US007122196B2

(12) United States Patent
Reed et al.

(10) Patent No.: US 7,122,196 B2
(45) Date of Patent: Oct. 17, 2006

(54) COMPOUNDS AND METHODS FOR DIAGNOSIS OF TUBERCULOSIS

(75) Inventors: Steven G. Reed, Bellevue, WA (US); Yasir A. W. Skeiky, Seattle, WA (US); Davin C. Dillon, Redmond, WA (US); Antonio Campos-Neto, Bainbridge Island, WA (US); Raymond Houghton, Bothell, WA (US); Thomas S. Vedvick, Federal Way, WA (US); Daniel R. Twardzik, Bainbridge Island, WA (US); Michael J. Lodes, Seattle, WA (US); Ronald C. Hendrickson, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 11/082,005

(22) Filed: Mar. 15, 2005

(65) Prior Publication Data

US 2005/0181419 A1    Aug. 18, 2005

Related U.S. Application Data

(60) Division of application No. 10/193,002, filed on Jul. 10, 2002, which is a continuation of application No. 09/072,596, filed on May 5, 1998, now Pat. No. 6,458,366, which is a continuation-in-part of application No. 09/024,753, filed on Feb. 18, 1998, now abandoned, which is a continuation-in-part of application No. 08/942,341, filed on Oct. 1, 1997, now abandoned, which is a continuation-in-part of application No. 08/818,111, filed on Mar. 13, 1997, now Pat. No. 6,338,852, which is a continuation-in-part of application No. 08/729,622, filed as application No. PCT/US96/14675 on Aug. 30, 1996, now abandoned, which is a continuation-in-part of application No. 08/680,574, filed on Jul. 12, 1996, now abandoned, which is a continuation-in-part of application No. 08/658,800, filed on Jun. 5, 1996, now abandoned, which is a continuation-in-part of application No. 08/620,280, filed on Mar. 22, 1996, now abandoned, which is a continuation-in-part of application No. 08/532,136, filed on Sep. 22, 1995, now abandoned, which is a continuation-in-part of application No. 08/523,435, filed on Sep. 1, 1995, now abandoned.

(51) Int. Cl.
| | |
|---|---|
| *A61K 39/04* | (2006.01) |
| *A61K 39/02* | (2006.01) |
| *A61K 39/00* | (2006.01) |
| *A61K 39/38* | (2006.01) |
| *C12Q 1/68* | (2006.01) |

(52) U.S. Cl. ................ 424/248.1; 424/130.1; 424/139.1; 424/150.1; 424/184.1; 424/185.1; 424/234.1; 435/6; 530/300; 530/350; 536/23.7

(58) Field of Classification Search ............ 424/130.1, 424/139.1, 150.1, 184.1, 185.1, 234.1, 248.1; 435/6; 530/300, 350; 536/23.7
See application file for complete search history.

(56) References Cited

U.S. PATENT DOCUMENTS

| 3,943,119 A | 3/1976 | Tsumita et al. |
|---|---|---|
| 5,108,745 A | 4/1992 | Horwitz |

FOREIGN PATENT DOCUMENTS

| EP | 419 355 A1 | 3/1991 |
|---|---|---|
| EP | 519 218 A2 | 12/1992 |
| FR | 2 244 539 | 5/1975 |
| FR | 2 265 402 | 11/1975 |
| WO | WO 88/05823 | 8/1988 |
| WO | WO 91/04272 | 4/1991 |
| WO | WO 91/14448 | 10/1991 |
| WO | WO 92/04049 | 3/1992 |
| WO | WO 92/14823 | 9/1992 |
| WO | WO 92/21758 | 12/1992 |
| WO | WO 94/00493 | 1/1994 |
| WO | WO 95/01440 | 1/1995 |
| WO | WO 95/01441 | 1/1995 |
| WO | WO 95/14713 | 6/1995 |
| WO | WO 95/31216 | 11/1995 |
| WO | WO 96/15241 | 5/1996 |
| WO | WO 96/23885 | 8/1996 |
| WO | WO 97/09428 | 3/1997 |
| WO | WO 97/09429 | 3/1997 |

OTHER PUBLICATIONS

Andersen and Hansen, "Structure and mapping antigenic domains of protein antigen b, a 38,000-molecular-weight protein of *Mycobacterium tuberculosis*," Infection and Immunity, vol. 37, No. 8; pp. 2481-2488 (1989).

Andersen et al., "Identficication of immunodominant antigens during infection with *Mycobacterium tuberculosis*," Scand. J. Immunol., vol. 36, pp. 823-831 (1992).

(Continued)

*Primary Examiner*—Rodney P Swartz
(74) *Attorney, Agent, or Firm*—Townsend and Townsend and Crew LLP

(57) ABSTRACT

Compounds and methods for diagnosing tuberculosis are disclosed. The compounds provided include polypeptides that contain at least one antigenic portion of one or more *M. tuberculosis* proteins, and DNA sequences encoding such polypeptides. Diagnostic kits containing such polypeptides or DNA sequences and a suitable detection reagent may be used for the detection of *M. tuberculosis* infection in patients and biological samples. Antibodies directed against such polypeptides are also provided.

5 Claims, 19 Drawing Sheets

OTHER PUBLICATIONS

Andersen, P., "Effective vaccination of mice against *Mycobacterium tuberculosis* with a soluble mixture of secreted mycobacterial proteins," Infection and Immunity, vol. 62, No. 6, pp. 2536-2544 (1994).

Ausebel et al., "Isolation of proteins for microsequence analysis," in: Current Protocols in Molecular Biology, Wiley & Sons, New York, pp. 10.19.1-12 (1993).

Barnes et al., "Immunoreactivity of a 10-kDa antigen of *Mycobacterium tuberculosis*," J. Immunol., vol. 148, No. 6; pp. 1835-1840 (1992).

Boesen et al., "Human T-cell responses to secreted antigen fractions of *Mycobacterium tuberculosis*," Infection and Immunity, vol. 63, No. 4; pp. 1491-1497 (1995).

Borremans et al., "Cloning, sequencing determination, and expression of a 32-kilodalton-protein gene of *Mycobacterium tuberculosis*," Infection and Immunity, vol. 57, No. 10; pp. 3123-3130 (1989).

Content et al., "The genes coding for antigen 85 complexes of *Mycobacterium tuberculosis* and *Mycobacterium bovis* BCG are members of a gene family: Cloning, sequence determination, and genomic organization of the gene coding for antigen 85-C of *M. tuberculosis*," Infection and Immunity, vol. 59; pp. 3205-3212 (1991).

Horowitz, et al., "Protective immunity against tuberculosis induced by vaccination with major extracellular proteins of *Mycobacterium tuberculosis*," PNAS USA, vol. 92; pp. 1530-1534 (1995).

Lowrie et al., "Towards a DNA vaccine against tuberculosis," Vaccine, vol. 12, No. 16; pp. 1537-1540 (1994).

Matsumoto et al, "Cloning and sequencing of a unique antigen MPT70 from *Mycobacterium tuberculosis* H37Rv and expression in BCG using *E. coli-Mycobacteria* shuttle vector," Scand. J. Immunol., vol. 41, pp. 281-287 (1995).

Nagai et al., "Isolation and partial characterization of major protein antigens in the culture fluid of *Mycobacterium tuberculosis*," Infection and Immunity, vol. 59, No. 1; pp. 372-382 (1991).

Oettinger and Andersen, "Cloning and B-cell-epitope mapping of MPT64 from *Mycobacterium tuberculosis* H37Rv," Infection and Immunity, vol. 62, No. 5; pp. 2058-2064 (1994).

Pal and Horwitz, "Immunization with extracellular proteins of *Mycobacterium tuberculosis* induces cell-mediated immune responses and substantial protective immunity in a guniea pig model of pulmonary tuberculosis," Infection and Immunity, vol. 60, No. 11; pp. 4781-4792 (1992).

Romain et al., "Isolation of a proline-rich mycobacterial protein eliciting delayed-type hypersensitivity reactions only in guinea pigs immunized with living mycobacteria," PNAS USA, vol. 90; pp. 5322-5326 (1993).

Wallis et al, "Identification of antigens of *Mycobacterium tuberculsosis* using human monoclonal antibodies," J. Clin. Invest., vol. 84; pp. 214-219 (1989).

Wiker and Harboe, "The antigen 85 complex: A major secretion product of *Mycobacterium tuberculosis*," Microbiological Reviews, vol. 56, No. 4; pp. 648-661 (1992).

Yamaguchi et al., "Cloning and characterization of the gene for immunogenic protein MPB64 of *Mycobacterium bovis* BCG," Infection and Immunity, vol. 57, No. 1; pp. 283-288 (1989).

Young et al., "Screening of a recombinant mycobacterial DNA library with polyclonal antiserum and molecular weight analysis of expressed antigens," Infection and Immunity, vol. 55, No. 6; pp. 1421-1425 (1987).

COMPOUNDS AND METHODS FOR DIAGNOSIS OF TUBERCULOSIS

CROSS-REFERENCE TO RELATED APPLICATIONS

This application is a division of U.S. application Ser. No. 10/193,002, filed Jul. 10, 2002, which is a continuation of U.S. application Ser. No. 09/072,596, filed May 5,1998, now U.S. Pat. No. 6,458,366; which is a continuation-in-part of U.S. application Ser. No. 09/024,753, filed Feb. 18, 1998, now abandoned; which is a continuation-in-part of U.S. application Ser. No. 08/942,341, filed Oct. 1, 1997, now abandoned; which is a continuation-in-part of U.S. application Ser. No. 08/818,111, filed Mar. 13, 1997, now U.S. Pat. No. 6,338,852; which is a continuation-in-part of U.S. application Ser. No. 08/729,622, filed Oct. 11, 1996, now abandoned; which claims priority from PCT Application No. PCT/US 96/14675, filed Aug. 30, 1996; and is a continuation-in-part of U.S. application Ser. No. 08/680,574, filed Jul. 12, 1996, now abandoned; which is a continuation-in-part of U.S. application Ser. No. 08/658,800, filed Jun. 5, 1996, now abandoned; which is a continuation-in-part of U.S. application Ser. No. 08/620,280, filed Mar. 22, 1996, now abandoned; which is a continuation-in-part of U.S. application Ser. No. 08/532,136, filed Sep. 22, 1995, now abandoned; which is a continuation-in-part of U.S. application Ser. No. 08/523,435, filed Sep. 1, 1995, now abandoned.

TECHNICAL FIELD

The present invention relates generally to the detection of *Mycobacterium tuberculosis* infection. The invention is more particularly related to polypeptides comprising a *Mycobacterium tuberculosis* antigen, or a portion or other variant thereof, and the use of such polypeptides for the serodiagnosis of *Mycobacterium tuberculosis* infection.

BACKGROUND OF THE INVENTION

Tuberculosis is a chronic, infectious disease, that is generally caused by infection with *Mycobacterium tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If left untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

Inhibiting the spread of tuberculosis will require effective vaccination and accurate, early diagnosis of the disease. Currently, vaccination with live bacteria is the most efficient method for inducing protective immunity. The most common *Mycobacterium* for this purpose is *Bacillus* Calmette-Guerin (BCG), an avirulent strain of *Mycobacterium bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable incubation at the injection site by 48–72 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. *Mycobacterium*-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25 dihydroxy-vitamin D3. Similarly, IL-12 has been shown to play a role in stimulating resistance to *M. tuberculosis* infection. For a review of the immunology of *M. tuberculosis* infection see Chan and Kaufmann, in *Tuberculosis: Pathogenesis, Protection and Control*, Bloom (ed.), ASM Press, Washington, D.C., 1994.

Accordingly, there is a need in the art for improved diagnostic methods for detecting tuberculosis. The present invention fulfills this need and further provides other related advantages.

SUMMARY OF THE INVENTION

Briefly stated, the present invention provides compositions and methods for diagnosing tuberculosis. In one aspect, polypeptides are provided comprising an antigenic portion of a soluble *M. tuberculosis* antigen, or a variant of such an antigen that differs only in conservative substitutions and/or modifications. In one embodiment of this aspect, the soluble antigen has one of the following N-terminal sequences:

(a)
Asp-Pro-Val-Asp-Ala-Val-Ile-Asn-Thr-Thr-Cys- Asn-Tyr-Gly-Gln-Val-Val-Ala-Ala-Leu; (SEQ ID NO: 115)

(b)
Ala-Val-Glu-Ser-Gly-Met-Leu-Ala-Leu-Gly-Thr-Pro-Ala-Pro-Ser; (SEQ ID NO: 116)

(c)
Ala-Ala-Met-Lys-Pro-Arg-Thr-Gly-Asp-Gly-Pro-Leu-Glu-Ala-Ala-Lys-Glu-Gly-Arg; (SEQ ID NO: 117)

(d)
Tyr-Tyr-Trp-Cys-Pro-Gly-Gln-Pro-Phe-Asp-Pro-Ala-Trp-Gly-Pro; (SEQ ID NO: 118)

(SEQ ID NO: 119)

-continued (e)
Asp-Ile-Gly-Ser-Glu-Ser-Thr-Glu-Asp-Gln-Gln-Xaa-
Ala-Val;

(SEQ ID NO: 120)
(f)
Ala-Glu-Glu-Ser-Ile-Ser-Thr-Xaa-Glu-Xaa-Ile-Val-
Pro;

(SEQ ID NO: 121)
(g)
Asp-Pro-Glu-Pro-Ala-Pro-Pro-Val-Pro-Thr-Thr-Ala-
Ala-Ser-Pro-Pro-Ser;

(SEQ ID NO: 122)
(h)
Ala-Pro-Lys-Thr-Tyr-Xaa-Glu-Glu-Leu-Lys-Gly-Thr-
Asp-Thr-Gly;

(SEQ ID NO: 123)
(i)
Asp-Pro-Ala-Ser-Ala-Pro-Asp-Val-Pro-Thr-Ala-Ala-
Gln-Leu-Thr-Ser-Leu-Leu-Asn-Ser-Leu-Ala-Asp-Pro-
Asn-Val-Ser-Phe-Ala-Asn;

(SEQ ID NO: 129)
(j)
Xaa-Asp-Ser-Glu-Lys-Ser-Ala-Thr-Ile-Lys-Val-Thr-
Asp-Ala-Ser;

(SEQ ID NO: 130)
(k)
Ala-Gly-Asp-Thr-Xaa-Ile-Tyr-Ile-Val-Gly-Asn-Leu-
Thr-Ala-Asp;
or (SEQ ID NO: 131)
(l)
Ala-Pro-Glu-Ser-Gly-Ala-Gly-Leu-Gly-Gly-Thr-Val-
Gln-Ala-Gly;

wherein Xaa may be any amino acid.

In a related aspect, polypeptides are provided comprising an immunogenic portion of an *M. tuberculosis* antigen, or a variant of such an antigen that differs only in conservative substitutions and/or modifications, the antigen having one of the following N-terminal sequences:

(SEQ ID NO: 132)
(m)
Xaa-Tyr-Ile-Ala-Tyr-Xaa-Thr-Thr-Ala-Gly-Ile-Val-
Pro-Gly-Lys-Ile-Asn-Val-His-Leu-Val;
or (SEQ ID NO: 124)
(n)
Asp-Pro-Pro-Asp-Pro-His-Gln-Xaa-Asp-Met-Thr-Lys-
Gly-Tyr-Tyr-Pro-Gly-Gly-Arg-Arg-Xaa-Phe;

wherein Xaa may be any amino acid.

In another embodiment, the soluble *M. tuberculosis* antigen comprises an amino acid sequence encoded by a DNA sequence selected from the group consisting of the sequences recited in SEQ ID NOS: 1, 2, 4–10, 13–25, 52, 94 and 96, the complements of said sequences, and DNA sequences that hybridize to a sequence recited in SEQ ID NOS: 1, 2, 4–10, 13–25, 52, 94 and 96 or a complement thereof under moderately stringent conditions.

In a related aspect, the polypeptides comprise an antigenic portion of a *M. tuberculosis* antigen, or a variant of such an antigen that differs only in conservative substitutions and/or modifications, wherein the antigen comprises an amino acid sequence encoded by a DNA sequence selected from the group consisting of the sequences recited in SEQ ID NOS: 26–51, 133, 134, 158–178, 184–88, 194–196, 198, 210–220, 232, 234, 235, 237–242, 248–251, 256–271, 287, 288, 290–293 and 298–337, the complements of said sequences, and DNA sequences that hybridize to a sequence recited in SEQ ID NOS: 26–51, 133, 134, 158–178, 184–188, 194–196, 198, 210–220, 232, 234, 235, 237–242, 248–251, 256–271, 287, 288, 290–293 and 298–337, or a complement thereof under moderately stringent conditions.

In related aspects, DNA sequences encoding the above polypeptides, recombinant expression vectors comprising these DNA sequences and host cells transformed or transfected with such expression vectors are also provided.

In another aspect, the present invention provides fusion proteins comprising a first and a second inventive polypeptide or, alternatively, an inventive polypeptide and a known *M. tuberculosis* antigen.

In further aspects of the subject invention, methods and diagnostic kits are provided for detecting tuberculosis in a patient. The methods comprise: (a) contacting a biological sample with at least one of the above polypeptides; and (b) detecting in the sample the presence of antibodies that bind to the polypeptide or polypeptides, thereby detecting *M. tuberculosis* infection in the biological sample. Suitable biological samples include whole blood, sputum, serum, plasma, saliva, cerebrospinal fluid and urine. The diagnostic kits comprise one or more of the above polypeptides in combination with a detection reagent.

The present invention also provides methods for detecting *M. tuberculosis* infection comprising: (a) obtaining a biological sample from a patient; (b) contacting the sample with at least one oligonucleotide primer in a polymerase chain reaction, the oligonucleotide primer being specific for a DNA sequence encoding the above polypeptides; and (c) detecting in the sample a DNA sequence that amplifies in the presence of the first and second oligonucleotide primers. In one embodiment, the oligonucleotide primer comprises at least about 10 contiguous nucleotides of such a DNA sequence.

In a further aspect, the present invention provides a method for detecting *M. tuberculosis* infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment, the oligonucleotide probe comprises at least about 15 contiguous nucleotides of such a DNA sequence.

In yet another aspect, the present invention provides antibodies, both polyclonal and monoclonal, that bind to the polypeptides described above, as well as methods for their use in the detection of *M. tuberculosis* infection.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIGS. 1A, 1B, 1C, and 1D illustrate the stimulation of proliferation and interferon-γ production in T cells derived from a first and a second *M. tuberculosis*-immune donor, respectively, by the 14 Kd, 20 Kd and 26 Kd antigens described in Example 1.

FIGS. 2A–D illustrate the reactivity of antisera raised against secretory *M. tuberculosis* proteins, the known *M.*

*tuberculosis* antigen 85b and the inventive antigens Tb38-1 and TbH-9, respectively, with *M. tuberculosis* lysate (lane 2), *M. tuberculosis* secretory proteins (lane 3), recombinant Tb38-1 (lane 4), recombinant TbH-9 (lane 5) and recombinant 85b (lane 5).

Figure 10:
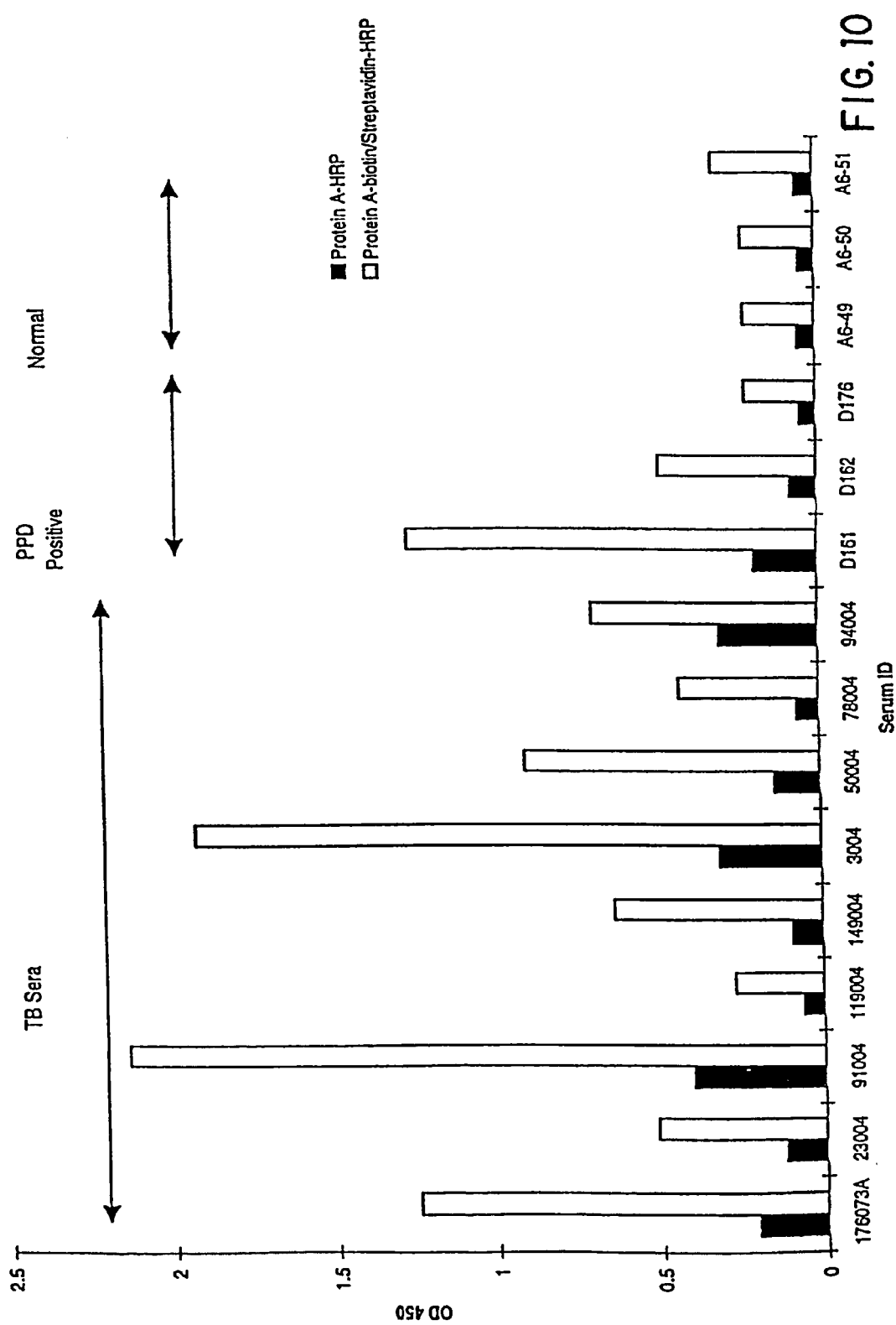
Figure 11:
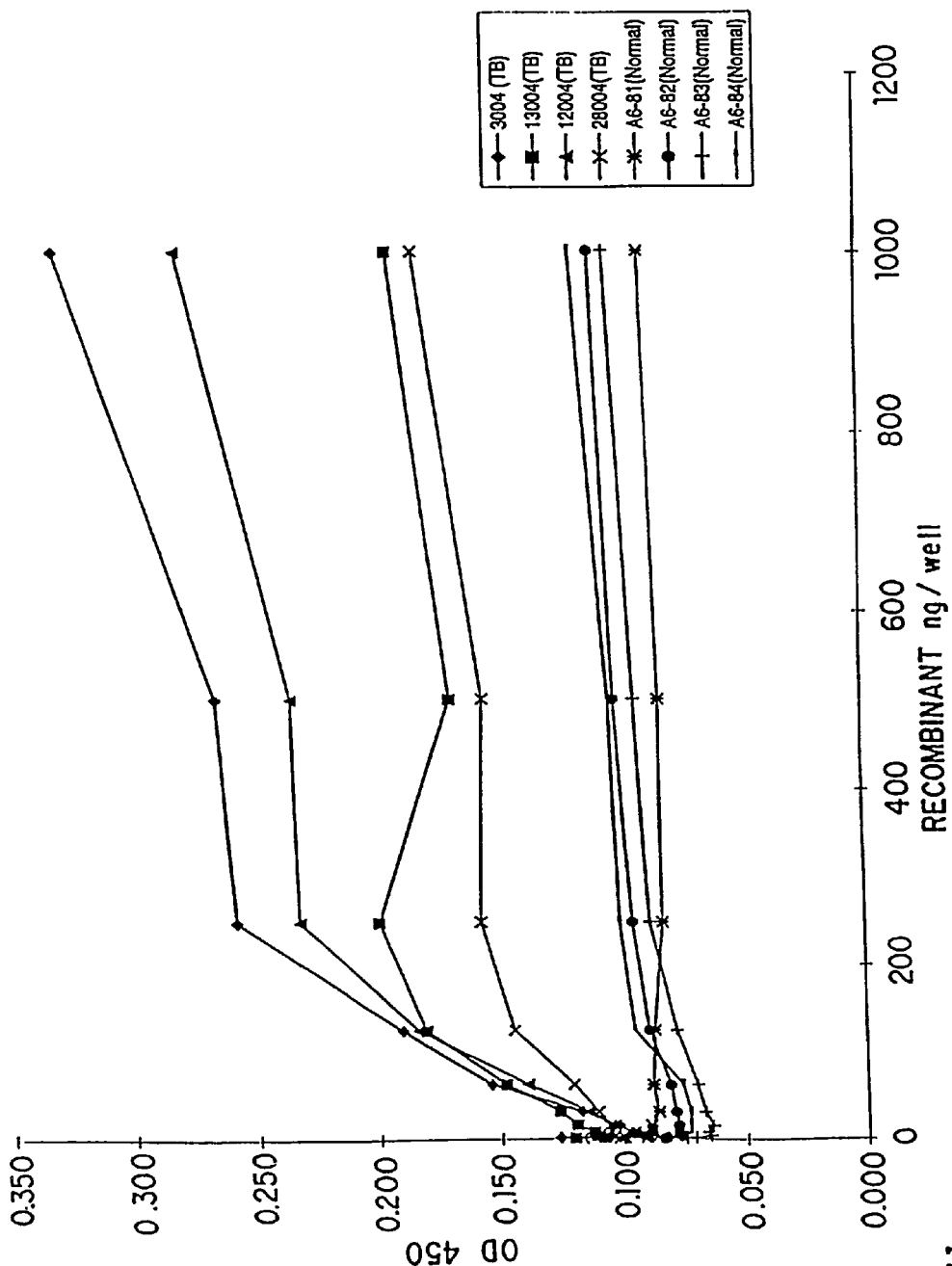
Figure 12A:
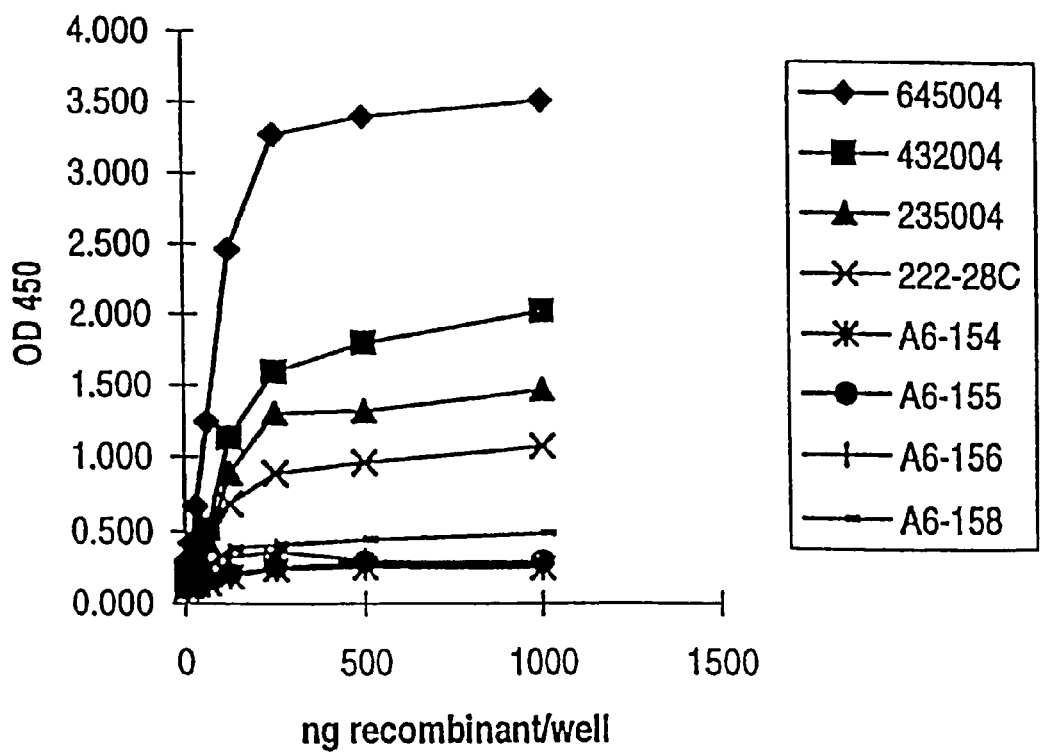
Figure 12B:
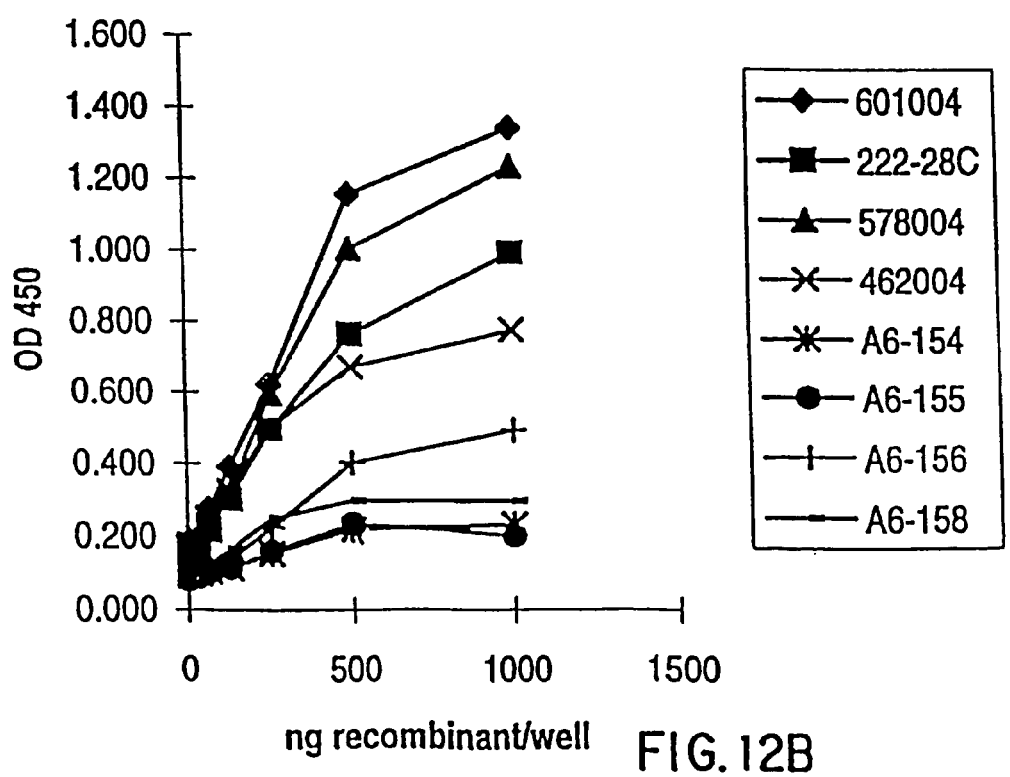
Figure 12C:
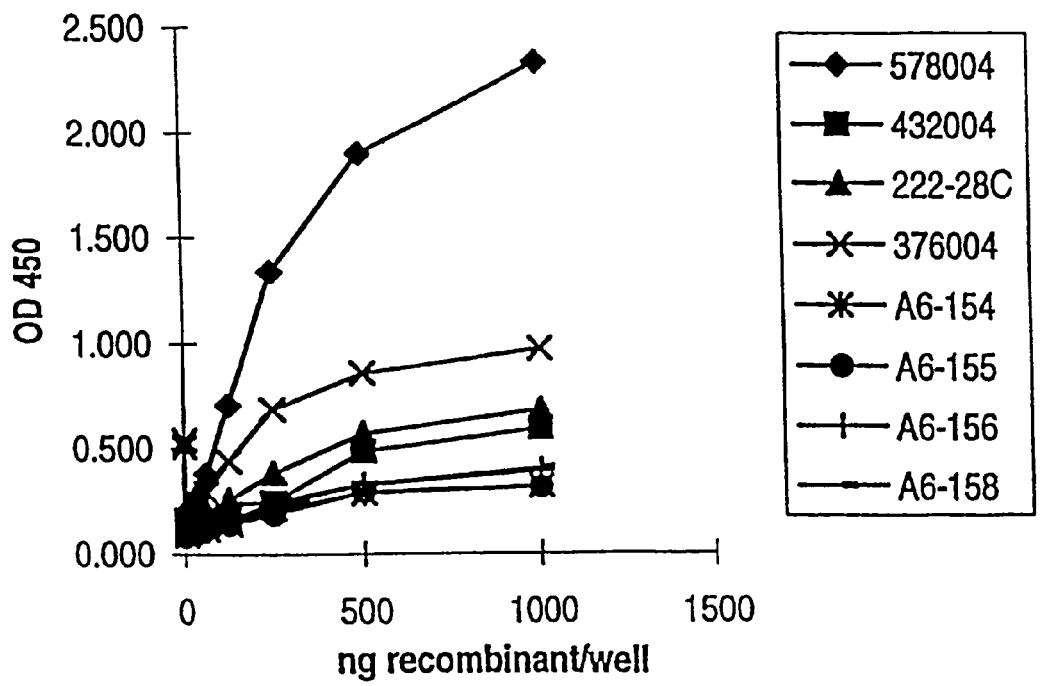
Figure 12D:
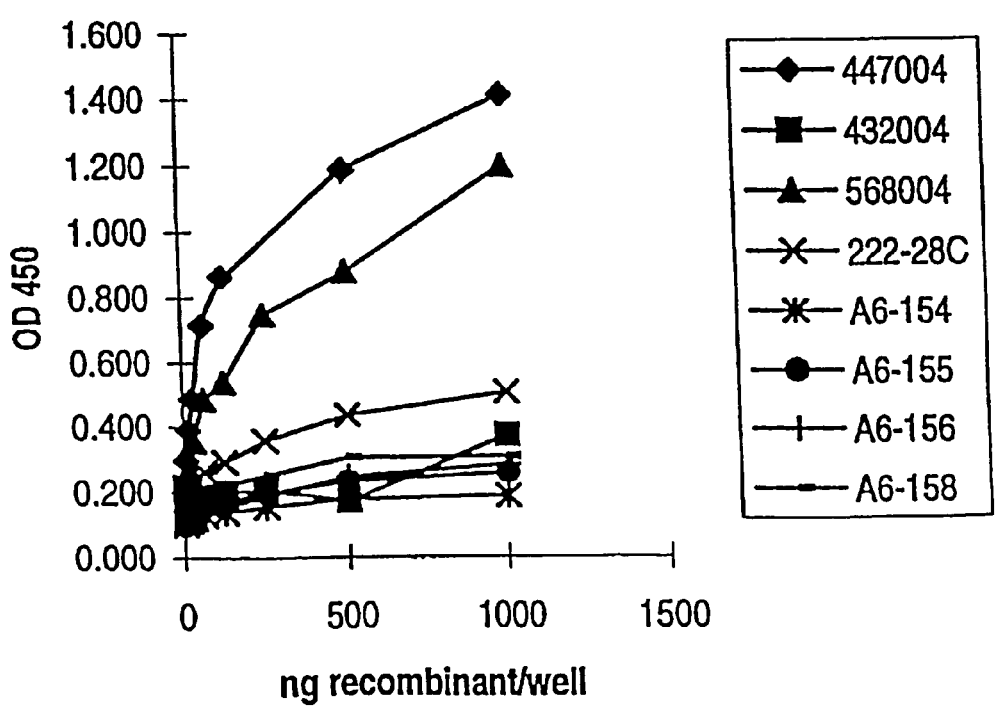
Figure 12E:
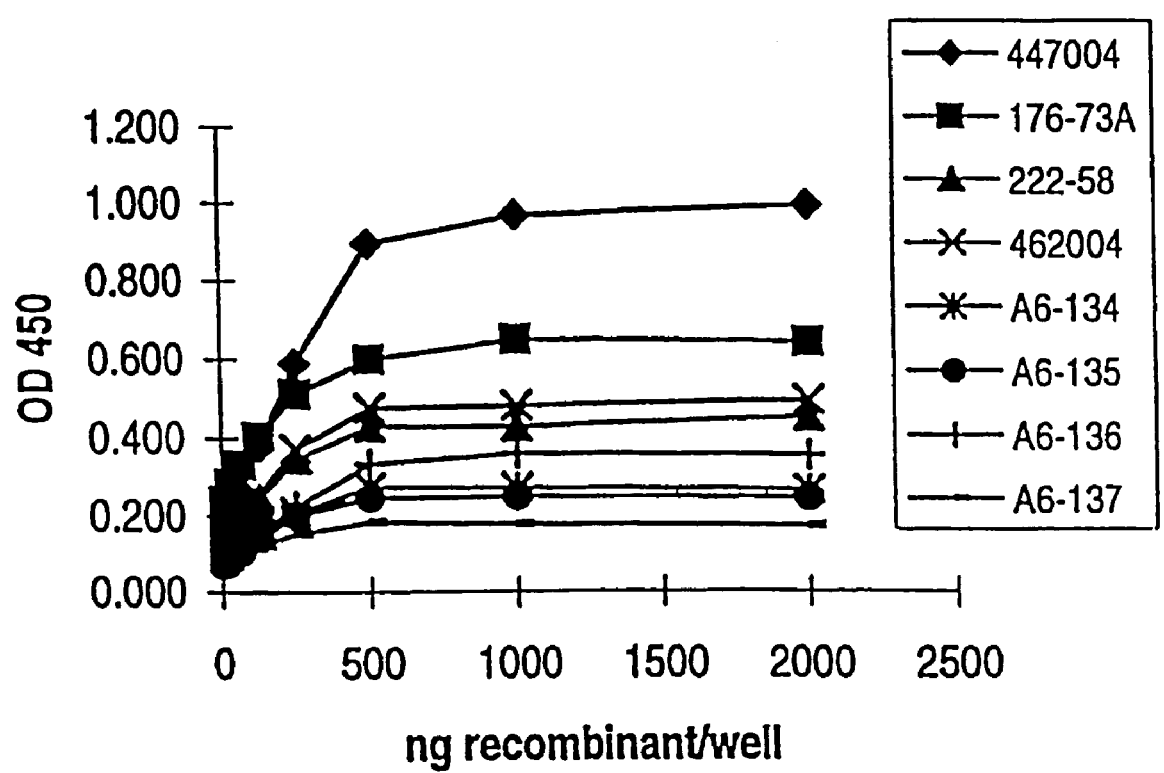

FIG. 10 illustrates the reactivity of the recombinant antigen TbH-33 (SEQ ID NO: 140) with sera from *M. tuberculosis* patients and from normal donors, and with a pool of sera from *M. tuberculosis* patients, as determined both by direct and indirect ELISA FIG. 11 illustrates the reactivity of increasing concentrations of the recombinant antigen TbH-33 (SEQ ID NO: 140) with sera from *M. tuberculosis* patients and from normal donors as determined by ELISA.

FIGS. 12A–E illustrate the reactivity of the recombinant antigens MO-1, MO-2, MO-4, MO-28 and MO-29, respectively, with sera from *M. tuberculosis* patients and from normal donors as determined by ELISA.

SEQ. ID NO. 1 is the DNA sequence of TbRa1.
SEQ. ID NO. 2 is the DNA sequence of TbRa10.
SEQ. ID NO. 3 is the DNA sequence of TbRa11.
SEQ. ID NO. 4 is the DNA sequence of TbRa12.
SEQ. ID NO. 5 is the DNA sequence of TbRa13.
SEQ. ID NO. 6 is the DNA sequence of TbRa16.
SEQ. ID NO. 7 is the DNA sequence of TbRa17.
SEQ. ID NO. 8 is the DNA sequence of TbRa18.
SEQ. ID NO. 9 is the DNA sequence of TbRa19.
SEQ. ID NO. 10 is the DNA sequence of TbRa24.
SEQ. ID NO. 11 is the DNA sequence of TbRa26.
SEQ. ID NO. 12 is the DNA sequence of TbRa28.
SEQ. ID NO. 13 is the DNA sequence of TbRa29.
SEQ. ID NO. 14 is the DNA sequence of TbRa2A.
SEQ. ID NO. 15 is the DNA sequence of TbRa3.
SEQ. ID NO. 16 is the DNA sequence of TbRa32.
SEQ. ID NO. 17 is the DNA sequence of TbRa35.
SEQ. ED NO. 18 is the DNA sequence of TbRa36.
SEQ. ID NO. 19 is the DNA sequence of TbRa4.
SEQ. ID NO. 20 is the DNA sequence of TbRa9.
SEQ. ID NO. 21 is the DNA sequence of TbRaB.
SEQ. ID NO. 22 is the DNA sequence of TbRaC.
SEQ. ID NO. 23 is the DNA sequence of TbRaD.
SEQ. ID NO. 24 is the DNA sequence of YYWCPG.
SEQ. ID NO. 25 is the DNA sequence of AAMK.
SEQ. ID NO. 26 is the DNA sequence of TbL-23.
SEQ. ID NO. 27 is the DNA sequence of TbL-24.
SEQ. ID NO. 28 is the DNA sequence of TbL-25.
SEQ. ID NO. 29 is the DNA sequence of TbL-8.
SEQ. ID NO. 30 is the DNA sequence of TbL-29.
SEQ. ID NO. 31 is the DNA sequence of TbH-5.
SEQ. ID NO. 32 is the DNA sequence of TbH-8.
SEQ. ID NO. 33 is the DNA sequence of TbH-9.
SEQ. ID NO. 34 is the DNA sequence of TbM-1.
SEQ. ID NO. 35 is the DNA sequence of TbM-3.
SEQ. ID NO. 36 is the DNA sequence of TbM-6.
SEQ. ID NO. 37 is the DNA sequence of TbM-7.
SEQ. ID NO. 38 is the DNA sequence of TbM-9.
SEQ. ID NO. 39 is the DNA sequence of TbM-12.
SEQ. ID NO. 40 is the DNA sequence of TbM-13.
SEQ. ID NO. 41 is the DNA sequence of TbM-14.
SEQ. ID NO. 42 is the DNA sequence of TbM-15.
SEQ. ID NO. 43 is the DNA sequence of TbH-4.
SEQ. ID NO. 44 is the DNA sequence of TbH-4-FWD.
SEQ. ID NO. 45 is the DNA sequence of TbH-12.
SEQ. ID NO. 46 is the DNA sequence of Tb38-1.
SEQ. ID NO. 47 is the DNA sequence of Tb38-4.
SEQ. ID NO. 48 is the DNA sequence of TbL-17.
SEQ. ID NO. 49 is the DNA sequence of TbL-20.
SEQ. ID NO. 50 is the DNA sequence of TbL-21.
SEQ. ID NO. 51 is the DNA sequence of TbH-16.
SEQ. ID NO. 52 is the DNA sequence of DPEP.
SEQ. ID NO. 53 is the deduced amino acid sequence of DPEP.
SEQ. ID NO. 54 is the protein sequence of DPV N-terminal Antigen.
SEQ. ID NO. 55 is the protein sequence of AVGS N-terminal Antigen.
SEQ. ID NO. 56 is the protein sequence of AAMK N-terminal Antigen.
SEQ. ID NO. 57 is the protein sequence of YYWC N-terminal Antigen.
SEQ. ID NO. 58 is the protein sequence of DIGS N-terminal Antigen.
SEQ. ID NO. 59 is the protein sequence of AEES N-terminal Antigen.
SEQ. ID NO. 60 is the protein sequence of DPEP N-terminal Antigen.
SEQ. ID NO. 61 is the protein sequence of APKT N-terminal Antigen.
SEQ. ID NO. 62 is the protein sequence of DPAS N-terminal Antigen.
SEQ. ID NO. 63 is the deduced amino acid sequence of TbM-1Peptide.
SEQ. ID NO. 64 is the deduced amino acid sequence of TbRa1.
SEQ. ID NO. 65 is the deduced amino acid sequence of TbRa10.
SEQ. ID NO. 66 is the deduced amino acid sequence of TbRa11.
SEQ. ID NO. 67 is the deduced amino acid sequence of TbRa12.
SEQ. ID NO. 68 is the deduced amino acid sequence of TbRa13.
SEQ. ID NO. 69 is the deduced amino acid sequence of TbRa16.
SEQ. ID NO. 70 is the deduced amino acid sequence of TbRa17.
SEQ. ID NO. 71 is the deduced amino acid sequence of TbRa18.

SEQ. ID NO. 72 is the deduced amino acid sequence of TbRa19.
SEQ. ID NO. 73 is the deduced amino acid sequence of TbRa24.
SEQ. ID NO. 74 is the deduced amino acid sequence of TbRa26.
SEQ. ID NO. 75 is the deduced amino acid sequence of TbRa28.
SEQ. ID NO. 76 is the deduced amino acid sequence of TbRa29.
SEQ. ID NO. 77 is the deduced amino acid sequence of TbRa2A.
SEQ. ID NO. 78 is the deduced amino acid sequence of TbRa3.
SEQ. ID NO. 79 is the deduced amino acid sequence of TbRa32.
SEQ. ID NO. 80 is the deduced amino acid sequence of TbRa35.
SEQ. ID NO. 81 is the deduced amino acid sequence of TbRa36.
SEQ. ID NO. 82 is the deduced amino acid sequence of TbRa4.
SEQ. ID NO. 83 is the deduced amino acid sequence of TbRa9.
SEQ. ID NO. 84 is the deduced amino acid sequence of TbRaB.
SEQ. ID NO. 85 is the deduced amino acid sequence of TbRaC.
SEQ. ID NO. 86 is the deduced amino acid sequence of TbRaD.
SEQ. ID NO. 87 is the deduced amino acid sequence of YYWCPG.
SEQ. ID NO. 88 is the deduced amino acid sequence of TbAAMK.
SEQ. ID NO. 89 is the deduced amino acid sequence of Tb38-1.
SEQ. ID NO. 90 is the deduced amino acid sequence of TbH-4.
SEQ. ID NO. 91 is the deduced amino acid sequence of TbH-8.
SEQ. ID NO. 92 is the deduced amino acid sequence of TbH-9.
SEQ. ID NO. 93 is the deduced amino acid sequence of TbH-12.
SEQ. ID NO. 94 is the DNA sequence of DPAS.
SEQ. ID NO. 95 is the deduced amino acid sequence of DPAS.
SEQ. ID NO. 96 is the DNA sequence of DPV.
SEQ. ID NO. 97 is the deduced amino acid sequence of DPV.
SEQ. ID NO. 98 is the DNA sequence of ESAT-6.
SEQ. ID NO. 99 is the deduced amino acid sequence of ESAT-6.
SEQ. ID NO. 100 is the DNA sequence of TbH-8-2.
SEQ. ID NO. 101 is the DNA sequence of TbH-9FL.
SEQ. ID NO. 102 is the deduced amino acid sequence of TbH-9FL.
SEQ. ID NO. 103 is the DNA sequence of TbH-9-1.
SEQ. ID NO. 104 is the deduced amino acid sequence of TbH-9-1.
SEQ. ID NO. 105 is the DNA sequence of TbH-9-4.
SEQ. ID NO. 106 is the deduced amino acid sequence of TbH-9-4.
SEQ. ID NO. 107 is the DNA sequence of Tb38-1F2 IN.
SEQ. ID NO. 108 is the DNA sequence of Tb38-1F2 RP.
SEQ. ID NO. 109 is the deduced amino acid sequence of Tb37-FL.
SEQ. ID NO. 110 is the deduced amino acid sequence of Tb38-IN.
SEQ. ID NO. 111 is the DNA sequence of Tb38-1F3.
SEQ. ID NO. 112 is the deduced amino acid sequence of Tb38-1F3.
SEQ. ID NO. 113 is the DNA sequence of Tb38-1F5.
SEQ. ID NO. 114 is the DNA sequence of Tb38-1F6.
SEQ. ID NO. 115 is the deduced N-terminal amino acid sequence of DPV.
SEQ. ID NO. 116 is the deduced N-terminal amino acid sequence of AVGS.
SEQ. ID NO. 117 is the deduced N-terminal amino acid sequence of AAMK
SEQ. ID NO. 118 is the deduced N-terminal amino acid sequence of YYWC
SEQ. ID NO. 119 is the deduced N-terminal amino acid sequence of DIGS.
SEQ. ID NO. 120 is the deduced N-terminal amino acid sequence of AAES.
SEQ. ID NO. 121 is the deduced N-terminal amino acid sequence of DPEP.
SEQ. ID NO. 122 is the deduced N-terminal amino acid sequence of APKT.
SEQ. ID NO. 123 is the deduced N-terminal amino acid sequence of DPAS.
SEQ ID NO. 124 is the protein sequence of DPPD N-terminal Antigen.
SEQ ID NO. 125–128 are the protein sequences of four DPPD cyanogen bromide fragments.
SEQ ID NO. 129 is the N-terminal protein sequence of XDS antigen.
SEQ ID NO. 130 is the N-terminal protein sequence of AGD antigen.
SEQ ID NO. 131 is the N-terminal protein sequence of APE antigen.
SEQ ID NO. 132 is the N-terminal protein sequence of XYI antigen.
SEQ ID NO. 133 is the DNA sequence of TbH-29.
SEQ ID NO. 134 is the DNA sequence of TbH-30.
SEQ ID NO. 135 is the DNA sequence of TbH-32.
SEQ ID NO. 136 is the DNA sequence of TbH-33.
SEQ ID NO. 137 is the predicted amino acid sequence of TbH-29.
SEQ ID NO. 138 is the predicted amino acid sequence of TbH-30.
SEQ ID NO. 139 is the predicted amino acid sequence of TbH-32.
SEQ ID NO. 140 is the predicted amino acid sequence of TbH-33.
SEQ ID NO: 141–146 are PCR primers used in the preparation of a fusion protein containing TbRa3, 38 kD and Tb38-1.
SEQ ID NO: 147 is the DNA sequence of the fusion protein containing TbRa3, 38 kD and Tb38-1.
SEQ ID NO: 148 is the amino acid sequence of the fusion protein containing TbRa3, 38 kD and Tb38-1.
SEQ ID NO: 149 is the DNA sequence of the *M. tuberculosis* antigen 38 kD.
SEQ ID NO: 150 is the amino acid sequence of the *M. tuberculosis* antigen 38 kD.
SEQ ID NO: 151 is the DNA sequence of XP14.
SEQ ID NO: 152 is the DNA sequence of XP24.
SEQ ID NO: 153 is the DNA sequence of XP31.
SEQ ID NO: 154 is the 5' DNA sequence of XP32.
SEQ ID NO: 155 is the 3' DNA sequence of XP32.
SEQ ID NO: 156 is the predicted amino acid sequence of XP14.

SEQ ID NO: 157 is the predicted amino acid sequence encoded by the reverse complement of XP14.
SEQ ID NO: 158 is the DNA sequence of XP27.
SEQ ID NO: 159 is the DNA sequence of XP36.
SEQ ID NO: 160 is the 5' DNA sequence of XP4.
SEQ ID NO: 161 is the 5' DNA sequence of XP5.
SEQ ID NO: 162 is the 5' DNA sequence of XP17.
SEQ ID NO: 163 is the 5' DNA sequence of XP30.
SEQ ID NO: 164 is the 5' DNA sequence of XP2.
SEQ ID NO: 165 is the 3' DNA sequence of XP2.
SEQ ID NO: 166 is the 5' DNA sequence of XP3.
SEQ ID NO: 167 is the 3' DNA sequence of XP3.
SEQ ID NO: 168 is the 5' DNA sequence of XP6.
SEQ ID NO: 169 is the 3' DNA sequence of XP6.
SEQ ID NO: 170 is the 5' DNA sequence of XP18.
SEQ ID NO: 171 is the 3' DNA sequence of XP18.
SEQ ID NO: 172 is the 5' DNA sequence of XP19.
SEQ ID NO: 173 is the 3' DNA sequence of XP19.
SEQ ID NO: 174 is the 5' DNA sequence of XP22.
SEQ ID NO: 175 is the 3' DNA sequence of XP22.
SEQ ID NO: 176 is the 5' DNA sequence of XP25.
SEQ ID NO: 177 is the 3' DNA sequence of XP25.
SEQ ID NO: 178 is the full-length DNA sequence of TbH 4-XP1.
SEQ ID NO: 179 is the predicted amino acid sequence of TbH 4-XP1.
SEQ ID NO: 180 is the predicted amino acid sequence encoded by the reverse complement of TbH 4-XP 1.
SEQ ID NO: 181 is a first predicted amino acid sequence encoded by XP36.
SEQ ID NO: 182 is a second predicted amino acid sequence encoded by XP36.
SEQ ID NO: 183 is the predicted amino acid sequence encoded by the reverse complement of XP36.
SEQ ID NO: 184 is the DNA sequence of RDIF2.
SEQ ID NO: 185 is the DNA sequence of RDIF5.
SEQ ID NO: 186 is the DNA sequence of RDIF8.
SEQ ID NO: 187 is the DNA sequence of RDIF10.
SEQ ID NO: 188 is the DNA sequence of RDIF11.
SEQ ID NO: 189 is the predicted amino acid sequence of RDIF2.
SEQ ID NO: 190 is the predicted amino acid sequence of RDIF5.
SEQ ID NO: 191 is the predicted amino acid sequence of RDIF8.
SEQ ID NO: 192 is the predicted amino acid sequence of RDIF10.
SEQ ID NO: 193 is the predicted amino acid sequence of RDIF11.
SEQ ID NO: 194 is the 5' DNA sequence of RDIF12.
SEQ ID NO: 195 is the 3' DNA sequence of RDIF12.
SEQ ID NO: 196 is the DNA sequence of RDIF7.
SEQ ID NO: 197 is the predicted amino acid sequence of RDIF7.
SEQ ID NO: 198 is the DNA sequence of DIF 2-1.
SEQ ID NO: 199 is the predicted amino acid sequence of DIF 2-1.
SEQ ID NO: 200–207 are PCR primers used in the preparation of a fusion protein containing TbRa3. 38 kD, Tb38-1 and DPEP (hereinafter referred to as TbF-2).
SEQ ID NO: 208 is the DNA sequence of the fusion protein TbF-2.
SEQ ID NO: 209 is the amino acid sequence of the fusion protein TbF-2.
SEQ ID NO: 210 is the 5' DNA sequence of MO-1.
SEQ ID NO: 211 is the 5' DNA sequence for MO-2.
SEQ ID NO: 212 is the 5' DNA sequence for MO-4.
SEQ ID NO: 213 is the 5' DNA sequence for MO-8.
SEQ ID NO: 214 is the 5' DNA sequence for MO-9.
SEQ ID NO: 215 is the 5' DNA sequence for MO-26.
SEQ ID NO: 216 is the 5' DNA sequence for MO-28.
SEQ ID NO: 217 is the 5' DNA sequence for MO-29.
SEQ ID NO: 218 is the 5' DNA sequence for MO-30.
SEQ ID NO: 219 is the 5' DNA sequence for MO-34.
SEQ ID NO: 220 is the 5' DNA sequence for MO-35.
SEQ ID NO: 221 is the predicted amino acid sequence for MO-1.
SEQ ID NO: 222 is the predicted amino acid sequence for MO-2.
SEQ ID NO: 223 is the predicted amino acid sequence for MO-4.
SEQ ID NO: 224 is the predicted amino acid sequence for MO-8.
SEQ ID NO: 225 is the predicted amino acid sequence for MO-9.
SEQ ID NO: 226 is the predicted amino acid sequence for MO-26.
SEQ ID NO: 227 is the predicted amino acid sequence for MO-28.
SEQ ID NO: 228 is the predicted amino acid sequence for MO-29.
SEQ ID NO: 229 is the predicted amino acid sequence for MO-30.
SEQ ID NO: 230 is the predicted amino acid sequence for MO-34.
SEQ ID NO: 231 is the predicted amino acid sequence for MO-35.
SEQ ID NO: 232 is the determined DNA sequence for MO-10.
SEQ ID NO: 233 is the predicted amino acid sequence for MO-10.
SEQ ID NO: 234 is the 3' DNA sequence for MO-27.
SEQ ID NO: 235 is the full-length DNA sequence for DPPD.
SEQ ID NO: 236 is the predicted full-length amino acid sequence for DPPD.
SEQ ID NO: 237 is the determined 5' cDNA sequence for LSER-10.
SEQ ID NO: 238 is the determined 5' cDNA sequence for LSER-11.
SEQ ID NO: 239 is the determined 5' cDNA sequence for LSER-12.
SEQ ID NO: 240 is the determined 5' cDNA sequence for LSER-13.
SEQ ID NO: 241 is the determined 5' cDNA sequence for LSER-16.
SEQ ID NO: 242 is the determined 5' cDNA sequence for LSER-25.
SEQ ID NO: 243 is the predicted amino acid sequence for LSER-10.
SEQ ID NO: 244 is the predicted amino acid sequence for LSER-12.
SEQ ID NO: 245 is the predicted amino acid sequence for LSER-13.
SEQ ID NO: 246 is the predicted amino acid sequence for LSER-16.
SEQ ID NO: 247 is the predicted amino acid sequence for LSER-25.
SEQ ID NO: 248 is the determined cDNA sequence for LSER-18.
SEQ ID NO: 249 is the determined cDNA sequence for LSER-23.
SEQ ID NO: 250 is the determined cDNA sequence for LSER-24.

SEQ ID NO: 251 is the determined cDNA sequence for LSER-27.
SEQ ID NO: 252 is the predicted amino acid sequence for LSER-18.
SEQ ID NO: 253 is the predicted amino acid sequence for LSER-23.
SEQ ID NO: 254 is the predicted amino acid sequence for LSER-24.
SEQ ID NO: 255 is the predicted amino acid sequence for LSER-27.
SEQ ID NO: 256 is the determined 5' cDNA sequence for LSER-1.
SEQ ID NO: 257 is the determined 5' cDNA sequence for LSER-3.
SEQ ID NO: 258 is the determined 5' cDNA sequence for LSER-4.
SEQ ID NO: 259 is the determined 5' cDNA sequence for LSER-5.
SEQ ID NO: 260 is the determined 5' cDNA sequence for LSER-6.
SEQ ID NO: 261 is the determined 5' cDNA sequence for LSER-8.
SEQ ID NO: 262 is the determined 5' cDNA sequence for LSER-14.
SEQ ID NO: 263 is the determined 5' cDNA sequence for LSER-15.
SEQ ID NO: 264 is the determined 5' cDNA sequence for LSER-17.
SEQ ID NO: 265 is the determined 5' cDNA sequence for LSER-19.
SEQ ID NO: 266 is the determined 5' cDNA sequence for LSER-20.
SEQ ID NO: 267 is the determined 5' cDNA sequence for LSER-22.
SEQ ID NO: 268 is the determined 5' cDNA sequence for LSER-26.
SEQ ID NO: 269 is the determined 5' cDNA sequence for LSER-28.
SEQ ID NO: 270 is the determined 5' cDNA sequence for LSER-29.
SEQ ID NO: 271 is the determined 5' cDNA sequence for LSER-30.
SEQ ID NO: 272 is the predicted amino acid sequence for LSER-1.
SEQ ID NO: 273 is the predicted amino acid sequence for LSER-3.
SEQ ID NO: 274 is the predicted amino acid sequence for LSER-5.
SEQ ID NO: 275 is the predicted amino acid sequence for LSER-6.
SEQ ID NO: 276 is the predicted amino acid sequence for LSER-8.
SEQ ID NO: 277 is the predicted amino acid sequence for LSER-14.
SEQ ID NO: 278 is the predicted amino acid sequence for LSER-15.
SEQ ID NO: 279 is the predicted amino acid sequence for LSER-17.
SEQ ID NO: 280 is the predicted amino acid sequence for LSER-19.
SEQ ID NO: 281 is the predicted amino acid sequence for LSER-20.
SEQ ID NO: 282 is the predicted amino acid sequence for LSER-22.
SEQ ID NO: 283 is the predicted amino acid sequence for LSER-26.
SEQ ID NO: 284 is the predicted amino acid sequence for LSER-28.
SEQ ID NO: 285 is the predicted amino acid sequence for LSER-29.
SEQ ID NO: 286 is the predicted amino acid sequence for LSER-30.
SEQ ID NO: 287 is the determined cDNA sequence for LSER-9.
SEQ ID NO: 288 is the determined cDNA sequence for the reverse complement of LSER-6.
SEQ ID NO: 289 is the predicted amino acid sequence for the reverse complement of LSER-6.
SEQ ID NO: 290 is the determined 5' cDNA sequence for MO-12.
SEQ ID NO: 291 is the determined 5' cDNA sequence for MO-13.
SEQ ID NO: 292 is the determined 5' cDNA sequence for MO-19.
SEQ ID NO: 293 is the determined 5' cDNA sequence for MO-39.
SEQ ID NO: 294 is the predicted amino acid sequence for MO-12.
SEQ ID NO: 295 is the predicted amino acid sequence for MO-13.
SEQ ID NO: 296 is the predicted amino acid sequence for MO-19.
SEQ ID NO: 297 is the predicted amino acid sequence for MO-39.
SEQ ID NO: 298 is the determined 5' cDNA sequence for Erdsn-1.
SEQ ID NO: 299 is the determined 5' cDNA sequence for Erdsn-2.
SEQ ID NO: 300 is the determined 5' cDNA sequence for Erdsn-4.
SEQ ID NO: 301 is the determined 5' cDNA sequence for Erdsn-5.
SEQ ID NO: 302 is the determined 5' cDNA sequence for Erdsn-6.
SEQ ID NO: 303 is the determined 5' cDNA sequence for Erdsn-7.
SEQ ID NO: 304 is the determined 5' cDNA sequence for Erdsn-8.
SEQ ID NO: 305 is the determined 5' cDNA sequence for Erdsn-9.
SEQ ID NO: 306 is the determined 5' cDNA sequence for Erdsn-10.
SEQ ID NO: 307 is the determined 5' cDNA sequence for Erdsn-12.
SEQ ID NO: 308 is the determined 5' cDNA sequence for Erdsn-13.
SEQ ID NO: 309 is the determined 5' cDNA sequence for Erdsn-14.
SEQ ID NO: 310 is the determined 5' cDNA sequence for Erdsn-15.
SEQ ID NO: 311 is the determined 5' cDNA sequence for Erdsn-16.
SEQ ID NO: 312 is the determined 5' cDNA sequence for Erdsn-17.
SEQ ID NO: 313 is the determined 5' cDNA sequence for Erdsn-18.
SEQ ID NO: 314 is the determined 5' cDNA sequence for Erdsn-21.
SEQ ID NO: 315 is the determined 5' cDNA sequence for Erdsn-22.
SEQ ID NO: 316 is the determined 5' cDNA sequence for Erdsn-23.

SEQ ID NO: 317 is the determined 5' cDNA sequence for Erdsn-25.

SEQ ID NO: 318 is the determined 3' cDNA sequence for Erdsn-1.

SEQ ID NO: 319 is the determined 3' cDNA sequence for Erdsn-2.

SEQ ID NO: 320 is the determined 3' cDNA sequence for Erdsn-4.

SEQ ID NO: 321 is the determined 3' cDNA sequence for Erdsn-5.

SEQ ID NO: 322 is the determined 3' cDNA sequence for Erdsn-7.

SEQ ID NO: 323 is the determined 3' cDNA sequence for Erdsn-8.

SEQ ID NO: 324 is the determined 3' cDNA sequence for Erdsn-9.

SEQ ID NO: 325 is the determined 3' cDNA sequence for Erdsn-10.

SEQ ID NO: 326 is the determined 3' cDNA sequence for Erdsn-12.

SEQ ID NO: 327 is the determined 3' cDNA sequence for Erdsn-13.

SEQ ID NO: 328 is the determined 3' cDNA sequence for Erdsn-14.

SEQ ID NO: 329 is the determined 3' cDNA sequence for Erdsn-15.

SEQ ID NO: 330 is the determined 3' cDNA sequence for Erdsn-16.

SEQ ID NO: 331 is the determined 3' cDNA sequence for Erdsn-17.

SEQ ID NO: 332 is the determined 3' cDNA sequence for Erdsn-18.

SEQ ID NO: 333 is the determined 3' cDNA sequence for Erdsn-21.

SEQ ID NO: 334 is the determined 3' cDNA sequence for Erdsn-22.

SEQ ID NO: 335 is the determined 3' cDNA sequence for Erdsn-23.

SEQ ID NO: 336 is the determined 3' cDNA sequence for Erdsn-25.

SEQ ID NO: 337 is the determined cDNA sequence for Erdsn-24.

SEQ ID NO: 338 is the determined amino acid sequence for a *M. tuberculosis* 85b precursor homolog.

SEQ ID NO: 339 is the determined amino acid sequence for spot 1.

SEQ ID NO: 340 is a determined amino acid sequence for spot 2.

SEQ ID NO: 341 is a determined amino acid sequence for spot 2.

SEQ ID NO: 342 is the determined amino acid seq for spot 4.

SEQ ID NO: 343 is the sequence of primer PDM-157.

SEQ ID NO: 344 is the sequence of primer PDM-160.

SEQ ID NO: 345 is the DNA sequence of the fusion protein TbF-6.

SEQ ID NO: 346 is the amino acid sequence of fusion protein TbF-6.

SEQ ID NO: 347 is the sequence of primer PDM-176.

SEQ ID NO: 348 is the sequence of primer PDM-175.

SEQ ID NO: 349 is the DNA sequence of the fusion protein TbF-8.

SEQ ID NO: 350 is the amino acid sequence of the fusion protein TbF-8.

DETAILED DESCRIPTION OF THE INVENTION

As noted above, the present invention is generally directed to compositions and methods for diagnosing tuberculosis. The compositions of the subject invention include polypeptides that comprise at least one antigenic portion of a *M. tuberculosis* antigen, or a variant of such an antigen that differs only in conservative substitutions and/or modifications. Polypeptides within the scope of the present invention include, but are not limited to, soluble *M. tuberculosis* antigens. A "soluble *M. tuberculosis* antigen" is a protein of *M. tuberculosis* origin that is present in *M. tuberculosis* culture filtrate. As used herein, the term "polypeptide" encompasses amino acid chains of any length, including full length proteins (i.e., antigens), wherein the amino acid residues are linked by covalent peptide bonds. Thus, a polypeptide comprising an antigenic portion of one of the above antigens may consist entirely of the antigenic portion, or may contain additional sequences. The additional sequences may be derived from the native *M. tuberculosis* antigen or may be heterologous, and such sequences may (but need not) be antigenic.

An "antigenic portion" of an antigen (which may or may not be soluble) is a portion that is capable of reacting with sera obtained from an *M. tuberculosis*-infected individual (i.e., generates an absorbance reading with sera from infected individuals that is at least three standard deviations above the absorbance obtained with sera from uninfected individuals, in a representative ELISA assay described herein). An "*M. tuberculosis*-infected individual" is a human who has been infected with *M. tuberculosis* (e.g., has an intradermal skin test response to PPD that is at least 0.5 cm in diameter). Infected individuals may display symptoms of tuberculosis or may be free of disease symptoms. Polypeptides comprising at least an antigenic portion of one or more *M. tuberculosis* antigens as described herein may generally be used, alone or in combination, to detect tuberculosis in a patient.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. For polypeptides with immunoreactive properties, variants may, alternatively, be identified by modifying the amino acid sequence of one of the above polypeptides, and evaluating the immunoreactivity of the modified polypeptide. For polypeptides useful for the generation of diagnostic binding agents, a variant may be identified by evaluating a modified polypeptide for the ability to generate antibodies that detect the presence or absence of tuberculosis. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*. 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. Such variant nucleotide sequences will generally hybridize to the recite nucleotide sequence under stringent conditions. As used herein, "stringent conditions" refers to prewashing in a solution of 6×SSC, 0.2% SDS; hybridizing at 65° C., 6×SSC, 0.20°% SDS overnight; followed by two washes of 30 minutes each in 1×SSC, 0.1% SDS at 65° C. and two washes of 30 minutes each in 0.2×SSC, 0.1% SDS at 65° C.

In a related aspect, combination, or fusion, polypeptides are disclosed. A "fusion polypeptide" is a polypeptide comprising at least one of the above antigenic portions and one or more additional antigenic *M. tuberculosis* sequences. which are joined via a peptide linkage into a single amino acid chain. The sequences may be joined directly (i.e., with no intervening amino acids) or may be joined by way of a linker sequence (e.g., Gly-Cys-Gly) that does not significantly diminish the antigenic properties of the component polypeptides.

In general, *M. tuberculosis* antigens, and DNA sequences encoding such antigens, may be prepared using any of a variety of procedures. For example, soluble antigens may be isolated from *M. tuberculosis* culture filtrate by procedures known to those of ordinary skill in the art, including anion-exchange and reverse phase chromatography. Purified antigens may then be evaluated for a desired property, such as the ability to react with sera obtained from an *M. tuberculosis*-infected individual. Such screens may be performed using the representative methods described herein. Antigens may then be partially sequenced using, for example, traditional Edman chemistry. See Edman and Berg, *Eur. J. Biochem.* 80:116–132, 1967.

Antigens may also be produced recombinantly using a DNA sequence that encodes the antigen, which has been inserted into an expression vector and expressed in an appropriate host. DNA molecules encoding soluble antigens may be isolated by screening an appropriate *M. tuberculosis* expression library with anti-sera (e.g., rabbit) raised specifically against soluble *M. tuberculosis* antigens. DNA sequences encoding antigens that may or may not be soluble may be identified by screening an appropriate *M. tuberculosis* genomic or cDNA expression library with sera obtained from patients infected with *M. tuberculosis*. Such screens may generally be performed using techniques well known in the art, such as those described in Sambrook et al., *Molecular Cloning: A Laboratory Manual*, Cold Spring Harbor Laboratories, Cold Spring Harbor, N.Y., 1989.

DNA sequences encoding soluble antigens may also be obtained by screening an appropriate *M. tuberculosis* cDNA or genomic DNA library for DNA sequences that hybridize to degenerate oligonucleotides derived from partial amino acid sequences of isolated soluble antigens. Degenerate oligonucleotide sequences for use in such a screen may be designed and synthesized, and the screen may be performed, as described (for example) in Sambrook et al., *Molecular Cloning: A Laboratory Manual*, Cold Spring Harbor Laboratories, Cold Spring Harbor, N.Y. (and references cited herein). Polymerase chain reaction (PCR) may also be employed, using the above oligonucleotides in methods well known in the art, to isolate a nucleic acid probe from a cDNA or genomic library. The library screen may then be performed using the isolated probe.

Regardless of the method of preparation, the antigens described herein are "antigenic." More specifically, the antigens have the ability to react with sera obtained from an *M. tuberculosis*-infected individual. Reactivity may be evaluated using, for example, the representative ELISA assays described herein, where an absorbance reading with sera from infected individuals that is at least three standard deviations above the absorbance obtained with sera from uninfected individuals is considered positive.

Antigenic portions of *M. tuberculosis* antigens may be prepared and identified using well known techniques, such as those summarized in Paul, *Fundamental Immunology*, 3d ed., Raven Press, 1993, pp. 243–247 and references cited therein. Such techniques include screening polypeptide portions of the native antigen for antigenic properties. The representative ELISAs described herein may generally be employed in these screens. An antigenic portion of a polypeptide is a portion that, within such representative assays, generates a signal in such assays that is substantially similar to that generated by the full length antigen. In other words, an antigenic portion of a *M. tuberculosis* antigen generates at least about 20%, and preferably about 100%, of the signal induced by the full length antigen in a model ELISA as described herein.

Portions and other variants of *M. tuberculosis* antigens may be generated by synthetic or recombinant means. Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc., Foster City, Calif., and may be operated according to the manufacturer's instructions. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art.

For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line, such as COS or CHO. The DNA sequences expressed in this manner may encode naturally occurring antigens, portions of naturally occurring antigens, or other variants thereof.

In general, regardless of the method of preparation, the polypeptides disclosed herein are prepared in substantially pure form. Preferably, the polypeptides are at least about 80% pure, more preferably at least about 90% pure and most preferably at least about 99% pure. For use in the methods described herein, however, such substantially pure polypeptides may be combined.

In certain specific embodiments, the subject invention discloses polypeptides comprising at least an antigenic portion of a soluble *M. tuberculosis* antigen (or a variant of such an antigen), where the antigen has one of the following N-terminal sequences:

(a) (SEQ ID NO: 115)
Asp-Pro-Val-Asp-Ala-Val-Ile-Asn-Thr-Thr-Cys-Asn-Tyr-Gly-Gln-Val-Val-Ala-Ala-Leu;

(b) (SEQ ID NO: 116)
Ala-Val-Glu-Ser-Gly-Met-Leu-Ala-Leu-Gly-Thr-Pro-Ala-Pro-Ser;

(c) (SEQ ID NO: 117)
Ala-Ala-Met-Lys-Pro-Arg-Thr-Gly-Asp-Gly-Pro-Leu-Glu-Ala-Ala-Lys-Glu-Gly-Arg;

(d) (SEQ ID NO: 118)
Tyr-Tyr-Trp-Cys-Pro-Gly-Gln-Pro-Phe-Asp-Pro-Ala-Trp-Gly-Pro;

(e) (SEQ ID NO: 119)
Asp-Ile-Gly-Ser-Glu-Ser-Thr-Glu-Asp-Gln-Gln-Xaa-Ala-Val;

(f) (SEQ ID NO: 120)
Ala-Glu-Glu-Ser-Ile-Ser-Thr-Xaa-Glu-Xaa-Ile-Val-Pro;

(g) (SEQ ID NO: 121)
Asp-Pro-Glu-Pro-Ala-Pro-Pro-Val-Pro-Thr-Thr-Ala-Ala-Ser-Pro-Pro-Ser;

(h) (SEQ ID NO: 122)
Ala-Pro-Lys-Thr-Tyr-Xaa-Glu-Glu-Leu-Lys-Gly-Thr-Asp-Thr-Gly;

(i) (SEQ ID NO: 123)
Asp-Pro-Ala-Ser-Ala-Pro-Asp-Val-Pro-Thr-Ala-Ala-Gln-Gln-Thr-Ser-Leu-Leu-Asn-Ser-Leu-Ala-Asp-Pro-Asn-Val-Ser-Phe-Ala-Asn;

(j) (SEQ ID NO: 129)
Xaa-Asp-Ser-Glu-Lys-Ser-Ala-Thr-Ile-Lys-Val-Thr-Asp-Ala-Ser;

(k) (SEQ ID NO: 130)
Ala-Gly-Asp-Thr-Xaa-Ile-Tyr-Ile-Val-Gly-Asn-Leu-Thr-Ala-Asp;

or (l) (SEQ ID NO: 131)
Ala-Pro-Glu-Ser-Gly-Ala-Gly-Leu-Gly-Gly-Thr-Val-Gln-Ala-Gly;

wherein Xaa may be any amino acid, preferably a cysteine residue. A DNA sequence encoding the antigen identified as (g) above is provided in SEQ ID NO: 52, the deduced amino acid sequence of which is provided in SEQ ID NO: 53. A DNA sequence encoding the antigen identified as (a) above is provided in SEQ ID NO: 96; its deduced amino acid sequence is provided in SEQ ID NO: 97. A DNA sequence corresponding to antigen (d) above is provided in SEQ ID NO: 24, a DNA sequence corresponding to antigen (c) is provided in SEQ ID NO: 25 and a DNA sequence corresponding to antigen (l) is disclosed in SEQ ID NO: 94 and its deduced amino acid sequence is provided in SEQ ID NO: 95.

In a further specific embodiment, the subject invention discloses polypeptides comprising at least an immunogenic portion of an *M. tuberculosis* antigen having one of the following N-terminal sequences, or a variant thereof that differs only in conservative substitutions and/or modifications:

(m) (SEQ ID NO: 132)
Xaa-Tyr-Ile-Ala-Tyr-Xaa-Thr-Thr-Ala-Gly-Ile-Val-Pro-Gly-Lys-Ile-Asn-Val-His-Leu-Val or (n) (SEQ ID NO: 124)
Asp-Pro-Pro-Asp-Pro-His-Gln-Xaa-Asp-Met-Thr-Lys-Gly-Tyr-Tyr-Pro-Gly-Gly-Arg-Arg-Xaa-Phe;

wherein Xaa may be any amino acid, preferably a cysteine residue. A DNA sequence encoding the antigen of (n) above is provided in SEQ ID NO: 235, with the corresponding predicted full-length amino acid sequence being provided in SEQ ID NO: 236.

In other specific embodiments, the subject invention discloses polypeptides comprising at least an antigenic portion of a soluble *M. tuberculosis* antigen (or a variant of such an antigen) that comprises one or more of the amino acid sequences encoded by (a) the DNA sequences of SEQ ID NOS: 1, 2, 410, 13–25, 52, 94 and 96, (b) the complements of such DNA sequences; or (c) DNA sequences substantially homologous to a sequence in (a) or (b).

In further specific embodiments, the subject invention discloses polypeptides comprising at least an antigenic portion of a *M. tuberculosis* antigen (or a variant of such an antigen), which may or may not be soluble, that comprises one or more of the amino acid sequences encoded by (a) the DNA sequences of SEQ ID NOS: 26–51, 133, 134, 158–178, 184–188, 194–196, 198, 210–220, 232, 234, 235, 237–242, 248–251, 256–271, 287, 288, 290–293 and 298–337, (b) the complements of such DNA sequences or (c) DNA sequences substantially homologous to a sequence in (a) or (b).

In a related aspect, the present invention provides fusion proteins comprising a first and a second inventive polypeptide or, alternatively, a polypeptide of the present invention and a known *M. tuberculosis* antigen, such as the 38 kD antigen described in Andersen and Hansen, *Infect. Immun.* 57:2481–2488, 1989, (Genbank Accession No. M30046) or ESAT-6 (SEQ ID NOS: 98 and 99), together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric hindrance.

In another aspect, the present invention provides methods for using the polypeptides described above to diagnose tuberculosis. In this aspect, methods are provided for detecting *M. tuberculosis* infection in a biological sample, using one or more of the above polypeptides, alone or in combination. In embodiments in which multiple polypeptides are employed, polypeptides other than those specifically described herein, such as the 38 kD antigen described in Andersen and Hansen, *Infect. Immun.* 57:2481–2488, 1989, may be included. As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient or a blood supply. The polypeptide(s) are used in an assay, as described below, to determine the presence or absence of antibodies to the polypeptide(s) in the sample, relative to a predetermined cut-off value. The presence of such antibodies indicates previous sensitization to mycobacterial antigens which may be indicative of tuberculosis.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *M. tuberculosis*. After determining which samples test positive (as described below) with each polypeptide, combinations of two or more polypeptides may be formulated that are capable of detecting infection in most, or all, of the samples tested. Such polypeptides are complementary. For example, approximately 25–30% of sera from tuberculosis-infected individuals are negative for antibodies to any single protein, such as the 38 kD antigen mentioned above. Complementary polypeptides may, therefore, be used in combination with the 38 kD antigen to improve sensitivity of a diagnostic test.

There are a variety of assay formats known to those of ordinary skill in the art for using one or more polypeptides to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 µg, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the to polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups, biotin and colloidal particles, such as colloidal gold and selenium. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*M. tuberculosis* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for tuberculosis. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for tuberculosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*M. tuberculosis* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 µg, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only.

In yet another aspect, the present invention provides antibodies to the inventive polypeptides. Antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Antibodies may be used in diagnostic tests to detect the presence of *M. tuberculosis* antigens using assays similar to those detailed above and other techniques well known to those of skill in the art, thereby providing a method for detecting *M. tuberculosis* infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify *M. tuberculosis*-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. *Ibid*; Ehrlich, *Ibid*). Primers or probes may thus be used to detect *M. tuberculosis*-specific sequences in biological samples. DNA probes or primers comprising oligonucleotide sequences described above may be used alone, in combination with each other, or with previously identified sequences, such as the 38 kD antigen discussed above.

The following Examples are offered by way of illustration and not by way of limitation.

EXAMPLES

Example 1

Purification and Characterization of Polypeptides from *M. Tuberculosis* Culture Filtrate This example illustrates the preparation of *M. tuberculosis* soluble polypeptides from culture filtrate. Unless otherwise noted, all percentages in the following example are weight per volume.

*M. tuberculosis* (either H37Ra, ATCC No. 25177, or H37Rv, ATCC No. 25618) was cultured in sterile GAS media at 37° C. for fourteen days. The media was then vacuum filtered (leaving the bulk of the cells) through a 0.45μ filter into a sterile 2.5 L bottle. The media was then filtered through a 0.2μ filter into a sterile 4 L bottle. $NaN_3$ was then added to the culture filtrate to a concentration of 0.04%. The is bottles were then placed in a 4° C. cold room.

The culture filtrate was concentrated by placing the filtrate in a 12 L reservoir that had been autoclaved and feeding the filtrate into a 400 ml Amicon stir cell which had been rinsed with ethanol and contained a 10,000 kDa MWCO membrane. The pressure was maintained at 60 psi using nitrogen gas. This procedure reduced the 12 L volume to approximately 50 ml.

The culture filtrate was then dialyzed into 0.1% ammonium bicarbonate using a 8,000 kDa MWCO cellulose ester membrane, with two changes of ammonium bicarbonate solution. Protein concentration was then determined by a commercially available BCA assay (Pierce, Rockford, Ill.).

The dialyzed culture filtrate was then lyophilized, and the polypeptides resuspended in distilled water. The polypeptides were then dialyzed against 0.01 mM 1,3 bis[tris(hydroxymethyl)-methylamino]propane, pH 7.5 (Bis-Tris propane buffer), the initial conditions for anion exchange chromatography. Fractionation was performed using gel profusion chromatography on a POROS 146 II Q/M anion exchange column 4.6 mm×100 mm (Perseptive BioSystems, Framingham, Mass.) equilibrated in 0.01 mM Bis-Tris propane buffer pH 7.5. Polypeptides were eluted with a linear 0–0.5 M NaCl gradient in the above buffer system. The column eluent was monitored at a wavelength of 220 nm.

The pools of polypeptides eluting from the ion exchange column were dialyzed against distilled water and lyophilized. The resulting material was dissolved in 0.1% trifluoroacetic acid (TFA) pH 1.9 in water, and the polypeptides were purified on a Delta-Pak C18 column (Waters, Milford, Mass.) 300 Angstrom pore size, 5 micron particle size (3.9×150 mm). The polypeptides were eluted from the column with a linear gradient from 0–60% dilution buffer (0.1% TFA in acetonitrile). The flow rate was 0.75 ml/minute and the HPLC eluent was monitored at 214 nm. Fractions containing the eluted polypeptides were collected to maximize the purity of the individual samples. Approximately 200 purified polypeptides were obtained.

The purified polypeptides were then screened for the ability to induce T-cell proliferation in PBMC preparations. The PBMCs from donors known to be PPD skin test positive and whose T cells were shown to proliferate in response to PPD and crude soluble proteins from MTB were cultured in medium comprising RPMI 1640 supplemented with 10% pooled human serum and 50 μg/ml gentamicin. Purified polypeptides were added in duplicate at concentrations of 0.5 to 10 μg/ml. After six days of culture in 96-well round-bottom plates in a volume of 200 μl 50 μl of medium was removed from each well for determination of IFN-γ levels, as described below.

The plates were then pulsed with 1 μCi/well of tritiated thymidine for a further 18 hours, harvested and tritium uptake determined using a gas scintillation counter. Fractions that resulted in proliferation in both replicates three fold greater than the proliferation observed in cells cultured in medium alone were considered positive.

IFN-γ was measured using an enzyme-linked immunosorbent assay (ELISA). ELISA plates were coated with a mouse monoclonal antibody directed to human IFN-γ (Chemicon) in PBS for four hours at room temperature. Wells were then blocked with PBS containing 5% (W/V) non-fat dried milk for 1 hour at room temperature. The plates were then washed six times in PBS/0.2% TWEEN-20 and samples diluted 1:2 in culture medium in the ELISA plates were incubated overnight at room temperature. The plates were again washed and a polyclonal rabbit anti-human IFN-γ serum diluted 1:3000 in PBS/10% normal goat serum was added to each well. The plates were then incubated for two hours at room temperature, washed and horseradish peroxidase-coupled anti-rabbit IgG (Jackson Labs.) was added at a 1:2000 dilution in PBS/5% non-fat dried milk. After a further two hour incubation at room temperature, the plates were washed and TMB substrate added. The reaction was stopped after 20 min with 1 N sulfuric acid. Optical density was determined at 450 nm using 570 nm as a reference wavelength. Fractions that resulted in both replicates giving an OD two fold greater than the mean OD from cells cultured in medium alone, plus 3 standard deviations, were considered positive.

For sequencing, the polypeptides were individually dried onto Biobrene™ (Perkin Elmer/Applied BioSystems Division, Foster City, Calif.) treated glass fiber filters. The filters with polypeptide were loaded onto a Perkin Elmer/Applied BioSystems Division Procise 492 protein sequencer. The polypeptides were sequenced from the amino terminal and using traditional Edman chemistry. The amino acid sequence was determined for each polypeptide by comparing the retention time of the PTH amino acid derivative to the appropriate PTH derivative standards.

Using the procedure described above, antigens having the following N-terminal sequences were isolated:

```
                                          (SEQ ID NO: 54)
(a)
Asp-Pro-Val-Asp-Ala-Val-Ile-Asn-Thr-Thr-Xaa-Asn-
Tyr-Gly-Gln-Val-Val-Ala-Ala-Leu;

(SEQ ID NO: 55)
(b)
Ala-Val-Glu-Ser-Gly-Met-Leu-Ala-Leu-Gly-Thr-Pro-
Ala-Pro-Ser;

(SEQ ID NO: 56)
(c)
Ala-Ala-Met-Lys-Pro-Arg-Thr-Gly-Asp-Gly-Pro-Leu-
Glu-Ala-Ala-Lys-Glu-Gly-Arg;

(SEQ ID NO: 57)
(d)
Tyr-Tyr-Trp-Cys-Pro-Gly-Gln-Pro-Phe-Asp-Pro-Ala-
Trp-Gly-Pro;

(SEQ ID NO: 58)
(e)
Asp-Ile-Gly-Ser-Glu-Ser-Thr-Glu-Asp-Gln-Gln-Xaa-
Ala-Val;

(SEQ ID NO: 59)
(f)
Ala-Glu-Glu-Ser-Ile-Ser-Thr-Xaa-Glu-Xaa-Glu-Xaa-
Ile-Val-Pro;

(SEQ ID NO: 60)
(g)
Asp-Pro-Glu-Pro-Ala-Pro-Pro-Val-Pro-Thr-Ala-Ala-
Ala-Ala-Pro-Pro-Ala;
and (SEQ ID NO: 61)
(h)
Ala-Pro-Lys-Thr-Tyr-Xaa-Glu-Glu-Leu-Lys-Gly-Thr-
Asp-Thr-Gly;
``` wherein Xaa may be any amino acid.

An additional antigen was isolated employing a microbore HPLC purification step in addition to the procedure described above. Specifically, 20 μl of a fraction comprising a mixture of antigens from the chromatographic purification step previously described, was purified on an Aquapore C18 column (Perkin Elmer/Applied Biosystems Division, Foster City, Calif.) with a 7 micron pore size, column size 1 mm×100 mm, in a Perkin Elmer/Applied Biosystems Division Model 172 HPLC. Fractions were eluted from the column with a linear gradient of 1%/minute of acetonitrile (containing 0.05% TFA) in water (0.05%

TFA) at a flow rate of 80 µl/minute. The eluent was monitored at 250 nm. The original fraction was separated into 4 major peaks plus other smaller components and a polypeptide was obtained which was shown to have a molecular weight of 12.054 Kd (by mass spectrometry) and the following N-terminal sequence:

(i)                                                                     (SEQ ID NO: 62)
Asp-Pro-Ala-Ser-Ala-Pro-Asp-Val-Pro-Thr-Ala-Ala-Gln-Gln-Thr-Ser-Leu-Leu-Asn-Asn-Leu-Ala-Asp-Pro-Asp-Val-Ser-Phe-Ala-Asp.

This polypeptide was shown to induce proliferation and IFN-γ production in PBMC preparations using the assays described above.

Additional soluble antigens were isolated from *M. tuberculosis* culture filtrate as follows. *M. tuberculosis* culture filtrate was prepared as described above.

Following dialysis against Bis-Tris propane buffer, at pH 5.5, fractionation was performed using anion exchange chromatography on a Poros QE column 4.6×100 mm (Perseptive Biosystems) equilibrated in Bis-Tris propane buffer pH 5.5. Polypeptides were eluted with a linear 0–1.5 M NaCl gradient in the above buffer system at a flow rate of 10 ml/min. The column eluent was monitored at a wavelength of 214 nm.

The fractions eluting from the ion exchange column were pooled and subjected to reverse phase chromatography using a Poros R2 column 4.6×100 mm (Perseptive Biosystems). Polypeptides were eluted from the column with a linear gradient from 0–100% acetonitrile (0.1% TFA) at a flow rate of 5 ml/min. The eluent was monitored at 214 nm.

Fractions containing the eluted polypeptides were lyophilized and resuspended in 80 µl of aqueous 0.1% TFA and further subjected to reverse phase chromatography on a Vydac C4 column 4.6×150 mm (Western Analytical, Temecula, Calif.) with a linear gradient of 0–100% acetonitrile (0.1% TFA) at a flow rate of 2 ml/min. Eluent was monitored at 214 nm.

The fraction with biological activity was separated into one major peak plus other smaller components. Western blot of this peak onto PVDF membrane revealed three major bands of molecular weights 14 Kd, 20 Kd and 26 Kd. These polypeptides were determined to have the following N-terminal sequences, respectively:

(j) Xaa-Asp-Ser-Glu-Lys-Ser-Ala-Thr-Ile-Lys-Val-Thr-Asp-Ala-Ser, (SEQ ID NO: 129)

(k) Ala-Gly-Asp-Thr-Xaa-Ile-Tyr-Ile-Val-Gly-Asn-Leu-Thr-Ala-Asp; (SEQ ID NO: 130) and (l) Ala-Pro-Glu-Ser-Gly-Ala-Gly-Leu-Gly-Gly-Thr-Val-Gln-Ala-Gly; (SEQ ID NO: 131), wherein Xaa may be any amino acid.

Figure 1A:
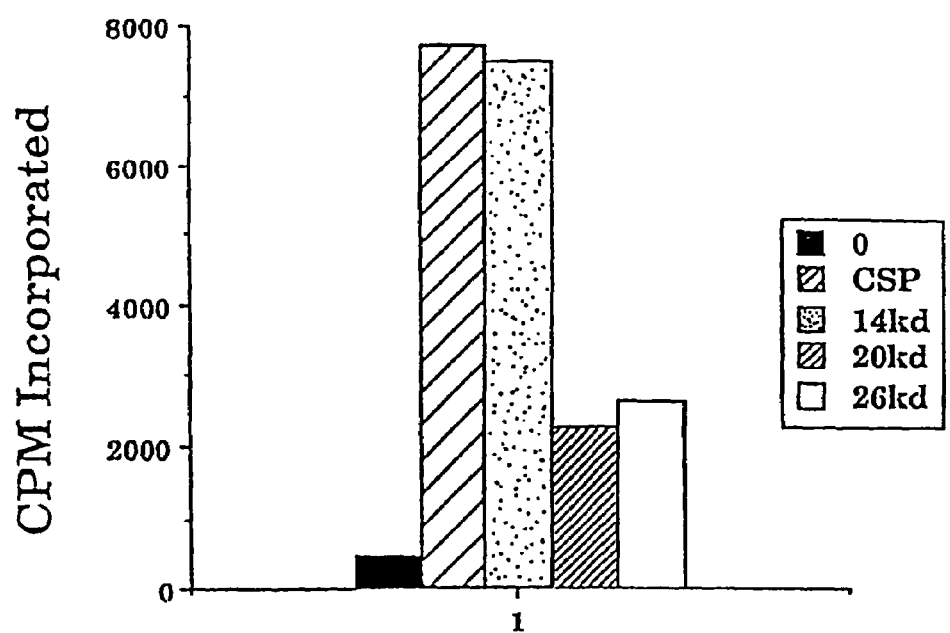
Figure 1B:
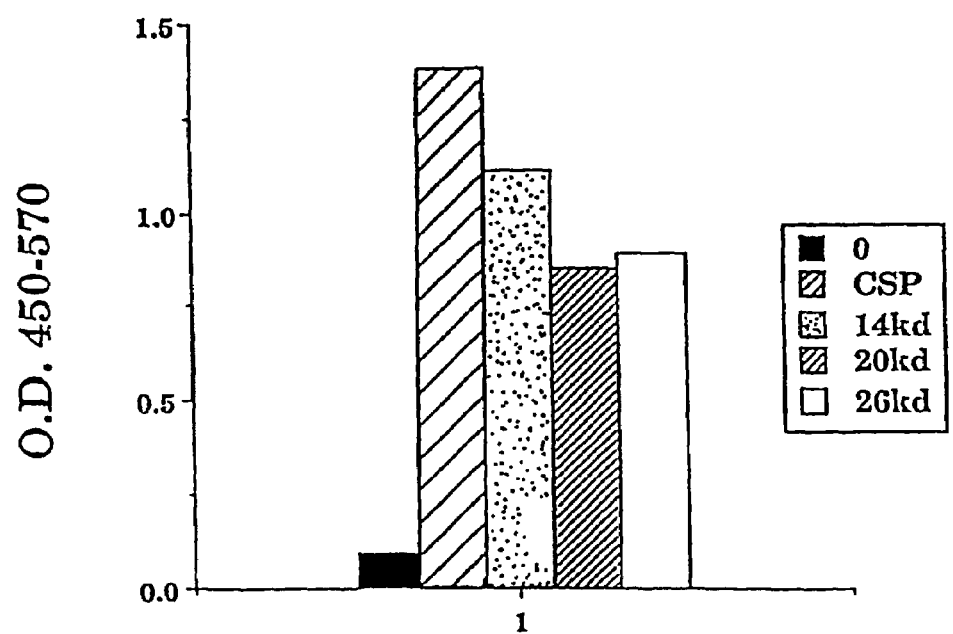
Figure 1C:
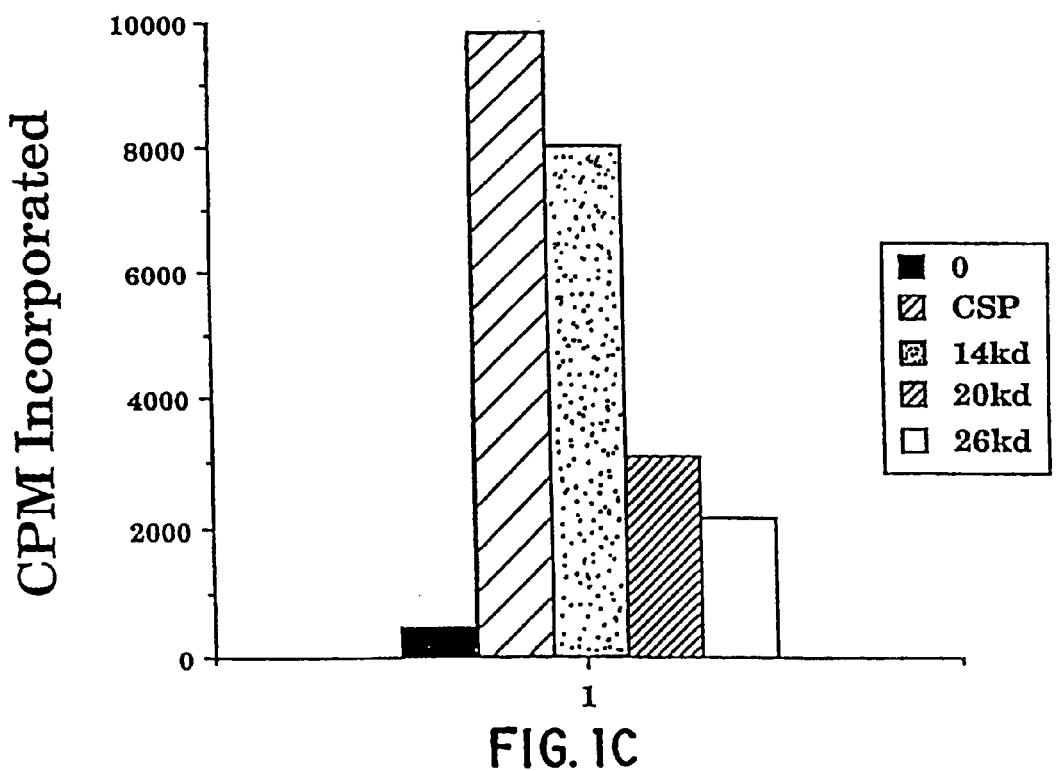
Figure 1D:
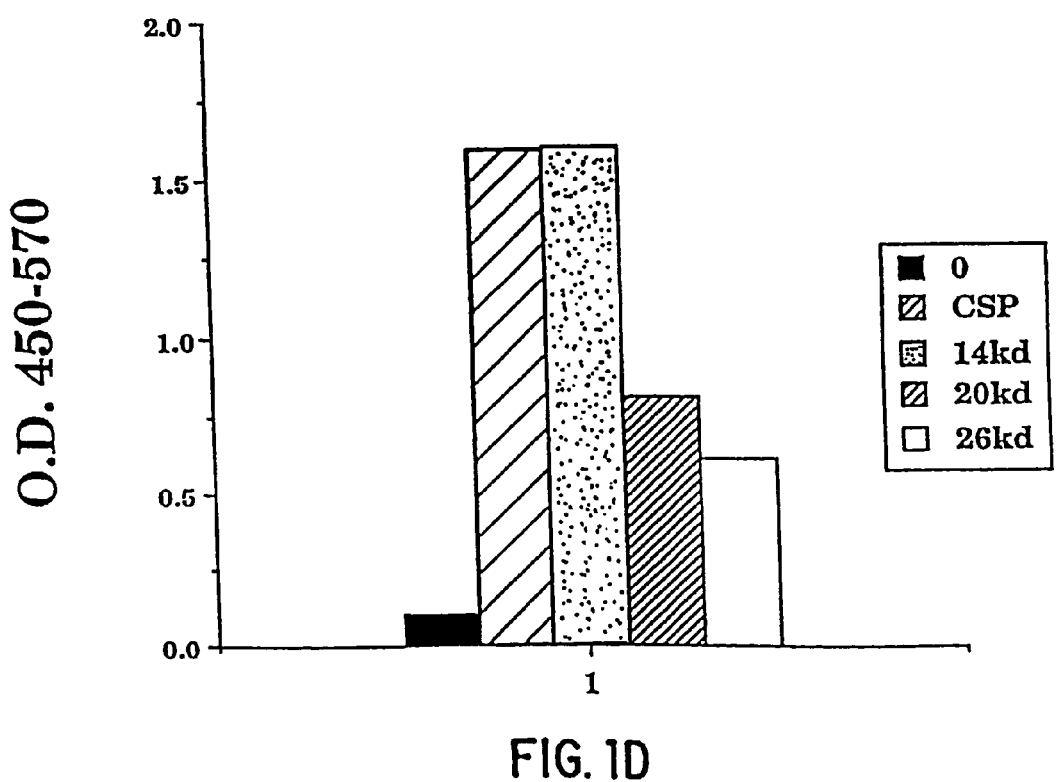
Figure 2A:
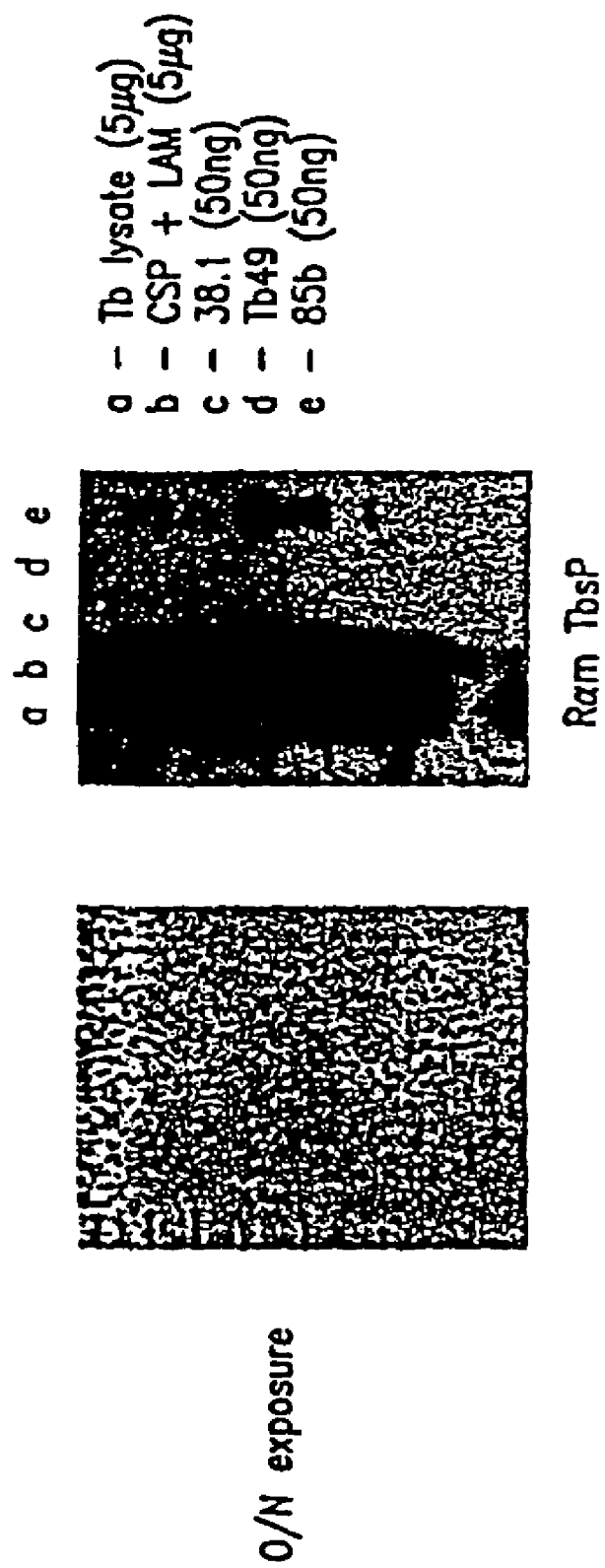
Figure 2B:
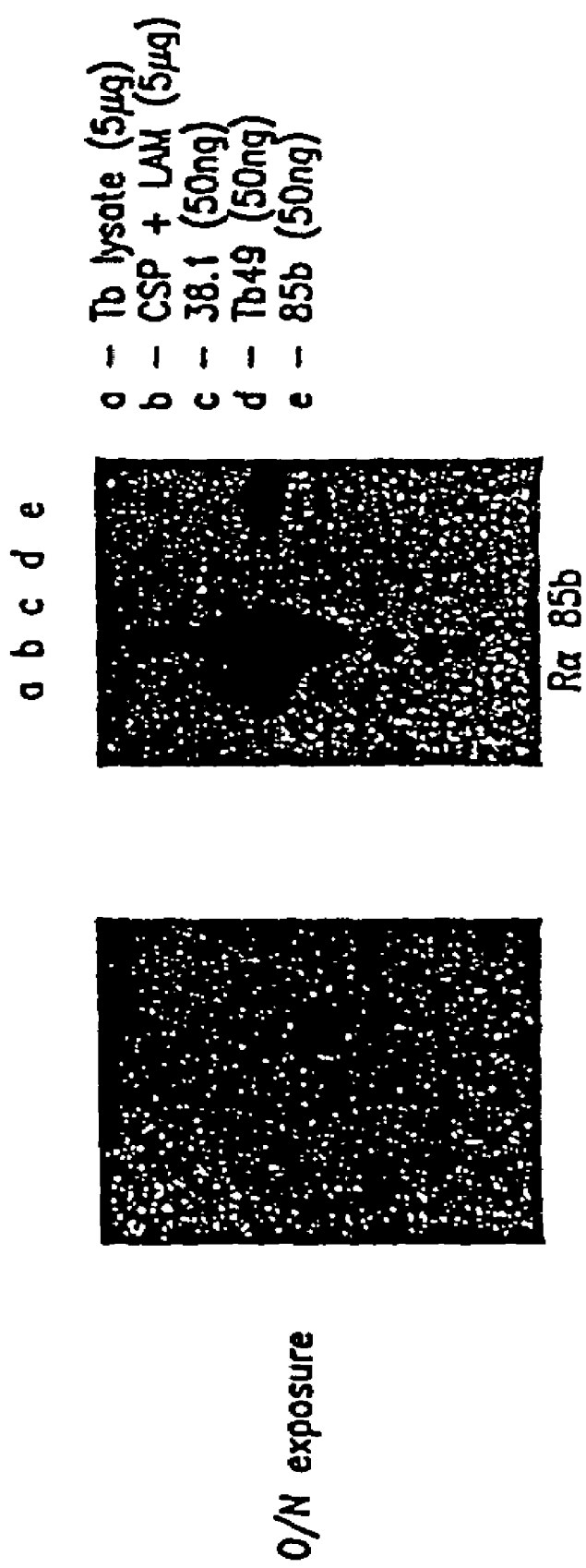
Figure 2C:
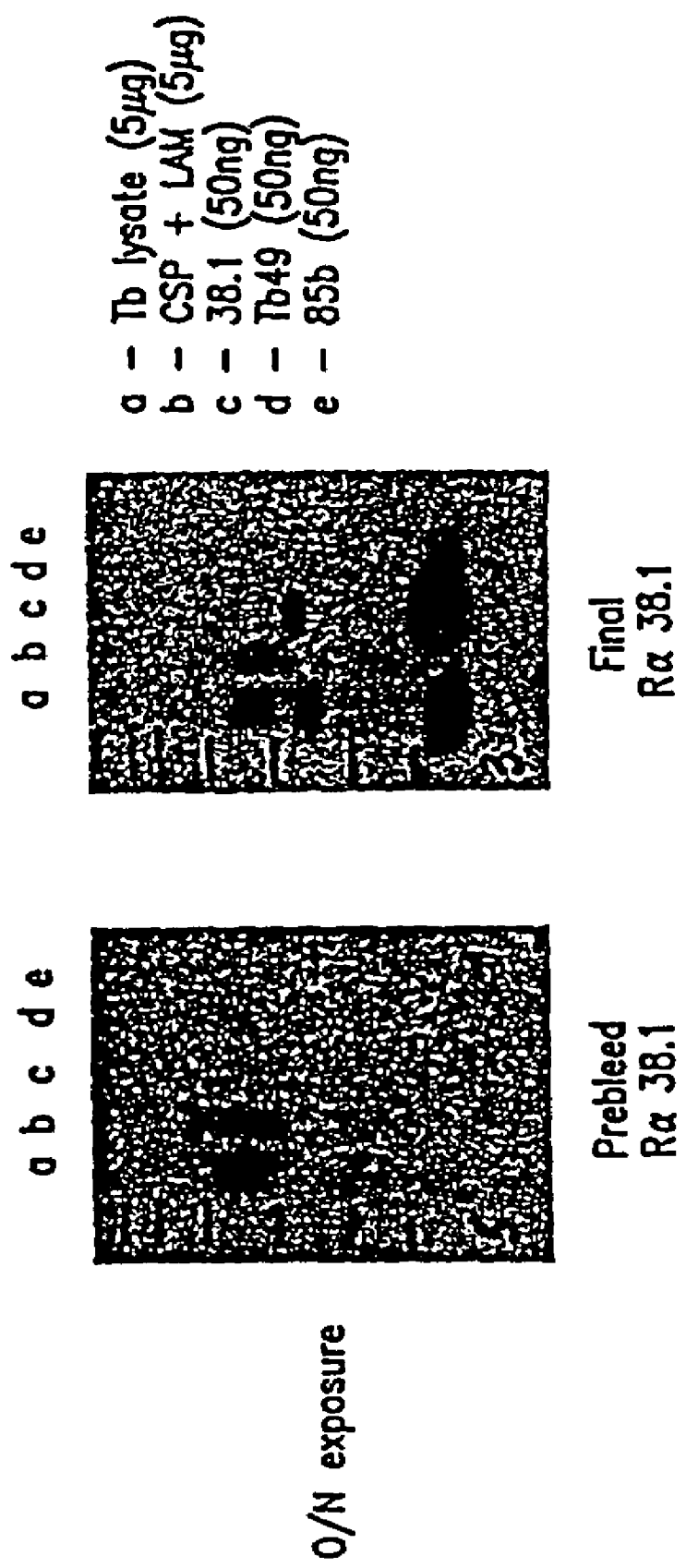
Figure 2D:
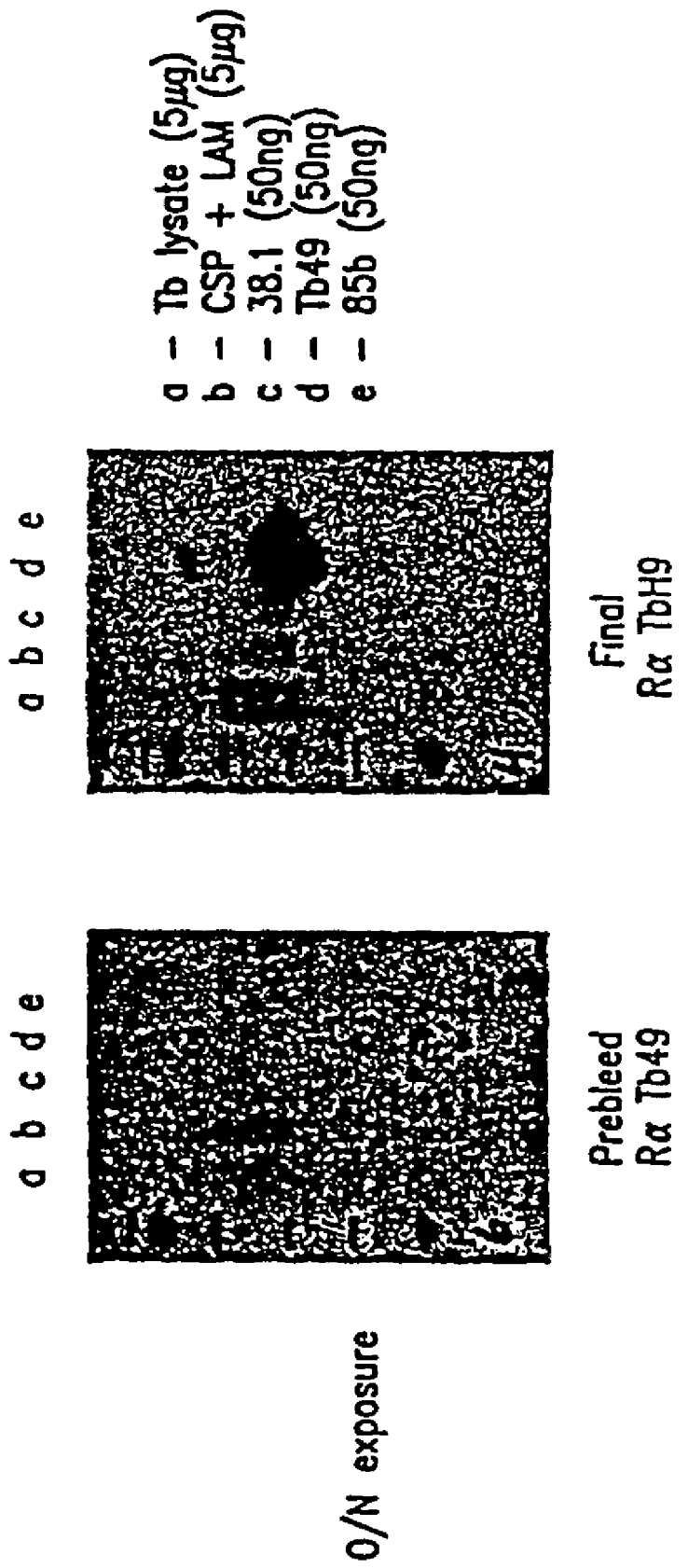
Figure 3A:
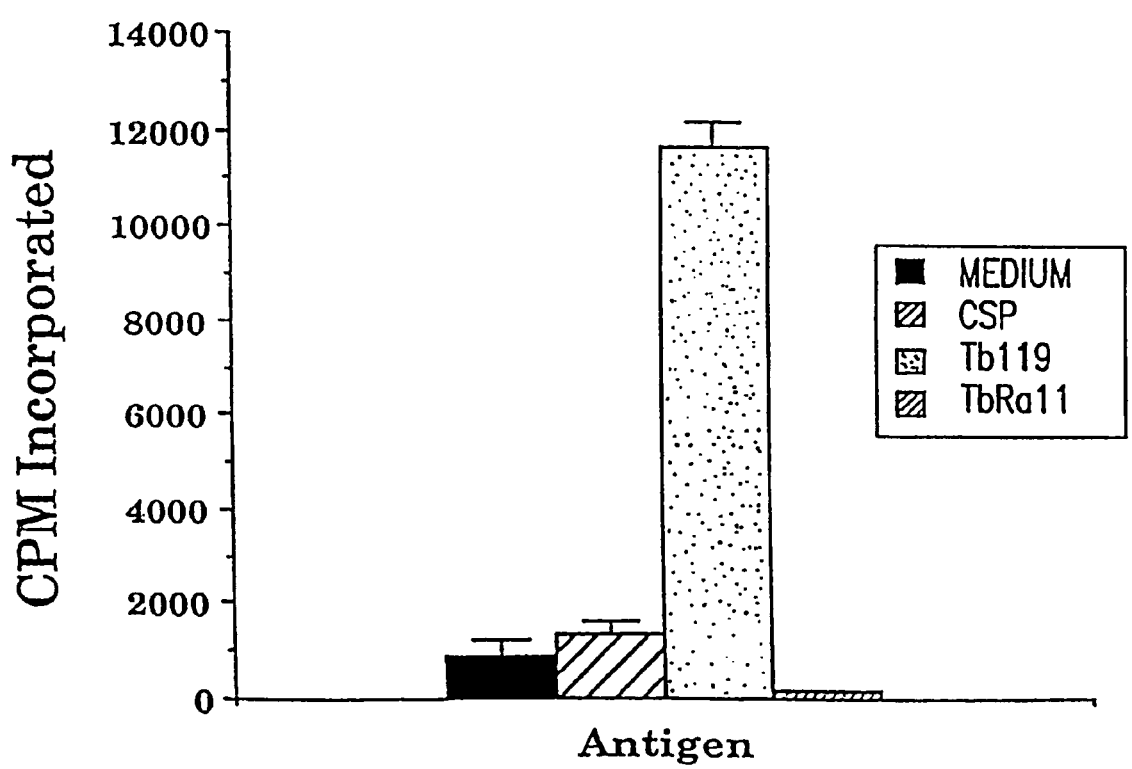
FIG. 3A illustrates the stimulation of proliferation in a TbH-9-specific T cell clone by secretory *M. tuberculosis* proteins, recombinant TbH-9 and a control antigen, TbRa11.
Figure 3B:
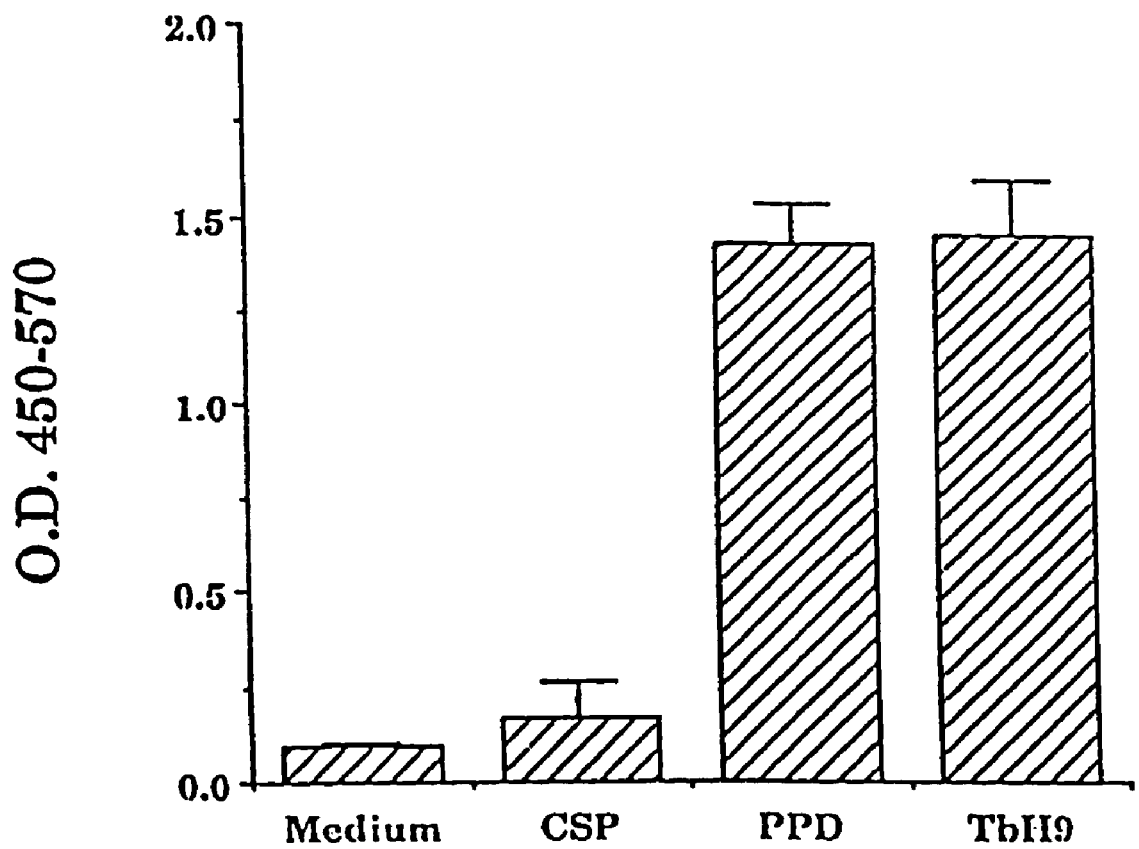
FIG. 3B illustrates the stimulation of interferon-γ production in a TbH-9-specific T cell clone by secretory *M. tuberculosis* proteins, PPD and recombinant TbH-9.

Using the assays described above, these polypeptides were shown to induce proliferation and IFN-γ production in PBMC preparations. FIGS. 1A and B show the results of such assays using PBMC preparations from a first and a second donor, respectively.

DNA sequences that encode the antigens designated as (a), (c), (d) and (g) above were obtained by screening a *M. tuberculosis* genomic library using $^{32}$P end labeled degenerate oligonucleotides corresponding to the N-terminal sequence and containing *M. tuberculosis* codon bias. The screen performed using a probe corresponding to antigen (a) above identified a clone having the sequence provided in SEQ ID NO: 96. The polypeptide encoded by SEQ ID NO: 96 is provided in SEQ ID NO: 97. The screen performed using a probe corresponding to antigen (g) above identified a clone having the sequence provided in SEQ ID NO: 52. The polypeptide encoded by SEQ ID NO: 52 is provided in SEQ ID NO: 53. The screen performed using a probe corresponding to antigen (d) above identified a clone having the sequence provided in SEQ ID NO: 24, and the screen performed with a probe corresponding to antigen (c) identified a clone having the sequence provided in SEQ ID NO: 25.

The above amino acid sequences were compared to known amino acid sequences in the gene bank using the DNA STAR system. The database searched contains some 173,000 proteins and is a combination of the Swiss, PIR databases along with translated protein sequences (Version 87). No significant homologies to the amino acid sequences for antigens (a)–(h) and (l) were detected.

The amino acid sequence for antigen (i) was found to be homologous to a sequence from *M. leprae*. The full length *M. leprae* sequence was amplified from genomic DNA using the sequence obtained from GENBANK. This sequence was then used to screen an *M. tuberculosis* library and a full length copy of the *M. tuberculosis* homologue was obtained (SEQ ID NO: 94).

The amino acid sequence for antigen (j) was found to be homologous to a known *M. tuberculosis* protein translated from a DNA sequence. To the best of the inventors' knowledge, this protein has not been previously shown to possess T-cell stimulatory activity. The amino acid sequence for antigen (k) was found to be related to a sequence from *M. leprae*.

In the proliferation and IFN-γ assays described above, using three PPD positive donors, the results for representative antigens provided above are presented in Table 1:

TABLE 1

RESULTS OF PBMC PROLIFERATION AND IFN-γ ASSAYS

| Sequence | Proliferation | IFN-γ |
| --- | --- | --- |
| (a) | + | − |
| (c) | +++ | +++ |
| (d) | ++ | ++ |
| (g) | +++ | +++ |
| (h) | +++ | +++ |

In Table 1, responses that gave a stimulation index (SI) of between 2 and 4 (compared to cells cultured in medium alone) were scored as +, as SI of 4–8 or 2–4 at a concentration of 1 µg or less was scored as ++ and an SI of greater than 8 was scored as +++. The antigen of sequence (i) was found to have a high SI (+++) for one donor and lower SI (++ and +) for the two other donors in both proliferation and IFN-γ assays. These results indicate that these antigens are capable of inducing proliferation and/or interferon-γ production.

Example 2

Use of Patient Sera to Isolate *M. Tuberculosis* Antigens

This example illustrates the isolation of antigens from *M. tuberculosis* lysate by screening with serum from *M. tuberculosis*-infected individuals.

Dessicated *M. tuberculosis* H37Ra (Difco Laboratories) was added to a 2% NP40 solution, and alternately homogenized and sonicated three times. The resulting suspension was centrifuged at 13,000 rpm in microfuge tubes and the supernatant put through a 0.2 micron syringe filter. The filtrate was bound to Macro Prep DEAE beads (BioRad, Hercules, Calif.). The beads were extensively washed with 20 mM Tris pH 7.5 and bound proteins eluted with 1M NaCl. The NaCl elute was dialyzed overnight against 10 mM Tris, pH 7.5. Dialyzed solution was treated with DNase and RNase at 0.05 mg/ml for 30 min. at room temperature and then with α-D-mannosidase, 0.5 U/mg at pH 4.5 for 3–4 hours at room temperature. After returning to pH 7.5, the material was fractionated via FPLC over a Bio Scale-Q-20 column (BioRad). Fractions were combined into nine pools, concentrated in a Centriprep 10 (Amicon, Beverley, Mass.) and screened by Western blot for serological activity using a serum pool from *M. tuberculosis*-infected patients which was not immunoreactive with other antigens of the present invention.

The most reactive fraction was run in SDS-PAGE and transferred to PVDF. A band at approximately 85 Kd was cut out yielding the sequence:

(m)   Xaa-Tyr-Ile-Ala-Tyr-Xaa-Thr-Thr-Ala-Gly-Ile-Val-Pro-Gly-Lys-Ile-Asn-Val-His-Leu-Val; (SEQ ID NO: 132), wherein Xaa may be any amino acid.

Comparison of this sequence with those in the gene bank as described above, revealed no significant homologies to known sequences.

A DNA sequence that encodes the antigen designated as (m) above was obtained by screening a genomic *M. tuberculosis* Erdman strain library using labeled degenerate oligonucleotides corresponding to the N-terminal sequence of SEQ ID NO: 137. A clone was identified having the DNA sequence provided in SEQ ID NO: 198. This sequence was found to encode the amino acid sequence provided in SEQ ID NO: 199. Comparison of these sequences with those in the genebank revealed some similarity to sequences previously identified in *M. tuberculosis* and *M. bovis*.

Example 3

Preparation of DNA Sequences Encoding *M. Tuberculosis* Antigens

This example illustrates the preparation of DNA sequences encoding *M. tuberculosis* antigens by screening a *M. tuberculosis* expression library with sera obtained from patients infected with *M. tuberculosis*, or with anti-sera raised against *M. tuberculosis* antigens.

A. Preparation of *M. Tuberculosis* Soluble Antigens Using Rabbit Anti-Sera Raised Against *M. Tuberculosis* Supernatant Genomic DNA was isolated from the *M. tuberculosis* strain H37Ra. The DNA was randomly sheared and used to construct an expression library using the Lambda ZAP expression system (Stratagene, La Jolla, Calif.). Rabbit anti-sera was generated against secretory proteins of the *M. tuberculosis* strains H37Ra, H37Rv and Erdman by immunizing a rabbit with concentrated supernatant of the *M. tuberculosis* cultures. Specifically, the rabbit was first immunized subcutaneously with 200 µg of protein antigen in a total volume of 2 ml containing 100 µg muramyl dipeptide (Calbiochem, La Jolla, Calif.) and 1 ml of incomplete Freund's adjuvant. Four weeks later the rabbit was boosted subcutaneously with 100 µg antigen in incomplete Freund's adjuvant. Finally, the rabbit was immunized intravenously four weeks later with 50 µg protein antigen. The anti-sera were used to screen the expression library as described in Sambrook et al., *Molecular Cloning: A Laboratory Manual*, Cold Spring Harbor Laboratories, Cold Spring Harbor, N.Y., 1989. Bacteriophage plaques expressing immunoreactive antigens were purified. Phagemid from the plaques was rescued and the nucleotide sequences of the *M. tuberculosis* clones deduced.

Thirty two clones were purified. Of these 25 represent sequences that have not been previously identified in *M. tuberculosis*. Proteins were induced by IPTG and purified by gel elution, as described in Skeiky et al., *J. Exp. Med.* 181:1527–1537, 1995. Representative partial sequences of DNA molecules identified in this screen are provided in SEQ ID NOS: 1–25. The corresponding predicted amino acid sequences are shown in SEQ ID NOS: 64–88.

On comparison of these sequences with known sequences in the gene bank using the databases described above, it was found that the clones referred to hereinafter as TbRA2A, TbRA16, TbRA18, and TbRA29 (SEQ ID NOS: 77, 69, 71, 76) show some homology to sequences previously identified in *Mycobacterium leprae* but not in *M. tuberculosis*. TbRA2A was found to be a lipoprotein, with a six residue lipidation sequence being located adjacent to a hydrophobic secretory sequence. TbRA11, TbRA26, TbRA28 and TbD-PEP (SEQ ID NOS: 66, 74, 75, 53) have been previously identified in *M. tuberculosis*. No significant homologies were found to TbRA1, TbRA3, TbRA4, TbRA9, TbRA10, TbRA13, TbRA17, TbRA19, TbRA29, TbRA32, TbRA36 and the overlapping clones TbRA35 and TbRA12 (SEQ ID NOS: 64, 78, 82, 83, 65, 68, 76, 72, 76, 79, 81, 80, 67, respectively). The clone TbRa24 is overlapping with clone TbRa29.

B. Use of Sera from Patients Having Pulmonary or Pleural Tuberculosis to Identify DNA Sequences Encoding *M. Tuberculosis* Antigens The genomic DNA library described above, and an additional H37Rv library, were screened using pools of sera obtained from patients with active tuberculosis. To prepare the H37Rv library, *M. tuberculosis* strain H37Rv genomic DNA was isolated, subjected to partial Sau3A digestion and used to construct an expression library using the Lambda Zap expression system (Stratagene, La Jolla, Calif.). Three different pools of sera, each containing sera obtained from three individuals with active pulmonary or pleural disease, were used in the expression screening. The pools were designated TbL, TbM and TbH, referring to relative reactivity with H37Ra lysate (i.e., TbL=low reactivity, TbM=medium reactivity and TbH=high reactivity) in both ELISA and immunoblot format. A fourth pool of sera from seven patients with active pulmonary tuberculosis was also employed. All of the sera lacked increased reactivity with the recombinant 38 kD *M. tuberculosis* H37Ra phosphate-binding protein.

All pools were pre-adsorbed with *E. coli* lysate and used to screen the H37Ra and H37Rv expression libraries as described in Sambrook et al., *Molecular Cloning: A Laboratory Manual*, Cold Spring Harbor Laboratories. Cold Spring Harbor. N.Y., 1989. Bacteriophage plaques expressing immunoreactive antigens were purified. Phagemid from the plaques was rescued and the nucleotide sequences of the *M. tuberculosis* clones deduced.

Thirty two clones were purified. Of these 31 represented sequences that had not been previously identified in human *M. tuberculosis*. Representative sequences of the DNA molecules identified are provided in SEQ ID NOS: 26–51 and 100. Of these, TbH-8–2 (SEQ. ID NO. 100) is a partial clone of TbH-8, and TbH-4 (SEQ. ID NO. 43) and TbH-4-FWD (SEQ. D NO. 44) are non-contiguous sequences from the same clone. Amino acid sequences for the antigens hereinafter identified as Tb38-1, TbH-4, TbH-8, TbH-9, and TbH-12 are shown in SEQ ID NOS.: 89–93. Comparison of these sequences with known sequences in the gene bank using the databases identified above revealed no significant homologies to TbH-4, TbH-8, TbH-9 and TbM-3, although weak homologies were found to TbH-9. TbH-12 was found to be homologous to a 34 kD antigenic protein previously identified in *M. paratuberculosis* (Acc. No. S28515). Tb38-1 was found to be located 34 base pairs upstream of the open reading frame for the antigen ESAT-6 previously identified in *M. bovis* (Acc. No. U 34848) and in *M. tuberculosis* (Sorensen et al., *Infec. Immun.* 63:1710–1717, 1995).

Probes derived from Tb38-1 and TbH-9, both isolated from an H37Ra library, were used to identify clones in an H37Rv library. Tb38-1 hybridized to Tb38-1F2, Tb38-1F3, Tb38-1F5and Tb38-1F6 (SEQ. ID NOS: 107, 108, 111, 113, and 114). (SEQ ID NOS: 107 and 108 are non-contiguous sequences from clone Tb38-1F2.) Two open reading frames were deduced in Tb38-IF2; one corresponds to Tb37FL (SEQ. ID. NO. 109), the second, a partial sequence, may be the homologue of Tb38-1 and is called Tb38-IN (SEQ. ID NO. 110). The deduced amino acid sequence of Tb38-IF3 is presented in SEQ. ED. NO. 112. A TbH-9 probe identified three clones in the H37Rv library: TbH-9-FL (SEQ. ID NO. 101), which may be the homologue of TbH-9 (R37Ra), TbH-9-1 (SEQ. ID NO. 103), and TbH-8-2 (SEQ. ID NO. 105) is a partial clone of TbH-8. The deduced amino acid sequences for these three clones are presented in SEQ ID NOS: 102, 104 and 106.

Further screening of the *M. tuberculosis* genomic DNA library, as described above, resulted in the recovery of ten additional reactive clones, representing seven different genes. One of these genes was identified as the 38 Kd antigen discussed above, one was determined to be identical to the 14 Kd alpha crystallin heat shock protein previously shown to be present in *M. tuberculosis*, and a third was determined to be identical to the antigen TbH-8 described above. The determined DNA sequences for the remaining five clones (hereinafter referred to as TbH-29, TbH-30, TbH-32 and TbH-33) are provided in SEQ ID NO: 133–136, respectively, with the corresponding predicted amino acid sequences being provided in SEQ ID NO: 137–140, respectively. The DNA and amino acid sequences for these antigens were compared with those in the gene bank as described above. No homologies were found to the 5' end of TbH-29 (which contains the reactive open reading frame), although the 3' end of TbH-29 was found to be identical to the *M. tuberculosis* cosmid Y 227. TbH-32 and TbH-33 were found to be identical to the previously identified *M. tuberculosis* insertion element IS6110 and to the *M. tuberculosis* cosmid Y50, respectively. No significant homologies to TbH-30 were found.

Positive phagemid from this additional screening were used to infect *E. coli* XL-1 Blue MRF', as described in Sambrook et al., supra. Induction of recombinant protein was accomplished by the addition of IPTG. Induced and uninduced lysates were run in duplicate on SDS-PAGE and transferred to nitrocellulose filters. Filters were reacted with human *M. tuberculosis* sera (1:200 dilution) reactive with TbH and a rabbit sera (1:200 or 1:250 dilution) reactive with the N-terminal 4 Kd portion of lacZ. Sera incubations were performed for 2 hours at room temperature. Bound antibody was detected by addition of $^{125}$I-labeled Protein A and subsequent exposure to film for variable times ranging from 16 hours to 11 days. The results of the immunoblots are summarized in Table 2.

TABLE 2

| Antigen | Human M. tb Sera | Anti-lacZ Sera |
|---|---|---|
| TbH-29 | 45 Kd | 45 Kd |
| TbH-30 | No reactivity | 29 Kd |
| TbH-32 | 12 Kd | 12 Kd |
| TbH-33 | 16 Kd | 16 Kd |

Positive reaction of the recombinant human *M. tuberculosis* antigens with both the human *M. tuberculosis* sera and anti-lacZ sera indicate that reactivity of the human *M. tuberculosis* sera is directed towards the fusion protein. Antigens reactive with the anti-lacZ sera but not with the human *M. tuberculosis* sera may be the result of the human *M. tuberculosis* sera recognizing conformational epitopes, or the antigen-antibody binding kinetics may be such that the 2 hour sera exposure in the immunoblot is not sufficient.

Studies were undertaken to determine whether the antigens TbH-9 and Tb38-1 represent cellular proteins or are secreted into *M. tuberculosis* culture media In the first study, rabbit sera were raised against A) secretory proteins of *M. tuberculosis*, B) the known secretory recombinant *M. tuberculosis* antigen 85b, C) recombinant Tb38-1 and D) recombinant TbH-9, using protocols substantially as described in Example 3A. Total *M. tuberculosis* lysate, concentrated supernatant of *M. tuberculosis* cultures and the recombinant antigens 85b, TbH-9 and Tb38-1 were resolved on denaturing gels, immobilized on nitrocellulose membranes and duplicate blots were probed using the rabbit sera described above.

The results of this analysis using control sera (panel I) and antisera (panel II) against secretory proteins, recombinant 85b, recombinant Tb38-1 and recombinant TbH-9 are shown in FIGS. 2A–D, respectively, wherein the lane designations are as follows: 1) molecular weight protein standards; 2) 5 μg of *M. tuberculosis* lysate; 3) 5 μg secretory proteins; 4) 50 ng recombinant Tb38-1; 5) 50 ng recombinant TbH-9; and 6) 50 ng recombinant 85b. The recombinant antigens were engineered with six terminal histidine residues and would therefore be expected to migrate with a mobility approximately 1 kD larger that the native protein. In FIG. 2D, recombinant TbH-9 is lacking approximately 10 kD of the full-length 42 kD antigen, hence the significant difference in the size of the immunoreactive native TbH-9 antigen in the lysate lane (indicated by an arrow). These results demonstrate that Tb38-1 and TbH-9 are intracellular antigens and are not actively secreted by *M. tuberculosis.*

The finding that TbH-9 is an intracellular antigen was confirmed by determining the reactivity of TbH-9-specific human T cell clones to recombinant TbH-9, secretory *M. tuberculosis* proteins and PPD. A TbH-9-specific T cell clone (designated 131TbH-9) was generated from PBMC of a healthy PPD-positive donor. The proliferative response of 131TbH-9 to secretory proteins, recombinant TbH-9 and a control *M. tuberculosis* antigen, TbRa11, was determined by measuring uptake of tritiated thymidine, as described in Example 1. As shown in FIG. 3A, the clone 131TbH-9 responds specifically to TbH-9, showing that TbH-9 is not a significant component of *M. tuberculosis* secretory proteins. FIG. 3B shows the production of IFN-γ by a second TbH-9-specific T cell clone (designated PPD 800-10) prepared from PBMC from a healthy PPD-positive donor, following stimulation of the T cell clone with secretory proteins, PPD or recombinant TbH-9. These results further confirm that TbH-9 is not secreted by *M. tuberculosis.*

C. Use of Sera from Patients Having Extrapulmonary Tuberculosis to Identify DNA Sequences Encoding *M. Tuberculosis* Antigens Genomic DNA was isolated from *M. tuberculosis* Erdman strain, randomly sheared and used to construct an expression library employing the Lambda ZAP expression system (Stratagene, La Jolla, Calif.). The resulting library was screened using pools of sera obtained from individuals with extrapulmonary tuberculosis, as described above in Example 3B, with the secondary antibody being goat anti-human IgG+A+M (H+L) conjugated with alkaline phosphatase.

Eighteen clones were purified. Of these, 4 clones (hereinafter referred to as XP14, NP24, XP31 and XP32) were found to bear some similarity to known sequences. The determined DNA sequences for XP14, XP24 and XP31 are provided in SEQ ID NOS: 151–153, respectively, with the 5' and 3' DNA sequences for XP32 being provided in SEQ ID NOS: 154 and 155, respectively. The predicted amino acid sequence for XP14 is provided in SEQ ID NO: 156. The reverse complement of XP14 was found to encode the amino acid sequence provided in SEQ ID NO: 157.

Comparison of the sequences for the remaining 14 clones (hereinafter referred to as XP1–XP6, XP17–XP19, XP22, XP25, XP27, XP30 and XP36) with those in the genebank as described above, revealed no homologies with the exception of the 3' ends of XP2 and XP6 which were found to bear some homology to known *M. tuberculosis* cosmids. The DNA sequences for XP27 and XP36 are shown in SEQ ID NOS: 158 and 159, respectively, with the 5' sequences for XP4, XP5, XP17 and XP30 being shown in SEQ ID NOS: 160–163, respectively, and the 5' and 3' sequences for XP2, XP3, XP6, XP18, XP19, XP22 and XP25 being shown in SEQ ID NOS: 164 and 165; 166 and 167; 168 and 169; 170 and 171; 172 and 173; 174 and 175; and 176 and 177, respectively. XP1 was found to overlap with the DNA sequences for TbH4, disclosed above. The full-length DNA sequence for TbH 4-XP1 is provided in SEQ ID NO: 178. This DNA sequence was found to contain an open reading frame encoding the amino acid sequence shown in SEQ ID NO: 179. The reverse complement of TbH4-XP1 was found to contain an open reading frame encoding the amino acid sequence shown in SEQ ID NO: 180. The DNA sequence for XP36 was found to contain two open reading frames encoding the amino acid sequence shown in SEQ ID NOS: 181 and 182, with the reverse complement containing an open reading frame encoding the amino acid sequence shown in SEQ ID NO: 183.

Recombinant XP1 protein was prepared as described above in Example 3B, with a metal ion affinity chromatography column being employed for purification. Recombinant XP1 was found to stimulate cell proliferation and IFN-γ production in T cells isolated from an *M. tuberculosis*-immune donors.

D. Use of a Lysate Positive Serum Pool from Patients Having Tuberculosis to Identify DNA Sequences Encoding *M. Tuberculosis* Antigens Genomic DNA was isolated from *M. tuberculosis* Erdman strain, randomly sheared and used to construct an expression library employing the Lambda Screen expression system (Novagen, Madison, Wis.), as described below in Example 6. Pooled serum obtained from *M. tuberculosis*-infected patients and that was shown to react with *M. tuberculosis* lysate but not with the previously expressed proteins 38 kD, Tb38-1, TbRa3, TbH4, DPEP and TbRa11, was used to screen the expression library as described above in Example 3B, with the secondary antibody being goat anti-human IgG+A+M (H+L) conjugated with alkaline phosphatase.

Twenty-seven clones were purified. Comparison of the determined cDNA sequences for these clones revealed no significant homologies to 10 of the clones (hereinafter referred to as LSER-10, LSER-11, LSER-12, LSER-13, LSER-16, LSER-18, LSER-23, LSER-24, LSER-25 and LSER-27). The determined 5' cDNA sequences for LSER-10, LSER-11, LSER-12, LSER-13, LSER-16 and LSER-25 are provided in SEQ ID NO: 237–242, respectively, with the corresponding predicted amino acid sequences for LSER-10, LSER-12, LSER-13, LSER-16 and LSER-25 being provided in SEQ ID NO: 243–247, respectively. The determined full-length cDNA sequences for LSER-18, LSER-23, LSER-24 and LSER-27 are shown in SEQ ID NO: 248–251, respectively, with the corresponding predicted amino acid sequences being provided in SEQ ID NO: 252–255. The remaining seventeen clones were found to show similarities to unknown sequences previously identified in *M. tuberculosis*. The determined 5' cDNA sequences for sixteen of these clones (hereinafter referred to as LSER-1, LSER-3, LSER-4, LSER-5, LSER-6, LSER-8, LSER-14, LSER-15, LSER-17, LSER-19, LSER-20, LSER-22, LSER-26, LSER-28, LSER-29 and LSER-30) are provided in SEQ ID NO: 256–271, respectively, with the corresponding predicted amino acid sequences for LSER-1, LSER-3, LSER-5, LSER-6, LSER-8, LSER-14, LSER-15, LSER-17, LSER-19, LSER-20, LSER-22, LSER-26, LSER-28, LSER-29 and LSER-30 being provided in SEQ ID NO: 272–286, respectively. The determined full-length cDNA sequence for the clone LSER-9 is provided in SEQ ID NO: 287. The reverse complement of LSER-6 (SEQ ID NO: 288) was found to encode the predicted amino acid sequence of SEQ ID NO: 289.

E. Preparation of *M. Tuberculosis* Soluble Antigens Using Rabbit Anti-Sera Raised Against *M. Tuberculosis* Fractionated Proteins

*M. tuberculosis* lysate was prepared as described above in Example 2. The resulting material was fractionated by HPLC and the fractions screened by Western blot for serological activity with a serum pool from *M. tuberculosis*-infected patients which showed little or no immunoreactivity with other antigens of the present invention. Rabbit anti-sera was generated against the most reactive fraction using the method described in Example 3A. The anti-sera was used to screen an *M. tuberculosis* Erdman strain genomic DNA expression library prepared as described above. Bacteriophage plaques expressing immunoreactive antigens were purified. Phagemid from the plaques was rescued and the nucleotide sequences of the *M. tuberculosis* clones determined.

Ten different clones were purified. Of these, one was found to be TbRa35, described above, and one was found to be the previously identified *M. tuberculosis* antigen, HSP60. Of the remaining eight clones, six (hereinafter referred to as RDIF2, RDIF5, RDIF8, RDIF10, RDIF11 and RDIF12) were found to bear some similarity to previously identified *M. tuberculosis* sequences. The determined DNA sequences for RDIF2, RDIF5, RDIF8, RDIF10 and RDIF11 are provided in SEQ ID NOS: 184–188, respectively, with the corresponding predicted amino acid sequences being provided in SEQ ID NOS: 189–193, respectively. The 5' and 3' DNA sequences for RDIF12 are provided in SEQ ID NOS: 194 and 195, respectively. No significant homologies were found to the antigen RDIF-7. The determined DNA and predicted amino acid sequences for RDIF7 are provided in SEQ ID NOS: 196 and 197, respectively. One additional clone, referred to as RDIF6 was isolated, however, this was found to be identical to RDIF5.

Recombinant RDIF6, RDIF8, RDIF10 and RDIF11 were prepared as described above. These antigens were found to stimulate cell proliferation and IFN-γ production in T cells isolated from *M. tuberculosis*-immune donors.

Example 4

Purification and Characterization of a Polypeptide from Tuberculin Purified Protein Derivative An *M. tuberculosis* polypeptide was isolated from tuberculin purified protein derivative (PPD) as follows.

PPD was prepared as published with some modification (Seibert, F. et al., Tuberculin purified protein derivative. Preparation and analyses of a large quantity for standard. *The American Review of Tuberculosis* 44:9–25, 1941). *M. tuberculosis* Rv strain was grown for 6 weeks in synthetic medium in roller bottles at 37° C. Bottles containing the bacterial growth were then heated to 100° C. in water vapor for 3 hours. Cultures were sterile filtered using a 0.22μ filter and the liquid phase was concentrated 20 times using a 3 kD cut-off membrane. Proteins were precipitated once with 50% ammonium sulfate solution and eight times with 25% ammonium sulfate solution. The resulting proteins (PPD) were fractionated by reverse phase liquid chromatography (RP-HPLC) using a C18 column (7.8×300 mM; Waters, Milford, Mass.) in a Biocad HPLC system (Perseptive Biosystems, Framingham, Mass.). Fractions were eluted from the column with a linear gradient from 0–100% buffer (0.1% TFA in acetonitrile). The flow rate was 10 ml/minute and eluent was monitored at 214 nm and 280 nm.

Six fractions were collected, dried, suspended in PBS and tested individually in *M. tuberculosis*-infected guinea pigs for induction of delayed type hypersensitivity (DTH) reaction. One fraction was found to induce a strong DTH reaction and was subsequently fractionated further by RP-HPLC on a microbore Vydac C18 column (Cat. No. 218TP5115) in a Perkin Elmer/Applied Biosystems Division Model 172 HPLC. Fractions were eluted with a linear gradient from 5–100% buffer (0.05% TFA in acetonitrile) with a flow rate of 80 μl/minute. Eluent was monitored at 215 nm. Eight fractions were collected and tested for induction of DTH in *M. tuberculosis*-infected guinea pigs. One fraction was found to induce strong DTH of about 16 mm induration. The other fractions did not induce detectable DTH. The positive fraction was submitted to SDS-PAGE gel electrophoresis and found to contain a single protein band of approximately 12 kD molecular weight.

This polypeptide, herein after referred to as DPPD, was sequenced from the amino terminal using a Perkin Elmer/Applied Biosystems Division Procise 492 protein sequencer as described above and found to have the N-terminal sequence shown in SEQ ID NO: 124. Comparison of this sequence with known sequences in the gene bank as described above revealed no known homologies. Four cyanogen bromide fragments of DPPD were isolated and found to have the sequences shown in SEQ ID NOS: 125–128. A subsequent search of the *M. tuberculosis* genome database releasedg by the Institute for Genomic Research revealed a match of the DPPD partial amino acid sequence with a sequence present within the *M. tuberculosis* cosmid MTY21C12. An open reading frame of 336 bp was identified. The full-length DNA sequence for DPPD is provided in SEQ ID NO: 235, with the corresponding full-length amino acid sequence being provided in SEQ ID NO: 236.

Example 5

Use of Sera from Tuberculosis-Infected Monkeys to Identify DNA Sequences Encoding *M. Tuberculosis* Antigens Genomic DNA was isolated from *M. tuberculosis* Erdman strain, randomly sheared and used to construct an expression library employing the Lambda ZAP expression system (Stratagene, La Jolla, Calif.). Serum samples were obtained from a cynomolgous monkey 18, 33, 51 and 56 days following infection with *M. tuberculosis* Erdman strain. These samples were pooled and used to screen the *M. tuberculosis* genomic DNA expression library using the procedure described above in Example 3C.

Twenty clones were purified. The determined 5' DNA sequences for the clones referred to as MO-1, MO-2, MO-4, MO-8, MO-9, MO-26, MO-28, MO-29, MO-30, MO-34 and MO-35 are provided in SEQ ID NO: 210–220, respectively, with the corresponding predicted amino acid sequences being provided in SEQ ID NO: 221–231. The full-length DNA sequence of the clone MO-10 is provided in SEQ ID NO: 232, with the corresponding predicted amino acid sequence being provided in SEQ ID NO: 233. The 3' DNA sequence for the clone MO-27 is provided in SEQ ID NO: 234.

Clones MO-1, MO-30 and MO-35 were found to show a high degree of relatedness and showed some homology to a previously identified unknown *M. tuberculosis* sequence and to cosmid MTC1237. MO-2 was found to show some homology to aspartokinase from *M. tuberculosis*. Clones MO-3, MO-7 and MO-27 were found to be identical and to show a high degree of relatedness to MO-5. All four of these clones showed some homology to *M. tuberculosis* heat shock protein 70. MO-27 was found to show some homology to *M. tuberculosis* cosmid MTCY339. MO-4 and MO-34 were found to show some homology to cosmid SCY21B4 and *M. smegmatis* integration host factor, and were both found to show some homology to a previously identified, unknown *M. tuberculosis* sequence. MO-6 was found to show some homology to *M. tuberculosis* heat shock protein 65. MO-8, MO-9, M 0–10, MO-26 and MO-29 were found to be highly related to each other and to show some homology to *M. tuberculosis* dihydrolipamide succinyltransferase. MO-28, MO-31 and MO-32 were found to be identical and to show some homology to a previously identified *M. tuberculosis* protein. MO-33 was found to show some homology to a previously identified 14 kDa *M. tuberculosis* heat shock protein.

Further studies using the above protocol resulted in the isolation of an additional four clones, hereinafter referred to as MO-12, M 0–13, MO-19 and MO-39. The determined 5' cDNA sequences for these clones are provided in SEQ ID NO: 290–293, respectively, with the corresponding predicted protein sequences being provided in SEQ ID NO: 294–297, respectively. Comparison of these sequences with those in the gene bank as described above revealed no significant homologies to MO-39. MO-12, MO-13 and MO-19 were found to show some homologies to unknown sequences previously isolated from *M. tuberculosis*.

Example 6

Isolation of DNA Sequences Encoding *M. Tuberculosis* Antigens by Screening of a Novel Expression Library This example illustrates isolation of DNA sequences encoding *M. tuberculosis* antigens by screening of a novel expression library with sera from *M. tuberculosis*-infected patients that were shown to be unreactive with a panel of the recombinant *M. tuberculosis* antigens TbRa11, TbRa3, Tb38-1, TbH4, TbF and 38 kD.

Genomic DNA from *M. tuberculosis* Erdman strain was randomly sheared to an average size of 2 kb, and blunt ended with Klenow polymerase, followed by the addition of EcoRI adaptors. The insert was subsequently ligated into the Screen phage vector (Novagen, Madison, Wis.) and packaged in vitro using the PhageMaker extract (Novagen). The resulting library was screened with sera from several *M. tuberculosis* donors that had been shown to be negative on a panel of previously identified *M. tuberculosis* antigens as described above in Example 3B.

A total of 22 different clones were isolated. By comparison, screening of the λZap library described above using the same sera did not result in any positive hits. One of the clones was found to represent TbRa11, described above. The determined 5' cDNA sequences for 19 of the remaining 21 clones (hereinafter referred to as Erdsn1, Erdsn2, Erdsn4–Erdsn10, Erdsn12–18, Erdsn21–Erdsn23 and Erdsn25) are provided in SEQ ID NO: 298–317, respectively, with the determined 3' cDNA sequences for Erdsn1, Erdsn2, Erdsn4, Erdsn5, Erdsn7–Erdsn10, Erdsn12–Erdsn18, Erdsn21–Erdsn23 and Erdsn25 being provided in SEQ ID NO: 318–336, respectively. The complete cDNA insert sequence for the clone Erdsn24 is provided in SEQ ID NO: 337. Comparison of the determined cDNA sequences with those in the gene bank revealed no significant homologies to the sequences provided in SEQ ID NO: 304, 311, 313–315, 317, 319, 324, 326, 329, 331, 333, 335 and 337. The sequences of SEQ ID NO: 298–303, 305–310, 312, 316, 318, 320–321, 324–326, 328, 330, 332, 334 and 336 were found to show some homology to unknown sequences previously identified in *M. tuberculosis*.

Example 7

Isolation of Soluble *M. Tuberculosis* Antigens Using Mass Spectrometry

This example illustrates the use of mass spectrometry to identify soluble *M. tuberculosis* antigens.

In a first approach, *M. tuberculosis* culture filtrate was screened by Western analysis using serum from a tuberculosis-infected individual. The reactive bands were excised from a silver stained gel and the amino acid sequences determined by mass spectrometry. The determined amino acid sequence for one of the isolated antigens is provided in SEQ ID NO: 338. Comparison of this sequence with those in the gene bank revealed homology to the 85b precursor antigen previously identified in *M. tuberculosis*.

In a second approach, the high molecular weight region of *M. tuberculosis* culture supernatant was studied. This area may contain immunodominant antigens which may be useful in the diagnosis of *M. tuberculosis* infection. Two known monoclonal antibodies, IT42 and IT57 (available from the Center for Disease Control, Atlanta, Ga.), show reactivity by Western analysis to antigens in this vicinity, although the identity of the antigens remains unknown. In addition, unknown high-molecular weight proteins have been described as containing a surrogate marker for *M. tuberculosis* infection in HIV-positive individuals (*Jnl. Infect. Dis.,* 176:133–143, 1997). To determine the identity of these antigens, two-dimensional gel electrophoresis and two-dimensional Western analysis were performed using the antibodies IT57 and IT42. Five protein spots in the high molecular weight region were identified, individually excised, enzymatically digested and subjected to mass spectrometric analysis.

The determined amino acid sequences for three of these spots (referred to as spots 1, 2 and 4) are provided in SEQ ID NO: 339, 340–341 and 342, respectively. Comparison of these sequences with those in the gene bank revealed that spot 1 is the previously identified PcK-1, a phosphoenolpyruvate kinase. The two sequences isolated from spot 2 were-determined to be from two DNAks, previously identified in *M. tuberculosis* as heat shock proteins. Spot 4 was determined to be the previously identified *M. tuberculosis* protein Kat G. To the best of the inventors' knowledge, neither PcK-1 nor the two DNAks have previously been shown to have utility in the diagnosis of *M. tuberculosis* infection.

Example 8

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation or labeling of the peptide. Cleavage of the peptides from the solid support may be carried out using the following cleavage mixture: trifluoroacetic acid: ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

This procedure was used to synthesize a TbM-1 peptide that contains one and a half repeats of a TbM-1 sequence. The TbM-1 peptide has the sequence GCGDRSGGNLDQIRLRRDRSGGNL (SEQ ID NO: 63).

Example 9

Use of Representative Antigens for Serodiagnosis of Tuberculosis

This Example illustrates the diagnostic properties of several representative antigens.

Assays were performed in 96-well plates were coated with 200 ng antigen diluted to 50 μL in carbonate coating buffer, pH 9.6. The wells were coated overnight at 4° C. (or 2 hours at 37° C.). The plate contents were then removed and the wells were blocked for 2 hours with 200 μL of PBS/1% BSA. After the blocking step, the wells were washed five times with PBS/0.1% Tween 20™. 50 μL sera, diluted 1:100 in PBS/0.1% Tween 20™/0.1% BSA, was then added to each well and incubated for 30 minutes at room temperature. The plates were then washed again five times with PBS/ 0.1% Tween 20™.

The enzyme conjugate (horseradish peroxidase—Protein A, Zymed, San Francisco, Calif.) was then diluted 1:10,000 in PBS/0.1% Tween 20™/0.1% BSA, and 50 µL of the diluted conjugate was added to each well and incubated for 30 minutes at room temperature. Following incubation, the wells were washed five times with PBS/0.1% Tween 20™. 100 µL of tetramethylbenzidine peroxidase (TMB) substrate (Kirkegaard and Perry Laboratories, Gaithersburg, Md.) was added, undiluted, and incubated for about 15 minutes. The reaction was stopped with the addition of 100 µL of 1 N $H_2SO_4$ to each well, and the plates were read at 450 nm.

compared to that of the 38 kD antigen described by Andersen and Hansen. *Infect. Immun.* 57:2481–2488, 1989. Again, all of the polypeptides tested differentiated positive from negative sera. Based on cut-off values obtained from receiver-operator curves, TbH4 detected 67 out of 126 positive sera, TbH12 detected 50 out of 125 positive sera, 38-1 detected 61 out of 101 positive sera and the TbM-1 peptide detected 25 out of 30 positive sera.

The reactivity of four antigens (TbRa3, TbRa9, TbH4 and TbH12) with sera from a group of *M. tuberculosis* infected patients with differing reactivity in the acid fast stain of sputum (Smithwick and David, *Tubercle* 52:226, 1971) was also examined, and compared to the reactivity of *M. tuberculosis* lysate and the 38 kD antigen. The results are presented in Table 3, below:

TABLE 3

REACTIVITY OF ANTIGENS WITH SERA FROM *M. TUBERCULOSIS* PATIENTS

| Patient | Acid Fast Sputum | ELISA Values | | | | | |
|---|---|---|---|---|---|---|---|
| | | Lysate | 38kD | TbRa9 | TbH12 | TbH4 | TbRa3 |
| Tb01B93I-2 | ++++ | 1.853 | 0.634 | 0.998 | 1.022 | 1.030 | 1.314 |
| Tb01B93I-19 | ++++ | 2.657 | 2.322 | 0.608 | 0.837 | 1.857 | 2.335 |
| Tb01B93I-8 | +++ | 2.703 | 0.527 | 0.492 | 0.281 | 0.501 | 2.002 |
| Tb01B93I-10 | +++ | 1.665 | 1.301 | 0.685 | 0.216 | 0.448 | 0.458 |
| Tb01B93I-11 | +++ | 2.817 | 0.697 | 0.509 | 0.301 | 0.173 | 2.608 |
| Tb01B93I-15 | +++ | 1.28 | 0.283 | 0.808 | 0.218 | 1.537 | 0.811 |
| Tb01B93I-16 | +++ | 2.908 | >3 | 0.899 | 0.441 | 0.593 | 1.080 |
| Tb01B93I-25 | +++ | 0.395 | 0.131 | 0.335 | 0.211 | 0.107 | 0.948 |
| Tb01B93I-87 | +++ | 2.653 | 2.432 | 2.282 | 0.977 | 1.221 | 0.857 |
| Tb01B93I-89 | +++ | 1.912 | 2.370 | 2.436 | 0.876 | 0.520 | 0.952 |
| Tb01B94I-108 | +++ | 1.639 | 0.341 | 0.797 | 0.368 | 0.654 | 0.798 |
| Tb01B94I-201 | +++ | 1.721 | 0.419 | 0.661 | 0.137 | 0.064 | 0.692 |
| Tb01B93I-88 | ++ | 1.939 | 1.269 | 2.519 | 1.381 | 0.214 | 0.530 |
| Tb01B93I-92 | ++ | 2.355 | 2.329 | 2.78 | 0.685 | 0.997 | 2.527 |
| Tb01B94I-109 | ++ | 0.993 | 0.620 | 0.574 | 0.441 | 0.5 | 2.558 |
| Tb01B94I-210 | ++ | 2.777 | >3 | 0.393 | 0.367 | 1.004 | 1.315 |
| Tb01B94I-224 | ++ | 2.913 | 0.476 | 0.251 | 1.297 | 1.990 | 0.256 |
| Tb01B93I-9 | + | 2.649 | 0.278 | 0.210 | 0.140 | 0.181 | 1.586 |
| Tb01B93I-14 | + | >3 | 1.538 | 0.282 | 0.291 | 0.549 | 2.880 |
| Tb01B93I-21 | + | 2.645 | 0.739 | 2.499 | 0.783 | 0.536 | 1.770 |
| Tb01B93I-22 | + | 0.714 | 0.451 | 2.082 | 0.285 | 0.269 | 1.159 |
| Tb01B93I-31 | + | 0.956 | 0.490 | 1.019 | 0.812 | 0.176 | 1.293 |
| Tb01B93I-32 | – | 2.261 | 0.786 | 0.668 | 0.273 | 0.535 | 0.405 |
| Tb01B93I-52 | – | 0.658 | 0.114 | 0.434 | 0.330 | 0.273 | 1.140 |
| Tb01B93I-99 | – | 2.118 | 0.584 | 1.62 | 0.119 | 0.977 | 0.729 |
| Tb01B94I-130 | – | 1.349 | 0.224 | 0.86 | 0.282 | 0.383 | 2.146 |
| Tb01B94I-131 | – | 0.685 | 0.324 | 1.173 | 0.059 | 0.118 | 1.431 |
| AT4-0070 | Normal | 0.072 | 0.043 | 0.092 | 0.071 | 0.040 | 0.039 |
| AT4-0105 | Normal | 0.397 | 0.121 | 0.118 | 0.103 | 0.078 | 0.390 |
| 3/15/94-1 | Normal | 0.227 | 0.064 | 0.098 | 0.026 | 0.001 | 0.228 |
| 4/15/93-2 | Normal | 0.114 | 0.240 | 0.071 | 0.034 | 0.041 | 0.264 |
| 5/26/94-4 | Normal | 0.089 | 0.259 | 0.096 | 0.046 | 0.008 | 0.053 |
| 5/26/94-3 | Normal | 0.139 | 0.093 | 0.085 | 0.019 | 0.067 | 0.01 |

Figure 4:
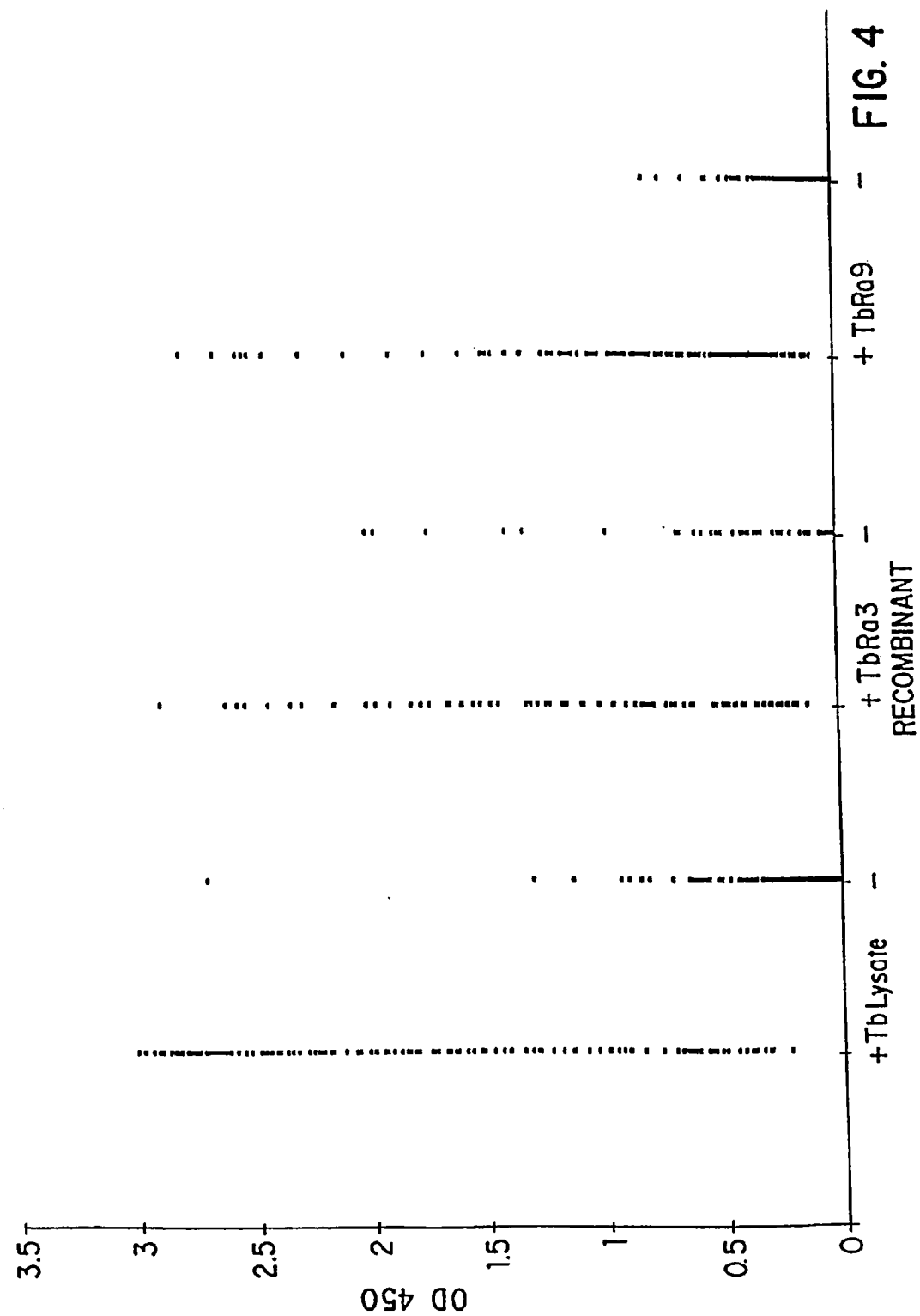
FIG. 4 illustrates the reactivity of two representative polypeptides with sera from *M. tuberculosis*-infected and uninfected individuals, as compared to the reactivity of bacterial lysate.

FIG. 4 shows the ELISA reactivity of two recombinant antigens isolated using method A in Example 3 (TbRa3 and TbRa9) with sera from *M. tuberculosis* positive and negative patients. The reactivity of these antigens is compared to that of bacterial lysate isolated from *M. tuberculosis* strain H37Ra (Difco. Detroit, Mich.). In both cases, the recombinant antigens differentiated positive from negative sera. Based on cut-off values obtained from receiver-operator curves, TbRa3 detected 56 out of 87 positive sera, and TbRa9 detected 111 out of 165 positive sera.

Figure 5:
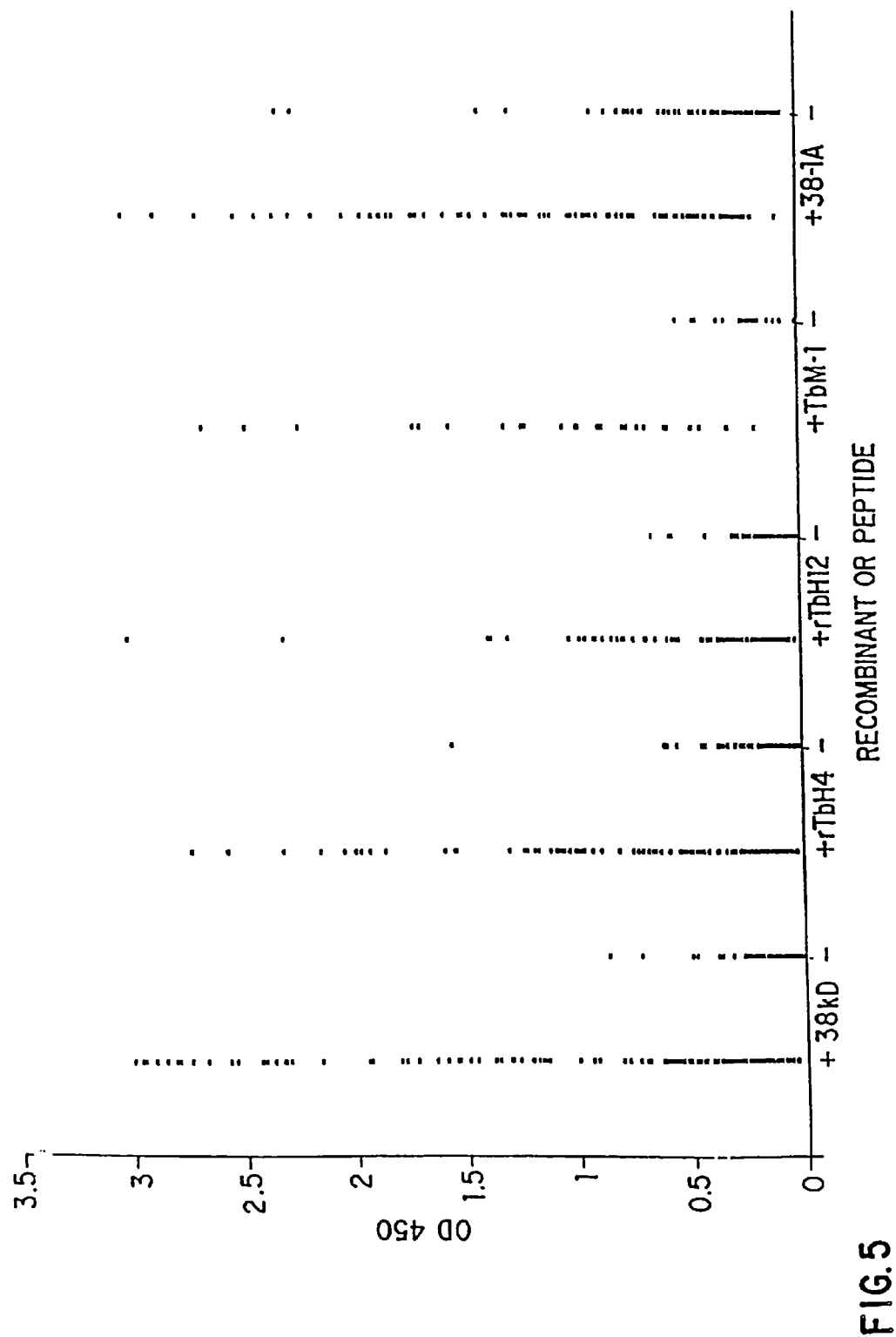
FIG. 5 shows the reactivity of four representative polypeptides with sera from *M. tuberculosis*-infected and uninfected individuals, as compared to the reactivity of the 38 kD antigen.

FIG. 5 illustrates the ELISA reactivity of representative antigens isolated using method B of Example 3. The reactivity of the recombinant antigens TbH 4, TbH12, Tb38-1 and the peptide TbM-1 (as described in Example 4) is Based on cut-off values obtained from receiver-operator curves, TbRa3 detected 23 out of 27 positive sera, T % TbRa9 detected 22 out of 27, TbH4 detected 18 out of 27 and TbH12 detected 15 out of 27. If used in combination, these four antigens would have a theoretical sensitivity of 27 out of 27, indicating that these antigens should complement each other in the serological detection of *M. tuberculosis* infection. In addition, several of the recombinant antigens detected positive sera that were not detected using the 38 kD antigen, indicating that these antigens may be complementary to the 38 kD antigen.

Figure 6:
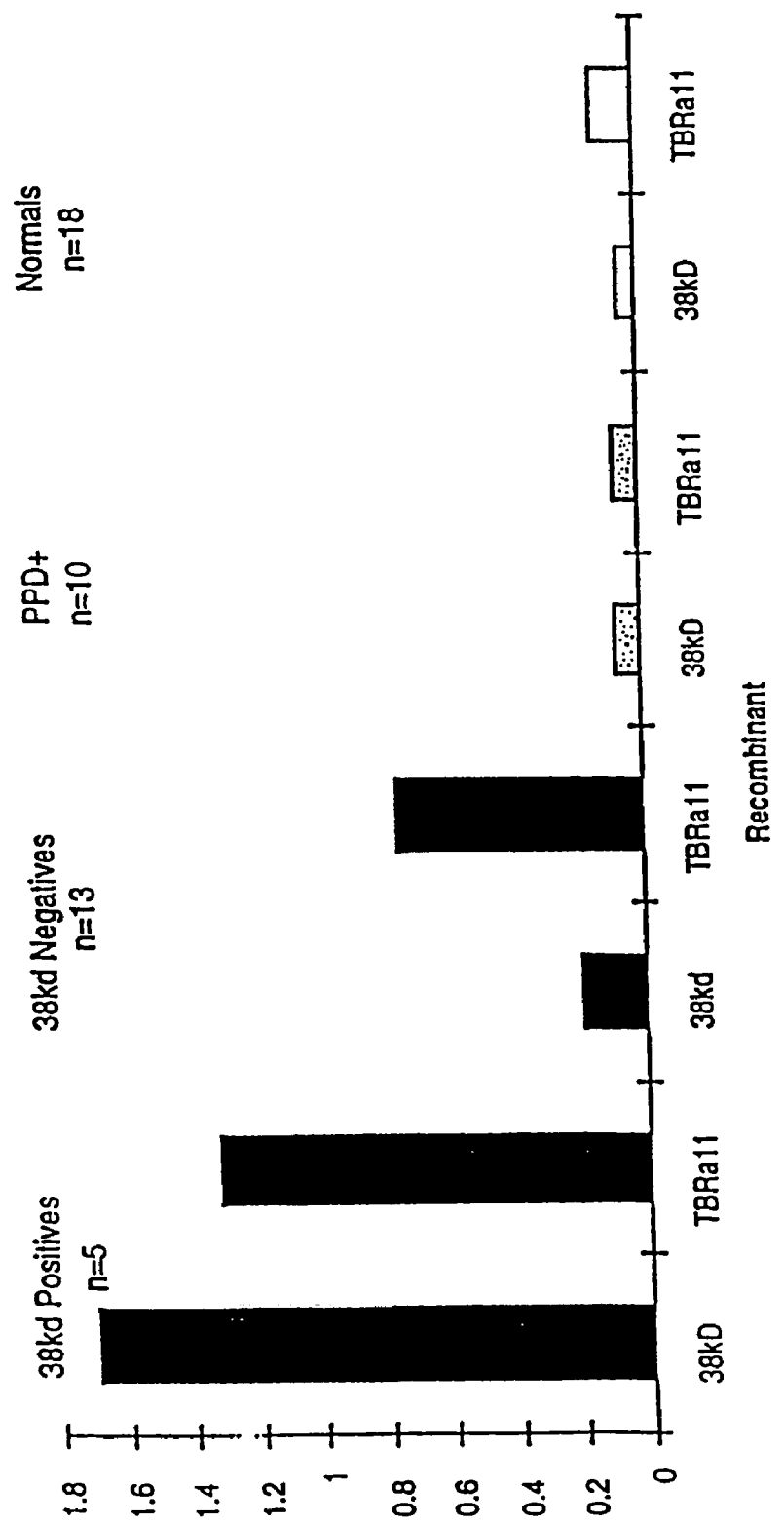
FIG. 6 shows the reactivity of recombinant 38 kD and TbRa11 antigens with sera from *M. tuberculosis* patients, PPD positive donors and normal donors.

The reactivity of the recombinant antigen TbRa11 with sera from *M. tuberculosis* patients shown to be negative for the 38 kD antigen, as well as with sera from PPD positive and normal donors, was determined by ELISA as described above. The results are shown in FIG. 6 which indicates that TbRa11, while being negative with sera from PPD positive and normal donors, detected sera that were negative with the 38 kD antigen. Of the thirteen 38 kD negative sera tested, nine were positive with TbRa11, indicating that this antigen may be reacting with a sub-group of 38 kD antigen negative sera. In contrast, in a group of 38 kD positive sera where TbRa11 was reactive, the mean OD 450 for TbRa11 was lower than that for the 38 kD antigen. The data indicate an inverse relationship between the presence of TbRa11 activity and 38 kD positivity.

Figure 7:
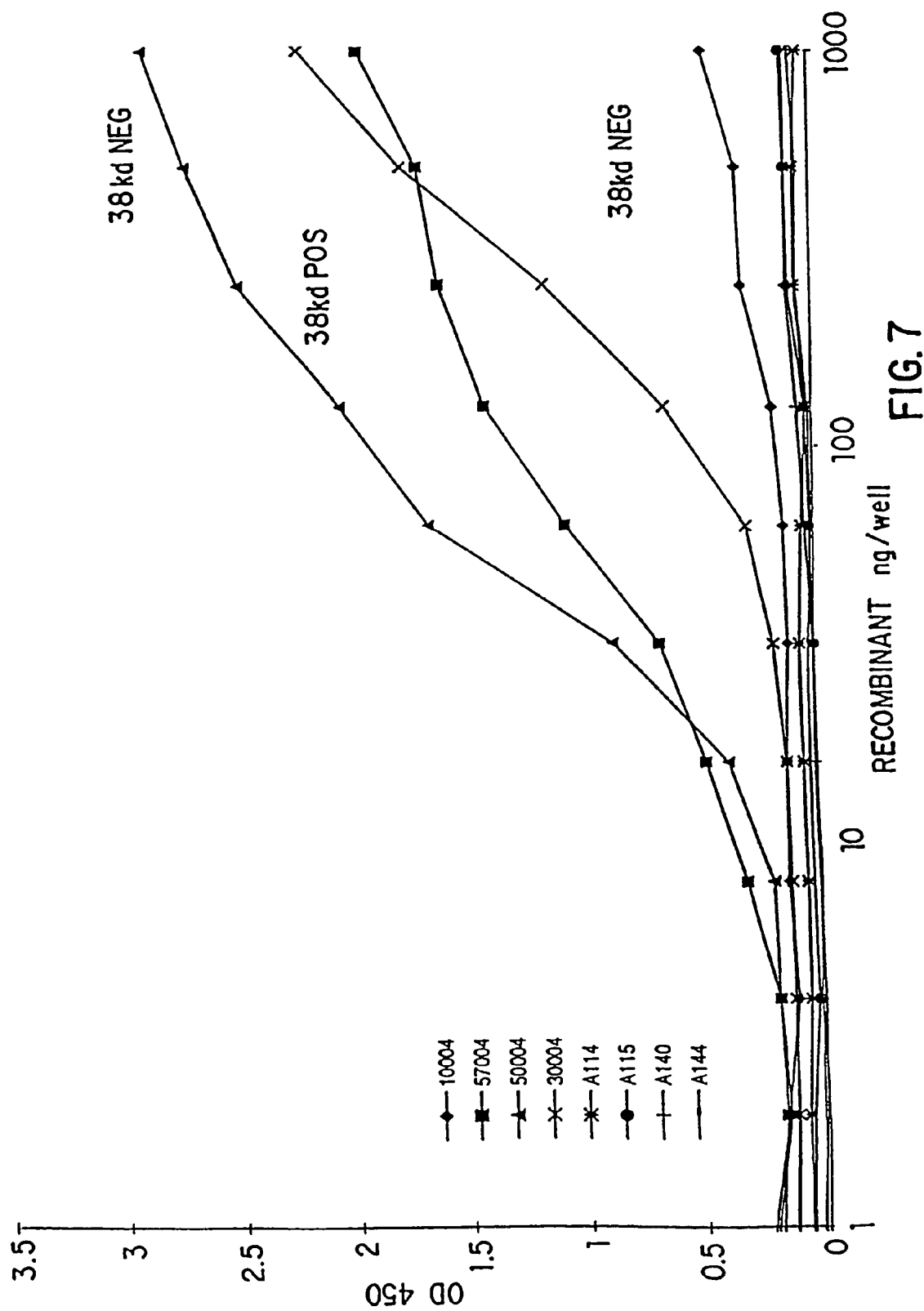
FIG. 7 shows the reactivity of the antigen TbRa2A with 38 kD negative sera.

The antigen TbRa2A was tested in an indirect ELISA using initially 50 μl of serum at 1:100 dilution for 30 minutes at room temperature followed by washing in PBS Tween and incubating for 30 minutes with biotinylated Protein A (Zymed, San Francisco, Calif.) at a 1:10,000 dilution. Following washing, 50 μl of streptavidin-horseradish peroxidase (Zymed) at 1:10,000 dilution was added and the mixture incubated for 30 minutes. After washing, the assay was developed with TMB substrate as described above. The reactivity of TbRa2A with sera from *M. tuberculosis* patients and normal donors in shown in Table 4. The mean value for reactivity of TbRa2A with sera from *M. tuberculosis* patients was 0.444 with a standard deviation of 0.309. The mean for reactivity with sera from normal donors was 0.109 with a standard deviation of 0.029. Testing of 38 kD negative sera (FIG. 7) also indicated that the TbRa2A antigen was capable of detecting sera in this category.

TABLE 4

REACTIVITY OF TBRA2A WITH SERA FROM
*M. TUBERCULOSIS* PATIENTS AND FROM NORMAL DONORS

| Serum ID | Status | OD 450 |
|---|---|---|
| Tb85 | TB | 0.680 |
| Tb86 | TB | 0.450 |
| Tb87 | TB | 0.263 |
| Tb88 | TB | 0.275 |
| Tb89 | TB | 0.403 |
| Tb91 | TB | 0.393 |
| Tb92 | TB | 0.401 |
| Tb93 | TB | 0.232 |
| Tb94 | TB | 0.333 |
| Tb95 | TB | 0.435 |
| Tb96 | TB | 0.284 |
| Tb97 | TB | 0.320 |
| Tb99 | TB | 0.328 |
| Tb100 | TB | 0.817 |
| Tb101 | TB | 0.607 |
| Tb102 | TB | 0.191 |
| Tb103 | TB | 0.228 |
| Tb107 | TB | 0.324 |
| Tb109 | TB | 1.572 |
| Tb112 | TB | 0.338 |
| DL4-0176 | Normal | 0.036 |
| AT4-0043 | Normal | 0.126 |
| AT4-0044 | Normal | 0.130 |
| AT4-0052 | Normal | 0.135 |
| AT4-0053 | Normal | 0.133 |
| AT4-0062 | Normal | 0.128 |
| AT4-0070 | Normal | 0.088 |
| AT4-0091 | Normal | 0.108 |
| AT4-0100 | Normal | 0.106 |
| AT4-0105 | Normal | 0.108 |
| AT4-0109 | Normal | 0.105 |

Figure 8:
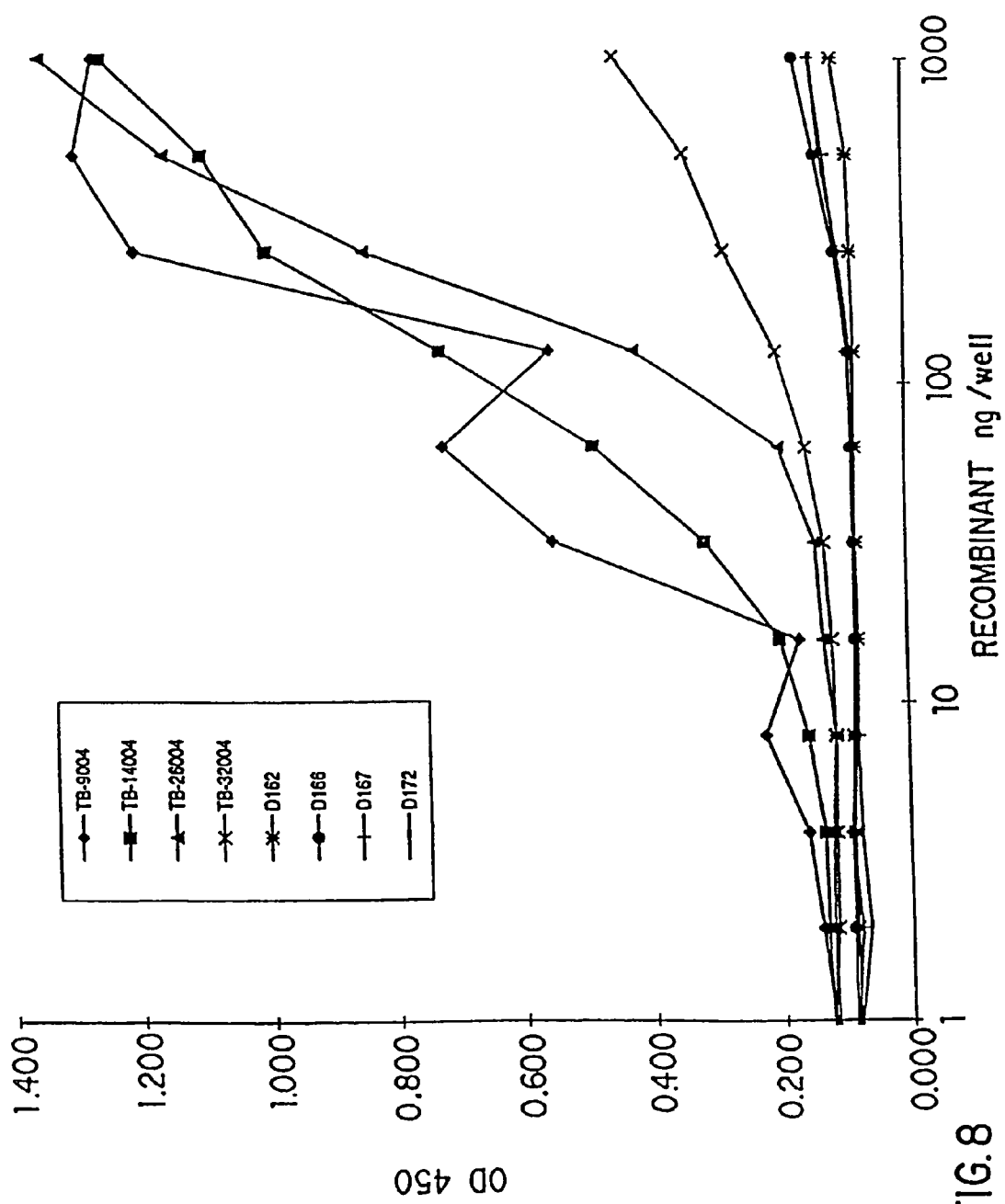
FIG. 8 shows the reactivity of the antigen of SEQ ID NO: 60 with sera from *M. tuberculosis* patients and normal donors.

The reactivity of the recombinant antigen (g) (SEQ ID NO: 60) with sera from *M. tuberculosis* patients and normal donors was determined by ELISA as described above. FIG. 8 shows the results of the titration of antigen (g) with four *M. tuberculosis* positive sera that were all reactive with the 38 kD antigen and with four donor sera, All four positive sera were reactive with antigen (g).

Figure 9:
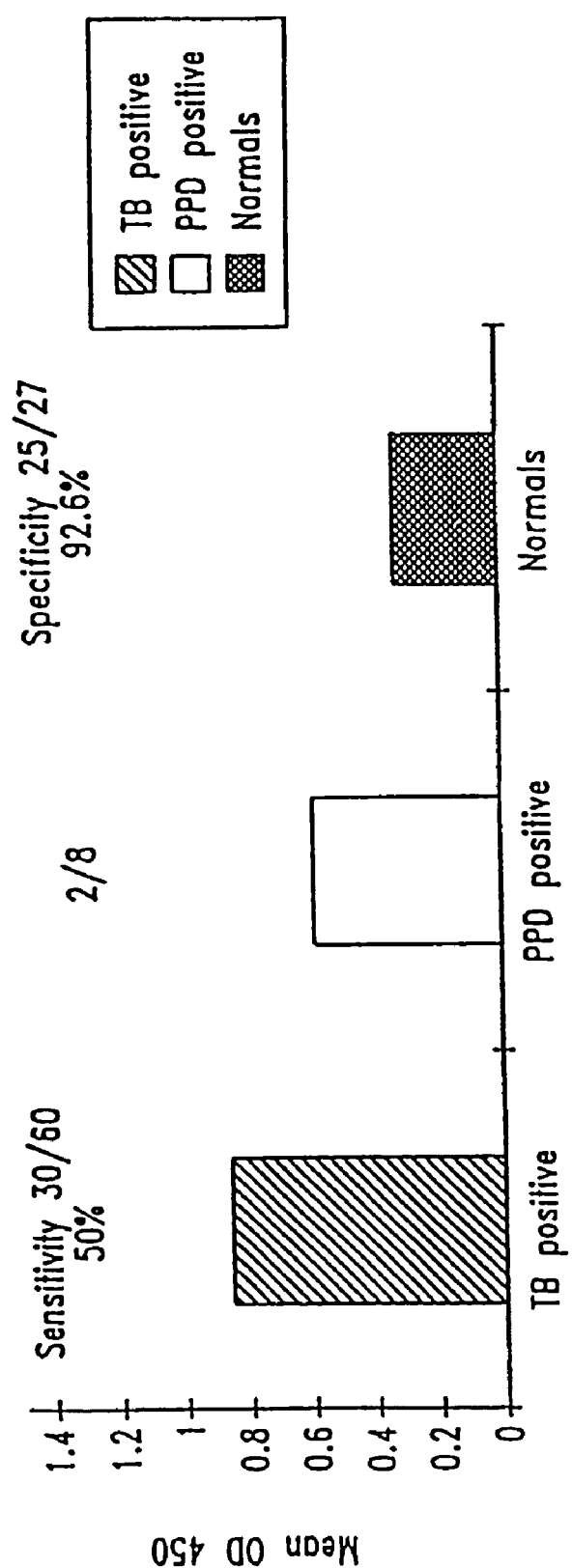
FIG. 9 illustrates the reactivity of the recombinant antigen TbH-29 (SEQ ID NO: 137) with sera from *M. tuberculosis* patients, PPD positive donors and normal donors as determined by indirect ELISA.

The reactivity of the recombinant antigen TbH-29 (SEQ ID NO: 137) with sera from *M. tuberculosis* patients, PPD positive donors and normal donors was determined by indirect ELISA as described above. The results are shown in FIG. 9. TbH-29 detected 30 out of 60 *M. tuberculosis* sera, 2 out of 8 PPD positive sera and 2 out of 27 normal sera.

FIG. 10 shows the results of ELISA tests (both direct and indirect) of the antigen TbH-33 (SEQ ID NO: 140) with sera from *M. tuberculosis* patients and from normal donors and with a pool of sera from *M. tuberculosis* patients. The mean OD 450 was demonstrated to be higher with sera from *M. tuberculosis* patients than from normal donors, with the mean OD 450 being significantly higher in the indirect ELISA than in the direct ELISA. FIG. 11 is a titration curve for the reactivity of recombinant TbH-33 with sera from *M. tuberculosis* patients and from normal donors showing an increase in OD 450 with increasing concentration of antigen.

The reactivity of the recombinant antigens RDIF6, RDIF8 and RDIF10 (SEQ ID NOS: 184–187, respectively) with sera from *M. tuberculosis* patients and normal donors was determined by ELISA as described above. RDIF6 detected 6 out of 32 *M. tuberculosis* sera and 0 out of 15 normal sera; RDIF8 detected 14 out of 32 *M. tuberculosis* sera and 0 out of 15 normal sera; and RDIF10 detected 4 out of 27 *M. tuberculosis* sera and 1 out of 15 normal sera. In addition, RDIF10 was found to detect 0 out of 5 sera from PPD-positive donors.

The antigens MO-1, MO-2, MO-4, MO-28 and MO-29 described above in Example 5, were expressed in *E. coli* and purified using a hexahistidine tag. The reactivity of these antigens with both *M. tuberculosis* positive and negative sera was examined by ELISA as described above. Titration curves showing the reactivity of MO-1, MO-2, MO-4, MO-28 and MO-29 at different solid phase coat levels when tested against four *M. tuberculosis* positive sera and four *M. tuberculosis* negative sera are shown in FIGS. 12A–E, respectively. Three of the clones, MO-1, MO-2 and MO-29 were further tested on panels of HIV positive/tuberculosis (HIV/TB) positive and extrapulmonary sera. MO-1 detected 3/20 extrapulmonary and 2/38 HIV/TB sera. On the same sera groups, MO-2 detected 2/20 and 10/38, and MO-29 detected 2/20 and 8/38 sera. In combination these three clones would have detected 4/20 extrapulmonary sera and 16/38 HIV/TB sera. In addition, MO-1 detected 6/17 sera that had previously been shown only to react with *M. tuberculosis* lysate and not with either 38 kD or with other antigens of the subject invention.

Example 10

Preparation and Characterization of *M. Tuberculosis* Fusion Proteins

A fusion protein containing TbRa3, the 38 kD antigen and Tb38-1 was prepared as follows.

Each of the DNA constructs TbRa3, 38 kD and Tb38-1 were modified by PCR in order to facilitate their fusion and the subsequent expression of the fusion protein TbRa3–38 kD-Tb38-1. TbRa3, 38 kD and Tb38-1 DNA was used to perform PCR using the primers PDM-64 and PDM-65 (SEQ ID NO: 141 and 142), PDM-57 and PDM-58 (SEQ ID NO: 143 and 144), and PDM-69 and PDM-60 (SEQ ID NO: 145–146), respectively. In each case, the DNA amplification was performed using 10 μl 10× Pfu buffer, 2 μl 10 mM dNTPs, 2 μl each of the PCR primers at 10 μM concentration, 81.5 μl water, 1.5 μl Pfu DNA polymerase (Stratagene, La Jolla, Calif.) and 1 μl DNA at either 70 ng/μl (for TbRa3) or 50 ng/μl (for 38 kD and Tb38-1). For TbRa3, denaturation at 94° C. was performed for 2 min, followed by 40 cycles of 96° C. for 15 sec and 72° C. for 1 min, and lastly by 72° C. for 4 min. For 38 kD, denaturation at 96° C. was performed for 2 min, followed by 40 cycles of 96° C. for 30 sec, 68° C. for 15 sec and 72° C. for 3 min, and finally by 72° C. for 4 min. For Tb38-1 denaturation at 94° C. for 2 min was followed by 10 cycles of 96° C. for 15 sec, 68° C. for 15 sec and 72° C. for 1.5 min, 30 cycles of 96° C. for 15 sec, 64° C. for 15 sec and 72° C. for 1.5, and finally by 72° C. for 4 min.

The TbRa3 PCR fragment was digested with NdeI and EcoRI and cloned directly into pT7^L2 IL 1 vector using NdeI and EcoRI sites. The 38 kD PCR fragment was digested with Sse8387 I, treated with T4 DNA polymerase to make blunt ends and then digested with EcoRI for direct cloning into the pT7^L2Ra3-1 vector which was digested with StuI and EcoRI. The 38-1 PCR fragment was digested with Eco47 III and EcoRI and directly subcloned into pT7^L2Ra3/38 kD-17 digested with the same enzymes. The whole fusion was then transferred to pET28b using NdeI and EcoRI sites. The fusion construct was confirmed by DNA sequencing.

The expression construct was transformed to BLR pLys S E. coli (Novagen, Madison, Wis.) and grown overnight in LB broth with kanamycin (30 μg/ml) and chloramphenicol (34 μg/ml). This culture (12 ml) was used to inoculate 500 ml 2XYT with the same antibiotics and the culture was induced with IPTG at an OD560 of 0.44 to a final concentration of 1.2 mM. Four hours post-induction, the bacteria were harvested and sonicated in 20 mM Tris (8.0), 100 mM NaCl, 0.1% DOC, 20 μg/ml Leupeptin, 20 mM PMSF followed by centrifugation at 26,000×g. The resulting pellet was resuspended in 8 M urea, 20 mM Tris (8.0), 100 mM NaCl and bound to Pro-bond nickel resin (Invitrogen, Carlsbad, Calif.). The column was washed several times with the above buffer then eluted with an imidazole gradient (50 mM, 100 mM, 500 mM imidazole was added to 8 M urea. 20 mM Tris (8.0), 100 mM NaCl). The eluates containing the protein of interest were then dialzyed against 10 mM Tris (8.0).

The DNA and amino acid sequences for the resulting fusion protein (hereinafter referred to as TbRa3–38 kD-Tb38-1) are provided in SEQ ED NO: 147 and 148, respectively.

A fusion protein containing the two antigens TbH-9 and TbH38-1 (hereinafter referred to as TbH9-Tb38-1) without a hinge sequence, was prepared using a similar procedure to that described above. The DNA sequence for the TbH9-TbH38-1 fusion protein is provided in SEQ ID NO: 151.

A fusion protein containing TbRa3, the antigen 38 kD, Tb38-1 and DPEP was prepared as follows.

Each of the DNA constructs TbRa3, 38 kD and Tb38-1 were modified by PCR and cloned into vectors essentially as described above, with the primers PDM-69 (SEQ ID NO:145 and PDM-83 (SEQ ID NO: 200) being used for amplification of the Tb38-1A fragment. Tb38-1A differs from Tb38-1 by a DraI site at the 3' end of the coding region that keeps the final amino acid intact while creating a blunt restriction site that is in frame. The TbRa3/38 kD/Tb38-1A fusion was then transferred to pET28b using NdeI and EcoRI sites.

DPEP DNA was used to perform PCR using the primers PDM-84 and PDM-85 (SEQ ID NO: 201 and 202, respectively) and 1 μl DNA at 50 ng/μl. Denaturation at 94° C. was performed for 2 min, followed by 10 cycles of 96° C. for 15 sec, 68° C. for 15 sec and 72° C. for 1.5 min; 30 cycles of 96° C. for 15 sec, 64° C. for 15 sec and 72° C. for 1.5 min; and finally by 72° C. for 4 min. The DPEP PCR fragment was digested with EcoRI and Eco72I and clones directly into the pET28Ra3/38 kD/38-1A construct which was digested with DraI and EcoRI. The fusion construct was confirmed to be correct by DNA sequencing. Recombinant protein was prepared as described above. The DNA and amino acid sequences for the resulting fusion protein (hereinafter referred to as TbF-2) are provided in SEQ ID NO: 203 and 204, respectively.

A fusion protein containing TbRa3, the antigen 38 kD, Tb38-1 and TbH4 was prepared as follows.

Genomic M. tuberculosis DNA was used to PCR full-length TbH4 (FL TbH4) with the primers PDM-157 and PDM-160 (SEQ ID NO: 343 and 344, respectively) and 2 μl DNA at 100 ng/μl. Denaturation at 96° C. was performed for 2 min, followed by 40 cycles of 96° C. for 30 sec, 61° C. for 20 sec and 72° C. for 5 min; and finally by annealing at 72° C. for 10 min. The FL TbH4 PCR fragment was digested with EcoRI and Sca I (New England Biolabs.) and cloned directly into the pET28Ra3/38kD/38-1A construct described above which was digested with DraI and EcoRI. The fusion construct was confirmed to be correct by DNA sequencing. Recombinant protein was prepared as described above. The DNA and amino acid sequences for the resulting fusion protein (hereinafter referred to as TbF-6) are provided in SEQ ID NO: 345 and 346, respectively.

A fusion protein containing the antigen 38 kD and DPEP separated by a linker was prepared as follows.

38 kD DNA was used to perform PCR using the primers PDM-176 and PDM-175 (SEQ ID NO: 347 and 348, respectively), and 1 μl PET28Ra3/38 kD/38-1/Ra2A-12 DNA at 110 ng/μl. Denaturation at 96° C. was performed for 2 min. followed by 40 cycles of 96° C. for 30 sec, 71° C. for 15 sec and 72° C. for 5 min and 40 sec; and finally by annealing at 72° C. for 4 min. The two sets of primers PDM-171. PDM-172, and PDM-173, PDM-174 were annealed by heating to 95° C. for 2 min and then ramping down to 25° C. slowly at 0.1° C./sec. DPEP DNA was used to perform PCR as described above. The 38 kD fragment was digested with Eco RI (New England Biolabs) and cloned into a modified pT7ΔL2 vector which was cut with Eco 72 I (Promega) and Eco RI. The modified pT7ΔL2 construct was designed to have a MGHHHHHH amino acid coding region in frame just 5' of the Eco 72 I site. The construct was digested with Kpn 2I (Gibco, BRL) and Pst I (New England Biolabs) and the annealed sets of phosphorylated primers (PDM-171, PDM-172 and PDM-173, PDM-174) were cloned in. The DPEP PCR fragment was digested with Eco RI and Eco 72 I and cloned into this second construct which was digested with Eco 47 III (New England Biolabs) and Eco RI. Ligations were done with a ligation kit from Panvera (Madison, Wis.). The resulting construct was digested with NdeI (New England Biolabs) and Eco RI, and transferred to a modified pET28 vector. The fusion construct was confirmed to be correct by DNA sequencing.

Recombinant protein was prepared essentially as described above. The DNA and amino acid sequences for the resulting fusion protein (hereinafter referred to as TbF-8) are provided in SEQ ID NO: 349 and 350, respectively.

Example 11

Use of *M. Tuberculosis* Fusion Proteins for Serodiagnosis of Tuberculosis

The effectiveness of the fusion protein TbRa3–38 kD-Tb38-1, prepared as described above, in the serodiagnosis of tuberculosis infection was examined by ELISA.

The ELISA protocol was as described above in Example 6, with the fusion protein being coated at 200 ng/well. A panel of sera was chosen from a group of tuberculosis patients previously shown, either by ELISA or by western blot analysis, to react with each of the three antigens individually or in combination. Such a panel enabled the dissection of the serological reactivity of the fusion protein to determine if all three epitopes functioned with the fusion protein. As shown in Table 5, all four sera that reacted with ThRa3 only were detectable with the fusion protein. Three sera that reacted only with Tb38-1 were also detectable, as were two sear that reacted with 38 kD alone. The remaining 15 sera were all positive with the fusion protein based on a cut-off in the assay of mean negatives +3 standard deviations. This data demonstrates the functional activity of all three epitopes in the fusion protein.

TABLE 5

REACTIVITY OF TRI-PEPTIDE FUSION PROTEIN WITH SERA FROM *M. TUBERCULOSIS* PATIENTS

| Serum ID | Status | ELISA and/or Western Blot Reactivity with Individual proteins | | | Fusion Recombinant OD 450 | Fusion Recombinant Status |
|---|---|---|---|---|---|---|
| | | 38kd | Tb38-1 | TbRa3 | | |
| 01B93I-40 | TB | − | − | + | 0.413 | + |
| 01B93I-41 | TB | − | + | + | 0.392 | + |
| 01B93I-29 | TB | + | − | + | 2.217 | + |
| 01B93I-109 | TB | + | ± | + | 0.522 | + |
| 01B93I-132 | TB | + | + | + | 0.937 | + |
| 5004 | TB | ± | + | ± | 1.098 | + |
| 15004 | TB | + | + | + | 2.077 | + |
| 39004 | TB | + | + | + | 1.675 | + |
| 68004 | TB | + | + | + | 2.388 | + |
| 99004 | TB | − | + | ± | 0.607 | + |
| 107004 | TB | − | + | ± | 0.667 | + |
| 92004 | TB | + | ± | ± | 1.070 | + |
| 97004 | TB | + | − | ± | 1.152 | + |
| 118004 | TB | + | − | ± | 2.694 | + |
| 173004 | TB | + | + | + | 3.258 | + |
| 175004 | TB | + | − | + | 2.514 | + |
| 274004 | TB | − | − | + | 3.220 | + |
| 276004 | TB | − | + | − | 2.991 | + |
| 282004 | TB | + | − | − | 0.824 | + |
| 289004 | TB | − | − | + | 0.848 | + |
| 308004 | TB | − | + | − | 3.338 | + |
| 314004 | TB | − | + | − | 1.362 | + |
| 317004 | TB | + | − | − | 0.763 | + |
| 312004 | TB | − | − | + | 1.079 | + |
| D176 | PPD | − | − | − | 0.145 | − |
| D162 | PPD | − | − | − | 0.073 | − |
| D161 | PPD | − | − | − | 0.097 | − |
| D27 | PPD | − | − | − | 0.082 | − |
| A6-124 | NORMAL | − | − | − | 0.053 | − |
| A6-125 | NORMAL | − | − | − | 0.087 | − |
| A6-126 | NORMAL | − | − | − | 0.346 | ± |
| A6-127 | NORMAL | − | − | − | 0.064 | − |
| A6-128 | NORMAL | − | − | − | 0.034 | − |
| A6-129 | NORMAL | − | − | − | 0.037 | − |
| A6-130 | NORMAL | − | − | − | 0.057 | − |
| A6-131 | NORMAL | − | − | − | 0.054 | − |
| A6-132 | NORMAL | − | − | − | 0.022 | − |
| A6-133 | NORMAL | − | − | − | 0.147 | − |
| A6-134 | NORMAL | − | − | − | 0.101 | − |
| A6-135 | NORMAL | − | − | − | 0.066 | − |
| A6-136 | NORMAL | − | − | − | 0.054 | − |
| A6-137 | NORMAL | − | − | − | 0.065 | − |
| A6-138 | NORMAL | − | − | − | 0.041 | − |
| A6-139 | NORMAL | − | − | − | 0.103 | − |
| A6-140 | NORMAL | − | − | − | 0.212 | − |
| A6-141 | NORMAL | − | − | − | 0.056 | − |
| A6-142 | NORMAL | − | − | − | 0.051 | − |

The reactivity of the fusion protein TbF-2 with sera from *M. tuberculosis*-infected patients was examined by ELISA using the protocol described above. The results of these studies (Table 6) demonstrate that all four antigens function independently in the fusion protein.

TABLE 6

REACTIVITY OF TBF-2 FUSION PROTEIN WITH TB AND NORMAL SERA

| | TbF | | TbF-2 | | ELISA Reactivity | | | |
|---|---|---|---|---|---|---|---|---|
| Serum ID | Status | OD450 | Status | OD450 | Status | 38kD | TbRa3 | Tb38-1 | DPEP |
| B931-40 | TB | 0.57 | + | 0.321 | + | − | + | − | + |
| B931-41 | TB | 0.601 | + | 0.396 | + | + | + | + | − |
| B931-109 | TB | 0.494 | + | 0.404 | + | + | + | ± | − |
| B931-132 | TB | 1.502 | + | 1.292 | + | + | + | + | ± |
| 5004 | TB | 1.806 | + | 1.666 | + | ± | ± | + | − |
| 15004 | TB | 2.862 | + | 2.468 | + | + | + | + | − |
| 39004 | TB | 2.443 | + | 1.722 | + | + | + | + | − |
| 68004 | TB | 2.871 | + | 2.575 | + | + | + | + | − |
| 99004 | TB | 0.691 | + | 0.971 | + | − | ± | − | − |
| 107004 | TB | 0.875 | + | 0.732 | + | − | ± | − | − |
| 92004 | TB | 1.632 | + | 1.394 | + | + | ± | ± | − |
| 97004 | TB | 1.491 | + | 1.979 | + | + | ± | − | + |
| 118004 | TB | 3.182 | + | 3.045 | + | + | ± | − | − |
| 173004 | TB | 3.644 | + | 3.578 | + | + | + | + | − |
| 175004 | TB | 3.332 | + | 2.916 | + | + | + | − | − |
| 274004 | TB | 3.696 | + | 3.716 | + | − | + | − | + |
| 276004 | TB | 3.243 | + | 2.56 | + | − | − | + | − |
| 282004 | TB | 1.249 | + | 1.234 | + | + | − | − | − |
| 289004 | TB | 1.373 | + | 1.17 | + | − | + | − | − |
| 308004 | TB | 3.708 | + | 3.355 | + | − | − | + | − |
| 314004 | TB | 1.663 | + | 1.399 | + | − | − | + | − |
| 317004 | TB | 1.163 | + | 0.92 | + | + | − | − | − |
| 312004 | TB | 1.709 | + | 1.453 | + | − | + | − | − |
| 380004 | TB | 0.238 | − | 0.461 | + | − | ± | − | + |
| 451004 | TB | 0.18 | − | 0.2 | − | − | − | − | ± |
| 478004 | TB | 0.188 | − | 0.469 | + | − | − | − | ± |
| 410004 | TB | 0.384 | + | 2.392 | + | ± | − | − | + |
| 411004 | TB | 0.306 | + | 0.874 | + | − | + | − | + |
| 421004 | TB | 0.357 | + | 1.456 | + | − | + | − | + |
| 528004 | TB | 0.047 | − | 0.196 | − | − | − | − | + |
| A6-87 | Normal | 0.094 | − | 0.063 | − | − | − | − | − |
| A6-88 | Normal | 0.214 | − | 0.19 | − | − | − | − | − |
| A6-89 | Normal | 0.248 | − | 0.125 | − | − | − | − | − |
| A6-90 | Normal | 0.179 | − | 0.206 | − | − | − | − | − |
| A6-91 | Normal | 0.135 | − | 0.151 | − | − | − | − | − |
| A6-92 | Normal | 0.064 | − | 0.097 | − | − | − | − | − |
| A6-93 | Normal | 0.072 | − | 0.098 | − | − | − | − | − |
| A6-94 | Normal | 0.072 | − | 0.064 | − | − | − | − | − |
| A6-95 | Normal | 0.125 | − | 0.159 | − | − | − | − | − |
| A6-96 | Normal | 0.121 | − | 0.12 | − | − | − | − | − |
| Cut-off | | 0.284 | | 0.266 | | | | | |

One of skill in the art will appreciate that the order of the individual antigens within the fusion protein may be changed and that comparable activity would be expected provided each of the epitopes is still functionally available. In addition, truncated forms of the proteins containing active epitopes may be used in the construction of fusion proteins.

From the foregoing, it will be appreciated that, although specific embodiments of the invention have been described herein for the purpose of illustration, various modifications may be made without deviating from the spirit and scope of the invention.

We claim:

1. An isolated polypeptide comprising an amino acid sequence as set forth in SEQ ID NO:102, 104, or 106 or an amino acid sequence comprising an immunogenic portion of SEQ ID NO:102, 104, or 106.

2. A fusion protein comprising a polypeptide according to claim 1.

3. A composition comprising a polypeptide of claim 1 or a fusion protein of claim 2 and a physiologically acceptable carrier.

4. The composition of claim 3, further comprising a non-specific immune response enhancer.

5. The composition of claim 4, wherein the non-specific immune response enhancer is an adjuvant.

* * * * *

SEQUENCE LISTING (1) GENERAL INFORMATION:

(iii) NUMBER OF SEQUENCES: 350

(2) INFORMATION FOR SEQ ID NO: 1:

(i) SEQUENCE CHARACTERISTICS:
    (A) LENGTH: 766 base pairs
    (B) TYPE: nucleic acid
    (C) STRANDEDNESS: single
    (D) TOPOLOGY: linear (xi) SEQUENCE DESCRIPTION: SEQ ID NO: 1:

```
CGAGGCACCG GTAGTTTGAA CCAAACGCAC AATCGACGGG CAAACGAACG GAAGAACACA      60
ACCATGAAGA TGGTGAAATC GATCGCCGCA GGTCTGACCG CCGCGGCTGC AATCGGCGCC     120
GCTGCGGCCG GTGTGACTTC GATCATGGCT GGCGGCCCGG TCGTATACCA GATGCAGCCG     180
GTCGTCTTCG GCGCGCCACT GCCGTTGGAC CCGGCATCCG CCCCTGACGT CCCGACCGCC     240
GCCCAGTTGA CCAGCCTGCT CAACAGCCTC GCCGATCCCA ACGTGTCGTT TGCGAACAAG     300
GGCAGTCTGG TCGAGGGCGG CATCGGGGGC ACCGAGGCGC GCATCGCCGA CCACAAGCTG     360
AAGAAGGCCG CCGAGCACGG GGATCTGCCG CTGTCGTTCA GCGTGACGAA CATCCAGCCG     420
GCGGCCGCCG GTTCGGCCAC CGCCGACGTT TCCGTCTCGG GTCCGAAGCT CTCGTCGCCG     480
GTCACGCAGA ACGTCACGTT CGTGAATCAA GGCGGCTGGA TGCTGTCACG CGCATCGGCG     540
ATGGAGTTGC TGCAGGCCGC AGGGAACTG ATTGGCGGGC CGGNTTCAGC CCGCTGTTCA      600
GCTACGCCGC CCGCCTGGTG ACGCGTCCAT GTCGAACACT CGCGCGTGTA GCACGGTGCG     660
GTNTGCGCAG GGNCGCACGC ACCGCCCGGT GCAAGCCGTC CTCGAGATAG GTGGTGNCTC     720
GNCACCAGNG ANCACCCCCN NNTCGNCNNT TCTCGNTGNT GNATGA                    766
```

(2) INFORMATION FOR SEQ ID NO: 2:

(i) SEQUENCE CHARACTERISTICS:
        (A) LENGTH: 752 base pairs
        (B) TYPE: nucleic acid
        (C) STRANDEDNESS: single
        (D) TOPOLOGY: linear (xi) SEQUENCE DESCRIPTION: SEQ ID NO: 2:

```
ATGCATCACC ATCACCATCA CGATGAAGTC ACGGTAGAGA CGACCTCCGT CTTCCGCGCA      60
GACTTCCTCA GCGAGCTGGA CGCTCCTGCG CAAGCGGGTA CGGAGAGCGC GGTCTCCGGG     120
GTGGAAGGGC TCCCGCCGGG CTCGGCGTTG CTGGTAGTCA AACGAGGCCC CAACGCCGGG     180
TCCCGGTTCC TACTCGACCA AGCCATCACG TCGGCTGGTC GGCATCCCGA CAGCGACATA     240
TTTCTCGACG ACGTGACCGT GAGCCGTCGC CATGCTGAAT TCCGGTTGGA AAACAACGAA     300
TTCAATGTCG TCGATGTCGG GAGTCTCAAC GGCACCTACG TCAACCGCGA GCCCGTGGAT     360
TCGGCGGTGC TGGCGAACGG CGACGAGGTC CAGATCGGCA AGCTCCGGTT GGTGTTCTTG     420
ACCGGACCCA AGCAAGGCGA GGATGACGGG AGTACCGGGG GCCCGTGAGC GCACCCGATA     480
GCCCCGCGCT GGCCGGGATG TCGATCGGGG CGGTCCTCCG ACCTGCTACG ACCGGATTTT     540
CCCTGATGTC CACCATCTCC AAGATTCGAT TCTTGGGAGG CTTGAGGGTC NGGGTGACCC     600
CCCCGCGGGC CTCATTCNGG GGTNTCGGCN GGTTTCACCC CNTACCNACT GCCNCCCGGN     660
TTGCNAATTC NTTCTTCNCT GCCCNNAAAG GGACCNTTAN CTTGCCGCTN GAAANGGTNA     720
TCCNGGGCCC NTCCTNGAAN CCCCNTCCCC CT                                   752
```

(2) INFORMATION FOR SEQ ID NO: 3:

(i) SEQUENCE CHARACTERISTICS:
        (A) LENGTH: 813 base pairs
        (B) TYPE: nucleic acid
        (C) STRANDEDNESS: single
        (D) TOPOLOGY: linear (xi) SEQUENCE DESCRIPTION: SEQ ID NO: 3:

```
CATATGCATC ACCATCACCA TCACACTTCT AACCGCCCAG CGCGTCGGGG GCGTCGAGCA    60

CCACGCGACA CCGGGCCCGA TCGATCTGCT AGCTTGAGTC TGGTCAGGCA TCGTCGTCAG   120

CAGCGCGATG CCCTATGTTT GTCGTCGACT CAGATATCGC GGCAATCCAA TCTCCCGCCT   180

GCGGCCGGCG GTGCTGCAAA CTACTCCCGG AGGAATTTCG ACGTGCGCAT CAAGATCTTC   240

ATGCTGGTCA CGGCTGTCGT TTTGCTCTGT TGTTCGGGTG TGGCCACGGC CGCGCCCAAG   300

ACCTACTGCG AGGAGTTGAA AGGCACCGAT ACCGGCCAGG CGTGCCAGAT TCAAATGTCC   360

GACCCGGCCT ACAACATCAA CATCAGCCTG CCCAGTTACT ACCCCGACCA GAAGTCGCTG   420

GAAAATTACA TCGCCCAGAC GCGCGACAAG TTCCTCAGCG CGGCCACATC GTCCACTCCA   480

CGCGAAGCCC CCTACGAATT GAATATCACC TCGGCCACAT ACCAGTCCGC GATACCGCCG   540

CGTGGTACGC AGGCCGTGGT GCTCAMGGTC TACCACAACG CCGGCGGCAC GCACCCAACG   600

ACCACGTACA AGGCCTTCGA TTGGGACCAG GCCTATCGCA AGCCAATCAC CTATGACACG   660

CTGTGGCAGG CTGACACCGA TCCGCTGCCA GTCGTCTTCC CCATTGTTGC AAGGTGAACT   720

GAGCAACGCA GACCGGGACA ACWGGTATCG ATAGCCGCCN AATGCCGGCT GGAACCCNG   780

TGAAATTATC ACAACTTCGC AGTCACNAAA NAA                                813
```

(2) INFORMATION FOR SEQ ID NO: 4:

(i) SEQUENCE CHARACTERISTICS:
        (A) LENGTH: 447 base pairs
        (B) TYPE: nucleic acid
        (C) STRANDEDNESS: single
        (D) TOPOLOGY: linear (xi) SEQUENCE DESCRIPTION: SEQ ID NO: 4:

```
CGGTATGAAC ACGGCCGCGT CCGATAACTT CCAGCTGTCC CAGGGTGGGC AGGGATTCGC    60

CATTCCGATC GGGCAGGCGA TGGCGATCGC GGGCCAGATC CGATCGGGTG GGGGGTCACC   120

CACCGTTCAT ATCGGGCCTA CCGCCTTCCT CGGCTTGGGT GTTGTCGACA CAACGGCAA    180

CGGCGCACGA GTCCAACGCG TGGTCGGGAG CGCTCCGGCG GCAAGTCTCG GCATCTCCAC   240

CGGCGACGTG ATCACCGCGG TCGACGGCGC TCCGATCAAC TCGGCCACCG CGATGGCGGA   300

CGCGCTTAAC GGGCATCATC CCGGTGACGT CATCTCGGTG AACTGGCAAA CCAAGTCGGG   360

CGGCACGCGT ACAGGGAACG TGACATTGGC CGAGGGACCC CCGGCCTGAT TCGTCGYGG   420

ATACCACCCG CCGGCCGGCC AATTGGA                                      447
```

(2) INFORMATION FOR SEQ ID NO: 5:

(i) SEQUENCE CHARACTERISTICS:
        (A) LENGTH: 604 base pairs
        (B) TYPE: nucleic acid
        (C) STRANDEDNESS: single
        (D) TOPOLOGY: linear (xi) SEQUENCE DESCRIPTION: SEQ ID NO: 5:

```
GTCCCACTGC GGTCGCCGAG TATGTCGCCC AGCAAATGTC TGGCAGCCGC CCAACGGAAT    60

CCGGTGATCC GACGTCGCAG GTTGTCGAAC CCGCCGCCGC GGAAGTATCG GTCCATGCCT   120

AGCCCGGCGA CGGCGAGCGC CGGAATGGCG CGAGTGAGGA GGCGGGCAAT TTGGCGGGGC   180

CCGGCGACGG NGAGCGCCGG AATGCGCGCA GTGAGGAGGT GGNCAGTCAT GCCCAGNGTG   240

ATCCAATCAA CCTGNATTCG GNCTGNGGGN CCATTTGACA ATCGAGGTAG TGAGCGCAAA   300
```

```
TGAATGATGG AAAACGGGNG GNGACGTCCG NTGTTCTGGT GGTGNTAGGT GNCTGNCTGG    360

NGTNGNGGNT ATCAGGATGT TCTTCGNCGA AANCTGATGN CGAGGAACAG GGTGTNCCCG    420

NNANNCCNAN GGNGTCCNAN CCCNNNNTCC TCGNCGANAT CANANAGNCG NTTGATGNGA    480

NAAAAGGGTG GANCAGNNNN AANTNGNGGN CCNAANAANC NNNANGNNG NNAGNTNGNT     540

NNNTNTTNNC ANNNNNNNTG NNGNNGNNCN NNNCAANCNN NTNNNNGNAA NNGGNTTNTT    600

NAAT                                                                604

(2) INFORMATION FOR SEQ ID NO: 6:

(i) SEQUENCE CHARACTERISTICS:
        (A) LENGTH: 633 base pairs
        (B) TYPE: nucleic acid
        (C) STRANDEDNESS: single
        (D) TOPOLOGY: linear (xi) SEQUENCE DESCRIPTION: SEQ ID NO: 6:

TTGCANGTCG AACCACCTCA CTAAAGGGAA CAAAAGCTNG AGCTCCACCG CGGTGGCGGC     60

CGCTCTAGAA CTAGTGKATM YYYCKGGCTG CAGSAATYCG GYACGAGCAT TAGGACAGTC    120

TAACGGTCCT GTTACGGTGA TCGAATGACC GACGACATCC TGCTGATCGA CACCGACGAA    180

CGGGTGCGAA CCCTCACCCT CAACCGGCCG CAGTCCCGYA ACGCGCTCTC GGCGGCGCTA    240

CGGGATCGGT TTTTCGCGGY GTTGGYCGAC GCCGAGGYCG ACGACGACAT CGACGTCGTC    300

ATCCTCACCG GYGCCGATCC GGTGTTCTGC GCCGGACTGG ACCTCAAGGT AGCTGGCCGG    360

GCAGACCGCG CTGCCGGACA TCTCACCGCG GTGGGCGGCC ATGACCAAGC CGGTGATCGG    420

CGCGATCAAC GGCGCCGCGG TCACCGGCGG GCTCGAACTG GCGCTGTACT GCGACATCCT    480

GATCGCCTCC GAGCACGCCC GCTTCGNCGA CACCCACGCC CGGGTGGGGC TGCTGCCCAC    540

CTGGGGACTC AGTGTGTGCT TGCCGCAAAA GGTCGGCATC GGNCTGGGCC GGTGGATGAG    600

CCTGACCGGC GACTACCTGT CCGTGACCGA CGC                                633

(2) INFORMATION FOR SEQ ID NO: 7:

(i) SEQUENCE CHARACTERISTICS:
        (A) LENGTH: 1362 base pairs
        (B) TYPE: nucleic acid
        (C) STRANDEDNESS: single
        (D) TOPOLOGY: linear (xi) SEQUENCE DESCRIPTION: SEQ ID NO: 7:

CGACGACGAC GGCGCCGGAG AGCGGGCGCG AACGGCGATC GACGCGGCCC TGGCCAGAGT     60

CGGCACCACC CAGGAGGGAG TCGAATCATG AAATTTGTCA ACCATATTGA GCCCGTCGCG    120

CCCCGCCGAG CCGGCGGCGC GGTCGCCGAG GTCTATGCCG AGGCCCGCCG CGAGTTCGGC    180

CGGCTGCCCG AGCCGCTCGC CATGCTGTCC CCGGACGAGG GACTGCTCAC CGCCGGCTGG    240

GCGACGTTGC GCGAGACACT GCTGGTGGGC CAGGTGCCGC GTGGCCGCAA GGAAGCCGTC    300

GCCGCCGCCG TCGCGGCCAG CCTGCGCTGC CCCTGGTGCG TCGACGCACA CACCACCATG    360

CTGTACGCGG CAGGCCAAAC CGACACCGCC GCGGCGATCT TGGCCGGCAC AGCACCTGCC    420

GCCGGTGACC CGAACGCGCC GTATGTGGCG TGGGCGGCAG GAACCGGGAC ACCGGCGGGA    480

CCGCCGGCAC CGTTCGGCCC GGATGTCGCC GCCGAATACC TGGGCACCGC GGTGCAATTC    540

CACTTCATCG CACGCCTGGT CCTGGTGCTG CTGGACGAAA CCTTCCTGCC GGGGGGCCCG    600

CGCGCCCAAC AGCTCATGCG CCGCGCCGGT GGACTGGTGT TCGCCCGCAA GGTGCGCGCG    660

GAGCATCGGC CGGGCCGCTC CACCCGCCGG CTCGAGCCGC GAACGCTGCC CGACGATCTG    720
```

```
GCATGGGCAA CACCGTCCGA GCCCATAGCA ACCGCGTTCG CCGCGCTCAG CCACCACCTG      780

GACACCGCGC CGCACCTGCC GCCACCGACT CGTCAGGTGG TCAGGCGGGT CGTGGGGTCG      840

TGGCACGGCG AGCCAATGCC GATGAGCAGT CGCTGGACGA ACGAGCACAC CGCCGAGCTG      900

CCCGCCGACC TGCACGCGCC CACCCGTCTT GCCCTGCTGA CCGGCCTGGC CCCGCATCAG      960

GTGACCGACG ACGACGTCGC CGCGGCCCGA TCCCTGCTCG ACACCGATGC GGCGCTGGTT     1020

GGCGCCCTGG CCTGGGCCGC CTTCACCGCC GCGCGGCGCA TCGGCACCTG GATCGGCGCC     1080

GCCGCCGAGG GCCAGGTGTC GCGGCAAAAC CCGACTGGGT GAGTGTGCGC GCCCTGTCGG     1140

TAGGGTGTCA TCGCTGGCCC GAGGGATCTC GCGGCGGCGA ACGGAGGTGG CGACACAGGT     1200

GGAAGCTGCG CCCACTGGCT TGCGCCCCAA CGCCGTCGTG GGCGTTCGGT TGGCCGCACT     1260

GGCCGATCAG GTCGGCGCCG GCCCTTGGCC GAAGGTCCAG CTCAACGTGC CGTCACCGAA     1320

GGACCGGACG GTCACCGGGG GTCACCCTGC GCGCCCAAGG AA                        1362
```

(2) INFORMATION FOR SEQ ID NO: 8:

(i) SEQUENCE CHARACTERISTICS:
        (A) LENGTH: 1458 base pairs
        (B) TYPE: nucleic acid
        (C) STRANDEDNESS: single
        (D) TOPOLOGY: linear (xi) SEQUENCE DESCRIPTION: SEQ ID NO: 8:

```
GCGACGACCC CGATATGCCG GGCACCGTAG CGAAAGCCGT CGCCGACGCA CTCGGGCGCG       60

GTATCGCTCC CGTTGAGGAC ATTCAGGACT GCGTGGAGGC CCGGCTGGGG GAAGCCGGTC      120

TGGATGACGT GGCCCGTGTT TACATCATCT ACCGGCAGCG GCGCGCCGAG CTGCGGACGG      180

CTAAGGCCTT GCTCGGCGTG CGGGACGAGT TAAAGCTGAG CTTGGCGGCC GTGACGGTAC      240

TGCGCGAGCG CTATCTGCTG CACGACGAGC AGGGCCGGCC GGCCGAGTCG ACCGGCGAGC      300

TGATGGACCG ATCGGCGCGC TGTGTCGCGG CGGCCGAGGA CCAGTATGAG CCGGGCTCGT      360

CGAGGCGGTG GGCCGAGCGG TTCGCCACGC TATTACGCAA CCTGGAATTC CTGCCGAATT      420

CGCCCACGTT GATGAACTCT GGCACCGACC TGGGACTGCT CGCCGGCTGT TTTGTTCTGC      480

CGATTGAGGA TTCGCTGCAA TCGATCTTTG CGACGCTGGG ACAGGCCGCC GAGCTGCAGC      540

GGGCTGGAGG CGGCACCGGA TATGCGTTCA GCCACCTGCG ACCCGCCGGG GATCGGGTGG      600

CCTCCACGGG CGGCACGGCC AGCGGACCGG TGTCGTTTCT ACGGCTGTAT GACAGTGCCG      660

CGGGTGTGGT CTCCATGGGC GGTCGCCGGC GTGGCGCCTG TATGGCTGTG CTTGATGTGT      720

CGCACCCGGA TATCTGTGAT TTCGTCACCG CCAAGGCCGA ATCCCCCAGC GAGCTCCCGC      780

ATTTCAACCT ATCGGTTGGT GTGACCGACG CGTTCCTGCG GGCCGTCGAA CGCAACGGCC      840

TACACCGGCT GGTCAATCCG CGAACCGGCA AGATCGTCGC GCGGATGCCC GCCGCCGAGC      900

TGTTCGACGC CATCTGCAAA GCCGCGCACG CCGGTGGCGA TCCCGGGCTG GTGTTTCTCG      960

ACACGATCAA TAGGGCAAAC CCGGTGCCGG GGAGAGGCCG CATCGAGGCG ACCAACCCGT     1020

GCGGGGAGGT CCCACTGCTG CCTTACGAGT CATGTAATCT CGGCTCGATC AACCTCGCCC     1080

GGATGCTCGC CGACGGTCGC GTCGACTGGG ACCGGCTCGA GGAGGTCGCC GGTGTGGCGG     1140

TGCGGTTCCT TGATGACGTC ATCGATGTCA GCCGCTACCC CTTCCCCGAA CTGGGTGAGG     1200

CGGCCCGCGC CACCCGCAAG ATCGGGCTGG GAGTCATGGG TTTGGCGGAA CTGCTTGCCG     1260

CACTGGGTAT TCCGTACGAC AGTGAAGAAG CCGTGCGGTT AGCCACCCGG CTCATGCGTC     1320

GCATACAGCA GGCGGCGCAC ACGGCATCGC GGAGGCTGGC CGAAGAGCGG GGCGCATTCC     1380
```

| CGGCGTTCAC CGATAGCCGG TTCGCGCGGT CGGGCCCGAG GCGCAACGCA CAGGTCACCT | 1440 |
| CCGTCGCTCC GACGGGCA | 1458 |

(2) INFORMATION FOR SEQ ID NO: 9:

(i) SEQUENCE CHARACTERISTICS:
        (A) LENGTH: 862 base pairs
        (B) TYPE: nucleic acid
        (C) STRANDEDNESS: single
        (D) TOPOLOGY: linear (xi) SEQUENCE DESCRIPTION: SEQ ID NO: 9:

| ACGGTGTAAT CGTGCTGGAT CTGGAACCGC GTGGCCCGCT ACCTACCGAG ATCTACTGGC | 60 |
| GGCGCAGGGG GCTGGCCCTG GCATCGCGG TCGTCGTAGT CGGGATCGCG GTGGCCATCG | 120 |
| TCATCGCCTT CGTCGACAGC AGCGCCGGTG CCAAACCGGT CAGCGCCGAC AAGCCGGCCT | 180 |
| CCGCCCAGAG CCATCCGGGC TCGCCGGCAC CCCAAGCACC CCAGCCGGCC GGGCAAACCG | 240 |
| AAGGTAACGC CGCCGCGGCC CCGCCGCAGG GCCAAAACCC CGAGACACCC ACGCCCACCG | 300 |
| CCGCGGTGCA GCCGCCGCCG GTGCTCAAGG AAGGGGACGA TTGCCCCGAT TCGACGCTGG | 360 |
| CCGTCAAAGG TTTGACCAAC GCGCCGCAGT ACTACGTCGG CGACCAGCCG AAGTTCACCA | 420 |
| TGGTGGTCAC CAACATCGGC CTGGTGTCCT GTAAACGCGA CGTTGGGGCC GCGGTGTTGG | 480 |
| CCGCCTACGT TTACTCGCTG GACAACAAGC GGTTGTGGTC CAACCTGGAC TGCGCGCCCT | 540 |
| CGAATGAGAC GCTGGTCAAG ACGTTTTCCC CCGGTGAGCA GGTAACGACC GCGGTGACCT | 600 |
| GGACCGGGAT GGGATCGGCG CCGCGCTGCC CATTGCCGCG GCCGGCGATC GGGCCGGGCA | 660 |
| CCTACAATCT CGTGGTACAA CTGGGCAATC TGCGCTCGCT GCCGGTTCCG TTCATCCTGA | 720 |
| ATCAGCCGCC GCCGCCGCCC GGGCCGGTAC CCGCTCCGGG TCCAGCGCAG GCGCCTCCGC | 780 |
| CGGAGTCTCC CGCGCAAGGC GGATAATTAT TGATCGCTGA TGGTCGATTC CGCCAGCTGT | 840 |
| GACAACCCCT CGCCTCGTGC CG | 862 |

(2) INFORMATION FOR SEQ ID NO: 10:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (xi) SEQUENCE DESCRIPTION: SEQ ID NO: 10:

| TTGATCAGCA CCGGCAAGGC GTCACATGCC TCCCTGGGTG TGCAGGTGAC CAATGACAAA | 60 |
| GACACCCCGG GCGCCAAGAT CGTCGAAGTA GTGGCCGGTG GTGCTGCCGC GAACGCTGGA | 120 |
| GTGCCGAAGG GCGTCGTTGT CACCAAGGTC GACGACCGCC CGATCAACAG CGCGGACGCG | 180 |
| TTGGTTGCCG CCGTGCGGTC CAAAGCGCCG GGCGCCACGG TGGCGCTAAC CTTTCAGGAT | 240 |
| CCCTCGGGCG GTAGCCGCAC AGTGCAAGTC ACCCTCGGCA AGGCGGAGCA GTGATGAAGG | 300 |
| TCGCCGCGCA GTGTTCAAAG CTCGGATATA CGGTGGCACC CATGGAACAG CGTGCGGAGT | 360 |
| TGGTGGTTGG CCGGGCACTT GTCGTCGTCG TTGACGATCG CACGGCGCAC GGCGATGAAG | 420 |
| ACCACAGCGG GCCGCTTGTC ACCGAGCTGC TCACCGAGGC CGGGTTTGTT GTCGACGGCG | 480 |
| TGGTGGCGGT GTCGGCCGAC GAGGTCGAGA TCCGAAATGC GCTGAACACA GCGGTGATCG | 540 |
| GCGGGGTGGA CCTGGTGGTG TCGGTCGGCG GGACCGGNGT GACGNCTCGC GATGTCACCC | 600 |
| CGGAAGCCAC CCGNGACATT CT | 622 |

(2) INFORMATION FOR SEQ ID NO: 11:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (xi) SEQUENCE DESCRIPTION: SEQ ID NO: 11:

```
GGCGCAGCGG TAAGCCTGTT GGCCGCCGGC ACACTGGTGT TGACAGCATG CGGCGGTGGC    60
ACCAACAGCT CGTCGTCAGG CGCAGGCGGA ACGTCTGGGT CGGTGCACTG CGGCGGCAAG   120
AAGGAGCTCC ACTCCAGCGG CTCGACCGCA CAAGAAAATG CCATGGAGCA GTTCGTCTAT   180
GCCTACGTGC GATCGTGCCC GGGCTACACG TTGGACTACA ACGCCAACGG GTCCGGTGCC   240
GGGGTGACCC AGTTTCTCAA CAACGAAACC GATTTCGCCG GCTCGGATGT CCCGTTGAAT   300
CCGTCGACCG GTCAACCTGA CCGGTCGGCG GAGCGGTGCG GTTCCCCGGC ATGGGACCTG   360
CCGACGGTGT TCGGCCCGAT CGCGATCACC TACAATATCA AGGGCGTGAG CACGCTGAAT   420
CTTGACGGAC CCACTACCGC CAAGATTTTC AACGGCACCA TCACCGTGTG GAATGATCCA   480
CAGATCCAAG CCCTCAACTC CGGCACCGAC CTGCCGCCAA CACCGATTAG CGTTATCTTC   540
CGCAGCGACA AGTCCGGTAC GTCGGACAAC TTCCAGAAAT ACCTCGACGG TGTATCCAAC   600
GGGGCGTGGG GCAAAGGCGC CAGCGAAACG TTCAGCGGGG GCGTCGGCGT CGGCGCCAGC   660
GGGAACAACG GAACGTCGGC CCTACTGCAG ACGACCGACG GGTCGATCAC CTACAACGAG   720
TGGTCGTTTG CGGTGGGTAA GCAGTTGAAC ATGGCCCAGA TCATCACGTC GGCGGGTCCG   780
GATCCAGTGG CGATCACCAC CGAGTCGGTC GGTAAGACAA TCGCCGGGGC CAAGATCATG   840
GGACAAGGCA ACGACCTGGT ATTGGACACG TCGTCGTTCT ACAGACCCAC CCAGCCTGGC   900
TCTTACCCGA TCGTGCTGGC GACCTATGAG ATCGTCTGCT CGAAATACCC GGATGCGACG   960
ACCGGTACTG CGGTAAGGGC GTTTATGCAA GCCGCGATTG GTCCAGGCCA AGAAGGCCTG  1020
GACCAATACG GCTCCATTCC GTTGCCCAAA TCGTTCCAAG CAAAATTGGC GGCCGCGGTG  1080
AATGCTATTT CTTGACCTAG TGAAGGGAAT TCGACGGTGA GCGATGCCGT TCCGCAGGTA  1140
GGGTCGCAAT TTGGGCCGTA TCAGCTATTG CGGCTGCTGG GCCGAGGCGG GATGGGCGAG  1200
```

(2) INFORMATION FOR SEQ ID NO: 12:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (xi) SEQUENCE DESCRIPTION: SEQ ID NO: 12:

```
GCAAGCAGCT GCAGGTCGTG CTGTTCGACG AACTGGGCAT GCCGAAGACC AAACGCACCA    60
AGACCGGCTA CACCACGGAT GCCGACGCGC TGCAGTCGTT GTTCGACAAG ACCGGGCATC   120
CGTTTCTGCA ACATCTGCTC GCCCACCGCG ACGTCACCCG GCTCAAGGTC ACCGTCGACG   180
GGTTGCTCCA AGCGGTGGCC GCCGACGGCC GCATCCACAC CACGTTCAAC CAGACGATCG   240
CCGCGACCGG CCGGCTCTCC TCGACCGAAC CCAACCTGCA GAACATCCCG ATCCGCACCG   300
ACGCGGGCCG GCGGATCCGG GACGCGTTCG TGGTCGGGGA CGGTTACGCC GAGTTGATGA   360
CGGCCGACTA CAGCCAGATC GAGATGCGGA TCATGGGCA CCTGTCCGGG GACGAGGGCC   420
TCATCGAGGC GTTCAACACC GGGGAGGACC TGTATTCGTT CGTCGCGTCC CGGGTGTTCG   480
GTGTGCCCAT CGACGAGGTC ACCGGCGAGT TGCGGCGCCG GGTCAAGGCG ATGTCCTACG   540
```

-continued

```
GGCTGGTTTA CGGGTTGAGC GCCTACGGCC TGTCGCAGCA GTTGAAAATC TCCACCGAGG      600

AAGCCAACGA GCAGATGGAC GCGTATTTCG CCCGATTCGG CGGGGTGCGC GACTACCTGC      660

GCGCCGTAGT CGAGCGGGCC CGCAAGGACG GCTACACCTC GACGGTGCTG GGCCGTCGCC      720

GCTACCTGCC CGAGCTGGAC AGCAGCAACC GTCAAGTGCG GGAGGCCGCC GAGCGGGCGG      780

CGCTGAACGC GCCGATCCAG GGCAGCGCGG CCGACATCAT CAAGGTGGCC ATGATCCAGG      840

TCGACAAGGC GCTCAACGAG GCACAGCTGG CGTCGCGCAT GCTGCTGCAG GTCCACGACG      900

AGCTGCTGTT CGAAATCGCC CCCGGTGAAC GCGAGCGGGT CGAGGCCCTG GTGCGCGACA      960

AGATGGGCGG CGCTTACCCG CTCGACGTCC CGCTGGAGGT GTCGGTGGGC TACGGCCGCA     1020

GCTGGGACGC GGCGGCGCAC TGAGTGCCGA GCGTGCATCT GGGGCGGGAA TTCGGCGATT     1080

TTTCCGCCCT GAGTTCACGC TCGGCGCAAT CGGGACCGAG TTTGTCCAGC GTGTACCCGT     1140

CGAGTAGCCT CGTCA                                                      1155
```

(2) INFORMATION FOR SEQ ID NO: 13:

(i) SEQUENCE CHARACTERISTICS:
        (A) LENGTH: 1771 base pairs
        (B) TYPE: nucleic acid
        (C) STRANDEDNESS: single
        (D) TOPOLOGY: linear (xi) SEQUENCE DESCRIPTION: SEQ ID NO: 13:

```
GAGCGCCGTC TGGTGTTTGA ACGGTTTTAC CGGTCGGCAT CGGCACGGGC GTTGCCGGGT       60

TCGGGCCTCG GGTTGGCGAT CGTCAAACAG GTGGTGCTCA ACCACGGCGG ATTGCTGCGC      120

ATCGAAGACA CCGACCCAGG CGGCCAGCCC CCTGGAACGT CGATTTACGT GCTGCTCCCC      180

GGCCGTCGGA TGCCGATTCC GCAGCTTCCC GGTGCGACGG CTGGCGCTCG GAGCACGGAC      240

ATCGAGAACT CTCGGGGTTC GGCGAACGTT ATCTCAGTGG AATCTCAGTC CACGCGCGCA      300

ACCTAGTTGT GCAGTTACTG TTGAAAGCCA CACCCATGCC AGTCCACGCA TGGCCAAGTT      360

GGCCCGAGTA GTGGGCCTAG TACAGGAAGA GCAACCTAGC GACATGACGA ATCACCCACG      420

GTATTCGCCA CCGCCGCAGC AGCCGGGAAC CCCAGGTTAT GCTCAGGGGC AGCAGCAAAC      480

GTACAGCCAG CAGTTCGACT GGCGTTACCC ACCGTCCCCG CCCCCGCAGC CAACCCAGTA      540

CCGTCAACCC TACGAGGCGT TGGGTGGTAC CCGGCCGGGT CTGATACCTG GCGTGATTCC      600

GACCATGACG CCCCCTCCTG GGATGGTTCG CCAACGCCCT CGTGCAGGCA TGTTGGCCAT      660

CGGCGCGGTG ACGATAGCGG TGGTGTCCGC CGGCATCGGC GGCGCGGCCG CATCCCTGGT      720

CGGGTTCAAC CGGGCACCCG CCGGCCCCAG CGGCGGCCCA GTGGCTGCCA GCGCGGCGCC      780

AAGCATCCCC GCAGCAAACA TGCCGCCGGG GTCGGTCGAA CAGGTGGCGG CCAAGGTGGT      840

GCCCAGTGTC GTCATGTTGG AAACCGATCT GGGCCGCCAG TCGGAGGAGG GCTCCGGCAT      900

CATTCTGTCT GCCGAGGGGC TGATCTTGAC CAACAACCAC GTGATCGCGG CGGCCGCCAA      960

GCCTCCCCTG GCAGTCCGC CGCCGAAAAC GACGGTAACC TTCTCTGACG GGCGGACCGC     1020

ACCCTTCACG GTGGTGGGGG CTGACCCCAC CAGTGATATC GCCGTCGTCC GTGTTCAGGG     1080

CGTCTCCGGG CTCACCCCGA TCTCCCTGGG TTCCTCCTCG GACCTGAGGG TCGGTCAGCC     1140

GGTGCTGGCG ATCGGGTCGC CGCTCGGTTT GGAGGGCACC GTGACCACGG GGATCGTCAG     1200

CGCTCTCAAC CGTCCAGTGT CGACGACCGG CGAGGCCGGC AACCAGAACA CCGTGCTGGA     1260

CGCCATTCAG ACCGACGCCG CGATCAACCC CGGTAACTCC GGGGGCGCGC TGGTGAACAT     1320

GAACGCTCAA CTCGTCGGAG TCAACTCGGC CATTGCCACG CTGGGCGCGG ACTCAGCCGA     1380
```

```
TGCGCAGAGC GGCTCGATCG GTCTCGGTTT TGCGATTCCA GTCGACCAGG CCAAGCGCAT    1440

CGCCGACGAG TTGATCAGCA CCGGCAAGGC GTCACATGCC TCCCTGGGTG TGCAGGTGAC    1500

CAATGACAAA GACACCCCGG GCGCCAAGAT CGTCGAAGTA GTGGCCGGTG GTGCTGCCGC    1560

GAACGCTGGA GTGCCGAAGG GCGTCGTTGT CACCAAGGTC GACGACCGCC CGATCAACAG    1620

CGCGGACGCG TTGGTTGCCG CCGTGCGGTC CAAAGCGCCG GGCGCCACGG TGGCGCTAAC    1680

CTTTCAGGAT CCCTCGGGCG GTAGCCGCAC AGTGCAAGTC ACCCTCGGCA AGGCGGAGCA    1740

GTGATGAAGG TCGCCGCGCA GTGTTCAAAG C                                   1771

(2) INFORMATION FOR SEQ ID NO: 14:

(i) SEQUENCE CHARACTERISTICS:
        (A) LENGTH: 1058 base pairs
        (B) TYPE: nucleic acid
        (C) STRANDEDNESS: single
        (D) TOPOLOGY: linear (xi) SEQUENCE DESCRIPTION: SEQ ID NO: 14:

CTCCACCGCG GTGGCGGCCG CTCTAGAACT AGTGGATCCC CCGGGCTGCA GGAATTCGGC      60

ACGAGGATCC GACGTCGCAG GTTGTCGAAC CCGCCGCCGC GGAAGTATCG GTCCATGCCT     120

AGCCCGGCGA CGGCGAGCGC CGGAATGGCG CGAGTGAGGA GGCGGGCAAT TTGGCGGGGC     180

CCGGCGACGG CGAGCGCCGG AATGGCGCGA GTGAGGAGGC GGGCAGTCAT GCCCAGCGTG     240

ATCCAATCAA CCTGCATTCG GCCTGCGGGC CCATTTGACA ATCGAGGTAG TGAGCGCAAA     300

TGAATGATGG AAAACGGGCG GTGACGTCCG CTGTTCTGGT GGTGCTAGGT GCCTGCCTGG     360

CGTTGTGGCT ATCAGGATGT TCTTCGCCGA AACCTGATGC CGAGGAACAG GGTGTTCCCG     420

TGAGCCCGAC GGCGTCCGAC CCCGCGCTCC TCGCCGAGAT CAGGCAGTCG CTTGATGCGA     480

CAAAAGGGTT GACCAGCGTG CACGTAGCGG TCCGAACAAC CGGGAAAGTC GACAGCTTGC     540

TGGGTATTAC CAGTGCCGAT GTCGACGTCC GGGCCAATCC GCTCGCGGCA AAGGGCGTAT     600

GCACCTACAA CGACGAGCAG GGTGTCCCGT TTCGGGTACA AGGCGACAAC ATCTCGGTGA     660

AACTGTTCGA CGACTGGAGC AATCTCGGCT CGATTTCTGA ACTGTCAACT TCACGCGTGC     720

TCGATCCTGC CGCTGGGGTG ACGCAGCTGC TGTCCGGTGT CACGAACCTC CAAGCGCAAG     780

GTACCGAAGT GATAGACGGA ATTTCGACCA CCAAAATCAC CGGGACCATC CCCGCGAGCT     840

CTGTCAAGAT GCTTGATCCT GGCGCCAAGA GTGCAAGGCC GGCGACCGTG TGGATTGCCC     900

AGGACGGCTC GCACCACCTC GTCCGAGCGA GCATCGACCT CGGATCCGGG TCGATTCAGC     960

TCACGCAGTC GAAATGGAAC GAACCCGTCA ACGTCGACTA GGCCGAAGTT GCGTCGACGC    1020

GTTGNTCGAA ACGCCCTTGT GAACGGTGTC AACGGNAC                           1058

(2) INFORMATION FOR SEQ ID NO: 15:

(i) SEQUENCE CHARACTERISTICS:
        (A) LENGTH: 542 base pairs
        (B) TYPE: nucleic acid
        (C) STRANDEDNESS: single
        (D) TOPOLOGY: linear (xi) SEQUENCE DESCRIPTION: SEQ ID NO: 15:

GAATTCGGCA CGAGAGGTGA TCGACATCAT CGGGACCAGC CCCACATCCT GGGAACAGGC      60

GGCGGCGGAG GCGGTCCAGC GGGCGCGGGA TAGCGTCGAT GACATCCGCG TCGCTCGGGT     120

CATTGAGCAG GACATGGCCG TGGACAGCGC CGGCAAGATC ACCTACCGCA TCAAGCTCGA     180
```

```
AGTGTCGTTC AAGATGAGGC CGGCGCAACC GCGCTAGCAC GGGCCGGCGA GCAAGACGCA        240

AAATCGCACG GTTTGCGGTT GATTCGTGCG ATTTTGTGTC TGCTCGCCGA GGCCTACCAG        300

GCGCGGCCCA GGTCCGCGTG CTGCCGTATC CAGGCGTGCA TCGCGATTCC GGCGGCCACG        360

CCGGAGTTAA TGCTTCGCGT CGACCCGAAC TGGGCGATCC GCCGGNGAGC TGATCGATGA        420

CCGTGGCCAG CCCGTCGATG CCCGAGTTGC CGAGGAAAC GTGCTGCCAG GCCGGTAGGA         480

AGCGTCCGTA GGCGGCGGTG CTGACCGGCT CTGCCTGCGC CCTCAGTGCG GCCAGCGAGC        540

GG                                                                      542
```

(2) INFORMATION FOR SEQ ID NO: 16:

(i) SEQUENCE CHARACTERISTICS:
        (A) LENGTH: 913 base pairs
        (B) TYPE: nucleic acid
        (C) STRANDEDNESS: single
        (D) TOPOLOGY: linear (xi) SEQUENCE DESCRIPTION: SEQ ID NO: 16:

```
CGGTGCCGCC CGCGCCTCCG TTGCCCCCAT TGCCGCCGTC GCCGATCAGC TGCGCATCGC         60

CACCATCACC GCCTTTGCCG CCGGCACCGC CGGTGGCGCC GGGGCCGCCG ATGCCACCGC        120

TTGACCCTGG CCGCCGGCGC CGCCATTGCC ATACAGCACC CCGCCGGGGG CACCGTTACC        180

GCCGTCGCCA CCGTCGCCGC CGCTGCCGTT TCAGGCCGGG GAGGCCGAAT GAACCGCCGC        240

CAAGCCCGCC GCCGGCACCG TTGCCGCCTT TTCCGCCCGC CCCGCCGGCG CCGCCAATTG        300

CCGAACAGCC AMGCACCGTT GCCGCCAGCC CCGCCGCCGT TAACGGCGCT GCCGGGCGCC        360

GCCGCCGGAC CCGCCATTAC CGCCGTTCCC GTTCGGTGCC CCGCCGTTAC CGGCGCCGCC        420

GTTTGCCGCC AATATTCGGC GGGCACCGCC AGACCCGCCG GGGCCACCAT TGCCGCCGGG        480

CACCGAAACA ACAGCCCAAC GGTGCCGCCG GCCCCGCCGT TGCCGCCAT CACCGGCCAT         540

TCACCGCCAG CACCGCCGTT AATGTTTATG AACCCGGTAC CGCCAGCGCG GCCCCTATTG        600

CCGGGCGCCG GAGNGCGTGC CCGCCGGCGC CGCCAACGCC CAAAAGCCCG GGGTTGCCAC        660

CGGCCCCGCC GGACCCACCG GTCCCGCCGA TCCCCCCGTT GCCGCCGGTG CCGCCGCCAT        720

TGGTGCTGCT GAAGCCGTTA GCGCCGGTTC CGCSGGTTCC GGCGGTGGCG CCNTGGCCGC        780

CGGCCCCGCC GTTGCCGTAC AGCCACCCCC CGGTGGCGCC GTTGCCGCCA TTGCCGCCAT        840

TGCCGCCGTT GCCGCCATTG CCGCCGTTCC CGCCGCCACC GCCGGNTTGG CCGCCGGCGC        900

CGCCGGCGGC CGC                                                          913
```

(2) INFORMATION FOR SEQ ID NO: 17:

(i) SEQUENCE CHARACTERISTICS:
        (A) LENGTH: 1872 base pairs
        (B) TYPE: nucleic acid
        (C) STRANDEDNESS: single
        (D) TOPOLOGY: linear (xi) SEQUENCE DESCRIPTION: SEQ ID NO: 17:

```
GACTACGTTG GTGTAGAAAA ATCCTGCCGC CCGGACCCTT AAGGCTGGGA CAATTTCTGA         60

TAGCTACCCC GACACAGGAG GTTACGGGAT GAGCAATTCG CGCCGCCGCT CACTCAGGTG        120

GTCATGGTTG CTGAGCGTGC TGGCTGCCGT CGGGCTGGGC CTGGCCACGG CGCCGGCCCA        180

GGCGGCCCCG CCGGCCTTGT CGCAGGACCG GTTCGCCGAC TTCCCCGCGC TGCCCCTCGA        240

CCCGTCCGCA TGGTCGCCC AAGTGGCGCC ACAGGTGGTC AACATCAACA CCAAACTGGG         300

CTACAACAAC GCCGTGGGCG CCGGGACCGG CATCGTCATC GATCCCAACG GTGTCGTGCT        360
```

```
GACCAACAAC CACGTGATCG CGGGCGCCAC CGACATCAAT GCGTTCAGCG TCGGCTCCGG      420

CCAAACCTAC GGCGTCGATG TGGTCGGGTA TGACCGCACC CAGGATGTCG CGGTGCTGCA      480

GCTGCGCGGT GCCGGTGGCC TGCCGTCGGC GGCGATCGGT GGCGGCGTCG CGGTTGGTGA      540

GCCCGTCGTC GCGATGGGCA ACAGCGGTGG GCAGGGCGGA ACGCCCCGTG CGGTGCCTGG      600

CAGGGTGGTC GCGCTCGGCC AAACCGTGCA GGCGTCGGAT TCGCTGACCG GTGCCGAAGA      660

GACATTGAAC GGGTTGATCC AGTTCGATGC CGCAATCCAG CCCGGTGATT CGGGCGGGCC      720

CGTCGTCAAC GGCCTAGGAC AGGTGGTCGG TATGAACACG GCCGCGTCCG ATAACTTCCA      780

GCTGTCCCAG GGTGGGCAGG GATTCGCCAT TCCGATCGGG CAGGCGATGG CGATCGCGGG      840

CCAAATCCGA TCGGGTGGGG GGTCACCCAC CGTTCATATC GGGCCTACCG CCTTCCTCGG      900

CTTGGGTGTT GTCGACAACA ACGGCAACGG CGCACGAGTC CAACGCGTGG TCGGAAGCGC      960

TCCGGCGGCA AGTCTCGGCA TCTCCACCGG CGACGTGATC ACCGCGGTCG ACGGCGCTCC     1020

GATCAACTCG GCCACCGCGA TGGCGGACGC GCTTAACGGG CATCATCCCG GTGACGTCAT     1080

CTCGGTGAAC TGGCAAACCA AGTCGGGCGG CACGCGTACA GGGAACGTGA CATTGGCCGA     1140

GGGACCCCCG GCCTGATTTG TCGCGGATAC CACCCGCCGG CCGGCCAATT GGATTGGCGC     1200

CAGCCGTGAT TGCCGCGTGA GCCCCCGAGT TCCGTCTCCC GTGCGCGTGG CATTGTGGAA     1260

GCAATGAACG AGGCAGAACA CAGCGTTGAG CACCCTCCCG TGCAGGGCAG TTACGTCGAA     1320

GGCGGTGTGG TCGAGCATCC GGATGCCAAG GACTTCGGCA GCGCCGCCGC CCTGCCCGCC     1380

GATCCGACCT GGTTTAAGCA CGCCGTCTTC TACGAGGTGC TGGTCCGGGC GTTCTTCGAC     1440

GCCAGCGCGG ACGGTTCCGN CGATCTGCGT GGACTCATCG ATCGCCTCGA CTACCTGCAG     1500

TGGCTTGGCA TCGACTGCAT CTGTTGCCGC CGTTCCTACG ACTCACCGCT GCGCGACGGC     1560

GGTTACGACA TTCGCGACTT CTACAAGGTG CTGCCCGAAT TCGGCACCGT CGACGATTTC     1620

GTCGCCCTGG TCGACACCGC TCACCGGCGA GGTATCCGCA TCATCACCGA CCTGGTGATG     1680

AATCACACCT CGGAGTCGCA CCCCTGGTTT CAGGAGTCCC GCCGCGACCC AGACGGACCG     1740

TACGGTGACT ATTACGTGTG GAGCGACACC AGCGAGCGCT ACACCGACGC CCGGATCATC     1800

TTCGTCGACA CCGAAGAGTC GAACTGGTCA TTCGATCCTG TCCGCCGACA GTTNCTACTG     1860

GCACCGATTC TT                                                        1872

(2) INFORMATION FOR SEQ ID NO: 18:

(i) SEQUENCE CHARACTERISTICS:
        (A) LENGTH: 1482 base pairs
        (B) TYPE: nucleic acid
        (C) STRANDEDNESS: single
        (D) TOPOLOGY: linear (xi) SEQUENCE DESCRIPTION: SEQ ID NO: 18:

CTTCGCCGAA ACCTGATGCC GAGGAACAGG GTGTTCCCGT GAGCCCGACG GCGTCCGACC       60

CCGCGCTCCT CGCCGAGATC AGGCAGTCGC TTGATGCGAC AAAAGGGTTG ACCAGCGTGC      120

ACGTAGCGGT CCGAACAACC GGGAAAGTCG ACAGCTTGCT GGGTATTACC AGTGCCGATG      180

TCGACGTCCG GGCCAATCCG CTCGCGGCAA AGGGCGTATG CACCTACAAC GACGAGCAGG      240

GTGTCCCGTT TCGGGTACAA GGCGACAACA TCTCGGTGAA ACTGTTCGAC GACTGGAGCA      300

ATCTCGGCTC GATTTCTGAA CTGTCAACTT CACGCGTGCT CGATCCTGCC GCTGGGGTGA      360

CGCAGCTGCT GTCCGGTGTC ACGAACCTCC AAGCGCAAGG TACCGAAGTG ATAGACGGAA      420

TTTCGACCAC CAAAATCACC GGGACCATCC CCGCGAGCTC TGTCAAGATG CTTGATCCTG      480
```

```
GCGCCAAGAG TGCAAGGCCG GCGACCGTGT GGATTGCCCA GGACGGCTCG CACCACCTCG      540

TCCGAGCGAG CATCGACCTC GGATCCGGGT CGATTCAGCT CACGCAGTCG AAATGGAACG      600

AACCCGTCAA CGTCGACTAG GCCGAAGTTG CGTCGACGCG TTGCTCGAAA CGCCCTTGTG      660

AACGGTGTCA ACGGCACCCG AAAACTGACC CCCTGACGGC ATCTGAAAAT TGACCCCCTA      720

GACCGGGCGG TTGGTGGTTA TTCTTCGGTG GTTCCGGCTG GTGGGACGCG GCCGAGGTCG      780

CGGTCTTTGA GCCGGTAGCT GTCGCCTTTG AGGGCGACGA CTTCAGCATG GTGGACGAGG      840

CGGTCGATCA TGGCGGCAGC AACGACGTCG TCGCCGCCGA AAACCTCGCC CCACCGGCCG      900

AAGGCCTTAT TGGACGTGAC GATCAAGCTG GCCCGCTCAT ACCGGGAGGA CACCAGCTGG      960

AAGAAGAGGT TGGCGGCCTC GGGCTCAAAC GGAATGTAAC CGACTTCGTC AACCACCAGG     1020

AGCGGATAGC GGCCAAACCG GGTGAGTTCG GCGTAGATGC GCCCGGCGTG GTGAGCCTCG     1080

GCGAACCGTG CTACCCATTC GGCGGCGGTG GCGAACAGCA CCCGATGACC GGCCTGACAC     1140

GCGCGTATCG CCAGGCCGAC CGCAAGATGA GTCTTCCCGG TGCCAGGCGG GGCCCAAAAA     1200

CACGACGTTA TCGCGGGCGG TGATGAAATC CAGGGTGCCC AGATGTGCGA TGGTGTCGCG     1260

TTTGAGGCCA CGAGCATGCT CAAAGTCGAA CTCTTCCAAC GACTTCCGAA CCGGGAAGCG     1320

GGCGGCGCGG ATGCGGCCCT CACCACCATG GGACTCCCGG GCTGACACTT CCCGCTGCAG     1380

GCAGGCGGCC AGGTATTCTT CGTGGCTCCA GTTCTCGGCG CGGGCGCGAT CGGCCAGCCG     1440

GGACACTGAC TCACGCAGGG TGGGAGCTTT CAATGCTCTT GT                        1482

(2) INFORMATION FOR SEQ ID NO: 19:

(i) SEQUENCE CHARACTERISTICS:
        (A) LENGTH: 876 base pairs
        (B) TYPE: nucleic acid
        (C) STRANDEDNESS: single
        (D) TOPOLOGY: linear (xi) SEQUENCE DESCRIPTION: SEQ ID NO: 19:

GAATTCGGCA CGAGCCGGCG ATAGCTTCTG GGCCGCGGCC GACCAGATGG CTCGAGGGTT       60

CGTGCTCGGG GCCACCGCCG GGCGCACCAC CCTGACCGGT GAGGGCCTGC AACACGCCGA      120

CGGTCACTCG TTGCTGCTGG ACGCCACCAA CCCGGCGGTG GTTGCCTACG ACCCGGCCTT      180

CGCCTACGAA ATCGGCTACA TCGNGGAAAG CGGACTGGCC AGGATGTGCG GGGAGAACCC      240

GGAGAACATC TTCTTCTACA TCACCGTCTA CAACGAGCCG TACGTGCAGC CGCCGGAGCC      300

GGAGAACTTC GATCCCGAGG GCGTGCTGGG GGGTATCTAC CGNTATCACG CGGCCACCGA      360

GCAACGCACC AACAAGGNGC AGATCCTGGC CTCCGGGGTA GCGATGCCCG CGGCGCTGCG      420

GGCAGCACAG ATGCTGGCCG CCGAGTGGGA TGTCGCCGCC GACGTGTGGT CGGTGACCAG      480

TTGGGGCGAG CTAAACCGCG ACGGGGTGGT CATCGAGACC GAGAAGCTCC GCCACCCCGA      540

TCGGCCGGCG GGCGTGCCCT ACGTGACGAG AGCGCTGGAG AATGCTCGGG GCCCGGTGAT      600

CGCGGTGTCG GACTGGATGC GCGCGGTCCC CGAGCAGATC CGACCGTGGG TGCCGGGCAC      660

ATACCTCACG TTGGGCACCG ACGGGTTCGG TTTTTCCGAC ACTCGGCCCG CCGGTCGTCG      720

TTACTTCAAC ACCGACGCCG AATCCCAGGT TGGTCGCGGT TTTGGGAGGG GTTGGCCGGG      780

TCGACGGGTG AATATCGACC CATTCGGTGC CGGTCGTGGG CCGCCCGCCC AGTTACCCGG      840

ATTCGACGAA GGTGGGGGGT TGCGCCCGAN TAAGTT                                876

(2) INFORMATION FOR SEQ ID NO: 20:
```

(i) SEQUENCE CHARACTERISTICS:
        (A) LENGTH: 1021 base pairs
        (B) TYPE: nucleic acid
        (C) STRANDEDNESS: single
        (D) TOPOLOGY: linear (xi) SEQUENCE DESCRIPTION: SEQ ID NO: 20:

```
ATCCCCCCGG GCTGCAGGAA TTCGGCACGA GAGACAAAAT TCCACGCGTT AATGCAGGAA    60

CAGATTCATA ACGAATTCAC AGCGGCACAA CAATATGTCG CGATCGCGGT TTATTTCGAC   120

AGCGAAGACC TGCCGCAGTT GGCGAAGCAT TTTTACAGCC AAGCGGTCGA GGAACGAAAC   180

CATGCAATGA TGCTCGTGCA ACACCTGCTC GACCGCGACC TTCGTGTCGA AATTCCCGGC   240

GTAGACACGG TGCGAAACCA GTTCGACAGA CCCCGCGAGG CACTGGCGCT GGCGCTCGAT   300

CAGGAACGCA CAGTCACCGA CCAGGTCGGT CGGCTGACAG CGGTGGCCCG CGACGAGGGC   360

GATTTCCTCG GCGAGCAGTT CATGCAGTGG TTCTTGCAGG AACAGATCGA AGAGGTGGCC   420

TTGATGGCAA CCCTGGTGCG GGTTGCCGAT CGGGCCGGGG CCAACCTGTT CGAGCTAGAG   480

AACTTCGTCG CACGTGAAGT GGATGTGGCG CCGGCCGCAT CAGGCGCCCC GCACGCTGCC   540

GGGGGCCGCC TCTAGATCCC TGGGGGGGAT CAGCGAGTGG TCCCGTTCGC CCGCCCGTCT   600

TCCAGCCAGG CCTTGGTGCG GCCGGGGTGG TGAGTACCAA TCCAGGCCAC CCCGACCTCC   660

CGGNAAAAGT CGATGTCCTC GTACTCATCG ACGTTCCAGG AGTACACCGC CCGGCCCTGA   720

GCTGCCGAGC GGTCAACGAG TTGCGGATAT TCCTTTAACG CAGGCAGTGA GGGTCCCACG   780

GCGGTTGGCC CGACCGCCGT GGCCGCACTG CTGGTCAGGT ATCGGGGGGT CTTGGCGAGC   840

AACAACGTCG GCAGGAGGGG TGGAGCCCGC CGGATCCGCA GACCGGGGGG GCGAAAACGA   900

CATCAACACC GCACGGGATC GATCTGCGGA GGGGGGTGCG GGAATACCGA ACCGGTGTAG   960

GAGCGCCAGC AGTTGTTTTT CCACCAGCGA AGCGTTTTCG GGTCATCGGN GGCNNTTAAG  1020

T                                                                 1021
```

(2) INFORMATION FOR SEQ ID NO: 21:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO: 21:

```
CGTGCCGACG AACGGAAGAA CACAACCATG AAGATGGTGA AATCGATCGC CGCAGGTCTG    60

ACCGCCGCGG CTGCAATCGG CGCCGCTGCG GCCGGTGTGA CTTCGATCAT GGCTGGCGGN   120

CCGGTCGTAT ACCAGATGCA GCCGGTCGTC TTCGGCGCGC CACTGCCGTT GGACCCGGNA   180

TCCGCCCCTG ANGTCCCGAC CGCCGCCCAG TGGACCAGNC TGCTCAACAG NCTCGNCGAT   240

CCCAACGTGT CGTTTGNGAA CAAGGGNAGT CTGGTCGAGG NGGNATCGG NGGNANCGAG    300

GGNGNGNATC GNCGANCACA A                                            321
```

(2) INFORMATION FOR SEQ ID NO: 22:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (xi) SEQUENCE DESCRIPTION: SEQ ID NO: 22:

```
TCTTATCGGT TCCGGTTGGC GACGGGTTTT GGGNGCGGGT GGTTAACCCG CTCGGCCAGC    60
```

```
CGATCGACGG GCGCGGAGAC GTCGACTCCG ATACTCGGCG CGCGCTGGAG CTCCAGGCGC    120

CCTCGGTGGT GNACCGGCAA GGCGTGAAGG AGCCGTTGNA GACCGGGATC AAGGCGATTG    180

ACGCGATGAC CCCGATCGGC CGCGGGCAGC GCCAGCTGAT CATCGGGGAC CGCAAGACCG    240

GCAAAAACCG CCGTCTGTGT CGGACACCAT CCTCAAACCA GCGGGAAGAA CTGGGAGTCC    300

GGTGGATCCC AAGAAGCAGG TGCGCTTGTG TATACGTTGG CCATCGGGCA AGAAGGGGAA    360

CTTACCATCG CCG                                                       373
```

(2) INFORMATION FOR SEQ ID NO: 23:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (xi) SEQUENCE DESCRIPTION: SEQ ID NO: 23:

```
GTGACGCCGT GATGGGATTC CTGGGCGGGG CCGGTCCGCT GGCGGTGGTG GATCAGCAAC     60

TGGTTACCCG GGTGCCGCAA GGCTGGTCGT TTGCTCAGGC AGCCGCTGTG CCGGTGGTGT    120

TCTTGACGGC CTGGTACGGG TTGGCCGATT TAGCCGAGAT CAAGGCGGGC GAATCGGTGC    180

TGATCCATGC CGGTACCGGC GGTGTGGGCA TGGCGGCTGT GCAGCTGGCT CGCCAGTGGG    240

GCGTGGAGGT TTTCGTCACC GCCAGCCGTG GNAAGTGGGA CACGCTGCGC GCCATNGNGT    300

TTGACGACGA NCCATATCGG NGATTCCCNC ACATNCGAAG TTCCGANGGA GA            352
```

(2) INFORMATION FOR SEQ ID NO: 24:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (xi) SEQUENCE DESCRIPTION: SEQ ID NO: 24:

```
GAAATCCGCG TTCATTCCGT TCGACCAGCG GCTGGCGATA ATCGACGAAG TGATCAAGCC     60

GCGGTTCGCG GCGCTCATGG GTCACAGCGA GTAATCAGCA AGTTCTCTGG TATATCGCAC    120

CTAGCGTCCA GTTGCTTGCC AGATCGCTTT CGTACCGTCA TCGCATGTAC CGGTTCGCGT    180

GCCGCACGCT CATGCTGGCG GCGTGCATCC TGGCCACGGG TGTGGCGGGT CTCGGGGTCG    240

GCGCGCAGTC CGCAGCCCAA ACCGCGCCGG TGCCCGACTA CTACTGGTGC CCGGGGCAGC    300

CTTTCGACCC CGCATGGGGG CCCAACTGGG ATCCCTACAC CTGCCATGAC GACTTCCACC    360

GCGACAGCGA CGGCCCCGAC CACAGCCGCG ACTACCCCGG ACCCATCCTC GAAGGTCCCG    420

TGCTTGACGA TCCCGGTGCT GCGCCGCCGC CCCCGGCTGC CGGTGGCGGC GCATAGCGCT    480

CGTTGACCGG GCCGCATCAG CGAATACGCG TATAAACCCG GGCGTGCCCC CGGCAAGCTA    540

CGACCCCCGG CGGGGCAGAT TTACGCTCCC GTGCCGATGG ATCGCGCCGT CCGATGACAG    600

AAAATAGGCG ACGGTTTTGG CAACCGCTTG GAGGACGCTT GAAGGGAACC TGTCATGAAC    660

GGCGACAGCG CCTCCACCAT CGACATCGAC AAGGTTGTTA CCCGCACACC CGTTCGCCGG    720

ATCGTG                                                               726
```

(2) INFORMATION FOR SEQ ID NO: 25:

(i) SEQUENCE CHARACTERISTICS:
        (A) LENGTH: 580 base pairs
        (B) TYPE: nucleic acid (C) STRANDEDNESS: single
        (D) TOPOLOGY: linear (xi) SEQUENCE DESCRIPTION: SEQ ID NO: 25:

CGCGACGACG ACGAACGTCG GGCCCACCAC CGCCTATGCG TTGATGCAGG CGACCGGGAT        60

GGTCGCCGAC CATATCCAAG CATGCTGGGT GCCCACTGAG CGACCTTTTG ACCAGCCGGG       120

CTGCCCGATG GCGGCCCGGT GAAGTCATTG CGCCGGGGCT TGTGCACCTG ATGAACCCGA       180

ATAGGGAACA ATAGGGGGGT GATTTGGCAG TTCAATGTCG GGTATGGCTG GAAATCCAAT       240

GGCGGGGCAT GCTCGGCGCC GACCAGGCTC GCGCAGGCGG GCCAGCCCGA ATCTGGAGGG       300

AGCACTCAAT GGCGGCGATG AAGCCCCGGA CCGGCGACGG TCCTTTGGAA GCAACTAAGG       360

AGGGGCGCGG CATTGTGATG CGAGTACCAC TTGAGGGTGG CGGTCGCCTG GTCGTCGAGC       420

TGACACCCGA CGAAGCCGCC GCACTGGGTG ACGAACTCAA AGGCGTTACT AGCTAAGACC       480

AGCCCAACGG CGAATGGTCG GCGTTACGCG CACACCTTCC GGTAGATGTC CAGTGTCTGC       540

TCGGCGATGT ATGCCCAGGA GAACTCTTGG ATACAGCGCT                            580

(2) INFORMATION FOR SEQ ID NO: 26:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (xi) SEQUENCE DESCRIPTION: SEQ ID NO: 26:

AACGGAGGCG CCGGGGGTTT TGGCGGGGCC GGGGCGGTCG GCGGCAACGG CGGGGCCGGC        60

GGTACCGCCG GGTTGTTCGG TGTCGGCGGG GCCGGTGGGG CCGGAGGCAA CGGCATCGCC       120

GGTGTCACGG GTACGTCGGC CAGCACACCG GGTGGATCCG                            160

(2) INFORMATION FOR SEQ ID NO: 27:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (xi) SEQUENCE DESCRIPTION: SEQ ID NO: 27:

GACACCGATA CGATGGTGAT GTACGCCAAC GTTGTCGACA CGCTCGAGGC GTTCACGATC        60

CAGCGCACAC CCGACGGCGT GACCATCGGC GATGCGGCCC CGTTCGCGGA GGCGGCTGCC       120

AAGGCGATGG GAATCGACAA GCTGCGGGTA ATTCATACCG GAATGGACCC CGTCGTCGCT       180

GAACGCGAAC AGTGGGACGA CGGCAACAAC ACGTTGGCGT TGGCGCCCGG TGTCGTTGTC       240

GCCTACGAGC GCAACGTACA GACCAACGCC CG                                    272

(2) INFORMATION FOR SEQ ID NO: 28:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (xi) SEQUENCE DESCRIPTION: SEQ ID NO: 28:

GCAGCCGGTG TTCTCGGAC TATCTGCGCA CGGTGACGCA GCGCGACGTG CGCGAGCTGA         60

AGCGGATCGA GCAGACGGAT CGCCTGCCGC GGTTCATGCG CTACCTGGCC GCTATCACCG       120

CGCAGGAGCT GAACGTGGCC GAAGCGGCGC GGGTCATCGG GGTCGACGCG GGGACGATCC       180

```
GTTCGGATCT GGCGTGGTTC GAGACGGTCT ATCTGGTACA TCGCCTGCCC GCCTGGTCGC      240

GGAATCTGAC CGCGAAGATC AAGAAGCGGT CAAAGATCCA CGTCGTCGAC AGTGGCTTCG      300

CGGCCTGGTT GCGCGGG                                                    317

(2) INFORMATION FOR SEQ ID NO: 29:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (xi) SEQUENCE DESCRIPTION: SEQ ID NO: 29:

GATCGTGGAG CTGTCGATGA ACAGCGTTGC CGGACGCGCG GCGGCCAGCA CGTCGGTGTA       60

GCAGCGCCGG ACCACCTCGC CGGTGGGCAG CATGGTGATG ACCACGTCGG CCTCGGCCAC      120

CGCTTCGGGC GCGCTACGAA ACACCGCGAC ACCGTGCGCG GCGGCGCCGG ACGCCGCCGT      180

GG                                                                    182

(2) INFORMATION FOR SEQ ID NO: 30:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (xi) SEQUENCE DESCRIPTION: SEQ ID NO: 30:

GATCGCGAAG TTTGGTGAGC AGGTGGTCGA CGCGAAAGTC TGGGCGCCTG CGAAGCGGGT       60

CGGCGTTCAC GAGGCGAAGA CACGCCTGTC CGAGCTGCTG CGGCTCGTCT ACGGCGGGCA      120

GAGGTTGAGA TTGCCCGCCG CGGCGAGCCG GTAGCAAAGC TTGTGCCGCT GCATCCTCAT      180

GAGACTCGGC GGTTAGGCAT TGACCATGGC GTGTACCGCG TGCCCGACGA TTTGGACGCT      240

CCGTTGTCAG ACGACGTGCT CGAACGCTTT CACCGGTGAA GCGCTACCTC ATCGACACCC      300

ACGTTTGG                                                              308

(2) INFORMATION FOR SEQ ID NO: 31:

(i) SEQUENCE CHARACTERISTICS:
        (A) LENGTH: 267 base pairs
        (B) TYPE: nucleic acid
        (C) STRANDEDNESS: single
        (D) TOPOLOGY: linear (xi) SEQUENCE DESCRIPTION: SEQ ID NO: 31:

CCGACGACGA GCAACTCACG TGGATGATGG TCGGCAGCGG CATTGAGGAC GGAGAGAATC       60

CGGCCGAAGC TGCCGCGCGG CAAGTGCTCA TAGTGACCGG CCGTAGAGGG CTCCCCCGAT      120

GGCACCGGAC TATTCTGGTG TGCCGCTGGC CGGTAAGAGC GGGTAAAAGA ATGTGAGGGG      180

ACACGATGAG CAATCACACC TACCGAGTGA TCGAGATCGT CGGGACCTCG CCCGACGGCG      240

TCGACGCGGC AATCCAGGGC GGTCTGG                                         267

(2) INFORMATION FOR SEQ ID NO: 32:

(i) SEQUENCE CHARACTERISTICS:
        (A) LENGTH: 1539 base pairs
        (B) TYPE: nucleic acid
        (C) STRANDEDNESS: single
        (D) TOPOLOGY: linear
```

(xi) SEQUENCE DESCRIPTION: SEQ ID NO: 32:

| | | | | | |
|---|---|---|---|---|---|
| CTCGTGCCGA | AAGAATGTGA | GGGGACACGA | TGAGCAATCA | CACCTACCGA | GTGATCGAGA | 60 |
| TCGTCGGGAC | CTCGCCCGAC | GGCGTCGACG | CGGCAATCCA | GGGCGGTCTG | GCCCGAGCTG | 120 |
| CGCAGACCAT | GCGCGCGCTG | GACTGGTTCG | AAGTACAGTC | AATTCGAGGC | CACCTGGTCG | 180 |
| ACGGAGCGGT | CGCGCACTTC | CAGGTGACTA | TGAAAGTCGG | CTTCCGCTGG | AGGATTCCTG | 240 |
| AACCTTCAAG | CGCGGCCGAT | AACTGAGGTG | CATCATTAAG | CGACTTTTCC | AGAACATCCT | 300 |
| GACGCGCTCG | AAACGCGGTT | CAGCCGACGG | TGGCTCCGCC | GAGGCGCTGC | CTCCAAAATC | 360 |
| CCTGCGACAA | TTCGTCGGCG | GCGCCTACAA | GGAAGTCGGT | GCTGAATTCG | TCGGGTATCT | 420 |
| GGTCGACCTG | TGTGGGCTGC | AGCCGGACGA | AGCGGTGCTC | GACGTCGGCT | GCGGCTCGGG | 480 |
| GCGGATGGCG | TTGCCGCTCA | CCGGCTATCT | GAACAGCGAG | GGACGCTACG | CCGGCTTCGA | 540 |
| TATCTCGCAG | AAAGCCATCG | CGTGGTGCCA | GGAGCACATC | ACCTCGGCGC | ACCCCAACTT | 600 |
| CCAGTTCGAG | GTCTCCGACA | TCTACAACTC | GCTGTACAAC | CCGAAAGGGA | AATACCAGTC | 660 |
| ACTAGACTTT | CGCTTTCCAT | ATCCGGATGC | GTCGTTCGAT | GTGGTGTTTC | TTACCTCGGT | 720 |
| GTTCACCCAC | ATGTTTCCGC | CGGACGTGGA | GCACTATCTG | GACGAGATCT | CCCGCGTGCT | 780 |
| GAAGCCCGGC | GGACGATGCC | TGTGCACGTA | CTTCTTGCTC | AATGACGAGT | CGTTAGCCCA | 840 |
| CATCGCGGAA | GGAAAGAGTG | CGCACAACTT | CCAGCATGAG | GGACCGGGTT | ATCGGACAAT | 900 |
| CCACAAGAAG | CGGCCCGAAG | AAGCAATCGG | CTTGCCGGAG | ACCTTCGTCA | GGGATGTCTA | 960 |
| TGGCAAGTTC | GGCCTCGCCG | TGCACGAACC | ATTGCACTAC | GGCTCATGGA | GTGGCCGGGA | 1020 |
| ACCACGCCTA | AGCTTCCAGG | ACATCGTCAT | CGCGACCAAA | ACCGCGAGCT | AGGTCGGCAT | 1080 |
| CCGGGAAGCA | TCGCGACACC | GTGGCGCCGA | GCGCCGCTGC | CGGCAGGCCG | ATTAGGCGGG | 1140 |
| CAGATTAGCC | CGCCGCGGCT | CCCGGCTCCG | AGTACGGCGC | CCCGAATGGC | GTCACCGGCT | 1200 |
| GGTAACCACG | CTTGCGCGCC | TGGGCGGCGG | CCTGCCGGAT | CAGGTGGTAG | ATGCCGACAA | 1260 |
| AGCCTGCGTG | ATCGGTCATC | ACCAACGGTG | ACAGCAGCCG | GTTGTGCACC | AGCGCGAACG | 1320 |
| CCACCCCGGT | CTCCGGGTCT | GTCCAGCCGA | TCGAGCCGCC | CAAGCCCACA | TGACCAAACC | 1380 |
| CCGGCATCAC | GTTGCCGATC | GGCATACCGT | GATAGCCAAG | ATGAAAATTT | AAGGGCACCA | 1440 |
| ATAGATTTCG | ATCCGGCAGA | ACTTGCCGTC | GGTTGCGGGT | CAGGCCCGTG | ACCAGCTCCC | 1500 |
| GCGACAAGAA | CCGTATGCCG | TCGATCTCGC | CTCGTGCCG | | | 1539 |

(2) INFORMATION FOR SEQ ID NO: 33:

(i) SEQUENCE CHARACTERISTICS:
        (A) LENGTH: 851 base pairs
        (B) TYPE: nucleic acid
        (C) STRANDEDNESS: single
        (D) TOPOLOGY: linear (xi) SEQUENCE DESCRIPTION: SEQ ID NO: 33:

| | | | | | |
|---|---|---|---|---|---|
| CTGCAGGGTG | GCGTGGATGA | GCGTCACCGC | GGGGCAGGCC | GAGCTGACCG | CCGCCCAGGT | 60 |
| CCGGGTTGCT | GCGGCGGCCT | ACGAGACGGC | GTATGGGCTG | ACGGTGCCCC | CGCCGGTGAT | 120 |
| CGCCGAGAAC | CGTGCTGAAC | TGATGATTCT | GATAGCGACC | AACCTCTTGG | GGCAAAACAC | 180 |
| CCCGGCGATC | GCGGTCAACG | AGGCCGAATA | CGGCGAGATG | TGGGCCCAAG | ACGCCGCCGC | 240 |
| GATGTTTGGC | TACGCCGCGG | CGACGGCGAC | GGCGACGGCG | ACGTTGCTGC | CGTTCGAGGA | 300 |
| GGCGCCGGAG | ATGACCAGCG | CGGGTGGGCT | CCTCGAGCAG | GCCGCCGCGG | TCGAGGAGGC | 360 |
| CTCCGACACC | GCCGCGGCGA | ACCAGTTGAT | GAACAATGTG | CCCCAGGCGC | TGAAACAGTT | 420 |

```
GGCCCAGCCC ACGCAGGGCA CCACGCCTTC TTCCAAGCTG GGTGGCCTGT GGAAGACGGT       480

CTCGCCGCAT CGGTCGCCGA TCAGCAACAT GGTGTCGATG GCCAACAACC ACATGTCGAT       540

GACCAACTCG GGTGTGTCGA TGACCAACAC CTTGAGCTCG ATGTTGAAGG CTTTGCTCC        600

GGCGGCGGCC GCCCAGGCCG TGCAAACCGC GGCGCAAAAC GGGGTCCGGG CGATGAGCTC       660

GCTGGGCAGC TCGCTGGGTT CTTCGGGTCT GGGCGGTGGG GTGGCCGCCA ACTTGGGTCG       720

GGCGGCCTCG GTACGGTATG GTCACCGGGA TGGCGGAAAA TATGCANAGT CTGGTCGGCG       780

GAACGGTGGT CCGGCGTAAG GTTTACCCCC GTTTTCTGGA TGCGGTGAAC TTCGTCAACG       840

GAAACAGTTA C                                                           851

(2) INFORMATION FOR SEQ ID NO: 34:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (xi) SEQUENCE DESCRIPTION: SEQ ID NO: 34:

GATCGATCGG GCGGAAATTT GGACCAGATT CGCCTCCGGC GATAACCCAA TCAATCGAAC        60

CTAGATTTAT TCCGTCCAGG GGCCCGAGTA ATGGCTCGCA GGAGAGGAAC CTTACTGCTG       120

CGGGCACCTG TCGTAGGTCC TCGATACGGC GGAAGGCGTC GACATTTTCC ACCGACACCC       180

CCATCCAAAC GTTCGAGGGC CACTCCAGCT TGTGAGCGAG GCGACGCAGT CGCAGGCTGC       240

GCTTGGTCAA GATC                                                        254

(2) INFORMATION FOR SEQ ID NO: 35:

(i) SEQUENCE CHARACTERISTICS:
        (A) LENGTH: 1227 base pairs
        (B) TYPE: nucleic acid
        (C) STRANDEDNESS: single
        (D) TOPOLOGY: linear (xi) SEQUENCE DESCRIPTION: SEQ ID NO: 35:

GATCCTGACC GAAGCGGCCG CCGCCAAGGC GAAGTCGCTG TTGGACCAGG AGGGACGGGA        60

CGATCTGGCG CTGCGGATCG CGGTTCAGCC GGGGGGGTGC GCTGGATTGC GCTATAACCT       120

TTTCTTCGAC GACCGGACGC TGGATGGTGA CCAAACCGCG GAGTTCGGTG GTGTCAGGTT       180

GATCGTGGAC CGGATGAGCG CGCCGTATGT GGAAGGCGCG TCGATCGATT TCGTCGACAC       240

TATTGAGAAG CAAGGTTCAC CATCGACAAT CCCAACGCCA CCGGCTCCTG CGCGTGCGGG       300

GATTCGTTCA ACTGATAAAA CGCTAGTACG ACCCCGCGGT GCGCAACACG TACGAGCACA       360

CCAAGACCTG ACCGCGCTGG AAAAGCAACT GAGCGATGCC TTGCACCTGA CCGCGTGGCG       420

GGCCGCCGGC GGCAGGTGTC ACCTGCATGG TGAACAGCAC CTGGGCCTGA TATTGCGACC       480

AGTACACGAT TTTGTCGATC GAGGTCACTT CGACCTGGGA GAACTGCTTG CGGAACGCGT       540

CGCTGCTCAG CTTGGCCAAG GCCTGATCGG AGCGCTTGTC GCGCACGCCG TCGTGGATAC       600

CGCACAGCGC ATTGCGAACG ATGGTGTCCA CATCGCGGTT CTCCAGCGCG TTGAGGTATC       660

CCTGAATCGC GGTTTTGGCC GGTCCCTCCG AGAATGTGCC TGCCGTGTTG GCTCCGTTGG       720

TGCGGACCCC GTATATGATC GCCGCCGTCA TAGCCGACAC CAGCGCGAGG GCTACCACAA       780

TGCCGATCAG CAGCCGCTTG TGCCGTCGCT TCGGGTAGGA CACCTGCGGC GGCACGCCGG       840

GATATGCGGC GGGCGGCAGC GCCGCGTCGT CTGCCGGTCC CGGGGCGAAG GCCGGTTCGG       900

CGGCGCCGAG GTCGTGGGGG TAGTCCAGGG CTTGGGGTTC GTGGGATGAG GGCTCGGGGT       960
```

```
ACGGCGCCGG TCCGTTGGTG CCGACACCGG GGTTCGGCGA GTGGGACCG  GGCATTGTGG    1020

TTCTCCTAGG GTGGTGGACG GGACCAGCTG CTAGGGCGAC AACCGCCCGT CGCGTCAGCC    1080

GGCAGCATCG GCAATCAGGT GAGCTCCCTA GGCAGGCTAG CGCAACAGCT GCCGTCAGCT    1140

CTCAACGCGA CGGGGCGGGC CGCGGCGCCG ATAATGTTGA AAGACTAGGC AACCTTAGGA    1200

ACGAAGGACG GAGATTTTGT GACGATC                                       1227
```

(2) INFORMATION FOR SEQ ID NO: 36:

(i) SEQUENCE CHARACTERISTICS:
        (A) LENGTH: 181 base pairs
        (B) TYPE: nucleic acid
        (C) STRANDEDNESS: single
        (D) TOPOLOGY: linear (xi) SEQUENCE DESCRIPTION: SEQ ID NO: 36:

```
GCGGTGTCGG CGGATCCGGC GGGTGGTTGA ACGGCAACGG CGGGGCCGGC GGGGCCGGCG     60

GGACCGGCGC TAACGGTGGT GCCGGCGGCA ACGCCTGGTT GTTCGGGGCC GGCGGGTCCG    120

GCGGNGCCGG CACCAATGGT GGNGTCGGCG GGTCCGGCGG ATTTGTCTAC GGCAACGGCG    180

G                                                                   181
```

(2) INFORMATION FOR SEQ ID NO: 37:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (xi) SEQUENCE DESCRIPTION: SEQ ID NO: 37:

```
GCGGTGTCGG CGGATCCGGC GGGTGGTTGA ACGGCAACGG CGGTGTCGGC GGCCGGGGCG     60

GCGACGGCGT CTTTGCCGGT GCCGGCGGCC AGGGCGGCCT CGGTGGGCAG GGCGGCAATG    120

GCGGCGGCTC CACCGGCGGC AACGGCGGTC TTGGCGGCGC GGGCGGTGGC GGAGGCAACG    180

CCCCGGACGG CGGCTTCGGT GGCAACGGCG GTAAGGGTGG CCAGGGCGGN ATTGGCGGCG    240

GCACTCAGAG CGCGACCGGC CTCGGNGGTG ACGGCGGTGA CGGCGGTGAC               290
```

(2) INFORMATION FOR SEQ ID NO: 38:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 38:

```
GATCCAGTGG CATGGNGGGT GTCAGTGGAA GCAT                                 34
```

(2) INFORMATION FOR SEQ ID NO: 39:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (xi) SEQUENCE DESCRIPTION: SEQ ID NO: 39:

```
GATCGCTGCT CGTCCCCCCC TTGCCGCCGA CGCCACCGGT CCCACCGTTA CCGAACAAGC     60

TGGCGTGGTC GCCAGCACCC CCGGCACCGC CGACGCCGGA GTCGAACAAT GGCACCGTCG    120
```

TATCCCCACC ATTGCCGCCG GNCCCACCGG CACCG     155

(2) INFORMATION FOR SEQ ID NO: 40:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO: 40:

ATGGCGTTCA CGGGGCGCCG GGGACCGGGC AGCCCGGNGG GGCCGGGGGG TGG     53

(2) INFORMATION FOR SEQ ID NO: 41:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (xi) SEQUENCE DESCRIPTION: SEQ ID NO: 41:

GATCCACCGC GGGTGCAGAC GGTGCCCGCG GCGCCACCCC GACCAGCGGC GGCAACGGCG     60

GCACCGGCGG CAACGGCGCG AACGCCACCG TCGTCGGNGG GGCCGGCGGG GCCGGCGGCA     120

AGGGCGGCAA CG     132

(2) INFORMATION FOR SEQ ID NO: 42:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (xi) SEQUENCE DESCRIPTION: SEQ ID NO: 42:

GATCGGCGGC CGGNACGGNC GGGGACGGCG GCAAGGGCGG NAACGGGGGC GCCGNAGCCA     60

CCNGCCAAGA ATCCTCCGNG TCCNCCAATG GCGCGAATGG CGGACAGGGC GGCAACGGCG     120

GCANCGGCGG CA     132

(2) INFORMATION FOR SEQ ID NO: 43:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (xi) SEQUENCE DESCRIPTION: SEQ ID NO: 43:

CGGCACGAGG ATCGGTACCC CGCGGCATCG GCAGCTGCCG ATTCGCCGGG TTTCCCCACC     60

CGAGGAAAGC CGCTACCAGA TGGCGCTGCC GAAGTAGGGC GATCCGTTCG CGATGCCGGC     120

ATGAACGGGC GGCATCAAAT TAGTGCAGGA ACCTTTCAGT TTAGCGACGA TAATGGCTAT     180

AGCACTAAGG AGGATGATCC GATATGACGC AGTCGCAGAC CGTGACGGTG GATCAGCAAG     240

AGATTTTGAA CAGGGCCAAC GAGGTGGAGG CCCCGATGGC GGACCCACCG ACTGATGTCC     300

CCATCACACC GTGCGAACTC ACGGNGGNTA AAAACGCCGC CAACAGNTG GTNTTGTCCG     360

CCGACAACAT GCGGGAATAC CTGGCGGCCG GTGCCAAAGA GCGGCAGCGT CTGGCGACCT     420

CGCTGCGCAA CGCGGCCAAG GNGTATGGCG AGGTTGATGA GGAGGCTGCG ACCGCGCTGG     480

ACAACGACGG CGAAGGAACT GTGCAGGCAG AATCGGCCGG GGCCGTCGGA GGGGACAGTT     540

CGGCCGAACT AACCGATACG CCGAGGGTGG CCACGGCCGG TGAACCCAAC TTCATGGATC     600

```
TCAAAGAAGC GGCAAGGAAG CTCGAAACGG GCGACCAAGG CGCATCGCTC GCGCACTGNG        660

GGGATGGGTG AACACTTNC ACCCTGACGC TGCAAGGCGA CG                            702

(2) INFORMATION FOR SEQ ID NO: 44:

(i) SEQUENCE CHARACTERISTICS:
        (A) LENGTH: 298 base pairs
        (B) TYPE: nucleic acid
        (C) STRANDEDNESS: single
        (D) TOPOLOGY: linear (xi) SEQUENCE DESCRIPTION: SEQ ID NO: 44:

GAAGCCGCAG CGCTGTCGGG CGACGTGGCG GTCAAAGCGG CATCGCTCGG TGGCGGTGGA         60

GGCGGCGGGG TGCCGTCGGC GCCGTTGGGA TCCGCGATCG GGGGCGCCGA ATCGGTGCGG        120

CCCGCTGGCG CTGGTGACAT TGCCGGCTTA GGCCAGGGAA GGGCCGGCGG CGGCGCCGCG        180

CTGGGCGGCG GTGGCATGGG AATGCCGATG GGTGCCGCGC ATCAGGGACA AGGGGCGCC        240

AAGTCCAAGG GTTCTCAGCA GGAAGACGAG GCGCTCTACA CCGAGGATCC TCGTGCCG         298

(2) INFORMATION FOR SEQ ID NO: 45:

(i) SEQUENCE CHARACTERISTICS:
        (A) LENGTH: 1058 base pairs
        (B) TYPE: nucleic acid
        (C) STRANDEDNESS: single
        (D) TOPOLOGY: linear (xi) SEQUENCE DESCRIPTION: SEQ ID NO: 45:

CGGCACGAGG ATCGAATCGC GTCGCCGGGA GCACAGCGTC GCACTGCACC AGTGGAGGAG         60

CCATGACCTA CTCGCCGGGT AACCCCGGAT ACCCGCAAGC GCAGCCCGCA GGCTCCTACG        120

GAGGCGTCAC ACCCTCGTTC GCCCACGCCG ATGAGGGTGC GAGCAAGCTA CCGATGTACC        180

TGAACATCGC GGTGGCAGTG CTCGGTCTGG CTGCGTACTT CGCCAGCTTC GGCCCAATGT        240

TCACCCTCAG TACCGAACTC GGGGGGGGTG ATGGCGCAGT GTCCGGTGAC ACTGGGCTGC        300

CGGTCGGGGT GGCTCTGCTG GCTGCGCTGC TTGCCGGGGT GGTTCTGGTG CCTAAGGCCA        360

AGAGCCATGT GACGGTAGTT GCGGTGCTCG GGGTACTCGG CGTATTTCTG ATGGTCTCGG        420

CGACGTTTAA CAAGCCCAGC GCCTATTCGA CCGGTTGGGC ATTGTGGGTT GTGTTGGCTT        480

TCATCGTGTT CCAGGCGGTT GCGGCAGTCC TGGCGCTCTT GGTGGAGACC GGCGCTATCA        540

CCGCGCCGGC GCCGCGGCCC AAGTTCGACC CGTATGGACA GTACGGGCGG TACGGGCAGT        600

ACGGGCAGTA CGGGGTGCAG CCGGGTGGGT ACTACGGTCA GCAGGGTGCT CAGCAGGCCG        660

CGGGACTGCA GTCGCCCGGC CCGCAGCAGT CTCCGCAGCC TCCCGGATAT GGGTCGCAGT        720

ACGGCGGCTA TTCGTCCAGT CCGAGCCAAT CGGGCAGTGG ATACACTGCT CAGCCCCCGG        780

CCCAGCCGCC GGCGCAGTCC GGGTCGCAAC AATCGCACCA GGGCCCATCC ACGCCACCTA        840

CCGGCTTTCC GAGCTTCAGC CCACCACCAC CGGTCAGTGC CGGGACGGGG TCGCAGGCTG        900

GTTCGGCTCC AGTCAACTAT TCAAACCCCA GCGGGGGCGA GCAGTCGTCG TCCCCCGGGG        960

GGGCGCCGGT CTAACCGGGC GTTCCCGCGT CCGGTCGCGC GTGTGCGCGA AGAGTGAACA       1020

GGGTGTCAGC AAGCGCGGAC GATCCTCGTG CCGAATTC                               1058

(2) INFORMATION FOR SEQ ID NO: 46:

(i) SEQUENCE CHARACTERISTICS:
        (A) LENGTH: 327 base pairs
        (B) TYPE: nucleic acid
```

```
        (C) STRANDEDNESS: single
        (D) TOPOLOGY: linear (xi) SEQUENCE DESCRIPTION: SEQ ID NO: 46:

CGGCACGAGA GACCGATGCC GCTACCCTCG CGCAGGAGGC AGGTAATTTC GAGCGGATCT      60

CCGGCGACCT GAAAACCCAG ATCGACCAGG TGGAGTCGAC GGCAGGTTCG TTGCAGGGCC     120

AGTGGCGCGG CGCGGCGGGG ACGGCCGCCC AGGCCGCGGT GGTGCGCTTC CAAGAAGCAG     180

CCAATAAGCA GAAGCAGGAA CTCGACGAGA TCTCGACGAA TATTCGTCAG GCCGGCGTCC     240

AATACTCGAG GGCCGACGAG GAGCAGCAGC AGGCGCTGTC CTCGCAAATG GGCTTCTGAC     300

CCGCTAATAC GAAAAGAAAC GGAGCAA                                        327

(2) INFORMATION FOR SEQ ID NO: 47:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (xi) SEQUENCE DESCRIPTION: SEQ ID NO: 47:

CGGTCGCGAT GATGGCGTTG TCGAACGTGA CCGATTCTGT ACCGCCGTCG TTGAGATCAA      60

CCAACAACGT GTTGGCGTCG GCAAATGTGC CGNACCCGTG GATCTCGGTG ATCTTGTTCT     120

TCTTCATCAG GAAGTGCACA CCGGCCACCC TGCCCTCGGN TACCTTTCGG                170

(2) INFORMATION FOR SEQ ID NO: 48:

(i) SEQUENCE CHARACTERISTICS:
        (A) LENGTH: 127 base pairs
        (B) TYPE: nucleic acid
        (C) STRANDEDNESS: single
        (D) TOPOLOGY: linear (xi) SEQUENCE DESCRIPTION: SEQ ID NO: 48:

GATCCGGCGG CACGGGGGGT GCCGGCGGCA GCACCGCTGG CGCTGGCGGC AACGGCGGGG      60

CCGGGGGTGG CGGCGGAACC GGTGGGTTGC TCTTCGGCAA CGGCGGTGCC GGCGGGCACG     120

GGGCCGT                                                              127

(2) INFORMATION FOR SEQ ID NO: 49:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO: 49:

CGGCGGCAAG GCGGCACCG CCGGCAACGG GAGCGGCGCG GCCGGCGGCA ACGGCGGCAA       60

CGGCGGCTCC GGCCTCAACG G                                               81

(2) INFORMATION FOR SEQ ID NO: 50:

(i) SEQUENCE CHARACTERISTICS:
        (A) LENGTH: 149 base pairs
        (B) TYPE: nucleic acid
        (C) STRANDEDNESS: single
        (D) TOPOLOGY: linear (xi) SEQUENCE DESCRIPTION: SEQ ID NO: 50:

GATCAGGGCT GGCCGGCTCC GGCCAGAAGG GCGGTAACGG AGGAGCTGCC GGATTGTTTG      60
```

```
GCAACGGCGG GGCCGGNGGT GCCGGCGCGT CCAACCAAGC CGGTAACGGC GGNGCCGGCG        120

GAAACGGTGG TGCCGGTGGG CTGATCTGG                                         149
```

(2) INFORMATION FOR SEQ ID NO: 51:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (xi) SEQUENCE DESCRIPTION: SEQ ID NO: 51:

```
CGGCACGAGA TCACACCTAC CGAGTGATCG AGATCGTCGG GACCTCGCCC GACGGTGTCG         60

ACGCGGNAAT CCAGGGCGGT CTGGCCCGAG CTGCGCAGAC CATGCGCGCG CTGGACTGGT        120

TCGAAGTACA GTCAATTCGA GGCCACCTGG TCGACGGAGC GGTCGCGCAC TTCCAGGTGA        180

CTATGAAAGT CGGCTTCCGC CTGGAGGATT CCTGAACCTT CAAGCGCGGC CGATAACTGA        240

GGTGCATCAT TAAGCGACTT TTCCAGAACA TCCTGACGCG CTCGAAACGC GGTTCAGCCG        300

ACGGTGGCTC CGCCGAGGCG CTGCCTCCAA AATCCCTGCG ACAATTCGTC GGCGG            355
```

(2) INFORMATION FOR SEQ ID NO: 52:

(i) SEQUENCE CHARACTERISTICS:
        (A) LENGTH: 999 base pairs
        (B) TYPE: nucleic acid
        (C) STRANDEDNESS: single
        (D) TOPOLOGY: linear (xi) SEQUENCE DESCRIPTION: SEQ ID NO: 52:

```
ATGCATCACC ATCACCATCA CATGCATCAG GTGGACCCCA ACTTGACACG TCGCAAGGGA         60

CGATTGGCGG CACTGGCTAT CGCGGCGATG GCCAGCGCCA GCCTGGTGAC CGTTGCGGTG        120

CCCGCGACCG CCAACGCCGA TCCGGAGCCA GCGCCCCCGG TACCCACAAC GGCCGCCTCG        180

CCGCCGTCGA CCGCTGCAGC GCCACCCGCA CCGGCGACAC CTGTTGCCCC CCCACCACCG        240

GCCGCCGCCA ACACGCCGAA TGCCCAGCCG GGCGATCCCA ACGCAGCACC TCCGCCGGCC        300

GACCCGAACG CACCGCCGCC ACCTGTCATT GCCCCAAACG CACCCCAACC TGTCCGGATC        360

GACAACCCGG TTGGAGGATT CAGCTTCGCG CTGCCTGCTG GCTGGGTGGA GTCTGACGCC        420

GCCCACTTCG ACTACGGTTC AGCACTCCTC AGCAAAACCA CCGGGGACCC GCCATTTCCC        480

GGACAGCCGC CGCCGGTGGC CAATGACACC CGTATCGTGC TCGGCCGGCT AGACCAAAAG        540

CTTTACGCCA GCGCCGAAGC CACCGACTCC AAGGCCGCGG CCCGGTTGGG CTCGGACATG        600

GGTGAGTTCT ATATGCCCTA CCCGGGCACC CGGATCAACC AGGAAACCGT CTCGCTCGAC        660

GCCAACGGGG TGTCTGGAAG CGCGTCGTAT TACGAAGTCA AGTTCAGCGA TCCGAGTAAG        720

CCGAACGGCC AGATCTGGAC GGGCGTAATC GGCTCGCCCG CGGCGAACGC ACCGGACGCC        780

GGGCCCCCTC AGCGCTGGTT TGTGGTATGG CTCGGGACCG CCAACAACCC GGTGGACAAG        840

GGCGCGGCCA AGGCGCTGGC CGAATCGATC CGGCCTTTGG TCGCCCCGCC GCCGGCGCCG        900

GCACCGGCTC CTGCAGAGCC CGCTCCGGCG CCGGCGCCGG CCGGGAAGT CGCTCCTACC        960

CCGACGACAC CGACACCGCA GCGGACCTTA CCGGCCTGA                              999
```

(2) INFORMATION FOR SEQ ID NO: 53:

(i) SEQUENCE CHARACTERISTICS:
        (A) LENGTH: 332 amino acids
        (B) TYPE: amino acid
        (C) STRANDEDNESS: single (D) TOPOLOGY: linear (xi) SEQUENCE DESCRIPTION: SEQ ID NO: 53:

```
Met His His His His His Met His Gln Val Asp Pro Asn Leu Thr
1               5                   10                  15

Arg Arg Lys Gly Arg Leu Ala Ala Leu Ala Ile Ala Ala Met Ala Ser
                20                  25                  30

Ala Ser Leu Val Thr Val Ala Val Pro Ala Thr Ala Asn Ala Asp Pro
            35                  40                  45

Glu Pro Ala Pro Pro Val Pro Thr Thr Ala Ala Ser Pro Pro Ser Thr
    50                  55                  60

Ala Ala Ala Pro Pro Ala Pro Ala Thr Pro Val Ala Pro Pro Pro
65                  70                  75                  80

Ala Ala Ala Asn Thr Pro Asn Ala Gln Pro Gly Asp Pro Asn Ala Ala
                85                  90                  95

Pro Pro Pro Ala Asp Pro Asn Ala Pro Pro Pro Val Ile Ala Pro
                100                 105                 110

Asn Ala Pro Gln Pro Val Arg Ile Asp Asn Pro Val Gly Gly Phe Ser
                115                 120                 125

Phe Ala Leu Pro Ala Gly Trp Val Glu Ser Asp Ala Ala His Phe Asp
    130                 135                 140

Tyr Gly Ser Ala Leu Leu Ser Lys Thr Thr Gly Asp Pro Pro Phe Pro
145                 150                 155                 160

Gly Gln Pro Pro Val Ala Asn Asp Thr Arg Ile Val Leu Gly Arg
                165                 170                 175

Leu Asp Gln Lys Leu Tyr Ala Ser Ala Glu Ala Thr Asp Ser Lys Ala
            180                 185                 190

Ala Ala Arg Leu Gly Ser Asp Met Gly Glu Phe Tyr Met Pro Tyr Pro
            195                 200                 205

Gly Thr Arg Ile Asn Gln Glu Thr Val Ser Leu Asp Ala Asn Gly Val
    210                 215                 220

Ser Gly Ser Ala Ser Tyr Tyr Glu Val Lys Phe Ser Asp Pro Ser Lys
225                 230                 235                 240

Pro Asn Gly Gln Ile Trp Thr Gly Val Ile Gly Ser Pro Ala Ala Asn
                245                 250                 255

Ala Pro Asp Ala Gly Pro Pro Gln Arg Trp Phe Val Val Trp Leu Gly
                260                 265                 270

Thr Ala Asn Asn Pro Val Asp Lys Gly Ala Ala Lys Ala Leu Ala Glu
        275                 280                 285

Ser Ile Arg Pro Leu Val Ala Pro Pro Ala Pro Ala Pro Ala Pro
290                 295                 300

Ala Glu Pro Ala Pro Ala Pro Ala Pro Gly Glu Val Ala Pro Thr
305                 310                 315                 320

Pro Thr Thr Pro Thr Pro Gln Arg Thr Leu Pro Ala
                325                 330
```

(2) INFORMATION FOR SEQ ID NO: 54:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (xi) SEQUENCE DESCRIPTION: SEQ ID NO: 54:

Asp Pro Val Asp Ala Val Ile Asn Thr Thr Xaa Asn Tyr Gly Gln Val

```
1               5                  10                 15
Val Ala Ala Leu
            20

(2) INFORMATION FOR SEQ ID NO: 55:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (xi) SEQUENCE DESCRIPTION: SEQ ID NO: 55:

Ala Val Glu Ser Gly Met Leu Ala Leu Gly Thr Pro Ala Pro Ser
1               5                  10                 15

(2) INFORMATION FOR SEQ ID NO: 56:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (xi) SEQUENCE DESCRIPTION: SEQ ID NO: 56:

Ala Ala Met Lys Pro Arg Thr Gly Asp Gly Pro Leu Glu Ala Ala Lys
1               5                  10                 15

Glu Gly Arg (2) INFORMATION FOR SEQ ID NO: 57:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (xi) SEQUENCE DESCRIPTION: SEQ ID NO: 57:

Tyr Tyr Trp Cys Pro Gly Gln Pro Phe Asp Pro Ala Trp Gly Pro
1               5                  10                 15

(2) INFORMATION FOR SEQ ID NO: 58:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 58:

Asp Ile Gly Ser Glu Ser Thr Glu Asp Gln Gln Xaa Ala Val
1               5                  10

(2) INFORMATION FOR SEQ ID NO: 59:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 59:

Ala Glu Glu Ser Ile Ser Thr Xaa Glu Xaa Ile Val Pro
1               5                  10

(2) INFORMATION FOR SEQ ID NO: 60:
```

```
    (i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (xi) SEQUENCE DESCRIPTION: SEQ ID NO: 60:

Asp Pro Glu Pro Ala Pro Pro Val Pro Thr Ala Ala Ala Pro Pro
1               5                  10                  15

Ala (2) INFORMATION FOR SEQ ID NO: 61:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (xi) SEQUENCE DESCRIPTION: SEQ ID NO: 61:

Ala Pro Lys Thr Tyr Xaa Glu Glu Leu Lys Gly Thr Asp Thr Gly
1               5                  10                  15

(2) INFORMATION FOR SEQ ID NO: 62:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (xi) SEQUENCE DESCRIPTION: SEQ ID NO: 62:

Asp Pro Ala Ser Ala Pro Asp Val Pro Thr Ala Ala Gln Gln Thr Ser
1               5                  10                  15

Leu Leu Asn Asn Leu Ala Asp Pro Asp Val Ser Phe Ala Asp
            20                  25                  30

(2) INFORMATION FOR SEQ ID NO: 63:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (xi) SEQUENCE DESCRIPTION: SEQ ID NO: 63:

Gly Cys Gly Asp Arg Ser Gly Gly Asn Leu Asp Gln Ile Arg Leu Arg
1               5                  10                  15

Arg Asp Arg Ser Gly Gly Asn Leu
            20

(2) INFORMATION FOR SEQ ID NO: 64:

(i) SEQUENCE CHARACTERISTICS:
        (A) LENGTH: 187 amino acids
        (B) TYPE: amino acid
        (C) STRANDEDNESS: single
        (D) TOPOLOGY: linear (xi) SEQUENCE DESCRIPTION: SEQ ID NO: 64:

Thr Gly Ser Leu Asn Gln Thr His Asn Arg Arg Ala Asn Glu Arg Lys
1               5                  10                  15

Asn Thr Thr Met Lys Met Val Lys Ser Ile Ala Ala Gly Leu Thr Ala
            20                  25                  30
```

```
Ala Ala Ala Ile Gly Ala Ala Ala Gly Val Thr Ser Ile Met Ala
            35                  40                  45
Gly Gly Pro Val Val Tyr Gln Met Gln Pro Val Phe Gly Ala Pro
 50                  55                  60
Leu Pro Leu Asp Pro Ala Ser Ala Pro Asp Val Pro Thr Ala Ala Gln
 65                  70                  75                  80
Leu Thr Ser Leu Leu Asn Ser Leu Ala Asp Pro Asn Val Ser Phe Ala
                 85                  90                  95
Asn Lys Gly Ser Leu Val Glu Gly Gly Ile Gly Gly Thr Glu Ala Arg
             100                 105                 110
Ile Ala Asp His Lys Leu Lys Lys Ala Ala Glu His Gly Asp Leu Pro
             115                 120                 125
Leu Ser Phe Ser Val Thr Asn Ile Gln Pro Ala Ala Gly Ser Ala
 130                 135                 140
Thr Ala Asp Val Ser Val Ser Gly Pro Lys Leu Ser Ser Pro Val Thr
 145                 150                 155                 160
Gln Asn Val Thr Phe Val Asn Gln Gly Gly Trp Met Leu Ser Arg Ala
                 165                 170                 175
Ser Ala Met Glu Leu Leu Gln Ala Ala Gly Xaa
             180                 185
```

(2) INFORMATION FOR SEQ ID NO: 65:

(i) SEQUENCE CHARACTERISTICS:
        (A) LENGTH: 148 amino acids
        (B) TYPE: amino acid
        (C) STRANDEDNESS: single
        (D) TOPOLOGY: linear (xi) SEQUENCE DESCRIPTION: SEQ ID NO: 65:

```
Asp Glu Val Thr Val Glu Thr Thr Ser Val Phe Arg Ala Asp Phe Leu
 1                   5                  10                  15
Ser Glu Leu Asp Ala Pro Ala Gln Ala Gly Thr Glu Ser Ala Val Ser
                 20                  25                  30
Gly Val Glu Gly Leu Pro Pro Gly Ser Ala Leu Leu Val Val Lys Arg
             35                  40                  45
Gly Pro Asn Ala Gly Ser Arg Phe Leu Leu Asp Gln Ala Ile Thr Ser
 50                  55                  60
Ala Gly Arg His Pro Asp Ser Asp Ile Phe Leu Asp Asp Val Thr Val
 65                  70                  75                  80
Ser Arg Arg His Ala Glu Phe Arg Leu Glu Asn Asn Glu Phe Asn Val
                 85                  90                  95
Val Asp Val Gly Ser Leu Asn Gly Thr Tyr Val Asn Arg Glu Pro Val
             100                 105                 110
Asp Ser Ala Val Leu Ala Asn Gly Asp Glu Val Gln Ile Gly Lys Leu
             115                 120                 125
Arg Leu Val Phe Leu Thr Gly Pro Lys Gln Gly Glu Asp Asp Gly Ser
             130                 135                 140
Thr Gly Gly Pro
 145
```

(2) INFORMATION FOR SEQ ID NO: 66:

(i) SEQUENCE CHARACTERISTICS:
        (A) LENGTH: 230 amino acids
        (B) TYPE: amino acid
        (C) STRANDEDNESS: single
        (D) TOPOLOGY: linear (xi) SEQUENCE DESCRIPTION: SEQ ID NO: 66:

```
Thr Ser Asn Arg Pro Ala Arg Arg Gly Arg Arg Ala Pro Arg Asp Thr
1               5                   10                  15

Gly Pro Asp Arg Ser Ala Ser Leu Ser Leu Val Arg His Arg Arg Gln
                20                  25                  30

Gln Arg Asp Ala Leu Cys Leu Ser Ser Thr Gln Ile Ser Arg Gln Ser
            35                  40                  45

Asn Leu Pro Pro Ala Ala Gly Gly Ala Ala Asn Tyr Ser Arg Arg Asn
        50                  55                  60

Phe Asp Val Arg Ile Lys Ile Phe Met Leu Val Thr Ala Val Val Leu
65                  70                  75                  80

Leu Cys Cys Ser Gly Val Ala Thr Ala Ala Pro Lys Thr Tyr Cys Glu
                85                  90                  95

Glu Leu Lys Gly Thr Asp Thr Gly Gln Ala Cys Gln Ile Gln Met Ser
                100                 105                 110

Asp Pro Ala Tyr Asn Ile Asn Ile Ser Leu Pro Ser Tyr Tyr Pro Asp
            115                 120                 125

Gln Lys Ser Leu Glu Asn Tyr Ile Ala Gln Thr Arg Asp Lys Phe Leu
    130                 135                 140

Ser Ala Ala Thr Ser Ser Thr Pro Arg Glu Ala Pro Tyr Glu Leu Asn
145                 150                 155                 160

Ile Thr Ser Ala Thr Tyr Gln Ser Ala Ile Pro Pro Arg Gly Thr Gln
                165                 170                 175

Ala Val Val Leu Xaa Val Tyr His Asn Ala Gly Thr His Pro Thr
                180                 185                 190

Thr Thr Tyr Lys Ala Phe Asp Trp Asp Gln Ala Tyr Arg Lys Pro Ile
            195                 200                 205

Thr Tyr Asp Thr Leu Trp Gln Ala Asp Thr Asp Pro Leu Pro Val Val
    210                 215                 220

Phe Pro Ile Val Ala Arg
225                 230
```

(2) INFORMATION FOR SEQ ID NO: 67:

(i) SEQUENCE CHARACTERISTICS:
        (A) LENGTH: 132 amino acids
        (B) TYPE: amino acid
        (C) STRANDEDNESS: single
        (D) TOPOLOGY: linear (xi) SEQUENCE DESCRIPTION: SEQ ID NO: 67:

```
Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Arg Ser
                20                  25                  30

Gly Gly Gly Ser Pro Thr Val His Ile Gly Pro Thr Ala Phe Leu Gly
            35                  40                  45

Leu Gly Val Val Asp Asn Asn Gly Asn Gly Ala Arg Val Gln Arg Val
        50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Asn Trp
                100                 105                 110
```

```
Gln Thr Lys Ser Gly Gly Thr Arg Thr Gly Asn Val Thr Leu Ala Glu
            115                 120                 125
Gly Pro Pro Ala
        130

(2) INFORMATION FOR SEQ ID NO: 68:

(i) SEQUENCE CHARACTERISTICS:
        (A) LENGTH: 100 amino acids
        (B) TYPE: amino acid
        (C) STRANDEDNESS: single
        (D) TOPOLOGY: linear (xi) SEQUENCE DESCRIPTION: SEQ ID NO: 68:

Val Pro Leu Arg Ser Pro Ser Met Ser Pro Ser Lys Cys Leu Ala Ala
1               5                   10                  15

Ala Gln Arg Asn Pro Val Ile Arg Arg Arg Leu Ser Asn Pro Pro
            20                  25                  30

Pro Arg Lys Tyr Arg Ser Met Pro Ser Pro Ala Thr Ala Ser Ala Gly
            35                  40                  45

Met Ala Arg Val Arg Arg Arg Ala Ile Trp Arg Gly Pro Ala Thr Xaa
        50                  55                  60

Ser Ala Gly Met Ala Arg Val Arg Arg Trp Xaa Val Met Pro Xaa Val
65                  70                  75                  80

Ile Gln Ser Thr Xaa Ile Arg Xaa Xaa Gly Pro Phe Asp Asn Arg Gly
                85                  90                  95

Ser Glu Arg Lys
            100

(2) INFORMATION FOR SEQ ID NO: 69:

(i) SEQUENCE CHARACTERISTICS:
        (A) LENGTH: 163 amino acids
        (B) TYPE: amino acid
        (C) STRANDEDNESS: single
        (D) TOPOLOGY: linear (xi) SEQUENCE DESCRIPTION: SEQ ID NO: 69:

Met Thr Asp Asp Ile Leu Leu Ile Asp Thr Asp Glu Arg Val Arg Thr
1               5                   10                  15

Leu Thr Leu Asn Arg Pro Gln Ser Arg Asn Ala Leu Ser Ala Ala Leu
            20                  25                  30

Arg Asp Arg Phe Phe Ala Xaa Leu Xaa Asp Ala Glu Xaa Asp Asp Asp
            35                  40                  45

Ile Asp Val Val Ile Leu Thr Gly Ala Asp Pro Val Phe Cys Ala Gly
        50                  55                  60

Leu Asp Leu Lys Val Ala Gly Arg Ala Asp Arg Ala Ala Gly His Leu
65                  70                  75                  80

Thr Ala Val Gly Gly His Asp Gln Ala Gly Asp Arg Asp Gln Arg
                85                  90                  95

Arg Arg Gly His Arg Arg Ala Arg Thr Gly Ala Val Leu Arg His Pro
            100                 105                 110

Asp Arg Leu Arg Ala Arg Pro Leu Arg Arg His Pro Arg Pro Gly Gly
            115                 120                 125

Ala Ala Ala His Leu Gly Thr Gln Cys Val Leu Ala Ala Lys Gly Arg
        130                 135                 140

His Arg Xaa Gly Pro Val Asp Glu Pro Asp Arg Arg Leu Pro Val Arg
145                 150                 155                 160
```

Asp Arg Arg (2) INFORMATION FOR SEQ ID NO: 70:

(i) SEQUENCE CHARACTERISTICS:
      (A) LENGTH: 344 amino acids
      (B) TYPE: amino acid
      (C) STRANDEDNESS: single
      (D) TOPOLOGY: linear (xi) SEQUENCE DESCRIPTION: SEQ ID NO: 70:

```
Met Lys Phe Val Asn His Ile Glu Pro Val Ala Pro Arg Arg Ala Gly
 1               5                  10                  15

Gly Ala Val Ala Glu Val Tyr Ala Glu Ala Arg Arg Glu Phe Gly Arg
                20                  25                  30

Leu Pro Glu Pro Leu Ala Met Leu Ser Pro Asp Glu Gly Leu Leu Thr
            35                  40                  45

Ala Gly Trp Ala Thr Leu Arg Glu Thr Leu Leu Val Gly Gln Val Pro
        50                  55                  60

Arg Gly Arg Lys Glu Ala Val Ala Ala Val Ala Ala Ser Leu Arg
 65                 70                  75                  80

Cys Pro Trp Cys Val Asp Ala His Thr Met Leu Tyr Ala Ala Gly
                85                  90                  95

Gln Thr Asp Thr Ala Ala Ile Leu Ala Gly Thr Ala Pro Ala Ala
                100                 105                 110

Gly Asp Pro Asn Ala Pro Tyr Val Ala Trp Ala Ala Gly Thr Gly Thr
                115                 120                 125

Pro Ala Gly Pro Pro Ala Pro Phe Gly Pro Asp Val Ala Ala Glu Tyr
        130                 135                 140

Leu Gly Thr Ala Val Gln Phe His Phe Ile Ala Arg Leu Val Leu Val
145                 150                 155                 160

Leu Leu Asp Glu Thr Phe Leu Pro Gly Gly Pro Arg Ala Gln Gln Leu
                165                 170                 175

Met Arg Arg Ala Gly Gly Leu Val Phe Ala Arg Lys Val Arg Ala Glu
                180                 185                 190

His Arg Pro Gly Arg Ser Thr Arg Arg Leu Glu Pro Arg Thr Leu Pro
                195                 200                 205

Asp Asp Leu Ala Trp Ala Thr Pro Ser Glu Pro Ile Ala Thr Ala Phe
        210                 215                 220

Ala Ala Leu Ser His His Leu Asp Thr Ala Pro His Leu Pro Pro Pro
225                 230                 235                 240

Thr Arg Gln Val Val Arg Arg Val Val Gly Ser Trp His Gly Glu Pro
                245                 250                 255

Met Pro Met Ser Ser Arg Trp Thr Asn Glu His Thr Ala Glu Leu Pro
                260                 265                 270

Ala Asp Leu His Ala Pro Thr Arg Leu Ala Leu Leu Thr Gly Leu Ala
            275                 280                 285

Pro His Gln Val Thr Asp Asp Val Ala Ala Arg Ser Leu Leu
        290                 295                 300

Asp Thr Asp Ala Ala Leu Val Gly Ala Leu Ala Trp Ala Ala Phe Thr
305                 310                 315                 320

Ala Ala Arg Arg Ile Gly Thr Trp Ile Gly Ala Ala Glu Gly Gln
                325                 330                 335

Val Ser Arg Gln Asn Pro Thr Gly
            340
```

(2) INFORMATION FOR SEQ ID NO: 71:

(i) SEQUENCE CHARACTERISTICS:
        (A) LENGTH: 485 amino acids
        (B) TYPE: amino acid
        (C) STRANDEDNESS: single
        (D) TOPOLOGY: linear (xi) SEQUENCE DESCRIPTION: SEQ ID NO: 71:

```
Asp Asp Pro Asp Met Pro Gly Thr Val Ala Lys Ala Val Ala Asp Ala
 1               5                  10                  15

Leu Gly Arg Gly Ile Ala Pro Val Glu Asp Ile Gln Asp Cys Val Glu
            20                  25                  30

Ala Arg Leu Gly Glu Ala Gly Leu Asp Asp Val Ala Arg Val Tyr Ile
        35                  40                  45

Ile Tyr Arg Gln Arg Arg Ala Glu Leu Arg Thr Ala Lys Ala Leu Leu
50                  55                  60

Gly Val Arg Asp Glu Leu Lys Leu Ser Leu Ala Ala Val Thr Val Leu
65                  70                  75                  80

Arg Glu Arg Tyr Leu Leu His Asp Glu Gln Gly Arg Pro Ala Glu Ser
                85                  90                  95

Thr Gly Glu Leu Met Asp Arg Ser Ala Arg Cys Val Ala Ala Ala Glu
            100                 105                 110

Asp Gln Tyr Glu Pro Gly Ser Ser Arg Arg Trp Ala Glu Arg Phe Ala
        115                 120                 125

Thr Leu Leu Arg Asn Leu Glu Phe Leu Pro Asn Ser Pro Thr Leu Met
130                 135                 140

Asn Ser Gly Thr Asp Leu Gly Leu Leu Ala Gly Cys Phe Val Leu Pro
145                 150                 155                 160

Ile Glu Asp Ser Leu Gln Ser Ile Phe Ala Thr Leu Gly Gln Ala Ala
                165                 170                 175

Glu Leu Gln Arg Ala Gly Gly Thr Gly Tyr Ala Phe Ser His Leu
            180                 185                 190

Arg Pro Ala Gly Asp Arg Val Ala Ser Thr Gly Thr Ala Ser Gly
        195                 200                 205

Pro Val Ser Phe Leu Arg Leu Tyr Asp Ser Ala Ala Gly Val Val Ser
210                 215                 220

Met Gly Gly Arg Arg Arg Gly Ala Cys Met Ala Val Leu Asp Val Ser
225                 230                 235                 240

His Pro Asp Ile Cys Asp Phe Val Thr Ala Lys Ala Glu Ser Pro Ser
                245                 250                 255

Glu Leu Pro His Phe Asn Leu Ser Val Gly Val Thr Asp Ala Phe Leu
            260                 265                 270

Arg Ala Val Glu Arg Asn Gly Leu His Arg Leu Val Asn Pro Arg Thr
        275                 280                 285

Gly Lys Ile Val Ala Arg Met Pro Ala Ala Glu Leu Phe Asp Ala Ile
290                 295                 300

Cys Lys Ala Ala His Ala Gly Gly Asp Pro Gly Leu Val Phe Leu Asp
305                 310                 315                 320

Thr Ile Asn Arg Ala Asn Pro Val Pro Gly Arg Gly Arg Ile Glu Ala
                325                 330                 335

Thr Asn Pro Cys Gly Glu Val Pro Leu Leu Pro Tyr Glu Ser Cys Asn
            340                 345                 350

Leu Gly Ser Ile Asn Leu Ala Arg Met Leu Ala Asp Gly Arg Val Asp
```

-continued

```
                355                 360                 365
Trp Asp Arg Leu Glu Glu Val Ala Gly Val Ala Val Arg Phe Leu Asp
        370                 375                 380

Asp Val Ile Asp Val Ser Arg Tyr Pro Phe Pro Glu Leu Gly Glu Ala
385                 390                 395                 400

Ala Arg Ala Thr Arg Lys Ile Gly Leu Gly Val Met Gly Leu Ala Glu
                405                 410                 415

Leu Leu Ala Ala Leu Gly Ile Pro Tyr Asp Ser Glu Glu Ala Val Arg
                420                 425                 430

Leu Ala Thr Arg Leu Met Arg Arg Ile Gln Gln Ala Ala His Thr Ala
                435                 440                 445

Ser Arg Arg Leu Ala Glu Glu Arg Gly Ala Phe Pro Ala Phe Thr Asp
        450                 455                 460

Ser Arg Phe Ala Arg Ser Gly Pro Arg Arg Asn Ala Gln Val Thr Ser
465                 470                 475                 480

Val Ala Pro Thr Gly
                485
```

(2) INFORMATION FOR SEQ ID NO: 72:

(i) SEQUENCE CHARACTERISTICS:
        (A) LENGTH: 267 amino acids
        (B) TYPE: amino acid
        (C) STRANDEDNESS: single
        (D) TOPOLOGY: linear (xi) SEQUENCE DESCRIPTION: SEQ ID NO: 72:

```
Gly Val Ile Val Leu Asp Leu Glu Pro Arg Gly Pro Leu Pro Thr Glu
1               5                   10                  15

Ile Tyr Trp Arg Arg Gly Leu Ala Leu Gly Ile Ala Val Val Val
                20                  25                  30

Val Gly Ile Ala Val Ala Ile Val Ile Ala Phe Val Asp Ser Ser Ala
                35                  40                  45

Gly Ala Lys Pro Val Ser Ala Asp Lys Pro Ala Ser Ala Gln Ser His
            50                  55                  60

Pro Gly Ser Pro Ala Pro Gln Ala Pro Gln Pro Ala Gly Gln Thr Glu
65                  70                  75                  80

Gly Asn Ala Ala Ala Pro Pro Gln Gly Gln Asn Pro Glu Thr Pro
                85                  90                  95

Thr Pro Thr Ala Ala Val Gln Pro Pro Val Leu Lys Glu Gly Asp
            100                 105                 110

Asp Cys Pro Asp Ser Thr Leu Ala Val Lys Gly Leu Thr Asn Ala Pro
            115                 120                 125

Gln Tyr Tyr Val Gly Asp Gln Pro Lys Phe Thr Met Val Val Thr Asn
            130                 135                 140

Ile Gly Leu Val Ser Cys Lys Arg Asp Val Gly Ala Ala Val Leu Ala
145                 150                 155                 160

Ala Tyr Val Tyr Ser Leu Asp Asn Lys Arg Leu Trp Ser Asn Leu Asp
                165                 170                 175

Cys Ala Pro Ser Asn Glu Thr Leu Val Lys Thr Phe Ser Pro Gly Glu
            180                 185                 190

Gln Val Thr Thr Ala Val Thr Trp Thr Gly Met Gly Ser Ala Pro Arg
            195                 200                 205

Cys Pro Leu Pro Arg Pro Ala Ile Gly Pro Gly Thr Tyr Asn Leu Val
210                 215                 220
```

```
Val Gln Leu Gly Asn Leu Arg Ser Leu Pro Val Pro Phe Ile Leu Asn
225                 230                 235                 240

Gln Pro Pro Pro Pro Gly Pro Val Pro Ala Pro Gly Pro Ala Gln
                245                 250                 255

Ala Pro Pro Glu Ser Pro Ala Gln Gly Gly
            260                 265
```

(2) INFORMATION FOR SEQ ID NO: 73:

(i) SEQUENCE CHARACTERISTICS:
        (A) LENGTH: 97 amino acids
        (B) TYPE: amino acid
        (C) STRANDEDNESS: single
        (D) TOPOLOGY: linear (xi) SEQUENCE DESCRIPTION: SEQ ID NO: 73:

```
Leu Ile Ser Thr Gly Lys Ala Ser His Ala Ser Leu Gly Val Gln Val
1               5                   10                  15

Thr Asn Asp Lys Asp Thr Pro Gly Ala Lys Ile Val Glu Val Val Ala
                20                  25                  30

Gly Gly Ala Ala Ala Asn Ala Gly Val Pro Lys Gly Val Val Val Thr
            35                  40                  45

Lys Val Asp Asp Arg Pro Ile Asn Ser Ala Asp Ala Leu Val Ala Ala
        50                  55                  60

Val Arg Ser Lys Ala Pro Gly Ala Thr Val Ala Leu Thr Phe Gln Asp
65                  70                  75                  80

Pro Ser Gly Gly Ser Arg Thr Val Gln Val Thr Leu Gly Lys Ala Glu
                85                  90                  95

Gln
```

(2) INFORMATION FOR SEQ ID NO: 74:

(i) SEQUENCE CHARACTERISTICS:
        (A) LENGTH: 364 amino acids
        (B) TYPE: amino acid
        (C) STRANDEDNESS: single
        (D) TOPOLOGY: linear (xi) SEQUENCE DESCRIPTION: SEQ ID NO: 74:

```
Gly Ala Ala Val Ser Leu Leu Ala Ala Gly Thr Leu Val Leu Thr Ala
1               5                   10                  15

Cys Gly Gly Gly Thr Asn Ser Ser Ser Gly Ala Gly Gly Thr Ser
                20                  25                  30

Gly Ser Val His Cys Gly Gly Lys Lys Glu Leu His Ser Ser Gly Ser
            35                  40                  45

Thr Ala Gln Glu Asn Ala Met Glu Gln Phe Val Tyr Ala Tyr Val Arg
        50                  55                  60

Ser Cys Pro Gly Tyr Thr Leu Asp Tyr Asn Ala Asn Gly Ser Gly Ala
65                  70                  75                  80

Gly Val Thr Gln Phe Leu Asn Asn Glu Thr Asp Phe Ala Gly Ser Asp
                85                  90                  95

Val Pro Leu Asn Pro Ser Thr Gly Gln Pro Asp Arg Ser Ala Glu Arg
                100                 105                 110

Cys Gly Ser Pro Ala Trp Asp Leu Pro Thr Val Phe Gly Pro Ile Ala
            115                 120                 125

Ile Thr Tyr Asn Ile Lys Gly Val Ser Thr Leu Asn Leu Asp Gly Pro
        130                 135                 140

Thr Thr Ala Lys Ile Phe Asn Gly Thr Ile Thr Val Trp Asn Asp Pro
```

-continued

```
                145                 150                 155                 160
Gln Ile Gln Ala Leu Asn Ser Gly Thr Asp Leu Pro Pro Thr Pro Ile
                    165                 170                 175
Ser Val Ile Phe Arg Ser Asp Lys Ser Gly Thr Ser Asp Asn Phe Gln
                    180                 185                 190
Lys Tyr Leu Asp Gly Val Ser Asn Gly Ala Trp Gly Lys Gly Ala Ser
                    195                 200                 205
Glu Thr Phe Ser Gly Gly Val Gly Val Gly Ala Ser Gly Asn Asn Gly
                    210                 215                 220
Thr Ser Ala Leu Leu Gln Thr Thr Asp Gly Ser Ile Thr Tyr Asn Glu
225                 230                 235                 240
Trp Ser Phe Ala Val Gly Lys Gln Leu Asn Met Ala Gln Ile Ile Thr
                    245                 250                 255
Ser Ala Gly Pro Asp Pro Val Ala Ile Thr Thr Glu Ser Val Gly Lys
                    260                 265                 270
Thr Ile Ala Gly Ala Lys Ile Met Gly Gln Gly Asn Asp Leu Val Leu
                    275                 280                 285
Asp Thr Ser Ser Phe Tyr Arg Pro Thr Gln Pro Gly Ser Tyr Pro Ile
                    290                 295                 300
Val Leu Ala Thr Tyr Glu Ile Val Cys Ser Lys Tyr Pro Asp Ala Thr
305                 310                 315                 320
Thr Gly Thr Ala Val Arg Ala Phe Met Gln Ala Ala Ile Gly Pro Gly
                    325                 330                 335
Gln Glu Gly Leu Asp Gln Tyr Gly Ser Ile Pro Leu Pro Lys Ser Phe
                    340                 345                 350
Gln Ala Lys Leu Ala Ala Ala Val Asn Ala Ile Ser
                    355                 360

(2) INFORMATION FOR SEQ ID NO: 75:

(i) SEQUENCE CHARACTERISTICS:
        (A) LENGTH: 309 amino acids
        (B) TYPE: amino acid
        (C) STRANDEDNESS: single
        (D) TOPOLOGY: linear (xi) SEQUENCE DESCRIPTION: SEQ ID NO: 75:

Gln Ala Ala Gly Arg Ala Val Arg Arg Thr Gly His Ala Glu Asp
1               5                   10                  15
Gln Thr His Gln Asp Arg Leu His His Gly Cys Arg Arg Ala Ala Val
                    20                  25                  30
Val Val Arg Gln Asp Arg Ala Ser Val Ser Ala Thr Ser Ala Arg Pro
                    35                  40                  45
Pro Arg Arg His Pro Ala Gln Gly His Arg Arg Arg Val Ala Pro Ser
    50                  55                  60
Gly Gly Arg Arg Arg Pro His Pro His Val Gln Pro Asp Asp Arg
65                  70                  75                  80
Arg Asp Arg Pro Ala Leu Leu Asp Arg Thr Gln Pro Ala Glu His Pro
                    85                  90                  95
Asp Pro His Arg Arg Gly Pro Ala Asp Pro Gly Arg Val Arg Gly Arg
                    100                 105                 110
Gly Arg Leu Arg Arg Val Asp Asp Gly Arg Leu Gln Pro Asp Arg Asp
                    115                 120                 125
Ala Asp His Gly Ala Pro Val Arg Gly Arg Gly Pro His Arg Gly Val
                    130                 135                 140
```

-continued

```
Gln His Arg Gly Gly Pro Val Phe Val Arg Arg Val Pro Gly Val Arg
145                 150                 155                 160

Cys Ala His Arg Arg Gly His Arg Arg Val Ala Ala Pro Gly Gln Gly
                165                 170                 175

Asp Val Leu Arg Ala Gly Leu Arg Val Glu Arg Leu Arg Pro Val Ala
            180                 185                 190

Ala Val Glu Asn Leu His Arg Gly Ser Gln Arg Ala Asp Gly Arg Val
        195                 200                 205

Phe Arg Pro Ile Arg Arg Gly Ala Arg Leu Pro Ala Arg Arg Ser Arg
    210                 215                 220

Ala Gly Pro Gln Gly Arg Leu His Leu Asp Gly Ala Gly Pro Ser Pro
225                 230                 235                 240

Leu Pro Ala Arg Ala Gly Gln Gln Gln Pro Ser Ser Ala Gly Gly Arg
                245                 250                 255

Arg Ala Gly Gly Ala Glu Arg Ala Asp Pro Gly Gln Arg Gly Arg His
            260                 265                 270

His Gln Gly Gly His Asp Pro Gly Arg Gln Gly Ala Gln Arg Gly Thr
        275                 280                 285

Ala Gly Val Ala His Ala Ala Gly Pro Arg Arg Ala Ala Val Arg
    290                 295                 300

Asn Arg Pro Arg Arg
305

(2) INFORMATION FOR SEQ ID NO: 76:

(i) SEQUENCE CHARACTERISTICS:
        (A) LENGTH: 580 amino acids
        (B) TYPE: amino acid
        (C) STRANDEDNESS: single
        (D) TOPOLOGY: linear (xi) SEQUENCE DESCRIPTION: SEQ ID NO: 76:

Ser Ala Val Trp Cys Leu Asn Gly Phe Thr Gly Arg His Arg His Gly
1               5                   10                  15

Arg Cys Arg Val Arg Ala Ser Gly Trp Arg Ser Ser Asn Arg Trp Cys
                20                  25                  30

Ser Thr Thr Ala Asp Cys Cys Ala Ser Lys Thr Pro Thr Gln Ala Ala
            35                  40                  45

Ser Pro Leu Glu Arg Arg Phe Thr Cys Cys Ser Pro Ala Val Gly Cys
    50                  55                  60

Arg Phe Arg Ser Phe Pro Val Arg Arg Leu Ala Leu Gly Ala Arg Thr
65                  70                  75                  80

Ser Arg Thr Leu Gly Val Arg Arg Thr Leu Ser Gln Trp Asn Leu Ser
                85                  90                  95

Pro Arg Ala Gln Pro Ser Cys Ala Val Thr Val Glu Ser His Thr His
            100                 105                 110

Ala Ser Pro Arg Met Ala Lys Leu Ala Arg Val Val Gly Leu Val Gln
        115                 120                 125

Glu Glu Gln Pro Ser Asp Met Thr Asn His Pro Arg Tyr Ser Pro Pro
    130                 135                 140

Pro Gln Gln Pro Gly Thr Pro Gly Tyr Ala Gln Gly Gln Gln Thr
145                 150                 155                 160

Tyr Ser Gln Gln Phe Asp Trp Arg Tyr Pro Pro Ser Pro Pro Gln
                165                 170                 175

Pro Thr Gln Tyr Arg Gln Pro Tyr Glu Ala Leu Gly Gly Thr Arg Pro
            180                 185                 190
```

-continued

```
Gly Leu Ile Pro Gly Val Ile Pro Thr Met Thr Pro Pro Gly Met
            195                 200                 205
Val Arg Gln Arg Pro Arg Ala Gly Met Leu Ala Ile Gly Ala Val Thr
210             215                 220
Ile Ala Val Val Ser Ala Gly Ile Gly Gly Ala Ala Ser Leu Val
225             230                 235                 240
Gly Phe Asn Arg Ala Pro Ala Gly Pro Ser Gly Gly Pro Val Ala Ala
            245                 250                 255
Ser Ala Ala Pro Ser Ile Pro Ala Ala Asn Met Pro Pro Gly Ser Val
            260                 265                 270
Glu Gln Val Ala Ala Lys Val Val Pro Ser Val Val Met Leu Glu Thr
            275                 280                 285
Asp Leu Gly Arg Gln Ser Glu Glu Gly Ser Gly Ile Ile Leu Ser Ala
            290                 295                 300
Glu Gly Leu Ile Leu Thr Asn Asn His Val Ile Ala Ala Ala Lys
305                 310                 315                 320
Pro Pro Leu Gly Ser Pro Pro Lys Thr Thr Val Thr Phe Ser Asp
                325                 330                 335
Gly Arg Thr Ala Pro Phe Thr Val Val Gly Ala Asp Pro Thr Ser Asp
                340                 345                 350
Ile Ala Val Val Arg Val Gln Gly Val Ser Gly Leu Thr Pro Ile Ser
                355                 360                 365
Leu Gly Ser Ser Ser Asp Leu Arg Val Gly Gln Pro Val Leu Ala Ile
            370                 375                 380
Gly Ser Pro Leu Gly Leu Glu Gly Thr Val Thr Thr Gly Ile Val Ser
385                 390                 395                 400
Ala Leu Asn Arg Pro Val Ser Thr Thr Gly Glu Ala Gly Asn Gln Asn
                405                 410                 415
Thr Val Leu Asp Ala Ile Gln Thr Asp Ala Ala Ile Asn Pro Gly Asn
                420                 425                 430
Ser Gly Gly Ala Leu Val Asn Met Asn Ala Gln Leu Val Gly Val Asn
            435                 440                 445
Ser Ala Ile Ala Thr Leu Gly Ala Asp Ser Ala Asp Ala Gln Ser Gly
450                 455                 460
Ser Ile Gly Leu Gly Phe Ala Ile Pro Val Asp Gln Ala Lys Arg Ile
465                 470                 475                 480
Ala Asp Glu Leu Ile Ser Thr Gly Lys Ala Ser His Ala Ser Leu Gly
                485                 490                 495
Val Gln Val Thr Asn Asp Lys Asp Thr Pro Gly Ala Lys Ile Val Glu
                500                 505                 510
Val Val Ala Gly Gly Ala Ala Asn Ala Gly Val Pro Lys Gly Val
            515                 520                 525
Val Val Thr Lys Val Asp Asp Arg Pro Ile Asn Ser Ala Asp Ala Leu
            530                 535                 540
Val Ala Ala Val Arg Ser Lys Ala Pro Gly Ala Thr Val Ala Leu Thr
545                 550                 555                 560
Phe Gln Asp Pro Ser Gly Gly Ser Arg Thr Val Gln Val Thr Leu Gly
                565                 570                 575
Lys Ala Glu Gln
            580
```

(2) INFORMATION FOR SEQ ID NO: 77:

```
    (i) SEQUENCE CHARACTERISTICS:
        (A) LENGTH: 233 amino acids
        (B) TYPE: amino acid
        (C) STRANDEDNESS: single
        (D) TOPOLOGY: linear (xi) SEQUENCE DESCRIPTION: SEQ ID NO: 77:

Met Asn Asp Gly Lys Arg Ala Val Thr Ser Ala Val Leu Val Val Leu
1               5                  10                  15

Gly Ala Cys Leu Ala Leu Trp Leu Ser Gly Cys Ser Ser Pro Lys Pro
                20                  25                  30

Asp Ala Glu Glu Gln Gly Val Pro Val Ser Pro Thr Ala Ser Asp Pro
            35                  40                  45

Ala Leu Leu Ala Glu Ile Arg Gln Ser Leu Asp Ala Thr Lys Gly Leu
    50                  55                  60

Thr Ser Val His Val Ala Val Arg Thr Thr Gly Lys Val Asp Ser Leu
65                  70                  75                  80

Leu Gly Ile Thr Ser Ala Asp Val Asp Val Arg Ala Asn Pro Leu Ala
                85                  90                  95

Ala Lys Gly Val Cys Thr Tyr Asn Asp Glu Gln Gly Val Pro Phe Arg
            100                 105                 110

Val Gln Gly Asp Asn Ile Ser Val Lys Leu Phe Asp Asp Trp Ser Asn
        115                 120                 125

Leu Gly Ser Ile Ser Glu Leu Ser Thr Ser Arg Val Leu Asp Pro Ala
    130                 135                 140

Ala Gly Val Thr Gln Leu Leu Ser Gly Val Thr Asn Leu Gln Ala Gln
145                 150                 155                 160

Gly Thr Glu Val Ile Asp Gly Ile Ser Thr Thr Lys Ile Thr Gly Thr
                165                 170                 175

Ile Pro Ala Ser Ser Val Lys Met Leu Asp Pro Gly Ala Lys Ser Ala
            180                 185                 190

Arg Pro Ala Thr Val Trp Ile Ala Gln Asp Gly Ser His His Leu Val
        195                 200                 205

Arg Ala Ser Ile Asp Leu Gly Ser Gly Ser Ile Gln Leu Thr Gln Ser
    210                 215                 220

Lys Trp Asn Glu Pro Val Asn Val Asp
225                 230

(2) INFORMATION FOR SEQ ID NO: 78:

(i) SEQUENCE CHARACTERISTICS:
        (A) LENGTH: 66 amino acids
        (B) TYPE: amino acid
        (C) STRANDEDNESS: single
        (D) TOPOLOGY: linear (xi) SEQUENCE DESCRIPTION: SEQ ID NO: 78:

Val Ile Asp Ile Ile Gly Thr Ser Pro Thr Ser Trp Glu Gln Ala Ala
1               5                  10                  15

Ala Glu Ala Val Gln Arg Ala Arg Asp Ser Val Asp Asp Ile Arg Val
                20                  25                  30

Ala Arg Val Ile Glu Gln Asp Met Ala Val Asp Ser Ala Gly Lys Ile
            35                  40                  45

Thr Tyr Arg Ile Lys Leu Glu Val Ser Phe Lys Met Arg Pro Ala Gln
    50                  55                  60

Pro Arg
65
```

(2) INFORMATION FOR SEQ ID NO: 79:

(i) SEQUENCE CHARACTERISTICS:
        (A) LENGTH: 69 amino acids
        (B) TYPE: amino acid
        (C) STRANDEDNESS: single
        (D) TOPOLOGY: linear (xi) SEQUENCE DESCRIPTION: SEQ ID NO: 79:

```
Val Pro Pro Ala Pro Pro Leu Pro Pro Leu Pro Pro Ser Pro Ile Ser
 1               5                  10                  15

Cys Ala Ser Pro Pro Ser Pro Pro Leu Pro Ala Pro Pro Val Ala
            20                  25                  30

Pro Gly Pro Pro Met Pro Pro Leu Asp Pro Trp Pro Pro Ala Pro Pro
            35                  40                  45

Leu Pro Tyr Ser Thr Pro Pro Gly Ala Pro Leu Pro Pro Ser Pro Pro
            50                  55                  60

Ser Pro Pro Leu Pro
 65
```

(2) INFORMATION FOR SEQ ID NO: 80:

(i) SEQUENCE CHARACTERISTICS:
        (A) LENGTH: 355 amino acids
        (B) TYPE: amino acid
        (C) STRANDEDNESS: single
        (D) TOPOLOGY: linear (xi) SEQUENCE DESCRIPTION: SEQ ID NO: 80:

```
Met Ser Asn Ser Arg Arg Arg Ser Leu Arg Trp Ser Trp Leu Leu Ser
 1               5                  10                  15

Val Leu Ala Ala Val Gly Leu Gly Leu Ala Thr Ala Pro Ala Gln Ala
            20                  25                  30

Ala Pro Pro Ala Leu Ser Gln Asp Arg Phe Ala Asp Phe Pro Ala Leu
            35                  40                  45

Pro Leu Asp Pro Ser Ala Met Val Ala Gln Val Ala Pro Gln Val Val
            50                  55                  60

Asn Ile Asn Thr Lys Leu Gly Tyr Asn Asn Ala Val Gly Ala Gly Thr
 65                  70                  75                  80

Gly Ile Val Ile Asp Pro Asn Gly Val Val Leu Thr Asn Asn His Val
                85                  90                  95

Ile Ala Gly Ala Thr Asp Ile Asn Ala Phe Ser Val Gly Ser Gly Gln
                100                 105                 110

Thr Tyr Gly Val Asp Val Val Gly Tyr Asp Arg Thr Gln Asp Val Ala
                115                 120                 125

Val Leu Gln Leu Arg Gly Ala Gly Leu Pro Ser Ala Ala Ile Gly
            130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
                165                 170                 175

Gly Gln Thr Val Gln Ala Ser Asp Ser Leu Thr Gly Ala Glu Glu Thr
            180                 185                 190

Leu Asn Gly Leu Ile Gln Phe Asp Ala Ala Ile Gln Pro Gly Asp Ser
            195                 200                 205

Gly Gly Pro Val Val Asn Gly Leu Gly Gln Val Val Gly Met Asn Thr
210                 215                 220
```

-continued

```
Ala Ala Ser Asp Asn Phe Gln Leu Ser Gln Gly Gly Gln Gly Phe Ala
225                 230                 235                 240

Ile Pro Ile Gly Gln Ala Met Ala Ile Ala Gly Gln Ile Arg Ser Gly
                245                 250                 255

Gly Gly Ser Pro Thr Val His Ile Gly Pro Thr Ala Phe Leu Gly Leu
                260                 265                 270

Gly Val Val Asp Asn Asn Gly Asn Gly Ala Arg Val Gln Arg Val Val
                275                 280                 285

Gly Ser Ala Pro Ala Ala Ser Leu Gly Ile Ser Thr Gly Asp Val Ile
                290                 295                 300

Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Asn Trp Gln
                325                 330                 335

Thr Lys Ser Gly Gly Thr Arg Thr Gly Asn Val Thr Leu Ala Glu Gly
                340                 345                 350

Pro Pro Ala
        355
```

(2) INFORMATION FOR SEQ ID NO: 81:

(i) SEQUENCE CHARACTERISTICS:
        (A) LENGTH: 205 amino acids
        (B) TYPE: amino acid
        (C) STRANDEDNESS: single
        (D) TOPOLOGY: linear (xi) SEQUENCE DESCRIPTION: SEQ ID NO: 81:

```
Ser Pro Lys Pro Asp Ala Glu Glu Gln Gly Val Pro Val Ser Pro Thr
1               5                   10                  15

Ala Ser Asp Pro Ala Leu Leu Ala Glu Ile Arg Gln Ser Leu Asp Ala
                20                  25                  30

Thr Lys Gly Leu Thr Ser Val His Val Ala Val Arg Thr Thr Gly Lys
                35                  40                  45

Val Asp Ser Leu Leu Gly Ile Thr Ser Ala Asp Val Asp Val Arg Ala
50                  55                  60

Asn Pro Leu Ala Ala Lys Gly Val Cys Thr Tyr Asn Asp Glu Gln Gly
65                  70                  75                  80

Val Pro Phe Arg Val Gln Gly Asp Asn Ile Ser Val Lys Leu Phe Asp
                85                  90                  95

Asp Trp Ser Asn Leu Gly Ser Ile Ser Glu Leu Ser Thr Ser Arg Val
                100                 105                 110

Leu Asp Pro Ala Ala Gly Val Thr Gln Leu Leu Ser Gly Val Thr Asn
                115                 120                 125

Leu Gln Ala Gln Gly Thr Glu Val Ile Asp Gly Ile Ser Thr Thr Lys
        130                 135                 140

Ile Thr Gly Thr Ile Pro Ala Ser Ser Val Lys Met Leu Asp Pro Gly
145                 150                 155                 160

Ala Lys Ser Ala Arg Pro Ala Thr Val Trp Ile Ala Gln Asp Gly Ser
                165                 170                 175

His His Leu Val Arg Ala Ser Ile Asp Leu Gly Ser Gly Ser Ile Gln
                180                 185                 190

Leu Thr Gln Ser Lys Trp Asn Glu Pro Val Asn Val Asp
        195                 200                 205
```

(2) INFORMATION FOR SEQ ID NO: 82:

(i) SEQUENCE CHARACTERISTICS:
    (A) LENGTH: 286 amino acids
    (B) TYPE: amino acid
    (C) STRANDEDNESS: single
    (D) TOPOLOGY: linear (xi) SEQUENCE DESCRIPTION: SEQ ID NO: 82:

```
Gly Asp Ser Phe Trp Ala Ala Asp Gln Met Ala Arg Gly Phe Val
 1               5                  10                  15

Leu Gly Ala Thr Ala Gly Arg Thr Thr Leu Thr Gly Glu Gly Leu Gln
                20                  25                  30

His Ala Asp Gly His Ser Leu Leu Leu Asp Ala Thr Asn Pro Ala Val
            35                  40                  45

Val Ala Tyr Asp Pro Ala Phe Ala Tyr Glu Ile Gly Tyr Ile Xaa Glu
 50                  55                  60

Ser Gly Leu Ala Arg Met Cys Gly Glu Asn Pro Glu Asn Ile Phe Phe
 65                  70                  75                  80

Tyr Ile Thr Val Tyr Asn Glu Pro Tyr Val Gln Pro Pro Glu Pro Glu
                85                  90                  95

Asn Phe Asp Pro Glu Gly Val Leu Gly Gly Ile Tyr Arg Tyr His Ala
            100                 105                 110

Ala Thr Glu Gln Arg Thr Asn Lys Xaa Gln Ile Leu Ala Ser Gly Val
        115                 120                 125

Ala Met Pro Ala Ala Leu Arg Ala Ala Gln Met Leu Ala Ala Glu Trp
    130                 135                 140

Asp Val Ala Asp Val Trp Ser Val Thr Ser Trp Gly Glu Leu Asn
145                 150                 155                 160

Arg Asp Gly Val Val Ile Glu Thr Glu Lys Leu Arg His Pro Asp Arg
                165                 170                 175

Pro Ala Gly Val Pro Tyr Val Thr Arg Ala Leu Glu Asn Ala Arg Gly
            180                 185                 190

Pro Val Ile Ala Val Ser Asp Trp Met Arg Ala Val Pro Glu Gln Ile
        195                 200                 205

Arg Pro Trp Val Pro Gly Thr Tyr Leu Thr Leu Gly Thr Asp Gly Phe
    210                 215                 220

Gly Phe Ser Asp Thr Arg Pro Ala Gly Arg Arg Tyr Phe Asn Thr Asp
225                 230                 235                 240

Ala Glu Ser Gln Val Gly Arg Gly Phe Gly Arg Gly Trp Pro Gly Arg
                245                 250                 255

Arg Val Asn Ile Asp Pro Phe Gly Ala Gly Arg Gly Pro Pro Ala Gln
            260                 265                 270

Leu Pro Gly Phe Asp Glu Gly Gly Gly Leu Arg Pro Xaa Lys
        275                 280                 285
```

(2) INFORMATION FOR SEQ ID NO: 83:

(i) SEQUENCE CHARACTERISTICS:
        (A) LENGTH: 173 amino acids
        (B) TYPE: amino acid
        (C) STRANDEDNESS: single
        (D) TOPOLOGY: linear (xi) SEQUENCE DESCRIPTION: SEQ ID NO: 83:

```
Thr Lys Phe His Ala Leu Met Gln Glu Gln Ile His Asn Glu Phe Thr
 1               5                  10                  15

Ala Ala Gln Gln Tyr Val Ala Ile Ala Val Tyr Phe Asp Ser Glu Asp
                20                  25                  30
```

```
Leu Pro Gln Leu Ala Lys His Phe Tyr Ser Gln Ala Val Glu Glu Arg
            35                  40                  45

Asn His Ala Met Met Leu Val Gln His Leu Leu Asp Arg Asp Leu Arg
 50                  55                  60

Val Glu Ile Pro Gly Val Asp Thr Val Arg Asn Gln Phe Asp Arg Pro
 65                  70                  75                  80

Arg Glu Ala Leu Ala Leu Ala Leu Asp Gln Gly Arg Thr Val Thr Asp
                85                  90                  95

Gln Val Gly Arg Leu Thr Ala Val Ala Arg Asp Glu Gly Asp Phe Leu
            100                 105                 110

Gly Glu Gln Phe Met Gln Trp Phe Leu Gln Glu Gln Ile Glu Glu Val
            115                 120                 125

Ala Leu Met Ala Thr Leu Val Arg Val Ala Asp Arg Ala Gly Ala Asn
            130                 135                 140

Leu Phe Glu Leu Glu Asn Phe Val Ala Arg Glu Val Asp Val Ala Pro
145                 150                 155                 160

Ala Ala Ser Gly Ala Pro His Ala Ala Gly Gly Arg Leu
                165                 170

(2) INFORMATION FOR SEQ ID NO: 84:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO: 84:

Arg Ala Asp Glu Arg Lys Asn Thr Thr Met Lys Met Val Lys Ser Ile
 1               5                   10                  15

Ala Ala Gly Leu Thr Ala Ala Ala Ile Gly Ala Ala Ala Ala Ala Gly
            20                  25                  30

Val Thr Ser Ile Met Ala Gly Gly Pro Val Val Tyr Gln Met Gln Pro
            35                  40                  45

Val Val Phe Gly Ala Pro Leu Pro Leu Asp Pro Xaa Ser Ala Pro Xaa
 50                  55                  60

Val Pro Thr Ala Ala Gln Trp Thr Xaa Leu Leu Asn Xaa Leu Xaa Asp
 65                  70                  75                  80

Pro Asn Val Ser Phe Xaa Asn Lys Gly Ser Leu Val Glu Gly Gly Ile
                85                  90                  95

Gly Gly Xaa Glu Gly Xaa Xaa Arg Arg Xaa Gln
            100                 105

(2) INFORMATION FOR SEQ ID NO: 85:

(i) SEQUENCE CHARACTERISTICS:
        (A) LENGTH: 125 amino acids
        (B) TYPE: amino acid
        (C) STRANDEDNESS: single
        (D) TOPOLOGY: linear (xi) SEQUENCE DESCRIPTION: SEQ ID NO: 85:

Val Leu Ser Val Pro Val Gly Asp Gly Phe Trp Xaa Arg Val Val Asn
 1               5                   10                  15

Pro Leu Gly Gln Pro Ile Asp Gly Arg Gly Asp Val Asp Ser Asp Thr
            20                  25                  30

Arg Arg Ala Leu Glu Leu Gln Ala Pro Ser Val Val Xaa Arg Gln Gly
            35                  40                  45
```

```
Val Lys Glu Pro Leu Xaa Thr Gly Ile Lys Ala Ile Asp Ala Met Thr
    50                  55                  60

Pro Ile Gly Arg Gly Gln Arg Gln Leu Ile Ile Gly Asp Arg Lys Thr
65                  70                  75                  80

Gly Lys Asn Arg Arg Leu Cys Arg Thr Pro Ser Ser Asn Gln Arg Glu
                85                  90                  95

Glu Leu Gly Val Arg Trp Ile Pro Arg Ser Arg Cys Ala Cys Val Tyr
            100                 105                 110

Val Gly His Arg Ala Arg Arg Gly Thr Tyr His Arg Arg
        115                 120                 125

(2) INFORMATION FOR SEQ ID NO: 86:

(i) SEQUENCE CHARACTERISTICS:
        (A) LENGTH: 117 amino acids
        (B) TYPE: amino acid
        (C) STRANDEDNESS: single
        (D) TOPOLOGY: linear (xi) SEQUENCE DESCRIPTION: SEQ ID NO: 86:

Cys Asp Ala Val Met Gly Phe Leu Gly Gly Ala Gly Pro Leu Ala Val
1               5                   10                  15

Val Asp Gln Gln Leu Val Thr Arg Val Pro Gln Gly Trp Ser Phe Ala
                20                  25                  30

Gln Ala Ala Ala Val Pro Val Val Phe Leu Thr Ala Trp Tyr Gly Leu
            35                  40                  45

Ala Asp Leu Ala Glu Ile Lys Ala Gly Glu Ser Val Leu Ile His Ala
    50                  55                  60

Gly Thr Gly Gly Val Gly Met Ala Ala Val Gln Leu Ala Arg Gln Trp
65                  70                  75                  80

Gly Val Glu Val Phe Val Thr Ala Ser Arg Gly Lys Trp Asp Thr Leu
                85                  90                  95

Arg Ala Xaa Xaa Phe Asp Asp Xaa Pro Tyr Arg Xaa Phe Pro His Xaa
            100                 105                 110

Arg Ser Ser Xaa Gly
        115

(2) INFORMATION FOR SEQ ID NO: 87:

(i) SEQUENCE CHARACTERISTICS:
        (A) LENGTH: 103 amino acids
        (B) TYPE: amino acid
        (C) STRANDEDNESS: single
        (D) TOPOLOGY: linear (xi) SEQUENCE DESCRIPTION: SEQ ID NO: 87:

Met Tyr Arg Phe Ala Cys Arg Thr Leu Met Leu Ala Ala Cys Ile Leu
1               5                   10                  15

Ala Thr Gly Val Ala Gly Leu Gly Val Gly Ala Gln Ser Ala Ala Gln
                20                  25                  30

Thr Ala Pro Val Pro Asp Tyr Tyr Trp Cys Pro Gly Gln Pro Phe Asp
            35                  40                  45

Pro Ala Trp Gly Pro Asn Trp Asp Pro Tyr Thr Cys His Asp Asp Phe
    50                  55                  60

His Arg Asp Ser Asp Gly Pro Asp His Ser Arg Asp Tyr Pro Gly Pro
65                  70                  75                  80

Ile Leu Glu Gly Pro Val Leu Asp Asp Pro Gly Ala Ala Pro Pro Pro
                85                  90                  95
```

```
Pro Ala Ala Gly Gly Gly Ala
            100
```

(2) INFORMATION FOR SEQ ID NO: 88:

(i) SEQUENCE CHARACTERISTICS:
        (A) LENGTH: 88 amino acids
        (B) TYPE: amino acid
        (C) STRANDEDNESS: single
        (D) TOPOLOGY: linear (xi) SEQUENCE DESCRIPTION: SEQ ID NO: 88:

```
Val Gln Cys Arg Val Trp Leu Glu Ile Gln Trp Arg Gly Met Leu Gly
1               5                   10                  15

Ala Asp Gln Ala Arg Ala Gly Gly Pro Ala Arg Ile Trp Arg Glu His
            20                  25                  30

Ser Met Ala Ala Met Lys Pro Arg Thr Gly Asp Gly Pro Leu Glu Ala
        35                  40                  45

Thr Lys Glu Gly Arg Gly Ile Val Met Arg Val Pro Leu Glu Gly Gly
    50                  55                  60

Gly Arg Leu Val Val Glu Leu Thr Pro Asp Ala Ala Ala Leu Leu Gly
65                  70                  75                  80

Asp Glu Leu Lys Gly Val Thr Ser
                85
```

(2) INFORMATION FOR SEQ ID NO: 89:

(i) SEQUENCE CHARACTERISTICS:
        (A) LENGTH: 95 amino acids
        (B) TYPE: amino acid
        (C) STRANDEDNESS: single
        (D) TOPOLOGY: linear (xi) SEQUENCE DESCRIPTION: SEQ ID NO: 89:

```
Thr Asp Ala Ala Thr Leu Ala Gln Glu Ala Gly Asn Phe Glu Arg Ile
1               5                   10                  15

Ser Gly Asp Leu Lys Thr Gln Ile Asp Gln Val Glu Ser Thr Ala Gly
            20                  25                  30

Ser Leu Gln Gly Gln Trp Arg Gly Ala Ala Gly Thr Ala Ala Gln Ala
        35                  40                  45

Ala Val Val Arg Phe Gln Glu Ala Ala Asn Lys Gln Lys Gln Glu Leu
    50                  55                  60

Asp Glu Ile Ser Thr Asn Ile Arg Gln Ala Gly Val Gln Tyr Ser Arg
65                  70                  75                  80

Ala Asp Glu Glu Gln Gln Gln Ala Leu Ser Ser Gln Met Gly Phe
                85                  90                  95
```

(2) INFORMATION FOR SEQ ID NO: 90:

(i) SEQUENCE CHARACTERISTICS:
        (A) LENGTH: 166 amino acids
        (B) TYPE: amino acid
        (C) STRANDEDNESS: single
        (D) TOPOLOGY: linear (xi) SEQUENCE DESCRIPTION: SEQ ID NO: 90:

```
Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Pro Thr Asp Val
            20                  25                  30
```

```
Pro Ile Thr Pro Cys Glu Leu Thr Xaa Xaa Lys Asn Ala Ala Gln Gln
        35                  40                  45

Xaa Val Leu Ser Ala Asp Asn Met Arg Glu Tyr Leu Ala Ala Gly Ala
    50                  55                  60

Lys Glu Arg Gln Arg Leu Ala Thr Ser Leu Arg Asn Ala Ala Lys Xaa
65                  70                  75                  80

Tyr Gly Glu Val Asp Glu Ala Ala Thr Ala Leu Asp Asn Asp Gly
                85                  90                  95

Glu Gly Thr Val Gln Ala Glu Ser Ala Gly Ala Val Gly Gly Asp Ser
                100                 105                 110

Ser Ala Glu Leu Thr Asp Thr Pro Arg Val Ala Thr Ala Gly Glu Pro
            115                 120                 125

Asn Phe Met Asp Leu Lys Glu Ala Ala Arg Lys Leu Glu Thr Gly Asp
            130                 135                 140

Gln Gly Ala Ser Leu Ala His Xaa Gly Asp Gly Trp Asn Thr Xaa Thr
145                 150                 155                 160

Leu Thr Leu Gln Gly Asp
                165

(2) INFORMATION FOR SEQ ID NO: 91:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 91:

Arg Ala Glu Arg Met
1               5

(2) INFORMATION FOR SEQ ID NO: 92:

(i) SEQUENCE CHARACTERISTICS:
        (A) LENGTH: 263 amino acids
        (B) TYPE: amino acid
        (C) STRANDEDNESS: single
        (D) TOPOLOGY: linear (xi) SEQUENCE DESCRIPTION: SEQ ID NO: 92:

Val Ala Trp Met Ser Val Thr Ala Gly Gln Ala Glu Leu Thr Ala Ala
1               5                   10                  15

Gln Val Arg Val Ala Ala Ala Tyr Glu Thr Ala Tyr Gly Leu Thr
            20                  25                  30

Val Pro Pro Pro Val Ile Ala Glu Asn Arg Ala Glu Leu Met Ile Leu
            35                  40                  45

Ile Ala Thr Asn Leu Leu Gly Gln Asn Thr Pro Ala Ile Ala Val Asn
    50                  55                  60

Glu Ala Glu Tyr Gly Glu Met Trp Ala Gln Asp Ala Ala Ala Met Phe
65                  70                  75                  80

Gly Tyr Ala Ala Ala Thr Ala Thr Ala Thr Ala Thr Leu Leu Pro Phe
                85                  90                  95

Glu Glu Ala Pro Glu Met Thr Ser Ala Gly Gly Leu Leu Glu Gln Ala
            100                 105                 110

Ala Ala Val Glu Glu Ala Ser Asp Thr Ala Ala Ala Asn Gln Leu Met
            115                 120                 125

Asn Asn Val Pro Gln Ala Leu Lys Gln Leu Ala Gln Pro Thr Gln Gly
            130                 135                 140
```

```
Thr Thr Pro Ser Ser Lys Leu Gly Gly Leu Trp Lys Thr Val Ser Pro
145                 150                 155                 160

His Arg Ser Pro Ile Ser Asn Met Val Ser Met Ala Asn Asn His Met
                165                 170                 175

Ser Met Thr Asn Ser Gly Val Ser Met Thr Asn Thr Leu Ser Ser Met
            180                 185                 190

Leu Lys Gly Phe Ala Pro Ala Ala Ala Gln Ala Val Gln Thr Ala
        195                 200                 205

Ala Gln Asn Gly Val Arg Ala Met Ser Ser Leu Gly Ser Ser Leu Gly
    210                 215                 220

Ser Ser Gly Leu Gly Gly Val Ala Ala Asn Leu Gly Arg Ala Ala
225                 230                 235                 240

Ser Val Arg Tyr Gly His Arg Asp Gly Gly Lys Tyr Ala Xaa Ser Gly
                245                 250                 255

Arg Arg Asn Gly Gly Pro Ala
            260
```

(2) INFORMATION FOR SEQ ID NO: 93:

(i) SEQUENCE CHARACTERISTICS:
        (A) LENGTH: 303 amino acids
        (B) TYPE: amino acid
        (C) STRANDEDNESS: single
        (D) TOPOLOGY: linear (xi) SEQUENCE DESCRIPTION: SEQ ID NO: 93:

```
Met Thr Tyr Ser Pro Gly Asn Pro Gly Tyr Pro Gln Ala Gln Pro Ala
1               5                   10                  15

Gly Ser Tyr Gly Gly Val Thr Pro Ser Phe Ala His Ala Asp Glu Gly
            20                  25                  30

Ala Ser Lys Leu Pro Met Tyr Leu Asn Ile Ala Val Ala Val Leu Gly
        35                  40                  45

Leu Ala Ala Tyr Phe Ala Ser Phe Gly Pro Met Phe Thr Leu Ser Thr
50                  55                  60

Glu Leu Gly Gly Gly Asp Gly Ala Val Ser Gly Asp Thr Gly Leu Pro
65                  70                  75                  80

Val Gly Val Ala Leu Leu Ala Ala Leu Leu Ala Gly Val Val Leu Val
                85                  90                  95

Pro Lys Ala Lys Ser His Val Thr Val Val Ala Val Leu Gly Val Leu
                100                 105                 110

Gly Val Phe Leu Met Val Ser Ala Thr Phe Asn Lys Pro Ser Ala Tyr
            115                 120                 125

Ser Thr Gly Trp Ala Leu Trp Val Val Leu Ala Phe Ile Val Phe Gln
        130                 135                 140

Ala Val Ala Ala Val Leu Ala Leu Leu Val Glu Thr Gly Ala Ile Thr
145                 150                 155                 160

Ala Pro Ala Pro Arg Pro Lys Phe Asp Pro Tyr Gly Gln Tyr Gly Arg
                165                 170                 175

Tyr Gly Gln Tyr Gly Gln Tyr Gly Val Gln Pro Gly Gly Tyr Tyr Gly
            180                 185                 190

Gln Gln Gly Ala Gln Gln Ala Ala Gly Leu Gln Ser Pro Gly Pro Gln
        195                 200                 205

Gln Ser Pro Gln Pro Pro Gly Tyr Gly Ser Tyr Gly Gly Tyr Ser
    210                 215                 220

Ser Ser Pro Ser Gln Ser Gly Ser Gly Tyr Thr Ala Gln Pro Pro Ala
225                 230                 235                 240
```

```
Gln Pro Pro Ala Gln Ser Gly Ser Gln Ser His Gln Gly Pro Ser
                245                 250                 255

Thr Pro Pro Thr Gly Phe Pro Ser Phe Ser Pro Pro Pro Val Ser
                260                 265                 270

Ala Gly Thr Gly Ser Gln Ala Gly Ser Ala Pro Val Asn Tyr Ser Asn
                275                 280                 285

Pro Ser Gly Gly Glu Gln Ser Ser Ser Pro Gly Gly Ala Pro Val
                290                 295                 300
```

(2) INFORMATION FOR SEQ ID NO: 94:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO: 94:

```
ATGAAGATGG TGAAATCGAT CGCCGCAGGT CTGACCGCCG CGGCTGCAAT CGGCGCCGCT      60

GCGGCCGGTG TGACTTCGAT CATGGCTGGC GGCCCGGTCG TATACCAGAT GCAGCCGGTC     120

GTCTTCGGCG CGCCACTGCC GTTGGACCCG GCATCCGCCC CTGACGTCCC GACCGCCGCC     180

CAGTTGACCA GCCTGCTCAA CAGCCTCGCC GATCCCAACG TGTCGTTTGC GAACAAGGGC     240

AGTCTGGTCG AGGGCGGCAT CGGGGGCACC GAGGCGCGCA TCGCCGACCA CAAGCTGAAG     300

AAGGCCGCCG AGCACGGGGA TCTGCCGCTG TCGTTCAGCG TGACGAACAT CCAGCCGGCG     360

GCCGCCGGTT CGGCCACCGC CGACGTTTCC GTCTCGGGTC CGAAGCTCTC GTCGCCGGTC     420

ACGCAGAACG TCACGTTCGT GAATCAAGGC GGCTGGATGC TGTCACGCGC ATCGGCGATG     480

GAGTTGCTGC AGGCCGCAGG GAACTGA                                         507
```

(2) INFORMATION FOR SEQ ID NO: 95:

(i) SEQUENCE CHARACTERISTICS:
        (A) LENGTH: 168 amino acids
        (B) TYPE: amino acid
        (C) STRANDEDNESS: single
        (D) TOPOLOGY: linear (xi) SEQUENCE DESCRIPTION: SEQ ID NO: 95:

```
Met Lys Met Val Lys Ser Ile Ala Ala Gly Leu Thr Ala Ala Ala
1               5                   10                  15

Ile Gly Ala Ala Ala Gly Val Thr Ser Ile Met Ala Gly Gly Pro
                20                  25                  30

Val Val Tyr Gln Met Gln Pro Val Val Phe Gly Ala Pro Leu Pro Leu
                35                  40                  45

Asp Pro Ala Ser Ala Pro Asp Val Pro Thr Ala Ala Gln Leu Thr Ser
    50                  55                  60

Leu Leu Asn Ser Leu Ala Asp Pro Asn Val Ser Phe Ala Asn Lys Gly
65                  70                  75                  80

Ser Leu Val Glu Gly Gly Ile Gly Gly Thr Glu Ala Arg Ile Ala Asp
                85                  90                  95

His Lys Leu Lys Lys Ala Ala Glu His Gly Asp Leu Pro Leu Ser Phe
                100                 105                 110

Ser Val Thr Asn Ile Gln Pro Ala Ala Ala Gly Ser Ala Thr Ala Asp
        115                 120                 125

Val Ser Val Ser Gly Pro Lys Leu Ser Ser Pro Val Thr Gln Asn Val
        130                 135                 140
```

```
Thr Phe Val Asn Gln Gly Gly Trp Met Leu Ser Arg Ala Ser Ala Met
145                 150                 155                 160

Glu Leu Leu Gln Ala Ala Gly Asn
            165
```

(2) INFORMATION FOR SEQ ID NO: 96:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (xi) SEQUENCE DESCRIPTION: SEQ ID NO: 96:

```
CGTGGCAATG TCGTTGACCG TCGGGGCCGG GGTCGCCTCC GCAGATCCCG TGGACGCGGT    60

CATTAACACC ACCTGCAATT ACGGGCAGGT AGTAGCTGCG CTCAACGCGA CGGATCCGGG   120

GGCTGCCGCA CAGTTCAACG CCTCACCGGT GGCGCAGTCC TATTTGCGCA ATTTCCTCGC   180

CGCACCGCCA CCTCAGCGCG CTGCCATGGC CGCGCAATTG CAAGCTGTGC CGGGGGCGGC   240

ACAGTACATC GGCCTTGTCG AGTCGGTTGC CGGCTCCTGC AACAACTATT AAGCCCATGC   300

GGGCCCCATC CCGCGACCCG GCATCGTCGC CGGGGCTAGG CCAGATTGCC CCGCTCCTCA   360

ACGGGCCGCA TCCCGCGACC CGGCATCGTC GCCGGGGCTA GGCCAGATTG CCCCGCTCCT   420

CAACGGGCCG CATCTCGTGC CGAATTCCTG CAGCCCGGGG GATCCACTAG TTCTAGAGCG   480

GCCGCCACCG CGGTGGAGCT                                              500
```

(2) INFORMATION FOR SEQ ID NO: 97:

(i) SEQUENCE CHARACTERISTICS:
        (A) LENGTH: 96 amino acids
        (B) TYPE: amino acid
        (C) STRANDEDNESS: single
        (D) TOPOLOGY: linear (xi) SEQUENCE DESCRIPTION: SEQ ID NO: 97:

```
Val Ala Met Ser Leu Thr Val Gly Ala Gly Val Ala Ser Ala Asp Pro
1               5                   10                  15

Val Asp Ala Val Ile Asn Thr Thr Cys Asn Tyr Gly Gln Val Val Ala
                20                  25                  30

Ala Leu Asn Ala Thr Asp Pro Gly Ala Ala Gln Phe Asn Ala Ser
            35                  40                  45

Pro Val Ala Gln Ser Tyr Leu Arg Asn Phe Leu Ala Ala Pro Pro Pro
    50                  55                  60

Gln Arg Ala Ala Met Ala Ala Gln Leu Gln Ala Val Pro Gly Ala Ala
65                  70                  75                  80

Gln Tyr Ile Gly Leu Val Glu Ser Val Ala Gly Ser Cys Asn Asn Tyr
                85                  90                  95
```

(2) INFORMATION FOR SEQ ID NO: 98:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (xi) SEQUENCE DESCRIPTION: SEQ ID NO: 98:

```
ATGACAGAGC AGCAGTGGAA TTTCGCGGGT ATCGAGGCCG CGGCAAGCGC AATCCAGGGA    60

AATGTCACGT CCATTCATTC CCTCCTTGAC GAGGGGAAGC AGTCCCTGAC CAAGCTCGCA   120
```

```
GCGGCCTGGG GCGGTAGCGG TTCGGAAGCG TACC                                154
```

(2) INFORMATION FOR SEQ ID NO: 99:

(i) SEQUENCE CHARACTERISTICS:
        (A) LENGTH: 51 amino acids
        (B) TYPE: amino acid
        (C) STRANDEDNESS: single
        (D) TOPOLOGY: linear (xi) SEQUENCE DESCRIPTION: SEQ ID NO: 99:

```
Met Thr Glu Gln Gln Trp Asn Phe Ala Gly Ile Glu Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr
    50
```

(2) INFORMATION FOR SEQ ID NO: 100:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (xi) SEQUENCE DESCRIPTION: SEQ ID NO: 100:

```
CGGTCGCGCA CTTCCAGGTG ACTATGAAAG TCGGCTTCCG NCTGGAGGAT TCCTGAACCT    60

TCAAGCGCGG CCGATAACTG AGGTGCATCA TTAAGCGACT TTTCCAGAAC ATCCTGACGC   120

GCTCGAAACG CGGCACAGCC GACGGTGGCT CCGNCGAGGC GCTGNCTCCA AAATCCCTGA   180

GACAATTCGN CGGGGCGCC TACAAGGAAG TCGGTGCTGA ATTCGNCGNG TATCTGGTCG   240

ACCTGTGTGG TCTGNAGCCG ACGAAGCGG TGCTCGACGT CG                     282
```

(2) INFORMATION FOR SEQ ID NO: 101:

(i) SEQUENCE CHARACTERISTICS:
        (A) LENGTH: 3058 base pairs
        (B) TYPE: nucleic acid
        (C) STRANDEDNESS: single
        (D) TOPOLOGY: linear (xi) SEQUENCE DESCRIPTION: SEQ ID NO: 101:

```
GATCGTACCC GTGCGAGTGC TCGGGCCGTT TGAGGATGGA GTGCACGTGT CTTTCGTGAT    60

GGCATACCCA GAGATGTTGG CGGCGGCGGC TGACACCCTG CAGAGCATCG GTGCTACCAC   120

TGTGGCTAGC AATGCCGCTG CGGCGGCCCC GACGACTGGG GTGGTGCCCC CCGCTGCCGA   180

TGAGGTGTCG GCGCTGACTG CGGCGCACTT CGCCGCACAT GCGGCGATGT ATCAGTCCGT   240

GAGCGCTCGG GCTGCTGCGA TTCATGACCA GTTCGTGGCC ACCCTTGCCA GCAGCGCCAG   300

CTCGTATGCG GCCACTGAAG TCGCCAATGC GGCGGCGGCC AGCTAAGCCA GGAACAGTCG   360

GCACGAGAAA CCACGAGAAA TAGGGACACG TAATGGTGGA TTTCGGGGCG TTACCACCGG   420

AGATCAACTC CGCGAGGATG TACGCCGGCC CGGGTTCGGC CTCGCTGGTG GCCGCGGCTC   480

AGATGTGGGA CAGCGTGGCG AGTGACCTGT TTTCGGCCGC GTCGGCGTTT CAGTCGGTGG   540

TCTGGGTCT GACGGTGGGG TCGTGGATAG GTTCGTCGGC GGGTCTGATG GTGGCGGCGG   600

CCTCGCCGTA TGTGGCGTGG ATGAGCGTCA CCGCGGGGCA GGCCGAGCTG ACCGCCGCCC   660
```

```
                                                              -continued

AGGTCCGGGT TGCTGCGGCG GCCTACGAGA CGGCGTATGG GCTGACGGTG CCCCCGCCGG      720

TGATCGCCGA GAACCGTGCT GAACTGATGA TTCTGATAGC GACCAACCTC TTGGGGCAAA      780

ACACCCCGGC GATCGCGGTC AACGAGGCCG AATACGGCGA GATGTGGGCC CAAGACGCCG      840

CCGCGATGTT TGGCTACGCC GCGGCGACGG CGACGGCGAC GGCGACGTTG CTGCCGTTCG      900

AGGAGGCGCC GGAGATGACC AGCGCGGGTG GGCTCCTCGA GCAGGCCGCC GCGGTCGAGG      960

AGGCCTCCGA CACCGCCGCG GCGAACCAGT TGATGAACAA TGTGCCCCAG GCGCTGCAAC     1020

AGCTGGCCCA GCCCACGCAG GGCACCACGC CTTCTTCCAA GCTGGGTGGC CTGTGGAAGA     1080

CGGTCTCGCC GCATCGGTCG CCGATCAGCA ACATGGTGTC GATGGCCAAC AACCACATGT     1140

CGATGACCAA CTCGGGTGTG TCGATGACCA ACACCTTGAG CTCGATGTTG AAGGGCTTTG     1200

CTCCGGCGGC GGCCGCCCAG GCCGTGCAAA CCGCGGCGCA AAACGGGGTC CGGGCGATGA     1260

GCTCGCTGGG CAGCTCGCTG GGTTCTTCGG GTCTGGGCGG TGGGGTGGCC GCCAACTTGG     1320

GTCGGGCGGC CTCGGTCGGT TCGTTGTCGG TGCCGCAGGC CTGGGCCGCG GCCAACCAGG     1380

CAGTCACCCC GGCGGCGCGG GCGCTGCCGC TGACCAGCCT GACCAGCGCC GCGGAAAGAG     1440

GGCCCGGGCA GATGCTGGGC GGGCTGCCGG TGGGGCAGAT GGGCGCCAGG GCCGGTGGTG     1500

GGCTCAGTGG TGTGCTGCGT GTTCCGCCGC GACCCTATGT GATGCCGCAT TCTCCGGCGG     1560

CCGGCTAGGA GAGGGGCGC AGACTGTCGT TATTTGACCA GTGATCGGCG GTCTCGGTGT     1620

TTCCGCGGCC GGCTATGACA ACAGTCAATG TGCATGACAA GTTACAGGTA TTAGGTCCAG     1680

GTTCAACAAG GAGACAGGCA ACATGGCCTC ACGTTTTATG ACGGATCCGC ACGCGATGCG     1740

GGACATGGCG GGCCGTTTTG AGGTGCACGC CCAGACGGTG GAGGACGAGG CTCGCCGGAT     1800

GTGGGCGTCC GCGCAAAACA TTTCCGGTGC GGGCTGGAGT GGCATGGCCG AGGCGACCTC     1860

GCTAGACACC ATGGCCCAGA TGAATCAGGC GTTTCGCAAC ATCGTGAACA TGCTGCACGG     1920

GGTGCGTGAC GGGCTGGTTC GCGACGCCAA CAACTACGAG CAGCAAGAGC AGGCCTCCCA     1980

GCAGATCCTC AGCAGCTAAC GTCAGCCGCT GCAGCACAAT ACTTTTACAA GCGAAGGAGA     2040

ACAGGTTCGA TGACCATCAA CTATCAATTC GGGGATGTCG ACGCTCACGG CGCCATGATC     2100

CGCGCTCAGG CCGGGTTGCT GGAGGCCGAG CATCAGGCCA TCATTCGTGA TGTGTTGACC     2160

GCGAGTGACT TTTGGGGCGG CGCCGGTTCG GCGGCCTGCC AGGGGTTCAT TACCCAGTTG     2220

GGCCGTAACT TCCAGGTGAT CTACGAGCAG GCCAACGCCC ACGGGCAGAA GGTGCAGGCT     2280

GCCGGCAACA ACATGGCGCA AACCGACAGC GCCGTCGGCT CCAGCTGGGC CTGACACCAG     2340

GCCAAGGCCA GGGACGTGGT GTACGAGTGA AGTTCCTCGC GTGATCCTTC GGGTGGCAGT     2400

CTAAGTGGTC AGTGCTGGGG TGTTGGTGGT TTGCTGCTTG GCGGGTTCTT CGGTGCTGGT     2460

CAGTGCTGCT CGGGCTCGGG TGAGGACCTC GAGGCCCAGG TAGCGCCGTC CTTCGATCCA     2520

TTCGTCGTGT TGTTCGGCGA GGACGGCTCC GACGAGGCGG ATGATCGAGG CGCGGTCGGG     2580

GAAGATGCCC ACGACGTCGG TTCGGCGTCG TACCTCTCGG TTGAGGCGTT CCTGGGGGTT     2640

GTTGGACCAG ATTTGGCGCC AGATCTGCTT GGGGAAGGCG GTGAACGCCA GCAGGTCGGT     2700

GCGGGCGGTG TCGAGGTGCT CGGCCACCGC GGGGAGTTTG TCGGTCAGAG CGTCGAGTAC     2760

CCGATCATAT TGGGCAACAA CTGATTCGGC GTCGGGCTGG TCGTAGATGG AGTGCAGCAG     2820

GGTGCGCACC CACGGCCAGG AGGGCTTCGG GGTGGCTGCC ATCAGATTGG CTGCGTAGTG     2880

GGTTCTGCAG CGCTGCCAGG CCGCTGCGGG CAGGGTGGCG CCGATCGCGG CCACCAGGCC     2940

GGCGTGGGCG TCGCTGGTGA CCAGCGCGAC CCCGGACAGG CCGCGGGCGA CCAGGTCGCG     3000
```

GAAGAACGCC AGCCAGCCGG CCCCGTCCTC GGCGGAGGTG ACCTGGATGC CCAGGATC        3058

(2) INFORMATION FOR SEQ ID NO: 102:

(i) SEQUENCE CHARACTERISTICS:
        (A) LENGTH: 391 amino acids
        (B) TYPE: amino acid
        (C) STRANDEDNESS: single
        (D) TOPOLOGY: linear (xi) SEQUENCE DESCRIPTION: SEQ ID NO: 102:

```
Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Gln Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Val Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Val Ile Ala
                100                 105                 110

Glu Asn Arg Ala Glu Leu Met Ile Leu Ile Ala Thr Asn Leu Leu Gly
                115                 120                 125

Gln Asn Thr Pro Ala Ile Ala Val Asn Glu Ala Glu Tyr Gly Glu Met
        130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
                180                 185                 190

Asp Thr Ala Ala Ala Asn Gln Leu Met Asn Asn Val Pro Gln Ala Leu
        195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
                340                 345                 350
```

```
Gln Met Leu Gly Gly Leu Pro Val Gly Gln Met Gly Ala Arg Ala Gly
        355                 360                 365

Gly Gly Leu Ser Gly Val Leu Arg Val Pro Pro Arg Pro Tyr Val Met
370                 375                 380

Pro His Ser Pro Ala Ala Gly
385                 390

(2) INFORMATION FOR SEQ ID NO: 103:

(i) SEQUENCE CHARACTERISTICS:
        (A) LENGTH: 1725 base pairs
        (B) TYPE: nucleic acid
        (C) STRANDEDNESS: single
        (D) TOPOLOGY: linear (xi) SEQUENCE DESCRIPTION: SEQ ID NO: 103:
```

| | | | | | |
|---|---|---|---|---|---|
| GACGTCAGCA | CCCGCCGTGC | AGGGCTGGAG | CGTGGTCGGT | TTTGATCTGC | GGTCAAGGTG | 60 |
| ACGTCCCTCG | GCGTGTCGCC | GGCGTGGATG | CAGACTCGAT | GCCGCTCTTT | AGTGCAACTA | 120 |
| ATTTCGTTGA | AGTGCCTGCG | AGGTATAGGA | CTTCACGATT | GGTTAATGTA | GCGTTCACCC | 180 |
| CGTGTTGGGG | TCGATTTGGC | CGGACCAGTC | GTCACCAACG | CTTGGCGTGC | GCGCCAGGCG | 240 |
| GGCGATCAGA | TCGCTTGACT | ACCAATCAAT | CTTGAGCTCC | CGGGCCGATG | CTCGGGCTAA | 300 |
| ATGAGGAGGA | GCACGCGTGT | CTTTCACTGC | GCAACCGGAG | ATGTTGGCGG | CCGCGGCTGG | 360 |
| CGAACTTCGT | TCCCTGGGGG | CAACGCTGAA | GGCTAGCAAT | GCCGCCGCAG | CCGTGCCGAC | 420 |
| GACTGGGGTG | GTGCCCCCGG | CTGCCGACGA | GGTGTCGCTG | CTGCTTGCCA | CACAATTCCG | 480 |
| TACGCATGCG | GCGACGTATC | AGACGGCCAG | CGCCAAGGCC | GCGGTGATCC | ATGAGCAGTT | 540 |
| TGTGACCACG | CTGGCCACCA | GCGCTAGTTC | ATATGCGGAC | ACCGAGGCCG | CCAACGCTGT | 600 |
| GGTCACCGGC | TAGCTGACCT | GACGGTATTC | GAGCGGAAGG | ATTATCGAAG | TGGTGGATTT | 660 |
| CGGGGCGTTA | CCACCGGAGA | TCAACTCCGC | GAGGATGTAC | GCCGGCCCGG | GTTCGGCCTC | 720 |
| GCTGGTGGCC | GCCGCGAAGA | TGTGGGACAG | CGTGGCGAGT | GACCTGTTTT | CGGCCGCGTC | 780 |
| GGCGTTTCAG | TCGGTGGTCT | GGGGTCTGAC | GGTGGGGTCG | TGGATAGGTT | CGTCGGCGGG | 840 |
| TCTGATGGCG | GCGGCGGCCT | CGCCGTATGT | GGCGTGGATG | AGCGTCACCG | CGGGGCAGGC | 900 |
| CCAGCTGACC | GCCGCCCAGG | TCCGGGTTGC | TGCGGCGGCC | TACGAGACAG | CGTATAGGCT | 960 |
| GACGGTGCCC | CCGCCGGTGA | TCGCCGAGAA | CCGTACCGAA | CTGATGACGC | TGACCGCGAC | 1020 |
| CAACCTCTTG | GGGCAAAACA | CGCCGGCGAT | CGAGGCCAAT | CAGGCCGCAT | ACAGCCAGAT | 1080 |
| GTGGGGCCAA | GACGCGGAGG | CGATGTATGG | CTACGCCGCC | ACGGCGGCGA | CGGCGACCGA | 1140 |
| GGCGTTGCTG | CCGTTCGAGG | ACGCCCCACT | GATCACCAAC | CCCGGCGGGC | TCCTTGAGCA | 1200 |
| GGCCGTCGCG | GTCGAGGAGG | CCATCGACAC | CGCCGCGGCG | AACCAGTTGA | TGAACAATGT | 1260 |
| GCCCCAAGCG | CTGCAACAGC | TGGCCCAGCC | AGCGCAGGGC | GTCGTACCTT | CTTCCAAGCT | 1320 |
| GGGTGGGCTG | TGGACGGCGG | TCTCGCCGCA | TCTGTCGCCG | CTCAGCAACG | TCAGTTCGAT | 1380 |
| AGCCAACAAC | CACATGTCGA | TGATGGGCAC | GGGTGTGTCG | ATGACCAACA | CCTTGCACTC | 1440 |
| GATGTTGAAG | GCCTTAGCTC | CGGCGGCGGC | TCAGGCCGTG | GAAACCGCGG | CGGAAAACGG | 1500 |
| GGTCTGGGCG | ATGAGCTCGC | TGGGCAGCCA | GCTGGGTTCG | TCGCTGGGTT | CTTCGGGTCT | 1560 |
| GGGCGCTGGG | GTGGCCGCCA | ACTTGGGTCG | GGCGGCCTCG | GTCGGTTCGT | TGTCGGTGCC | 1620 |
| GCCAGCATGG | GCCGCGGCCA | ACCAGGCGGT | CACCCCGGCG | GCGCGGGCGC | TGCCGCTGAC | 1680 |
| CAGCCTGACC | AGCGCCGCCC | AAACCGCCCC | CGGACACATG | CTGGG | | 1725 |

-continued (2) INFORMATION FOR SEQ ID NO: 104:

(i) SEQUENCE CHARACTERISTICS:
        (A) LENGTH: 359 amino acids
        (B) TYPE: amino acid
        (C) STRANDEDNESS: <Unknown>
        (D) TOPOLOGY: linear (xi) SEQUENCE DESCRIPTION: SEQ ID NO: 104:

```
Val Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
            35                  40                  45

Val Val Trp Gly Leu Thr Val Gly Ser Trp Ile Gly Ser Ser Ala Gly
50                  55                  60

Leu Met Ala Ala Ala Ser Pro Tyr Val Ala Trp Met Ser Val Thr
65                  70                  75                  80

Ala Gly Gln Ala Gln Leu Thr Ala Ala Gln Val Arg Val Ala Ala
                85                  90                  95

Ala Tyr Glu Thr Ala Tyr Arg Leu Thr Val Pro Pro Val Ile Ala
                100                 105                 110

Glu Asn Arg Thr Glu Leu Met Thr Leu Thr Ala Thr Asn Leu Leu Gly
                115                 120                 125

Gln Asn Thr Pro Ala Ile Glu Ala Asn Gln Ala Ala Tyr Ser Gln Met
            130                 135                 140

Trp Gly Gln Asp Ala Glu Ala Met Tyr Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
                180                 185                 190

Asp Thr Ala Ala Ala Asn Gln Leu Met Asn Asn Val Pro Gln Ala Leu
            195                 200                 205

Gln Gln Leu Ala Gln Pro Ala Gln Gly Val Val Pro Ser Ser Lys Leu
210                 215                 220

Gly Gly Leu Trp Thr Ala Val Ser Pro His Leu Ser Pro Leu Ser Asn
225                 230                 235                 240

Val Ser Ser Ile Ala Asn Asn His Met Ser Met Met Gly Thr Gly Val
                245                 250                 255

Ser Met Thr Asn Thr Leu His Ser Met Leu Lys Gly Leu Ala Pro Ala
                260                 265                 270

Ala Ala Gln Ala Val Glu Thr Ala Glu Asn Gly Val Trp Ala Met
            275                 280                 285

Ser Ser Leu Gly Ser Gln Leu Gly Ser Ser Leu Gly Ser Ser Gly Leu
            290                 295                 300

Gly Ala Gly Val Ala Ala Asn Leu Gly Arg Ala Ala Ser Val Gly Ser
305                 310                 315                 320

Leu Ser Val Pro Pro Ala Trp Ala Ala Ala Asn Gln Ala Val Thr Pro
                325                 330                 335

Ala Ala Arg Ala Leu Pro Leu Thr Ser Leu Thr Ser Ala Ala Gln Thr
                340                 345                 350

Ala Pro Gly His Met Leu Gly
            355
```

(2) INFORMATION FOR SEQ ID NO: 105:

(i) SEQUENCE CHARACTERISTICS:
        (A) LENGTH: 3027 base pairs
        (B) TYPE: nucleic acid
        (C) STRANDEDNESS: single
        (D) TOPOLOGY: linear (xi) SEQUENCE DESCRIPTION: SEQ ID NO: 105:

```
AGTTCAGTCG AGAATGATAC TGACGGGCTG TATCCACGAT GGCTGAGACA ACCGAACCAC      60

CGTCGGACGC GGGGACATCG CAAGCCGACG CGATGGCGTT GGCCGCCGAA GCCGAAGCCG     120

CCGAAGCCGA AGCGCTGGCC GCCGCGGCGC GGGCCCGTGC CCGTGCCGCC CGGTTGAAGC     180

GTGAGGCGCT GGCGATGGCC CCAGCCGAGG ACGAGAACGT CCCCGAGGAT ATGCAGACTG     240

GGAAGACGCC GAAGACTATG ACGACTATGA CGACTATGAG GCCGCAGACC AGGAGGCCGC     300

ACGGTCGGCA TCCTGGCGAC GGCGGTTGCG GGTGCGGTTA CCAAGACTGT CCACGATTGC     360

CATGGCGGCC GCAGTCGTCA TCATCTGCGG CTTCACCGGG CTCAGCGGAT ACATTGTGTG     420

GCAACACCAT GAGGCCACCG AACGCCAGCA GCGCGCCGCG GCGTTCGCCG CCGGAGCCAA     480

GCAAGGTGTC ATCAACATGA CCTCGCTGGA CTTCAACAAG GCCAAAGAAG ACGTCGCGCG     540

TGTGATCGAC AGCTCCACCG GCGAATTCAG GGATGACTTC CAGCAGCGGG CAGCCGATTT     600

CACCAAGGTT GTCGAACAGT CCAAAGTGGT CACCGAAGGC ACGGTGAACG CGACAGCCGT     660

CGAATCCATG AACGAGCATT CCGCCGTGGT GCTCGTCGCG GCGACTTCAC GGGTCACCAA     720

TTCCGCTGGG GCGAAAGACG AACCACGTGC GTGGCGGCTC AAAGTGACCG TGACCGAAGA     780

GGGGGGACAG TACAAGATGT CGAAAGTTGA GTTCGTACCG TGACCGATGA CGTACGCGAC     840

GTCAACACCG AAACCACTGA CGCCACCGAA GTCGCTGAGA TCGACTCAGC CGCAGGCGAA     900

GCCGGTGATT CGGCGACCGA GGCATTTGAC ACCGACTCTG CAACGGAATC TACCGCGCAG     960

AAGGGTCAGC GGCACCGTGA CCTGTGGCGA ATGCAGGTTA CCTTGAAACC CGTTCCGGTG    1020

ATTCTCATCC TGCTCATGTT GATCTCTGGG GGCGCGACGG GATGGCTATA CCTTGAGCAA    1080

TACGACCCGA TCAGCAGACG GACTCCGGCG CCGCCCGTGC TGCCGTCGCC GCGGCGTCTG    1140

ACGGGACAAT CGCGCTGTTG TGTATTCACC CGACACGTCG ACCAAGACTT CGCTACCGCC    1200

AGGTCGCACC TCGCCGGCGA TTTCCTGTCC TATACGACCA GTTCACGCAG CAGATCGTGG    1260

CTCCGGCGGC CAAACAGAAG TCACTGAAAA CCACCGCCAA GGTGGTGCGC GCGGCCGTGT    1320

CGGAGCTACA TCCGGATTCG GCCGTCGTTC TGGTTTTTGT CGACCAGAGC ACTACCAGTA    1380

AGGACAGCCC CAATCCGTCG ATGGCGGCCA GCAGCGTGAT GGTGACCCTA GCCAAGGTCG    1440

ACGGCAATTG GCTGATCACC AAGTTCACCC CGGTTTAGGT TGCCGTAGGC GGTCGCCAAG    1500

TCTGACGGGG GCGCGGGTGG CTGCTCGTGC GAGATACCGG CCGTTCTCCG GACAATCACG    1560

GCCCGACCTC AAACAGATCT CGGCCGCTGT CTAATCGGCC GGGTTATTTA AGATTAGTTG    1620

CCACTGTATT TACCTGATGT TCAGATTGTT CAGCTGGATT TAGCTTCGCG GCAGGGCGGC    1680

TGGTGCACTT TGCATCTGGG GTTGTGACTA CTTGAGAGAA TTTGACCTGT TGCCGACGTT    1740

GTTTGCTGTC CATCATTGGT GCTAGTTATG GCCGAGCGGA AGGATTATCG AAGTGGTGGA    1800

CTTCGGGGCG TTACCACCGG AGATCAACTC CGCGAGGATG TACGCCGGCC CGGGTTCGGC    1860

CTCGCTGGTG GCCGCCGCGA AGATGTGGGA CAGCGTGGCG AGTGACCTGT TTTCGGCCGC    1920

GTCGGCGTTT CAGTCGGTGG TCTGGGGTCT GACGACGGGA TCGTGGATAG GTTCGTCGGC    1980

GGGTCTGATG GTGGCGGCGG CCTCGCCGTA TGTGGCGTGG ATGAGCGTCA CCGCGGGGCA    2040
```

-continued

```
GGCCGAGCTG ACCGCCGCCC AGGTCCGGGT TGCTGCGGCG GCCTACGAGA CGGCGTATGG    2100

GCTGACGGTG CCCCCGCCGG TGATCGCCGA GAACCGTGCT GAACTGATGA TTCTGATAGC    2160

GACCAACCTC TTGGGGCAAA ACACCCCGGC GATCGCGGTC AACGAGGCCG AATACGGGGA    2220

GATGTGGGCC CAAGACGCCG CCGCGATGTT TGGCTACGCC GCCACGGCGG CGACGGCGAC    2280

CGAGGCGTTG CTGCCGTTCG AGGACGCCCC ACTGATCACC AACCCCGGCG GGCTCCTTGA    2340

GCAGGCCGTC GCGGTCGAGG AGGCCATCGA CACCGCCGCG GCGAACCAGT TGATGAACAA    2400

TGTGCCCCAA GCGCTGCAAC AACTGGCCCA GCCCACGAAA AGCATCTGGC CGTTCGACCA    2460

ACTGAGTGAA CTCTGGAAAG CCATCTCGCC GCATCTGTCG CCGCTCAGCA ACATCGTGTC    2520

GATGCTCAAC AACCACGTGT CGATGACCAA CTCGGGTGTG TCGATGGCCA GCACCTTGCA    2580

CTCAATGTTG AAGGGCTTTG CTCCGGCGGC GGCTCAGGCC GTGGAAACCG CGGCGCAAAA    2640

CGGGGTCCAG GCGATGAGCT CGCTGGGCAG CCAGCTGGGT TCGTCGCTGG GTTCTTCGGG    2700

TCTGGGCGCT GGGGTGGCCG CCAACTTGGG TCGGGCGGCC TCGGTCGGTT CGTTGTCGGT    2760

GCCGCAGGCC TGGGCCGCGG CCAACCAGGC GGTCACCCCG GCGGCGCGGG CGCTGCCGCT    2820

GACCAGCCTG ACCAGCGCCG CCCAAACCGC CCCCGGACAC ATGCTGGGCG GGCTACCGCT    2880

GGGGCAACTG ACCAATAGCG GCGGCGGGTT CGGCGGGGTT AGCAATGCGT TGCGGATGCC    2940

GCCGCGGGCG TACGTAATGC CCCGTGTGCC CGCCGCCGGG TAACGCCGAT CCGCACGCAA    3000

TGCGGGCCCT CTATGCGGGC AGCGATC                                       3027
```

(2) INFORMATION FOR SEQ ID NO: 106:

(i) SEQUENCE CHARACTERISTICS:
        (A) LENGTH: 396 amino acids
        (B) TYPE: amino acid
        (C) STRANDEDNESS: <Unknown>
        (D) TOPOLOGY: linear (xi) SEQUENCE DESCRIPTION: SEQ ID NO: 106:

```
Val Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
            35                  40                  45

Val Val Trp Gly Leu Thr Thr Gly Ser Trp Ile Gly Ser Ser Ala Gly
    50                  55                  60

Leu Met Val Ala Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Val Ile Ala
            100                 105                 110

Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
```

-continued

```
            180                 185                 190
Asp Thr Ala Ala Ala Asn Gln Leu Met Asn Asn Val Pro Gln Ala Leu
        195                 200                 205

Gln Gln Leu Ala Gln Pro Thr Lys Ser Ile Trp Pro Phe Asp Gln Leu
    210                 215                 220

Ser Glu Leu Trp Lys Ala Ile Ser Pro His Leu Ser Pro Leu Ser Asn
225                 230                 235                 240

Ile Val Ser Met Leu Asn Asn His Val Ser Met Thr Asn Ser Gly Val
                245                 250                 255

Ser Met Ala Ser Thr Leu His Ser Met Leu Lys Gly Phe Ala Pro Ala
        260                 265                 270

Ala Ala Gln Ala Val Glu Thr Ala Ala Gln Asn Gly Val Gln Ala Met
    275                 280                 285

Ser Ser Leu Gly Ser Gln Leu Gly Ser Ser Leu Gly Ser Ser Gly Leu
    290                 295                 300

Gly Ala Gly Val Ala Ala Asn Leu Gly Arg Ala Ala Ser Val Gly Ser
305                 310                 315                 320

Leu Ser Val Pro Gln Ala Trp Ala Ala Ala Asn Gln Ala Val Thr Pro
                325                 330                 335

Ala Ala Arg Ala Leu Pro Leu Thr Ser Leu Thr Ser Ala Ala Gln Thr
            340                 345                 350

Ala Pro Gly His Met Leu Gly Gly Leu Pro Leu Gly Gln Leu Thr Asn
        355                 360                 365

Ser Gly Gly Gly Phe Gly Gly Val Ser Asn Ala Leu Arg Met Pro Pro
    370                 375                 380

Arg Ala Tyr Val Met Pro Arg Val Pro Ala Ala Gly
385                 390                 395
```

(2) INFORMATION FOR SEQ ID NO: 107:

(i) SEQUENCE CHARACTERISTICS:
        (A) LENGTH: 1616 base pairs
        (B) TYPE: nucleic acid
        (C) STRANDEDNESS: single
        (D) TOPOLOGY: linear (xi) SEQUENCE DESCRIPTION: SEQ ID NO: 107:

```
CATCGGAGGG AGTGATCACC ATGCTGTGGC ACGCAATGCC ACCGGAGTAA ATACCGCACG      60

GCTGATGGCC GGCGCGGGTC CGGCTCCAAT GCTTGCGGCG GCCGCGGGAT GGCAGACGCT     120

TTCGGCGGCT CTGGACGCTC AGGCCGTCGA GTTGACCGCG CGCCTGAACT CTCTGGGAGA     180

AGCCTGGACT GGAGGTGGCA GCGACAAGGC GCTTGCGGCT GCAACGCCGA TGGTGGTCTG     240

GCTACAAACC GCGTCAACAC AGGCCAAGAC CCGTGCGATG CAGGCGACGG CGCAAGCCGC     300

GGCATACACC CAGGCCATGG CCACGACGCC GTCGCTGCCG GAGATCGCCG CCAACCACAT     360

CACCCAGGCC GTCCTTACGG CCACCAACTT CTTCGGTATC AACACGATCC CGATCGCGTT     420

GACCGAGATG GATTATTTCA TCCGTATGTG GAACCAGGCA GCCCTGGCAA TGGAGGTCTA     480

CCAGGCCGAG ACCGCGGTTA ACACGCTTTT CGAGAAGCTC GAGCCGATGG CGTCGATCCT     540

TGATCCCGGC GCGAGCCAGA GCACGACGAA CCCGATCTTC GGAATGCCCT CCCCTGGCAG     600

CTCAACACCG GTTGGCCAGT TGCCGCCGGC GGCTACCCAG ACCCTCGGCC AACTGGGTGA     660

GATGAGCGGC CCGATGCAGC AGCTGACCCA GCCGCTGCAG CAGGTGACGT CGTTGTTCAG     720

CCAGGTGGGC GGCACCGGCG GCGGCAACCC AGCCGACGAG GAAGCCGCGC AGATGGGCCT     780

GCTCGGCACC AGTCCGCTGT CGAACCATCC GCTGGCTGGT GGATCAGGCC CCAGCGCGGG     840
```

```
CGCGGGCCTG CTGCGCGCGG AGTCGCTACC TGGCGCAGGT GGGTCGTTGA CCCGCACGCC      900

GCTGATGTCT CAGCTGATCG AAAAGCCGGT TGCCCCCTCG GTGATGCCGG CGGCTGCTGC      960

CGGATCGTCG GCGACGGGTG GCGCCGCTCC GGTGGGTGCG GGAGCGATGG GCCAGGGTGC     1020

GCAATCCGGC GGCTCCACCA GGCCGGGTCT GGTCGCGCCG GCACCGCTCG CGCAGGAGCG     1080

TGAAGAAGAC GACGAGGACG ACTGGGACGA AGAGGACGAC TGGTGAGCTC CCGTAATGAC     1140

AACAGACTTC CCGGCCACCC GGGCCGGAAG ACTTGCCAAC ATTTTGGCGA GGAAGGTAAA     1200

GAGAGAAAGT AGTCCAGCAT GGCAGAGATG AAGACCGATG CCGCTACCCT CGCGCAGGAG     1260

GCAGGTAATT TCGAGCGGAT CTCCGGCGAC CTGAAAACCC AGATCGACCA GGTGGAGTCG     1320

ACGGCAGGTT CGTTGCAGGG CCAGTGGCGC GGCGCGGCGG GGACGGCCGC CCAGGCCGCG     1380

GTGGTGCGCT TCCAAGAAGC AGCCAATAAG CAGAAGCAGG AACTCGACGA GATCTCGACG     1440

AATATTCGTC AGGCCGGCGT CCAATACTCG AGGGCCGACG AGGAGCAGCA GCAGGCGCTG     1500

TCCTCGCAAA TGGGCTTCTG ACCCGCTAAT ACGAAAAGAA ACGGAGCAAA AACATGACAG     1560

AGCAGCAGTG GAATTTCGCG GGTATCGAGG CCGCGGCAAG CGCAATCCAG GGAAAT         1616
```

(2) INFORMATION FOR SEQ ID NO: 108:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (xi) SEQUENCE DESCRIPTION: SEQ ID NO: 108:

```
CTAGTGGATG GGACCATGGC CATTTTCTGC AGTCTCACTG CCTTCTGTGT TGACATTTTG       60

GCACGCCGGC GGAAACGAAG CACTGGGGTC GAAGAACGGC TGCGCTGCCA TATCGTCCGG      120

AGCTTCCATA CCTTCGTGCG GCCGGAAGAG CTTGTCGTAG TCGGCCGCCA TGACAACCTC      180

TCAGAGTGCG CTCAAACGTA TAAACACGAG AAAGGGCGAG ACCGACGGAA GGTCGAACTC      240

GCCCGATCCC GTGTTTCGCT ATTCTACGCG AACTCGGCGT TGCCCTATGC GAACATCCCA      300

GTGACGTTGC CTTCGGTCGA AGCCATTGCC TGACCGGCTT CGCTGATCGT CCGCGCCAGG      360

TTCTGCAGCG CGTTGTTCAG CTCGGTAGCC GTGGCGTCCC ATTTTTGCTG GACACCCTGG      420

TACGCCTCCG AA                                                         432
```

(2) INFORMATION FOR SEQ ID NO: 109:

(i) SEQUENCE CHARACTERISTICS:
        (A) LENGTH: 368 amino acids
        (B) TYPE: amino acid
        (C) STRANDEDNESS: single
        (D) TOPOLOGY: linear (xi) SEQUENCE DESCRIPTION: SEQ ID NO: 109:

```
Met Leu Trp His Ala Met Pro Pro Glu Xaa Asn Thr Ala Arg Leu Met
1               5                   10                  15

Ala Gly Ala Gly Pro Ala Pro Met Leu Ala Ala Ala Gly Trp Gln
            20                  25                  30

Thr Leu Ser Ala Ala Leu Asp Ala Gln Ala Val Glu Leu Thr Ala Arg
        35                  40                  45

Leu Asn Ser Leu Gly Glu Ala Trp Thr Gly Gly Ser Asp Lys Ala
    50                  55                  60

Leu Ala Ala Ala Thr Pro Met Val Val Trp Leu Gln Thr Ala Ser Thr
65                  70                  75                  80
```

-continued

```
Gln Ala Lys Thr Arg Ala Met Gln Ala Thr Ala Gln Ala Ala Tyr
                 85                  90                  95
Thr Gln Ala Met Ala Thr Thr Pro Ser Leu Pro Glu Ile Ala Ala Asn
            100                 105                 110
His Ile Thr Gln Ala Val Leu Thr Ala Thr Asn Phe Phe Gly Ile Asn
            115                 120                 125
Thr Ile Pro Ile Ala Leu Thr Glu Met Asp Tyr Phe Ile Arg Met Trp
            130                 135                 140
Asn Gln Ala Ala Leu Ala Met Glu Val Tyr Gln Ala Glu Thr Ala Val
145                 150                 155                 160
Asn Thr Leu Phe Glu Lys Leu Glu Pro Met Ala Ser Ile Leu Asp Pro
                165                 170                 175
Gly Ala Ser Gln Ser Thr Thr Asn Pro Ile Phe Gly Met Pro Ser Pro
                180                 185                 190
Gly Ser Ser Thr Pro Val Gly Gln Leu Pro Pro Ala Ala Thr Gln Thr
                195                 200                 205
Leu Gly Gln Leu Gly Glu Met Ser Gly Pro Met Gln Gln Leu Thr Gln
210                 215                 220
Pro Leu Gln Gln Val Thr Ser Leu Phe Ser Gln Val Gly Gly Thr Gly
225                 230                 235                 240
Gly Gly Asn Pro Ala Asp Glu Glu Ala Ala Gln Met Gly Leu Leu Gly
                245                 250                 255
Thr Ser Pro Leu Ser Asn His Pro Leu Ala Gly Gly Ser Gly Pro Ser
                260                 265                 270
Ala Gly Ala Gly Leu Leu Arg Ala Glu Ser Leu Pro Gly Ala Gly Gly
                275                 280                 285
Ser Leu Thr Arg Thr Pro Leu Met Ser Gln Leu Ile Glu Lys Pro Val
                290                 295                 300
Ala Pro Ser Val Met Pro Ala Ala Ala Gly Ser Ser Ala Thr Gly
305                 310                 315                 320
Gly Ala Ala Pro Val Gly Ala Gly Ala Met Gly Gln Gly Ala Gln Ser
                325                 330                 335
Gly Gly Ser Thr Arg Pro Gly Leu Val Ala Pro Ala Pro Leu Ala Gln
                340                 345                 350
Glu Arg Glu Glu Asp Asp Glu Asp Asp Trp Asp Glu Gly Asp Asp Trp
                355                 360                 365
```

(2) INFORMATION FOR SEQ ID NO: 110:

(i) SEQUENCE CHARACTERISTICS:
        (A) LENGTH: 100 amino acids
        (B) TYPE: amino acid
        (C) STRANDEDNESS: <Unknown>
        (D) TOPOLOGY: linear (xi) SEQUENCE DESCRIPTION: SEQ ID NO: 110:

```
Met Ala Glu Met Lys Thr Asp Ala Ala Thr Leu Ala Gln Glu Ala Gly
1               5                   10                  15
Asn Phe Glu Arg Ile Ser Gly Asp Leu Lys Thr Gln Ile Asp Gln Val
                20                  25                  30
Glu Ser Thr Ala Gly Ser Leu Gln Gly Gln Trp Arg Gly Ala Ala Gly
            35                  40                  45
Thr Ala Ala Gln Ala Ala Val Val Arg Phe Gln Glu Ala Ala Asn Lys
50                  55                  60
Gln Lys Gln Glu Leu Asp Glu Ile Ser Thr Asn Ile Arg Gln Ala Gly
```

```
                65                  70                  75                  80
Val Gln Tyr Ser Arg Ala Asp Glu Glu Gln Gln Gln Ala Leu Ser Ser
                    85                  90                  95

Gln Met Gly Phe
            100
```

(2) INFORMATION FOR SEQ ID NO: 111:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (xi) SEQUENCE DESCRIPTION: SEQ ID NO: 111:

```
GATCTCCGGC GACCTGAAAA CCCAGATCGA CCAGGTGGAG TCGACGGCAG GTTCGTTGCA       60

GGGCCAGTGG CGCGGCGCGG CGGGGACGGC CGCCCAGGCC GCGGTGGTGC GCTTCCAAGA      120

AGCAGCCAAT AAGCAGAAGC AGGAACTCGA CGAGATCTCG ACGAATATTC GTCAGGCCGG      180

CGTCCAATAC TCGAGGGCCG ACGAGGAGCA GCAGCAGGCG CTGTCCTCGC AAATGGGCTT      240

CTGACCCGCT AATACGAAAA GAAACGGAGC AAAAACATGA CAGAGCAGCA GTGGAATTTC      300

GCGGGTATCG AGGCCGCGGC AAGCGCAATC CAGGGAAATG TCACGTCCAT TCATTCCCTC      360

CTTGACGAGG GGAAGCAGTC CCTGACCAAG CTCGCA                                396
```

(2) INFORMATION FOR SEQ ID NO: 112:

(i) SEQUENCE CHARACTERISTICS:
        (A) LENGTH: 80 amino acids
        (B) TYPE: amino acid
        (C) STRANDEDNESS: single
        (D) TOPOLOGY: linear (xi) SEQUENCE DESCRIPTION: SEQ ID NO: 112:

```
Ile Ser Gly Asp Leu Lys Thr Gln Ile Asp Gln Val Glu Ser Thr Ala
1                5                  10                  15

Gly Ser Leu Gln Gly Gln Trp Arg Gly Ala Ala Gly Thr Ala Ala Gln
                20                  25                  30

Ala Ala Val Val Arg Phe Gln Glu Ala Ala Asn Lys Gln Lys Gln Glu
            35                  40                  45

Leu Asp Glu Ile Ser Thr Asn Ile Arg Gln Ala Gly Val Gln Tyr Ser
        50                  55                  60

Arg Ala Asp Glu Glu Gln Gln Gln Ala Leu Ser Ser Gln Met Gly Phe
65                  70                  75                  80
```

(2) INFORMATION FOR SEQ ID NO: 113:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (xi) SEQUENCE DESCRIPTION: SEQ ID NO: 113:

```
GTGGATCCCG ATCCCGTGTT TCGCTATTCT ACGCGAACTC GGCGTTGCCC TATGCGAACA       60

TCCCAGTGAC GTTGCCTTCG GTCGAAGCCA TTGCCTGACC GGCTTCGCTG ATCGTCCGCG      120

CCAGGTTCTG CAGCGCGTTG TTCAGCTCGG TAGCCGTGGC GTCCCATTTT TGCTGGACAC      180

CCTGGTACGC CTCCGAACCG CTACCGCCCC AGGCCGCTGC GAGCTTGGTC AGGGACTGCT      240

TCCCCTCGTC AAGGAGGGAA TGAATGGACG TGACATTTCC CTGGATTGCG CTTGCCGCGG      300
```

```
CCTCGATACC CGCGAAATTC CACTGCTGCT CTGTCATGTT TTTGCTCCGT TCTTTTCGT    360

ATTAGCGGGT CAGAAGCCCA TTTGCGA                                      387
```

(2) INFORMATION FOR SEQ ID NO: 114:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (xi) SEQUENCE DESCRIPTION: SEQ ID NO: 114:

```
CGGCACGAGG ATCTCGGTTG GCCCAACGGC GCTGGCGAGG GCTCCGTTCC GGGGGCGAGC    60

TGCGCGCCGG ATGCTTCCTC TGCCCGCAGC CGCGCCTGGA TGGATGGACC AGTTGCTACC   120

TTCCCGACGT TCGTTCGGT GTCTGTGCGA TAGCGGTGAC CCCGGCGCGC ACGTCGGGAG    180

TGTTGGGGGG CAGGCCGGGT CGGTGGTTCG GCCGGGACG CAGACGGTCT GGACGGAACG    240

GGCGGGGGTT CGCCGATTGG CATCTTTGCC CA                                272
```

(2) INFORMATION FOR SEQ ID NO: 115:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (xi) SEQUENCE DESCRIPTION: SEQ ID NO: 115:

```
Asp Pro Val Asp Ala Val Ile Asn Thr Thr Cys Asn Tyr Gly Gln Val
1               5                   10                  15

Val Ala Ala Leu
            20
```

(2) INFORMATION FOR SEQ ID NO: 116:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (xi) SEQUENCE DESCRIPTION: SEQ ID NO: 116:

```
Ala Val Glu Ser Gly Met Leu Ala Leu Gly Thr Pro Ala Pro Ser
1               5                   10                  15
```

(2) INFORMATION FOR SEQ ID NO: 117:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (xi) SEQUENCE DESCRIPTION: SEQ ID NO: 117:

```
Ala Ala Met Lys Pro Arg Thr Gly Asp Gly Pro Leu Glu Ala Ala Lys
1               5                   10                  15

Glu Gly Arg
```

(2) INFORMATION FOR SEQ ID NO: 118:

(i) SEQUENCE CHARACTERISTICS:
        (A) LENGTH: 15 amino acids
        (B) TYPE: amino acid (C) STRANDEDNESS: <Unknown>
        (D) TOPOLOGY: linear (xi) SEQUENCE DESCRIPTION: SEQ ID NO: 118:

Tyr Tyr Trp Cys Pro Gly Gln Pro Phe Asp Pro Ala Trp Gly Pro
1               5                   10                  15

(2) INFORMATION FOR SEQ ID NO: 119:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 119:

Asp Ile Gly Ser Glu Ser Thr Glu Asp Gln Gln Xaa Ala Val
1               5                   10

(2) INFORMATION FOR SEQ ID NO: 120:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 120:

Ala Glu Glu Ser Ile Ser Thr Xaa Glu Xaa Ile Val Pro
1               5                   10

(2) INFORMATION FOR SEQ ID NO: 121:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (xi) SEQUENCE DESCRIPTION: SEQ ID NO: 121:

Asp Pro Glu Pro Ala Pro Pro Val Pro Thr Thr Ala Ala Ser Pro Pro
1               5                   10                  15

Ser (2) INFORMATION FOR SEQ ID NO: 122:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (xi) SEQUENCE DESCRIPTION: SEQ ID NO: 122:

Ala Pro Lys Thr Tyr Xaa Glu Glu Leu Lys Gly Thr Asp Thr Gly
1               5                   10                  15

(2) INFORMATION FOR SEQ ID NO: 123:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (xi) SEQUENCE DESCRIPTION: SEQ ID NO: 123:

Asp Pro Ala Ser Ala Pro Asp Val Pro Thr Ala Ala Gln Leu Thr Ser
1               5                   10                  15

```
Leu Leu Asn Ser Leu Ala Asp Pro Asn Val Ser Phe Ala Asn
            20                  25                  30
```

(2) INFORMATION FOR SEQ ID NO: 124:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (xi) SEQUENCE DESCRIPTION: SEQ ID NO: 124:

```
Asp Pro Pro Asp Pro His Gln Xaa Asp Met Thr Lys Gly Tyr Tyr Pro
1               5                   10                  15
Gly Gly Arg Arg Xaa Phe
            20
```

(2) INFORMATION FOR SEQ ID NO: 125:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (xi) SEQUENCE DESCRIPTION: SEQ ID NO: 125:

```
Asp Pro Gly Tyr Thr Pro Gly
1               5
```

(2) INFORMATION FOR SEQ ID NO: 126:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ix) FEATURE:
        (D) OTHER INFORMATION: /note= "The Second Residue Can Be
            Either a Pro or Thr"

(xi) SEQUENCE DESCRIPTION: SEQ ID NO: 126:

```
Xaa Xaa Gly Phe Thr Gly Pro Gln Phe Tyr
1               5                   10
```

(2) INFORMATION FOR SEQ ID NO: 127:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ix) FEATURE:
        (D) OTHER INFORMATION: /note= "The Third Residue Can Be Either
            a Gln or Leu"

(xi) SEQUENCE DESCRIPTION: SEQ ID NO: 127:

```
Xaa Pro Xaa Val Thr Ala Tyr Ala Gly
1               5
```

(2) INFORMATION FOR SEQ ID NO: 128:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (xi) SEQUENCE DESCRIPTION: SEQ ID NO: 128:

Xaa Xaa Xaa Glu Lys Pro Phe Leu Arg
1               5

(2) INFORMATION FOR SEQ ID NO: 129:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (xi) SEQUENCE DESCRIPTION: SEQ ID NO: 129:

Xaa Asp Ser Glu Lys Ser Ala Thr Ile Lys Val Thr Asp Ala Ser
1               5                   10                  15

(2) INFORMATION FOR SEQ ID NO: 130:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (xi) SEQUENCE DESCRIPTION: SEQ ID NO: 130:

Ala Gly Asp Thr Xaa Ile Tyr Ile Val Gly Asn Leu Thr Ala Asp
1               5                   10                  15

(2) INFORMATION FOR SEQ ID NO: 131:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: linear (xi) SEQUENCE DESCRIPTION: SEQ ID NO: 131:

Ala Pro Glu Ser Gly Ala Gly Leu Gly Gly Thr Val Gln Ala Gly
1               5                   10                  15

(2) INFORMATION FOR SEQ ID NO: 132:

(i) SEQUENCE CHARACTERISTICS:
            (A) LENGTH: 21 amino acids
            (B) TYPE: amino acid
            (C) STRANDEDNESS: <Unknown>
            (D) TOPOLOGY: linear (xi) SEQUENCE DESCRIPTION: SEQ ID NO: 132:

Xaa Tyr Ile Ala Tyr Xaa Thr Thr Ala Gly Ile Val Pro Gly Lys Ile
1               5                   10                  15

Asn Val His Leu Val
            20

(2) INFORMATION FOR SEQ ID NO: 133:

(i) SEQUENCE CHARACTERISTICS:
            (A) LENGTH: 882 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 133:

GCAACGCTGT CGTGGCCTTT GCGGTGATCG GTTTCGCCTC GCTGGCGGTG GCGGTGGCGG      60

```
TCACCATCCG ACCGACCGCG GCCTCAAAAC CGGTAGAGGG ACACCAAAAC GCCCAGCCAG        120

GGAAGTTCAT GCCGTTGTTG CCGACGCAAC AGCAGGCGCC GGTCCCGCCG CCTCCGCCCG        180

ATGATCCCAC CGCTGGATTC CAGGGCGGCA CCATTCCGGC TGTACAGAAC GTGGTGCCGC        240

GGCCGGGTAC CTCACCCGGG GTGGGTGGGA CGCCGGCTTC GCCTGCGCCG GAAGCGCCGG        300

CCGTGCCCGG TGTTGTGCCT GCCCCGGTGC AATCCCGGT CCCGATCATC ATTCCCCCGT         360

TCCCGGGTTG GCAGCCTGGA ATGCCGACCA TCCCCACCGC ACCGCCGACG ACGCCGGTGA        420

CCACGTCGGC GACGACGCCG CCGACCACGC CGCCGACCAC GCCGGTGACC ACGCCGCCAA        480

CGACGCCGCC GACCACGCCG GTGACCACGC CGCCAACGAC GCCGCCGACC ACGCCGGTGA        540

CCACGCCACC AACGACCGTC GCCCCGACGA CCGTCGCCCC GACGACGGTC GCTCCGACCA        600

CCGTCGCCCC GACCACGGTC GCTCCAGCCA CCGCCACGCC GACGACCGTC GCTCCGCAGC        660

CGACGCAGCA GCCCACGCAA CAACCAACCC AACAGATGCC AACCCAGCAG CAGACCGTGG        720

CCCCGCAGAC GGTGGCGCCG GCTCCGCAGC CGCCGTCCGG TGGCCGCAAC GGCAGCGGCG        780

GGGGCGACTT ATTCGGCGGG TTCTGATCAC GGTCGCGGCT TCACTACGGT CGGAGGACAT        840

GGCCGGTGAT GCGGTGACGG TGGTGCTGCC CTGTCTCAAC GA                          882

(2) INFORMATION FOR SEQ ID NO: 134:

(i) SEQUENCE CHARACTERISTICS:
        (A) LENGTH: 815 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 134:

CCATCAACCA ACCGCTCGCG CCGCCCGCGC CGCCGGATCC GCCGTCGCCG CCACGCCCGC         60

CGGTGCCTCC GGTGCCCCCG TTGCCGCCGT CGCCGCCGTC GCCGCCGACC GGCTGGGTGC        120

CTAGGGCGCT GTTACCGCCC TGGTTGGCGG GGACGCCGCC GGCACCACCG GTACCGCCGA        180

TGGCGCCGTT GCCGCCGGCG GCACCGTTGC CACCGTTGCC ACCGTTGCCA CCGTTGCCGA        240

CCAGCCACCC GCCGCGACCA CCGGCACCGC CGGCGCCGCC CGCACCGCCG GCGTGCCCGT        300

TCGTGCCCGT ACCGCCGGCA CCGCCGTTGC CGCCGTCACC GCCGACGGAA CTACCGGCGG        360

ACGCGGCCTG CCCGCCGGCG CCGCCCGCAC CGCCATTGGC ACCGCCGTCA CCGCCGGCTG        420

GGAGTGCCGC GATTAGGGCA CTGACCGGCG CAACCAGCGC AAGTACTCTC GGTCACCGAG        480

CACTTCCAGA CGACACCACA GCACGGGGTT GTCGGCGGAC TGGGTGAAAT GGCAGCCGAT        540

AGCGGCTAGC TGTCGGCTGC GGTCAACCTC GATCATGATG TCGAGGTGAC CGTGACCGCG        600

CCCCCCGAAG GAGGCGCTGA ACTCGGCGTT GAGCCGATCG GCGATCGGTT GGGGCAGTGC        660

CCAGGCCAAT ACGGGGATAC CGGGTGTCNA AGCCGCCGCG AGCGCAGCTT CGGTTGCGCG        720

ACNGTGGTCG GGGTGGCCTG TTACGCCGTT GTCNTCGAAC ACGAGTAGCA GGTCTGCTCC        780

GGCGAGGGCA TCCACCACGC GTTGCGTCAG CTCGT                                  815

(2) INFORMATION FOR SEQ ID NO: 135:

(i) SEQUENCE CHARACTERISTICS:
        (A) LENGTH: 1152 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 135:

```
ACCAGCCGCC GGCTGAGGTC TCAGATCAGA GAGTCTCCGG ACTCACCGGG GCGGTTCAGC      60
CTTCTCCCAG AACAACTGCT GAAGATCCTC GCCCGCGAAA CAGGCGCTGA TTTGACGCTC     120
TATGACCGGT TGAACGACGA GATCATCCGG CAGATTGATA TGGCACCGCT GGGCTAACAG     180
GTGCGCAAGA TGGTGCAGCT GTATGTCTCG GACTCCGTGT CGCGGATCAG CTTTGCCGAC     240
GGCCGGGTGA TCGTGTGGAG CGAGGAGCTC GGCGAGAGCC AGTATCCGAT CGAGACGCTG     300
GACGGCATCA CGCTGTTTGG GCGGCCGACG ATGACAACGC CCTTCATCGT TGAGATGCTC     360
AAGCGTGAGC GCGACATCCA GCTCTTCACG ACCGACGGCC ACTACCAGGG CCGGATCTCA     420
ACACCCGACG TGTCATACGC GCCGCGGCTC CGTCAGCAAG TTCACCGCAC CGACGATCCT     480
GCGTTCTGCC TGTCGTTAAG CAAGCGGATC GTGTCGAGGA AGATCCTGAA TCAGCAGGCC     540
TTGATTCGGG CACACACGTC GGGGCAAGAC GTTGCTGAGA GCATCCGCAC GATGAAGCAC     600
TCGCTGGCCT GGGTCGATCG ATCGGGCTCC CTGGCGGAGT TGAACGGGTT CGAGGGAAAT     660
GCCGCAAAGG CATACTTCAC CGCGCTGGGG CATCTCGTCC CGCAGGAGTT CGCATTCCAG     720
GGCCGCTCGA CTCGGCCGCC GTTGGACGCC TTCAACTCGA TGGTCAGCCT CGGCTATTCG     780
CTGCTGTACA AGAACATCAT AGGGGCGATC GAGCGTCACA GCCTGAACGC GTATATCGGT     840
TTCCTACACC AGGATTCACG AGGGCACGCA ACGTCTCGTG CCGAATTCGG CACGAGCTCC     900
GCTGAAACCG CTGGCCGGCT GCTCAGTGCC CGTACGTAAT CCGCTGCGCC CAGGCCGGCC     960
CGCCGGCCGA ATACCAGCAG ATCGGACAGC GAATTGCCGC CCAGCCGGTT GGAGCCGTGC    1020
ATACCGCCGG CACACTCACC GGCAGCGAAC AGGCCTGGCA CCGTGGCGGC GCCGGTGTCC    1080
GCGTCTACTT CGACACCGCC CATCACGTAG TGACACGTCG GCCCGACTTC CATTGCCTGC    1140
GTTCGGCACG AG                                                       1152
```

(2) INFORMATION FOR SEQ ID NO: 136:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 136:

```
CTCGTGCCGA TTCGGCAGGG TGTACTTGCC GGTGGTGTAN GCCGCATGAG TGCCGACGAC      60
CAGCAATGCG GCAACAGCAC GGATCCCGGT CAACGACGCC ACCCGGTCCA CGTGGGCGAT     120
CCGCTCGAGT CCGCCCTGGG CGGCTCTTTC CTTGGGCAGG GTCATCCGAC GTGTTTCCGC     180
CGTGGTTTGC CGCCATTATG CCGGCGCGCC GCGTCGGGCG GCCGGTATGG CCGAANGTCG     240
ATCAGCACAC CCGAGATACG GGTCTGTGCA AGCTTTTTGA GCGTCGCGCG GGGCAGCTTC     300
GCCGGCAATT CTACTAGCGA GAAGTCTGGC CCGATACGGA TCTGACCGAA GTCGCTGCGG     360
TGCAGCCCAC CCTCATTGGC GATGGCGCCG ACGATGGCGC CTGGACCGAT CTTGTGCCGC     420
TTGCCGACGG CGACGCGGTA GGTGGTCAAG TCCGGTCTAC GCTTGGGCCT TTGCGGACGG     480
TCCCGACGCT GGTCGCGGTT GCGCCGCGAA AGCGGCGGGT CGGGTGCCAT CAGGAATGCC     540
TCACCGCCGC GGCACTGCAC GGCCAGTGCC GCGGCGATGT CAGCCATCGG GACATCATGC     600
TCGCGTTCAT ACTCCTCGAC CAGTCGGCGG AACAGCTCGA TTCCCGGACC GCCCA         655
```

(2) INFORMATION FOR SEQ ID NO: 137:

(i) SEQUENCE CHARACTERISTICS:
        (A) LENGTH: 267 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 137:

```
Asn Ala Val Val Ala Phe Ala Val Ile Gly Phe Ala Ser Leu Ala Val
 1               5                  10                  15

Ala Val Ala Val Thr Ile Arg Pro Thr Ala Ala Ser Lys Pro Val Glu
            20                  25                  30

Gly His Gln Asn Ala Gln Pro Gly Lys Phe Met Pro Leu Leu Pro Thr
        35                  40                  45

Gln Gln Gln Ala Pro Val Pro Pro Pro Pro Asp Asp Pro Thr Ala
 50                  55                  60

Gly Phe Gln Gly Gly Thr Ile Pro Ala Val Gln Asn Val Val Pro Arg
 65                  70                  75                  80

Pro Gly Thr Ser Pro Gly Val Gly Gly Thr Pro Ala Ser Pro Ala Pro
                85                  90                  95

Glu Ala Pro Ala Val Pro Gly Val Val Pro Ala Pro Val Pro Ile Pro
                100                 105                 110

Val Pro Ile Ile Ile Pro Pro Phe Pro Gly Trp Gln Pro Gly Met Pro
            115                 120                 125

Thr Ile Pro Thr Ala Pro Pro Thr Thr Pro Val Thr Thr Ser Ala Thr
        130                 135                 140

Thr Pro Pro Thr Thr Pro Thr Thr Pro Val Thr Thr Pro Pro Thr
145                 150                 155                 160

Thr Pro Pro Thr Thr Pro Val Thr Thr Pro Pro Thr Thr Pro Pro Thr
                165                 170                 175

Thr Pro Val Thr Thr Pro Pro Thr Thr Val Ala Pro Thr Thr Val Ala
            180                 185                 190

Pro Thr Thr Val Ala Pro Thr Thr Val Ala Pro Thr Thr Val Ala Pro
            195                 200                 205

Ala Thr Ala Thr Pro Thr Thr Val Ala Pro Gln Pro Thr Gln Gln Pro
        210                 215                 220

Thr Gln Gln Pro Thr Gln Gln Met Pro Thr Gln Gln Gln Thr Val Ala
225                 230                 235                 240

Pro Gln Thr Val Ala Pro Ala Pro Gln Pro Pro Ser Gly Gly Arg Asn
                245                 250                 255

Gly Ser Gly Gly Gly Asp Leu Phe Gly Phe
                260                 265
```

(2) INFORMATION FOR SEQ ID NO: 138:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 138:

```
Ile Asn Gln Pro Leu Ala Pro Pro Ala Pro Asp Pro Pro Ser Pro
 1               5                  10                  15
```

```
Pro Arg Pro Pro Val Pro Pro Val Pro Leu Pro Pro Ser Pro Pro
            20                  25                  30

Ser Pro Pro Thr Gly Trp Val Pro Arg Ala Leu Leu Pro Pro Trp Leu
            35                  40                  45

Ala Gly Thr Pro Pro Ala Pro Pro Val Pro Pro Met Ala Pro Leu Pro
 50                  55                  60

Pro Ala Ala Pro Leu Pro Pro Leu Pro Pro Leu Pro Pro Leu Pro Thr
 65                  70                  75                  80

Ser His Pro Pro Arg Pro Pro Ala Pro Ala Pro Pro Ala Pro Pro
            85                  90                  95

Ala Cys Pro Phe Val Pro Val Pro Pro Ala Pro Pro Leu Pro Pro Ser
            100                 105                 110

Pro Pro Thr Glu Leu Pro Ala Asp Ala Ala Cys Pro Pro Ala Pro Pro
            115                 120                 125

Ala Pro Pro Leu Ala Pro Pro Ser Pro Pro Ala Gly Ser Ala Ala Ile
 130                 135                 140

Arg Ala Leu Thr Gly Ala Thr Ser Ala Ser Thr Leu Gly His Arg Ala
145                 150                 155                 160

Leu Pro Asp Asp Thr Thr Ala Arg Gly Cys Arg Arg Thr Gly
            165                 170
```

(2) INFORMATION FOR SEQ ID NO: 139:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 139:

```
Gln Pro Pro Ala Glu Val Ser Asp Gln Arg Val Ser Gly Leu Thr Gly
 1               5                  10                  15

Ala Val Gln Pro Ser Pro Arg Thr Thr Ala Glu Asp Pro Arg Pro Arg
            20                  25                  30

Asn Arg Arg
         35
```

(2) INFORMATION FOR SEQ ID NO: 140:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 140:

```
Arg Ala Asp Ser Ala Gly Cys Thr Cys Arg Trp Cys Xaa Pro His Glu
 1               5                  10                  15

Cys Arg Arg Pro Ala Met Arg Gln Gln His Gly Ser Arg Ser Thr Thr
            20                  25                  30

Pro Pro Gly Pro Arg Gly Arg Ser Ala Arg Val Arg Pro Gly Arg Leu
            35                  40                  45

Phe Pro Trp Ala Gly Ser Ser Asp Val Phe Pro Pro Trp Phe Ala Ala
 50                  55                  60

Ile Met Pro Ala Arg Arg Val Gly Arg Pro Val Trp Pro Xaa Val Asp
```

-continued

```
            65                  70                  75                  80
       Gln His Thr Arg Asp Thr Gly Leu Cys Lys Leu Phe Glu Arg Arg Ala
                       85                  90                  95
       Gly Gln Leu Arg Arg Gln Phe Tyr
                      100
```

(2) INFORMATION FOR SEQ ID NO: 141:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO: 141:

GGATCCATAT GGGCCATCAT CATCATCATC ACGTGATCGA CATCATCGGG ACC          53

(2) INFORMATION FOR SEQ ID NO: 142:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR Primer"

(vi) ORIGINAL SOURCE:
        (A) ORGANISM: Mycobacterium tuberculosis (xi) SEQUENCE DESCRIPTION: SEQ ID NO: 142:

CCTGAATTCA GGCCTCGGTT GCGCCGGCCT CATCTTGAAC GA                  42

(2) INFORMATION FOR SEQ ID NO: 143:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR Primer"

(vi) ORIGINAL SOURCE:
        (A) ORGANISM: Mycobacterium tuberculosis (xi) SEQUENCE DESCRIPTION: SEQ ID NO: 143:

GGATCCTGCA GGCTCGAAAC CACCGAGCGG T                              31

(2) INFORMATION FOR SEQ ID NO: 144:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO: 144:

CTCTGAATTC AGCGCTGGAA ATCGTCGCGA T                                          31

(2) INFORMATION FOR SEQ ID NO: 145:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO: 145:

GGATCCAGCG CTGAGATGAA GACCGATGCC GCT                                        33

(2) INFORMATION FOR SEQ ID NO: 146:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO: 146:

GAGAGAATTC TCAGAAGCCC ATTTGCGAGG ACA                                        33

(2) INFORMATION FOR SEQ ID NO: 147:

(i) SEQUENCE CHARACTERISTICS:
        (A) LENGTH: 1993 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium tuberculosis (ix) FEATURE:
        (A) NAME/KEY: CDS
        (B) LOCATION: 152..1273

(xi) SEQUENCE DESCRIPTION: SEQ ID NO: 147:

TGTTCTTCGA CGGCAGGCTG GTGGAGGAAG GGCCCACCGA ACAGCTGTTC TCCTCGCCGA            60

AGCATGCGGA AACCGCCCGA TACGTCGCCG GACTGTCGGG GGACGTCAAG GACGCCAAGC           120

GCGGAAATTG AAGAGCACAG AAAGGTATGG C GTG AAA ATT CGT TTG CAT ACG              172
                                  Val Lys Ile Arg Leu His Thr
                                    1               5

CTG TTG GCC GTG TTG ACC GCT GCG CCG CTG CTG CTA GCA GCG GCG GGC             220
Leu Leu Ala Val Leu Thr Ala Ala Pro Leu Leu Leu Ala Ala Ala Gly
         10                  15                  20

TGT GGC TCG AAA CCA CCG AGC GGT TCG CCT GAA ACG GGC GCC GGC GCC             268
Cys Gly Ser Lys Pro Pro Ser Gly Ser Pro Glu Thr Gly Ala Gly Ala
     25                  30                  35

```
                                                      -continued

GGT ACT GTC GCG ACT ACC CCC GCG TCG TCG CCG GTG ACG TTG GCG GAG       316
Gly Thr Val Ala Thr Thr Pro Ala Ser Ser Pro Val Thr Leu Ala Glu
 40              45              50              55

ACC GGT AGC ACG CTG CTC TAC CCG CTG TTC AAC CTG TGG GGT CCG GCC       364
Thr Gly Ser Thr Leu Leu Tyr Pro Leu Phe Asn Leu Trp Gly Pro Ala
             60              65              70

TTT CAC GAG AGG TAT CCG AAC GTC ACG ATC ACC GCT CAG GGC ACC GGT       412
Phe His Glu Arg Tyr Pro Asn Val Thr Ile Thr Ala Gln Gly Thr Gly
         75              80              85

TCT GGT GCC GGG ATC GCG CAG GCC GCC GCC GGG ACG GTC AAC ATT GGG       460
Ser Gly Ala Gly Ile Ala Gln Ala Ala Ala Gly Thr Val Asn Ile Gly
     90              95             100

GCC TCC GAC GCC TAT CTG TCG GAA GGT GAT ATG GCC GCG CAC AAG GGG       508
Ala Ser Asp Ala Tyr Leu Ser Glu Gly Asp Met Ala Ala His Lys Gly
105             110             115

CTG ATG AAC ATC GCG CTA GCC ATC TCC GCT CAG CAG GTC AAC TAC AAC       556
Leu Met Asn Ile Ala Leu Ala Ile Ser Ala Gln Gln Val Asn Tyr Asn
120             125             130             135

CTG CCC GGA GTG AGC GAG CAC CTC AAG CTG AAC GGA AAA GTC CTG GCG       604
Leu Pro Gly Val Ser Glu His Leu Lys Leu Asn Gly Lys Val Leu Ala
                140             145             150

GCC ATG TAC CAG GGC ACC ATC AAA ACC TGG GAC GAC CCG CAG ATC GCT       652
Ala Met Tyr Gln Gly Thr Ile Lys Thr Trp Asp Asp Pro Gln Ile Ala
            155             160             165

GCG CTC AAC CCC GGC GTG AAC CTG CCC GGC ACC GCG GTA GTT CCG CTG       700
Ala Leu Asn Pro Gly Val Asn Leu Pro Gly Thr Ala Val Val Pro Leu
        170             175             180

CAC CGC TCC GAC GGG TCC GGT GAC ACC TTC TTG TTC ACC CAG TAC CTG       748
His Arg Ser Asp Gly Ser Gly Asp Thr Phe Leu Phe Thr Gln Tyr Leu
    185             190             195

TCC AAG CAA GAT CCC GAG GGC TGG GGC AAG TCG CCC GGC TTC GGC ACC       796
Ser Lys Gln Asp Pro Glu Gly Trp Gly Lys Ser Pro Gly Phe Gly Thr
200             205             210             215

ACC GTC GAC TTC CCG GCG GTG CCG GGT GCG CTG GGT GAG AAC GGC AAC       844
Thr Val Asp Phe Pro Ala Val Pro Gly Ala Leu Gly Glu Asn Gly Asn
            220             225             230

GGC GGC ATG GTG ACC GGT TGC GCC GAG ACA CCG GGC TGC GTG GCC TAT       892
Gly Gly Met Val Thr Gly Cys Ala Glu Thr Pro Gly Cys Val Ala Tyr
        235             240             245

ATC GGC ATC AGC TTC CTC GAC CAG GCC AGT CAA CGG GGA CTC GGC GAG       940
Ile Gly Ile Ser Phe Leu Asp Gln Ala Ser Gln Arg Gly Leu Gly Glu
    250             255             260

GCC CAA CTA GGC AAT AGC TCT GGC AAT TTC TTG TTG CCC GAC GCG CAA       988
Ala Gln Leu Gly Asn Ser Ser Gly Asn Phe Leu Leu Pro Asp Ala Gln
265             270             275

AGC ATT CAG GCC GCG GCG GCT GGC TTC GCA TCG AAA ACC CCG GCG AAC      1036
Ser Ile Gln Ala Ala Ala Ala Gly Phe Ala Ser Lys Thr Pro Ala Asn
280             285             290             295

CAG GCG ATT TCG ATG ATC GAC GGG CCC GCC CCG GAC GGC TAC CCG ATC      1084
Gln Ala Ile Ser Met Ile Asp Gly Pro Ala Pro Asp Gly Tyr Pro Ile
            300             305             310

ATC AAC TAC GAG TAC GCC ATC GTC AAC AAC CGG CAA AAG GAC GCC GCC      1132
Ile Asn Tyr Glu Tyr Ala Ile Val Asn Asn Arg Gln Lys Asp Ala Ala
        315             320             325

ACC GCG CAG ACC TTG CAG GCA TTT CTG CAC TGG GCG ATC ACC GAC GGC      1180
Thr Ala Gln Thr Leu Gln Ala Phe Leu His Trp Ala Ile Thr Asp Gly
    330             335             340

AAC AAG GCC TCG TTC CTC GAC CAG GTT CAT TTC CAG CCG CTG CCG CCC      1228
Asn Lys Ala Ser Phe Leu Asp Gln Val His Phe Gln Pro Leu Pro Pro
345             350             355
```

```
GCG GTG GTG AAG TTG TCT GAC GCG TTG ATC GCG ACG ATT TCC AGC      1273
Ala Val Val Lys Leu Ser Asp Ala Leu Ile Ala Thr Ile Ser Ser
360                 365                 370

TAGCCTCGTT GACCACCACG CGACAGCAAC CTCCGTCGGG CCATCGGGCT GCTTTGCGGA      1333

GCATGCTGGC CCGTGCCGGT GAAGTCGGCC GCGCTGGCCC GGCCATCCGG TGGTTGGGTG      1393

GGATAGGTGC GGTGATCCCG CTGCTTGCGC TGGTCTTGGT GCTGGTGGTG CTGGTCATCG      1453

AGGCGATGGG TGCGATCAGG CTCAACGGGT TGCATTTCTT CACCGCCACC GAATGGAATC      1513

CAGGCAACAC CTACGGCGAA ACCGTTGTCA CCGACGCGTC GCCCATCCGG TCGGCGCCTA      1573

CTACGGGGCG TTGCCGCTGA TCGTCGGGAC GCTGGCGACC TCGGCAATCG CCCTGATCAT      1633

CGCGGTGCCG GTCTCTGTAG AGCGGCGCT GGTGATCGTG GAACGGCTGC CGAAACGGTT      1693

GGCCGAGGCT GTGGGAATAG TCCTGGAATT GCTCGCCGGA ATCCCCAGCG TGGTCGTCGG      1753

TTTGTGGGGG GCAATGACGT TCGGGCCGTT CATCGCTCAT CACATCGCTC CGGTGATCGC      1813

TCACAACGCT CCCGATGTGC CGGTGCTGAA CTACTTGCGC GGCGACCCGG GCAACGGGGA      1873

GGGCATGTTG GTGTCCGGTC TGGTGTTGGC GGTGATGGTC GTTCCCATTA TCGCCACCAC      1933

CACTCATGAC CTGTTCCGGC AGGTGCCGGT GTTGCCCCGG GAGGGCGCGA TCGGGAATTC      1993
```

(2) INFORMATION FOR SEQ ID NO: 148:

(i) SEQUENCE CHARACTERISTICS:
        (A) LENGTH: 374 amino acids
        (B) TYPE: amino acid
        (D) TOPOLOGY: linear (ii) MOLECULE TYPE: protein (xi) SEQUENCE DESCRIPTION: SEQ ID NO: 148:

```
Val Lys Ile Arg Leu His Thr Leu Leu Ala Val Leu Thr Ala Ala Pro
 1               5                  10                  15

Leu Leu Leu Ala Ala Gly Cys Gly Ser Lys Pro Pro Ser Gly Ser
            20                  25                  30

Pro Glu Thr Gly Ala Gly Ala Gly Thr Val Ala Thr Thr Pro Ala Ser
        35                  40                  45

Ser Pro Val Thr Leu Ala Glu Thr Gly Ser Thr Leu Leu Tyr Pro Leu
    50                  55                  60

Phe Asn Leu Trp Gly Pro Ala Phe His Glu Arg Tyr Pro Asn Val Thr
65                  70                  75                  80

Ile Thr Ala Gln Gly Thr Gly Ser Gly Ala Gly Ile Ala Gln Ala Ala
                85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
        115                 120                 125

Ala Gln Gln Val Asn Tyr Asn Leu Pro Gly Val Ser Glu His Leu Lys
    130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
        195                 200                 205
```

```
Lys Ser Pro Gly Phe Gly Thr Thr Val Asp Phe Pro Ala Val Pro Gly
    210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
            260                 265                 270

Phe Leu Leu Pro Asp Ala Gln Ser Ile Gln Ala Ala Ala Gly Phe
        275                 280                 285

Ala Ser Lys Thr Pro Ala Asn Gln Ala Ile Ser Met Ile Asp Gly Pro
    290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
                325                 330                 335

His Trp Ala Ile Thr Asp Gly Asn Lys Ala Ser Phe Leu Asp Gln Val
            340                 345                 350

His Phe Gln Pro Leu Pro Pro Ala Val Val Lys Leu Ser Asp Ala Leu
        355                 360                 365

Ile Ala Thr Ile Ser Ser
    370
```

(2) INFORMATION FOR SEQ ID NO: 149:

(i) SEQUENCE CHARACTERISTICS:
        (A) LENGTH: 1993 base pairs
        (B) TYPE: nucleic acid
        (C) STRANDEDNESS: single
        (D) TOPOLOGY: linear (xi) SEQUENCE DESCRIPTION: SEQ ID NO: 149:

```
TGTTCTTCGA CGGCAGGCTG GTGGAGGAAG GGCCCACCGA ACAGCTGTTC TCCTCGCCGA      60

AGCATGCGGA AACCGCCCGA TACGTCGCCG GACTGTCGGG GGACGTCAAG GACGCCAAGC     120

GCGGAAATTG AAGAGCACAG AAAGGTATGG CGTGAAAATT CGTTTGCATA CGCTGTTGGC     180

CGTGTTGACC GCTGCGCCGC TGCTGCTAGC AGCGGCGGGC TGTGGCTCGA ACCACCGAG      240

CGGTTCGCCT GAAACGGGCG CCGGCGCCGG TACTGTCGCG ACTACCCCCG CGTCGTCGCC     300

GGTGACGTTG GCGGAGACCG GTAGCACGCT GCTCTACCCG CTGTTCAACC TGTGGGGTCC     360

GGCCTTTCAC GAGAGGTATC CGAACGTCAC GATCACCGCT CAGGGCACCG GTTCTGGTGC     420

CGGGATCGCG CAGGCCGCCG CCGGGACGGT CAACATTGGG GCCTCCGACG CCTATCTGTC     480

GGAAGGTGAT ATGGCCGCGC ACAAGGGGCT GATGAACATC GCGCTAGCCA TCTCCGCTCA     540

GCAGGTCAAC TACAACCTGC CCGGAGTGAG CGAGCACCTC AAGCTGAACG GAAAAGTCCT     600

GGCGGCCATG TACCAGGGCA CCATCAAAAC CTGGGACGAC CCGCAGATCG CTGCGCTCAA     660

CCCCGGCGTG AACCTGCCCG GCACCGCGGT AGTTCCGCTG CACCGCTCCG ACGGGTCCGG     720

TGACACCTTC TTGTTCACCC AGTACCTGTC CAAGCAAGAT CCCGAGGGCT GGGGCAAGTC     780

GCCCGGCTTC GGCACCACCG TCGACTTCCC GGCGGTGCCG GGTGCGCTGG GTGAGAACGG     840

CAACGGCGGC ATGGTGACCG GTTGCGCCGA GACACCGGGC TGCGTGGCCT ATATCGGCAT     900

CAGCTTCCTC GACCAGGCCA GTCAACGGGG ACTCGGCGAG GCCCAACTAG GCAATAGCTC     960

TGGCAATTTC TTGTTGCCCG ACGCGCAAAG CATTCAGGCC GCGGCGGCTG GCTTCGCATC    1020
```

```
GAAAACCCCG GCGAACCAGG CGATTTCGAT GATCGACGGG CCCGCCCCGG ACGGCTACCC    1080

GATCATCAAC TACGAGTACG CCATCGTCAA CAACCGGCAA AAGGACGCCG CCACCGCGCA    1140

GACCTTGCAG GCATTTCTGC ACTGGGCGAT CACCGACGGC AACAAGGCCT CGTTCCTCGA    1200

CCAGGTTCAT TTCCAGCCGC TGCCGCCCGC GGTGGTGAAG TTGTCTGACG CGTTGATCGC    1260

GACGATTTCC AGCTAGCCTC GTTGACCACC ACGCGACAGC AACCTCCGTC GGGCCATCGG    1320

GCTGCTTTGC GGAGCATGCT GGCCCGTGCC GGTGAAGTCG GCCGCGCTGG CCCGGCCATC    1380

CGGTGGTTGG GTGGGATAGG TGCGGTGATC CCGCTGCTTG CGCTGGTCTT GGTGCTGGTG    1440

GTGCTGGTCA TCGAGGCGAT GGGTGCGATC AGGCTCAACG GGTTGCATTT CTTCACCGCC    1500

ACCGAATGGA ATCCAGGCAA CACCTACGGC GAAACCGTTG TCACCGACGC GTCGCCCATC    1560

CGGTCGGCGC CTACTACGGG GCGTTGCCGC TGATCGTCGG GACGCTGGCG ACCTCGGCAA    1620

TCGCCCTGAT CATCGCGGTG CCGGTCTCTG TAGGAGCGGC GCTGGTGATC GTGGAACGGC    1680

TGCCGAAACG GTTGGCCGAG GCTGTGGGAA TAGTCCTGGA ATTGCTCGCC GGAATCCCCA    1740

GCGTGGTCGT CGGTTTGTGG GGGGCAATGA CGTTCGGGCC GTTCATCGCT CATCACATCG    1800

CTCCGGTGAT CGCTCACAAC GCTCCCGATG TGCCGGTGCT GAACTACTTG CGCGGCGACC    1860

CGGGCAACGG GGAGGGCATG TTGGTGTCCG GTCTGGTGTT GGCGGTGATG GTCGTTCCCA    1920

TTATCGCCAC CACCACTCAT GACCTGTTCC GGCAGGTGCC GGTGTTGCCC CGGGAGGGCG    1980

CGATCGGGAA TTC                                                      1993

(2) INFORMATION FOR SEQ ID NO: 150:

(i) SEQUENCE CHARACTERISTICS:
        (A) LENGTH: 374 amino acids
        (B) TYPE: amino acid
        (C) STRANDEDNESS: <Unknown>
        (D) TOPOLOGY: linear (xi) SEQUENCE DESCRIPTION: SEQ ID NO: 150:

Met Lys Ile Arg Leu His Thr Leu Leu Ala Val Leu Thr Ala Ala Pro
1               5                   10                  15

Leu Leu Leu Ala Ala Ala Gly Cys Gly Ser Lys Pro Pro Ser Gly Ser
            20                  25                  30

Pro Glu Thr Gly Ala Gly Ala Gly Thr Val Ala Thr Thr Pro Ala Ser
        35                  40                  45

Ser Pro Val Thr Leu Ala Glu Thr Gly Ser Thr Leu Leu Tyr Pro Leu
    50                  55                  60

Phe Asn Leu Trp Gly Pro Ala Phe His Glu Arg Tyr Pro Asn Val Thr
65                  70                  75                  80

Ile Thr Ala Gln Gly Thr Gly Ser Gly Ala Gly Ile Ala Gln Ala Ala
                85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
        115                 120                 125

Ala Gln Gln Val Asn Tyr Asn Leu Pro Gly Val Ser Glu His Leu Lys
    130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
```

-continued

```
                    180                 185                 190
Phe Leu Phe Thr Gln Tyr Leu Ser Lys Gln Asp Pro Glu Gly Trp Gly
            195                 200                 205
Lys Ser Pro Gly Phe Gly Thr Thr Val Asp Phe Pro Ala Val Pro Gly
210                 215                 220
Ala Leu Gly Glu Asn Gly Asn Gly Gly Met Val Thr Gly Cys Ala Glu
225                 230                 235                 240
Thr Pro Gly Cys Val Ala Tyr Ile Gly Ile Ser Phe Leu Asp Gln Ala
                245                 250                 255
Ser Gln Arg Gly Leu Gly Glu Ala Gln Leu Gly Asn Ser Ser Gly Asn
            260                 265                 270
Phe Leu Leu Pro Asp Ala Gln Ser Ile Gln Ala Ala Ala Gly Phe
            275                 280                 285
Ala Ser Lys Thr Pro Ala Asn Gln Ala Ile Ser Met Ile Asp Gly Pro
290                 295                 300
Ala Pro Asp Gly Tyr Pro Ile Ile Asn Tyr Glu Tyr Ala Ile Val Asn
305                 310                 315                 320
Asn Arg Gln Lys Asp Ala Ala Thr Ala Gln Thr Leu Gln Ala Phe Leu
                325                 330                 335
His Trp Ala Ile Thr Asp Gly Asn Lys Ala Ser Phe Leu Asp Gln Val
            340                 345                 350
His Phe Gln Pro Leu Pro Pro Ala Val Val Lys Leu Ser Asp Ala Leu
            355                 360                 365
Ile Ala Thr Ile Ser Ser
    370

(2) INFORMATION FOR SEQ ID NO: 151:

(i) SEQUENCE CHARACTERISTICS:
        (A) LENGTH: 1777 base pairs
        (B) TYPE: nucleic acid
        (C) STRANDEDNESS: single
        (D) TOPOLOGY: linear (xi) SEQUENCE DESCRIPTION: SEQ ID NO: 151:

GGTCTTGACC ACCACCTGGG TGTCGAAGTC GGTGCCCGGA TTGAAGTCCA GGTACTCGTG     60

GGTGGGGCGG GCGAAACAAT AGCGACAAGC ATGCGAGCAG CCGCGGTAGC CGTTGACGGT    120

GTAGCGAAAC GGCAACGCGG CCGCGTTGGG CACCTTGTTC AGCGCTGATT TGCACAACAC    180

CTCGTGGAAG GTGATGCCGT CGAATTGTGG CGCGCGAACG CTGCGGACCA GGCCGATCCG    240

CTGCAACCCG GCAGCGCCCG TCGTCAACGG GCATCCCGTT CACCGCGACG GCTTGCCGGG    300

CCCAACGCAT ACCATTATTC GAACAACCGT TCTATACTTT GTCAACGCTG GCCGCTACCG    360

AGCGCCGCAC AGGATGTGAT ATGCCATCTC TGCCCGCACA GACAGGAGCC AGGCCTTATG    420

ACAGCATTCG GCGTCGAGCC CTACGGGCAG CCGAAGTACC TAGAAATCGC CGGGAAGCGC    480

ATGGCGTATA TCGACGAAGG CAAGGGTGAC GCCATCGTCT TTCAGCACGG CAACCCCACG    540

TCGTCTTACT TGTGGCGCAA CATCATGCCG CACTTGGAAG GGCTGGGCCG GCTGGTGGCC    600

TGCGATCTGA TCGGGATGGG CGCGTCGGAC AAGCTCAGCC CATCGGGACC CGACCGCTAT    660

AGCTATGGCG AGCAACGAGA CTTTTTGTTC GCGCTCTGGG ATGCGCTCGA CCTCGGCGAC    720

CACGTGGTAC TGGTGCTGCA CGACTGGGGC TCGGCGCTCG GCTTCGACTG GCTAACCAG    780

CATCGCGACC GAGTGCAGGG GATCGCGTTC ATGGAAGCGA TCGTCACCCC GATGACGTGG    840

GCGGACTGGC CGCCGGCCGT GCGGGGTGTG TTCCAGGGTT CCGATCGCC TCAAGGCGAG    900
```

```
CCAATGGCGT TGGAGCACAA CATCTTTGTC GAACGGGTGC TGCCCGGGGC GATCCTGCGA    960

CAGCTCAGCG ACGAGGAAAT GAACCACTAT CGGCGGCCAT TCGTGAACGG CGGCGAGGAC   1020

CGTCGCCCCA CGTTGTCGTG GCCACGAAAC CTTCCAATCG ACGGTGAGCC CGCCGAGGTC   1080

GTCGCGTTGG TCAACGAGTA CCGGAGCTGG CTCGAGGAAA CCGACATGCC GAAACTGTTC   1140

ATCAACGCCG AGCCCGGCGC GATCATCACC GGCCGCATCC GTGACTATGT CAGGAGCTGG   1200

CCCAACCAGA CCGAAATCAC AGTGCCCGGC GTGCATTTCG TTCAGGAGGA CAGCGATGGC   1260

GTCGTATCGT GGGCGGGCGC TCGGCAGCAT CGGCGACCTG GGAGCGCTCT CATTTCACGA   1320

GACCAAGAAT GTGATTTCCG GCGAAGGCGG CGCCCTGCTT GTCAACTCAT AAGACTTCCT   1380

GCTCCGGGCA GAGATTCTCA GGGAAAAGGG CACCAATCGC AGCCGCTTCC TTCGCAACGA   1440

GGTCGACAAA TATACGTGGC AGGACAAAGG TCTTCCTATT TGCCCAGCGA ATTAGTCGCT   1500

GCCTTTCTAT GGGCTCAGTT CGAGGAAGCC GAGCGGATCA CGCGTATCCG ATTGGACCTA   1560

TGGAACCGGT ATCATGAAAG CTTCGAATCA TTGAACAGC GGGGGCTCCT GCGCCGTCCG   1620

ATCATCCCAC AGGGCTGCTC TCACAACGCC CACATGTACT ACGTGTTACT AGCGCCCAGC   1680

GCCGATCGGG AGGAGGTGCT GGCGCGTCTG ACGAGCGAAG GTATAGGCGC GGTCTTTCAT   1740

TACGTGCCGC TTCACGATTC GCCGGCCGGG CGTCGCT                            1777

(2) INFORMATION FOR SEQ ID NO: 152:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (xi) SEQUENCE DESCRIPTION: SEQ ID NO: 152:

GAGATTGAAT CGTACCGGTC TCCTTAGCGG CTCCGTCCCG TGAATGCCCA TATCACGCAC     60

GGCCATGTTC TGGCTGTCGA CCTTCGCCCC ATGCCCGGAC GTTGGTAAAC CCAGGGTTTG    120

ATCAGTAATT CCGGGGACG GTTGCGGGAA GGCGGCCAGG ATGTGCGTGA GCCGCGGCGC    180

CGCCGTCGCC CAGGCGACCG CTGGATGCTC AGCCCCGGTG CGGCGACGTA GCCAGCGTTT    240

GGCGCGTGTC GTCCACAGTG GTACTCCGGT GACGACGCGG CGCGGTGCCT GGGTGAAGAC    300

CGTGACCGAC GCCGCCGATT CAGA                                          324

(2) INFORMATION FOR SEQ ID NO: 153:

(i) SEQUENCE CHARACTERISTICS:
        (A) LENGTH: 1338 base pairs
        (B) TYPE: nucleic acid
        (C) STRANDEDNESS: single
        (D) TOPOLOGY: linear (xi) SEQUENCE DESCRIPTION: SEQ ID NO: 153:

GCGGTACCGC CGCGTTGCGC TGGCACGGGA CCTGTACGAC CTGAACCACT TCGCCTCGCG     60

AACGATTGAC GAACCGCTCG TGCGGCGGCT GTGGGTGCTC AAGGTGTGGG GTGATGTCGT    120

CGATGACCGG CGCGGCACCC GGCCACTACG CGTCGAAGAC GTCCTCGCCG CCCGCAGCGA    180

GCACGACTTC CAGCCCGACT CGATCGGCGT GCTGACCCGT CCTGTCGCTA TGGCTGCCTG    240

GGAAGCTCGC GTTCGGAAGC GATTTGCGTT CCTCACTGAC CTCGACGCCG ACGAGCAGCG    300

GTGGGCCGCC TGCGACGAAC GGCACCGCCG CGAAGTGGAG AACGCGCTGG CGGTGCTGCG    360

GTCCTGATCA ACCTGCCGGC GATCGTGCCG TTCCGCTGGC ACGGTTGCGG CTGGACGCGG    420

CTGAATCGAC TAGATGAGAG CAGTTGGGCA CGAATCCGGC TGTGGTGGTG AGCAAGACAC    480
```

```
GAGTACTGTC ATCACTATTG GATGCACTGG ATGACCGGCC TGATTCAGCA GGACCAATGG      540

AACTGCCCGG GGCAAAACGT CTCGGAGATG ATCGGCGTCC CCTCGGAACC CTGCGGTGCT      600

GGCGTCATTC GGACATCGGT CCGGCTCGCG GGATCGTGGT GACGCCAGCG CTGAAGGAGT      660

GGAGCGCGGC GGTGCACGCG CTGCTGGACG GCCGGCAGAC GGTGCTGCTG CGTAAGGGCG      720

GGATCGGCGA GAAGCGCTTC GAGGTGGCGG CCCACGAGTT CTTGTTGTTC CCGACGGTCG      780

CGCACAGCCA CGCCGAGCGG GTTCGCCCCG AGCACCGCGA CCTGCTGGGC CCGGCGGCCG      840

CCGACAGCAC CGACGAGTGT GTGCTACTGC GGGCCGCAGC GAAAGTTGTT GCCGCACTGC      900

CGGTTAACCG GCCAGAGGGT CTGGACGCCA TCGAGGATCT GCACATCTGG ACCGCCGAGT      960

CGGTGCGCGC CGACCGGCTC GACTTTCGGC CCAAGCACAA ACTGGCCGTC TTGGTGGTCT     1020

CGGCGATCCC GCTGGCCGAG CCGGTCCGGC TGGCGCGTAG GCCCGAGTAC GGCGGTTGCA     1080

CCAGCTGGGT GCAGCTGCCG GTGACGCCGA CGTTGGCGGC GCCGGTGCAC GACGAGGCCG     1140

CGCTGGCCGA GGTCGCCGCC CGGGTCCGCG AGGCCGTGGG TTGACTGGGC GGCATCGCTT     1200

GGGTCTGAGC TGTACGCCCA GTCGGCGCTG CGAGTGATCT GCTGTCGGTT CGGTCCCTGC     1260

TGGCGTCAAT TGACGGCGCG GGCAACAGCA GCATTGGCGG CGCCATCCTC CGCGCGGCCG     1320

GCGCCCACCG CTACAACC                                                   1338

(2) INFORMATION FOR SEQ ID NO: 154:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO: 154:

CCGGCGGCAC CGGCGGCACC GGCGGTACCG GCGGCAACGG CGCTGACGCC GCTGCTGTGG       60

TGGGCTTCGG CGCGAACGGC GACCCTGGCT TCGCTGGCGG CAAAGGCGGT AACGGCGGAA      120

TAGGTGGGGC CGCGGTGACA GGCGGGGTCG CCGGCGACGG CGGCACCGGC GGCAAAGGTG      180

GCACCGGCGG TGCCGGCGGC GCCGGCAACG ACGCCGGCAG CACCGGCAAT CCCGGCGGTA      240

AGGGCGGCGA CGGCGGGATC GGCGGTGCCG GCGGGGCCGG CGGCGCGGCC GGCACCGGCA      300

ACGGCGGCCA TGCCGGCAAC C                                                321

(2) INFORMATION FOR SEQ ID NO: 155:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (xi) SEQUENCE DESCRIPTION: SEQ ID NO: 155:

GAAGACCCGG CCCCGCCATA TCGATCGGCT CGCCGACTAC TTTCGCCGAA CGTGCACGCG       60

GCGGCGTCGG GCTGATCATC ACCGGTGGCT ACGCGCCCAA CCGCACCGGA TGGCTGCTGC      120

CGTTCGCCTC CGAACTCGTC ACTTCGGCGC AAGCCCGACG GCACCGCCGA ATCACCAGGG      180

CGGTCCACGA TTCGGGTGCA AAGATCCTGC TGCAAATCCT GCACGCCGGA CGCTACGCCT      240

ACCACCCACT TGCGGTCAGC GCCTCGCCGA TCAAGGCGCC GATCACCCCG TTTCGTCCGC      300

GAGCACTATC GGCTCGCGGG GTCGAAGCGA CCATCGCGGA TTTCGCCCGC TGCGCGCAGT      360

TGGCCCGCGA TGCCGGCTAC GACGGCGTCG AAATCATGGG CAGCGAAGGG TATCTGCTCA      420
```

```
ATCAGTTCCT GGCGCCGCGC ACCAACAAGC GCACCGACTC GTGGGGCGGC ACACCGGCCA      480

ACCGTCGCCG GT                                                         492
```

(2) INFORMATION FOR SEQ ID NO: 156:

(i) SEQUENCE CHARACTERISTICS:
        (A) LENGTH: 536 amino acids
        (B) TYPE: amino acid
        (C) STRANDEDNESS: <Unknown>
        (D) TOPOLOGY: linear (xi) SEQUENCE DESCRIPTION: SEQ ID NO: 156:

```
Phe Ala Gln His Leu Val Glu Gly Asp Ala Val Glu Leu Trp Arg Ala
 1               5                  10                  15

Asn Ala Ala Asp Gln Ala Asp Pro Leu Gln Pro Gly Ser Ala Arg Arg
                20                  25                  30

Gln Arg Ala Ser Arg Ser Pro Arg Arg Leu Ala Gly Pro Asn Ala Tyr
            35                  40                  45

His Tyr Ser Asn Asn Arg Ser Ile Leu Cys Gln Arg Trp Pro Leu Pro
        50                  55                  60

Ser Ala Ala Gln Asp Val Ile Cys His Leu Cys Pro His Arg Gln Glu
65                  70                  75                  80

Pro Gly Leu Met Thr Ala Phe Gly Val Glu Pro Tyr Gly Gln Pro Lys
                85                  90                  95

Tyr Leu Glu Ile Ala Gly Lys Arg Met Ala Tyr Ile Asp Glu Gly Lys
                100                 105                 110

Gly Asp Ala Ile Val Phe Gln His Gly Asn Pro Thr Ser Ser Tyr Leu
            115                 120                 125

Trp Arg Asn Ile Met Pro His Leu Glu Gly Leu Gly Arg Leu Val Ala
        130                 135                 140

Cys Asp Leu Ile Gly Met Gly Ala Ser Asp Lys Leu Ser Pro Ser Gly
145                 150                 155                 160

Pro Asp Arg Tyr Ser Tyr Gly Glu Gln Arg Asp Phe Leu Phe Ala Leu
                165                 170                 175

Trp Asp Ala Leu Asp Leu Gly Asp His Val Val Leu Val Leu His Asp
                180                 185                 190

Trp Gly Ser Ala Leu Gly Phe Asp Trp Ala Asn Gln His Arg Asp Arg
            195                 200                 205

Val Gln Gly Ile Ala Phe Met Glu Ala Ile Val Thr Pro Met Thr Trp
        210                 215                 220

Ala Asp Trp Pro Pro Ala Val Arg Gly Val Phe Gln Gly Phe Arg Ser
225                 230                 235                 240

Pro Gln Gly Glu Pro Met Ala Leu Glu His Asn Ile Phe Val Glu Arg
                245                 250                 255

Val Leu Pro Gly Ala Ile Leu Arg Gln Leu Ser Asp Glu Glu Met Asn
                260                 265                 270

His Tyr Arg Arg Pro Phe Val Asn Gly Gly Glu Asp Arg Arg Pro Thr
            275                 280                 285

Leu Ser Trp Pro Arg Asn Leu Pro Ile Asp Gly Glu Pro Ala Glu Val
        290                 295                 300

Val Ala Leu Val Asn Glu Tyr Arg Ser Trp Leu Glu Glu Thr Asp Met
305                 310                 315                 320

Pro Lys Leu Phe Ile Asn Ala Glu Pro Gly Ala Ile Ile Thr Gly Arg
                325                 330                 335

Ile Arg Asp Tyr Val Arg Ser Trp Pro Asn Gln Thr Glu Ile Thr Val
```

```
                    340                 345                 350
Pro Gly Val His Phe Val Gln Glu Asp Ser Asp Gly Val Val Ser Trp
                355                 360                 365
Ala Gly Ala Arg Gln His Arg Arg Pro Gly Ser Ala Leu Ile Ser Arg
            370                 375                 380
Asp Gln Glu Cys Asp Phe Arg Arg Arg Arg Pro Ala Cys Gln Leu
385                 390                 395                 400
Ile Arg Leu Pro Ala Pro Gly Arg Asp Ser Gln Gly Lys Gly His Gln
                405                 410                 415
Ser Gln Pro Leu Pro Ser Gln Arg Gly Arg Gln Ile Tyr Val Ala Gly
                420                 425                 430
Gln Arg Ser Ser Tyr Leu Pro Ser Glu Leu Val Ala Ala Phe Leu Trp
                435                 440                 445
Ala Gln Phe Glu Glu Ala Glu Arg Ile Thr Arg Ile Arg Leu Asp Leu
            450                 455                 460
Trp Asn Arg Tyr His Glu Ser Phe Glu Ser Leu Glu Gln Arg Gly Leu
465                 470                 475                 480
Leu Arg Arg Pro Ile Ile Pro Gln Gly Cys Ser His Asn Ala His Met
                485                 490                 495
Tyr Tyr Val Leu Leu Ala Pro Ser Ala Asp Arg Glu Glu Val Leu Ala
                500                 505                 510
Arg Leu Thr Ser Glu Gly Ile Gly Ala Val Phe His Tyr Val Pro Leu
            515                 520                 525
His Asp Ser Pro Ala Gly Arg Arg
            530                 535

(2) INFORMATION FOR SEQ ID NO: 157:

(i) SEQUENCE CHARACTERISTICS:
        (A) LENGTH: 284 amino acids
        (B) TYPE: amino acid
        (C) STRANDEDNESS: <Unknown>
        (D) TOPOLOGY: linear (xi) SEQUENCE DESCRIPTION: SEQ ID NO: 157:

Asn Glu Ser Ala Pro Arg Ser Pro Met Leu Pro Ser Ala Arg Pro Arg
1               5                   10                  15
Tyr Asp Ala Ile Ala Val Leu Leu Asn Glu Met His Ala Gly His Cys
                20                  25                  30
Asp Phe Gly Leu Val Gly Pro Ala Pro Asp Ile Val Thr Asp Ala Ala
            35                  40                  45
Gly Asp Asp Arg Ala Gly Leu Gly Val Asp Glu Gln Phe Arg His Val
50              55                  60
Gly Phe Leu Glu Pro Ala Pro Val Leu Val Asp Gln Arg Asp Asp Leu
65                  70                  75                  80
Gly Gly Leu Thr Val Asp Trp Lys Val Ser Trp Pro Arg Gln Arg Gly
                85                  90                  95
Ala Thr Val Leu Ala Ala Val His Glu Trp Pro Pro Ile Val Val His
            100                 105                 110
Phe Leu Val Ala Glu Leu Ser Gln Asp Arg Pro Gly Gln His Pro Phe
            115                 120                 125
Asp Lys Asp Val Val Leu Gln Arg His Trp Leu Ala Leu Arg Arg Ser
            130                 135                 140
Glu Thr Leu Glu His Thr Pro His Gly Arg Arg Pro Val Arg Pro Arg
145                 150                 155                 160
```

```
His Arg Gly Asp Asp Arg Phe His Glu Arg Asp Pro Leu His Ser Val
                165                 170                 175

Ala Met Leu Val Ser Pro Val Glu Ala Glu Arg Arg Ala Pro Val Val
            180                 185                 190

Gln His Gln Tyr His Val Val Ala Glu Val Glu Arg Ile Pro Glu Arg
            195                 200                 205

Glu Gln Lys Val Ser Leu Leu Ala Ile Ala Ile Ala Val Gly Ser Arg
        210                 215                 220

Trp Ala Glu Leu Val Arg Arg Ala His Pro Asp Gln Ile Ala Gly His
225                 230                 235                 240

Gln Pro Ala Gln Pro Phe Gln Val Arg His Asp Val Ala Pro Gln Val
                245                 250                 255

Arg Arg Arg Gly Val Ala Val Leu Lys Asp Asp Gly Val Thr Leu Ala
                260                 265                 270

Phe Val Asp Ile Arg His Ala Leu Pro Gly Asp Phe
            275                 280
```

(2) INFORMATION FOR SEQ ID NO: 158:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (xi) SEQUENCE DESCRIPTION: SEQ ID NO: 158:

```
ATGAACATGT CGTCGGTGGT GGGTCGCAAG GCCTTTGCGC GATTCGCCGG CTACTCCTCC    60

GCCATGCACG CGATCGCCGG TTTCTCCGAT GCGTTGCGCC AAGAGCTGCG GGGTAGCGGA   120

ATCGCCGTCT CGGTGATCCA CCCGGCGCTG ACCCAGACAC CGCTGTTGGC CAACGTCGAC   180

CCCGCCGACA TGCCGCCGCC GTTTCGCAGC CTCACGCCCA TTCCCGTTCA CTGGGTCGCG   240

GCAGCGGTGC TTGACGGTGT GGCG                                         264
```

(2) INFORMATION FOR SEQ ID NO: 159:

(i) SEQUENCE CHARACTERISTICS:
        (A) LENGTH: 1171 base pairs
        (B) TYPE: nucleic acid
        (C) STRANDEDNESS: single
        (D) TOPOLOGY: linear (xi) SEQUENCE DESCRIPTION: SEQ ID NO: 159:

```
TAGTCGGCGA CGATGACGTC GCGGTCCAGG CCGACCGCTT CAAGCACCAG CGCGACCACG    60

AAGCCGGTGC GATCCTTACC CGCGAAGCAG TGGGTGAGCA CCGGGCGTCC GGCGGCAAGC   120

AGTGTGACGA CACGATGTAG CGCGCGCTGT GCTCCATTGC GCGTTGGGAA TTGGCGATAC   180

TCGTCGGTCA TGTAGCGGGT GGCCGCGTCA TTTATCGACT GGCTGGATTC GCCGGACTCG   240

CCGTTGGACC CGTCATTGGT TAGCAGCCTC TTGAATGCGG TTTCGTGCGG CGCTGAGTCG   300

TCGGCGTCAT CATCGGCGAG GTCGGGGAAC GGCAGCAGGT GGACGTCGAT GCCGTCCGGA   360

ACCCGTCCTG GACCGCGGCG GGCAACCTCC CGGGACGACC GCAGGTCGGC AACGTCGGTG   420

ATCCCCAGCC GGCGCAGCGT TGCCCCTCGT GCCGAATTCG GCACGAGGCT GGCGAGCCAC   480

CGGGCATCAC CAAGCAACGC TTGCCCAGTA CGGATCGTCA CTTCCGCATC CGGCAGACCA   540

ATCTCCTCGC CGCCCATCGT CAGATCCCGC TCGTGCGTTG ACAAGAACGG CCGCAGATGT   600

GCCAGCGGGT ATCGGAGATT GAACCGCGCA CGCAGTTCTT CAATCGCTGC GCGCTGCCGC   660

ACTATTGGCA CTTTCCGGCG GTCGCGGTAT TCAGCAAGCA TGCGAGTCTC GACGAACTCG   720
```

```
CCCCACGTAA CCCACGGCGT AGCTCCCGGC GTGACGCGGA GGATCGGCGG GTGATCTTTG        780

CCGCCACGCT CGTAGCCGTT GATCCACCGC TTCGCGGTGC CGGCGGGGAG GCCGATCAGC        840

TTATCGACCT CGGCGTATGC CGACGGCAAG CTGGGCGCGT TCGTCGAGGT CAAGAACTCC        900

ACCATCGGCA CCGGCACCAA GGTGCCGCAC CTGACCTACG TCGGCGACGC CGACATCGGC        960

GAGTACAGCA ACATCGGCGC CTCCAGCGTG TTCGTCAACT ACGACGGTAC GTCCAAACGG       1020

CGCACCACCG TCGGTTCGCA CGTACGGACC GGGTCCGACA CCATGTTCGT GGCCCCAGTA       1080

ACCATCGGCG ACGGCGCGTA TACCGGGGCC GGCACAGTGG TGCGGGAGGA TGTCCCGCCG       1140

GGGGCGCTGG CAGTGTCGGC GGGTCCGCAA C                                      1171

(2) INFORMATION FOR SEQ ID NO: 160:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (xi) SEQUENCE DESCRIPTION: SEQ ID NO: 160:

GCAAAGGCGG CACCGGCGGG GCCGGCATGA ACAGCCTCGA CCCGCTGCTA GCCGCCCAAG         60

ACGGCGGCCA AGGCGGCACC GGCGGCACCG GCGGCAACGC CGGCGCCGGC GGCACCAGCT        120

TCACCCAAGG CGCCGACGGC AACGCCGGCA ACGGCGGTGA CGGCGGGGTC GGCGGCAACG        180

GCGGAAACGG CGGAAACGGC GCAGACAACA CCACCACCGC CGCCGCC                     227

(2) INFORMATION FOR SEQ ID NO: 161:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (xi) SEQUENCE DESCRIPTION: SEQ ID NO: 161:

CCTCGCCACC ATGGGCGGGC AGGGCGGTAG CGGTGGCGCC GGCTCTACCC CAGGCGCCAA         60

GGGCGCCCAC GGCTTCACTC CAACCAGCGG CGGCGACGGC GGCGACGGCG GCAACGGCGG        120

CAACTCCCAA GTGGTCGGCG GCAACGGCGG CGACGGCGGC AATGGCGGCA ACGGCGGCAG        180

CGCCGGCACG GGCGGCAACG GCGGCCGCGG CGGCGACGGC GCGTTTGGTG GCATGAGTGC        240

CAACGCCACC AACCCTGGTG AAAACGGGCC AAACGGTAAC CCCGGCGGCA ACGGTGGCGC        300

CGGC                                                                    304

(2) INFORMATION FOR SEQ ID NO: 162:

(i) SEQUENCE CHARACTERISTICS:
        (A) LENGTH: 1439 base pairs
        (B) TYPE: nucleic acid
        (C) STRANDEDNESS: single
        (D) TOPOLOGY: linear (xi) SEQUENCE DESCRIPTION: SEQ ID NO: 162:

GTGGGACGCT GCCGAGGCTG TATAACAAGG ACAACATCGA CCAGCGCCGG CTCGGTGAGC         60

TGATCGACCT ATTTAACAGT GCGCGCTTCA GCCGGCAGGG CGAGCACCGC GCCCGGGATC        120

TGATGGGTGA GGTCTACGAA TACTTCCTCG GCAATTTCGC TCGCGCGGAA GGGAAGCGGG        180

GTGGCGAGTT CTTTACCCCG CCCAGCGTGG TCAAGGTGAT CGTGGAGGTG CTGGAGCCGT        240

CGAGTGGGCG GGTGTATGAC CCGTGCTGCG GTTCCGGAGG CATGTTTGTG CAGACCGAGA        300
```

```
AGTTCATCTA CGAACACGAC GGCGATCCGA AGGATGTCTC GATCTATGGC CAGGAAAGCA      360

TTGAGGAGAC CTGGCGGATG GCGAAGATGA ACCTCGCCAT CCACGGCATC GACAACAAGG      420

GGCTCGGCGC CCGATGGAGT GATACCTTCG CCCGCGACCA GCACCCGGAC GTGCAGATGG      480

ACTACGTGAT GGCCAATCCG CCGTTCAACA TCAAAGACTG GCCCGCAAC GAGGAAGACC       540

CACGCTGGCG CTTCGGTGTT CCGCCCGCCA ATAACGCCAA CTACGCATGG ATTCAGCACA      600

TCCTGTACAA CTTGGCGCCG GGAGGTCGGG CGGGCGTGGT GATGGCCAAC GGGTCGATGT      660

CGTCGAACTC CAACGGCAAG GGGGATATTC GCGCGCAAAT CGTGGAGGCG GATTTGGTTT      720

CCTGCATGGT CGCGTTACCC ACCCAGCTGT TCCGCAGCAC CGGAATCCCG GTGTGCCTGT      780

GGTTTTTCGC CAAAAACAAG GCGGCAGGTA AGCAAGGGTC TATCAACCGG TGCGGGCAGG      840

TGCTGTTCAT CGACGCTCGT GAACTGGGCG ACCTAGTGGA CCGGGCCGAG CGGGCGCTGA      900

CCAACGAGGA GATCGTCCGC ATCGGGGATA CCTTCCACGC GAGCACGACC ACCGGCAACG      960

CCGGCTCCGG TGGTGCCGGC GGTAATGGGG GCACTGGCCT CAACGGCGCG GGCGGTGCTG     1020

GCGGGGCCGG CGGCAACGCG GGTGTCGCCG GCGTGTCCTT CGGCAACGCT GTGGGCGGCG     1080

ACGGCGGCAA CGGCGGCAAC GGCGGCCACG GCGGCGACGG CACGACGGGC GGCGCCGGCG     1140

GCAAGGGCGG CAACGCAGC AGCGGTGCCG CCAGCGGCTC AGGCGTCGTC AACGTCACCG      1200

CCGGCCACGG CGGCAACGGC GGCAATGGCG GCAACGGCGG CAACGGCTCC GCGGGCGCCG     1260

GCGGCCAGGG CGGTGCCGGC GGCAGCGCCG GCAACGGCGG CCACGGCGGC GGTGCCACCG     1320

GCGGCGCCAG CGGCAAGGGC GGCAACGGCA CCAGCGGTGC CGCCAGCGGC TCAGGCGTCA     1380

TCAACGTCAC CGCCGGCCAC GGCGGCAACG GCGGCAATGG CCGCAACGGC GGCAACGGC     1439

(2) INFORMATION FOR SEQ ID NO: 163:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (xi) SEQUENCE DESCRIPTION: SEQ ID NO: 163:

GGGCCGGCGG GGCCGGATTT TCTCGTGCCT TGATTGTCGC TGGGGATAAC GGCGGTGATG       60

GTGGTAACGG CGGGATGGGC GGGGCTGGCG GGGCTGGCGG CCCCGGCGGG GCCGGCGGCC      120

TGATCAGCCT GCTGGGCGGC CAAGGCGCCG GCGGGGCCGG CGGGACCGGC GGGGCCGGCG      180

GTGTTGGCGG TGACGGCGGG GCCGGCGGCC CCGGCAACCA GGCCTTCAAC GCAGGTGCCG      240

GCGGGGCCGG CGGCCTGATC AGCCTGCTGG GCGGCCAAGG CGCCGGCGGG GCCGGCGGGA      300

CCGGCGGGGC CGGCGGTGTT GGCGGTGAC                                       329

(2) INFORMATION FOR SEQ ID NO: 164:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 164:

GCAACGGTGG CAACGGCGGC ACCAGCACGA CCGTGGGGAT GGCCGGAGGT AACTGTGGTG       60

CCGCCGGGCT GATCGGCAAC                                                  80

(2) INFORMATION FOR SEQ ID NO: 165:
```

(i) SEQUENCE CHARACTERISTICS:
    (A) LENGTH: 392 base pairs
    (B) TYPE: nucleic acid
    (C) STRANDEDNESS: single
    (D) TOPOLOGY: linear (xi) SEQUENCE DESCRIPTION: SEQ ID NO: 165:

```
GGGCTGTGTC GCACTCACAC CGCCGCATTC GGCGACGTTG GCCGCCCAAT ATCCAGCTCA    60
AGGCCTACTA CTTACCGTCG GAGGACCGCC GCATCAAGGT GCGGGTCAGC GCCCAAGGAA   120
TCAAGGTCAT CGACCGCGAC GGGCATCGAG GCCGTCGTCG CGCGGCTCGG GCAGGATCCG   180
CCCCGGCGCA CTTCGCGCGC CAAGCGGGCT CATCGCTCCG AACGCGGCG ATCCTGTGAG    240
CACAACTGAT GGCGCGCAAC GAGATTCGTC CAATTGTCAA GCCGTGTTCG ACCGCAGGGA   300
CCGGTTATAC GTATGTCAAC CTATGTCACT CGCAAGAACC GGCATAACGA TCCCGTGATC   360
CGCCGACAGC CCACGAGTGC AAGACCGTTA CA                                  392
```

(2) INFORMATION FOR SEQ ID NO: 166:

(i) SEQUENCE CHARACTERISTICS:
    (A) LENGTH: 535 base pairs
    (B) TYPE: nucleic acid
    (C) STRANDEDNESS: single
    (D) TOPOLOGY: linear (xi) SEQUENCE DESCRIPTION: SEQ ID NO: 166:

```
ACCGGCGCCA CCGGCGGCAC CGGGTTCGCC GGTGGCGCCG GCGGGGCCGG CGGGCAGGGC    60
GGTATCAGCG GTGCCGGCGG CACCAACGGC TCTGGTGGCG CTGGCGGCAC CGGCGGACAA   120
GGCGGCGCCG GGGGCGCTGG CGGGGCCGGC GCCGATAACC CCACCGGCAT CGGCGGCGCC   180
GGCGGCACCG GCGGCACCGG CGGAGCGGCC GGAGCCGGCG GGGCCGGTGG CGCCATCGGT   240
ACCGGCGGCA CCGGCGGCGC GGTGGGCAGC GTCGGTAACG CCGGGATCGG CGGTACCGGC   300
GGTACGGGTG GTGTCGGTGG TGCTGGTGGT GCAGGTGCGG CTGCGGCCGC TGGCAGCAGC   360
GCTACCGGTG GCGCCGGGTT CGCCGGCGGC GCCGGCGGAG AAGGCGGACC GGGCGGCAAC   420
AGCGGTGTGG GCGGCACCAA CGGCTCCGGC GGCGCCGGCG GTGCAGGCGG CAAGGGCGGC   480
ACCGGAGGTG CCGGCGGGTC CGGCGCGGAC AACCCCACCG GTGCTGGTTT CGCCG        535
```

(2) INFORMATION FOR SEQ ID NO: 167:

(i) SEQUENCE CHARACTERISTICS:
    (A) LENGTH: 690 base pairs
    (B) TYPE: nucleic acid
    (C) STRANDEDNESS: single
    (D) TOPOLOGY: linear (xi) SEQUENCE DESCRIPTION: SEQ ID NO: 167:

```
CCGACGTCGC CGGGGCGATA CGGGGGTCAC CGACTACTAC ATCATCCGCA CCGAGAATCG    60
GCCGCTGCTG CAACCGCTGC GGGCGGTGCC GGTCATCGGA GATCCGCTGG CCGACCTGAT   120
CCAGCCGAAC CTGAAGGTGA TCGTCAACCT GGGCTACGGC GACCCGAACT ACGGCTACTC   180
GACGAGCTAC GCCGATGTGC GAACGCCGTT CGGGCTGTGG CCGAACGTGC CGCCTCAGGT   240
CATCGCCGAT GCCCTGGCCG CCGGAACACA AGAAGGCATC CTTGACTTCA CGGCCGACCT   300
GCAGGCGCTG TCCGCGCAAC CGCTCACGCT CCCGCAGATC CAGCTGCCGC AACCCGCCGA   360
TCTGGTGGCC GCGGTGGCCG CCGCACCGAC GCCGGCCGAG GTGGTGAACA CGCTCGCCAG   420
GATCATCTCA ACCAACTACG CCGTCCTGCT GCCCACCGTG GACATCGCCC TCGCCTGGTC   480
```

```
ACCACCCTGC CGCTGTACAC CACCCAACTG TTCGTCAGGC AACTCGCTGC GGGCAATCTG    540

ATCAACGCGA TCGGCTATCC CCTGGCGGCC ACCGTAGGTT TAGGCACGAT CGATAGCGGG    600

CGGCGTGGAA TTGCTCACCC TCCTCGCGGC GGCCTCGGAC ACCGTTCGAA ACATCGAGGG    660

CCTCGTCACC TAACGGATTC CCGACGGCAT                                    690
```

(2) INFORMATION FOR SEQ ID NO: 168:

(i) SEQUENCE CHARACTERISTICS:
        (A) LENGTH: 407 base pairs
        (B) TYPE: nucleic acid
        (C) STRANDEDNESS: single
        (D) TOPOLOGY: linear (xi) SEQUENCE DESCRIPTION: SEQ ID NO: 168:

```
ACGGTGACGG CGGTACTGGC GGCGGCCACG GCGGCAACGG CGGGAATCCC GGGTGGCTCT     60

TGGGCACAGC CGGGGGTGGC GGCAACGGTG GCGCCGGCAG CACCGGTACT GCAGGTGGCG    120

GCTCTGGGGG CACCGGCGGC GACGGCGGGA CCGGCGGGCG TGGCGGCCTG TTAATGGGCG    180

CCGGCGCCGG CGGGCACGGT GGCACTGGCG GCGCGGGCGG TGCCGGTGTC GACGGTGGCG    240

GCGCCGGCGG GGCCGGCGGG GCCGGCGGCA ACGGCGGCGC CGGGGGTCAA GCCGCCCTGC    300

TGTTCGGGCG CGGCGGCACC GGCGGAGCCG GCGGCTACGG CGGCGATGGC GGTGGCGGCG    360

GTGACGGCTT CGACGGCACG ATGGCCGGCC TGGGTGGTAC CGGTGGC                 407
```

(2) INFORMATION FOR SEQ ID NO: 169:

(i) SEQUENCE CHARACTERISTICS:
        (A) LENGTH: 468 base pairs
        (B) TYPE: nucleic acid
        (C) STRANDEDNESS: single
        (D) TOPOLOGY: linear (xi) SEQUENCE DESCRIPTION: SEQ ID NO: 169:

```
GATCGGTCAG CGCATCGCCC TCGGCGGCAA GCGATTCCGC GGTCTCACCG AAGAACATCG     60

TGCACGCGGC GGCGCGGACC AGCCCGCTGC GCTGCGGCGC GTCGAACGCC TCCAGCAGGC    120

ACAGCCAGTC CTTGGCGGCC TGCGAGGCGA ACACGTCGGT GTCACCGGTG TAGATCGCCG    180

GGATGCCCGC CTCCGCCAAC GCATTCCGGC ACGCCCGCGC GTCTTTGTGA TGCTCGACGA    240

TCACCGCGAT GTCTGCGGCC ACCACGGGCC GCCCGGCGAA GGTGGCCCCG CTGGCCAGTA    300

GCGCCGCGAC GTCGGCGGCC AGGTCGTCGG GGATGTGCCG GCGCAGCGCT CCGGCGCGAC    360

GCCCGAAAAA CGACCCCTCA CCCAGCTGGG TCCCGCTGGC ATATCCCTTG CCGTCCTGGG    420

CGATATTGGA CGCGCATGCC CCGACCGCGT ACAGGCCGGC CACCACCG                468
```

(2) INFORMATION FOR SEQ ID NO: 170:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (xi) SEQUENCE DESCRIPTION: SEQ ID NO: 170:

```
GGTGGTAACG GCGGCCAGGG TGGCATCGGC GGCGCCGGCG AGAGAGGCGC CGACGGCGCC     60

GGCCCCAATG CTAACGGCGC AAACGGCGAG AACGGCGGTA GCGGTGGTAA CGGTGGCGAC    120

GGCGGCGCCG GCGGCAATGG CGGCGCGGGC GGCAACGCGC AGGCGGCCGG GTACACCGAC    180

GGCGCCACGG GCACCGGCGG CGACGGCGGC AACGGCGGC                          219
```

(2) INFORMATION FOR SEQ ID NO: 171:

(i) SEQUENCE CHARACTERISTICS:
        (A) LENGTH: 494 base pairs
        (B) TYPE: nucleic acid
        (C) STRANDEDNESS: single
        (D) TOPOLOGY: linear (xi) SEQUENCE DESCRIPTION: SEQ ID NO: 171:

```
TAGCTCCGGC GAGGGCGGCA AGGGCGGCGA CGGTGGCCAC GGCGGTGACG GCGTCGGCGG    60

CAACAGTTCC GTCACCCAAG GCGGCAGCGG CGGTGGCGGC GGCGCCGGCG GCGCCGGCGG   120

CAGCGGCTTT TTCGGCGGCA AGGGCGGCTT CGGCGGCGAC GGCGGTCAGG GCGGCCCCAA   180

CGGCGGCGGT ACCGTCGGCA CCGTGGCCGG TGGCGGCGGC AACGGCGGTG TCGGCGGCCG   240

GGGCGGCGAC GGCGTCTTTG CCGGTGCCGG CGGCCAGGGC GGCCTCGGTG GCAGGGCGG    300

CAATGGCGGC GGCTCCACCG GCGGCAACGG CGGCCTTGGC GGCGCGGGCG GTGGCGGAGG   360

CAACGCCCCG GCTCGTGCCG AATCCGGGCT GACCATGGAC AGCGCGGCCA AGTTCGCTGC   420

CATCGCATCA GGCGCGTACT GCCCCGAACA CCTGGAACAT CACCCGAGTT AGCGGGGCGC   480

ATTTCCTGAT CACC                                                    494
```

(2) INFORMATION FOR SEQ ID NO: 172:

(i) SEQUENCE CHARACTERISTICS:
        (A) LENGTH: 220 base pairs
        (B) TYPE: nucleic acid
        (C) STRANDEDNESS: single
        (D) TOPOLOGY: linear (xi) SEQUENCE DESCRIPTION: SEQ ID NO: 172:

```
GGGCCGGTGG TGCCGCGGGC CAGCTCTTCA GCGCCGGAGG CGCGGCGGGT GCCGTTGGGG    60

TTGGCGGCAC CGGCGGCCAG GGTGGGGCTG GCGGTGCCGG AGCGGCCGGC GCCGACGCCC   120

CCGCCAGCAC AGGTCTAACC GGTGGTACCG GGTTCGCTGG CGGGGCCGGC GGCGTCGGCG   180

GCCAGAGCGG CAACGCCATT GCCGGCGGCA TCAACGGCTC                         220
```

(2) INFORMATION FOR SEQ ID NO: 173:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (xi) SEQUENCE DESCRIPTION: SEQ ID NO: 173:

```
ATGGCGGCAA CGGGGCCCC GGCGGTGCTG GCGGGGCCGG CGACTACAAT TTCCAACGGC     60

GGGCAGGGTG GTGCCGGCGG CCAAGGCGGC CAAGGCGGCC TGGGCGGGGC AAGCACCACC   120

TGATCGGCCT AGCCGCACCC GGGAAAGCCG ATCCAACAGG CGACGATGCC GCCTTCCTTG   180

CCGCGTTGGA CCAGGCCGGC ATCACCTACG CTGACCCAGG CCACGCCATA ACGGCCGCCA   240

AGGCGATGTG TGGGCTGTGT GCTAACGGCG TAACAGGTCT ACAGCTGGTC GCGGACCTGC   300

GGGACTACAA TCCCGGGCTG ACCATGGACA GCGCGGCCAA GTTCGCTGCC ATCGCATCAG   360

GCGCGTACTG CCCCGAACAC CTGGAACA                                     388
```

(2) INFORMATION FOR SEQ ID NO: 174:

(i) SEQUENCE CHARACTERISTICS:
        (A) LENGTH: 400 base pairs
        (B) TYPE: nucleic acid

```
        (C) STRANDEDNESS: single
        (D) TOPOLOGY: linear (xi) SEQUENCE DESCRIPTION: SEQ ID NO: 174:

GCAAAGGCGG CACCGGCGGG GCCGGCATGA ACAGCCTCGA CCCGCTGCTA GCCGCCCAAG      60

ACGGCGGCCA AGGCGGCACC GGCGGCACCG GCGGCAACGC CGGCGCCGGC GGCACCAGCT     120

TCACCCAAGG CGCCGACGGC AACGCCGGCA ACGGCGGTGA CGGCGGGGTC GGCGGCAACG     180

GCGGAAACGG CGGAAACGGC GCAGACAACA CCACCACCGC CGCCGCCGGC ACCACAGGCG     240

GCGACGGCGG GGCCGGCGGG GCCGGCGGAA CCGGCGGAAC CGGCGGAGCC GCCGGCACCG     300

GCACCGGCGG CCAACAAGGC AACGGCGGCA ACGGCGGCAC CGGCGGCAAA GGCGGCACCG     360

GCGGCGACGG TGCACTCTCA GGCAGCACCG GTGGTGCCGG                           400

(2) INFORMATION FOR SEQ ID NO: 175:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (xi) SEQUENCE DESCRIPTION: SEQ ID NO: 175:

GGCAACGGCG GCAACGGCGG CATCGCCGGC ATTGGGCGGC AACGGCGTTC CGGGACGGGC      60

AGCGGCAACG GCGGCCAACG GCGGCAGCGG CGGCAACGGC GGCAACGCCG GCATGGGCGG     120

CAACAGCGGC ACCGGCAGCG GCGACGGCGG TGCCGGCGGG AACGGCGGCG CGGCGGGCAC     180

GGGCGGCACC GGCGGCGACG GCGGCCTCAC CGGTACTGGC GGCACCGGCG GCAGCGGTGG     240

CACCGGCGGT GACGGCGGTA ACGGCGGCAA CGGAGCAGAT AACACCGCAA ACATGACTGC     300

GCAGGCGGGC GGTGACGGTG GCAACGGCGG CGACGGTGGC TTCGGCGGCG GGCCGGGGC     360

CGGCGGCGGT GGCTTGACCG CTGGCGCCAA CGGCACCGGC GGGCAAGGCG GCGCCGGCGG     420

CGATGGCGGC AACGGGGCCA TCGGCGGCCA CGGCCCACTC ACTGACGACC CCGGCGGCAA     480

CGGGGGCACC GGCGGCAACG GCGGCACCGG CGGCACCGGC GGCGCGGGCA TCGGCAGC      538

(2) INFORMATION FOR SEQ ID NO: 176:

(i) SEQUENCE CHARACTERISTICS:
        (A) LENGTH: 239 base pairs
        (B) TYPE: nucleic acid
        (C) STRANDEDNESS: single
        (D) TOPOLOGY: linear (xi) SEQUENCE DESCRIPTION: SEQ ID NO: 176:

GGGCCGGTGG TGCCGCGGGC CAGCTCTTCA GCGCCGGAGG CGCGGCGGGT GCCGTTGGGG      60

TTGGCGGCAC CGGCGGCCAG GGTGGGGCTG GCGGTGCCGG AGCGGCCGGC GCCGACGCCC     120

CCGCCAGCAC AGGTCTAACC GGTGGTACCG GGTTCGCTGG CGGGGCCGGC GGCGTCGGCG     180

GCCACGGCGG CAACGCCATT GCCGGCGGCA TCAACGGCTC CGGTGGTGCC GGCGGCACC      239

(2) INFORMATION FOR SEQ ID NO: 177:

(i) SEQUENCE CHARACTERISTICS:
        (A) LENGTH: 985 base pairs
        (B) TYPE: nucleic acid
        (C) STRANDEDNESS: single
        (D) TOPOLOGY: linear (xi) SEQUENCE DESCRIPTION: SEQ ID NO: 177:

AGCAGCGCTA CCGGTGGCGC CGGGTTCGCC GGCGGCGCCG GCGGAGAAGG CGGAGCGGGC      60
```

```
GGCAACAGCG GTGTGGGCGG CACCAACGGC TCCGGCGGCG CCGGCGGTGC AGGCGGCAAG      120

GGCGGCACCG GAGGTGCCGG CGGGTCCGGC GCGGACAACC CCACCGGTGC TGGTTTCGCC      180

GGTGGCGCCG GCGGCACAGG TGGCGCGGCC GGCGCCGGCG GGGCCGGCGG GGCGACCGGT      240

ACCGGCGGCA CCGGCGGCGT TGTCGGCGCC ACCGGTAGTG CAGGCATCGG CGGGGCCGGC      300

GGCCGCGGCG GTGACGGCGG CGATGGGGCC AGCGGTCTCG GCCTGGGCCT CTCCGGCTTT      360

GACGGCGGCC AAGGCGGCCA AGGCGGGGCC GGCGGCAGCG CCGGCGCCGG CGGCATCAAC      420

GGGGCCGGCG GGGCCGGCGG CAACGGCGGC GACGGCGGGG ACGGCGCAAC CGGTGCCGCA      480

GGTCTCGGCG ACAACGGCGG GGTCGGCGGT GACGGTGGGG CCGGTGGCGC CGCCGGCAAC      540

GGCGGCAACG CGGGCGTCGG CCTGACAGCC AAGGCCGGCG ACGGCGGCGC CGCGGGCAAT      600

GGCGGCAACG GGGGCGCCGG CGGTGCTGGC GGGGCCGGCG ACAACAATTT CAACGGCGGC      660

CAGGGTGGTG CCGGCGGCCA AGGCGGCCAA GGCGGCTTGG GCGGGGCAAG CACCACCTGA      720

TCGGCCTAGC CGCACCCGGG AAAGCCGATC AACAGGCGA CGATGCCGCC TTCCTTGCCG       780

CGTTGGACCA GGCCGGCATC ACCTACGCTG ACCCAGGCCA CGCCATAACG GCCGCCAAGG      840

CGATGTGTGG GCTGTGTGCT AACGGCGTAA CAGGTCTACA GCTGGTCGCG GACCTGCGGG      900

AATACAATCC CGGGCTGACC ATGGACAGCG CGGCCAAGTT CGCTGCCATC GCATCAGGCG      960

CGTACTGCCC CGAACACCTG GAACA                                           985

(2) INFORMATION FOR SEQ ID NO: 178:

(i) SEQUENCE CHARACTERISTICS:
        (A) LENGTH: 2138 base pairs
        (B) TYPE: nucleic acid
        (C) STRANDEDNESS: single
        (D) TOPOLOGY: linear (xi) SEQUENCE DESCRIPTION: SEQ ID NO: 178:

CGGCACGAGG ATCGGTACCC CGCGGCATCG GCAGCTGCCG ATTCGCCGGG TTTCCCCACC       60

CGAGGAAAGC CGCTACCAGA TGGCGCTGCC GAAGTAGGGC GATCCGTTCG CGATGCCGGC      120

ATGAACGGGC GGCATCAAAT TAGTGCAGGA ACCTTTCAGT TTAGCGACGA TAATGGCTAT      180

AGCACTAAGG AGGATGATCC GATATGACGC AGTCGCAGAC CGTGACGGTG GATCAGCAAG      240

AGATTTTGAA CAGGGCCAAC GAGGTGGAGG CCCCGATGGC GGACCCACCG ACTGATGTCC      300

CCATCACACC GTGCGAACTC ACGGCGGCTA AAAACGCCGC CCAACAGCTG GTATTGTCCG      360

CCGACAACAT GCGGGAATAC CTGGCGGCCG GTGCCAAAGA GCGGCAGCGT CTGGCGACCT      420

CGCTGCGCAA CGCGGCCAAG GCGTATGGCG AGGTTGATGA GGAGGCTGCG ACCGCGCTGG      480

ACAACGACGG CGAAGGAACT GTGCAGGCAG AATCGGCCGG GGCCGTCGGA GGGGACAGTT      540

CGGCCGAACT AACCGATACG CCGAGGGTGG CCACGGCCGG TGAACCCAAC TTCATGGATC      600

TCAAAGAAGC GGCAAGGAAG CTCGAAACGG GCGACCAAGG CGCATCGCTC GCGCACTTTG      660

CGGATGGGTG GAACACTTTC AACCTGACGC TGCAAGGCGA CGTCAAGCGG TTCCGGGGGT      720

TTGACAACTG GGAAGGCGAT GCGGCTACCG CTTGCGAGGC TTCGCTCGAT CAACAACGGC      780

AATGGATACT CCACATGGCC AAATTGAGCG CTGCGATGGC CAAGCAGGCT CAATATGTCG      840

CGCAGCTGCA CGTGTGGGCT AGGCGGGAAC ATCGACTTA TGAAGACATA GTCGGGCTCG       900

AACGGCTTTA CGCGGAAAAC CCTTCGGCCC GCGACCAAAT TCTCCCGGTG TACGCGGAGT      960

ATCAGCAGAG GTCGGAGAAG GTGCTGACCG AATACAACAA CAAGGCAGCC CTGGAACCGG     1020

TAAACCCGCC GAAGCCTCCC CCCGCCATCA AGATCGACCC GCCCCCGCCT CCGCAAGAGC     1080
```

```
AGGGATTGAT CCCTGGCTTC CTGATGCCGC CGTCTGACGG CTCCGGTGTG ACTCCCGGTA   1140

CCGGGATGCC AGCCGCACCG ATGGTTCCGC CTACCGGATC GCCGGGTGGT GGCCTCCCGG   1200

CTGACACGGC GGCGCAGCTG ACGTCGGCTG GGCGGGAAGC CGCAGCGCTG TCGGGCGACG   1260

TGGCGGTCAA AGCGGCATCG CTCGGTGGCG GTGGAGGCGG CGGGGTGCCG TCGGCGCCGT   1320

TGGGATCCGC GATCGGGGGC GCCGAATCGG TGCGGCCCGC TGGCGCTGGT GACATTGCCG   1380

GCTTAGGCCA GGGAAGGGCC GGCGGCGGCG CCGCGCTGGG CGGCGGTGGC ATGGGAATGC   1440

CGATGGGTGC CGCGCATCAG GGACAAGGGG GCGCCAAGTC CAAGGGTTCT CAGCAGGAAG   1500

ACGAGGCGCT CTACACCGAG GATCGGGCAT GGACCGAGGC CGTCATTGGT AACCGTCGGC   1560

GCCAGGACAG TAAGGAGTCG AAGTGAGCAT GGACGAATTG GACCCGCATG TCGCCCGGGC   1620

GTTGACGCTG GCGGCGCGGT TTCAGTCGGC CCTAGACGGG ACGCTCAATC AGATGAACAA   1680

CGGATCCTTC CGCGCCACCG ACGAAGCCGA GACCGTCGAA GTGACGATCA ATGGGCACCA   1740

GTGGCTCACC GGCCTGCGCA TCGAAGATGG TTTGCTGAAG AAGCTGGGTG CCGAGGCGGT   1800

GGCTCAGCGG GTCAACGAGG CGCTGCACAA TGCGCAGGCC GCGGCGTCCG CGTATAACGA   1860

CGCGGCGGGC GAGCAGCTGA CCGCTGCGTT ATCGGCCATG TCCCGCGCGA TGAACGAAGG   1920

AATGGCCTAA GCCCATTGTT GCGGTGGTAG CGACTACGCA CCGAATGAGC GCCGCAATGC   1980

GGTCATTCAG CGCGCCCGAC ACGGCGTGAG TACGCATTGT CAATGTTTTG ACATGGATCG   2040

GCCGGGTTCG GAGGGCGCCA TAGTCCTGGT CGCCAATATT GCCGCAGCTA GCTGGTCTTA   2100

GGTTCGGTTA CGCTGGTTAA TTATGACGTC CGTTACCA                          2138
```

(2) INFORMATION FOR SEQ ID NO: 179:

(i) SEQUENCE CHARACTERISTICS:
        (A) LENGTH: 460 amino acids
        (B) TYPE: amino acid
        (C) STRANDEDNESS: <Unknown>
        (D) TOPOLOGY: linear (xi) SEQUENCE DESCRIPTION: SEQ ID NO: 179:

```
Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Thr Asp Val
            20                  25                  30

Pro Ile Thr Pro Cys Glu Leu Thr Ala Ala Lys Asn Ala Ala Gln Gln
            35                  40                  45

Leu Val Leu Ser Ala Asp Asn Met Arg Glu Tyr Leu Ala Ala Gly Ala
        50                  55                  60

Lys Glu Arg Gln Arg Leu Ala Thr Ser Leu Arg Asn Ala Ala Lys Ala
65                  70                  75                  80

Tyr Gly Glu Val Asp Glu Glu Ala Ala Thr Ala Leu Asp Asn Asp Gly
                    85                  90                  95

Glu Gly Thr Val Gln Ala Glu Ser Ala Gly Ala Val Gly Gly Asp Ser
                100                 105                 110

Ser Ala Glu Leu Thr Asp Thr Pro Arg Val Ala Thr Ala Gly Glu Pro
            115                 120                 125

Asn Phe Met Asp Leu Lys Glu Ala Ala Arg Lys Leu Glu Thr Gly Asp
            130                 135                 140

Gln Gly Ala Ser Leu Ala His Phe Ala Asp Gly Trp Asn Thr Phe Asn
145                 150                 155                 160

Leu Thr Leu Gln Gly Asp Val Lys Arg Phe Arg Gly Phe Asp Asn Trp
```

-continued

```
                165                 170                 175
Glu Gly Asp Ala Ala Thr Ala Cys Glu Ala Ser Leu Asp Gln Gln Arg
            180                 185                 190
Gln Trp Ile Leu His Met Ala Lys Leu Ser Ala Met Ala Lys Gln
        195                 200                 205
Ala Gln Tyr Val Ala Gln Leu His Val Trp Ala Arg Arg Glu His Pro
    210                 215                 220
Thr Tyr Glu Asp Ile Val Gly Leu Glu Arg Leu Tyr Ala Glu Asn Pro
225                 230                 235                 240
Ser Ala Arg Asp Gln Ile Leu Pro Val Tyr Ala Glu Tyr Gln Gln Arg
                245                 250                 255
Ser Glu Lys Val Leu Thr Glu Tyr Asn Asn Lys Ala Ala Leu Glu Pro
            260                 265                 270
Val Asn Pro Pro Lys Pro Pro Pro Ala Ile Lys Ile Asp Pro Pro
        275                 280                 285
Pro Pro Gln Glu Gln Gly Leu Ile Pro Gly Phe Leu Met Pro Pro Ser
    290                 295                 300
Asp Gly Ser Gly Val Thr Pro Gly Thr Gly Met Pro Ala Ala Pro Met
305                 310                 315                 320
Val Pro Pro Thr Gly Ser Pro Gly Gly Leu Pro Ala Asp Thr Ala
                325                 330                 335
Ala Gln Leu Thr Ser Ala Gly Arg Glu Ala Ala Ala Leu Ser Gly Asp
            340                 345                 350
Val Ala Val Lys Ala Ala Ser Leu Gly Gly Gly Gly Gly Gly Val
        355                 360                 365
Pro Ser Ala Pro Leu Gly Ser Ala Ile Gly Gly Ala Glu Ser Val Arg
    370                 375                 380
Pro Ala Gly Ala Gly Asp Ile Ala Gly Leu Gly Gln Gly Arg Ala Gly
385                 390                 395                 400
Gly Gly Ala Ala Leu Gly Gly Gly Met Gly Met Pro Met Gly Ala
                405                 410                 415
Ala His Gln Gly Gln Gly Gly Ala Lys Ser Lys Gly Ser Gln Gln Glu
            420                 425                 430
Asp Glu Ala Leu Tyr Thr Glu Asp Arg Ala Trp Thr Glu Ala Val Ile
        435                 440                 445
Gly Asn Arg Arg Arg Gln Asp Ser Lys Glu Ser Lys
    450                 455                 460

(2) INFORMATION FOR SEQ ID NO: 180:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: linear (xi) SEQUENCE DESCRIPTION: SEQ ID NO: 180:

Ala Gly Asn Val Thr Ser Ala Ser Gly Pro His Arg Phe Gly Ala Pro
1               5                   10                  15

Asp Arg Gly Ser Gln Arg Arg Arg His Pro Ala Ala Ser Thr Ala
            20                  25                  30

Thr Glu Arg Cys Arg Phe Asp Arg His Val Ala Arg Gln Arg Cys Gly
        35                  40                  45

Phe Pro Pro Ser Arg Arg Gln Leu Arg Arg Arg Val Ser Arg Glu Ala
    50                  55                  60
```

-continued

```
Thr Thr Arg Arg Ser Gly Arg Arg Asn His Arg Cys Gly Trp His Pro
 65                  70                  75                  80

Gly Thr Gly Ser His Thr Gly Ala Val Arg Arg His Gln Glu Ala
                 85                  90                  95

Arg Asp Gln Ser Leu Leu Leu Arg Arg Gly Arg Val Asp Leu Asp
                100                 105                 110

Gly Gly Gly Arg Leu Arg Arg Val Tyr Arg Phe Gln Gly Cys Leu Val
            115                 120                 125

Val Val Phe Gly Gln His Leu Leu Arg Pro Leu Leu Ile Leu Arg Val
        130                 135                 140

His Arg Glu Asn Leu Val Ala Gly Arg Arg Val Phe Arg Val Lys Pro
145                 150                 155                 160

Phe Glu Pro Asp Tyr Val Phe Ile Ser Arg Met Phe Pro Pro Ser Pro
                165                 170                 175

His Val Gln Leu Arg Asp Ile Leu Ser Leu Leu Gly His Arg Ser Ala
                180                 185                 190

Gln Phe Gly His Val Glu Tyr Pro Leu Pro Leu Leu Ile Glu Arg Ser
            195                 200                 205

Leu Ala Ser Gly Ser Arg Ile Ala Phe Pro Val Val Lys Pro Pro Glu
    210                 215                 220

Pro Leu Asp Val Ala Leu Gln Arg Gln Val Glu Ser Val Pro Pro Ile
225                 230                 235                 240

Arg Lys Val Arg Glu Arg Cys Ala Leu Val Ala Arg Phe Glu Leu Pro
                245                 250                 255

Cys Arg Phe Phe Glu Ile His Glu Val Gly Phe Thr Gly Arg Gly His
                260                 265                 270

Pro Arg Arg Ile Gly
            275

(2) INFORMATION FOR SEQ ID NO: 181:

(i) SEQUENCE CHARACTERISTICS:
        (A) LENGTH: 192 amino acids
        (B) TYPE: amino acid
        (C) STRANDEDNESS: <Unknown>
        (D) TOPOLOGY: linear (xi) SEQUENCE DESCRIPTION: SEQ ID NO: 181:

Arg Val Ala Ala Ser Phe Ile Asp Trp Leu Asp Ser Pro Asp Ser Pro
 1               5                  10                  15

Leu Asp Pro Ser Leu Val Ser Ser Leu Leu Asn Ala Val Ser Cys Gly
                20                  25                  30

Ala Glu Ser Ser Ala Ser Ser Ala Arg Ser Gly Asn Gly Ser Arg
                35                  40                  45

Trp Thr Ser Met Pro Ser Gly Thr Arg Pro Gly Pro Arg Arg Ala Thr
         50                  55                  60

Ser Arg Asp Asp Arg Arg Ser Ala Thr Ser Val Ile Pro Ser Arg Arg
 65                  70                  75                  80

Ser Val Ala Pro Arg Ala Glu Phe Gly Thr Arg Leu Ala Ser His Arg
                 85                  90                  95

Ala Ser Pro Ser Asn Ala Cys Pro Val Arg Ile Val Thr Ser Ala Ser
                100                 105                 110

Gly Arg Pro Ile Ser Ser Pro Ile Val Arg Ser Arg Ser Cys Val
            115                 120                 125

Asp Lys Asn Gly Arg Arg Cys Ala Ser Gly Tyr Arg Arg Leu Asn Arg
    130                 135                 140
```

```
Ala Arg Ser Ser Ser Ile Ala Ala Arg Cys Arg Thr Ile Gly Thr Phe
145                 150                 155                 160

Arg Arg Ser Arg Tyr Ser Ala Ser Met Arg Val Ser Thr Asn Ser Pro
            165                 170                 175

His Val Thr His Gly Val Ala Pro Gly Val Thr Arg Arg Ile Gly Gly
            180                 185                 190
```

(2) INFORMATION FOR SEQ ID NO: 182:

(i) SEQUENCE CHARACTERISTICS:
        (A) LENGTH: 196 amino acids
        (B) TYPE: amino acid
        (C) STRANDEDNESS: <Unknown>
        (D) TOPOLOGY: linear (xi) SEQUENCE DESCRIPTION: SEQ ID NO: 182:

```
Gln Glu Arg Pro Gln Met Cys Gln Arg Val Ser Glu Ile Glu Pro Arg
1               5                   10                  15

Thr Gln Phe Phe Asn Arg Cys Ala Leu Pro His Tyr Trp His Phe Pro
            20                  25                  30

Ala Val Ala Val Phe Ser Lys His Ala Ser Leu Asp Glu Leu Ala Pro
        35                  40                  45

Arg Asn Pro Arg Arg Ser Ser Arg Arg Asp Ala Glu Asp Arg Arg Val
50                  55                  60

Ile Phe Ala Ala Thr Leu Val Ala Val Asp Pro Pro Leu Arg Gly Ala
65                  70                  75                  80

Gly Gly Glu Ala Asp Gln Leu Ile Asp Leu Gly Val Cys Arg Arg Gln
                85                  90                  95

Ala Gly Arg Val Arg Arg Gly Gln Glu Leu His His Arg His Arg His
                100                 105                 110

Gln Gly Ala Ala Pro Asp Leu Arg Arg Arg Arg His Arg Arg Val
            115                 120                 125

Gln Gln His Arg Arg Leu Gln Arg Val Arg Gln Leu Arg Arg Tyr Val
130                 135                 140

Gln Thr Ala His His Arg Arg Phe Ala Arg Thr Asp Arg Val Arg His
145                 150                 155                 160

His Val Arg Gly Pro Ser Asn His Arg Arg Arg Val Tyr Arg Gly
            165                 170                 175

Arg His Ser Gly Ala Gly Gly Cys Pro Ala Gly Gly Ala Gly Ser Val
            180                 185                 190

Gly Gly Ser Ala
        195
```

(2) INFORMATION FOR SEQ ID NO: 183:

(i) SEQUENCE CHARACTERISTICS:
        (A) LENGTH: 311 amino acids
        (B) TYPE: amino acid
        (C) STRANDEDNESS: <Unknown>
        (D) TOPOLOGY: linear (xi) SEQUENCE DESCRIPTION: SEQ ID NO: 183:

```
Val Arg Cys Gly Thr Leu Val Pro Val Pro Met Val Glu Phe Leu Thr
1               5                   10                  15

Ser Thr Asn Ala Pro Ser Leu Pro Ser Ala Tyr Ala Glu Val Asp Lys
            20                  25                  30

Leu Ile Gly Leu Pro Ala Gly Thr Ala Lys Arg Trp Ile Asn Gly Tyr
        35                  40                  45
```

```
Glu Arg Gly Gly Lys Asp His Pro Pro Ile Leu Arg Val Thr Pro Gly
 50                  55                  60

Ala Thr Pro Trp Val Thr Trp Gly Glu Phe Val Glu Thr Arg Met Leu
 65                  70                  75                  80

Ala Glu Tyr Arg Asp Arg Arg Lys Val Pro Ile Val Arg Gln Arg Ala
                 85                  90                  95

Ala Ile Glu Glu Leu Arg Ala Arg Phe Asn Leu Arg Tyr Pro Leu Ala
                100                 105                 110

His Leu Arg Pro Phe Leu Ser Thr His Glu Arg Asp Leu Thr Met Gly
                115                 120                 125

Gly Glu Glu Ile Gly Leu Pro Asp Ala Glu Val Thr Ile Arg Thr Gly
                130                 135                 140

Gln Ala Leu Leu Gly Asp Ala Arg Trp Leu Ala Ser Leu Val Pro Asn
145                 150                 155                 160

Ser Ala Arg Gly Ala Thr Leu Arg Arg Leu Gly Ile Thr Asp Val Ala
                165                 170                 175

Asp Leu Arg Ser Ser Arg Glu Val Ala Arg Arg Gly Pro Gly Arg Val
                180                 185                 190

Pro Asp Gly Ile Asp Val His Leu Leu Pro Phe Pro Asp Leu Ala Asp
                195                 200                 205

Asp Asp Ala Asp Asp Ser Ala Pro His Glu Thr Ala Phe Lys Arg Leu
                210                 215                 220

Leu Thr Asn Asp Gly Ser Asn Gly Glu Ser Gly Glu Ser Ser Gln Ser
225                 230                 235                 240

Ile Asn Asp Ala Ala Thr Arg Tyr Met Thr Asp Glu Tyr Arg Gln Phe
                245                 250                 255

Pro Thr Arg Asn Gly Ala Gln Arg Ala Leu His Arg Val Val Thr Leu
                260                 265                 270

Leu Ala Ala Gly Arg Pro Val Leu Thr His Cys Phe Ala Gly Lys Asp
                275                 280                 285

Arg Thr Gly Phe Val Val Ala Leu Val Leu Glu Ala Val Gly Leu Asp
                290                 295                 300

Arg Asp Val Ile Val Ala Asp
305                 310

(2) INFORMATION FOR SEQ ID NO: 184:

(i) SEQUENCE CHARACTERISTICS:
        (A) LENGTH: 2072 base pairs
        (B) TYPE: nucleic acid
        (C) STRANDEDNESS: single
        (D) TOPOLOGY: linear (xi) SEQUENCE DESCRIPTION: SEQ ID NO: 184:

CTCGTGCCGA TTCGGCACGA GCTGAGCAGC CCAAGGGGCC GTTCGGCGAA GTCATCGAGG      60

CATTCGCCGA CGGGCTGGCC GGCAAGGGTA AGCAAATCAA CACCACGCTG AACAGCCTGT     120

CGCAGGCGTT GAACGCCTTG AATGAGGGCC GCGGCGACTT CTTCGCGGTG GTACGCAGCC     180

TGGCGCTATT CGTCAACGCG CTACATCAGG ACGACCAACA GTTCGTCGCG TTGAACAAGA     240

ACCTTGCGGA GTTCACCGAC AGGTTGACCC ACTCCGATGC GGACCTGTCG AACGCCATCC     300

AGCAATTCGA CAGCTTGCTC GCCGTCGCGC GCCCGTTCTT CGCCAAGAAC CGCGAGGTGC     360

TGACGCATGA CGTCAATAAT CTCGCGACCG TGACCACCAC GTTGCTGCAG CCCGATCCGT     420

TGGATGGGTT GGAGACCGTC CTGCACATCT TCCCGACGCT GGCGGCGAAC ATTAACCAGC     480
```

```
TTTACCATCC GACACACGGT GGCGTGGTGT CGCTTTCCGC GTTCACGAAT TTCGCCAACC      540

CGATGGAGTT CATCTGCAGC TCGATTCAGG CGGGTAGCCG GCTCGGTTAT CAAGAGTCGG      600

CCGAACTCTG TGCGCAGTAT CTGGCGCCAG TCCTCGATGC GATCAAGTTC AACTACTTTC      660

CGTTCGGCCT GAACGTGGCC AGCACCGCCT CGACACTGCC TAAAGAGATC GCGTACTCCG      720

AGCCCCGCTT GCAGCCGCCC AACGGGTACA AGGACACCAC GGTGCCCGGC ATCTGGGTGC      780

CGGATACGCC GTTGTCACAC CGCAACACGC AGCCCGGTTG GGTGGTGGCA CCCGGGATGC      840

AAGGGGTTCA GGTGGGACCG ATCACGCAGG GTTTGCTGAC GCCGGAGTCC CTGGCCGAAC      900

TCATGGGTGG TCCCGATATC GCCCCTCCGT CGTCAGGGCT GCAAACCCCG CCCGGACCCC      960

CGAATGCGTA CGACGAGTAC CCCGTGCTGC CGCCGATCGG TTTACAGGCC CCACAGGTGC     1020

CGATACCACC GCCGCCTCCT GGGCCCGACG TAATCCCGGG TCCGGTGCCA CCGGTCTTGG     1080

CGGCGATCGT GTTCCAAGA GATCGCCCGG CAGCGTCGGA AAACTTCGAC TACATGGGCC     1140

TCTTGTTGCT GTCGCCGGGC CTGGCGACCT TCCTGTTCGG GGTGTCATCT AGCCCCGCCC     1200

GTGGAACGAT GGCCGATCGG CACGTGTTGA TACCGGCGAT CACCGGCCTG GCGTTGATCG     1260

CGGCATTCGT CGCACATTCG TGGTACCGCA CAGAACATCC GCTCATAGAC ATGCGCTTGT     1320

TCCAGAACCG AGCGGTCGCG CAGGCCAACA TGACGATGAC GGTGCTCTCC CTCGGGCTGT     1380

TTGGCTCCTT CTTGCTGCTC CCGAGCTACC TCCAGCAAGT GTTGCACCAA TCACCGATGC     1440

AATCGGGGGT GCATATCATC CCACAGGGCC TCGGTGCCAT GCTGGCGATG CCGATCGCCG     1500

GAGCGATGAT GGACCGACGG GGACCGGCCA AGATCGTGCT GGTTGGGATC ATGCTGATCG     1560

CTGCGGGGTT GGGCACCTTC GCCTTTGGTG TCGCGCGGCA AGCGGACTAC TTACCCATTC     1620

TGCCGACCGG GCTGGCAATC ATGGGCATGG GCATGGGCTG CTCCATGATG CCACTGTCCG     1680

GGGCGGCAGT GCAGACCCTG GCCCCACATC AGATCGCTCG CGGTTCGACG CTGATCAGCG     1740

TCAACCAGCA GGTGGGCGGT TCGATAGGGA CCGCACTGAT GTCGGTGCTG CTCACCTACC     1800

AGTTCAATCA CAGCGAAATC ATCGCTACTG CAAAGAAAGT CGCACTGACC CCAGAGAGTG     1860

GCGCCGGGCG GGGGCGGCG GTTGACCCTT CCTCGCTACC GCGCCAAACC AACTTCGCGG     1920

CCCAACTGCT GCATGACCTT TCGCACGCCT ACGCGGTGGT ATTCGTGATA GCGACCGCGC     1980

TAGTGGTCTC GACGCTGATC CCCGCGGCAT TCCTGCCGAA ACAGCAGGCT AGTCATCGAA     2040

GAGCACCGTT GCTATCCGCA TGACGTCTGC TT                                   2072

(2) INFORMATION FOR SEQ ID NO: 185:

(i) SEQUENCE CHARACTERISTICS:
        (A) LENGTH: 1923 base pairs
        (B) TYPE: nucleic acid
        (C) STRANDEDNESS: single
        (D) TOPOLOGY: linear (xi) SEQUENCE DESCRIPTION: SEQ ID NO: 185:

TCACCCCGGA GAAGTCGTTC GTCGACGACC TGGACATCGA CTCGCTGTCG ATGGTCGAGA       60

TCGCCGTGCA GACCGAGGAC AAGTACGGCG TCAAGATCCC CGACGAGGAC CTCGCCGGTC      120

TGCGTACCGT CGGTGACGTT GTCGCCTACA TCCAGAAGCT CGAGGAAGAA AACCCGGAGG      180

CGGCTCAGGC GTTGCGCGCG AAGATTGAGT CGGAGAACCC CGATGCGGCA CGAGCAGATC      240

GGTGCGTTTC ACCCACATCG CAAGCTCGAG ACGCCCGTCG TCCTCTTGCA CGCTCAGCCA      300

GGTTGGCGTG TCGCCGCCTT CCAGCAAGTG TTCCCACCAC ACGAAGGGAC CCTCGCGAAA      360

GGTGACTGAT CCGCGGACCA CATAGTCGAT GCCACCGTGG CTGACAATTG CGCCGGGTCC      420
```

```
GAGTTGGCGG GGGCCGAATT GCGGCATTGC GTCGAAGGCC AGCGGATCCC GGCGCCCGCC      480

CGGCGTGGCT GGTGTTTTGG GCCGCCGGAT GGCCACGACG AGAACGACGA TGGCGGCGAT      540

GAACAGCGCC ACGGCAATCA CGACCAGCAG ATTTCCCACG CATACCCTCT CGTACCGCTG      600

CGCCGCGGTT GGTCGATCGG TCGCATATCG ATGGCGCCGT TTAACGTAAC AGCTTTCGCG      660

GGACCGGGGG TCACAACGGG CGAGTTGTCC GGCCGGGAAC CCGGCAGGTC TCGGCCGCGG      720

TCACCCCAGC TCACTGGTGC ACCATCCGGG TGTCGGTGAG CGTGCAACTC AAACACACTC      780

AACGGCAACG GTTTCTCAGG TCACCAGCTC AACCTCGACC CGCAATCGCT CGTACGTTTC      840

GACCGCGCGC AGGTCGCGAG TCAGCAGCTT TGCGCCGGCA GCTTTCGCCG TGAAGCCGAC      900

CAGGGCATCG TAGGTTGCGC CACCGGTGAC ATCGTGCTCG GCGAGGTGGT CGGTCAAGCC      960

GCGATATGAG CAGGCATCCA GTGCCAGGTA GTTGCTGGAG GTGATGTCCG CCAAGTAGGC     1020

GTGGACGGCA ACAGGGGCAA TACGATGCGG CGGTGGTAGC CGGGTCAAGA CCGAATAGGT     1080

TTCCACAGCC GCGTGCGCGA TCAGATGGAC GCCACGGTTG AGCGCGCGCA CGGCGGCCTC     1140

GTGCCCTTCG TGCCAGGTCG CGAATCCGGC AACCAGCACG CTGGTGTCTG GTGCGATCAC     1200

CGCCGTGTGC GATCGAGCGT TTCCCGAACG ATTTCGTCGG TCAACGGGGG CAGGGGACGT     1260

TCTGGCCGTG CGACGAGAAC CGAGCCTTCC CGAACGAGTT CGACACCGGT CGGGGCCGGC     1320

TCAATCTCGA TGCGCCCATC GCGCTCGGTG ATCTCCACCT GGTCGTTCCC GCGCAAGCCA     1380

AGGCGCTCGC GAATCCGCTT GGGAATCACC AGACGTCCTG CGACATCGAT GGTTGTTCGC     1440

ATGGTAGGAA ATTTACCATC GCACGTTCCA TAGGCGTGTC CTGCGCGGGA TGTCGGGACG     1500

ATCCGCTAGC GTATCGAACG ATTGTTTCGG AAATGGCTGA GGGAGCGTGC GGTGCGGGTG     1560

ATGGGTGTCG ATCCCGGGTT GACCCGATGC GGGCTGTCGC TCATCGAGAG TGGGCGTGGT     1620

CGGCAGCTCA CCGCGCTGGA TGTCGACGTG GTGCGCACAC CGTCGGATGC GGCCTTGGCG     1680

CAGCGCCTGT TGGCCATCAG CGATGCCGTC GAGCACTGGC TGGACACCCA TCATCCGGAG     1740

GTGGTGGCTA TCGAACGGGT GTTCTCTCAG CTCAACGTGA CCACGGTGAT GGGCACCGCG     1800

CAGGCCGGCG GCGTGATCGC CCTGGCGGCG GCCAAACGTG GTGTCGACGT GCATTTCCAT     1860

ACCCCCAGCG AGGTCAAGGC GGCGGTCACT GGCAACGGTT CCGCAGACAA GGCTCAGGTC     1920

ACC                                                                 1923

(2) INFORMATION FOR SEQ ID NO: 186:

(i) SEQUENCE CHARACTERISTICS:
        (A) LENGTH: 1055 base pairs
        (B) TYPE: nucleic acid
        (C) STRANDEDNESS: single
        (D) TOPOLOGY: linear (xi) SEQUENCE DESCRIPTION: SEQ ID NO: 186:

CTGGCGTGCC AGTGTCACCG GCGATATGAC GTCGGCATTC AATTTCGCGG CCCCGCCGGA       60

CCCGTCGCCA CCCAATCTGG ACCACCCGGT CCGTCAATTG CCGAAGGTCG CCAAGTGCGT      120

GCCCAATGTG GTGCTGGGTT TCTTGAACGA AGGCCTGCCG TATCGGGTGC CCTACCCCCA      180

AACAACGCCA GTCCAGGAAT CCGGTCCCGC GCGGCCGATT CCCAGCGGCA TCTGCTAGCC      240

GGGGATGGTT CAGACGTAAC GGTTGGCTAG GTCGAAACCC GCGCCAGGGC CGCTGGACGG      300

GCTCATGGCA GCGAAATTAG AAAACCCGGG ATATTGTCCG CGGATTGTCA TACGATGCTG      360

AGTGCTTGGT GGTTCGTGTT TAGCCATTGA GTGTGGATGT GTTGAGACCC TGGCCTGGAA      420

GGGGACAACG TGCTTTTGCC TCTTGGTCCG CCTTTGCCGC CCGACGCGGT GGTGGCGAAA      480
```

```
CGGGCTGAGT CGGGAATGCT CGGCGGGTTG TCGGTTCCGC TCAGCTGGGG AGTGGCTGTG      540

CCACCCGATG ATTATGACCA CTGGGCGCCT GCGCCGGAGG ACGGCGCCGA TGTCGATGTC      600

CAGGCGGCCG AAGGGGCGGA CGCAGAGGCC GCGGCCATGG ACGAGTGGGA TGAGTGGCAG      660

GCGTGGAACG AGTGGGTGGC GGAGAACGCT GAACCCCGCT TTGAGGTGCC ACGGAGTAGC      720

AGCAGCGTGA TTCCGCATTC TCCGGCGGCC GGCTAGGAGA GGGGGCGCAG ACTGTCGTTA      780

TTTGACCAGT GATCGGCGGT CTCGGTGTTC CCGCGGCCGG CTATGACAAC AGTCAATGTG      840

CATGACAAGT TACAGGTATT AGGTCCAGGT TCAACAAGGA GACAGGCAAC ATGGCAACAC      900

GTTTTATGAC GGATCCGCAC GCGATGCGGG ACATGGCGGG CCGTTTTGAG GTGCACGCCC      960

AGACGGTGGA GGACGAGGCT CGCCGGATGT GGGCGTCCGC GCAAAACATC TCGGGNGCGG     1020

GCTGGAGTGG CATGGCCGAG GCGACCTCGC TAGAC                                 1055

(2) INFORMATION FOR SEQ ID NO: 187:

(i) SEQUENCE CHARACTERISTICS:
        (A) LENGTH: 359 base pairs
        (B) TYPE: nucleic acid
        (C) STRANDEDNESS: single
        (D) TOPOLOGY: linear (xi) SEQUENCE DESCRIPTION: SEQ ID NO: 187:

CCGCCTCGTT GTTGGCATAC TCCGCCGCGG CCGCCTCGAC CGCACTGGCC GTGGCGTGTG       60

TCCGGGCTGA CCACCGGGAT CGCCGAACCA TCCGAGATCA CCTCGCAATG ATCCACCTCG      120

CGCAGCTGGT CACCCAGCCA CCGGGCGGTG TGCGACAGCG CCTGCATCAC CTTGGTATAG      180

CCGTCGCGCC CCAGCCGCAG GAAGTTGTAG TACTGGCCCA CCACCTGGTT ACCGGGACGG      240

GAGAAGTTCA GGGTGAAGGT CGGCATGTCG CCGCCGAGGT AGTTGACCCG GAAAACCAGA      300

TCCTCCGGCA GGTGCTCGGG CCCGCGCCAC ACGACAAACC CGACGCCGGG ATAGGTCAG       359

(2) INFORMATION FOR SEQ ID NO: 188:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (xi) SEQUENCE DESCRIPTION: SEQ ID NO: 188:

AACGGGCCCG TGGGCACCGC TCCTCTAAGG GCTCTCGTTG GTCGCATGAA GTGCTGGAAG       60

GATGCATCTT GGCAGATTCC CGCCAGAGCA AAACAGCCGC TAGTCCTAGT CCGAGTCGCC      120

CGCAAAGTTC CTCGAATAAC TCCGTACCCG GAGCGCCAAA CCGGGTCTCC TTCGCTAAGC      180

TGCGCGAACC ACTTGAGGTT CCGGGACTCC TTGACGTCCA GACCGATTCG TTCGAGTGGC      240

TGATCGGTTC GCCGCGCTGG CGCGAATCCG CCGCCGAGCG GGGTGATGTC AACCCAGTGG      300

GTGGCCTGGA AGAGGTGCTC TACGAGCTGT CTCCGATCGA GGACTTCTCC                 350

(2) INFORMATION FOR SEQ ID NO: 189:

(i) SEQUENCE CHARACTERISTICS:
        (A) LENGTH: 679 amino acids
        (B) TYPE: amino acid
        (C) STRANDEDNESS: <Unknown>
        (D) TOPOLOGY: linear (xi) SEQUENCE DESCRIPTION: SEQ ID NO: 189:

Glu Gln Pro Lys Gly Pro Phe Gly Glu Val Ile Glu Ala Phe Ala Asp
1               5                   10                  15
```

```
Gly Leu Ala Gly Lys Gly Lys Gln Ile Asn Thr Thr Leu Asn Ser Leu
                20                  25                  30

Ser Gln Ala Leu Asn Ala Leu Asn Glu Gly Arg Gly Asp Phe Phe Ala
            35                  40                  45

Val Val Arg Ser Leu Ala Leu Phe Val Asn Ala Leu His Gln Asp Asp
        50                  55                  60

Gln Gln Phe Val Ala Leu Asn Lys Asn Leu Ala Glu Phe Thr Asp Arg
65                  70                  75                  80

Leu Thr His Ser Asp Ala Asp Leu Ser Asn Ala Ile Gln Gln Phe Asp
                85                  90                  95

Ser Leu Leu Ala Val Ala Arg Pro Phe Phe Ala Lys Asn Arg Glu Val
            100                 105                 110

Leu Thr His Asp Val Asn Asn Leu Ala Thr Val Thr Thr Leu Leu
        115                 120                 125

Gln Pro Asp Pro Leu Asp Gly Leu Glu Thr Val Leu His Ile Phe Pro
130                 135                 140

Thr Leu Ala Ala Asn Ile Asn Gln Leu Tyr His Pro Thr His Gly Gly
145                 150                 155                 160

Val Val Ser Leu Ser Ala Phe Thr Asn Phe Ala Asn Pro Met Glu Phe
            165                 170                 175

Ile Cys Ser Ser Ile Gln Ala Gly Ser Arg Leu Gly Tyr Gln Glu Ser
            180                 185                 190

Ala Glu Leu Cys Ala Gln Tyr Leu Ala Pro Val Leu Asp Ala Ile Lys
            195                 200                 205

Phe Asn Tyr Phe Pro Phe Gly Leu Asn Val Ala Ser Thr Ala Ser Thr
210                 215                 220

Leu Pro Lys Glu Ile Ala Tyr Ser Glu Pro Arg Leu Gln Pro Pro Asn
225                 230                 235                 240

Gly Tyr Lys Asp Thr Thr Val Pro Gly Ile Trp Val Pro Asp Thr Pro
            245                 250                 255

Leu Ser His Arg Asn Thr Gln Pro Gly Trp Val Val Ala Pro Gly Met
            260                 265                 270

Gln Gly Val Gln Val Gly Pro Ile Thr Gln Gly Leu Leu Thr Pro Glu
            275                 280                 285

Ser Leu Ala Glu Leu Met Gly Gly Pro Asp Ile Ala Pro Pro Ser Ser
290                 295                 300

Gly Leu Gln Thr Pro Pro Gly Pro Pro Asn Ala Tyr Asp Glu Tyr Pro
305                 310                 315                 320

Val Leu Pro Pro Ile Gly Leu Gln Ala Pro Gln Val Pro Ile Pro Pro
            325                 330                 335

Pro Pro Pro Gly Pro Asp Val Ile Pro Gly Pro Val Pro Pro Val Leu
            340                 345                 350

Ala Ala Ile Val Phe Pro Arg Asp Arg Pro Ala Ser Glu Asn Phe
            355                 360                 365

Asp Tyr Met Gly Leu Leu Leu Ser Pro Gly Leu Ala Thr Phe Leu
370                 375                 380

Phe Gly Val Ser Ser Ser Pro Ala Arg Gly Thr Met Ala Asp Arg His
385                 390                 395                 400

Val Leu Ile Pro Ala Ile Thr Gly Leu Ala Leu Ile Ala Ala Phe Val
            405                 410                 415

Ala His Ser Trp Tyr Arg Thr Glu His Pro Leu Ile Asp Met Arg Leu
            420                 425                 430
```

```
Phe Gln Asn Arg Ala Val Ala Gln Ala Asn Met Thr Met Thr Val Leu
            435                 440                 445

Ser Leu Gly Leu Phe Gly Ser Phe Leu Leu Pro Ser Tyr Leu Gln
        450                 455                 460

Gln Val Leu His Gln Ser Pro Met Gln Ser Gly Val His Ile Ile Pro
465                 470                 475                 480

Gln Gly Leu Gly Ala Met Leu Ala Met Pro Ile Ala Gly Ala Met Met
                485                 490                 495

Asp Arg Arg Gly Pro Ala Lys Ile Val Leu Val Gly Ile Met Leu Ile
            500                 505                 510

Ala Ala Gly Leu Gly Thr Phe Ala Phe Gly Val Ala Arg Gln Ala Asp
            515                 520                 525

Tyr Leu Pro Ile Leu Pro Thr Gly Leu Ala Ile Met Gly Met Gly Met
            530                 535                 540

Gly Cys Ser Met Met Pro Leu Ser Gly Ala Ala Val Gln Thr Leu Ala
545                 550                 555                 560

Pro His Gln Ile Ala Arg Gly Ser Thr Leu Ile Ser Val Asn Gln Gln
                565                 570                 575

Val Gly Gly Ser Ile Gly Thr Ala Leu Met Ser Val Leu Leu Thr Tyr
            580                 585                 590

Gln Phe Asn His Ser Glu Ile Ile Ala Thr Ala Lys Lys Val Ala Leu
            595                 600                 605

Thr Pro Glu Ser Gly Ala Gly Arg Gly Ala Ala Val Asp Pro Ser Ser
            610                 615                 620

Leu Pro Arg Gln Thr Asn Phe Ala Ala Gln Leu Leu His Asp Leu Ser
625                 630                 635                 640

His Ala Tyr Ala Val Val Phe Val Ile Ala Thr Ala Leu Val Val Ser
            645                 650                 655

Thr Leu Ile Pro Ala Ala Phe Leu Pro Lys Gln Gln Ala Ser His Arg
            660                 665                 670

Arg Ala Pro Leu Leu Ser Ala
            675

(2) INFORMATION FOR SEQ ID NO: 190:

(i) SEQUENCE CHARACTERISTICS:
        (A) LENGTH: 120 amino acids
        (B) TYPE: amino acid
        (C) STRANDEDNESS: <Unknown>
        (D) TOPOLOGY: linear (xi) SEQUENCE DESCRIPTION: SEQ ID NO: 190:

Thr Pro Glu Lys Ser Phe Val Asp Asp Leu Asp Ile Asp Ser Leu Ser
1               5                   10                  15

Met Val Glu Ile Ala Val Gln Thr Glu Asp Lys Tyr Gly Val Lys Ile
                20                  25                  30

Pro Asp Glu Asp Leu Ala Gly Leu Arg Thr Val Gly Asp Val Val Ala
            35                  40                  45

Tyr Ile Gln Lys Leu Glu Glu Asn Pro Glu Ala Ala Gln Ala Leu
50                  55                  60

Arg Ala Lys Ile Glu Ser Glu Asn Pro Asp Ala Ala Arg Ala Asp Arg
65                  70                  75                  80

Cys Val Ser Pro Thr Ser Gln Ala Arg Asp Ala Arg Arg Pro Leu Ala
                85                  90                  95

Arg Ser Ala Arg Leu Ala Cys Arg Leu Pro Ala Ser Val Pro Thr
            100                 105                 110
```

```
Thr Arg Arg Asp Pro Arg Glu Arg
        115                 120

(2) INFORMATION FOR SEQ ID NO: 191:

(i) SEQUENCE CHARACTERISTICS:
        (A) LENGTH: 89 amino acids
        (B) TYPE: amino acid
        (C) STRANDEDNESS: <Unknown>
        (D) TOPOLOGY: linear (xi) SEQUENCE DESCRIPTION: SEQ ID NO: 191:

Leu Ala Cys Gln Cys His Arg Arg Tyr Asp Val Gly Ile Gln Phe Arg
1               5                   10                  15

Gly Pro Ala Gly Pro Val Ala Thr Gln Ser Gly Pro Pro Gly Pro Ser
            20                  25                  30

Ile Ala Glu Gly Arg Gln Val Arg Ala Gln Cys Gly Ala Gly Phe Leu
            35                  40                  45

Glu Arg Arg Pro Ala Val Ser Gly Ala Leu Pro Pro Asn Asn Ala Ser
50                  55                  60

Pro Gly Ile Arg Ser Arg Ala Ala Asp Ser Gln Arg His Leu Leu Ala
65                  70                  75                  80

Gly Asp Gly Ser Asp Val Thr Val Gly
                85

(2) INFORMATION FOR SEQ ID NO: 192:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (xi) SEQUENCE DESCRIPTION: SEQ ID NO: 192:

Ala Ser Leu Leu Ala Tyr Ser Ala Ala Ala Ser Thr Ala Leu Ala
1               5                   10                  15

Val Ala Cys Val Arg Ala Asp His Arg Asp Arg Arg Thr Ile Arg Asp
            20                  25                  30

His Leu Ala Met Ile His Leu Ala Gln Leu Val Thr Gln Pro Pro Gly
            35                  40                  45

Gly Val Arg Gln Arg Leu His His Leu Gly Ile Ala Val Ala Pro Gln
            50                  55                  60

Pro Gln Glu Val Val Val Leu Ala His His Leu Val Thr Gly Thr Gly
65                  70                  75                  80

Glu Val Gln Gly Glu Gly Arg His Val Ala Ala Glu Val Val Asp Pro
                85                  90                  95

Glu Asn Gln Ile Leu Arg Gln Val Leu Gly Pro Ala Pro His Asp Lys
            100                 105                 110

Pro Asp Ala Gly Ile Gly Gln
        115

(2) INFORMATION FOR SEQ ID NO: 193:

(i) SEQUENCE CHARACTERISTICS:
        (A) LENGTH: 116 amino acids
        (B) TYPE: amino acid
        (C) STRANDEDNESS: <Unknown>
        (D) TOPOLOGY: linear (xi) SEQUENCE DESCRIPTION: SEQ ID NO: 193:
```

```
Arg Ala Arg Gly His Arg Ser Ser Lys Gly Ser Arg Trp Ser His Glu
1               5                   10                  15

Val Leu Glu Gly Cys Ile Leu Ala Asp Ser Arg Gln Ser Lys Thr Ala
                20                  25                  30

Ala Ser Pro Ser Pro Ser Arg Pro Gln Ser Ser Ser Asn Asn Ser Val
            35                  40                  45

Pro Gly Ala Pro Asn Arg Val Ser Phe Ala Lys Leu Arg Glu Pro Leu
        50                  55                  60

Glu Val Pro Gly Leu Leu Asp Val Gln Thr Asp Ser Phe Glu Trp Leu
65                  70                  75                  80

Ile Gly Ser Pro Arg Trp Arg Glu Ser Ala Ala Glu Arg Gly Asp Val
                85                  90                  95

Asn Pro Val Gly Gly Leu Glu Glu Val Leu Tyr Glu Leu Ser Pro Ile
            100                 105                 110

Glu Asp Phe Ser
        115
```

(2) INFORMATION FOR SEQ ID NO: 194:

(i) SEQUENCE CHARACTERISTICS:
        (A) LENGTH: 811 base pairs
        (B) TYPE: nucleic acid
        (C) STRANDEDNESS: single
        (D) TOPOLOGY: linear (xi) SEQUENCE DESCRIPTION: SEQ ID NO: 194:

```
TGCTACGCAG CAATCGCTTT GGTGACAGAT GTGGATGCCG GCGTCGCTGC TGGCGATGGC        60

GTGAAAGCCG CCGACGTGTT CGCCGCATTC GGGGAGAACA TCGAACTGCT CAAAAGGCTG       120

GTGCGGGCCG CCATCGATCG GGTCGCCGAC GAGCGCACGT GCACGCACTG TCAACACCAC       180

GCCGGTGTTC CGTTGCCGTT CGAGCTGCCA TGAGGGTGCT GCTGACCGGC GCGGCCGGCT       240

TCATCGGGTC GCGCGTGGAT GCGGCGTTAC GGGCTGCGGG TCACGACGTG GTGGGCGTCG       300

ACGCGCTGCT GCCCGCCGCG CACGGGCCAA ACCCGGTGCT GCCACCGGGC TGCCAGCGGG       360

TCGACGTGCG CGACGCCAGC GCGCTGGCCC CGTTGTTGGC CGGTGTCGAT CTGGTGTGTC       420

ACCAGGCCGC CATGGTGGGT GCCGGCGTCA ACGCCGCCGA CGCACCCGCC TATGGCGGCC       480

ACAACGATTT CGCCACCACG GTGCTGCTGG CGCAGATGTT CGCCGCCGGG GTCCGCCGTT       540

TGGTGCTGGC GTCGTCGATG GTGGTTTACG GGCAGGGGCG CTATGACTGT CCCCAGCATG       600

GACCGGTCGA CCCGCTGCCG CGGCGGCGAG CCGACCTGGA CAATGGGGTC TTCGAGCACC       660

GTTGCCCGGG GTGCGGCGAG CCAGTCATCT GGCAATTGGT CGACGAAGAT GCCCCGTTGC       720

GCCCGCGCAG CCTGTACGCG GCAGCAAGAC CGCGCAGGAG CACTACGCGC TGGCGTGGTC       780

GGAAACGAAT GGCGGTTCCG TGGTGGCGTT G                                      811
```

(2) INFORMATION FOR SEQ ID NO: 195:

(i) SEQUENCE CHARACTERISTICS:
        (A) LENGTH: 966 base pairs
        (B) TYPE: nucleic acid
        (C) STRANDEDNESS: single
        (D) TOPOLOGY: linear (xi) SEQUENCE DESCRIPTION: SEQ ID NO: 195:

```
GTCCCGCGAT GTGGCCGAGC ATGACTTTCG GCAACACCGG CGTAGTAGTC GAAGATATCG        60

GACTTTGTGG TCCCGGTGGC GGGATAGAGC ACCTGTCGGC GTTGGTCAGC GTCACCCGTT       120

GCTCGGACGC CGAACCCATG CTTTCAACGT AGCCTGTCGG TCACACAAGT CGCGAGCGTA       180
```

```
ACGTCACGGT CAAATATCGC GTGGAATTTC GCCGTGACGT TCCGCTCGCG GACAATCAAG      240

GCATACTCAC TTACATGCGA GCCATTTGGA CGGGTTCGAT CGCCTTCGGG CTGGTGAACG      300

TGCCGGTCAA GGTGTACAGC GCTACCGCAG ACCACGACAT CAGGTTCCAC CAGGTGCACG      360

CCAAGGACAA CGGACGCATC CGGTACAAGC GCGTCTGCGA GGCGTGTGGC GAGGTGGTCG      420

ACTACCGCGA TCTTGCCCGG GCCTACGAGT CCGGCGACGG CCAAATGGTG GCGATCACCG      480

ACGACGACAT CGCCAGCTTG CCTGAAGAAC GCAGCCGGGA GATCGAGGTG TTGGAGTTCG      540

TCCCCGCCGC CGACGTGGAC CCGATGATGT TCGACCGCAG CTACTTTTTG GAGCCTGATT      600

CGAAGTCGTC GAAATCGTAT GTGCTGCTGG CTAAGACACT CGCCGAGACC GACCGGATGG      660

CGATCGTGGA TCGCCCCACC GGCCGTGAAT GCAGGAAAAA TAAGAGCCGC TATCCACAAT      720

TCGGCGTCGA GCTCGGCTAC CACAAACGGT AGAACGATCG AGACATTCCC GAGCTGAAGT      780

GCGGCGCTAT AGAAGCCGCT CTGCGCGATT ATCAAACGCA AAATACGCTT ACTCATGCCA      840

TCGGCGCTGC TCACCCGATG CGACGTTTTT GCCACGCTCC ACCGCCTGCC GCGCGACCTC      900

AAGTGGGCAT GCATCCCACC CGTTCCCGGA AACCGGTTCC GGCGGGTCGG CTCATCGCTT      960

CATCCT                                                                966

(2) INFORMATION FOR SEQ ID NO: 196:

(i) SEQUENCE CHARACTERISTICS:
        (A) LENGTH: 2367 base pairs
        (B) TYPE: nucleic acid
        (C) STRANDEDNESS: single
        (D) TOPOLOGY: linear (xi) SEQUENCE DESCRIPTION: SEQ ID NO: 196:

CCGCACCGCC GGCAATACCG CCAGCGCCAC CGTTACCGCC GTTTGCGCCG TTGCCCCCGT       60

TGCCGCCCGT CCCGCCGGCC CCGCCGATGG AGTTCTCATC GCCAAAAGTA CTGGCGTTGC      120

CACCGGAGCC GCCGTTGCCG CCGTCACCGC CAGCCCCGCC GACTCCACCG GCCCCACCGA      180

CTCCGCCGCT GCCACCGTTG CCGCCGTTGC CGATCAACAT GCCGCTGGCG CCACCCTTGC      240

CACCCACGCC ACCGGCTCCG CCCACCCCGC CGACACCAAG CGAGCTGCCG CCGGAGCCAC      300

CATCACCACC TACGCCACCG ACCGCCCAGA CACCAGCGAC CGGGTCTTCG TGAAACGTCG      360

CGGTGCCACC ACCGCCGCCG TTACCGCCAA CCCCACCGGC AACGCCGGCG CCGCCATCCC      420

CGCCGGCCCC GGCGTTGCCG CCGTTGCCGC CGTTGCCGAA CAACAACCCG CCGGCGCCGC      480

CGTTGCCGCC CGCGCCGCCG GTCCCGCCGG CGCCGCCGAC GCCAAGGCCG CTGCCGCCCT      540

TGCCGCCATC ACCACCCTTG CCGCCGACCA CATCGGGTTC TGCCTCGGGG TCTGGGCTGT      600

CAAACCTCGC GATGCCAGCG TTGCCGCCGC TTCCCCCGGG CCCCCCGTG GCGCCGTCAC      660

CACCGATACC ACCCGCGCCA CCGGCGCCAC CGTTGCCGCC ATCACCGAAT AGCAACCCGC      720

CGGCGCCACC ATTGCCGCCA GCTCCCCCTG CGCCACCGTC GGCGCCGGAG GCGGCACTGG      780

CAGCCCCGTT ACCACCGAAA CCGCCGCTAC CACCGGTAGA GGTGGCAGTG GCGATGTGTA      840

CGAAAGCGCC GCCTCCGGCG CCGCCGCTAC CACCCCCACT GCCGGCGGCT ACACCGTCGG      900

ACCCGTTGCC ACCATCACCG CCAAAGGCGC TCGCAATGTC GCCCTGCGCG ACTCCGCCGT      960

CGCCGCCGTT GCCGCCGCCG CCACCGGCAG CGGCGGTACC GCCGTCACCA CCGGCACCGC     1020

CGGTGGCCTT GCCCGAGCCT GCCGTCGCGG TGGCACCGTC GCCGCCGGTG CCACCGGTCG     1080

GCGTGCCGGC AGTGCCATGG CCGCCCGTGC CGCCGTCGCC GCCGGTTTGA TCACCGATGC     1140

CGGACACATC TGCCGGGCTG TCCCCGGTGC TGGCCGCGGG GCCGGGCGTG GGATTGACCC     1200
```

-continued

```
CGTTTGCCCC GGCGAGGCCG GCGCCGCCGG TACCACCGGC GCCGCCATGG CCGAACAGCC    1260

CGGCGTTGCC GCCGTTACCG CCCGCACCCC CGATGCCTGC GGCCACGCTG GTGCCGCCGA    1320

CACCGCCGTT GCCGCCGTTG CCCCACAACC ACCCCCCGTT CCCACCGGCA CCGCCGGCCG    1380

CGCCGGTACC ACCGGCCCCG CCGTTGCCGC CGTTGCCGAT CAACCCGGCC GCGCCTCCGC    1440

TGCCGCCGGT TTGACCGAAC CCGCCAGCCG CGCCGTTGCC ACCGTTGCCA AACAGCAACC    1500

CGCCGGCCGC GCCAGGCTGC CCGGGTGCCG TCCCGTCGGC GCCGTTTCCG ATCAACGGGC    1560

GCCCCAAAAG CGCCTCGGTG GGCGCATTCA CCGCACCCAG CAGACTCCGC TCAACAGCGG    1620

CTTCAGTGCT GGCATACCGA CCCGCGGCCG CAGTCAACGC CTGCACAAAC TGCTCGTGAA    1680

ACGCTGCCAC CTGTACGCTG AGCGCCTGAT ACTGCCGAGC ATGGGCCCCG AACAACCCCG    1740

CAATCGCCGC CGACACTTCA TCGGCAGCCG CAGCCACCAC TTCCGTCGTC GGGATCGCCG    1800

CGGCCGCATT AGCCGCGCTC ACCTGCGAAC CAATAGTCGA TAAATCCAAA GCCGCAGTTG    1860

CCAGCAGCTG CGGCGTCGCG ATCACCAAGG ACACCTCGCA CCTCCGGATA CCCCATATCG    1920

CCGCACCGTG TCCCCAGCGG CCACGTGACC TTTGGTCGCT GGCTGGCGGC CCTGACTATG    1980

GCCGCGACGG CCCTCGTTCT GATTCGCCCC GGCGCGCAGC TTGTTGCGCG AGTTGAAGAC    2040

GGGAGGACAG GCCGAGCTTG GTGTAGACGT GGGTCAAGTG GAATGCACG GTCCGCGGCG    2100

AGATGAATAG GCGGACGCCG ATCTCCTTGT TGCTGAGTCC CTCACCGACC AGTAGAGCCA    2160

CCTCAAGCTC TGTCGGTGTC AACGCGCCCC AGCCACTTGT CGGGCGTTTC CGTGCACCGC    2220

GGCCTCGTTG CGCGTACGCG ATCGCCTCAT CGATCGATAA CGCAGTTCCT TCGGCCCAGG    2280

CATCGTCGAA CTCGCTGTCA CCCATGGATT TTCGAAGGGT GGCTAGCGAC GAGTTACAGC    2340

CCGCCTGGTA GATCCCGAAG CGGACCG                                       2367
```

(2) INFORMATION FOR SEQ ID NO: 197:

(i) SEQUENCE CHARACTERISTICS:
        (A) LENGTH: 376 amino acids
        (B) TYPE: amino acid
        (C) STRANDEDNESS: <Unknown>
        (D) TOPOLOGY: linear (xi) SEQUENCE DESCRIPTION: SEQ ID NO: 197:

```
Gln Pro Ala Gly Ala Thr Ile Ala Ala Ser Ser Pro Cys Ala Thr Val
1               5                   10                  15

Gly Ala Gly Gly Gly Thr Gly Ser Pro Val Thr Thr Glu Thr Ala Ala
            20                  25                  30

Thr Thr Gly Arg Gly Gly Ser Gly Asp Val Tyr Glu Ser Ala Ala Ser
        35                  40                  45

Gly Ala Ala Thr Thr Pro Thr Ala Gly Gly Tyr Thr Val Gly Pro
    50                  55                  60

Val Ala Thr Ile Thr Ala Lys Gly Ala Arg Asn Val Ala Leu Arg Asp
65                  70                  75                  80

Ser Ala Val Ala Ala Val Ala Ala Ala Thr Gly Ser Gly Gly Thr
                85                  90                  95

Ala Val Thr Thr Gly Thr Ala Gly Gly Leu Ala Arg Ala Cys Arg Arg
            100                 105                 110

Gly Gly Thr Val Ala Ala Gly Ala Thr Gly Arg Arg Ala Gly Ser Ala
        115                 120                 125

Met Ala Ala Arg Ala Ala Val Ala Ala Gly Leu Ile Thr Asp Ala Gly
    130                 135                 140
```

```
His Ile Cys Arg Ala Val Pro Gly Ala Gly Arg Gly Ala Gly Arg Gly
145                 150                 155                 160

Ile Asp Pro Val Cys Pro Gly Glu Ala Gly Ala Ala Gly Thr Thr Gly
                165                 170                 175

Ala Ala Met Ala Glu Gln Pro Gly Val Ala Ala Val Thr Ala Arg Thr
            180                 185                 190

Pro Asp Ala Cys Gly His Ala Gly Ala Ala Asp Thr Ala Val Ala Ala
        195                 200                 205

Val Ala Pro Gln Pro Pro Val Pro Thr Gly Thr Ala Gly Arg Ala
    210                 215                 220

Gly Thr Thr Gly Pro Ala Val Ala Ala Val Ala Asp Gln Pro Gly Arg
225                 230                 235                 240

Ala Ser Ala Ala Ala Gly Leu Thr Glu Pro Ala Ser Arg Ala Val Ala
                245                 250                 255

Thr Val Ala Lys Gln Gln Pro Ala Gly Arg Ala Arg Leu Pro Gly Cys
                260                 265                 270

Arg Pro Val Gly Ala Val Ser Asp Gln Arg Ala Pro Gln Lys Arg Leu
            275                 280                 285

Gly Gly Arg Ile His Arg Thr Gln Gln Thr Pro Leu Asn Ser Gly Phe
    290                 295                 300

Ser Ala Gly Ile Pro Thr Arg Gly Arg Ser Gln Arg Leu His Lys Leu
305                 310                 315                 320

Leu Val Lys Arg Cys His Leu Tyr Ala Glu Arg Leu Ile Leu Pro Ser
                325                 330                 335

Met Gly Pro Glu Gln Pro Arg Asn Arg Arg His Phe Ile Gly Ser
                340                 345                 350

Arg Ser His His Phe Arg Arg Asp Arg Arg Gly Arg Ile Ser Arg
        355                 360                 365

Ala His Leu Arg Thr Asn Ser Arg
    370                 375

(2) INFORMATION FOR SEQ ID NO: 198:

(i) SEQUENCE CHARACTERISTICS:
        (A) LENGTH: 2852 base pairs
        (B) TYPE: nucleic acid
        (C) STRANDEDNESS: single
        (D) TOPOLOGY: linear (xi) SEQUENCE DESCRIPTION: SEQ ID NO: 198:

GGCCAAAACG CCCCGGCGAT CGCGGCCACC GAGGCCGCCT ACGACCAGAT GTGGGCCCAG      60

GACGTGGCGG CGATGTTTGG CTACCATGCC GGGGCTTCGG CGGCCGTCTC GGCGTTGACA     120

CCGTTCGGCC AGGCGCTGCC GACCGTGGCG GGCGGCGGTG CGCTGGTCAG CGCGGCCGCG     180

GCTCAGGTGA CCACGCGGGT CTTCCGCAAC CTGGGCTTGG CGAACGTCCG CGAGGGCAAC     240

GTCCGCAACG GTAATGTCCG GAACTTCAAT CTCGGCTCGG CCAACATCGG CAACGGCAAC     300

ATCGGCAGCG GCAACATCGG CAGCTCCAAC ATCGGGTTTG CAACGTGGG TCCTGGGTTG      360

ACCGCAGCGC TGAACAACAT CGGTTTCGGC AACACCGGCA GCAACAACAT CGGGTTTGGC     420

AACACCGGCA GCAACAACAT CGGGTTCGGC AATACCGGAG ACGGCAACCG AGGTATCGGG     480

CTCACGGGTA GCGGTTTGTT GGGGTTCGGC GGCCTGAACT CGGGCACCGG CAACATCGGT     540

CTGTTCAACT CGGGCACCGG AAACGTCGGC ATCGGCAACT CGGGTACCGG GAACTGGGGC     600

ATTGGCAACT CGGGCAACAG CTACAACACC GGTTTTGGCA ACTCCGGCGA CGCCAACACG     660

GGCTTCTTCA ACTCCGGAAT AGCCAACACC GGCGTCGGCA ACGCCGGCAA CTACAACACC     720
```

-continued

```
GGTAGCTACA ACCCGGGCAA CAGCAATACC GGCGGCTTCA ACATGGGCCA GTACAACACG      780

GGCTACCTGA ACAGCGGCAA CTACAACACC GGCTTGGCAA ACTCCGGCAA TGTCAACACC      840

GGCGCCTTCA TTACTGGCAA CTTCAACAAC GGCTTCTTGT GGCGCGGCGA CCACCAAGGC      900

CTGATTTTCG GGAGCCCCGG CTTCTTCAAC TCGACCAGTG CGCCGTCGTC GGGATTCTTC      960

AACAGCGGTG CCGGTAGCGC GTCCGGCTTC CTGAACTCCG GTGCCAACAA TTCTGGCTTC     1020

TTCAACTCTT CGTCGGGGGC CATCGGTAAC TCCGGCCTGG CAAACGCGGG CGTGCTGGTA     1080

TCGGGCGTGA TCAACTCGGG CAACACCGTA TCGGGTTTGT TCAACATGAG CCTGGTGGCC     1140

ATCACAACGC CGGCCTTGAT CTCGGGCTTC TTCAACACCG GAAGCAACAT GTCGGGATTT     1200

TTCGGTGGCC CACCGGTCTT CAATCTCGGC CTGGCAAACC GGGGCGTCGT GAACATTCTC     1260

GGCAACGCCA ACATCGGCAA TTACAACATT CTCGGCAGCG GAAACGTCGG TGACTTCAAC     1320

ATCCTTGGCA GCGGCAACCT CGGCAGCCAA AACATCTTGG GCAGCGGCAA CGTCGGCAGC     1380

TTCAATATCG GCAGTGGAAA CATCGGAGTA TTCAATGTCG GTTCCGGAAG CCTGGGAAAC     1440

TACAACATCG GATCCGGAAA CCTCGGGATC TACAACATCG GTTTTGGAAA CGTCGGCGAC     1500

TACAACGTCG GCTTCGGGAA CGCGGGCGAC TTCAACCAAG GCTTTGCCAA CACCGGCAAC     1560

AACAACATCG GGTTCGCCAA CACCGGCAAC AACAACATCG GCATCGGGCT GTCCGGCGAC     1620

AACCAGCAGG GCTTCAATAT TGCTAGCGGC TGGAACTCGG GCACCGGCAA CAGCGGCCTG     1680

TTCAATTCGG GCACCAATAA CGTTGGCATC TTCAACGCGG GCACCGGAAA CGTCGGCATC     1740

GCAAACTCGG GCACCGGGAA CTGGGGTATC GGGAACCCGG GTACCGACAA TACCGGCATC     1800

CTCAATGCTG GCAGCTACAA CACGGGCATC CTCAACGCCG GCGACTTCAA CACGGGCTTC     1860

TACAACACGG GCAGCTACAA CACCGGCGGC TTCAACGTCG GTAACACCAA CACCGGCAAC     1920

TTCAACGTGG GTGACACCAA TACCGGCAGC TATAACCCGG GTGACACCAA CACCGGCTTC     1980

TTCAATCCCG GCAACGTCAA TACCGGCGCT TTCGACACGG GCGACTTCAA CAATGGCTTC     2040

TTGGTGGCGG GCGATAACCA GGGCCAGATT GCCATCGATC TCTCGGTCAC CACTCCATTC     2100

ATCCCCATAA ACGAGCAGAT GGTCATTGAC GTACACAACG TAATGACCTT CGGCGGCAAC     2160

ATGATCACGG TCACCGAGGC CTCGACCGTT TTCCCCCAAA CCTTCTATCT GAGCGGTTTG     2220

TTCTTCTTCG GCCCGGTCAA TCTCAGCGCA TCCACGCTGA CCGTTCCGAC GATCACCCTC     2280

ACCATCGGCG GACCGACGGT GACCGTCCCC ATCAGCATTG TCGGTGCTCT GGAGAGCCGC     2340

ACGATTACCT TCCTCAAGAT CGATCCGGCG CCGGGCATCG GAAATTCGAC CACCAACCCC     2400

TCGTCCGGCT TCTTCAACTC GGGCACCGGT GGCACATCTG GCTTCCAAAA CGTCGGCGGC     2460

GGCAGTTCAG GCGTCTGGAA CAGTGGTTTG AGCAGCGCGA TAGGGAATTC GGGTTTCCAG     2520

AACCTCGGCT CGCTGCAGTC AGGCTGGGCG AACCTGGGCA ACTCCGTATC GGGCTTTTTC     2580

AACACCAGTA CGGTGAACCT CTCCACGCCG GCCAATGTCT CGGGCCTGAA CAACATCGGC     2640

ACCAACCTGT CCGGCGTGTT CCGCGGTCCG ACCGGGACGA TTTTCAACGC GGGCCTTGCC     2700

AACCTGGGCC AGTTGAACAT CGGCAGCGCC TCGTGCCGAA TTCGGCACGA GTTAGATACG     2760

GTTTCAACAA TCATATCCGC GTTTTGCGGC AGTGCATCAG ACGAATCGAA CCCGGGAAGC     2820

GTAAGCGAAT AAACCGAATG GCGGCCTGTC AT                                   2852
```

(2) INFORMATION FOR SEQ ID NO: 199:

(i) SEQUENCE CHARACTERISTICS:
        (A) LENGTH: 943 amino acids
        (B) TYPE: amino acid (C) STRANDEDNESS: <Unknown>
(D) TOPOLOGY: linear (xi) SEQUENCE DESCRIPTION: SEQ ID NO: 199:

```
Gly Gln Asn Ala Pro Ala Ile Ala Ala Thr Glu Ala Ala Tyr Asp Gln
1               5                   10                  15

Met Trp Ala Gln Asp Val Ala Ala Met Phe Gly Tyr His Ala Gly Ala
            20                  25                  30

Ser Ala Ala Val Ser Ala Leu Thr Pro Phe Gly Gln Ala Leu Pro Thr
        35                  40                  45

Val Ala Gly Gly Gly Ala Leu Val Ser Ala Ala Ala Gln Val Thr
    50                  55                  60

Thr Arg Val Phe Arg Asn Leu Gly Leu Ala Asn Val Arg Glu Gly Asn
65                  70                  75                  80

Val Arg Asn Gly Asn Val Arg Asn Phe Asn Leu Gly Ser Ala Asn Ile
                85                  90                  95

Gly Asn Gly Asn Ile Gly Ser Gly Asn Ile Gly Ser Ser Asn Ile Gly
            100                 105                 110

Phe Gly Asn Val Gly Pro Gly Leu Thr Ala Ala Leu Asn Asn Ile Gly
        115                 120                 125

Phe Gly Asn Thr Gly Ser Asn Asn Ile Gly Phe Gly Asn Thr Gly Ser
    130                 135                 140

Asn Asn Ile Gly Phe Gly Asn Thr Gly Asp Gly Asn Arg Gly Ile Gly
145                 150                 155                 160

Leu Thr Gly Ser Gly Leu Leu Gly Phe Gly Leu Asn Ser Gly Thr
                165                 170                 175

Gly Asn Ile Gly Leu Phe Asn Ser Gly Thr Gly Asn Val Gly Ile Gly
            180                 185                 190

Asn Ser Gly Thr Gly Asn Trp Gly Ile Gly Asn Ser Gly Asn Ser Tyr
        195                 200                 205

Asn Thr Gly Phe Gly Asn Ser Gly Asp Ala Asn Thr Gly Phe Phe Asn
    210                 215                 220

Ser Gly Ile Ala Asn Thr Gly Val Gly Asn Ala Gly Asn Tyr Asn Thr
225                 230                 235                 240

Gly Ser Tyr Asn Pro Gly Asn Ser Asn Thr Gly Gly Phe Asn Met Gly
                245                 250                 255

Gln Tyr Asn Thr Gly Tyr Leu Asn Ser Gly Asn Tyr Asn Thr Gly Leu
            260                 265                 270

Ala Asn Ser Gly Asn Val Asn Thr Gly Ala Phe Ile Thr Gly Asn Phe
        275                 280                 285

Asn Asn Gly Phe Leu Trp Arg Gly Asp His Gln Gly Leu Ile Phe Gly
    290                 295                 300

Ser Pro Gly Phe Phe Asn Ser Thr Ser Ala Pro Ser Ser Gly Phe Phe
305                 310                 315                 320

Asn Ser Gly Ala Gly Ser Ala Ser Gly Phe Leu Asn Ser Gly Ala Asn
                325                 330                 335

Asn Ser Gly Phe Phe Asn Ser Ser Gly Ala Ile Gly Asn Ser Gly
            340                 345                 350

Leu Ala Asn Ala Gly Val Leu Val Ser Gly Val Ile Asn Ser Gly Asn
        355                 360                 365

Thr Val Ser Gly Leu Phe Asn Met Ser Leu Val Ala Ile Thr Thr Pro
    370                 375                 380

Ala Leu Ile Ser Gly Phe Phe Asn Thr Gly Ser Asn Met Ser Gly Phe
385                 390                 395                 400
```

```
Phe Gly Gly Pro Pro Val Phe Asn Leu Gly Leu Ala Asn Arg Gly Val
                405                 410                 415

Val Asn Ile Leu Gly Asn Ala Asn Ile Gly Asn Tyr Asn Ile Leu Gly
            420                 425                 430

Ser Gly Asn Val Gly Asp Phe Asn Ile Leu Gly Ser Gly Asn Leu Gly
        435                 440                 445

Ser Gln Asn Ile Leu Gly Ser Gly Asn Val Gly Ser Phe Asn Ile Gly
    450                 455                 460

Ser Gly Asn Ile Gly Val Phe Asn Val Gly Ser Gly Ser Leu Gly Asn
465                 470                 475                 480

Tyr Asn Ile Gly Ser Gly Asn Leu Gly Ile Tyr Asn Ile Gly Phe Gly
            485                 490                 495

Asn Val Gly Asp Tyr Asn Val Gly Phe Gly Asn Ala Gly Asp Phe Asn
        500                 505                 510

Gln Gly Phe Ala Asn Thr Gly Asn Asn Asn Ile Gly Phe Ala Asn Thr
    515                 520                 525

Gly Asn Asn Asn Ile Gly Ile Gly Leu Ser Gly Asp Asn Gln Gln Gly
530                 535                 540

Phe Asn Ile Ala Ser Gly Trp Asn Ser Gly Thr Gly Asn Ser Gly Leu
545                 550                 555                 560

Phe Asn Ser Gly Thr Asn Asn Val Gly Ile Phe Asn Ala Gly Thr Gly
                565                 570                 575

Asn Val Gly Ile Ala Asn Ser Gly Thr Gly Asn Trp Gly Ile Gly Asn
            580                 585                 590

Pro Gly Thr Asp Asn Thr Gly Ile Leu Asn Ala Gly Ser Tyr Asn Thr
        595                 600                 605

Gly Ile Leu Asn Ala Gly Asp Phe Asn Thr Gly Phe Tyr Asn Thr Gly
    610                 615                 620

Ser Tyr Asn Thr Gly Gly Phe Asn Val Gly Asn Thr Asn Thr Gly Asn
625                 630                 635                 640

Phe Asn Val Gly Asp Thr Asn Thr Gly Ser Tyr Asn Pro Gly Asp Thr
                645                 650                 655

Asn Thr Gly Phe Phe Asn Pro Gly Asn Val Asn Thr Gly Ala Phe Asp
            660                 665                 670

Thr Gly Asp Phe Asn Asn Gly Phe Leu Val Ala Gly Asp Asn Gln Gly
        675                 680                 685

Gln Ile Ala Ile Asp Leu Ser Val Thr Thr Pro Phe Ile Pro Ile Asn
    690                 695                 700

Glu Gln Met Val Ile Asp Val His Asn Val Met Thr Phe Gly Gly Asn
705                 710                 715                 720

Met Ile Thr Val Thr Glu Ala Ser Thr Val Phe Pro Gln Thr Phe Tyr
                725                 730                 735

Leu Ser Gly Leu Phe Phe Gly Pro Val Asn Leu Ser Ala Ser Thr
            740                 745                 750

Leu Thr Val Pro Thr Ile Thr Leu Thr Ile Gly Gly Pro Thr Val Thr
        755                 760                 765

Val Pro Ile Ser Ile Val Gly Ala Leu Glu Ser Arg Thr Ile Thr Phe
    770                 775                 780

Leu Lys Ile Asp Pro Ala Pro Gly Ile Gly Asn Ser Thr Thr Asn Pro
785                 790                 795                 800

Ser Ser Gly Phe Phe Asn Ser Gly Thr Gly Thr Ser Gly Phe Gln
                805                 810                 815
```

```
Asn Val Gly Gly Gly Ser Ser Gly Val Trp Asn Ser Gly Leu Ser Ser
            820                 825                 830

Ala Ile Gly Asn Ser Gly Phe Gln Asn Leu Gly Ser Leu Gln Ser Gly
        835                 840                 845

Trp Ala Asn Leu Gly Asn Ser Val Ser Gly Phe Phe Asn Thr Ser Thr
    850                 855                 860

Val Asn Leu Ser Thr Pro Ala Asn Val Ser Gly Leu Asn Asn Ile Gly
865                 870                 875                 880

Thr Asn Leu Ser Gly Val Phe Arg Gly Pro Thr Gly Thr Ile Phe Asn
                885                 890                 895

Ala Gly Leu Ala Asn Leu Gly Gln Leu Asn Ile Gly Ser Ala Ser Cys
            900                 905                 910

Arg Ile Arg His Glu Leu Asp Thr Val Ser Thr Ile Ile Ser Ala Phe
        915                 920                 925

Cys Gly Ser Ala Ser Asp Glu Ser Asn Pro Gly Ser Val Ser Glu
    930                 935                 940
```

(2) INFORMATION FOR SEQ ID NO: 200:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO: 200:

```
GGATCCATAT GGGCCATCAT CATCATCATC ACGTGATCGA CATCATCGGG ACC         53
```

(2) INFORMATION FOR SEQ ID NO: 201:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 201:

```
CCTGAATTCA GGCCTCGGTT GCGCCGGCCT CATCTTGAAC GA                     42
```

(2) INFORMATION FOR SEQ ID NO: 202:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 202:

```
GGATCCTGCA GGCTCGAAAC CACCGAGCGG T                                 31
```

(2) INFORMATION FOR SEQ ID NO: 203:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 203:

```
CTCTGAATTC AGCGCTGGAA ATCGTCGCGA T                                 31
```

(2) INFORMATION FOR SEQ ID NO: 204:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 204:

GGATCCAGCG CTGAGATGAA GACCGATGCC GCT                                33

(2) INFORMATION FOR SEQ ID NO: 205:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 205:

GGATATCTGC AGAATTCAGG TTTAAAGCCC ATTTGCGA                           38

(2) INFORMATION FOR SEQ ID NO: 206:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 206:

CCGCATGCGA GCCACGTGCC CACAACGGCC                                    30

(2) INFORMATION FOR SEQ ID NO: 207:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 207:

CTTCATGGAA TTCTCAGGCC GGTAAGGTCC GCTGCGG                            37

(2) INFORMATION FOR SEQ ID NO: 208:

(i) SEQUENCE CHARACTERISTICS:
        (A) LENGTH: 7676 base pairs
        (B) TYPE: nucleic acid
        (C) STRANDEDNESS: single
        (D) TOPOLOGY: linear (xi) SEQUENCE DESCRIPTION: SEQ ID NO: 208:

TGGCGAATGG GACGCGCCCT GTAGCGGCGC ATTAAGCGCG GCGGGTGTGG TGGTTACGCG    60

CAGCGTGACC GCTACACTTG CCAGCGCCCT AGCGCCCGCT CCTTTCGCTT TCTTCCCTTC   120

CTTTCTCGCC ACGTTCGCCG GCTTTCCCCG TCAAGCTCTA AATCGGGGGC TCCCTTTAGG   180

GTTCCGATTT AGTGCTTTAC GGCACCTCGA CCCCAAAAAA CTTGATTAGG GTGATGGTTC   240

ACGTAGTGGG CCATCGCCCT GATAGACGGT TTTTCGCCCT TGACGTTGG AGTCCACGTT    300

CTTTAATAGT GGACTCTTGT TCCAAACTGG AACAACACTC AACCCTATCT CGGTCTATTC   360

TTTTGATTTA TAAGGGATTT TGCCGATTTC GGCCTATTGG TTAAAAAATG AGCTGATTTA   420

ACAAAAATTT AACGCGAATT TTAACAAAAT ATTAACGTTT ACAATTTCAG GTGGCACTTT   480

TCGGGGAAAT GTGCGCGGAA CCCCTATTTG TTTATTTTTC TAAATACATT CAAATATGTA   540

TCCGCTCATG AATTAATTCT TAGAAAAACT CATCGAGCAT CAAATGAAAC TGCAATTTAT   600

```
TCATATCAGG ATTATCAATA CCATATTTTT GAAAAAGCCG TTTCTGTAAT GAAGGAGAAA    660

ACTCACCGAG GCAGTTCCAT AGGATGGCAA GATCCTGGTA TCGGTCTGCG ATTCCGACTC    720

GTCCAACATC AATACAACCT ATTAATTTCC CCTCGTCAAA AATAAGGTTA TCAAGTGAGA    780

AATCACCATG AGTGACGACT GAATCCGGTG AGAATGGCAA AAGTTTATGC ATTTCTTTCC    840

AGACTTGTTC AACAGGCCAG CCATTACGCT CGTCATCAAA ATCACTCGCA TCAACCAAAC    900

CGTTATTCAT TCGTGATTGC GCCTGAGCGA GACGAAATAC GCGATCGCTG TTAAAAGGAC    960

AATTACAAAC AGGAATCGAA TGCAACCGGC GCAGGAACAC TGCCAGCGCA TCAACAATAT    1020

TTTCACCTGA ATCAGGATAT TCTTCTAATA CCTGGAATGC TGTTTTCCCG GGATCGCAG    1080

TGGTGAGTAA CCATGCATCA TCAGGAGTAC GGATAAAATG CTTGATGGTC GGAAGAGGCA    1140

TAAATTCCGT CAGCCAGTTT AGTCTGACCA TCTCATCTGT AACATCATTG GCAACGCTAC    1200

CTTTGCCATG TTTCAGAAAC AACTCTGGCG CATCGGGCTT CCCATACAAT CGATAGATTG    1260

TCGCACCTGA TTGCCCGACA TTATCGCGAG CCCATTTATA CCCATATAAA TCAGCATCCA    1320

TGTTGGAATT TAATCGCGGC CTAGAGCAAG ACGTTTCCCG TTGAATATGG CTCATAACAC    1380

CCCTTGTATT ACTGTTTATG TAAGCAGACA GTTTTATTGT TCATGACCAA AATCCCTTAA    1440

CGTGAGTTTT CGTTCCACTG AGCGTCAGAC CCCGTAGAAA AGATCAAAGG ATCTTCTTGA    1500

GATCCTTTTT TTCTGCGCGT AATCTGCTGC TTGCAAACAA AAAAACCACC GCTACCAGCG    1560

GTGGTTTGTT TGCCGGATCA AGAGCTACCA ACTCTTTTTC CGAAGGTAAC TGGCTTCAGC    1620

AGAGCGCAGA TACCAAATAC TGTCCTTCTA GTGTAGCCGT AGTTAGGCCA CCACTTCAAG    1680

AACTCTGTAG CACCGCCTAC ATACCTCGCT CTGCTAATCC TGTTACCAGT GGCTGCTGCC    1740

AGTGGCGATA AGTCGTGTCT TACCGGGTTG GACTCAAGAC GATAGTTACC GGATAAGGCG    1800

CAGCGGTCGG GCTGAACGGG GGGTTCGTGC ACACAGCCCA GCTTGGAGCG AACGACCTAC    1860

ACCGAACTGA GATACCTACA GCGTGAGCTA TGAGAAAGCG CCACGCTTCC CGAAGGGAGA    1920

AAGGCGGACA GGTATCCGGT AAGCGGCAGG GTCGGAACAG GAGAGCGCAC GAGGGAGCTT    1980

CCAGGGGGAA ACGCCTGGTA TCTTTATAGT CCTGTCGGGT TTCGCCACCT CTGACTTGAG    2040

CGTCGATTTT TGTGATGCTC GTCAGGGGGG CGGAGCCTAT GGAAAAACGC CAGCAACGCG    2100

GCCTTTTTAC GGTTCCTGGC CTTTTGCTGG CCTTTTGCTC ACATGTTCTT TCCTGCGTTA    2160

TCCCCTGATT CTGTGGATAA CCGTATTACC GCCTTTGAGT GAGCTGATAC CGCTCGCCGC    2220

AGCCGAACGA CCGAGCGCAG CGAGTCAGTG AGCGAGGAAG CGGAAGAGCG CCTGATGCGG    2280

TATTTTCTCC TTACGCATCT GTGCGGTATT TCACACCGCA TATATGGTGC ACTCTCAGTA    2340

CAATCTGCTC TGATGCCGCA TAGTTAAGCC AGTATACACT CCGCTATCGC TACGTGACTG    2400

GGTCATGGCT GCGCCCCGAC ACCCGCCAAC ACCCGCTGAC GCGCCCTGAC GGGCTTGTCT    2460

GCTCCCGGCA TCCGCTTACA GACAAGCTGT GACCGTCTCC GGGAGCTGCA TGTGTCAGAG    2520

GTTTTCACCG TCATCACCGA AACGCGCGAG GCAGCTGCGG TAAAGCTCAT CAGCGTGGTC    2580

GTGAAGCGAT TCACAGATGT CTGCCTGTTC ATCCGCGTCC AGCTCGTTGA GTTTCTCCAG    2640

AAGCGTTAAT GTCTGGCTTC TGATAAAGCG GGCCATGTTA AGGGCGGTTT TTTCCTGTTT    2700

GGTCACTGAT GCCTCCGTGT AAGGGGGATT TCTGTTCATG GGGTAATGA TACCGATGAA    2760

ACGAGAGAGG ATGCTCACGA TACGGGTTAC TGATGATGAA CATGCCCGGT TACTGGAACG    2820

TTGTGAGGGT AAACAACTGG CGGTATGGAT GCGGCGGGAC CAGAGAAAAA TCACTCAGGG    2880

TCAATGCCAG CGCTTCGTTA ATACAGATGT AGGTGTTCCA CAGGGTAGCC AGCAGCATCC    2940
```

```
TGCGATGCAG ATCCGGAACA TAATGGTGCA GGGCGCTGAC TTCCGCGTTT CCAGACTTTA    3000

CGAAACACGG AAACCGAAGA CCATTCATGT TGTTGCTCAG GTCGCAGACG TTTTGCAGCA    3060

GCAGTCGCTT CACGTTCGCT CGCGTATCGG TGATTCATTC TGCTAACCAG TAAGGCAACC    3120

CCGCCAGCCT AGCCGGGTCC TCAACGACAG GAGCACGATC ATGCGCACCC GTGGGCCGC     3180

CATGCCGGCG ATAATGGCCT GCTTCTCGCC GAAACGTTTG GTGGCGGGAC CAGTGACGAA    3240

GGCTTGAGCG AGGGCGTGCA AGATTCCGAA TACCGCAAGC GACAGGCCGA TCATCGTCGC    3300

GCTCCAGCGA AAGCGGTCCT CGCCGAAAAT GACCCAGAGC GCTGCCGGCA CCTGTCCTAC    3360

GAGTTGCATG ATAAAGAAGA CAGTCATAAG TGCGGCGACG ATAGTCATGC CCCGCGCCCA    3420

CCGGAAGGAG CTGACTGGGT TGAAGGCTCT CAAGGGCATC GGTCGAGATC CCGGTGCCTA    3480

ATGAGTGAGC TAACTTACAT TAATTGCGTT GCGCTCACTG CCCGCTTTCC AGTCGGGAAA    3540

CCTGTCGTGC CAGCTGCATT AATGAATCGG CCAACGCGCG GGAGAGGCG GTTTGCGTAT     3600

TGGGCGCCAG GGTGGTTTTT CTTTTCACCA GTGAGACGGG CAACAGCTGA TTGCCCTTCA    3660

CCGCCTGGCC CTGAGAGAGT TGCAGCAAGC GGTCCACGCT GGTTTGCCCC AGCAGGCGAA    3720

AATCCTGTTT GATGGTGGTT AACGGCGGGA TATAACATGA GCTGTCTTCG GTATCGTCGT    3780

ATCCCACTAC CGAGATATCC GCACCAACGC GCAGCCCGGA CTCGGTAATG GCGCGCATTG    3840

CGCCCAGCGC CATCTGATCG TTGGCAACCA GCATCGCAGT GGGAACGATG CCCTCATTCA    3900

GCATTTGCAT GGTTTGTTGA AAACCGGACA TGGCACTCCA GTCGCCTTCC CGTTCCGCTA    3960

TCGGCTGAAT TTGATTGCGA GTGAGATATT TATGCCAGCC AGCCAGACGC AGACGCGCCG    4020

AGACAGAACT TAATGGGCCC GCTAACAGCG CGATTTGCTG GTGACCCAAT GCGACCAGAT    4080

GCTCCACGCC CAGTCGCGTA CCGTCTTCAT GGGAGAAAAT AATACTGTTG ATGGGTGTCT    4140

GGTCAGAGAC ATCAAGAAAT AACGCCGGAA CATTAGTGCA GGCAGCTTCC ACAGCAATGG    4200

CATCCTGGTC ATCCAGCGGA TAGTTAATGA TCAGCCCACT GACGCGTTGC GCGAGAAGAT    4260

TGTGCACCGC CGCTTTACAG GCTTCGACGC CGCTTCGTTC TACCATCGAC ACCACCACGC    4320

TGGCACCCAG TTGATCGGCG CGAGATTTAA TCGCCGCGAC AATTTGCGAC GGCGCGTGCA    4380

GGGCCAGACT GGAGGTGGCA ACGCCAATCA GCAACGACTG TTTGCCCGCC AGTTGTTGTG    4440

CCACGCGGTT GGGAATGTAA TTCAGCTCCG CCATCGCCGC TTCCACTTTT TCCCGCGTTT    4500

TCGCAGAAAC GTGGCTGGCC TGGTTCACCA CGCGGGAAAC GGTCTGATAA GAGACACCGG    4560

CATACTCTGC GACATCGTAT AACGTTACTG GTTTCACATT CACCACCCTG AATTGACTCT    4620

CTTCCGGGCG CTATCATGCC ATACCGCGAA AGGTTTTGCG CCATTCGATG GTGTCCGGGA    4680

TCTCGACGCT CTCCCTTATG CGACTCCTGC ATTAGGAAGC AGCCCAGTAG TAGGTTGAGG    4740

CCGTTGAGCA CCGCCGCCGC AAGGAATGGT GCATGCAAGG AGATGGCGCC CAACAGTCCC    4800

CCGGCCACGG GGCCTGCCAC CATACCCACG CCGAAACAAG CGCTCATGAG CCCGAAGTGG    4860

CGAGCCCGAT CTTCCCCATC GGTGATGTCG GCGATATAGG CGCCAGCAAC CGCACCTGTG    4920

GCGCCGGTGA TGCCGGCCAC GATGCGTCCG GCGTAGAGGA TCGAGATCTC GATCCCGCGA    4980

AATTAATACG ACTCACTATA GGGGAATTGT GAGCGGATAA CAATTCCCCT CTAGAAATAA    5040

TTTTGTTTAA CTTTAAGAAG GAGATATACA TATGGGCCAT CATCATCATC ATCACGTGAT    5100

CGACATCATC GGGACCAGCC CCACATCCTG GAACAGGCG GCGGCGGAGG CGGTCCAGCG     5160

GGCGCGGGAT AGCGTCGATG ACATCCGCGT CGCTCGGGTC ATTGAGCAGG ACATGGCCGT    5220

GGACAGCGCG GCAAGATCA CCTACCGCAT CAAGCTCGAA GTGTCGTTCA AGATGAGGCC     5280

GGCGCAACCG AGGGGCTCGA AACCACCGAG CGGTTCGCCT GAAACGGGCG CCGGCGCCGG    5340
```

-continued

```
TACTGTCGCG ACTACCCCCG CGTCGTCGCC GGTGACGTTG GCGGAGACCG GTAGCACGCT    5400

GCTCTACCCG CTGTTCAACC TGTGGGGTCC GGCCTTTCAC GAGAGGTATC CGAACGTCAC    5460

GATCACCGCT CAGGGCACCG GTTCTGGTGC CGGGATCGCG CAGGCCGCCG CCGGGACGGT    5520

CAACATTGGG GCCTCCGACG CCTATCTGTC GGAAGGTGAT ATGGCCGCGC ACAAGGGGCT    5580

GATGAACATC GCGCTAGCCA TCTCCGCTCA GCAGGTCAAC TACAACCTGC CCGGAGTGAG    5640

CGAGCACCTC AAGCTGAACG GAAAAGTCCT GGCGGCCATG TACCAGGGCA CCATCAAAAC    5700

CTGGGACGAC CCGCAGATCG CTGCGCTCAA CCCCGGCGTG AACCTGCCCG GCACCGCGGT    5760

AGTTCCGCTG CACCGCTCCG ACGGGTCCGG TGACACCTTC TTGTTCACCC AGTACCTGTC    5820

CAAGCAAGAT CCCGAGGGCT GGGGCAAGTC GCCCGGCTTC GGCACCACCG TCGACTTCCC    5880

GGCGGTGCCG GGTGCGCTGG GTGAGAACGG CAACGGCGGC ATGGTGACCG GTTGCGCCGA    5940

GACACCGGGC TGCGTGGCCT ATATCGGCAT CAGCTTCCTC GACCAGGCCA GTCAACGGGG    6000

ACTCGGCGAG GCCCAACTAG GCAATAGCTC TGGCAATTTC TTGTTGCCCG ACGCGCAAAG    6060

CATTCAGGCC GCGGCGGCTG GCTTCGCATC GAAAACCCCG GCGAACCAGG CGATTTCGAT    6120

GATCGACGGG CCCGCCCCGG ACGGCTACCC GATCATCAAC TACGAGTACG CCATCGTCAA    6180

CAACCGGCAA AAGGACGCCG CCACCGCGCA GACCTTGCAG GCATTTCTGC ACTGGGCGAT    6240

CACCGACGGC AACAAGGCCT CGTTCCTCGA CCAGGTTCAT TTCCAGCCGC TGCCGCCCGC    6300

GGTGGTGAAG TTGTCTGACG CGTTGATCGC GACGATTTCC AGCGCTGAGA TGAAGACCGA    6360

TGCCGCTACC CTCGCGCAGG AGGCAGGTAA TTTCGAGCGG ATCTCCGGCG ACCTGAAAAC    6420

CCAGATCGAC CAGGTGGAGT CGACGGCAGG TTCGTTGCAG GGCCAGTGGC GCGGCGCGGC    6480

GGGGACGGCC GCCCAGGCCG CGGTGGTGCG CTTCCAAGAA GCAGCCAATA AGCAGAAGCA    6540

GGAACTCGAC GAGATCTCGA CGAATATTCG TCAGGCCGGC GTCCAATACT CGAGGGCCGA    6600

CGAGGAGCAG CAGCAGGCGC TGTCCTCGCA AATGGGCTTT GTGCCCACAA CGGCCGCCTC    6660

GCCGCCGTCG ACCGCTGCAG CGCCACCCGC ACCGGCGACA CCTGTTGCCC CCCACCACC    6720

GGCCGCCGCC AACACGCCGA ATGCCCAGCC GGGCGATCCC AACGCAGCAC CTCCGCCGGC    6780

CGACCCGAAC GCACCGCCGC CACCTGTCAT TGCCCCAAAC GCACCCCAAC CTGTCCGGAT    6840

CGACAACCCG GTTGGAGGAT TCAGCTTCGC GCTGCCTGCT GGCTGGGTGG AGTCTGACGC    6900

CGCCCACTTC GACTACGGTT CAGCACTCCT CAGCAAAACC ACCGGGGACC CGCCATTTCC    6960

CGGACAGCCG CCGCCGGTGG CCAATGACAC CCGTATCGTG CTCGGCCGGC TAGACCAAAA    7020

GCTTTACGCC AGCGCCGAAG CCACCGACTC CAAGGCCGCG GCCCGGTTGG GCTCGGACAT    7080

GGGTGAGTTC TATATGCCCT ACCCGGGCAC CCGGATCAAC CAGGAAACCG TCTCGCTTGA    7140

CGCCAACGGG GTGTCTGGAA GCGCGTCGTA TTACGAAGTC AAGTTCAGCG ATCCGAGTAA    7200

GCCGAACGGC CAGATCTGGA CGGGCGTAAT CGGCTCGCCC GCGGCGAACG CACCGGACGC    7260

CGGGCCCCCT CAGCGCTGGT TTGTGGTATG GCTCGGGACC GCCAACAACC CGGTGGACAA    7320

GGGCGCGGCC AAGGCGCTGG CCGAATCGAT CCGGCCTTTG GTCGCCCCGC CGCCGGCGCC    7380

GGCACCGGCT CCTGCAGAGC CCGCTCCGGC GCCGGCGCCG GCCGGGGAAG TCGCTCCTAC    7440

CCCGACGACA CCGACACCGC AGCGGACCTT ACCGGCCTGA GAATTCTGCA GATATCCATC    7500

ACACTGGCGG CCGCTCGAGC ACCACCACCA CCACCACTGA GATCCGGCTG CTAACAAAGC    7560

CCGAAAGGAA GCTGAGTTGG CTGCTGCCAC CGCTGAGCAA TAACTAGCAT AACCCCTTGG    7620

GGCCTCTAAA CGGGTCTTGA GGGGTTTTTT GCTGAAAGGA GGAACTATAT CCGGAT       7676
```

(2) INFORMATION FOR SEQ ID NO: 209:

(i) SEQUENCE CHARACTERISTICS:
        (A) LENGTH: 802 amino acids
        (B) TYPE: amino acid
        (C) STRANDEDNESS: single
        (D) TOPOLOGY: linear (xi) SEQUENCE DESCRIPTION: SEQ ID NO: 209:

```
Met Gly His His His His His Val Ile Asp Ile Ile Gly Thr Ser
1               5                   10                  15

Pro Thr Ser Trp Glu Gln Ala Ala Glu Ala Val Gln Arg Ala Arg
            20                  25                  30

Asp Ser Val Asp Ile Arg Val Ala Arg Val Ile Glu Gln Asp Met
        35                  40                  45

Ala Val Asp Ser Ala Gly Lys Ile Thr Tyr Arg Ile Lys Leu Glu Val
50                  55                  60

Ser Phe Lys Met Arg Pro Ala Gln Pro Arg Gly Ser Lys Pro Pro Ser
65              70                  75                  80

Gly Ser Pro Glu Thr Gly Ala Gly Ala Gly Thr Val Ala Thr Thr Pro
                85                  90                  95

Ala Ser Ser Pro Val Thr Leu Ala Glu Thr Gly Ser Thr Leu Leu Tyr
            100                 105                 110

Pro Leu Phe Asn Leu Trp Gly Pro Ala Phe His Glu Arg Tyr Pro Asn
            115                 120                 125

Val Thr Ile Thr Ala Gln Gly Thr Gly Ser Gly Ala Gly Ile Ala Gln
            130                 135                 140

Ala Ala Ala Gly Thr Val Asn Ile Gly Ala Ser Asp Ala Tyr Leu Ser
145                 150                 155                 160

Glu Gly Asp Met Ala Ala His Lys Gly Leu Met Asn Ile Ala Leu Ala
                165                 170                 175

Ile Ser Ala Gln Gln Val Asn Tyr Asn Leu Pro Gly Val Ser Glu His
            180                 185                 190

Leu Lys Leu Asn Gly Lys Val Leu Ala Ala Met Tyr Gln Gly Thr Ile
            195                 200                 205

Lys Thr Trp Asp Asp Pro Gln Ile Ala Ala Leu Asn Pro Gly Val Asn
            210                 215                 220

Leu Pro Gly Thr Ala Val Val Pro Leu His Arg Ser Asp Gly Ser Gly
225                 230                 235                 240

Asp Thr Phe Leu Phe Thr Gln Tyr Leu Ser Lys Gln Asp Pro Glu Gly
                245                 250                 255

Trp Gly Lys Ser Pro Gly Phe Gly Thr Thr Val Asp Phe Pro Ala Val
            260                 265                 270

Pro Gly Ala Leu Gly Glu Asn Gly Asn Gly Gly Met Val Thr Gly Cys
            275                 280                 285

Ala Glu Thr Pro Gly Cys Val Ala Tyr Ile Gly Ile Ser Phe Leu Asp
            290                 295                 300

Gln Ala Ser Gln Arg Gly Leu Gly Glu Ala Gln Leu Gly Asn Ser Ser
305                 310                 315                 320

Gly Asn Phe Leu Leu Pro Asp Ala Gln Ser Ile Gln Ala Ala Ala
                325                 330                 335

Gly Phe Ala Ser Lys Thr Pro Ala Asn Gln Ala Ile Ser Met Ile Asp
            340                 345                 350

Gly Pro Ala Pro Asp Gly Tyr Pro Ile Ile Asn Tyr Glu Tyr Ala Ile
            355                 360                 365
```

```
Val Asn Asn Arg Gln Lys Asp Ala Ala Thr Ala Gln Thr Leu Gln Ala
    370                 375                 380

Phe Leu His Trp Ala Ile Thr Asp Gly Asn Lys Ala Ser Phe Leu Asp
385                 390                 395                 400

Gln Val His Phe Gln Pro Leu Pro Pro Ala Val Lys Leu Ser Asp
                405                 410                 415

Ala Leu Ile Ala Thr Ile Ser Ser Ala Glu Met Lys Thr Asp Ala Ala
            420                 425                 430

Thr Leu Ala Gln Glu Ala Gly Asn Phe Glu Arg Ile Ser Gly Asp Leu
        435                 440                 445

Lys Thr Gln Ile Asp Gln Val Glu Ser Thr Ala Gly Ser Leu Gln Gly
    450                 455                 460

Gln Trp Arg Gly Ala Ala Gly Thr Ala Ala Gln Ala Ala Val Val Arg
465                 470                 475                 480

Phe Gln Glu Ala Ala Asn Lys Gln Lys Gln Glu Leu Asp Glu Ile Ser
                485                 490                 495

Thr Asn Ile Arg Gln Ala Gly Val Gln Tyr Ser Arg Ala Asp Glu Glu
            500                 505                 510

Gln Gln Gln Ala Leu Ser Ser Gln Met Gly Phe Val Pro Thr Thr Ala
        515                 520                 525

Ala Ser Pro Pro Ser Thr Ala Ala Pro Pro Ala Pro Ala Thr Pro
    530                 535                 540

Val Ala Pro Pro Pro Ala Ala Ala Asn Thr Pro Asn Ala Gln Pro
545                 550                 555                 560

Gly Asp Pro Asn Ala Ala Pro Pro Ala Asp Pro Asn Ala Pro Pro
                565                 570                 575

Pro Pro Val Ile Ala Pro Asn Ala Pro Gln Pro Val Arg Ile Asp Asn
            580                 585                 590

Pro Val Gly Gly Phe Ser Phe Ala Leu Pro Ala Gly Trp Val Glu Ser
        595                 600                 605

Asp Ala Ala His Phe Asp Tyr Gly Ser Ala Leu Leu Ser Lys Thr Thr
    610                 615                 620

Gly Asp Pro Pro Phe Pro Gly Gln Pro Pro Val Ala Asn Asp Thr
625                 630                 635                 640

Arg Ile Val Leu Gly Arg Leu Asp Gln Lys Leu Tyr Ala Ser Ala Glu
                645                 650                 655

Ala Thr Asp Ser Lys Ala Ala Arg Leu Gly Ser Asp Met Gly Glu
            660                 665                 670

Phe Tyr Met Pro Tyr Pro Gly Thr Arg Ile Asn Gln Glu Thr Val Ser
        675                 680                 685

Leu Asp Ala Asn Gly Val Ser Gly Ser Ala Ser Tyr Tyr Glu Val Lys
    690                 695                 700

Phe Ser Asp Pro Ser Lys Pro Asn Gly Gln Ile Trp Thr Gly Val Ile
705                 710                 715                 720

Gly Ser Pro Ala Ala Asn Ala Pro Asp Ala Gly Pro Pro Gln Arg Trp
                725                 730                 735

Phe Val Val Trp Leu Gly Thr Ala Asn Asn Pro Val Asp Lys Gly Ala
            740                 745                 750

Ala Lys Ala Leu Ala Glu Ser Ile Arg Pro Leu Val Ala Pro Pro
        755                 760                 765

Ala Pro Ala Pro Ala Pro Ala Glu Pro Ala Pro Ala Pro Ala
    770                 775                 780
```

```
Gly Glu Val Ala Pro Thr Pro Thr Thr Pro Thr Pro Gln Arg Thr Leu
785                 790             795                 800

Pro Ala (2) INFORMATION FOR SEQ ID NO: 210:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 210:

GTGGCGGCGC TGCGGCCGGC CAGCAGAGCG ATGTGCATCC GTTCGCGAAC CTGATCGCGG      60

TCGACGATGA GCGCGCCGAA CGCCGCGACG ACGAAGAACG TCAGGAAGCC GTCCAGCAGC     120

GCGGTCCGCG CGGTGACGAA GCTGACCCCG TCGCAGATCA GCAGCACCCC GGCGATGGCG     180

CCGACCAATG TCGACCGGCT GATCCGCCGC ACGATCCGCA CCACCAGCGC CACCAGGACC     240

ACACCCAGCA GGGCGCCGGT GAACCGCCAG CCGAATCCGT TGTGACCGAA GATGGCCTCC     300

CCGATCGCGA TCAGCTGCTT ACCGACCGGC GGGTGAACCA CCAGGCCGTA CCCGGGGTTG     360

TCTTCCACCC CATGGTTGTT CAGCACCTGC CAGGCCTGGC GGTGCGTAAT GCTTCTCGTC     420

GAAGATGGGG GTGCCGGCAT CCGTCACCGA GCCC                                 454

(2) INFORMATION FOR SEQ ID NO: 211:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 211:

TGCAGAAGTA CGGCGGATCC TCGGTGGCCG ACGCCGAACG GATTCGCCGC GTCGCCGAAC      60

GCATCGTCGC CACCAAGAAG CAAGGCAATG ACGTCGTCGT CGTCGTCTCT GCCATGGGGG     120

ATACCACCGA CGACCTGCTG GATCTGGCTC AGCAGGTGTG CCCGGCGCCG CCGCCTCGGG     180

AGCTGGACAT GCTGCTTACC GCCGGTGAAC GCATCTCGAA TGCGTTGGTG GCCATGGCCA     240

TCGAGTCGCT CGGCGCGCAT GCCCGGTCGT TCACCGGTTC GCAGGCCGGG GTGATCACCA     300

CCGGCACCCA CGGCAACGCC AAGATCATCG ACGTCACGCC GGGGCGGCTG CAAACCGCCC     360

TTGAGGAAGG GCGGGTCGTC TTGGTGGCCG GATTCCAAGG GGTCAGCCAG GACACCAAGG     420

ATGTCACGAC GTTGGGCCGC GGCGGCTCGG ACACCACCGC CGTCGCCATG                470

(2) INFORMATION FOR SEQ ID NO: 212:

(i) SEQUENCE CHARACTERISTICS:
        (A) LENGTH: 279 base pa irs
        (B) TYPE: nucleic acid
        (C) STRANDEDNESS: sin gle
        (D) TOPOLOGY: linear (ii) MOLECULE TYPE: Genomic DNA (xi) SEQUENCE DESCRIPTION: SEQ ID NO: 212:

GGCCGGCGTA CCCGGCCGGG ACAAACAACG ATCGATTGAT ATCGATGAGA GACGGAGGAA      60

TCGTGGCCCT TCCCCAGTTG ACCGACGAGC AGCGCGCGGC CGCGTTGGAG AAGGCTGCTG     120
```

```
CCGCACGTCG AGCGCGAGCA GAGCTCAAGG ATCGGCTCAA GCGTGGCGGC ACCAACCTCA        180

CCCAGGTCCT CAAGGACGCG GAGAGCGATG AAGTCTTGGG CAAAATGAAG GTGTCTGCGC        240

TGCTTGAGGC CTTGCCAAAG GTGGGCAAGG TCCAGGCGC                               279
```

(2) INFORMATION FOR SEQ ID NO: 213:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 213:

```
ACACGGTCGA ACTCGACGAG CCCCTCGTGG AGGTGTCGAC CGACAAGGTC GACACCGAAA         60

TCCCTCGCCG GCCGCGGGTG TGCTGACCAA GATCATCGCC CAAGAAGATG ACACGGTCGA        120

GGTCGGCGGC GAGCTCTCTG TCATTGGCGA CGCCCATGAT GCCGGCGAGG CCGCGGTCCC        180

GGCACCCCAG AAAGTCTCTG CCGGCCCAAC CCGAATCCA                               219
```

(2) INFORMATION FOR SEQ ID NO: 214:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 214:

```
TCGCTGCCGA CATCGGCGCC GCGCCCGCCC CCAAGCCCGC ACCCAAGCCC GTCCCCGAGC         60

CAGCGCCGAC GCCGAAGGCC GAACCCGCAC CATCGCCGCC GGCGGCCCAG CCAGCCGGTG        120

CGGCCGAGGG CGCACCGTAC GTGACGCCGC TGGTGCGAAA GCTGGCGTCG GAAAACAACA        180

TCGACCTCGC CGGGGTGACC GGCACCGGAG TGGGTGGTCG CATCCGCAAA CAGGATGTGC        240

TGGCCGCGGC TGAACAAAAG AAGCGGGCGA AAGCACCGGC GCCGGCCGCC CAGGCCGCCG        300

CCGCGCCGGC CCCGAAAGCG CCGCCTGAAG ATCCGATGCC GC                          342
```

(2) INFORMATION FOR SEQ ID NO: 215:

(i) SEQUENCE CHARACTERISTICS:
        (A) LENGTH: 515 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 215:

```
GGGTCTTGGT CAGTATCAGC GCCGACGAGG ACGCCACGGT GCCCGTCGGC GGCGAGTTGG         60

CCCGGATCGG TGTCGCTGCC GACATCGGCG CCGCGCCCGC CCCCAAGCCC GCACCCAAGC        120

CCGTCCCCGA GCCAGCGCCG ACGCCGAAGG CCGAACCCGC ACCATCGCCG CCGGCGGCCC        180

AGCCAGCCGG TGCGGCCGAG GGCGCACCGT ACGTGACGCC GCTGGTGCGA AAGCTGGCGT        240

CGGAAAACAA CATCGACCTC GCCGGGGTGA CCGGCACCGG AGTGGGTGGT CGCATCCGCA        300

AACAGGATGT GCTGGCCGCG GCTGAACAAA AGAAGCGGGC GAAAGCACCG GCGCCCTGAG        360

CGCTTCATCA CCCGGTTAAC CAGCTTGCCC CAGAAGCCGG CTTCGACCTC TTCGCGGGTC        420
```

```
TTGGTCCGCT GCAGGCGGTC GGCGAGCCAG TTCAGGTTAG GCGGCCGAAA TCTTCCAGTT      480

CGCCAGGAAG GGCACCCGGA ACAGGGTCCG CACCC                                 515

(2) INFORMATION FOR SEQ ID NO: 216:

(i) SEQUENCE CHARACTERISTICS:
        (A) LENGTH: 557 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 216:

CCGACCCCAA GGTGCAGATT CAACAGGCCA TGAGGAAGC ACAGCGCACC CACCAAGCGC        60

TGACTCAACA GGCGGCGCAA GTGATCGGTA ACCAGCGTCA ATTGGAGATG CGACTCAACC      120

GACAGCTGGC GGACATCGAA AAGCTTCAGG TCAATGTGCG CCAAGCCCTG ACGCTGGCCG      180

ACCAGGCCAC CGCCGCCGGA GACGCTGCCA AGGCCACCGA ATACAACAAC GCCGCCGAGG      240

CGTTCGCAGC CCAGCTGGTG ACCGCCGAGC AGAGCGTCGA AGACCTCAAG ACGCTGCATG      300

ACCAGGCGCT TAGCGCCGCA GCTCAGGCCA AGAAGGCCGT CGAACGAAAT GCGATGGTGC      360

TGCAGCAGAA GATCGCCGAG CGAACCAAGC TGCTCAGCCA GCTCGAGCAG GCGAAGATGC      420

AGGAGCAGGT CAGCGCATCG TTGCGGTCGA TGAGTGAGCT CGCCGCGCCA GGCAACACGC      480

CGAGCCTCGA CGAGGTGCGC GACAAGATCG AGCGTCGCTA CGCCAACGCG ATCGGTTCGG      540

CTGAACTTGC CGAGAGT                                                    557

(2) INFORMATION FOR SEQ ID NO: 217:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 217:

CAGGATAGGT TTCGACATCC ACCTGGGTTC CGCACCCGGT GCGCGACCGT GTGATAGGCC       60

AGAGGTGGAC CTGCGCCGAC CGACGATCGA TCGAGGAGTC AACAGAAATG GCCTTCTCCG      120

TCCAGATGCC GGCACTCGGT GAGAGCGTCA CCGAGGGGAC GGTTACCCGC TGGCTCAAAC      180

AGGAAGGCGA CACGGTCGAA CTCGACGAGC CCTCGTGGA GGT                         223

(2) INFORMATION FOR SEQ ID NO: 218:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 218:

AAGAAGTACA TCTGCCGGTC GATGTCGGCG AACCACGGCA GCCAACCGGC GCAGTAGCCG       60

ACCAGGACCA CCGCATAACG CCAGTCCCGG CGCACAAACA TACGCCACCC CGCGTATGCC      120

AGGACTGGCA CCGCCAGCCA CCACATCGCG GGCGTGCCGA CCAGCATCTC GGCCTTGACG      180

CACGACTGTG CGCCGCAGCC TGCAACGTCT TGCTGGTCGA TGGCGTACAG CACCGGCCGC      240
```

```
AACGACATGG GCCAGGTCCA CGGTTTGGAT TCCCAAGGGT GGTAGTTGCC TGCGGAATTC        300

GTCAGGCCCG CGTGGAAGTG GAACGCTTTG GCGGTGTATT GCCAGAGCGA GCGCACGGCG        360

TCGGGCAGCG GAACAACCGA GTTGCGACCG ACCGCTTGAC CGACCGCATG CCGATCGATC        420

GCGGTCTCGG ACGCGAACCA CGGAGCGTAG GTGGCCAGAT AGACCGCGAA CGGGATCAAC        480

CCCAGCGCAT ACCCGCTGGG AAGCACGTCA CGCCGCACTG TTCCCAGCCA CGGTCTTTGC        540

ACTTGGTATG AACGTCGCGC CGCCACGTCA ACGCCAGC                                578

(2) INFORMATION FOR SEQ ID NO: 219:

(i) SEQUENCE CHARACTERISTICS:
        (A) LENGTH: 484 base pa irs
        (B) TYPE: nucleic acid
        (C) STRANDEDNESS: sin gle
        (D) TOPOLOGY: linear (ii) MOLECULE TYPE: Genomic DNA (xi) SEQUENCE DESCRIPTION: SEQ ID NO: 219:

ACAACGATCG ATTGATATCG ATGAGAGACG GAGGAATCGT GGCCCTTCCC CAGTTGACCG         60

ACGAGCAGCG CGCGGCCGCG TTGGAGAAGG CTGCTGCCGC ACGTCGAGCG CGAGCAGAGC        120

TCAAGGATCG GCTCAAGCGT GGCGGCACCA ACCTCACCCA GGTCCTCAAG GACGCGGAGA        180

GCGATGAAGT CTTGGGCAAA ATGAAGGTGT CTGCGCTGCT TGAGGCCTTG CCAAAGGTGG        240

GCAAGGTCAA GGCGCAGGAG ATCATGACCG AGCTGGAAAT TGCGCCCCAC CCCGCCGCCT        300

TCGTGGCCTC GGTGACCGTC AGCGCAAGGC CCTGCTGGAA AAGTTCGGCT CCGCCTAACC        360

CCGCCGGCCG ACGATGCGGG CCGGAAGGCC TGTGGTGGGC GTACCCCGC ATACGGGGGA        420

GAAGCGGCCT GACAGGGCCA GCTCACAATT CAGGCCGAAC GCCCCGGTGG GGGGGAACCC        480

GCCC                                                                    484

(2) INFORMATION FOR SEQ ID NO: 220:

(i) SEQUENCE CHARACTERISTICS:
        (A) LENGTH: 537 base pa irs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 220:

AGGACTGGCA CCGCCAGCCA CCACATCGCG GGCGTGCCGA CCAGCATCTC GGCCTTGACG         60

CACGACTGTG CGCCGCAGCC TGCAACGTCT TGCTGGTCGA TGGCGTACAG CACCGGCCGC        120

AACGACATGG GCCAGGTCCA CGGTTTGGAT TCCCAAGGGT GGTAGTTGCC TGCGGAATTC        180

GTCAGGCCCG CGTGGAAGTG GAACGCTTTG GCGGTGTAGT GCCAGAGCGA GCGCACGGCG        240

TCGGGCAGCG GAACAACCGA GTTGCGACCG ACCGCTTGAC CGACCGCATG CCGATCGATC        300

GCGGTCTCGG ACGCGAACCA CGGAGCGTAG GTGGCCAGAT AGACCGCGAA CGGGATCAAC        360

CCCAGCGCAT ACCCGCTGGG AAGCACGTCA CGCCGCACTG TCCCCAGCCA CGGTCTTTGC        420

ACTTGGTACT GACGTCGCGC CGCCACGTCG AACGCCAGCG CCATCGCGCC GAAGAACAGC        480

ACGAAGTACA CGCCGGACCA CTTGGTGGCG CAAGCCAATC CCAAGCAGCA CCCCGGC          537

(2) INFORMATION FOR SEQ ID NO: 221:

(i) SEQUENCE CHARACTERISTICS:
```

```
          (A) LENGTH: 135 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 221:

Gly Gly Ala Ala Ala Gly Gln Gln Ser Asp Val His Pro Phe Ala Asn
  1               5                  10                  15

Leu Ile Ala Val Asp Asp Glu Arg Ala Glu Arg Arg Asp Asp Glu Glu
                20                  25                  30

Arg Gln Glu Ala Val Gln Arg Gly Pro Arg Gly Asp Glu Ala Asp
             35                  40                  45

Pro Val Ala Asp Gln Gln His Pro Gly Asp Gly Ala Asp Gln Cys Arg
         50                  55                  60

Pro Ala Asp Pro Pro His Asp Pro His His Gln Arg His Gln Asp His
 65                  70                  75                  80

Thr Gln Gln Gly Ala Gly Glu Pro Pro Ala Glu Ser Val Val Thr Glu
                 85                  90                  95

Asp Gly Leu Pro Asp Arg Asp Gln Leu Leu Thr Asp Arg Arg Val Asn
                100                 105                 110

His Gln Ala Val Pro Gly Val Val Phe His Pro Met Val Val Gln His
             115                 120                 125

Leu Pro Gly Leu Ala Val Arg
            130             135

(2) INFORMATION FOR SEQ ID NO: 222:

(i) SEQUENCE CHARACTERISTICS:
          (A) LENGTH: 156 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 222:

Gln Lys Tyr Gly Gly Ser Ser Val Ala Asp Ala Glu Arg Ile Arg Arg
  1               5                  10                  15

Val Ala Glu Arg Ile Val Ala Thr Lys Lys Gln Gly Asn Asp Val Val
                 20                  25                  30

Val Val Val Ser Ala Met Gly Asp Thr Thr Asp Asp Leu Leu Asp Leu
                 35                  40                  45

Ala Gln Gln Val Cys Pro Ala Pro Pro Arg Glu Leu Asp Met Leu
 50                  55                  60

Leu Thr Ala Gly Glu Arg Ile Ser Asn Ala Leu Val Ala Met Ala Ile
 65                  70                  75                  80

Glu Ser Leu Gly Ala His Ala Arg Ser Phe Thr Gly Ser Gln Ala Gly
                 85                  90                  95

Val Ile Thr Thr Gly Thr His Gly Asn Ala Lys Ile Ile Asp Val Thr
                100                 105                 110

Pro Gly Arg Leu Gln Thr Ala Leu Glu Glu Gly Arg Val Val Leu Val
             115                 120                 125

Ala Gly Phe Gln Gly Val Ser Gln Asp Thr Lys Asp Val Thr Thr Leu
             130                 135                 140

Gly Arg Gly Gly Ser Asp Thr Thr Ala Val Ala Met
145                 150                 155
```

(2) INFORMATION FOR SEQ ID NO: 223:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 223:

Pro Ala Tyr Pro Ala Gly Thr Asn Asn Asp Arg Leu Ile Ser Met Arg
 1               5                  10                  15

Asp Gly Gly Ile Val Ala Leu Pro Gln Leu Thr Asp Glu Gln Arg Ala
            20                  25                  30

Ala Ala Leu Glu Lys Ala Ala Ala Arg Arg Ala Arg Ala Glu Leu
        35                  40                  45

Lys Asp Arg Leu Lys Arg Gly Gly Thr Asn Leu Thr Gln Val Leu Lys
 50                  55                  60

Asp Ala Glu Ser Asp Glu Val Leu Gly Lys Met Lys Val Ser Ala Leu
65                  70                  75                  80

Leu Glu Ala Leu Pro Lys Val Gly Lys Val Gln Ala
                85                  90

(2) INFORMATION FOR SEQ ID NO: 224:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 224:

Thr Val Glu Leu Asp Glu Pro Leu Val Glu Val Ser Thr Asp Lys Val
 1               5                  10                  15

Asp Thr Glu Ile Pro Ser Pro Ala Ala Gly Val Leu Thr Lys Ile Ile
            20                  25                  30

Ala Gln Glu Asp Asp Thr Val Glu Val Gly Gly Glu Leu Ser Val Ile
        35                  40                  45

Gly Asp Ala His Asp Ala Gly Glu Ala Ala Val Pro Ala Pro Gln Lys
 50                  55                  60

Val Ser Ala Gly Pro Thr Arg Ile
65                  70

(2) INFORMATION FOR SEQ ID NO: 225:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 225:

Ala Ala Asp Ile Gly Ala Ala Pro Ala Pro Lys Pro Ala Pro Lys Pro
 1               5                  10                  15

Val Pro Glu Pro Ala Pro Thr Pro Lys Ala Glu Pro Ala Pro Ser Pro
            20                  25                  30

Pro Ala Ala Gln Pro Ala Gly Ala Ala Glu Gly Ala Pro Tyr Val Thr

```
               35                  40                  45
Pro Leu Val Arg Lys Leu Ala Ser Glu Asn Asn Ile Asp Leu Ala Gly
        50                  55                  60

Val Thr Gly Thr Gly Val Gly Gly Arg Ile Arg Lys Gln Asp Val Leu
 65                  70                  75                  80

Ala Ala Ala Glu Gln Lys Lys Arg Ala Lys Ala Pro Ala Pro Ala Ala
                85                  90                  95

Gln Ala Ala Ala Ala Pro Ala Pro Lys Ala Pro Pro Glu Asp Pro Met
                100                 105                 110

Pro (2) INFORMATION FOR SEQ ID NO: 226:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 226:

Val Leu Val Ser Ile Ser Ala Asp Glu Asp Ala Thr Val Pro Val Gly
 1               5                  10                  15

Gly Glu Leu Ala Arg Ile Gly Val Ala Ala Asp Ile Gly Ala Ala Pro
                20                  25                  30

Ala Pro Lys Pro Ala Pro Lys Pro Val Pro Glu Pro Ala Pro Thr Pro
                35                  40                  45

Lys Ala Glu Pro Ala Pro Ser Pro Pro Ala Ala Gln Pro Ala Gly Ala
        50                  55                  60

Ala Glu Gly Ala Pro Tyr Val Thr Pro Leu Val Arg Lys Leu Ala Ser
 65                  70                  75                  80

Glu Asn Asn Ile Asp Leu Ala Gly Val Thr Gly Thr Gly Val Gly Gly
                85                  90                  95

Arg Ile Arg Lys Gln Asp Val Leu Ala Ala Ala Glu Gln Lys Lys Arg
                100                 105                 110

Ala Lys Ala Pro Ala Pro
        115

(2) INFORMATION FOR SEQ ID NO: 227:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 227:

Asp Pro Lys Val Gln Ile Gln Gln Ala Ile Glu Glu Ala Gln Arg Thr
 1               5                  10                  15

His Gln Ala Leu Thr Gln Gln Ala Ala Gln Val Ile Gly Asn Gln Arg
                20                  25                  30

Gln Leu Glu Met Arg Leu Asn Arg Gln Leu Ala Asp Ile Glu Lys Leu
        35                  40                  45

Gln Val Asn Val Arg Gln Ala Leu Thr Leu Ala Asp Gln Ala Thr Ala
        50                  55                  60

Ala Gly Asp Ala Ala Lys Ala Thr Glu Tyr Asn Asn Ala Ala Glu Ala
```

```
                 65                  70                  75                  80
Phe Ala Ala Gln Leu Val Thr Ala Glu Gln Ser Val Glu Asp Leu Lys
                 85                  90                  95

Thr Leu His Asp Gln Ala Leu Ser Ala Ala Gln Ala Lys Lys Ala
                100                 105                 110

Val Glu Arg Asn Ala Met Val Leu Gln Gln Lys Ile Ala Glu Arg Thr
                115                 120                 125

Lys Leu Leu Ser Gln Leu Glu Gln Ala Lys Met Gln Glu Gln Val Ser
        130                 135                 140

Ala Ser Leu Arg Ser Met Ser Glu Leu Ala Ala Pro Gly Asn Thr Pro
145                 150                 155                 160

Ser Leu Asp Glu Val Arg Asp Lys Ile Glu Arg Arg Tyr Ala Asn Ala
                165                 170                 175

Ile Gly Ser Ala Glu Leu Ala Glu Ser
                180                 185
```

(2) INFORMATION FOR SEQ ID NO: 228:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 228:

```
Val Ser Thr Ser Thr Trp Val Pro His Pro Val Arg Asp Arg Val Ile
 1               5                  10                  15

Gly Gln Arg Trp Thr Cys Ala Asp Arg Arg Ser Ile Glu Glu Ser Thr
                20                  25                  30

Glu Met Ala Phe Ser Val Gln Met Pro Ala Leu Gly Glu Ser Val Thr
                35                  40                  45

Glu Gly Thr Val Thr Arg Trp Leu Lys Gln Glu Gly Asp Thr Val Glu
        50                  55                  60

Leu Asp Glu Pro Leu Val Glu
65                  70
```

(2) INFORMATION FOR SEQ ID NO: 229:

(i) SEQUENCE CHARACTERISTICS:
        (A) LENGTH: 182 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 229:

```
Glu Val His Leu Pro Val Asp Val Gly Glu Pro Arg Gln Pro Thr Gly
 1               5                  10                  15

Ala Val Ala Asp Gln Asp His Arg Ile Thr Pro Val Pro Ala His Lys
                20                  25                  30

His Thr Pro Pro Arg Val Cys Gln Asp Trp His Arg Gln Pro Pro His
                35                  40                  45

Arg Gly Arg Ala Asp Gln His Leu Gly Leu Asp Ala Arg Leu Cys Ala
        50                  55                  60

Ala Ala Cys Asn Val Leu Leu Val Asp Gly Val Gln His Arg Pro Gln
65                  70                  75                  80
```

```
Arg His Gly Pro Gly Pro Arg Phe Gly Phe Pro Arg Val Val Val Ala
                85                  90                  95

Cys Gly Ile Arg Gln Ala Arg Val Glu Val Glu Arg Phe Gly Gly Val
            100                 105                 110

Leu Pro Glu Arg Ala His Gly Val Gly Gln Arg Asn Asn Arg Val Ala
            115                 120                 125

Thr Asp Arg Leu Thr Asp Arg Met Pro Ile Asp Arg Gly Leu Gly Arg
130                 135                 140

Glu Pro Arg Ser Val Gly Gly Gln Ile Asp Arg Glu Arg Asp Gln Pro
145                 150                 155                 160

Gln Arg Ile Pro Ala Gly Lys His Val Thr Pro His Cys Ser Gln Pro
                165                 170                 175

Arg Ser Leu His Leu Val
            180
```

(2) INFORMATION FOR SEQ ID NO: 230:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 230:

```
Asn Asp Arg Leu Ile Ser Met Arg Asp Gly Gly Ile Val Ala Leu Pro
1               5                   10                  15

Gln Leu Thr Asp Glu Gln Arg Ala Ala Ala Leu Glu Lys Ala Ala Ala
            20                  25                  30

Ala Arg Arg Ala Arg Ala Glu Leu Lys Asp Arg Leu Lys Arg Gly Gly
            35                  40                  45

Thr Asn Leu Thr Gln Val Leu Lys Asp Ala Glu Ser Asp Glu Val Leu
50                  55                  60

Gly Lys Met Lys Val Ser Ala Leu Leu Glu Ala Leu Pro Lys Val Gly
65                  70                  75                  80

Lys Val Lys Ala Gln Glu Ile Met Thr Glu Leu Glu Ile Ala Pro His
                85                  90                  95

Pro Ala Ala Phe Val Ala Ser Val Thr Val Ser Ala Arg Pro Cys Trp
            100                 105                 110

Lys Ser Ser Ala Pro Pro Asn Pro Ala Gly Arg Arg Cys Gly Pro Glu
            115                 120                 125

Gly Leu Trp Trp Ala Tyr Pro Arg Ile Arg Gly Arg Ser Gly Leu Thr
130                 135                 140

Gly Pro Ala His Asn Ser Gly Arg Thr Pro Arg Trp Gly Gly Thr Arg
145                 150                 155                 160
```

(2) INFORMATION FOR SEQ ID NO: 231:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 231:

```
Asp Trp His Arg Gln Pro Pro His Arg Gly Arg Ala Asp Gln His Leu
1               5                   10                  15
```

```
Gly Leu Asp Ala Arg Leu Cys Ala Ala Cys Asn Val Leu Leu Val
             20                  25                  30

Asp Gly Val Gln His Arg Pro Gln Arg His Gly Pro Gly Arg Phe
             35                  40                  45

Gly Phe Pro Arg Val Val Ala Cys Gly Ile Arg Gln Ala Arg Val
             50                  55                  60

Glu Val Glu Arg Phe Gly Gly Val Pro Glu Arg Ala His Gly Val
 65                  70                  75                  80

Gly Gln Arg Asn Asn Arg Val Ala Thr Asp Arg Leu Thr Asp Arg Met
                 85                  90                  95

Pro Ile Asp Arg Gly Leu Gly Arg Glu Pro Arg Ser Val Gly Gly Gln
                100                 105                 110

Ile Asp Arg Glu Arg Asp Gln Pro Gln Arg Ile Pro Ala Gly Lys His
                115                 120                 125

Val Thr Pro His Cys Pro Gln Pro Arg Ser Leu His Leu Val Leu Thr
                130                 135                 140

Ser Arg Arg His Val Glu Arg Gln Arg His Arg Ala Glu Gln His
145                 150                 155                 160

Glu Val His Ala Gly Pro Leu Gly Gly Ala Ser Gln Ser Gln Ala Ala
                165                 170                 175

Pro Arg
```

(2) INFORMATION FOR SEQ ID NO: 232:

(i) SEQUENCE CHARACTERISTICS:
        (A) LENGTH: 271 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 232:

```
ATGCCAAGCC GGTGCTGATG CCCGAGCTCG GCGAATCGGT GACCGAGGGG ACCGTCATTC    60

GTTGGCTGAA GAAGATCGGG GATTCGGTTC AGGTTGACGA GCCACTCGTG GAGGTGTCCA   120

CCGACAAGGT GGACACCGAG ATCCCGTCCC CGGTGGCTGG GGTCTTGGTC AGTATCAGCG   180

CCGACGAGGA CGCCACGGTG CCCGTCGGCG GCGAGTTGGC CCGGATCGGT GTCGCTGCCG   240

AGATCGGCGC CGCGCCCGCC CCCAAGCCCC C                                  271
```

(2) INFORMATION FOR SEQ ID NO: 233:

(i) SEQUENCE CHARACTERISTICS:
        (A) LENGTH: 89 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 233:

```
Ala Lys Pro Val Leu Met Pro Glu Leu Gly Glu Ser Val Thr Glu Gly
 1               5                  10                  15

Thr Val Ile Arg Trp Leu Lys Lys Ile Gly Asp Ser Val Gln Val Asp
             20                  25                  30

Glu Pro Leu Val Glu Val Ser Thr Asp Lys Val Asp Thr Glu Ile Pro
             35                  40                  45

Ser Pro Val Ala Gly Val Leu Val Ser Ile Ser Ala Asp Glu Asp Ala
```

```
                50                   55                  60
Thr Val Pro Val Gly Gly Glu Leu Ala Arg Ile Gly Val Ala Ala Glu
65                  70                  75                  80

Ile Gly Ala Ala Pro Ala Pro Lys Pro
                85
```

(2) INFORMATION FOR SEQ ID NO: 234:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 234:

```
GAGGTAGCGG ATGGCCGGAG GAGCACCCCA GGACCGCGCC CGAACCGCGG GTGCCGGTCA    60

TCGATATGTG GGCACCGTTC GTTCCGTCCG CCGAGGTCAT TGACGAT               107
```

(2) INFORMATION FOR SEQ ID NO: 235:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 235:

```
ATGAAGTTGA AGTTTGCTCG CCTGAGTACT GCGATACTGG GTTGTGCAGC GGCGCTTGTG    60

TTTCCTGCCT CGGTTGCCAG CGCAGATCCA CCTGACCCGC ATCAGCCGGA CATGACGAAA   120

GGCTATTGCC CGGGTGGCCG ATGGGGTTTT GGCGACTTGG CCGTGTGCGA CGGCGAGAAG   180

TACCCCGACG GCTCGTTTTG GCACCAGTGG ATGCAAACGT GGTTTACCGG CCCACAGTTT   240

TACTTCGATT GTGTCAGCGG CGGTGAGCCC CTCCCCGGCC CGCCGCCACC GGGTGGTTGC   300

GGTGGGGCAA TTCCGTCCGA GCAGCCCAAC GCTCCCTGA                         339
```

(2) INFORMATION FOR SEQ ID NO: 236:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 236:

```
Met Lys Leu Lys Phe Ala Arg Leu Ser Thr Ala Ile Leu Gly Cys Ala
1               5                   10                  15

Ala Ala Leu Val Phe Pro Ala Ser Val Ala Ser Ala Asp Pro Pro Asp
                20                  25                  30

Pro His Gln Pro Asp Met Thr Lys Gly Tyr Cys Pro Gly Gly Arg Trp
            35                  40                  45

Gly Phe Gly Asp Leu Ala Val Cys Asp Gly Glu Lys Tyr Pro Asp Gly
        50                  55                  60

Ser Phe Trp His Gln Trp Met Gln Thr Trp Phe Thr Gly Pro Gln Phe
65                  70                  75                  80

Tyr Phe Asp Cys Val Ser Gly Gly Glu Pro Leu Pro Gly Pro Pro Pro
```

```
                85              90              95
Pro Gly Gly Cys Gly Gly Ala Ile Pro Ser Glu Gln Pro Asn Ala Pro
            100             105             110
```

(2) INFORMATION FOR SEQ ID NO: 237:

(i) SEQUENCE CHARACTERISTICS:
        (A) LENGTH: 371 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 237:

```
GTGACCACGG TGGGCCTGCC ACCAACCCGG GCAGCGGCAG CCGCGGCGGC GCCGGCGGCT      60

CCGGCGGCAA CGGTGGCGCC GGGGGTAACG CCACCGGCTC AGGCGGCAAG GGCGGCGCCG     120

GTGGCAATGG CGGTGATGGG AGCTTCGGCG CTACCAGCGG CCCCGCCTCC ATCGGGTCA      180

CGGGCGCCCC CGGCGGCAAC GGCGGCAAGG GCGGCGCCGG TGGCAGCAAC CCCAACGGCT     240

CAGGTGGCGA CGGCGGCAAA GGCGGCAACG GCGGTGCCGG CGGCAACGGG GGCTCGATCG     300

GCGCCAACAG CGGCATCGTC GGCGGTTCCG GTGGGGCCGG TGGCGCTGGC GGCGCCGGCG     360

GAAACGGCAG C                                                         371
```

(2) INFORMATION FOR SEQ ID NO: 238:

(i) SEQUENCE CHARACTERISTICS:
        (A) LENGTH: 424 base pa irs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 238:

```
GTCCGGGTCC CACCACCGCG CCGGCGCGCC CCTAGCGGCC GGGCGCACCA GCCCCTTTTC      60

TTGACTCGTT CAAGAAAAGG GCCTTCTGTT TGGTCGGCCA TGTTGGCATG ATCGTGACCC     120

ATGGGCAACA TCGACGTCGA CATCTCGGCC AAGGTCTAGC TCCATGCGAA TCGCCGCCGC     180

GGTGGTGAGC ATCGGTCTAG CCGTCATAGC AGGGTTCGCG GTACCTGTTG CCGACGCACA     240

CCCGTCGGAG CCCGGGGTTG TGTCCTACGC GGTGCTCGGA AAGGGGTCGG TCGGCAACAT     300

CGTCGGCGCC CCAATGGGGT GGGAGGCGGT GTTCACCAAG CCGTTCCAGG CGTTTTGGGT     360

CGAACTACCG GCGTGCAACA ACTGGGTGGA CATCGGGCTG CCCGAGGTGT ACGACGATCC     420

CGAC                                                                 424
```

(2) INFORMATION FOR SEQ ID NO: 239:

(i) SEQUENCE CHARACTERISTICS:
        (A) LENGTH: 317 base pa irs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 239:

```
GCGATGGCGG CCGCGGGTAC CACCGCCAAT GTGGAACGGT TTCCCAACCC CAACGATCCT      60

TTGCATCTGG CGTCAATTGA CTTCAGCCCG GCCGATTTCG TCACCGAGGG CCACCGTCTA     120

AGGGCGGATG CGATCCTACT GCGCCGTACC GACCGGCTGC CTTTCGCCGA GCCGCCGGAT     180
```

```
TGGGACTTGG TGGAGTCGCA GTTGCGCACG ACCGTCACCG CCGACACGGT GCGCATCGAC      240

GTCATCGCCG ACGATATGCG TCCCGAACTG GCGGCGGCGT CCAAACTCAC CGAATCGCTG      300

CGGCTCTACG ATTCGTC                                                    317

(2) INFORMATION FOR SEQ ID NO: 240:

(i) SEQUENCE CHARACTERISTICS:
        (A) LENGTH: 422 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 240:

TGGCGTATGC GCTTCGCAGC CGGTGCCGCG TCAACGCGCC GGAGGCAATC GCTTCGCTGC       60

CGAGGAATGG TTCGATCACG ATCGCAGTGT GCCGTCGTGC ACCGACACCG CCGTCCAACG      120

TGAACTGAGG GCGGAAAATC GGCCGAAATC TCGCCCTCAG TTCACGCTCG GCGCCTAACG      180

GTTCTGGAAG TTGGGTGCGC GCTTCTCGGC GAACGCGCGC GGGCCTTCCT TGGCGTCGTC      240

GGACAGGAAG ACCTTGATGC CGATCTGGGT GTCGATCTTG AACGCCTCGT TTTCGGGCAT      300

GCACTCGGTC TCGCGGATGG ACCGCAAGAT GGCCTGCACG GCCAGGGGTC CGTTAGCCGA      360

GATGGCGTCG GCAAGTTCTA GAACCTTGGT CAACGCCTGG CCGTCGGGCA CACGTGGCCG      420

AT                                                                    422

(2) INFORMATION FOR SEQ ID NO: 241:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 241:

GCGTGCCGCT GAACACCAGC CCGCGGCTGC CAGATCTCCC GGACTCGGTA GTGCCGCCGG       60

TGGCGTCGTT GCTCTCCTGA CGGGGCGCGG CGACCATAAG GTCGCTAATG CCCAGGTAGC      120

GGCCCAGGTG CATGGAGTCG ATGATGATGC GACTCTCCAG CTCGCCGACC GGGAGCTTGG      180

CATCGGGCCT GATCAGCCAG GACGCGTAGG ACAAGTCGAT CGAATGCATA GTGGCCTCCA      240

GAGTGGCCGT GCCACTTCCG GCGTGCTCCA CGGCAAATGC CTTGATTTCT AGCTCCGCGT      300

AGTGTTCCCG CATCGCCTGC GGGATGAATG GGAACCGCAG GATGGCGACA AACGGGTCTG      360

ACCTCAGGTT TGCCGCTTTG CGCACAGTGG TCGACAGCCG GTACTCGGCA TAAATGCTGG      420

CCCCGA                                                                426

(2) INFORMATION FOR SEQ ID NO: 242:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 242:

AGACCGGCGA GGGTGTGGTC GCTGCCCGCG GCATTGTCGA TAATCTGCGC TGGGTCGACG       60
```

```
CGCCGATCAA CTAGTGAGGC GCAACGCTAG GCTTTGGGAT ACCCACAGCT AAAAAGTTTA      120

TCAAAGAAAC GAAGAAGGTT GCCATGAGCA CTGTTGCCGC CTACGCCGCC ATGTCGGCGA      180

CCGAACCCCT GACCAAGACC ACGATCACCC GTCGCGACCC GGGCCCGCAC GACATGGCGA      240

TCGACATCAA ATTCGCCGGA ATCTGTCGCT CGGACATCCA TACCGTCCAA ACCGAATGGG      300

GGCAACCGAA TTTACCTGTG GTCCCTG                                          327
```

(2) INFORMATION FOR SEQ ID NO: 243:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 243:

```
Asp His Gly Gly Pro Ala Thr Asn Pro Gly Ser Gly Ser Arg Gly Gly
 1               5                  10                  15

Ala Gly Gly Ser Gly Gly Asn Gly Gly Ala Gly Asn Ala Thr Gly
            20                  25                  30

Ser Gly Gly Lys Gly Gly Ala Gly Gly Asn Gly Asp Gly Ser Phe
        35                  40                  45

Gly Ala Thr Ser Gly Pro Ala Ser Ile Gly Val Thr Gly Ala Pro Gly
 50                  55                  60

Gly Asn Gly Gly Lys Gly Gly Ala Gly Gly Ser Asn Pro Asn Gly Ser
 65                  70                  75                  80

Gly Gly Asp Gly Gly Lys Gly Gly Asn Gly Ala Gly Gly Asn Gly
            85                  90                  95

Gly Ser Ile Gly Ala Asn Ser Gly Ile Val Gly Gly Ser Gly Gly Ala
                100                 105                 110

Gly Gly Ala Gly Gly Ala Gly Gly Asn Gly Ser
            115                 120
```

(2) INFORMATION FOR SEQ ID NO: 244:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 244:

```
Met Ala Ala Ala Gly Thr Thr Ala Asn Val Glu Arg Phe Pro Asn Pro
 1               5                  10                  15

Asn Asp Pro Leu His Leu Ala Ser Ile Asp Phe Ser Pro Ala Asp Phe
            20                  25                  30

Val Thr Glu Gly His Arg Leu Arg Ala Asp Ala Ile Leu Leu Arg Arg
        35                  40                  45

Thr Asp Arg Leu Pro Phe Ala Glu Pro Pro Asp Trp Asp Leu Val Glu
 50                  55                  60

Ser Gln Leu Arg Thr Thr Val Thr Ala Asp Thr Val Arg Ile Asp Val
 65                  70                  75                  80

Ile Ala Asp Asp Met Arg Pro Glu Leu Ala Ala Ser Lys Leu Thr
            85                  90                  95
```

```
Glu Ser Leu Arg Leu Tyr Asp Ser
            100
```

(2) INFORMATION FOR SEQ ID NO: 245:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 245:

```
Ala Tyr Ala Leu Arg Ser Arg Cys Arg Val Asn Ala Pro Glu Ala Ile
 1               5                  10                  15

Ala Ser Leu Pro Arg Asn Gly Ser Ile Thr Ile Ala Val Cys Arg Arg
            20                  25                  30

Ala Pro Thr Pro Pro Ser Asn Val Asn
            35                  40
```

(2) INFORMATION FOR SEQ ID NO: 246:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 246:

```
Val Pro Leu Asn Thr Ser Pro Arg Leu Pro Asp Leu Pro Asp Ser Val
 1               5                  10                  15

Val Pro Pro Val Ala Ser Leu Leu Ser
            20                  25
```

(2) INFORMATION FOR SEQ ID NO: 247:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 247:

```
Met Ser Thr Val Ala Ala Tyr Ala Ala Met Ser Ala Thr Glu Pro Leu
 1               5                  10                  15

Thr Lys Thr Thr Ile Thr Arg Arg Asp Pro Gly Pro His Asp Met Ala
            20                  25                  30

Ile Asp Ile Lys Phe Ala Gly Ile Cys Arg Ser Asp Ile His Thr Val
            35                  40                  45

Gln Thr Glu Trp Gly Gln Pro Asn Leu Pro Val Val Pro
     50                  55                  60
```

(2) INFORMATION FOR SEQ ID NO: 248:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 248:

| | | | | | |
|---|---|---|---|---|---|
|GCTTGGAGCC|CTGGAGCGAC|GGTGTGGGTC|TGGGGGTCGA|TTCGTTCTCG|GCGAAAGTCA|60|
|ACTAAAGACC|ACGTTGACAC|CCAACCGGCG|GCCCGGCATG|GGCCGTCGCG|GCGTAGAAGC|120|
|TTTGACCGCG|GCGCGAAACG|TTCGCTGCTG|CGGCCCATGC|AGATCGCACA|CGCTTGCTTG|180|
|AACATCGGGT|GGAGCCGGTG|GTAACGCCAG|GCT| | |213|

(2) INFORMATION FOR SEQ ID NO: 249:

(i) SEQUENCE CHARACTERISTICS:
        (A) LENGTH: 367 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 249:

| | | | | | |
|---|---|---|---|---|---|
|CCGAGCTGCT|GTTCGGCGCC|GGCGGTGCGG|GCGGCGCGGG|TGGGGCGGGC|ACCGACGGCG|60|
|GGCCCGGTGC|TACCGGCGGG|ACCGGCGGAC|ACGGCGGAGT|CGGCGGCGAC|GGCGGATGGC|120|
|TGGCACCCGG|CGGGGCCGGC|GGGGCCGGCG|GGCAAGGCGG|GGCAGGTGGT|GCCCGCAGCG|180|
|ATGGTGGCGC|GTTGGGTGGT|ACCGGCGGGA|CGGGCGGTAC|CGGCGGCGCC|GGTGGCGCCG|240|
|GCGGTCGCGG|CACACTGCTG|CTGGGCGCTG|GCGGACAGGG|CGGCCTCGGC|GGCGCCGGCG|300|
|GACAAGGCGG|CACCGGCGGG|GGCCGGCGGA|GATGGCGTTC|TGGGGGGTGT|CAGTGGCACT|360|
|GGTGGTA| | | | | |367|

(2) INFORMATION FOR SEQ ID NO: 250:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 250:

| | | | | | |
|---|---|---|---|---|---|
|AAGGCGTGAT|TGGCAAGGCG|ACCGCGCAGC|GGCCCGTAGC|CGCGGGACGG|CCCAGGCCCC|60|
|GACCGCAGCG|GCCGGTGTCT|GACCGGGTCA|GCGACCAGCG|GCGCTGACCG|TGCCGCTCGT|120|
|CTACTTCGAC|GCCAGCGCCT|TCGTCAAACT|TCTCACCACC|GAGACAGGGA|GCTCGCTGGC|180|
|GTCCGCTCTA|TGGGACGGCT|GCGACGCCGC|ATTGTCCAAC|CGCCTGGCCT|ACCCCGAAGT|240|
|CCGCGCCGCA|CTCGCTGCAA|CGGGCCGCAA|TCACGACCTA|ACCGAATCCG|AGCTCGCCGA|300|
|CGCCGAGCGT|GACTGGGAGG|ACTTCTGGGC|CGCACCCGCC|CAGTCGAACT|CACCGCGACG|360|
|GTTGAACAGC|ACGCCGGGCA|CCTCGCCCGA|ACACATGCCT|TACGCGGAGC|CGACACCGTT|420|

(2) INFORMATION FOR SEQ ID NO: 251:

(i) SEQUENCE CHARACTERISTICS:
        (A) LENGTH: 299 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 251:

| | | | | | |
|---|---|---|---|---|---|
|CTCTTGTCGG|TGGCATCGGC|GGTACCGGCG|GAACCGGCGG|CAACGCCGGT|ATGCTCGCCG|60|

```
GCGCCGCCGG GGCCGGCGGT GCCGGCGGGT TCAGCTTCAG CACTGCCGGT GGGGCTGGCG      120

GCGCCGGCGG GGCCGGTGGG CTGTTCACCA CCGGCGGTGT CGGCGGCGCC GGTGGGCAGG      180

GTCACACGGG CGGGGCGGGC GGCGCCGGCG GGGCCGGCGG GTTGTTTGGT GCCGGCGGCA      240

TGGGCGGGGC GGGCGGATTC GGGGATCACG GAACGCTCGG CACCGGCGGG GCCGGCGGG       299
```

(2) INFORMATION FOR SEQ ID NO: 252:

(i) SEQUENCE CHARACTERISTICS:
  (A) LENGTH: 20 amino ac ids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO: 252:

```
Leu Glu Pro Trp Ser Asp Gly Val Gly Leu Gly Val Asp Ser Phe Ser
 1               5                  10                  15

Ala Lys Val Asn
            20
```

(2) INFORMATION FOR SEQ ID NO: 253:

(i) SEQUENCE CHARACTERISTICS:
  (A) LENGTH: 121 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO: 253:

```
Glu Leu Leu Phe Gly Ala Gly Gly Ala Gly Gly Ala Gly Gly Ala Gly
 1               5                  10                  15

Thr Asp Gly Gly Pro Gly Ala Thr Gly Gly Thr Gly Gly His Gly Gly
            20                  25                  30

Val Gly Gly Asp Gly Gly Trp Leu Ala Pro Gly Ala Gly Gly Ala
        35                  40                  45

Gly Gly Gln Gly Gly Ala Gly Gly Ala Arg Ser Asp Gly Gly Ala Leu
    50                  55                  60

Gly Gly Thr Gly Gly Thr Gly Gly Thr Gly Gly Ala Gly Gly Ala Gly
65                  70                  75                  80

Gly Arg Gly Thr Leu Leu Leu Gly Ala Gly Gly Gln Gly Gly Leu Gly
                85                  90                  95

Gly Ala Gly Gly Gln Gly Gly Thr Gly Gly Gly Arg Arg Arg Trp Arg
            100                 105                 110

Ser Gly Gly Cys Gln Trp His Trp Trp
        115                 120
```

(2) INFORMATION FOR SEQ ID NO: 254:

(i) SEQUENCE CHARACTERISTICS:
  (A) LENGTH: 34 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO: 254:

Gly Val Ile Gly Lys Ala Thr Ala Gln Arg Pro Val Ala Ala Gly Arg

```
                1               5              10              15
Pro Arg Pro Arg Pro Gln Arg Pro Val Ser Asp Arg Val Ser Asp Gln
               20              25              30
Arg Arg
```

(2) INFORMATION FOR SEQ ID NO: 255:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 255:

```
Leu Val Gly Gly Ile Gly Gly Thr Gly Gly Thr Gly Gly Asn Ala Gly
 1               5              10              15

Met Leu Ala Gly Ala Ala Gly Ala Gly Gly Ala Gly Gly Phe Ser Phe
               20              25              30

Ser Thr Ala Gly Gly Ala Gly Gly Ala Gly Gly Ala Gly Gly Leu Phe
           35              40              45

Thr Thr Gly Gly Val Gly Gly Ala Gly Gln Gly His Thr Gly Gly
       50              55              60

Ala Gly Gly Ala Gly Gly Ala Gly Gly Leu Phe Gly Ala Gly Gly Met
65              70              75              80

Gly Gly Ala Gly Gly Phe Gly Asp His Gly Thr Leu Gly Thr Gly Gly
               85              90              95

Ala Gly Gly
```

(2) INFORMATION FOR SEQ ID NO: 256:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 256:

```
TCCTGTTCGG CGCCGGCGGG GTGGGCGGTG TTGGCGGTGA CGGTGTGGCA TTCCTGGGCA    60

CCGCCCCCGG CGGGCCCGGT GGTGCCGGCG GGGCCGGTGG GCTGTTCAGC GTCGGTGGGG   120

CCGGCGGCGC CGGCGGAATC GGATTGGTCG GAACAGCGG  TGCCGGGGGG TCCGGCGGGT   180

CCGCCCTGCT CTGGGGCGAC GGCGGTGCCG GCGGCGCGGG TGGGGTCGGG TCCACTACCG   240

GCGGTGCCGG CGGGGCGGGC GGCAACGCCA GCCTGCTGGT AA                     282
```

(2) INFORMATION FOR SEQ ID NO: 257:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 257:

```
CGGCACGAGC CGTGCTACTG GTCAACTGAT GCCCTGATTG TGACCTTCCC GGCGCCGGAT    60

CAGTGCTTCT CAGGACCGAC GTAATATTCG AAAACCAATC CGGCCGCCGA GGCGAGGATG   120
```

```
AATGCCACAC CGGCGGCGAT CAGCCACGGG AGCCACAACG CGATGCCGAC CGCTGCCACC       180

GAGCCGGACA ACGCGACCAT GATCGGCCAC CAGCTATGCG GACTGAAGAA TCCAAGTTCT       240

CCTGCGCCGT CGCTGATTTC AGCGCCTTCG TAGTCCTCGG GCCGGGAATC TAACCGGCGG       300

GCCACAAACC GGAAGAAGGT GGCGACGATC AACGCCATGC CGCCGGTGAG CGCCAACGCA       360

ATGGTGCCAG CCCACTCGAC ACCACCGGTG GCGAACATCG AGGTCAACAC GCCGT           415

(2) INFORMATION FOR SEQ ID NO: 258:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 258:

TCACCGCGTG AACGGTTCGT AACACTGATA CGTATGCTTG TCAGCGAGCA GATCAAGTCC       60

AGTCCGACCA ATGCCAGGAG ATCATCGGCT AGGCTCACGG TTTCGCCTGG GACGAGACGG      120

TATTGAGTTC TGGCGTTGGA CGGTCCGTGG CGTGGTGGGA AGTCTGACGC GGCATCAGAA      180

CGGTTGTCAA TACCAGTCTT TGGGGGATAT GGCCTATTTG GTGTCGTCGG GCCGCTCCAC      240

CGGATCCCTT TTCGAACGTT GCGCAAGCGC GGTCCAGTTA CGGCCTGTTC ACTGCGCGCT      300

GGCGTAGCTG CGCGGCCTCG ATCGGTTTGA ACGTCATCGC AATTCCCGCA ATGGGTGAGT      360

ACCTGACGCT CCT                                                         373

(2) INFORMATION FOR SEQ ID NO: 259:

(i) SEQUENCE CHARACTERISTICS:
        (A) LENGTH: 423 base pa irs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 259:

CCAAACCGGA CAGGCCGGCA GCGACGGTCG GAAGTTGCAC CACGGTGCGC GCTCCATGTA       60

GCCAACCGGT GACCACGGCG TAGACAGCAG ATCCGTGGAT CGCGCGTTCG GTGTCGTCCG      120

GGCCGAGTAC CCGCGGGCCG AACCGCAGCG ACCAAAGCAA CGCGATCGAT ACGGGGATCG      180

CCACTCGTGC CGAATTCGAG CTCCGTCGAC AAGCTTGCGG CCGCACTCGA ACCCGGGTGA      240

ATGATTGAGT TTAAACCGCT TAGCAATAAC TAGCATAACC CCTTGGGGCC TCTAAACGGG      300

TCTTGAGGGG TTTTTTGCTG AAAGGAGGAA CTATATCCGG ATAACCTGGC GTAGTAGCGA      360

AGAGGCCCGC ACCGATCGCC CTTCCCAACA GTTGCGCAGC CTGAATGGCG AATGGACGCG      420

CCC                                                                    423

(2) INFORMATION FOR SEQ ID NO: 260:

(i) SEQUENCE CHARACTERISTICS:
        (A) LENGTH: 404 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 260:
```

```
AGTGGCCAGC CGGTCGGCCA ATGCATCCAG CTCCCGGTAC GTCAGCTGAC CATCCGCCCA      60

ACTGACCGCC ACCGAGTCAG GCTGTGCCGC AGCGATTTCG GCGAACCGGG TATGCACCGC     120

GGGTGCCGAC GTCGTCACAT CCGGCAGGCC GGGTGCGGTC GGATCGTGCT CGCCGTCCAG     180

CAGAATGTCG ACGTCGCGCA GCGGCCGATC CCACCGGCTG ACCAAGCGCT GTAACACAGC     240

CAGCACCCGC CTGCCGAGGC TTTCGGGCGC CATCGTGCCC AGCGCACCGT CGAGCACCTC     300

CACTAGCAGC GTGAGCTCAC CGGTGCTGCG GTGCGCGGCG ACGGTCACCG GAAAGTGCGA     360

CAAACTCTCT AGCGCCACCG GACGGAACGT CACCCCGTTT GCGA                     404

(2) INFORMATION FOR SEQ ID NO: 261:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 261:

GTCCTGGTCG CAGGCTGTTC TTCGAACCCG CTGGCTAACT TCGCACCCGG GTATCCGCCC      60

ACCATCGAAC CGCCCAACC GGCGGTGTCA CCGCCTACTT CGCAAGACCC GGCCGGTGCA     120

GTGCGACCAC TGAGCGGCCA CCCCCGGGCG GCACTATTCG ACAACGGCAC CCGCCAATTG     180

GTGGCTCTGC GCCCGGGCGC CGATTCGGCG GCACCCGCCA GCATCATGGT CTTCGATGAC     240

ATGCACGTTG CACCGCGCGT CATTTTTCTG CCGGGCCCGG CAGCCGCGTT GACCAGCGAC     300

GACCACGGCA CGGCCTTCCT TGCCGCCCGC GGCGGCTACT TCGTGGCCGA CCTGTCCTCC     360

GGTCACACCG CACGAGTGAA TGTCGCTGAC GCAGCGCACA CCGATTTCAC CGCGATCGCC     420

C                                                                     421

(2) INFORMATION FOR SEQ ID NO: 262:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 262:

ATGCATATCA CGCTCAACGC CATCCTGCGT GCGATCTTCG GGGCCGGCGG CAGTGAACTA      60

GACGAGCTGC GCCGCCTCAT TCCGCCGTGG GTCACGCTGG GCTCGCGCCT GGCGGCGCTA     120

CCGAAACCCA AACGCGACTA TGGCCGCCTT AGCCCGTGGG GCCGGCTGGC CGAGTGGCGG     180

CGCCAGTACG ACACTGTCAT CGACGAGCTC ATCAAGCCG AGCGGGCCGA CCCGAACTTC     240

GCCGATCGGA CCGACGTTTT GGCGTTGATG CTGCGCAGCA CTTACGACGA CGGTTCCATC     300

ATGTCGCGCA AGGACATTGG CGACGAACTG CTCACGCTGC TTGCCGCCGG GCACGAAACC     360

ACGGCGGCGA CATGGGCTGG GCGTTCGAAC GGCTCAACCG GCACCCCGAC GTGCTCGCGG     420

CTCTGG                                                                426

(2) INFORMATION FOR SEQ ID NO: 263:

(i) SEQUENCE CHARACTERISTICS:
        (A) LENGTH: 522 base pairs
        (B) TYPE: nucleic acid
```

(C) STRANDEDNESS: single
        (D) TOPOLOGY: linear (ii) MOLECULE TYPE: cDNA (xi) SEQUENCE DESCRIPTION: SEQ ID NO: 263:

GTCCTGGTCG CAGGCTGTTC TTCGAACCCG CTGGCTAACT TCGCACCCGG GTATCCGCCC    60

ACCATCGAAC CCGCCCAACC GGCGGTGTCA CCGCCTACTT CGCAAGACCC GGCCGGTGCA   120

GTGCGACCAC TGAGCGGCCA CCCCCGGGCG GCACTATTCG ACAACGGCAC CCGCCAATTG   180

GTGGCTCTGC GCCCGGGCGC CGATTCGGCG GCACCCGCCA GCATCATGGT CTTCGATGAC   240

GTGCACGTTG CACCGCGCGT CATTTTTCTG CCGGGCCCGG CAGCCGCGTT GACCAGCGAC   300

GACCACGGCA CGGCCTTCCT TGCCGCCCGC GGCGGCTACT TCGTGGCCGA CCTGTCCTCC   360

GGTCACACCG CACGAGTGAA TGTCGCTGAC GCAGCGCACA CCGATTTCAC CGCGATCGCC   420

CGCCGCTCCG ACGGCAAGCT GGTGCTGGGC AGCGCAGATG GCGCCGTCTA CACGCTTGCC   480

AAGAACCCGC AGTTGACCGG CGTCGGCGCC GCCACCGTAG CC                      522

(2) INFORMATION FOR SEQ ID NO: 264:

(i) SEQUENCE CHARACTERISTICS:
        (A) LENGTH: 739 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 264:

GCTGGGGCGC ACCGCCGTCC GGCGGCCCCA GCCCCTGGGC CCAGACCCCG CGCAAAACCA    60

ACCCGTGGCC CTTAGTGGCC GGCGCCGCCG CCGTCGTGCT CGTCCTCGTG TTGGGCGCCA   120

TCGGCATCTG GATCGCCATC CGGCCCAAGC CGGTACAGCC GCCTCAGCCG GTTGCGGAGG   180

AGCGCCTTAG CGCCCTACTG CTGAACTCCT CAGAAGTCAA CGCCGTGATG GGCTCGTCGT   240

CCATGCAGCC GGGCAAACCG ATCACATCGA TGGACTCTTC GCCGGTGACG GTGTCCCTGC   300

CGGACTGCCA GGGCGCGCTG TATACCAGCC AGGATCCGGT GTATGCCGGC ACCGGCTACA   360

CCGCCATCAA CGGCTTGATT TCATCCGAGC CGGGCGACAA CTACGAACAT TGGGTGAACC   420

AAGCCGTCGT CGCCTTTCCG ACCGCCGACA AGCCCGCGC GTTCGTGCAG ACTTCGGCCG   480

ACAAATGGAA GAACTGCGCA GGCAAGACGG TCACCGTCAC GAATAAGGCC AAGACCTACC   540

GGTGGACGTT TGCCGACGTC AAAGGCAGCC CGCCGACGAT CACGGTGATA GACACCCAAG   600

AAGGCGCTGA GGGCTGGGAA TGCCAACGCG CGATGAGCGT GGCCAACAAT GTGGTTGTCG   660

ACGTCAACGC ATGCGGGTAC CAGATCACCA ATCAAGCAGG CCAGATCGCC GCCAAGATCT   720

GTTGACAAAG TCAACAAGG                                                739

(2) INFORMATION FOR SEQ ID NO: 265:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 265:

AGACGTCGTC GAGGCCGCCA TCGCCCGCGC CGAAGCCGTT AACCCGGCAC TGAACGCGTT    60

```
GGCGTATGC                                                                  69

(2) INFORMATION FOR SEQ ID NO: 266:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 266:

ACTGCACCCG GCAGGCGCGA CCAACGGATC GGGTCAACTA GCACTGCCGG TGGAGGCGCC       60

CCCGCGGTCT GTGCCTTCCC ACGGGGAACC CTTGGGCAGC GCGGCTCCAG AAGGGTTGGA      120

GGGAGAGTTC GACGACCGTA TCGACGAGCG GTTCCCGGTC TTCAGCTCGG CCAGTCTCGC      180

CGAAGCGCTG CCGGGTCCGC TGACCCCGAT GACGCTGGAT GTCCAGTTGA GTGGACTGCG      240

CGCGGCCGGT CGGGCGATGG GTCGGGTACT GGCGCTTGGC GGTGTCGTTG CCGATGAGTG      300

GGAGAGAAGA GCCATCGCGG TGTTCGGTCA CCGCCCGTAT ATCGGAGTGT CGGCCAATAT      360

TGTGGCCGCC GCCCAACTGC CGGGGTGGGA CGCGCAGGCC GTAACCCGGC GGGCACTGGG      420

CGAGCAACCG CAGGTCACTG AGCTGCTTCC GTTTGGTCGA CCGCAACTTG CGGGCGGACC      480

GCTCGGCTCG GTCGCGAAGG TGGTCGTGAC GGCACGGTCG CTG                        523

(2) INFORMATION FOR SEQ ID NO: 267:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 267:

GTGTCGGTGT CGTCGGGGTA GGAGCGACTT CCCCGGCCGG CGCCGGCGCC GGAGCGGGCT       60

CTGCAGGAAC CGGTGCCGGC GCCGGCGGCG GGGCGACCAA AGGCCGGATC GATTCGGCCA      120

GCGCCTTGGC CGCGCCCTTG TCCACCGGGT TGTTGGCGGT CCCGAGCCAT ACCACAAACC      180

AACGCTGAAG GGGCCCGGCG TCCGGTGCGT TCGCCGCGGG CGAC                       224

(2) INFORMATION FOR SEQ ID NO: 268:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 268:

TGAACTGACT GCCCCGCTCG ATCGGCGGCG GCGGCGTGTC ATAGCTGCGC CGCCAGGCCA       60

TGAACTGCTC TTCGCCATAG CGGGCCTTGG TCTCGGCCTT GTCCAAACCC TGCAGCGCGC      120

CGTAGTGGCG TTCGTTGAGC CGCCAGCTAC GCCGCACGGG AATCCAGAGC CGATCGGCGC      180

TGTCCAACGC CAGATGCGCG GTGGTGATCG CGCGCCGCAG CAACGAGGTG TAGAGCACGT      240

CGGGCAATAG GTCGTGTTCC GCGATCAGCT CGCCGCTTCG AACCGCCTCT GCCTGGCCCT      300

TGTCCGTCAG GCCGACATCG ACCCAGCCGG TGAACAGGTT GAGGGCATTC CAGTCGCTCT      360
```

```
CGCCGTGGCG CAGCAACACC AGGCTGCCAG TGTTTGCCAT ACCGGCAAGT CTCTCACGCA       420

CTCCCGCACT CCTCATCGTG GACCAAAATG CCCGAATTCT CCTCGGTCCG CTGCGCAGCG       480

CGTTCATACC GCCGAGGTGG TCGGCACCGT AACGGCCGGT T                          521

(2) INFORMATION FOR SEQ ID NO: 269:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 269:

CTCCAGGCTC ATTCGCTCGA ACAAAGCCAC CCGGCCGTAC AGCGGACGCC CCCATTCGTT        60

GTCGTGATAG TCGCGGTACA GCTGGGCATC GGGCCCTGGA CGAACCTCCG CCCAGGGGCA       120

GCGAACCAGC CCGTCGCCGC TCACGCGGGG TCAGAACGGT AGTGCACGAC AGTCTCGCCG       180

CGCGAAGGGT TTGACGCGTC AGACTCGGCC TCGGCGTCTT CCGACGAGGC GTGGATCGCC       240

CCGAGCTGAG AGCGTAGCGC CTCGAGCTCA CGGCCGAGCC GTTCCAGCAC CCAGTCCACC       300

TCGCTGGTCT TGTTCCCGCG CAGCACCTGC GTGAACTTGA CCGCGTCGAC ATCGGCGCGG       360

GTGACCCCGA ACGCCGGCAG CGTCGTCGCC GTCGTCGCCC GCGGCAGGGG CGGCAACTGC       420

TCGCCA                                                                 426

(2) INFORMATION FOR SEQ ID NO: 270:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 270:

GCGGACACGG CGGACAAAGC GCAATCGGCC TCGGCGGCGG CGCCGGCGGC GACGGGGGCC        60

AGGGCGGCGC CGGCCGCGGA CTGTGGGGTA CTGGCGGCGC CGGCGGACAC GGCGGGGCAA       120

GGCGGTGGTA CCGGGGGCCC ACCGCTGCCC GGTCAGGCAG GCATGGGCGC CGCGGGTGGC       180

GCCGGTGGGC TGATCGGCAA CGGCGGGGCC GGCGGCGAC                             219

(2) INFORMATION FOR SEQ ID NO: 271:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 271:

AAGATCATCG GCGCCGCTCC TTAGCATCGC TGCGCTCTGC ATCGTCGCCG GCGCGGATCA        60

CGGAGGTCCG GCCTTGTACC CCACTCCTCG AACGGTCAGC ACCACAGTCG GGTTCTCGGG       120

ATCCTTTTCG ACCTTGGCCC GCAGACGCTG GACATGCACG TTCACCAGCC TGGTATCGGC       180

TGGGTGCCGG TAACCCCATA CCTGTTCGAG CAGCACATCA CGAGTAAACA CCTGGCGCGG       240

CTTGCGCGCC AATGCGACCA ACAGGTCGAA TTCCAGCGGT GTCAACGAGA TCTGCTCACC       300
```

-continued

```
GTTGCGAGTG ACCTTGTGCG CCGGTACGTC GATTTCTACG TCGGCGATGG ACAGCATCTC    360

GGCGGGTTCG TCGTCGTTGC GGCGCAGCCG CGCCCGCACC CGCGCAACCA GCTCCTTGGG    420

CTTGAACGGC TTCATGATGT AGTCGTCGGC GCCCGACTCC AGACCCAGCA CCACATCCAC    480

GGTGTCGGTC TTTGCGGTGA GCATCACGAT CGGAACACCG GAATCGGCGC GCAACACCCG    540

GCACACGTCG ATGCCGTTCA TACCGGGGCA A                                   571
```

(2) INFORMATION FOR SEQ ID NO: 272:

(i) SEQUENCE CHARACTERISTICS:
        (A) LENGTH: 93 amino ac ids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 272:

```
Leu Phe Gly Ala Gly Gly Val Gly Gly Val Gly Gly Asp Gly Val Ala
 1               5                  10                  15

Phe Leu Gly Thr Ala Pro Gly Gly Pro Gly Gly Ala Gly Gly Ala Gly
            20                  25                  30

Gly Leu Phe Ser Val Gly Gly Ala Gly Gly Ala Gly Gly Ile Gly Leu
        35                  40                  45

Val Gly Asn Ser Gly Ala Gly Gly Ser Gly Gly Ser Ala Leu Leu Trp
    50                  55                  60

Gly Asp Gly Gly Ala Gly Gly Ala Gly Gly Val Gly Ser Thr Thr Gly
65                  70                  75                  80

Gly Ala Gly Gly Ala Gly Gly Asn Ala Ser Leu Leu Val
                85                  90
```

(2) INFORMATION FOR SEQ ID NO: 273:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 273:

```
Met Pro Pro Val Ser Ala Asn Ala Met Val Pro Ala His Ser Thr Pro
 1               5                  10                  15

Pro Val Ala Asn Ile Glu Val Asn Thr Pro
            20                  25
```

(2) INFORMATION FOR SEQ ID NO: 274:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 274:

```
Lys Pro Asp Arg Pro Ala Ala Thr Val Gly Ser Cys Thr Thr Val Arg
 1               5                  10                  15

Ala Pro Cys Ser Gln Pro Val Thr Thr Ala
            20                  25
```

(2) INFORMATION FOR SEQ ID NO: 275:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 275:

Trp Pro Ala Gly Arg Pro Met His Pro Ala Pro Gly Thr Ser Ala Asp
1               5                   10                  15

His Pro Pro Asn
            20

(2) INFORMATION FOR SEQ ID NO: 276:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 276:

Val Leu Val Ala Gly Cys Ser Ser Asn Pro Leu Ala Asn Phe Ala Pro
1               5                   10                  15

Gly Tyr Pro Pro Thr Ile Glu Pro Ala Gln Pro Ala Val Ser Pro Pro
                20                  25                  30

Thr Ser Gln Asp Pro Ala Gly Ala Val Arg Pro Leu Ser Gly His Pro
            35                  40                  45

Arg Ala Ala Leu Phe Asp Asn Gly Thr Arg Gln Leu Val Ala Leu Arg
        50                  55                  60

Pro Gly Ala Asp Ser Ala Ala Pro Ala Ser Ile Met Val Phe Asp Asp
65                  70                  75                  80

Met His Val Ala Pro Arg Val Ile Phe Leu Pro Gly Pro Ala Ala Ala
                85                  90                  95

Leu Thr Ser Asp Asp His Gly Thr Ala Phe Leu Ala Ala Arg Gly Gly
                100                 105                 110

Tyr Phe Val Ala Asp Leu Ser Ser Gly His Thr Ala Arg Val Asn Val
            115                 120                 125

Ala Asp Ala Ala His Thr Asp Phe Thr Ala Ile Ala
        130                 135                 140

(2) INFORMATION FOR SEQ ID NO: 277:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 277:

Met His Ile Thr Leu Asn Ala Ile Leu Arg Ala Ile Phe Gly Ala Gly
1               5                   10                  15

Gly Ser Glu Leu Asp Glu Leu Arg Arg Leu Ile Pro Pro Trp Val Thr
                20                  25                  30

Leu Gly Ser Arg Leu Ala Ala Leu Pro Lys Pro Lys Arg Asp Tyr Gly

```
                  35                  40                  45
Arg Leu Ser Pro Trp Gly Arg Leu Ala Glu Trp Arg Arg Gln Tyr Asp
 50                  55                  60

Thr Val Ile Asp Glu Leu Ile Glu Ala Glu Arg Ala Asp Pro Asn Phe
 65                  70                  75                  80

Ala Asp Arg Thr Asp Val Leu Ala Leu Met Leu Arg Ser Thr Tyr Asp
                 85                  90                  95

Asp Gly Ser Ile Met Ser Arg Lys Asp Ile Gly Asp Glu Leu Leu Thr
                100                 105                 110

Leu Leu Ala Ala Gly His Glu Thr Thr Ala Ala Thr Trp Ala Gly Arg
            115                 120                 125

Ser Asn Gly Ser Thr Gly Thr Pro Thr Cys Ser Arg Leu Trp
130                 135                 140
```

(2) INFORMATION FOR SEQ ID NO: 278:

(i) SEQUENCE CHARACTERISTICS:
        (A) LENGTH: 163 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 278:

```
Val Leu Val Ala Gly Cys Ser Ser Asn Pro Leu Ala Asn Phe Ala Pro
  1                   5                  10                  15

Gly Tyr Pro Pro Thr Ile Glu Pro Ala Gln Pro Ala Val Ser Pro Pro
                 20                  25                  30

Thr Ser Gln Asp Pro Ala Gly Ala Val Arg Pro Leu Ser Gly His Pro
             35                  40                  45

Arg Ala Ala Leu Phe Asp Asn Gly Thr Arg Gln Leu Val Ala Leu Arg
 50                  55                  60

Pro Gly Ala Asp Ser Ala Ala Pro Ala Ser Ile Met Val Phe Asp Asp
 65                  70                  75                  80

Val His Val Ala Pro Arg Val Ile Phe Leu Pro Gly Pro Ala Ala Ala
                 85                  90                  95

Leu Thr Ser Asp Asp His Gly Thr Ala Phe Leu Ala Ala Arg Gly Gly
            100                 105                 110

Tyr Phe Val Ala Asp Leu Ser Ser Gly His Thr Ala Arg Val Asn Val
            115                 120                 125

Ala Asp Ala Ala His Thr Asp Phe Thr Ala Ile Ala Arg Arg Ser Asp
            130                 135                 140

Gly Lys Leu Val Leu Gly Ser Ala Asp Gly Ala Val Tyr Thr Leu Ala
145                 150                 155                 160

Lys Asn Pro
```

(2) INFORMATION FOR SEQ ID NO: 279:

(i) SEQUENCE CHARACTERISTICS:
        (A) LENGTH: 240 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 279:

Trp Gly Ala Pro Pro Ser Gly Gly Pro Ser Pro Trp Ala Gln Thr Pro

```
                1               5                      10                     15
            Arg Lys Thr Asn Pro Trp Pro Leu Val Ala Gly Ala Ala Val Val
                            20                   25                  30
            Leu Val Leu Val Leu Gly Ala Ile Gly Ile Trp Ile Ala Ile Arg Pro
                            35                   40                  45
            Lys Pro Val Gln Pro Pro Gln Pro Val Ala Glu Glu Arg Leu Ser Ala
            50                           55                   60
            Leu Leu Leu Asn Ser Ser Glu Val Asn Ala Val Met Gly Ser Ser Ser
            65                   70                   75                  80
            Met Gln Pro Gly Lys Pro Ile Thr Ser Met Asp Ser Ser Pro Val Thr
                            85                   90                  95
            Val Ser Leu Pro Asp Cys Gln Gly Ala Leu Tyr Thr Ser Gln Asp Pro
                            100                  105                 110
            Val Tyr Ala Gly Thr Gly Tyr Thr Ala Ile Asn Gly Leu Ile Ser Ser
                            115                  120                 125
            Glu Pro Gly Asp Asn Tyr Glu His Trp Val Asn Gln Ala Val Val Ala
                            130                  135                 140
            Phe Pro Thr Ala Asp Lys Ala Arg Ala Phe Val Gln Thr Ser Ala Asp
            145                          150                  155                 160
            Lys Trp Lys Asn Cys Ala Gly Lys Thr Val Thr Val Thr Asn Lys Ala
                            165                  170                 175
            Lys Thr Tyr Arg Trp Thr Phe Ala Asp Val Lys Gly Ser Pro Pro Thr
                            180                  185                 190
            Ile Thr Val Ile Asp Thr Gln Glu Gly Ala Glu Gly Trp Glu Cys Gln
                            195                  200                 205
            Arg Ala Met Ser Val Ala Asn Asn Val Val Asp Val Asn Ala Cys
                            210                  215                 220
            Gly Tyr Gln Ile Thr Asn Gln Ala Gly Gln Ile Ala Ala Lys Ile Cys
            225                          230                  235                 240

(2) INFORMATION FOR SEQ ID NO: 280:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 280:

Asp Val Val Glu Ala Ala Ile Ala Arg Ala Glu Ala Val Asn Pro Ala
    1               5                      10                     15
    Leu Asn Ala Leu Ala Tyr
                    20

(2) INFORMATION FOR SEQ ID NO: 281:

(i) SEQUENCE CHARACTERISTICS:
            (A) LENGTH: 174 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 281:

Leu His Pro Ala Gly Ala Thr Asn Gly Ser Gly Gln Leu Ala Leu Pro
    1               5                      10                     15
```

-continued

Val Glu Ala Pro Pro Arg Ser Val Pro Ser His Gly Glu Pro Leu Gly
                20                  25                  30

Ser Ala Ala Pro Glu Gly Leu Glu Gly Glu Phe Asp Asp Arg Ile Asp
            35                  40                  45

Glu Arg Phe Pro Val Phe Ser Ser Ala Ser Leu Ala Glu Ala Leu Pro
 50                      55                  60

Gly Pro Leu Thr Pro Met Thr Leu Asp Val Gln Leu Ser Gly Leu Arg
 65                  70                  75                  80

Ala Ala Gly Arg Ala Met Gly Arg Val Leu Ala Leu Gly Gly Val Val
                85                  90                  95

Ala Asp Glu Trp Glu Arg Arg Ala Ile Ala Val Phe Gly His Arg Pro
            100                 105                 110

Tyr Ile Gly Val Ser Ala Asn Ile Val Ala Ala Gln Leu Pro Gly
            115                 120                 125

Trp Asp Ala Gln Ala Val Thr Arg Arg Ala Leu Gly Glu Gln Pro Gln
 130                 135                 140

Val Thr Glu Leu Leu Pro Phe Gly Arg Pro Gln Leu Ala Gly Gly Pro
 145                 150                 155                 160

Leu Gly Ser Val Ala Lys Val Val Val Thr Ala Arg Ser Leu
                165                 170

(2) INFORMATION FOR SEQ ID NO: 282:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 282:

Val Gly Val Val Gly Val Gly Ala Thr Ser Pro Ala Gly Ala Gly Ala
 1                   5                  10                  15

Gly Ala Gly Ser Ala Gly Thr Gly Ala Gly Ala Gly Gly Ala Thr
                20                  25                  30

Lys Gly Arg Ile Asp Ser Ala Ser Ala Leu Ala Ala Pro Leu Ser Thr
            35                  40                  45

Gly Leu Leu Ala Val Pro Ser His Thr Thr Asn Gln Arg
 50                  55                  60

(2) INFORMATION FOR SEQ ID NO: 283:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 283:

Met Ala Asn Thr Gly Ser Leu Val Leu Leu Arg His Gly Glu Ser Asp
 1                   5                  10                  15

Trp Asn Ala Leu Asn Leu Phe Thr Gly Trp Val Asp Val Gly Leu Thr
                20                  25                  30

Asp Lys Gly Gln Ala Glu Ala Val Arg Ser Gly Glu Leu Ile Ala Glu
            35                  40                  45

His Asp Leu Leu Pro Asp Val Leu Tyr Thr Ser Leu Leu Arg Arg Ala
 50                  55                  60

```
Ile Thr Thr Ala His Leu Ala Leu Asp Ser Ala Asp Arg Leu Trp Ile
 65                  70                  75                  80

Pro Val Arg Arg Ser Trp Arg Leu Asn Glu Arg His Tyr Gly Ala Leu
                 85                  90                  95

Gln Gly Leu Asp Lys Ala Glu Thr Lys Ala Arg Tyr Gly Glu Glu Gln
            100                 105                 110

Phe Met Ala Trp Arg Arg Ser Tyr Asp Thr Pro Pro Pro Ile Glu
        115                 120                 125

Arg Gly Ser Gln Phe
    130
```

(2) INFORMATION FOR SEQ ID NO: 284:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 284:

```
Pro Gly Ser Phe Ala Arg Thr Lys Pro Pro Gly Arg Thr Ala Asp Ala
  1               5                  10                  15

Pro Ile Arg Cys Arg Asp Ser Arg Gly Thr Ala Gly His Arg Ala Leu
             20                  25                  30

Asp Glu Pro Pro Pro Arg Gly Ser Glu Pro Ala Arg Arg Ser Arg
        35                  40                  45

Gly Val Arg Thr Val Val His Asp Ser Leu Ala Ala Arg Arg Val
    50                  55                  60
```

(2) INFORMATION FOR SEQ ID NO: 285:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 285:

```
Gly His Gly Gly Gln Ser Ala Ile Gly Leu Gly Gly Ala Gly Gly
  1               5                  10                  15

Asp Gly Gly Gln Gly Gly Ala Gly Arg Gly Leu Trp Gly Thr Gly Gly
             20                  25                  30

Ala Gly Gly His Gly Gly Ala Arg Arg Trp Tyr Arg Gly Pro Thr Ala
            35                  40                  45

Ala Arg Ser Gly Arg His Gly Arg Arg Gly Trp Arg Trp Ala Asp
    50                  55                  60

Arg Gln Arg Arg Gly Arg Arg Arg
 65                  70
```

(2) INFORMATION FOR SEQ ID NO: 286:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 286:

Asp His Arg Arg Arg Ser Leu Ala Ser Leu Arg Ser Ala Ser Ser Pro
1               5                   10                  15

Ala Arg Ile Thr Glu Val Arg Pro Cys Thr Pro Leu Leu Glu Arg Ser
            20                  25                  30

Ala Pro Gln Ser Gly Ser Arg Asp Pro Phe Arg Pro Trp Pro Ala Asp
        35                  40                  45

Ala Gly His Ala Arg Ser Pro Ala Trp Tyr Arg Leu Gly Ala Gly Asn
    50                  55                  60

Pro Ile Pro Val Arg Ala Ala His His Glu
65                  70

(2) INFORMATION FOR SEQ ID NO: 287:

(i) SEQUENCE CHARACTERISTICS:
        (A) LENGTH: 174 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 287:

CCGCACGTAA CACCGTGAAT TGAAGGGAGC CGCTGGTCAT GGGCCGATTC TATCCGTGGG      60

CGAACGGTTA TTGACGGCCC GGAGGCCACT CCGCTGCCAC CAAGTGGTGA CTCAGCGCGT     120

TTTCACGGCA ACGAACGGCG GACACACCAC TTGACATTCG ACAGCACGGC CGCG           174

(2) INFORMATION FOR SEQ ID NO: 288:

(i) SEQUENCE CHARACTERISTICS:
        (A) LENGTH: 404 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 288:

TCGCAAACGG GGTGACGTTC CGTCCGGTGG CGCTAGAGAG TTTGTCGCAC TTTCCGGTGA      60

CCGTCGCCGC GCACCGCAGC ACCGGTGAGC TCACGCTGCT AGTGGAGGTG CTCGACGGTG     120

CGCTGGGCAC GATGGCGCCC GAAAGCCTCG GCAGGCGGGT GCTGGCTGTG TTACAGCGCT     180

TGGTCAGCCG GTGGGATCGG CCGCTGCGCG ACGTCGACAT TCTGCTGGAC GGCGAGCACG     240

ATCCGACCGC ACCCGGCCTG CCGGATGTGA CGACGTCGGC ACCCGCGGTG CATACCCGGT     300

TCGCCGAAAT CGCTGCGGCA CAGCCTGACT CGGTGGCGGT CAGTTGGGCG GATGGTCAGC     360

TGACGTACCG GGAGCTGGAT GCATTGGCCG ACCGGCTGGC CACT                      404

(2) INFORMATION FOR SEQ ID NO: 289:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 289:

Ala Asn Gly Val Thr Phe Arg Pro Val Ala Leu Glu Ser Leu Ser His
1               5                   10                  15

```
Phe Pro Val Thr Val Ala Ala His Arg Ser Thr Gly Glu Leu Thr Leu
            20                  25                  30

Leu Val Glu Val Leu Asp Gly Ala Leu Gly Thr Met Ala Pro Glu Ser
        35                  40                  45

Leu Gly Arg Arg Val Leu Ala Val Leu Gln Arg Leu Val Ser Arg Trp
    50                  55                  60

Asp Arg Pro Leu Arg Asp Val Asp Ile Leu Leu Asp Gly Glu His Asp
65                  70                  75                  80

Pro Thr Ala Pro Gly Leu Pro Asp Val Thr Thr Ser Ala Pro Ala Val
                85                  90                  95

His Thr Arg Phe Ala Glu Ile Ala Ala Ala Gln Pro Asp Ser Val Ala
            100                 105                 110

Val Ser Trp Ala Asp Gly Gln Leu Thr Tyr Arg Glu Leu Asp Ala Leu
        115                 120                 125

Ala Asp Arg Leu Ala Thr
    130
```

(2) INFORMATION FOR SEQ ID NO: 290:

(i) SEQUENCE CHARACTERISTICS:
        (A) LENGTH: 526 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 290:

```
GCTTCGACGG CTACGAGTAC CTGTTCTGGG TGGGTTGTGC GGGCGCCTAC GACGACAAGG    60
CCAAGAAGAC CACCAAGGCC GTCGCCGAGC TGTTCGCCGT CGCCGGGGTG AAATACTTGG   120
TGCTGGGCGC TGGGGAAACC TGCAACGGCG ACTCGGCGCG CCGCTCCGGC AACGAGTTCC   180
TCTTCCAGCA GCTGGCACAA CAGGCCGTCG AGACCCTGGA CGGTTTGTTC GAGGGTGTGG   240
AGACCGTCGA CCGCAAGATC GTTGTCACCT GCCCGCACTG CTTCAACACC ATCGGCAAGG   300
AATATCGGCA GCTGGGCGCC AACTACACCG TGCTGCACCA CACCCAGCTG CTCAATCGGT   360
TGGTGCGCGA CAAGAGGCTG GTCCCTGTCA CTCCGGTTTC TCAGGACATC ACCTACCACG   420
ACCCGTGCTA CCTGGGTCGG CACAACAAGG TCTACGAGGC ACCACGGGAG CTGATCGGTG   480
CCGCGGGGGC CACCTGAGCC GAGATGCCGC GCCATGCCGA CCGCAG             526
```

(2) INFORMATION FOR SEQ ID NO: 291:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 291:

```
CTCGCCGCCG TGATCTGGCC GGCGAACTTC GTCAGTGCAT CCAGACCCCA ACGATCATCG    60
ATCAGGCCGA TGCCCATGAT CACCGCACCG GCCACCAGCA CCGCGGGCAT GCCGGTGGAA   120
TAGACGAACC CCCGGGTGAG TGCCGGAAGC TGGGAGGCAA GAAAGACGGC GCCGACAATG   180
CCCAGGAACA TCGCCAACCC ACCCATCCGA GGGGTAGGCG TGACGTGCAC ATCTCGCTCC   240
CGCGGGTAGG CGACGGCTCC CAGGCGACTG GCCAGCATCC GCACCGGACC GGTCGCAAAA   300
```

```
TAGGTGATGA TCGCCGCGGT CAGCCCGACC AGCGCAAGCT CACGCAGCGG GACACCGGCG      360

CCGCGATAGG ACAGGGCGAG CAAGCCACCG GCAACGCCGG CCACATCGCT GGACACCTCG      420

AGACCGTACT GCACCAACCT GAAGAGCTGA ACACTCGCCG AACGTGCAAC AGCTGCGAAC      480

AATTGGG                                                                487
```

(2) INFORMATION FOR SEQ ID NO: 292:

(i) SEQUENCE CHARACTERISTICS:
        (A) LENGTH: 528 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 292:

```
ACGAAGCGCG AGAATATGAG CCGGGGCAAC CCGGCATGTA CGAGCTTGAG TTCCCGGCGC       60

CTCAGCTGTC GTCGTCCGAC GGCCGTGGTC CGGTGTTGGT GCACGCTTTG GAAGGTTTCT      120

CCGACGCCGG CCATGCGATC CGGCTGGCCG CCGCCCACCT CAAGGCGGCC CTGGACACAG      180

AGCTGGTCGC GTCCTTCGCG ATCGATGAAC TACTGGACTA CCGCTCGCGG CGGCCATTAA      240

TGACTTTCAA GACCGATCAT TTCACCCACT CCGATGATCC TGAGCTAAGC CTGTATGCGC      300

TGCGCGACAG CATCGGCACC CCATTTCTGC TGCTGGCGGG TTTGGAGCCG GACCTGAAGT      360

GGGAGCGGTT CATCACCGCC GTCCGATTGC TGGCCGAGCG CCTGGGTGTA CGGCAGAACC      420

ATCGGCCTGG GCACCGTCCC GATGGCCGTT CCGCACACAC GACCGATCAC GATGACCGCT      480

CATTCCAACA ACCGGGAGCT ATCTCCGATT TCAACCGTT CGATCTCC                    528
```

(2) INFORMATION FOR SEQ ID NO: 293:

(i) SEQUENCE CHARACTERISTICS:
        (A) LENGTH: 610 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 293:

```
CCAAGCCCGT CAAGGAGCCG GTGCCGGCCT TGCCTCCGGT GCCGCCGACG CCGGCGTTGC       60

CGCCGTTGCC GCCGTTGCCG CCGGTACCGG GGTTTCCTAC GGTGCCGCCG CCCGGCAGCA      120

TGGCCCCGCT GTTTAGGCCG TTTTCGCCGG CCCCGCCGTC ACCGGCTTTG CCGCCATCGC      180

CGCCGTTGCC GCCGCTGGTG GGGGTGGCGG CCTGGTTGAC GTATTGTTCC ACCGGCCCGG      240

CCCTTGACCC TTTGGCGGTG TCGATCGCGG CGTCGATGGA TCCGCCGACC ACGACGTGCG      300

AAGCCTCGCC TGCCGCCGCA GCCGCCCAAC TGTGTCGCGG CTCCTGCGAT TTGGCCCCGG      360

CCGACGAGAT GATGGGCACC ACCGGAGCCT GCGGCCGTCT GGGGGAGGCC AGCGCGGGTT      420

CGCGGTCACG CCATACGCGA CGGTGCGCCG CCGCTTCGGA GATTTGCAGG CTGCGTTGCA      480

CCAGATCGAG CAGCGGTGTG CCCAGGGACT GGGTTAGCCC GTTGGCGCCG CCGTTGTAGC      540

GGCGAGCGCA ATATCGGTGC CCACTCGACC CAACCGCGAC TCCATAAGCG ACACCATTCG      600

CGGTTGATGC                                                            610
```

(2) INFORMATION FOR SEQ ID NO: 294:

(i) SEQUENCE CHARACTERISTICS:
        (A) LENGTH: 164 amino acids

```
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 294:

Phe Asp Gly Tyr Glu Tyr Leu Phe Trp Val Gly Cys Ala Gly Ala Tyr
 1               5                  10                  15

Asp Asp Lys Ala Lys Lys Thr Thr Lys Ala Val Ala Glu Leu Phe Ala
            20                  25                  30

Val Ala Gly Val Lys Tyr Leu Val Leu Gly Ala Gly Glu Thr Cys Asn
        35                  40                  45

Gly Asp Ser Ala Arg Arg Ser Gly Asn Glu Phe Leu Phe Gln Gln Leu
    50                  55                  60

Ala Gln Gln Ala Val Glu Thr Leu Asp Gly Leu Phe Glu Gly Val Glu
65                  70                  75                  80

Thr Val Asp Arg Lys Ile Val Val Thr Cys Pro His Cys Phe Asn Thr
                85                  90                  95

Ile Gly Lys Glu Tyr Arg Gln Leu Gly Ala Asn Tyr Thr Val Leu His
            100                 105                 110

His Thr Gln Leu Leu Asn Arg Leu Val Arg Asp Lys Arg Leu Val Pro
        115                 120                 125

Val Thr Pro Val Ser Gln Asp Ile Thr Tyr His Asp Pro Cys Tyr Leu
    130                 135                 140

Gly Arg His Asn Lys Val Tyr Glu Ala Pro Arg Glu Leu Ile Gly Ala
145                 150                 155                 160

Ala Gly Ala Thr (2) INFORMATION FOR SEQ ID NO: 295:

(i) SEQUENCE CHARACTERISTICS:
            (A) LENGTH: 161 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 295:

Arg Arg Arg Asp Leu Ala Gly Glu Leu Arg Gln Cys Ile Gln Thr Pro
 1               5                  10                  15

Thr Ile Ile Asp Gln Ala Asp Ala His Asp His Arg Thr Gly His Gln
            20                  25                  30

His Arg Gly His Ala Gly Gly Ile Asp Glu Pro Pro Gly Glu Cys Arg
        35                  40                  45

Lys Leu Gly Gly Lys Lys Asp Gly Ala Asp Asn Ala Gln Glu His Arg
    50                  55                  60

Gln Pro Thr His Pro Arg Gly Arg Arg Asp Val His Ile Ser Leu Pro
65                  70                  75                  80

Arg Val Gly Asp Gly Ser Gln Ala Thr Gly Gln His Pro His Arg Thr
                85                  90                  95

Gly Arg Lys Ile Gly Asp Asp Arg Arg Gly Gln Pro Asp Gln Arg Lys
            100                 105                 110

Leu Thr Gln Arg Asp Thr Gly Ala Ala Ile Gly Gln Gly Glu Gln Ala
        115                 120                 125

Thr Gly Asn Ala Gly His Ile Ala Gly His Leu Glu Thr Val Leu His
    130                 135                 140
```

```
Gln Pro Glu Glu Leu Asn Thr Arg Arg Thr Cys Asn Ser Cys Glu Gln
145                 150                 155                 160

Leu (2) INFORMATION FOR SEQ ID NO: 296:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 296:

Glu Ala Arg Glu Tyr Glu Pro Gly Gln Pro Gly Met Tyr Glu Leu Glu
1               5                   10                  15

Phe Pro Ala Pro Gln Leu Ser Ser Asp Gly Arg Gly Pro Val Leu
            20                  25                  30

Val His Ala Leu Glu Gly Phe Ser Asp Ala Gly His Ala Ile Arg Leu
        35                  40                  45

Ala Ala Ala His Leu Lys Ala Ala Leu Asp Thr Glu Leu Val Ala Ser
        50                  55                  60

Phe Ala Ile Asp Glu Leu Leu Asp Tyr Arg Ser Arg Arg Pro Leu Met
65                  70                  75                  80

Thr Phe Lys Thr Asp His Phe Thr His Ser Asp Asp Pro Glu Leu Ser
                85                  90                  95

Leu Tyr Ala Leu Arg Asp Ser Ile Gly Thr Pro Phe Leu Leu Leu Ala
            100                 105                 110

Gly Leu Glu Pro Asp Leu Lys Trp Glu Arg Phe Ile Thr Ala Val Arg
        115                 120                 125

Leu Leu Ala Glu Arg Leu Gly Val Arg Gln Asn His Arg Pro Gly His
    130                 135                 140

Arg Pro Asp Gly Arg Ser Ala His Thr Thr Asp His Asp Asp Arg Ser
145                 150                 155                 160

Phe Gln Gln Pro Gly Ala Ile Ser Asp Phe Gln Pro Phe Asp Leu
                165                 170                 175

(2) INFORMATION FOR SEQ ID NO: 297:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 297:

Lys Pro Val Lys Glu Pro Val Pro Ala Leu Pro Val Pro Pro Thr
1               5                   10                  15

Pro Ala Leu Pro Pro Leu Pro Pro Leu Pro Val Pro Gly Phe Pro
            20                  25                  30

Thr Val Pro Pro Pro Gly Ser Met Ala Pro Leu Phe Arg Pro Phe Ser
            35                  40                  45

Pro Ala Pro Pro Ser Pro Ala Leu Pro Pro Ser Pro Pro Leu Pro Pro
        50                  55                  60

Leu Val Gly Val Ala Ala Trp Leu Thr Tyr Cys Ser Thr Gly Pro Ala
65                  70                  75                  80
```

```
Leu Asp Pro Leu Ala Val Ser Ile Ala Ala Ser Met Asp Pro Pro Thr
                85                  90                  95

Thr Thr Cys Glu Ala Ser Pro Ala Ala Ala Ala Gln Leu Cys Arg
            100                 105                 110

Gly Ser Cys Asp Leu Ala Pro Ala Asp Glu Met Met Gly Thr Thr Gly
            115                 120                 125

Ala Cys Gly Arg Leu Gly Glu Ala Ser Ala Gly Ser Arg Ser Arg His
            130                 135                 140

Thr Arg Arg Cys Ala Ala Ala Ser Glu Ile Cys Arg Leu Arg Cys Thr
145                 150                 155                 160

Arg Ser Ser Ser Gly Val Pro Arg Asp Trp Val Ser Pro Leu Ala Pro
                165                 170                 175

Pro Leu (2) INFORMATION FOR SEQ ID NO: 298:

(i) SEQUENCE CHARACTERISTICS:
        (A) LENGTH: 921 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 298:

AATTCGGCAC GARCAGCACC AACACCGGCT TCTTCAACTC CGGCGACGTC AATACCGGTA      60

TCGGCAACAC CGGCAGCTTC AACACCGGCA GCTTCAATCC GGGCGATTCC AACACCGGGG     120

ATTTCAACCC ANGCAGCTAC CACACGGGGA CTCGGAAACA CCGGCGATTT TACACCGGCS     180

CCTTCATCTC CGGCAGCTAC AGCAACGGGT CTTGTGGAGT GGAAATTATC AGGGCTCATT     240

GGNTGCACCC GGSCTTRCGA ATCCCTCGKG CCAATTCAAC TCCTCNACAA GCTTGCGGCC     300

GCACTCSAGC CCGGGTGAAT GATTGAGTTT AACCGCTNAN CAATAACTAG CATAACCCCT     360

TKGGGCCTCT AAACGGGTCT TGAAGGGTTT TTTGCTGAAA GGANGAACTA TATCCGGATA     420

ACTGGCGTAN TACGAAAAGC CGCACCGATC GCCTTCCCAA CAGTTGCGCA CCKGAATGGC     480

AATGGACCNC CCTKTTACCG GSCATTAACN CGGGGGTGTN GGKGTTACCC CCACGTNACC     540

GCTACCTTGC CANNSSCCTN RSGCCGTCTT TCSTTTCTTC CTTCCTTCTC CCMCTTCGCC     600

GGTTCCCNTC AGCTCTAAAT CGGGGNNCCC TTTMGGGTTC CAATTATTGC TTACNGSCCC     660

CCACCCCAAA AAYTNATTNG GGTTAATGTC CCTTMTTGGG CNTCCCCCTA WTNANNGTTT     720

TCCCCCTTNA CTTTGRSTCC CTTCYTTATW NTGAMNCTNT TTCCACYGGA AAAMNCTCCA     780

CCNTTYSSGS TTTCCTTTGA WTTATMRGGR AATTSCAATY CCGCYTTKGG TTMAANTTAA     840

CYTATTTCNA ATTTTCCCGM TTTTMMNATR TTNSNCKCGM KNCTCCNRKA SSGNTTTCCT     900

CCCCCYTTSS GKTYCCCCRN G                                              921

(2) INFORMATION FOR SEQ ID NO: 299:

(i) SEQUENCE CHARACTERISTICS:
        (A) LENGTH: 1082 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 299:
```

```
AATTCGGCAC GAGATANGGG CGCACCGGGG TCCGCAGCCG GCGGGACCGT CGCCAGCACC      60

ACCGGGGTCA ACAGCACCAC GGTGGCGTCC ANGCAGAGCG CCGCGGTGAT GGCGGCCGAG     120

ACGGCRAACA CCTGCCGTAG CAGTCGGTGC GACTCCGCGC TCGCTCGANC CATGGCCGCG     180

CCGGCTGCCT CGAACANGCC TTCGTCGTCC ACAGCTTAGC CAGCANCCAA ACCGCACCCA     240

GAAACCCACA CGCCCGCCGC CCCGGANACC TGCGCCATCG KCTGCTGGGG CGANATCCCC     300

CGATCGCTNA CANGATGACC GCTGCCGGAA CGCCGCCGCT GCCTCCGGGC AGCCGCGTGG     360

GCSGGGCAAC CGCGAACCCA NGAACACGGC AAGCAGTATC ANCGCAACAG CAATTGTCAA     420

GGGCTAAACG CTTCACATCC AGGGATCTCG CGGCGCCACA CCGTCGGMTC TGCAGSGCGA     480

CCCCNTCCTN GGGCGGNCAC TCNTCAAAGA TGCNGATCNA CAGKCTAGGT CTTCGGCCGA     540

TATGSAAGGN CCCAACGGNT TTAAAGCGGC SAAAAAASTC TCCCANTGGA TAAAATCAGC     600

CGGGGANCCC CCCGTGSCMM NGTCYCGGKC ATTNTTCAAC MGGTTTNACG GCGGKTGCNG     660

GCCAACTKGC CAAAMTTAAG KTNGGGGNTY CGGGGCGGTA ACCGGCNNTK NGCCCCTTAA     720

AAAACCGGNC YTTTCTKGAT TAMMACCGGN CCCCCAWTGG CGGKTGKTCC CANGNTYAAC     780

AMCCYCCCSS MNGGGKTGGS SAACCCTTCC CGNGGGGTTC NTKGTTSCYT AWMCCCCCGG     840

AAAACCSGKYG GGKTGGCRTN WASSAMNCCC CMNGYYTCTT TAAAGGCCAN KNRAAWGKYT     900

CCTTGGGAAW CCTNCAATYC GAAAAYYCTC CTYMMGSSCN CTTKCWRTYN NRNGGGAACS     960

AMWTNYCCNC GWTTCAWTCG GGTCCGASMN AAACKCTTTY TTTTYCGSSC STCCMGGSNC    1020

SGGTKNANAN AAASATTTMC YYCNNNANKK YYYCSSGCTT CYKMGRRNRR GMGAACCCGR    1080

GS                                                                  1082

(2) INFORMATION FOR SEQ ID NO: 300:

(i) SEQUENCE CHARACTERISTICS:
        (A) LENGTH: 990 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 300:

AATTGGCACG AGTGATCGCG CTGAAGCCGG TAGCGCGGGT GGCTCGGGTG GTTTGCGAAC      60

RAAATCCGCT CGANGTGGTC TCGGTAGGCG GTGTCCANAA CGGTGGCGCG GTGCCGGCGG     120

ATCTGATCGG CGCGGCCGTA GTGCACGTCG GCGGGCGTGT GCAGTCCGAT GCCGGAATGC     180

TTGTGTTCGT GGTTGTACCA GCCGAAGAAC CGGTCGCAGT GCACCCGGGC CGCCTCGATC     240

GACTCGAACC GTTTCGGGAA ATCGGGCCGG TACTTGAAGG TCTYGAACTG GCCTCAGAC     300

AACGGGTTGT CTTGCTGGTG TGCGGGCGTG AGTGCGACTT GGTGACACCG AAGTCGGCCA     360

NCANCAATGC CACCGGTTTG GAACTCATCC ACAACCCCCG TCCGCGTCMA GGTCACTTGT     420

NCGGCGCTAA TTTNYTGGGC GGCAAGGGTT TGCCGAYCAN KCCGCTCGGC CAAAACTTCG     480

ANTCNCSCCA AGGCCNCCAT CCNCCCAAAC AMGTTACGGG ANAAAANATY CAAAGAYCAC     540

CYTCCGGKTN TTATANCTYC CCYTTTGSTY GGGCCCCCCN CYYTGKKNAT ACCCCTNCCA     600

AWTCCCAACN CCCKCCAANA RCYKGGGGCC CCCNCCAACC CGGGKGAAKA WTAATTTAAA     660

CCCYAACMAW ACTWMMNACC CNNGGGSCCY AAMCGTYYNR AGGTTTTSCT NAAAGAAASA     720

ANTCGGAAMC CGGNTSTACC AAAAASCCCK CCNWTCCCTC CRASATTGSC NCCSAAWKSA     780

AKGCCCCCNY TCSGCNWNNC CSGCGGKKKT KKGTTNCCCT WMRCWMWYTS GGCCNASCCN     840
```

```
CKYYSSMYCC CCCCTCCCCM CTCCGNKTCC CCAMCCYANC MGGCCCCYTM GKKCCCWKNT     900

YKGCCCCCCC AMMNNNGGGG WGACCCTNGG CCCCMKRRGM TCCCNANTGA MCCTCWGNRA     960

MKCYCCNRAR ANMCCSCNCC NGCNCRCKNN                                     990
```

(2) INFORMATION FOR SEQ ID NO: 301:

(i) SEQUENCE CHARACTERISTICS:
  (A) LENGTH: 223 base pairs
  (B) TYPE: nucleic acid
  (C) STRANDEDNESS: single
  (D) TOPOLOGY: linear (ii) MOLECULE TYPE: Genomic DNA (xi) SEQUENCE DESCRIPTION: SEQ ID NO: 301:

```
AATTCGGGTG GCAACGCGGG CCTGTTCGGC AACGGCGGCG CCGGTGGTGC CGGTGGGGCT      60

GGTGGTGGCG CCGGCGGCGC GGGCGGTAAC GCGGGGTGGT TTGGTCATGG GGGCGCTGGC     120

GGCGTGGGTG GTGTANGTGC GGCCGGGGCC AACGGTGCTA CGCCCGGTCA GGATGGGGCG     180

GCTGGTGTTG CCGGGTCGGA CRACRCTCGT GCCGCTCGTG CCG                       223
```

(2) INFORMATION FOR SEQ ID NO: 302:

(i) SEQUENCE CHARACTERISTICS:
  (A) LENGTH: 418 base pairs
  (B) TYPE: nucleic acid
  (C) STRANDEDNESS: single
  (D) TOPOLOGY: linear (ii) MOLECULE TYPE: Genomic DNA (xi) SEQUENCE DESCRIPTION: SEQ ID NO: 302:

```
AATTCGGCAC GANGCGGCAA CGGTGGCAGC GGCGGCACGT CNGTTGCCAC CGGGGGGGCC      60

GGGAACGGCG GTGCCGGCGG CGCCGGCGGC GGGGCCGGGC TGATCGGCAA CGGCSGCAAC     120

GGCGGCAGTG GCGGAATGGG CGATGCCCCG GCGGCACCG  GCGTCNGCGG CATCRGTGGG     180

CTGTTGTTGG GTTTGGACRG CGCCAACGCC CCGGCCAGCA CCAACCCGCT GCACACCGCG     240

CAGCACAGGC GTTGGCCGCA GTCAACGCGC CCATCCAGGC CGTGACCGGG CGCCCCTGAT     300

CGGCAACGCG CCAACGGCGC CCCGGGCAAC GGGGCCCCCG GCRGGCACGG CGGGTGGTTG     360

TTCGGCGGCG GAAGGAACGG CGGGTCCGGC GTCANCRGCG GGGCGGGCGG AAATGCCG       418
```

(2) INFORMATION FOR SEQ ID NO: 303:

(i) SEQUENCE CHARACTERISTICS:
  (A) LENGTH: 1049 base p airs
  (B) TYPE: nucleic acid
  (C) STRANDEDNESS: single
  (D) TOPOLOGY: linear (ii) MOLECULE TYPE: Genomic DNA (xi) SEQUENCE DESCRIPTION: SEQ ID NO: 303:

```
AATTCGGCAC GAGGGGCACG ATCGCATACA GCGCTCGCGG CAGACCCGCC CGATACAGCA      60

GCTCGGCACA CGCGAGCGCA CAATACGGCG TCTGGCTGTC CGGCTTGARC ACCACCGCGT     120

TACCGGCCAC CAGCGCGGGC ACCGAGTCCG ACACCGTAAG CGTCATGGGG TAGTTCCACG     180

GCGAGATCAC CCCCACCACG CCCTTCGGTT GATAGCACAC CGTGGTCTTG CCTATCCCGG     240

GCAGCAGCGG CTGTGCCTTA CGGGGCTTCA GCAGGTCCAC ACAGACTCGT GCSTTATAAT     300

TNCGCSTTCC GCGATCAGAT CGACAATTTC CTCTTGCGCC GCCCATCGGG CCTTGCCCGC     360
```

| | |
|---|---|
| CTCGGCTTGC AGGAAGTCCA TGAAGAACTC GCGGTTCTCG ATNAACAGGT CGCGATAGCG | 420 |
| GCSGATGACT GCAGCTCGCT CGATNACGGG ACCTTCGCCA GTCGGTCTGC GCCGCGCGAN | 480 |
| CTTCCGCGAA TGCCGCTTCG ACTTCCGCGG NCGTGCCAAC GGAATCNTAT CACGGGTTGC | 540 |
| CGGTTAAAAC TCCTCAATST NCYGGTCGAA ATTCGGCAAC TTCTTATCCC GGCAGGTRCC | 600 |
| AACSANNCAA ACCTCGGCAA GGTTAGGMTT TCCCCCNCTT YCAAAAATNC GGKTTTTGGN | 660 |
| CMAATTTCGC CKCNATGKTG MCAAGGMTCT CKAANAAKCS GGGTCYTCTN NTCNGKGGAK | 720 |
| CCAAAMGGKT TTGGGGMAGC GKNMNCCAAN CCTWACCCTG KTKAANGGNW TTCCCCCCGG | 780 |
| GGGAKKGNGA ATYCYCCSNA NCCCRGGGGG GNMCARATTC TYCCGGMCTC CTCKGGAWTC | 840 |
| WGMGSTTTCC CAAAAAACSC CCCAAATTMM TTTTTCCRCN TRTTGANACW CTTTTKARCA | 900 |
| MMCSSAARNS ANMCNCTCYC CKCTKTGKTK AAAAAGNAYW CCCCMAAATT TYTAWTTSSC | 960 |
| CCSCGCGGGN CCCNCTNTTT TSCNMTWCTM WNYTNCRMCC MMMSNCKSNG KKGGNRCCNN | 1020 |
| CRCCSNCCCM AAWYNTKGYN KNTATMAGC | 1049 |

(2) INFORMATION FOR SEQ ID NO: 304:

(i) SEQUENCE CHARACTERISTICS:
        (A) LENGTH: 1036 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 304:

| | |
|---|---|
| AATTCGGCAC GAGGGAATCG AGAATCCCGG AATGGTGAAG CCTCGGTGCC TGCCGTTACG | 60 |
| CCAAGAKTCA GGGTGAGCGG CCCCCCGGTG GGAATGCTGA SGCCAACCGG GAAAAGGGTG | 120 |
| AGGGCTGGGG TGGAATAACT GAANGTTACT GGGATGGAAA ACCCGGTATT GATATGTATT | 180 |
| GGGCCGATCA ANGTTGTGGG AATGGGGGAA GGCTGAGGGC GACCTGTTGG ATTTGGGGAA | 240 |
| TTGTYRTGGA CRAKACWGGC CAGCCMGCGT GATGGTTTGG TTSAANTTTT GTGCCGSCCA | 300 |
| CANGGTGATG GGATTGATTT TGATGGGGCC SATCGAAATA TTGGGTATGC CNACGCCSAA | 360 |
| CGAGATYGCC GGGACGTTCA TGGGCGGGAC AACCMASGGT CCSANGTAAK GGTTTCCTTN | 420 |
| ATNTTGATCG GGATTCCGGA ACTMTSTCGA TGSGCTCSAY MTSATSGCCC NACNCCWCCG | 480 |
| YTTATTTCMS GCTNAYGGGA ATBAMRGGAA CAAYNTCCCT CCCMGGAAAA ACCAACMSGC | 540 |
| CCTGGTNSYC CNCCCRCCNC AKAACCCRTT KCTGTRSTMC CCSMAAATNA CSCCCSCTTS | 600 |
| NACTCCNCSG AANTNSCCCC CCCSCKNNTT ATSTYCCCGK GTTCCCCCMC CCCTTNAAMC | 660 |
| TCCCCGGTTA ACCCCWTNT SNCNCCCCCS YTAAKMNCRG GCTTSTTNCT CCCCCYTRMK | 720 |
| CNCCCCCTCK SAMCWNCCNC CTCKAACNAC CCCKCYKGSM TNCCCAATNT WCMWCKCCNS | 780 |
| KTTNTMCTKC CCAAYTNCRC CCNCRCTCCC CCKSTSTCAM WTATAAAACC WCWYAWYNNK | 840 |
| KCNCWMAWTA MGACWCTCNY NCCCCNCNCK NTTKTAMWCC CKMCCCKCSW TWCYCKCSCC | 900 |
| CCMTCTMNAC YCCCCCKKTY NKWMCCCTTC CCCCCCTCCC MCNMBMKTCT YCSGKTWCWC | 960 |
| NCYNTTMTCN CYNANMCKCK KTCTCTTCCN CRNTCTCCCC CCWCCCCCCV KKCTCTSKCC | 1020 |
| CNCNCTCCSC MMKGSC | 1036 |

(2) INFORMATION FOR SEQ ID NO: 305:

(i) SEQUENCE CHARACTERISTICS:
        (A) LENGTH: 1036 base pairs
        (B) TYPE: nucleic acid

```
        (C) STRANDEDNESS: single
        (D) TOPOLOGY: linear (ii) MOLECULE TYPE: Genomic DNA (xi) SEQUENCE DESCRIPTION: SEQ ID NO: 305:

AATTCGGCAC GAGATCATGA ATAGCGGGCT GGTCAGCACC GAAGTGGTCG GCGATCTCGC      60

GAGCAAGTCT CGTCTGCTCG CCCAGCAGGA GGTCGGCATC GATGCGGACA CCTGCGATGT     120

CTTGGATGGT GTTCAGTTGC AGGTAAGGCC GACGCCGCAG CTTTGCTAGC AGGGTGTCTT     180

GGCTCTTCGC ACGTGAGGTA ACCAATAACT CCGACGCAGA CCAACTCCGG CCCTCGATCC     240

GGGTACCAGG CTCCGCCGGA GCCAGCCGTT GTGCCCCTG GGCCGAAGGT CAGCTGCTGT      300

GCGATCGAAG TAAGAAACCG CGCCATGCCC GTCGCCAAGT ACGACTGACC GAGCAAACGA     360

ACGATCGTCG TCCTTTCCGT GGGGGTAATC GANCCCAGCA ACCGCACGAG CCACCAATCA     420

TTGGGATTCG GCCACTGACC GACCAACCGC CTGTGCGACA CCCCAGCGGA ATTGGTGGTC     480

TTCCGCGGGG CCGCNAACGG AATCANCGSG ACGCGCTCGC CGAASCANCC GCATANCCNT     540

ACATANCAAC GGNNTCTGCG CCCACATTTC GGGSTTMTGC CCCTCNGCAA CSSNAAYNCC     600

CCCAATTCYG AACNAAAAAA TTGGYCCATY ARNGTYCTCM CCAAAAACCN AWTCCCCKTA     660

TCCCCCGGGG GGGRCCCCYY NMNAAAACGG CCCWWAANCC CCSGGGCSCC CGGGTTRWTN     720

CCCCTTGTCG GCCCNCCSGG TTTGGTCMCM GGSCMMTNWN GGGNTGCSCC CCCNCNAAAA     780

AAAAAYCKNG NCAAATYAAA CCCKYCMAAA ASKTGGGSSC CCCMARCCGG GGKAAKKWWA     840

ANTTAANCCN KAAAAAAAWW NCANNMCCCC NGGGNCCTAA GGKYTTAGGG GTTSTTNANG     900

ARAAAATMTC CANATMNSSK TTNNAAAAAA ASCCSWAKCC CCCNNNKKNN CCAAWKAARR     960

SRCCTTCGGG TNWNSGGGGG KKKKKTNCMS KMNMMTTWGR CCCNCCGCCN NNTWKCCTTN    1020

TCCNYGGNGC RNCAGN                                                   1036

(2) INFORMATION FOR SEQ ID NO: 306:

(i) SEQUENCE CHARACTERISTICS:
        (A) LENGTH: 1060 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 306:

AATTCGGCAC GAGTCGATTC GATCGAACAC GCCCGCACCT GGCCAGGCCA CATGGGCGCG      60

GCCATGGCCA ACGCCTACTC GGCCAACCCG AATCCATTCG GCGTCTCACC GCAACCCCCG     120

AAACCGGCGA CCGCGGCATG GATCAACCCG CCCACCCCAG ATCCGAAATA GCGTCCACAT     180

AATGAGACAC TGGCGCAAAG AGCTTGACAG GCGCCGCACC ACGCAAGCTG TTAGACGTGT     240

CGGTCTTGCA AGAAGCGGGT TGGCCACCCA AGATCACGCC GCCCAAGGGC ATCGAGTCAA     300

CGTTGCGGTG GTATCGCGCT AACGTCGGCG CCGCCAAGAA ATGACGGTGC GCATTACCAT     360

GGCCCTGCTG ATCACCTTTG GCCACCTGCG CACCANAACT ATGANCAGCC TTATGCCGAG     420

TCTCGTGGAC ATCGGCAGCC GCTTCAAAAA CTCCTTGTCG ACAATSGTAT TGCTGANCCG     480

CCGAATTCTT NTRCTTGCAA SAACACTNCA TGTTNCSGGT NAACAACCYT GGTTNGAAAA     540

ACANCCAATA TTGAANTCCC ANTCGGGCAM GAACCNGTTM CGGAAGKTGK TGGGAACGAA     600

TGKTGCCCAA AAATCCCGGG NGGTRAAAWW CCCNSNATGG MSAATTTTSC CTNGAACAAM     660

AAAAGGTCCA AGKYCAAAGG NGCCCCCCCC SGNAAATTGG TGAACSCAKA WYANRTTCCC     720
```

```
WWWTNCAAAT MTTNGGGTCC KNNTCCCCWT AAANGGGSCN CCCCNCCRGG GMGTYTCCCC      780

NWNMGGGMGN CYYCSCCCCA AAAAAAAMMM MTTTCSGKGG SMGGKKCCCC CCSGGTYWGG      840

GKKYTTAAAC CCGGKGGGTN CAAAAAANAN ACCCCCCAMS NGGGGGGAAA ATTTGNAAWT      900

AAGGKKKTKC SCMACCCCAA AAANMMNNCN AWNCCCGMGK SARGGGGRNY TTMKAGGGMG      960

GNYCCCCCCW YCGGGGGGNA NAAYAAAAGK NGSNGRGAAT NTTNTTTTGK RSSSRNKTTT     1020

TYNTCCTYCN CCNMGNRWWG SRAMNTGKTS NSSGGGSGGC                          1060

(2) INFORMATION FOR SEQ ID NO: 307:

(i) SEQUENCE CHARACTERISTICS:
        (A) LENGTH: 1040 base p airs
        (B) TYPE: nucleic acid
        (C) STRANDEDNESS: si ngle
        (D) TOPOLOGY: linear (ii) MOLECULE TYPE: Genomic DNA (xi) SEQUENCE DESCRIPTION: SEQ ID NO: 307:

AATTCGGCAC GAGCTTCACC AAAGAGCTGA CATGCCGGGT GATGCGACAT CGCATCGAGG       60

GCAATACGGG CATGGATGAN CCGAANGGAN TCTGGCGTTC GCTCAACTGG ATTACGGTTC      120

CCAAGGTGAA ACGCTTTGCG GCGAAAGATG CGACGCTTAA CTTGCGCTTC CACCGTGCAA      180

TGTTNGTATG GATGCTGGAA CCGCGCTGAC NGATAANGAA TTCGCTGGTC GCCGGGCACN      240

ATGGATGGTC CKSTTTTCNC TCCGCSGTTA AATTGCSTGT GCATCATCTG GCAGGCTATG      300

TTCCCGCTAC RCTGCAGCCC ATCATGGATG TGCGGCTAAC GAANAAGTTA TGACATGGCG      360

CAAGCGAMTC GGGCATSCNC GCGGCAMTTT CGCAACCTGC TGTGTNTGAA GCGTMTCAAC      420

CGAATGCGGC GCTYAAAAGC NGGCTTGCGT TGATTMMAAC CNAACCCNTN CNATYCTTTG      480

CCGNGNMNTG CGTTCTCTCC AACTCCGKKG SYTGCCNCCG TGAAACCCMA CTNCCCCCCC      540

GTTGGACTTA MRTNTTCAAA AAMCGGMTNA ACCSGAATNN SAACCTNCCR TCAAANTAMM      600

SAANTCGGGC TTYGGGNRCC CCCCNGAAYW TTCKNCNGGG GMNNTYCTCN GGTTYNGGCG      660

SAAACNTTTG CCRTNCYMNN TTTACAMGGC NCMTNMTTGM GGGSCSNNAS GWCCCGGGKK      720

TNTTTNCAAW TCNCNSKTTT TTKGGGGGGG GGCYGRTRMC NCGGGCCCCC GGCCCKKMAA      780

AAAAAMCMSA RRCCNCYGGG KKCCCCCCCM NNATNGGGCG YKCRAAACAA ACCCCAANRA      840

TNGNGMGGGC SMACCSGNGN GYNAAAKGGT TSNSCTMANM MKGMANNNCT SGMSCCMNSN      900

NCTGMGGGKT TTKGNNGARN AANAMKMGGM RCGGNCGCNN GAAAGGGSMS GSCKSCNNGN      960

NGASNGWMGN CRNNGANRCC NCNGYGNMRN NNGNNNGNNN GGGRKNNACN NMKMCAWSMC     1020

NSNMMGNNNS CGYMTNKCGC                                                1040

(2) INFORMATION FOR SEQ ID NO: 308:

(i) SEQUENCE CHARACTERISTICS:
        (A) LENGTH: 348 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 308:

AATTCGGCAC GAGACAANGG CGTGAAATGG GATCCGGCCG AGCTGGGGCC CGTCGTCAGC       60

GACCTGTTGG CCAAGTCGCG GCCGCCGGTT CCGGTCTATG GGCCTAGTT ATCTGCGCCG      120
```

-continued

```
AGCGTGAACT CAGGGCGAGA TTTCGGCCGT TTTCTCGCCC TGGCTTCACG TTCGGCGAAG      180

TKGGGAACGG TCAGGGTTCG CAAACCACGA TCGGGATCGT GCGGTCGGTC CAGGACTGGT      240

ANTCCTGATA CTTKGGTACA TCGTGACCAA CTGTGGNCAA TATTCGGCGC GCTCCTCGTC      300

NGTCGCGTCC CGCGCGGTAA GGTCCANCAC TTCCTTTTTC TCGTGCCG                  348
```

(2) INFORMATION FOR SEQ ID NO: 309:

(i) SEQUENCE CHARACTERISTICS:
        (A) LENGTH: 332 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 309:

```
AATTCGGCAC GAGAGACCGG GTCGTTGACC AACGGACGCT TGGGCGCGGG CCCCTTGCGT       60

GGCATCAGCC CTTCTCCTTC TTAGCGCCGT AACGGCTGCG TGCCTGTTTG CGGTTCTTGA      120

CACCCTGCGT ATCCAGCGAA CCGCGGATGA TCTTGTAGCG CACACCAGGC AGGTCCTTCA      180

CCCGGCCGCC GCGCACCAGC ACCATCGAGT GCTCCTGCAG GTTGTGGCCC TCGCCGGGAA      240

TGTACGCCGT GACCTCGAAC TGACTCGTCA CTTCACGCGG GCAACCTTCC GAAGCGCCGA      300

GTTCGGCTTC TTCGGAGTGG TGGCTCGTGC CG                                   332
```

(2) INFORMATION FOR SEQ ID NO: 310:

(i) SEQUENCE CHARACTERISTICS:
        (A) LENGTH: 962 base p airs
        (B) TYPE: nucleic acid
        (C) STRANDEDNESS: si ngle
        (D) TOPOLOGY: linear (ii) MOLECULE TYPE: Genomic DNA (xi) SEQUENCE DESCRIPTION: SEQ ID NO: 310:

```
AATTCGGCAC RAGTCGGTCT AGACGGATTC AATGCTCCCG CGAGCACCTC GCCACTGCAC       60

ACCCTGCAGC AAAATGTGCT CAATGTGGTG AACGAGCCCT TCCAGACGCT CACCGGCCGC      120

CCGCTGATCG GCAACGGCGC CAACGGGACT CCTGGAACCG GGGCTGACGC GGGGCCGGCG      180

GGTGGCTGTT CGGCAACGGC GGCAACGGCG GGTCCGGGGC GAACGGAACC AACGGCGGGG      240

ACGTGGGGAC GCGCCCGGCG GGATTTCTTC GCACCGGSGC ACCGGCGGGG CCGGCGGCGT      300

CGCACAACGG CACCGGCGGG GACGCNGCGC CCGTNGGGCG GCTTCTKGAT GGGCTCCGGC      360

GGTNACGCGG CACGGCGGCG CCCGGCTCAC CGCCNGTTGG GACGCGGGGA CGCGTNACCC      420

CGATCTTCTT CCGCNCCCCG GAAACCGCGG GGCCGGCCCC ACATTAKACC CGGCGGNACC      480

GCGGMCCCGG CGGAACGGNG GGYNTTTTCC AACGGCGGGG CCGCGGAACC GNMGGSTGTT      540

CCTTNGGSGA AGGNCCAAKT CCCGKCTANC YYAATCCCCG ANGGKTGAMC CTSATGSNCA      600

MYTTMAGGAA CYTNCCCANT KTTSGRACCW CRCCNGGAAA ASRAWNKNGT KGGCAAACNA      660

NNTNCYTTKN NATTKGGNNA AAAANCCCTY CCWCSGRACT NCCCCCCNGM GRGMCNNTNN      720

NTTTYGNCNN CCCGGSNAAM RNTTKATTTC NGGGGGNTCN GGGTKMNNNA AACCCCAAAM      780

MNRNNKCSCA ANGGGKSNGC NKNNMMNSGT TTTYCKNMRA MRNWTYKNKN NTCNGARSRN      840

NAAMCNNSNK NGKKKNNKAA ARNNTTWKTN KNSCNNNCNN GRRNGVRGGC CKMKGSNMNG      900

MCWHNAWRNG NNGSNCNCKC NNKMNAAAAA AASGGVNCKS NSMKNKKKKG NRGGGGGGGG      960

GG                                                                    962
```

(2) INFORMATION FOR SEQ ID NO: 311:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 311:

```
AATTCGGCAC RAGAAGACGC CCGAANGTTT GCGCTGGCTC TACAACTTCA TCAARGCGCA      60

GGGGGAACGC AACTTCGGCA AGATCTACGT TCGCTTCCCC GAAGCGGTCT CGATGCGCCA     120

GTACCTCGGC GCACCGCACG GCGAGCTGAC CCAGGATCCG GCCGCGAAAC GGCTTGCGTT     180

GCAGAAGATG TCGTTCGAGG TGGCCTGGAG GATTTTGCAN GCGACGCCNG TGACCGCGAC     240

GGGTTTKGTG TCCGCACTGC TGCTCACCAC CCGCGGCACC GCGTTGACCT CGACCAGCTG     300

CACCACTCGT GCCGCTCGTG CCG                                              323
```

(2) INFORMATION FOR SEQ ID NO: 312:

(i) SEQUENCE CHARACTERISTICS:
        (A) LENGTH: 1034 base p airs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 312:

```
AATTCGCAGT GTGTGTGGCG GCGTCCAGAA GAAGATGATC GCGAACATCG CCAGCGCCGG      60

CCAGGCTATG GTGCCGGTGA TGGCCGACCA GCCGATCATC ACCGGCATAC AGCCGGCCGC     120

CCCACCCCAC ACCACGTTCT GTGACGTGCG TCGCTTGAGC CAAAGCGTGT AGACRAACAC     180

ATAAAACGCG ACGGTGACCA GGGCCAGCAC CCCCGCCAGC AGGTTCGTGG CGCACCATAG     240

CCAGAAGAAC GAGATCACCG TCNACGTCAC CCGAGTGCCA ACGCGTTTCG GGTCGGCACC     300

GCTTCCCGCG CCAAGGGCCG GCGCGCGGTT CGCTTCATCA CCTTGTCGAT ATCGGCGTCG     360

GCNACCAGTT GAGCGTGTTG GCGCCGGCGG CSGCCATCAT CCCGCCGACN ANCGTGTTGA     420

GCATGANCAG CGGATGAATG GCGCCGCGGC TCGTGCCGCT CGTGCCGAAT TCAACTCCGT     480

CNACAACTTG CGGNCGCACT CGAACCCGGG TGAATGAWTG AATTTAAACC GSTSAACANT     540

AACTACATAA CCCTTGGGGG CTCTTAACCG GTYYTGAANG GGTTTTTTGC TTAAAGGAAG     600

AACYATTTCC GGATANCTGG CSTTNWTARC GAAAAGGCCC CRCCCATNGC CCTCCACAGT     660

TTSCCCCTGA ATGGSAATGG MNCNCCYKNR CNGGGNCTTT AACRCSGGCG GGNTTTTGKT     720

MCCCNNCTKA CNTTMMMTGC ARNNCNGGCC SKCCCTTCCK TNTYCCCTCC NTCCCCCNST     780

TNCNGKTCCC CNNAMNYTNW ACGGGGGGCC YTNGGGKCRM TWTKKTTTGG GCCCCMCCCC     840

MAAANASAAN GGGGKRNGTY CSTTTGGCNC CCCAMAARGG NYCCCCCCAM YTNRRKMCSY     900

CNNTNKGGNN CTGTNCKNCG GAARAMAMCC KCCCCGNSTS STTNGTYWAG GNRWKGNSRG     960

CCSCCCCGGY MNNNAAYAWN WMNATNCNNS STNANMAKKN NNNNNNNSCN WNGNGNNTCN    1020

SCNSNGGKBC CSCC                                                     1034
```

(2) INFORMATION FOR SEQ ID NO: 313:

(i) SEQUENCE CHARACTERISTICS:

(A) LENGTH: 331 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 313:

AATTCGGCAC GAGCCCACAT CCGGGGCCGC TCGTTGCATG ACTCGTTCGT CATCGTCGAC        60

RAGGCACAGT CGCTGGAGCG CAATGTGTTG CTGACCGTGC TGTCCCGGTT GGGGACCGGT       120

TCCCGGGTGG TGTTGACCCA CGACATCGCC CAGCGCGACA ACCTGCGGGT CGGCCGCCAC       180

GACGGGTCGC CGCGGTGATC GAGAAGCTCA AAGGTCATCC GTTGTTCGCC CACATCACCT       240

TGCTGCGCAG TGAGCGCTCG CCGATCGCCG CGCTGGTCAC GAGATGCTCG ANGAGATCAC       300

CGGGCCGCGC TGAGTGCGCC TCCCGCGAGC A                                    331

(2) INFORMATION FOR SEQ ID NO: 314:

(i) SEQUENCE CHARACTERISTICS:
        (A) LENGTH: 1026 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 314:

AATTCGGCAC GAGATCGTCA CCCTGGCGAC CAGTGCACCC AGGCCACGCC ACCAGTTACG        60

GCTGATGGGC CAGAAGATGG ACCAGGTGCT GCCCATCCCG CCCACCGCAC TGCAGCTGAG       120

CACCGGGATC GCGGTCCTCA GCTACGGCGA TRAGCTGGTG TTCGGCATCA CCGCTGACTA       180

TGACGCCGCG TCCGAAATGC AGCAGCTGGT CAACGGTATC GAACTGGGTG TGGCGCGTCT       240

GGTGGCGCTC ANCGACAATT CCGTGCTGCT GTTTACAAGG ATCGGCSTAA GCGTTCATCC       300

CGCGCACTCC CCANCGCCGC GCGGCSGGGG CGGCCCTCTG TGCCGACCGC CCGAGCGCGT       360

CACTGACGCC ATCTCCGTCG GCGTTAACCC CGTGAGAAGG TGGGTCGTGC GCAAGTTGGG       420

CCCGGTCACC ATCNATCCGC GCCGCCATGA CGCNGTGCTG TTCCACACCA CNTSNGACNC       480

CCCCCAGGAA CTGGTCCGGC AMTNCAGGAA NTYCGTGTGG GCACCNGCTT CTTCCGKTRT       540

GGCYTAAACT TCCNATSTTN CSGCSGGCCT CTGGCGTTNC GNCCGGGCCG NTCTTNCCAA       600

ATCGGSMMAA ATCCCCANMC AAACCCCCCG GGTCTTGSGG GCSGGGNGGC GGCCNAWNCC       660

AAACCCCCCC NTTAAANTCT TTGKTNCCNN CNCSGGCNCC NCNAANSCAN CCCTTTKGGC       720

NCTTCCCCCC CCCAWTTTAA CCGAKCGSCN AAYCCCAAGY TMMGKCCYCY KNAAAAAAAA       780

AATTTGSCSG CCCCAANTAA ATTCCCNGGC CCYTTGGGGG CGRANCNYNT TTTMCCSNSS       840

TKGNNNAAMC NGGANCCSGG KAAYTMMTKG NAAYCGCCSN AAMBNTTTTC TAANNCCCCN       900

YNCCCSGAAA ATTNNAMAAM CMNNKTGSNG GGGGKTTSNC SGKKGRAGGM AAAAAANRSN       960

SKTTNMCNNN SANMNCNSNN SGGNSNNNNN NNNCNCGYKC CSNAANMCCC CGCGGGGGGG      1020

CCMMCC                                                                1026

(2) INFORMATION FOR SEQ ID NO: 315:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 315:

| | | | | | |
|---|---|---|---|---|---|
| AATTCGGCAC | GAGAAGACGC | CCGARNGTST | GCGCTGGCTC | TACAACTTCA | TCAARGCGCA | 60 |
| NGGGGAACGC | AACTTCGGCA | AGATCTACGT | TCGCTTCCCC | GAAGCGGTCT | CGATGCGCCA | 120 |
| GTACCTCGGC | GCACCGCACG | GCGAGCTGAC | CCAGGATCCG | GCCGCGAAAC | GGCTTGCGTT | 180 |
| GCAGAAGATG | TCGTTCGAGG | TGGCCTGGAN | GATTTTGCAN | GCGACGCCNG | TNACCGCGAC | 240 |
| GGGTTTKGTG | TCCGCACTGC | TGCTCACCAC | CCGCSGCACC | GCGTTGACGC | TCGACCAGCT | 300 |
| GCACCACTCG | TGCCGCTCGT | GCCG | | | | 324 |

(2) INFORMATION FOR SEQ ID NO: 316:

(i) SEQUENCE CHARACTERISTICS:
        (A) LENGTH: 1010 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 316:

| | | | | | |
|---|---|---|---|---|---|
| AATTCGGCAC | GANGCGTGCC | GCTNAACACC | AGCCCGCGGC | TGCCAGATAT | CCCGGACTCG | 60 |
| GTAGTGCCGC | CGGTGGCGTC | GTTGCTCTCC | TGACGGGGCG | CGGCGACCAT | AAGGTCGCTM | 120 |
| ATGCCCAGGT | AGCGGCCCAG | GTGCATGGAG | TCGATGATGA | TGCGACTCTC | CAGCTCGCCG | 180 |
| ACCGGGAGCT | TGGCATCGGG | CCTGATCAGC | CAGGACGCGT | AGGACAAGTC | GATCGAATGC | 240 |
| ATAGTGGCCT | CCAGAGTGGC | CGTGCAMTTC | CNGCGTGCTC | CACGGCAAAT | GCCTTGATTT | 300 |
| CTACTCCGCG | TANTGTTCCC | GCATCGCCTG | CGGGATGAAT | GGGAACCGCA | SGATGGCGAC | 360 |
| GAACGGGTCT | GANCTCAGGT | TTGCCGCTTT | GCGCACAGTG | GTCNACANCC | GGTACTCGGC | 420 |
| ATANATCTGG | CCCNAAATCG | GCGCCGACGG | CGCCCACNAT | AANAACGGGC | ACNACAATCG | 480 |
| CCGCCCCGGT | CACCCNAACA | ACANCTTGSC | ATCGGATTTT | GTCCCCANCG | CTCAANCCGT | 540 |
| CCCGAACGCC | TCNTCCGGCG | NACTTTTCTT | NNAWTAACTG | CCGCTTCCGK | CCCTGGNGCA | 600 |
| WTAAATGGGA | AACCCTTNCC | CCACCTTGAA | GGGGTTGTTG | NATTTTTACT | GSTAACCCCG | 660 |
| AATTNTTCCG | GANTCGGTCN | KCCGGGSTTT | YSTNTTCCCC | ACCTTNGNAN | GGGCCGGCCA | 720 |
| AGSTTTTCTT | SYTGAAGGGG | GAAACCCAAC | TTTNTYTYYN | AACCSCMNAA | MYMTTTYCSG | 780 |
| MNAASCCNKT | CCCCTTTAAC | CAMGGSGGTN | AACCGKTMNG | NGGKTAAAAA | GGGSKNNKTG | 840 |
| NCCCCYMANG | GGGGGRAAAA | TSTKTCNNCG | GGGCCKAAAW | ACCMMMMYGN | GTGKKKNKSS | 900 |
| GCSAAATTTT | NMMRAACTKN | GGGGCCSSGA | NNTTTNAAAG | MSCCCCCSNN | GSTGKCCCNN | 960 |
| NTTTCCNNAA | WMKKGKNWNM | SNMNSCSNGG | GKYNSGGSNN | NNAAGMGGGG | | 1010 |

(2) INFORMATION FOR SEQ ID NO: 317:

(i) SEQUENCE CHARACTERISTICS:
        (A) LENGTH: 1010 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 317:

| | | | | | |
|---|---|---|---|---|---|
| AATTCGGCAC | GANGCGTGCC | GCTNAACACC | AGCCCGCGGC | TGCCAGATAT | CCCGGACTCG | 60 |
| GTAGTGCCGC | CGGTGGCGTC | GTTGCTCTCC | TGACGGGGCG | CGGCGACCAT | AAGGTCGCTM | 120 |

```
ATGCCCAGGT AGCGGCCCAG GTGCATGGAG TCGATGATGA TGCGACTCTC CAGCTCGCCG      180

ACCGGGAGCT TGGCATCGGG CCTGATCAGC CAGGACGCGT AGGACAAGTC GATCGAATGC      240

ATAGTGGCCT CCAGAGTGGC CGTGCAMTTC CNGCGTGCTC CACGGCAAAT GCCTTGATTT      300

CTACTCCGCG TANTGTTCCC GCATCGCCTG CGGGATGAAT GGGAACCGCA SGATGGCGAC      360

GAACGGGTCT GANCTCAGGT TTGCCGCTTT GCGCACAGTG GTCNACANCC GGTACTCGGC      420

ATANATCTGG CCCNAAATCG GCGCCGACGG CGCCCACNAT AANAACGGGC ACNACAATCG      480

CCGCCCCGGT CACCCNAACA ACANCTTGSC ATCGGATTTT GTCCCCANCG CTCAANCCGT      540

CCCGAACGCC TCNTCCGGCG NACTTTTCTT NNAWTAACTG CCGCTTCCGK CCCTGGNGCA      600

WTAAATGGGA AACCCTTNCC CCACCTTGAA GGGGTTGTTG NATTTTTACT GSTAACCCCG      660

AATTNTTCCG GANTCGGTCN KCCGGGSTTT YSTNTTCCCC ACCTTNGNAN GGGCCGGCCA      720

AGSTTTTCTT SYTGAAGGGG GAAACCCAAC TTTNTYTYYN AACCSCMNAA MYMTTTYCSG      780

MNAASCCNKT CCCCTTTAAC CAMGGSGGTN AACCGKTMNG NGGKTAAAAA GGGSKNNKTG      840

NCCCCYMANG GGGGGRAAAA TSTKTCNNCG GGGCCKAAAW ACCMMMMYGN GTGKKKNKSS      900

GCSAAATTTT NMMRAACTKN GGGGCCSSGA NNTTTNAAAG MSCCCCCSNN GSTGKCCCNN      960

NTTTCCNNAA WMKKGKNWNM SNMNSCSNGG GKYNSGGSNN NNAAGMGGGG               1010
```

(2) INFORMATION FOR SEQ ID NO: 318:

(i) SEQUENCE CHARACTERISTICS:
        (A) LENGTH: 1092 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 318:

```
NGNGGGGWNS NTCAYCAYCA YCACSGGGYW CWATTGCGGC CGCAWCTTGT MAASAGATCT       60

CGAAYTCGGC AMGAGGGAMT CKCTMGCNCC GCTGTGCAAN CCAATRAGGC CTRATAATTY      120

CCACTCCACA AAAAACCGTT GTGTGTAYYT SCCGRAAATR AAGGCGCCGG TNTCAACWYC      180

GCCGGTKTTY CCRATYCCCG TKTTGTAMCT GCCKGGGTSR AAAYCCCCGG TGTTGGAYCC      240

CCGGATTGAA ACTGCCGGKT TGAAACTGCC GKTTTSGCSA TCCGGKWATT GAMSTCRCGG      300

ATTAAAAAAC CGGKKTTGGN GCTGSNCGTG CCAAATNCGR AYCCRATAYC CCATGGCCTG      360

KYCTYCTCCK YCGGTACCCA AAYCTGGGTA TCCTATACTG GYCCCTAAAK GCAAWYCKGG      420

GCTGYCMMTK TTGCKGGSGT CCNAATTTAS CACCASCGGT TCCTTCCATA CCNAAACNCG      480

CKTGGGCWCC AGMCCGRAAA AAAKAATAAT RAKAAKGGTG CATNYCCAAA ACCNCCGCCN      540

CCCNANTNCN ATCCGNTNCC MSCNCCCCCA GCGGTNAAGK TKSGGAAYTT CTMMAACCCC      600

CAAANCCCCA TAACNTNCGR GAASAAACCC CTYCNCGGGG GYCNWNCAAA ACASCNTTAT      660

TTGCTKSTTT CGGGMWCCGT GCCGCCNAAA YCCCAAASTA CTTTYTGGGT CCNAGAKAAA      720

ACCNCGGGCN CCMCCCSNAA NWTATYTCTT KGGCAANCCC CSAAACCTTR TCMNACCNCK      780

ATRMTCCCTT CCCCVSCAAT TGGYCGGRAT NCGSNCCYTY TCAAAKKKSC CAKWWNNGNG      840

GRRNNACCMA ACCCCAAGTY CCMNAAAATN GKCCCCGCTC CNAACACGNK TYYTCCSAAA      900

ASCCCWCCCC CCCCCCCCRAA AACCCCCCNA RKANTNCCCA AAAACNYNGK GGCCCCCCCC      960

CAAACMAAAA AMCCCCCSGM RMACSGGGGN NMCCCCGKKK KKTTTTCTTT TKCCMRSCCC     1020

AAMGCAMWSY KSKTNMAAAA GGAAGRANCN TYCCSANANM TCCCNYWRSW CCGSWGMGNA     1080
```

GAASMCCCCC CS								1092

(2) INFORMATION FOR SEQ ID NO: 319:

(i) SEQUENCE CHARACTERISTICS:
        (A) LENGTH: 1251 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 319:

GGGGGGGNNN NATACATCWT CYGTGYACCG GGGMTCTAKT GGCGGGCCGC AATCTNGTCA   60

ASAGATCTCT NAMTTCGGGC ACAAAAACTW GACAAASYMT CGNGCNMTCC GTGTCCTNKA  120

TCGCAAAACG NGTRACASAC ASACACRTAT GTGTGCCCAC CASCAAYTCK TTGGGACCTC  180

GCTRACCGGY TGCCCRNACG CCACGYTGCS CWTCTATCCC RACGCCGGCC ACGGGYGGGG  240

ATATTCCAGG CACCACGCCC AGTTTGGTGG ACAATGCCCT GGCAKTTTCC TCRAANTTCG  300

TGAAACCGAA TTCNSMTTGA ACCNCCAARG CCCCSNCCNR AACARTTGGG WTCCGCGGTT  360

CTCCCCACCG KTTTCCGGGG GTNTCGGCAN AANCGCACCC WTGGWTTCTM TCNCCGCACC  420

GGGCGGACAA NTCGGGTTGC AATTTTGCRA AYCGGGGCCG GGATTCCSCA AACGGGTGCC  480

GAAACTGTTY YCRAAMACCG GGAKCCGCAA TTTCCGGGCR ANAAATTTCN YCNCACCACT  540

GCTTRTACTT CCCCGACCGT AACMANTTTC ATCGTCNTNN CCTCTGCCCT TGGGGCAGGG  600

CKAAAYACCG CMTTKGGTTT CGCAACCTGC GGCCCAANTC CCNAMCCRCA CTTTCNATTT  660

GGNTCGAATT SCCCCCCGGT RANAACCSCC NTGGCCNNYT CGGASSAAAA NGGGCCCTNT  720

KGGCNSCCCC AGTAANACCC TACCNNAYTS CAWTCTTTGC CAAASTTKGG ACGAANSKTG  780

GGNTTCCGGK ATTTYYTTGS GGNCNCCCTN TATNGGSNTN GGGCCKCYNC NCSTKTGKCA  840

NASSKAYCCS NGNKGGGGGT ACCCCCCTMG GGGGGTTTTT NSSGCCCCCC AWAYGNKSTG  900

GCCCCCNNGG GGAAKAATWT MWWTMCNSGG GGGAAWTTTT NTSTGGAMCS SGGACYCCCR  960

GGGGGKTTTT TCCCCCNCSA NNAWANGGGG GGGGGANAYT NTGNSGNGGG KWNTTTATTT 1020

YTYYCYCCTM TKACMSGGGG GTTTKKAKNG GGGGAGAAA ANAAAAAAAA RAKGGYKNTT 1080

TSKNCACNCT GKWNWNWANR NAGAGKTCCT CKCKCCNCSG SNTTTCTTTT MGNSGSYGGG 1140

GNNGNNNAAA ACNKSRMMAC KCSYTYCCCG CGYCTCCTCC NCNGGGGYGS NGSCGNSTYN 1200

GNNKGRKWTA TNTMGNCGTN SCCTCCNCCC GCKNKNTGTC TMTCNMYGSG C         1251

(2) INFORMATION FOR SEQ ID NO: 320:

(i) SEQUENCE CHARACTERISTICS:
        (A) LENGTH: 1099 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 320:

AAYTCGGCAC MGAGTATCAC CAAKCTGYGT GGCCCAGCAA AGTGGAGCTA TTACTACCTG   60

TATGTGATCC TCRACATCTY CTCCCGCTAC KTGGTCGGGT GGATGGTGGC CTCGCKTGAK  120

TCRAAGGTCT TGGCCRAACG GCTGATCGCG CAAACCCTTG CGCCCAGCAC ATCAKCGCCG  180

AACAGCTGAC CTGCMCGCCG ACCGGGGGYC GNCAATAACT CCAAACCGGT GGCMCTGCTG  240

```
CTGGCCNACY CCGTGTCCCA ANTCGAACTC ASCCSGCNMA CCAKMAACKA NAACCGTTGT      300

CTGAAGCCCA GTTCAAAAAC CTCAAGTWCC GGCCCRACTT CCCGAAACGG TNCGAGTCKA      360

TCRSAGGSGG CCGGGTGCMC TGCAACCGGT TCTTCGGNTG GTRCAMCCCN AAAMCAAGCA      420

TTCCGGGMTC CGMMTGCCCA CGCCGCCAAS TTTMCTACGG GCSGSCCNAT CAAATTCGCC      480

GGGAACSGSN CCMCCKTCNK GGAMACGCCC TWCCAAAACC CYCGAACGGK ATCCTTCKGY      540

NAACNCCCGA RCNCCCKSKT TCCGGGCTTC NMSGCGAATA CCCKNSCMNT CCGAATCCAA      600

TTCCCMKYGG CTTTTYYYCC CCCCGGCCCC AAAYNGGGYC CCTASSNMKC KNCCAMNANT      660

CCNWATCTGG NGGTCCCNAN KYYGGCGTTC NMAATSAMNA NMNRGGGTYT TSCYACCMMN      720

AACCGKNNKG KCCCCMKCTK MANAAAKATT RATCAMKWNG GGNKCKCNCN NAAMACCSCN      780

CNCYNCWYTC TMYCSSKWGC GCSMYNANCA SNGGGGAGGW GGSGRMKMCT CTMTCTCNCT      840

MGCGCCKNTN TYCKSGAKAT ACASMNKTCC GCGCNGCGCN MAAMANRAKA CTAKCCGYGN      900

CCSNSTMTYN CTSNNMKMNN TCCWMWNATC NTYYGKKCNN KCTMKATNWC CSCTSKCNCK      960

MRAMTCKTYG SNMTCCTCCA TCNCTCKKSC SNMSKNTCKC KSCNCCNCWN CNKCNMKCWN     1020

GGNSTCRCCY TCTMNNNTCS AGCKCGSKNC WACNCACACK NGWCTYTTCC WKNNMKCNKM     1080

TCKCKCACRG MTMTCWCCS                                                 1099

(2) INFORMATION FOR SEQ ID NO: 321:

(i) SEQUENCE CHARACTERISTICS:
        (A) LENGTH: 296 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 321:

GNGNTATACA TCWCTGTGYA CCSAGGATCW ANTGCGGCCG MAAKCTWSTM CASAGATCTC       60

AAAYTCTGCA MGAGCGGCAC AKAKYSTCGT CCMRACCCGG CAYACWCCWG CNCGCCCCWT      120

CTTRGACCGG GGCKATASMC ACCGTTGGCC CCGGCNCGCA CCTACACCAC CCACGCCGCC      180

AGCGCCCCCW TRAMCAAACC ACCCCGCKTT TACCGCCCGC GCCGCCGGGG CCACCACCAG      240

CCCCACCGGC ACCACCGGCG CCGCCGTTGC CAAAACAGGC CCGCKTTTGC CACCRA         296

(2) INFORMATION FOR SEQ ID NO: 322:

(i) SEQUENCE CHARACTERISTICS:
        (A) LENGTH: 1073 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 322:

NGNGSGNKMY ATCATCWTTC TGCACCSNGG MTCWATTGCG GCCGCAATCT TSTMNASAGA       60

TCTCGAAYTC GGCAMGARCA TCTGCGCGGN GAATGTCCAA AWGTCWKTAA CGGCMATCGG      120

TTTGCCGYCA ACCACKCTRT SCAKATGCGG GCCAMWTYCA AACCRATTAT TGGGYCGAG      180

AAAATTTMCG CKTGTRASCA ACCTGCAGCG GGTCAASCAA CAGCCTCTRA ACCGTAAATY      240

CKTAGGTNKT YCCGGCAACA ASCYCRATAA TSCGGCCCGC AMCCACAAAA CCTGANTNGT      300

TNTTCNCRAA NCCGGTYCCC GRAGGGGTSA ACTGCSGTAR GCTTNTCWYC NCCTTRACAT      360

TAAACCCCCC CGGNTCWTCG CCGCGCCCAA ATYCYTGCCC WTKGCNACCA YCCCANCCTG      420
```

```
CSGTATGGTS RAANCASTSG GCRAACGGTM MCCSTACCKC TGGCTGATYC KTCGGNTCCS      480

SNAATTCGGG GATTTACGGS CAMGGTTAAY CCAGGYCCCC TNTGCYTCKY CNACAACCSG      540

ATCMWCNCCG TACCTKTTAA AATTCTTTGT GGTGGAACCC AWYCKAAAAA NMTNTYCCCN      600

TCCAMMGGGG CYCGGAAKKT CNACNTGGKT NACCCCTNCC YTTGAASTTT TCYTGNCCCC      660

GGCCCKAAAS ANACCSGAKC CCCGGAAYCS WTAGGCYTCN TGCCCCSTTA AATTKGNCYC      720

AATCCKCCAA CGCTCCCCGG GGTCSSCCMT TAAAMTTCCC CCCKSCASNG GAATYCYKSG      780

GCWGTMATTW CCNCCCNTTT CYYGKNAAAC SCCCCCWKGN GSCTYCCCCN SNTTSSGCCS      840

GGTTSGAMYC AAAAWTNGGG MMCNRAGNCG SGNAMCCSCN GKKGGGSATW TKAAYYCYGG      900

GGGGGTCNYC CCCCRCSNAA AAGYGTKGGC KCCSSSCCYC CCMARTTTYT CNGGMRCMAM      960

ACCANGGGNG CTCCCGTNCW WGGCTCCCSN SNSMAMAAAN NKCKCCKGGS CKGARRNMNA    1020

MCTCSNGNGG WTCCCKNKTC NSCNSGNCGS YGGNSASWCC YNYCNCCACA ANC           1073

(2) INFORMATION FOR SEQ ID NO: 323:

(i) SEQUENCE CHARACTERISTICS:
        (A) LENGTH: 1166 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 323:

CGCCCCGTTC TTMMMTTCAY TCATTCACCG GGMTCTAGTG CGGCCGCAAK CTTGTCKACA       60

GATCTCGAAY TCGGCAMGAS ACAATSTCGG GTKGGGCAAT GTCNGGTGGG GCAACTTTGG      120

GCTCGGRAAT YCGGGGTTAA CGCCGGGTCT RATGGGTSTG GGTAATATCG GGTTTGGTAA      180

TGCCGGCAGC TACAATTTCG GTTTGGCAAA ATATGGGTGT GGGCAATATN GGGTYCGCTA      240

ACACCGSCAS TGGRAATTYC GGTATTSGGT NACCGGTRAY AAYCTGACCG GGTNCGGTGG      300

TTYCAATACC GGTAACGGGA ATGTSGGTTS YYYYACYCCGS GSAACGGNWW YTTNGKTCCT      360

TMMCNCTSSM CCKSAAMTSM KMGGTSTYCT MTYCNNGGAS TAMTYNMCCC CCGWAYCKSC      420

WAYCCCTCGT CATYCCMCMC SGSGYCCTCA MNCCACCYTG NGYYCCCTCC MKMTCYCAYT      480

CMNTCCGGTW CCTNTMMNCC CSCNCRYCTC AMCNCTKSGK CACCNATMYC CSACKCHTCT      540

MCYMCSCAKN MTTCCCCTCN CCTYTNNCCA MCMCSCTCTM TCMAACTCKC CCGGYCKCNC      600

MYCTCTCKCC AYNMAACCKK TYCYWCNWYC YMYCKCKCAG WYKNMCTCCW ACTCTMYNTT      660

TCTCTCNKCC CMKACCKNTT CTCWCSCCCC CCACAKAYMC YAWCMTMTCC MCTCKACSCC      720

CYYCNNYCCM NMCWCMTCWC TWNAKCANCN TTCTTCTCTC MMYMTMACKC WCNNTCNCCK      780

SGACCYTCTC ACTKMKCCCKM TCTCCTTMCK CCYMWCNTCC MKYNCCCTCC NMTCMTCKYT      840

CCTCNCNMRY CYYYAKCAKC NMCTCCCCAN KMCAKCTKCT CCCCCAKMKS ACNCKCCCWC      900

CCTCCTATCC WCTCTCWCTY ATCTCKCTCW CNYCMYMKMC ACNCKCYAYT CNACTMNMWN      960

CCANCNCTCT CTNYCTCWCK ACGTYCKCCK CTMCKCNYMC NRWCTYRCCT CKKCCNCCRN    1020

CKNMCMKCTM CTCTCCWMKM TCCCWCCCAT CTMMKSTCTC WCNCMTCCCT CNKCCYNYNT    1080

KCYTYCCMYG CTTCKNTCMT MCCWCCYATC TCTMKCCTCT CWCACYMCAC WMTTACWNCC    1140

ACTCTCTRCW CKCCKCMCCR MTCTCB                                         1166

(2) INFORMATION FOR SEQ ID NO: 324:
```

(i) SEQUENCE CHARACTERISTICS:
    (A) LENGTH: 1230 base pairs
    (B) TYPE: nucleic acid
    (C) STRANDEDNESS: single
    (D) TOPOLOGY: linear (ii) MOLECULE TYPE: Genomic DNA (xi) SEQUENCE DESCRIPTION: SEQ ID NO: 324:

| | | | | |
|---|---|---|---|---|
| NGNGGNNNNT | CWTACATCWN | TCTNCACCSG | NGMTCWATTG | CGCGCCGCAW | NCTTGTMNAS | 60 |
| AGAATCTCNN | AAYTCGGCAC | ANATGTCTTT | TSTMTAKTGT | GGCGGGGNGC | CACGCCKTAT | 120 |
| GTGYGCCTGG | GYTRACCCAA | CCCCGCGGCS | CGGGCCRACC | AGGCGGGGRA | TSCAGGCCGC | 180 |
| GGCGGCCGCG | GCGGYTATAT | RAAGCGCCGY | TTTTKTRATA | ACGGTSCCGC | CGCCGGGTRA | 240 |
| TTACGGGCAA | AAYCGGKKTT | TTGGGTRTAT | AACGCTAATT | GCAACCAWTT | TTTYCGGGTC | 300 |
| AAAAACYCGG | CGWGCANATC | NCGGGYCNCT | RAGGCGCATT | YMCGCCAAAA | WTNTGGGCGC | 360 |
| AAAACCCCKT | TSYTATTTTN | TGGGCTATSC | GGYTGCTTCG | GCAAACGCTY | CCCGGGTTAA | 420 |
| TCCCKTCCGC | GGCGCCGCCN | AAAAACCACC | AATYCCGYTG | GGGGTGKYCC | CMCAGGCSGT | 480 |
| TGCTYCGNGY | CACCTGGCCA | AAYYCCCAWT | AKATTGGGTG | SCYCKTSCGG | TTSYTGGGCY | 540 |
| CAATTACCCC | CNCGGGNAAA | GRRAAAANAA | ATCNTCCNTT | TGCTCGGYCA | YCTTTMTTGG | 600 |
| SAAAAGGGGC | ATGGCSCGGT | TYYTTTACCT | CAAYCCCCNA | NCANTWACCT | YTCCSCCCGG | 660 |
| GGGGNCANAA | CGSTTNGCTC | CGSGGNAKCC | TKGTMCCCGN | ATCNAAAGGC | CNGAATTTGG | 720 |
| TYYSSTYCNA | ATTWTWKKKY | CCCCWCNTTG | YAAAAAKCCA | AAASAKCCCK | YCNCAMMYKT | 780 |
| NGGGGTYSSG | GCCKNYCTTK | SNMTTAAACC | CYCCCCAAAA | YYNSGGGKKT | TCCGCYNSAT | 840 |
| KCCACCNCCK | GNGGGGGNA | SAAAAAAAAY | TTTYCCSAAA | ATCCCACCYY | TCYKTKSTRY | 900 |
| AMACCCCCTT | TYYMKKAYTC | CKYSCNATTC | SGMTTCWAAA | TYCCGYGGCT | TNTTCCCCCK | 960 |
| CSGGNGCCCC | AAWTTTGKTT | YNCNANTTYC | CCCNAAMNCM | AWTMGGGGKS | KCCATTCTGG | 1020 |
| SCYTMAANTA | AAANAANGGG | NKTTTYYCTY | MANAAACACN | GTGKCNCNCN | CNAAMAAASN | 1080 |
| AKMAAAKAGN | KKKMTKNNSA | AANCCNCCCC | CTSTYTNYTT | NKTNMNCKCC | CYGGKKNKGM | 1140 |
| SWSWYNTTCT | NCCCRCCCCC | YNYNKTGANA | AAMMNCYCCS | GGSTMCRNAN | ASNMNTTTCK | 1200 |
| STSTNGMGCC | KMBASNANAN | MCAMWKWYCC | | | | 1230 |

(2) INFORMATION FOR SEQ ID NO: 325:

(i) SEQUENCE CHARACTERISTICS:
    (A) LENGTH: 1022 base pairs
    (B) TYPE: nucleic acid
    (C) STRANDEDNESS: single
    (D) TOPOLOGY: linear (ii) MOLECULE TYPE: Genomic DNA (xi) SEQUENCE DESCRIPTION: SEQ ID NO: 325:

| | | | | |
|---|---|---|---|---|
| NGNGGGKNNA | TMAYCWTCTC | ACSSGGTCTA | TGCGGCGCAW | CTMGTMAASA | GATCTCNAAY | 60 |
| TCGGCAMNAN | GCATMTCMMC | CATATATAAC | CATTGCGTCS | GYWTGCAWCT | CRAAWCTGTC | 120 |
| CTTCSKGCCG | TTKTACRAAG | GTGGMWTGYT | CWTYCCTRAA | SCCCTCRATC | TCKTKTATYC | 180 |
| CTKGGGCTYC | ACTTTAACSG | RATKSCTGCC | TTKTAYCATT | RATGCAAWTA | WTGGYCRAWT | 240 |
| KTTGCAGGCC | RACGGCWYCT | TTTYCCGCRA | GRACAATGA | TTGGAWYCGC | TYCGCRAGGC | 300 |
| CCGGCACCAR | ACCGGGCNCC | AAAGGYCCGC | GCAAWTSCCT | GGKTCAAAAA | TGGTGCAAAC | 360 |
| AAAMCNATCC | CCGGYTTRAC | CGCAGYTAMC | ACAAKAAAAT | TCCCWTGGCC | GCACCAWNNT | 420 |

```
TTYCRATCWY CWYCCCCACC TTRAACTTGK YTGCSGTATT GCCTKCCTGC CTCRACAGCM      480

YCNCCCKTCA AACCTGCGGT GACTCCAACT GGTCTGGYCG AASGGGGGYT CAMCGGACAA      540

AACCCCRANN TCGCCAAATT TTCNCCCCCC CYCGGGAAAN GKTGATMTTC TCSNAACCSA      600

CMGGGNNYTW NAACCCTGAA CSSSGSNKGA MYNSCCSGGA ANTTTTCCCT TYNGGGCGRN      660

AAANCCTTTT AAGGTACCCC KGGNGGGGKG CCCYYTTGGG AAAACAACCC CKATTGGKTT      720

TGGAAATNTT TKCNCCCCCA TTCNSGGGGG GGGCCCCAMC CCMMCTTTTN TCMSCNMTYY      780

YCYYGGGAAT TNYTCGCCSG GAAYYCGGSM CCKGYCCTAA NCCCCMNWGG GKYSTGSNAR      840

GGRATMAWWT TYSTTTYYMC CCGGCNNCCC CCCKAKMCNT KGNTGAACMA AAAKCSGGGG      900

GSCNMYMWYY YCNNNGNRTT TNRGGSSNMT TYMAAAMMAN GGGGKYWTYY CKCCNGSCNN      960

GKTYSGGGST TTTCCNTTTS GGGSSATYKG MACCCCKTMT AYCCGGGGGT NTKTKYCCCC     1020

SC                                                                   1022

(2) INFORMATION FOR SEQ ID NO: 326:

(i) SEQUENCE CHARACTERISTICS:
        (A) LENGTH: 1083 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 326:

NNCGNNKNTA TAMAYCWYCT NCACCSGGGA TCWATTGCGG CCGCAATCTT STMAASAGAT       60

CTCKAAYTCG GCAMGANCCG CAWCTATTTG KGTGRASCGC ACCAGCGRGA CCTCGCSGKT      120

CKTTYCTTGC AGRGAGGCCK TGGGTGGCRC CGGTGGCAAT GCCAACCGCC CCCCAAAACN     180

CCGCAAATMY CRAAAAACAA CCCSGGGGTA GKTCCSGGCC GCCAAATMAA TAACCGTKTT      240

AACKCAGGCN ACGGCCAACC GGYCCCGCCC AACCAAGCNA CCTCCCCSCC NATAGGYCCG      300

GTGGGGGCTG CCKTATYKCC AASTCGTCAY CTCNACGGGM CGGYCCMCWT TCCGCCTCAT      360

CCGTCTCTCC TTMMATTTTC CRTCCACYKG GCGGGGAACY TTTTTNYCNC CCTTGSCMAN      420

CACCNAAGGY CNAAAATTNC CCMTGCCKYG SNNCAAAYGR GATTGGGGTY CGKKTTTTNT      480

TCNMCCMAAC CCCCNTTTNA CGCCCCMATC CCYTWATACC CCCWWMCMNS ANGKTTGNSA      540

AAKTNNCCCC AAATRCCAAA MTTCTTCGCC NTTTMTWMCY YYCCTTTCCC CMCCCWNAAA      600

GGSCCRCCYY TCGGGAANTY TCCCCNCAAA AWTCAMWCCM TTTCCCNCCA AGAAWTTCSG      660

SACTCCTTTN TTCNGGGNAM ATANATYYTT YCKTNGGGSK TTCCGMTCNC AMMAATNTCC      720

RGGGKAAMCC AGKNTNNTCC YYYYCCCCAA NNTYCCYKGG RMCYNNYYCY TTAAANRASR      780

SAACCCKSGG GKCYNCNCSS TARCCCCCAM KAAAATTTCC CCCSSKTTTC TYYNNKKMRW      840

GCCCCCSAAM ACTMTWAYTT TCCCKCGNNN TTTSYCCKCS KCAMWMWMTG KKNCTTTTTT      900

YCSCMATAMA CTTNGGKCCT NTCNYGSGCG CMAAANAAGG CGCGSTTCTN TTCWMAMACA      960

YNTSGNMMMA SAAKAKWATA AWNNTRKKYK TKNNCCCNCC CKCKCTTSNN TNKCCMCSKS     1020

GGGKNWNKKR GWCTCCWCNC CKCCCNCKNK CCKWATMCCC CCCCSKCCGM NCMMNTTTKT    1080

CCC                                                                 1083

(2) INFORMATION FOR SEQ ID NO: 327:

(i) SEQUENCE CHARACTERISTICS:
        (A) LENGTH: 1069 base pairs
        (B) TYPE: nucleic acid
```

(C) STRANDEDNESS: single
        (D) TOPOLOGY: linear (ii) MOLECULE TYPE: Genomic DNA (xi) SEQUENCE DESCRIPTION: SEQ ID NO: 327:

```
GGGGNNKYAT MCAYCWTCTS YACSGGGMNC TATTGCGGCC GCAWYTNGTM GASAGATCTC        60

GAAYTCGGCA MGAAAAAAGW GATGTGCTGG ACCTTMCCGC GCGGGACGCR ACCRACAAAG       120

RAASCGCGCC ANAATATTGG CCACAKTTGG TCACATATTT ACCCAATTMT AYCAGGGAYT       180

MCCATTCCKG GGACCRACCG CACAATCCCR ATSKTGGTTT GCRAACCCTR ACCGTCCCCA       240

MYTYCGCCRA STTGAACCAG GGCRAAAAAA CGGCCRAAWY CTCGCCCTGA NTCCCGCTCS       300

GCGCNAATAA CTAGGCCCAT TKAACGGAAC CGGNGGCCSC NANTTGGCCA ACAGGTCCTR       360

ACAAAGGGGC CCCASYYCGG CCGGWTCCCW TTYCACNCCC TNKTCTCKTG CCGAATYCGG       420

WTCCRATNYC CCWTGGGCCT TKTCKYCKYC KYCGGTNCCA AWTCTNGGTA TNCTATRGKG       480

TCCCCTAAAT SCANATCTGG GCKYCCATTT NCTGGSNTTC NATTTAMMAN SRRCGGTTCT       540

TTCWTTCCRA AACCGSNTGG GCCCNNMCCA AAAAATGATN ATAATAATGK YGSCTTTCAA       600

ACCCCGCCCC CCCATTCRWT CSGTTCCANC CCCCNGNGGT TAAGKTGGGA ATTTYTNAMC       660

YCNARGCCCT NATTTSGGNA AAACCYCYC GGGYCTCAAA CMNYTTTTTT GSKSSNTCGG        720

GCTCRTTCSC CAAAACCCAA ATTNTYNYGG GGYCCKTNAA ACMCGGYCRC RCCGGAAATT       780

TTTYTGGTTC AACCCCAACC TTTTCAASCC NTTTTYTYYT TRCCSSCSMN TNGSSGGGNT       840

KSSCCNTTCY RARKKCCNMN GGGGGWYCYN CCCCRMNTTT CTTTTTTTTT CCGTNNMAAM       900

NGKTTCTTCA AASMCCCCCC SCCCCCNSAA ACCCCCTNAR GTTTTYCMMA AANNWYNNGN       960

KNCCCCCCCC MMNAAAAAAY YCSCCCGNRN ACSMSNGGGA MCCCCCGGSN NTTRKTTTTT      1020

TNCMSGYCCC CSRMASYYTT TKAMAMANRR GAMNSMTTTY TNNRGNWNK                  1069
```

(2) INFORMATION FOR SEQ ID NO: 328:

(i) SEQUENCE CHARACTERISTICS:
        (A) LENGTH: 1210 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 328:

```
NGNGGGKWK MATACATCWT TCTTCACGSG GGATCWATTG CGGGCCGCAW TCTNGTMCAA         60

SAGATCTCGA TYTCGGGCAM NACCCACCWC TCCRAAAAAA ACCCRAAWCT CGGGSKCTYC       120

GARAAGTGTT GCCCGCKTTR AATTTAACAA ATTCAGTGTC ANAGTGTCAC GGCKTTACWT       180

YCCCGGCAAA GGGGCCACAA CCTGCAGRGA SCACYCRATG GKTGYTGKTS CNCGGGCGGG      240

CCGGKTNAAG GGACCTGCCT GGGTKTGCSC TMCAAANATC WYCCGCGGGT YCGCTGGRAT       300

MCNCAGGGGT GTCAAAAAAC CGCAAACAGG CACSCCANCC NTTTACGGGS CTTAAAANGA       360

AAAAGGGCTG ATGCCCCCAA GGGGGCCCGC NCCCAACCTT CCGTTGGTCA ACAACCCGGT       420

CTCTCKTGCC RAATCCGRWT CCRATNYCNC CWTGGCCTTK TCKYCTYCTY CGGTACCCAA      480

ATCTGGGTAT CCTATASTGT CCCCTAAWTT CCAAATCTGG GCTGTCCATT TSCTTGGCNT       540

TCCAAATTTA CCANCAACGG TTTCTTNCAT NCCAAAAACC GNTKGGCKCC NRACCCRAAA       600

AAATGAATAA TAATAANNGG KCNNTTYCNA ACCNCCCCCC CCCNATTCCA TYSNGTTCCA       660

NMNCCCCCAG NGGKTAGGTK GGGAAANYYC TCMACCYYCA ANCCCTWARS TTTTNGRAAT       720
```

```
KAAACCCTYC YCNGGGTCWW TYMAAAAAMA NTTATTTGGN NGNTTTCGGG MWNCKRKNST        780

SCCAAAATCC MAAATANTTT YYTGGTYCNA TWAAAAAMCG YGNCCMNCCC GGAAAAWTTT        840

TTNTGKTTSA ACCCCAAAAC YTTTTCMNAA NCSSKTTTTY CYTTCCCCCC AMNWTGGGYS        900

GGGNATKGYG SCYTNTCTTA TKTKYTYMTW CMGGGGGGNN MKMTCMMCCC CCMTTTYYCY        960

NYWRTTTTTN KCCCCKTNMR NNRAANNGGN YTCSYNANAA AAGCNCCCCC SCCKNCCCNA       1020

AAAAWCCCCN NNNARAKTNT TTMKANNRMN SCKCNKNGKY YCCCCCCCWC YNMNNAAAAA       1080

AATMYCCNCC RASANMCASM NMGGRGNRSC CCCCCCCSTT NNNNTMTTNT TTTTTTCSRA       1140

GAGCKCCSCG MNNANMKNCK CTTTTTKCNC NNGNNGNGNN GGNGMNCKCC CCNAGAAMWK       1200

CTKSTCCCKS                                                             1210

(2) INFORMATION FOR SEQ ID NO: 329:

(i) SEQUENCE CHARACTERISTICS:
        (A) LENGTH: 1105 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 329:

NGSSSNGNNA TMCATCWYCT GYACSGGGMT CWATTGCGGC CGCAACTNGT MAASAGATCT         60

CGAAYTCGGC AAKANACACC ACCGCCGTGT MTATACACCG CAAATGTTCT GTKTGCCAAA        120

ACCGAGACGC GCCGGCCGCG GGGYTCCAAC GCKTTACYTR ACCCGCCAGY TCAGTGTTRA        180

AACCGGTGYT RAGGGCCGCA CCCAACWTAA ACGCTTTAKC CAAGRAWYTG GKTGGCCCGC        240

AGCCACCTGY TGTGGYTGCC CTCWYCGGTG GTAGCGCCGG TTANCGCCGG TTGCGCGYTC        300

AMCASCSCGC CGGTRATCCC AKCNWTCCCC CGGCCMRACC CACCGGGCAC TTTGRACGGT        360

GCCGCCAATT CAAAYCKYCT GRWTCCTTCM AAACACCACR AAGGCCACCM CCMSCACCNA        420

ATMGGGRACT TTAAGGCCCA GGCAAAAACCT NTRAKCNCCT CCCGGGCRAA GGTCCSGCAA       480

SCRATCCMAA AAAAKCKNAT TTCCCCCAGC AKCAACCCAA MMCGSTTTGC TGCTTCCGGA        540

TTCGAAMCCA ATTMCWGGKT NCNWGGGAAA AACASCNNCC NWTAKCCMGG CCCMCGGGCA        600

ATTTCSGRAA SAACCCCTNY CCCGGGTTTT YCCTGCTCMG GCCCAANACC CCCGGGAATC        660

AAAAASGGTC GGNCAAANGG GCMAAACCCS SACCCMACTT WTTCCRCTTN GGGGGGSCWN        720

CCKNGTTTAA AWKSCCTCYY CTSCCCAAAY TCGGKCMAAA NNGRKTTGGK TTNGGCNACC        780

NTTTCCGGKC CCGGGKGKGK WGKYCTMNMA CSTTTNTTTT SCCCCYKAAA NYSCCCCCCC        840

CGGSSCCCCG CCCGGGGGGA NNTTTTTAMA GKKTYCCCCT CCCCAMAAAA ANACCCCNYC        900

CCSGGSCCCT TTKRWAAAMN KCTSCCCCNG GNNGGGGKCM GGKTTATTMT NNNCCSCCCC        960

TCCGCGSAAA AAATAKMTTT SYCCCCCCNC CTCCKNCKNR GKAMSMSCGC TCCCYCTCNC       1020

GCNKNTWAAN ARSNCCKKNN CCNCYKCCGS NSNGKCNWCD NCCSTSSNCT NKGCNCKNCN       1080

KAAANAAYNC NGSMSTSSMN CNKCC                                            1105

(2) INFORMATION FOR SEQ ID NO: 330:

(i) SEQUENCE CHARACTERISTICS:
        (A) LENGTH: 936 base pairs
        (B) TYPE: nucleic acid
        (C) STRANDEDNESS: single
        (D) TOPOLOGY: linear
```

(ii) MOLECULE TYPE: Genomic DNA (xi) SEQUENCE DESCRIPTION: SEQ ID NO: 330:

| | | | | | |
|---|---|---|---|---|---|
| NGSNSNKNNN | TAMAYCWYYC | TSCACSNGGA | ACWANTGCGG | CCRMAWCTNS | TMKASAGATC | 60 |
| TMGAAYTCGG | CAAGAGCGGC | AAGAGTGTGT | GCATCTGGTC | ANAGTSTMMA | CRCGGTGCCG | 120 |
| CSGGTGKGTR | GASCACMCAT | NTGCGRACAC | CAAACCCKTC | GCGGGYCACC | GGCKTCGCCT | 180 |
| GCAAAWYCCT | CCAGGCCACC | TCRAACAAYW | YCTYCTGCAA | CGCARGCCGT | TYCGCGGCCG | 240 |
| RATCCTGGKT | CASYYCGCCK | TGCGGTGCCC | AAGKTACTGG | CSCAYCAAAA | CCGCTCCGGG | 300 |
| RAACRAACKT | AAWTYTGCCG | AATTTCNTTC | CCCTGCGCCT | TGATAAATTT | NTNAAGCCAC | 360 |
| CGCAAMCCTY | CGGGCKTCTC | CTCKTGCCRA | ATYCGRWTCC | RATAYCGCCA | TGGCCTNKTC | 420 |
| KYCTYCKYCS | GTACCCAAAT | CTTGGGTATC | CTATANTKYC | CCWAAANRCA | AWTCTGGGCK | 480 |
| KTCCATKTSC | TGGSKTCCRA | ATTTAMMACA | NCGGTTTCTT | TCWTACCAAA | AACCSNTGGG | 540 |
| CCCCRACCRA | AAAAKGATAA | TAATAAKGTG | CWWWCAAAAC | CCCGCCCCCC | RRTTCAAYCG | 600 |
| GTCCARCACC | CCANGNGGTN | AGGTNGGAAT | TYTMAACCCC | CAGCCCATAA | SNTTNSGNAA | 660 |
| AAACCCCCCN | GGGYMYCAAA | AMMCTTTTTG | GGGMTTCSGS | CCATKGYKCC | AAAACCAAAA | 720 |
| TMTTTCYGGT | CRWAAAAACC | GGCCCNCCCG | NAAATTTTTT | GKCAACCCCA | AACCTTTMAM | 780 |
| CCNNNTTCYY | YCCCNSACAA | TNGGSGGNKN | NGSSCNTTYT | TWTTTYYNNA | GGGGGGRRWC | 840 |
| SNCCCCNAAN | YYCCNAANKG | NKCCCGSNMA | AAAGAGANTT | YCMKAAAAAC | CCCCNCNCCC | 900 |
| NAAAYACCCC | MAAAKWTTCM | AAASMSCNNG | YCCCCC | | | 936 |

(2) INFORMATION FOR SEQ ID NO: 331:

(i) SEQUENCE CHARACTERISTICS:
        (A) LENGTH: 1042 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 331:

| | | | | | |
|---|---|---|---|---|---|
| NNNGNKNNNY | ATMMAYTCWY | YCTSCACCSG | GGNNWCWATT | GCGGCCRMAW | KCTTGTMAAS | 60 |
| AGATCTMNAA | YTCGGCACAG | ASSSGCACAG | ASCCGCGGCG | CTATYCMYCC | GYTGCTCATG | 120 |
| CTCAACACGC | TCKTCGGCGW | GRATAATGGC | NCGCCGCCGG | CGCCAACACG | YTCAAYTGCT | 180 |
| TCGCCAACGC | CATATNTCAA | CAAGGTRATA | AAASCAAAAC | CGCSCGCCGY | GCCCTTGGGC | 240 |
| SCGGRAASCG | GTGCCAACCC | RAAACNCKTT | GGGCACYCGG | KTSRACTTTA | AASGGTAATC | 300 |
| TCKTCCTCCT | GGGCTATGGT | GCGCCACAAA | CCTSYTGGCG | WGGGTCTGGC | CCTGGGYCAC | 360 |
| CGYCRCNTTT | TATNTNTCCK | YCTACACNCT | TKGGTYCAAC | CAACCCACTT | CACMAAATTG | 420 |
| TTTTGGGKTG | GGGSSGCCGG | YTGTNNCCGK | TAATAATCSG | NTGKTCSGCC | MYCACCGGWA | 480 |
| CCATANCCTG | GCCGGCSCTG | GCAAATTTCC | SAAATCATYT | CCTTCTGRAC | CCCCACAMRC | 540 |
| CTNSAAATCC | GRATCAATNC | CCCNKGGCTT | NTCYCTCTCN | GTRCCCAATY | TGGTTTCTAT | 600 |
| RKTNCCCYAA | TSCAATTGGS | TTYCCRTTSC | YGSTTCCAAN | TTNACAAMAS | GGTTTYTCMT | 660 |
| ACCAAAACCC | NTGGSCCNNA | CMNAAAAKNA | RAAAANAKGG | KCTTTYAAAC | CCCCCCCTAT | 720 |
| TCAWYCGGTN | CMRNWCCCCG | NGKAAGGKGN | GAAAYTTHRA | CCCAANCCMT | ARSTTSGNAK | 780 |
| AAACCCYYCG | GGGTSMCAAA | MKNTWTTSSC | CTTCGGMCTT | YCCAAATMSA | AAATYYTCKK | 840 |
| KRMNAAAAMC | YGNCCCCSAA | ANATTTTTGT | NAAMCCCKMA | YYTRTTWMCC | WTTTTCCYCC | 900 |

```
CCMCNNSNSG GNTNCCCTTY TYATTTCYMM MCRNNSGACN CCCCMNTYTT TWTTCKCWCN        960

MMARGSNNYT RGRMMNMNCC CCNCCCCNAK MTCCNCAAAK NTTTNAACNN NNKYCKCCCC       1020

CCCMWMNKNC CCCCMNCMTT TM                                                1042

(2) INFORMATION FOR SEQ ID NO: 332:

(i) SEQUENCE CHARACTERISTICS:
        (A) LENGTH: 1073 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 332:

NNSGSGMKKK ATAMATCWCT CTSYACCSNG GMTCWATTGC GGCCGMAWTC TNGTMAASAG         60

ATCTCGAAYT CGGCAAANAK ACGCMAYGTC AAGTGTRAYY CGGTCACATA TCMTCGCGNG        120

TCAACMCCAA AGCCGNGTCA CCGYCTCCCT GGGGCGCCAC CCCCATCGGT RATGCAACYT       180

CGCGCGCCAC CGYCAAAAGG KTCWTTRAGG CGCTAAAGGT CAMCAATTCC TRAGGTYMCN       240

CACCGTTNTT TGGCCCGCCC RAWTYCTRAC CCGCAATWTC GGTAATCGGR AATTTGGGCW       300

YCGGCTTGGG CAATAAGKTN TTGGGCAACG GCGGRWTCYC NCTGGCCGRA ATTCCCNCAT       360

TCCKTTAACG GKTGRACCGT TTYCCCGGYT GCCGTAAYTG YTYCNTGGGC GCCYTCGGCC       420

CRNAGCASYY CRCTAACGGY CMCCAGGCAA TACCKTTGGC TTTRAACCAC CGGRATNAAY       480

TGKTACCCAC YTCAASSGTS CTGRANTTRK TNTCNTGRAA AANMCCACCN AACCCGGNTT       540

RATCTGCTTC MTCANCWTTT SCCGGGTTCT GCCGTTTTGR AAYCTTNATC CMTYCAAAAG       600

GTTTAMTTTC CCAANRAATT CGGYTTGCCA CCTTGGCCGS GGCTGGTTTM CGMWCCTTRR       660

AMATCCNCCS GCGGGSAAAN AMTTSGGNTT SGSCCGGTCC CCCGNAATAT YCNTGGNCCT       720

GNAAATTGSS GGGATCCCCN GSGNAYCCGG CCWTKGGGGK TNCCCAGTTG GWACAATTYC       780

WKCCGTTCCA AACCCGGGNC CGGGGGGTGG GSCCCNTTTT CCTMYNNAAA AAGKGTTTGN      840

NYYTTTTCCG CNRAANTTCA CCSKCNKTNT GGNCCNAACY YYYCAANTTC CANACCTTTA       900

AASAAANCYK YGKTYYCCCC TTTTMCCSGS SANCCCCCCM NMSSKNCGGG AAAAAAAGNK       960

TYNGCCTTAN CNSNKTKTTT TNKTYCCCCC NMWNNSNMCY NCBKKCNKRY NGNSNMNCCT      1020

MKYSKCNNNN SNNNNNKCGN GSNCSGMKYM CMNNCNGMYK NGNKSNNCCC MSC              1073

(2) INFORMATION FOR SEQ ID NO: 333:

(i) SEQUENCE CHARACTERISTICS:
        (A) LENGTH: 1061 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 333:

GNSNGNKNTN TMCAYCWYCT SCACSGGGTC TATTGCGGCC GCAATYTNGT CKASAGATCT         60

CGATYTCGGC AMNANAARTG TCGTCGTCAA TTTCAGKKTG GTCKTCAAAY GGGCCAGGCC       120

GNGACCRACA CCCTGNGTCA CCCAAAANAC CAACAGCWTC AAATWTCAAG GCCRAGGCSC       180

TRTCAATYCC CRASCAKTTA ACCGTKTCCW TCRAAGGTGC CRAACCAGGC ACCCAGYTCA       240

CCGCCSGGCA AWTCGCGCTG CCGGCCGGTN TCAGCCTGAT TYCTGACCCT RWTCTGTSGG       300

TGGYCAMCNT GGTGAAGGCC CWWCCGCCNA AGAACTGGAG GGCRAATTCC CAGGANCCNA      360
```

```
GRAACCCNAG GAACCCGCGG TAKAANCCGG CRAAACCRAG GCCGYTGGCN ATTCCNATTA       420

NAMSGGTTTG CRACNTGGCC RAACCGTTTY CTTGGTCGGC CTCGGCAACC CTGGACCANT       480

TACCCCKTNC CCGGNMCMAC CYCGGGTNCT TGKYCCCAAT NTGCYCCCGC GNRANTNGGC       540

CNAATTCCAG GGCNCCANCT TTCCGGCCCN AATTCCCYTG GTTAATCACC GGGCNCNCCT       600

GGTTTTGGGC AACCCCNCYS CTTMTTTAAA CATTCCGSCC CAAATGGGNC STTGGSAAAT       660

TCTNTYCGGT GGGGCSGGCR ANMYTTCTCT YCCCNAASAN CTTAMYCCAN TTCGSSNTCC       720

CGGKCAAAWS NGGGGGGGNA AAGGGCCCCC CGGNTSCKCC GGGGKKGCCC CYGGKTTCAA       780

AANTTTCSGG GKTSTMSCGG NVTCSCCCCC CSGCCAAGRA CCGNGGTTTT TTTTTGAACC       840

KCMANTCSSA AMCCGCCSSC CCCMAAAGGS GCCTNAAWGR RAYTTNKSCC CNNAAACSGG       900

CCCCCAKYTY SGGKTTCNNC CNCCSGKKGT CCMTSTTTMM MRCCCTTTGN GNKTTTTTAN       960

MGSCCTTNNC CACCCCCYCK GGGKCSMNNA GAAKTMYWKC CNGGGGNNAN RSCCCCCCNN      1020

GSGKGGGGKG MGAGYSCCKT CTKGCGNCNN YKNTTTCCCC C                          1061

(2) INFORMATION FOR SEQ ID NO: 334:

(i) SEQUENCE CHARACTERISTICS:
        (A) LENGTH: 986 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 334:

GNNGNNNKWN ATMCAYCWYY CTSCACCSGG GMTCWATTGC GGCCGCAWKY TNGTMAASAG        60

ATCTMGAAYT CGGCACANAG CGGCACAGAG TGTGTGCATC TGTGTCANAG CTGTCAACGC       120

GGTGCCGCSG GTGGTRASCA CMCATTGCGR AACACCAAAC CCGTCCGCGG GYCACCGGCK       180

TCGCCTGCAA AAYCCTCCAG GCCACCYCRA AACAAYWYCT CCTGCAACSC ARSCCGTTYC       240

GCGGCCGRAT CCTGGKYCAS YTCGCCKTGC GGTGCGCCAA GGTACTGGCS CWYCRANACC       300

GCTYCGGGRA ACCNAACGTA AATCTTGCCN AATTTGCNTT CCCCCTSCCC TTRATNAATT       360

TGTTAAACCA CGCAAACCTY CGGGCKTCTC CTCKTGCCRA WTCCGRWTCC RATNYCGCCA       420

TGGCCTNKTC KYCTYCKYCS GTMCCCAAAT CTTGGTATCC TATATTGTCC CTAAATGCAA       480

ATCTKGGCTG TCCATNTGCT GGCGTTCAAA TTWAMANCAG NGGTTTCTTY CTTCCNAAAC       540

CCSTTGGCCC CAAACCNAAA AATGATNATA ATAATGGTGC TNTCAAACCC CGCNCCCATY       600

CNATCSGKCC AMMCCCCRGN GGKTANKKGG GNAATTCTMM AACCCCAAGC CATAASNTTG       660

SGANAAACCY NCNCMGGYCA CCAAAACANY NTTNTTGGNY SSNTTCGGMN YCATGGCTNN       720

CMAAAACCCA AATACTNYYG GGYCCAATAA AAMMMSGGYC SAMCCGGAAA WTTTTYTTGN       780

KYNAAACCNA AAKCCTTTTT CNAACCCDAN WNTYCCTNCC RCRCMANTGG CNSGGARTKT       840

SSSCTTNCCA ATGKYCCMAA AGNGGGRANA CCARCCCCAA TTCCTNNNTN KNKNCCCNST       900

TRNAAAAGGG GKNTYNCMAA AASCNCCNCC NCNCTCCCAA AAKAMCCCCN AAAGAKNTCN       960

NAAANASKYSN NNNSCCCCCC CCMMMN                                          986

(2) INFORMATION FOR SEQ ID NO: 335:

(i) SEQUENCE CHARACTERISTICS:
        (A) LENGTH: 1074 base pairs
        (B) TYPE: nucleic acid
        (C) STRANDEDNESS: single
```

(D) TOPOLOGY: linear (ii) MOLECULE TYPE: Genomic DNA (xi) SEQUENCE DESCRIPTION: SEQ ID NO: 335:

NGNGGGNKRN ATMMAYCWCT SATYYACCSN GGMNMWATTG CGGCCRMAWT CTNGTMKASA        60

GATCTMGAAA YTCGGCAAAG AGYATKCTCG GGGGCCAGAT TTNTGGCCCG CAACCGCCGC       120

ACTTTGCAYW TCAACAKTCC SGGTGCCCCA AAAAAWTCWT ACCCCCATMC TYCKTGCASM       180

ASYTGCGCCC RATTRAACAC CCGGCCGGCW TGCTGCGCCA GGTATTYCAS CAGYTCAAAY       240

YCTTTKTAGK TAAAATCCAG CSGGCGGCCA CNCAGCCGGG CGGTKTAGGT GCCTYCRTCA       300

ATMACCAGCY CGCCCAGGGY CACCTTGCCC AAAAYCTCCT GGGTCAGCCA AATTYCCGCS       360

CCGGCCAACM ACCANCCGCA TYCTGGCNTC AATCYCACCG GGCCCGGTGY TAAAMMANMA       420

GRATCTCKTC MANCCCCCAN TCAGCSYTNA CNGCMACAGC CCGCCTTCTT CAMACCGCCA       480

RTACCGGGWT CAACCGGCCS GTCAAACTCA ACAGGCGGNC AGGCCTCCCC CGGANSAAAG       540

GTCTTACSCC NNYAANAAAA MAAGNTCTGT TTTCCCCCTC CASAASNAAA AANCCCCSGC       600

CGGGCCTTCN NMMGGGTTTG GGGMANANAA AARCNCCGGN GGAACGNATC CGAAAMCTCC       660

CAAGTCNCMT TWAWAACYCN NNAACCCCCC ANTTTTGGGA AAGGNTCCCC NTTMYCCCCC       720

TTTTASGKTS GGGMMYYCTY TAAAAAAATT CCCCAAAAAG CCCCGGGAAG GGTCMAMCTG       780

GGNAAATTTC CAAMCCNWGK TTNTTYNGGT TMCGGGGRA AATTYCNCTC CCYYNNNGGG       840

CSSGSNNNAT TAYGGMSNMT TTTNNAAWTM NSGKKTSAMM YNNKCCMNNN SNNMSMANNK       900

TNAMCKCCCN CCTCNGNGKY CSCYNCCCSG GNAGNGGRAS MKCCNANMAA AYASGNTTNK       960

CGGAAMMCNN AATKGNNNSC CCGGASMCMN NNNMAAATMT CNCNKCNSNN AANRGMRACN      1020

CCCNSNSGMN RRGAARMTNY YCCCCCGSKM GKGNKAAAAW GKYCCCCCCM AAAG           1074

(2) INFORMATION FOR SEQ ID NO: 336:

(i) SEQUENCE CHARACTERISTICS:
        (A) LENGTH: 1195 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 336:

NGNGNCNKNT MTACATCWTT CTGCACCSGG GNTCWANTGC GGCCGCAWKY TTGTCGASAG        60

ATCTCGAAYT CGGCAMGAGG ACWCTCGCRA CGCCCCCACA NACTCTGGCG TGTGTACCCC      120

ATTGNGCGCK TCACGCGCCC AYTGANCCAK TNCACTGGGG TGCCGTYCGC CKTGCGCGGC      180

GGCCTCACGG CKCTSCWTCT RAAGGCWTGG CGCACCGCAT TCGGTTTTCT RAACGCTGGG      240

AAAWTGGCCA GCCGTCTGGC TCATGGGNTC TACGCAACGC CNGCCCCCAA CRCTTTCTTA     300

AATCCGGYCC NTCCTGANCS CTTTGAAYCC CGGGGSAAGA ACTGGTTGCS CNCGAYCTGC     360

TCGAACTTRK TCNAAATCCC GCANAKTGTT TCNTAMGYCC CNCCGGAAGG NGAACCTACT     420

TTCNGGWANG TCGGCNKCCG GCGCTTATCA STCCTGATCA ACGGGGAACT GGYKNNSTTG     480

KGGGAAAAAG RRCCTCAATG MTYGGTCCKC GCTGCGKANC CGCSCCCTGK GYCGCNAATG     540

GAAGGCSMAG GGTTAANGCC MTTYCNYCCR RSCCGTSTGA SGKWTTYCGG MGGANKAMNN     600

NNKMAMWTTK TCRGNGGCCW ATSTSCCGGG CKSTTAKAGA ANACTYCCKW WCCGTNTYSC      660

SAAAGNTKCS GCGMGTTTTS SCCKMGANGN YCTGATTTSA GGGGGKYKCC CCCGGGGTYC      720

```
CGAAWKWRKY CCYAGGGGGM GNYCSAGCSC CGMNNATNAG AGNAAGGKTT RYGSTSKNCC      780

TYTNKGGACC WSCNNCWSAK ANAACNNKKT TGCSCCNTMS AGNKTNKGRT YCCNKTSTTC      840

TAAGAGGAGC TATKMKCGCC CKTGGANGMM GAGWGMGCGC KYCCCSNKRT TCNTNGWAAA      900

TATKSAGMGG TKCCGMAGMK CCSCGTTTKT TKTGANAAMN MSMRKNKKTG CGMGYTCTSC      960

GGGNTTTGTA GAGTAKTCGS CSCSSMWGAC WCSGMCMGNG AGKNKTNNTS YANTGARCGY     1020

MNNSKTMKMT MSCSCGCGNA GGAGNGCCCC CSANGMSTGY NKGGNMSSNG ARAKGATGGS     1080

GGCCNCGMNN MGMGGANMGA SANNGMGGMR GGGGGKTGKC TCKCSCCGNS CSANGRAGAA     1140

GKTCNGSCGC CGMGGKYGKT KTKTKNKTGG YSTCMSSMMM NAGAAAAGAG AGGGC          1195

(2) INFORMATION FOR SEQ ID NO: 337:

(i) SEQUENCE CHARACTERISTICS:
        (A) LENGTH: 3572 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 337:

CCATCTGATC GTTGGCAACC AGCATCGCAG TGGGAACGAT GCCCTCATTC AGCATTTGCA       60

TGGTTTGTTG AAAACCGGAC ATGGCACTCC AGTCGCCTTC CCGTTCCGCT ATCGGCTGAA      120

TTTGATTGCG AGTGAGATAT TTATGCCAGC CAGCCAGACG CAGACGCGCC GAGACAGAAC      180

TTAATGGGCC CGCTAACAGC GCGATTTGCT GGTGACCCAA TGCGACCAGA TGCTCCACGC      240

CCAGTCGCGT ACCGTCTTCA TGGGAGAAAA TAATACTGTT GATGGGTGTC TGGTCAGAGA      300

CATCAAGAAA TAACGCCGGA ACATTAGTGC AGGCAGCTTC CACAGCAATG GCATCCTGGT      360

CATCCAGCGG ATAGTTAATG ATCAGCCCAC TGACGCGTTG CGCGAGAAGA TTGTGCACCG      420

CCGCTTTACA GGCTTCGACG CCGCTTCGTT CTACCATCGA CACCACCACG CTGGCACCCA      480

GTTGATCGGC GCGAGATTTA ATCGCCGCGA CAATTTGCGA CGGCGCGTGC AGGGCCAGAC      540

TGGAGGTGGC AACGCCAATC AGCAACGACT GTTTGCCCGC CAGTTGTTGT GCCACGCGGT      600

TGGGAATGTA ATTCAGCTCC GCCATCGCCG CTTCCACTTT TTCCCGCGTT TTCGCAGAAA      660

CGTGGCTGGC CTGGTTCACC ACGCGGGAAA CGGTCTGATA AGAGACACCG GCATACTCTG      720

CGACATCGTA TAACGTTACT GGTTTCACAT TCACCACCCT GAATTGACTC TCTTCCGGGC      780

GCTATCATGC CATACCGCGA AAGGTTTTGC GCCATTCGAT GGTGTCCGGG ATCTCGACGC      840

TCTCCCTTAT GCGACTCCTG CATTAGGAAG CAGCCCAGTA GTAGGTTGAG GCCGTTGAGC      900

ACCGCCGCCG CAAGGAATGG TGCATGCAAG GAGATGGCGC CCAACAGTCC CCCGGCCACG      960

GGGCCTGCCA CCATACCCAC GCCGAAACAA GCGCTCATGA GCCCGAAGTG GCGAGCCCGA     1020

TCTTCCCCAT CGGTGATGTC GGCGATATAG GCGCCAGCAA CCGCACCTGT GGCGCCGGTG     1080

ATGCCGGCCA CGATGCGTCC GGCGTAGAGG ATCGAGATCT CGATCCCGCG AAATTAATAC     1140

GACTCACTAT AGGGGAATTG TGAGCGGATA ACAATTCCCC TCTAGAAATA ATTTTGTTTA     1200

ACTTTAAGAA GGAGATATAC ATATGGGCCA TCATCATCAT CATCACGTGA TCGACATCAT     1260

CGGGACCAGC CCCACATCCT GGGAACAGGC GGCGGCGGAG GCGGTCCAGC GGGCGCGGGA     1320

TAGCGTCGAT GACATCCGCG TCGCTCGGGT CATTGAGCAG GACATGGCCG TGGACAGCGC     1380

CGGCAAGATC ACCTACCGCA TCAAGCTCGA AGTGTCGTTC AAGATGAGGC CGGCGCAACC     1440

GAGGGGCTCG AAACCACCGA GCGGTTCGCC TGAAACGGGC GCCGGCGCCG GTACTGTCGC     1500
```

```
GACTACCCCC GCGTCGTCGC CGGTGACGTT GGCGGAGACC GGTAGCACGC TGCTCTACCC    1560

GCTGTTCAAC CTGTGGGGTC CGGCCTTTCA CGAGAGGTAT CCGAACGTCA CGATCACCGC    1620

TCAGGGCACC GGTTCTGGTG CCGGGATCGC GCAGGCCGCC GCCGGGACGG TCAACATTGG    1680

GGCCTCCGAC GCCTATCTGT CGGAAGGTGA TATGGCCGCG CACAAGGGGC TGATGAACAT    1740

CGCGCTAGCC ATCTCCGCTC AGCAGGTCAA CTACAACCTG CCCGGAGTGA GCGAGCACCT    1800

CAAGCTGAAC GGAAAAGTCC TGGCGGCCAT GTACCAGGGC ACCATCAAAA CCTGGGACGA    1860

CCCGCAGATC GCTGCGCTCA ACCCCGGCGT GAACCTGCCC GGCACCGCGG TAGTTCCGCT    1920

GCACCGCTCC GACGGGTCCG GTGACACCTT CTTGTTCACC CAGTACCTGT CCAAGCAAGA    1980

TCCCGAGGGC TGGGGCAAGT CGCCCGGCTT CGGCACCACC GTCGACTTCC GGCGGTGCC    2040

GGGTGCGCTG GGTGAGAACG GCAACGGCGG CATGGTGACC GGTTGCGCCG AGACACCGGG    2100

CTGCGTGGCC TATATCGGCA TCAGCTTCCT CGACCAGGCC AGTCAACGGG GACTCGGCGA    2160

GGCCCAACTA GGCAATAGCT CTGGCAATTT CTTGTTGCCC GACGCGCAAA GCATTCAGGC    2220

CGCGGCGGCT GGCTTCGCAT CGAAAACCCC GGCGAACCAG GCGATTTCGA TGATCGACGG    2280

GCCCGCCCCG GACGGCTACC CGATCATCAA CTACGAGTAC GCCATCGTCA CAACCGGCA    2340

AAAGGACGCC GCCACCGCGC AGACCTTGCA GGCATTTCTG CACTGGGCGA TCACCGACGG    2400

CAACAAGGCC TCGTTCCTCG ACCAGGTTCA TTTCCAGCCG CTGCCGCCCG CGGTGGTGAA    2460

GTTGTCTGAC GCGTTGATCG CGACGATTTC CAGCGCTGAG ATGAAGACCG ATGCCGCTAC    2520

CCTCGCGCAG GAGGCAGGTA ATTTCGAGCG GATCTCCGGC GACCTGAAAA CCCAGATCGA    2580

CCAGGTGGAG TCGACGGCAG GTTCGTTGCA GGGCCAGTGG CGCGGCGCGG CGGGGACGGC    2640

CGCCCAGGCC GCGGTGGTGC GCTTCCAAGA AGCAGCCAAT AAGCAGAAGC AGGAACTCGA    2700

CGAGATCTCG ACGAATATTC GTCAGGCCGG CGTCCAATAC TCGAGGGCCG ACGAGGAGCA    2760

GCAGCAGGCG CTGTCCTCGC AAATGGGCTT TGGATTCAGC TTCGCGCTGC CTGCTGGCTG    2820

GGTGGAGTCT GACGCCGCCC ACTTCGACTA CGGTTCAGCA CTCCTCAGCA AAACCACCGG    2880

GGACCCGCCA TTTCCCGGAC AGCCGCCGCC GGTGGCCAAT GACACCCGTA TCGTGCTCGG    2940

CCGGCTAGAC CAAAAGCTTT ACGCCAGCGC CGAAGCCACC GACTCCAAGG CCGCGGCCCG    3000

GTTGGGCTCG GACATGGGTG AGTTCTATAT GCCCTACCCG GGCACCCGGA TCAACCAGGA    3060

AACCGTCTCG CTYGACGCCA ACGGGGTGTC TGGAAGCGCG TCGTATTACG AAGTCAAGTT    3120

CAGCGATCCG AGTAAGCCGA ACGGCCAGAT CTGGACGGGC GTAATCGGCT CGCCCGCGGC    3180

GAACGCACCG GACGCCGGGC CCCCTCAGCG CTGGTTTGTG GTATGGCTCG GGACCGCCAA    3240

CAACCCGGTG GACAAGGGCG CGGCCAAGGC GCTGGCCGAA TCGATCCGGC CTTTGGTCGC    3300

CCCGCCGCCG GCGCCGGCCG GGGAAGTCGC TCCTACCCCG ACGACACCGA CACCGCAGCG    3360

GACCTTACCG GCCTGAGAAT TCTGCAGATA TCCATCACAC TGGCGGCCGC TCGAGCACCA    3420

CCACCACCAC CACTGAGATC CGGCTGCTAA CAAAGCCCGA AAGGAAGCTG AGTTGGCTGC    3480

TGCCACCGCT GAGCAATAAC TAGCATAACC CCTTGGGGCC TCTAAACGGG TCTTGAGGGG    3540

TTTTTTGCTG AAAGGAGGAA CTATATCCGG AT                                  3572
```

(2) INFORMATION FOR SEQ ID NO: 338:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 338:

Val Gln Phe Gln Ser Gly Gly Asp Asn Ser Pro Ala Val Tyr Xaa Xaa
1               5                   10                  15

Asp Gly Xaa Arg
            20

(2) INFORMATION FOR SEQ ID NO: 339:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 339:

Thr Thr Val Pro Xaa Val Thr Glu Ala Arg
1               5                   10

(2) INFORMATION FOR SEQ ID NO: 340:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 340:

Thr Thr Pro Ser Xaa Val Ala Phe Ala Arg
1               5                   10

(2) INFORMATION FOR SEQ ID NO: 341:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 341:

Asp Ala Gly Lys Xaa Ala Gly Xaa Asp Val Xaa Arg
1               5                   10

(2) INFORMATION FOR SEQ ID NO: 342:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 342:

Thr Xaa Glu Glu Xaa Gln Glu Ser Phe Asn Ser Ala Ala Pro Gly Asn
1               5                   10                  15

Xaa Lys (2) INFORMATION FOR SEQ ID NO: 343:

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 343:

CTAGTTAGTA CTCAGTCGCA GACCGTG                                         27

(2) INFORMATION FOR SEQ ID NO: 344:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 344:

GCAGTGACGA ATTCACTTCG ACTCC                                           25

(2) INFORMATION FOR SEQ ID NO: 345:

(i) SEQUENCE CHARACTERISTICS:
        (A) LENGTH: 2412 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 345:

CATATGGGCC ATCATCATCA TCATCACGTG ATCGACATCA TCGGGACCAG CCCCACATCC     60

TGGGAACAGG CGGCGGCGGA GGCGGTCCAG CGGGCGCGGG ATAGCGTCGA TGACATCCGC    120

GTCGCTCGGG TCATTGAGCA GGACATGGCC GTGGACAGCG CCGGCAAGAT CACCTACCGC    180

ATCAAGCTCG AAGTGTCGTT CAAGATGAGG CCGGCGCAAC CGAGGGGCTC GAAACCACCG    240

AGCGGTTCGC CTGAAACGGG CGCCGGCGCC GGTACTGTCG CGACTACCCC CGCGTCGTCG    300

CCGGTGACGT TGGCGGAGAC CGGTAGCACG CTGCTCTACC CGCTGTTCAA CCTGTGGGGT    360

CCGGCCTTTC ACGAGAGGTA TCCGAACGTC ACGATCACCG CTCAGGGCAC CGGTTCTGGT    420

GCCGGGATCG CGCAGGCCGC CGCCGGGACG GTCAACATTG GGCCTCCGA CGCCTATCTG     480

TCGGAAGGTG ATATGGCCGC GCACAAGGGG CTGATGAACA TCGCGCTAGC CATCTCCGCT    540

CAGCAGGTCA ACTACAACCT GCCCGGAGTG AGCGAGCACC TCAAGCTGAA CGGAAAAGTC    600

CTGGCGGCCA TGTACCAGGG CACCATCAAA ACCTGGGACG ACCCGCAGAT CGCTGCGCTC    660

AACCCCGGCG TGAACCTGCC CGGCACCGCG GTAGTTCCGC TGCACCGCTC CGACGGGTCC    720

GGTGACACCT TCTTGTTCAC CCAGTACCTG TCCAAGCAAG ATCCCGAGGG CTGGGGCAAG    780

TCGCCCGGCT TCGGCACCAC CGTCGACTTC CCGGCGGTGC CGGGTGCGCT GGGTGAGAAC    840

GGCAACGGCG GCATGGTGAC CGGTTGCGCC GAGACACCGG GCTGCGTGGC CTATATCGGC    900

ATCAGCTTCC TCGACCAGGC CAGTCAACGG GGACTCGGCG AGGCCCAACT AGGCAATAGC    960

TCTGGCAATT TCTTGTTGCC CGACGCGCAA AGCATTCAGG CCGCGGCGGC TGGCTTCGCA   1020

TCGAAAACCC CGGCGAACCA GGCGATTTCG ATGATCGACG GGCCCGCCCC GGACGGCTAC   1080

CCGATCATCA ACTACGAGTA CGCCATCGTC AACAACCGGC AAAAGGACGC CGCCACCGCG   1140

CAGACCTTGC AGGCATTTCT GCACTGGGCG ATCACCGACG GCAACAAGGC CTCGTTCCTC   1200
```

-continued

```
GACCAGGTTC ATTTCCAGCC GCTGCCGCCC GCGGTGGTGA AGTTGTCTGA CGCGTTGATC    1260

GCGACGATTT CCAGCGCTGA GATGAAGACC GATGCCGCTA CCCTCGCGCA GGAGGCAGGT    1320

AATTTCGAGC GGATCTCCGG CGACCTGAAA ACCCAGATCG ACCAGGTGGA GTCGACGGCA    1380

GGTTCGTTGC AGGGCCAGTG GCGCGGCGCG GCGGGGACGG CCGCCCAGGC CGCGGTGGTG    1440

CGCTTCCAAG AAGCAGCCAA TAAGCAGAAG CAGGAACTCG ACGAGATCTC GACGAATATT    1500

CGTCAGGCCG GCGTCCAATA CTCGAGGGCC GACGAGGAGC AGCAGCAGGC GCTGTCCTCG    1560

CAAATGGGCT TTGTGCCCAC AACGGCCGCC TCGCCGCCGT CGACCGCTGC AGCGCCACCC    1620

GCACCGGCGA CACCTGTTGC CCCCCCACCA CCGGCCGCCG CCAACACGCC GAATGCCCAG    1680

CCGGGCGATC CCAACGCAGC ACCTCCGCCG GCCGACCCGA ACGCACCGCC GCCACCTGTC    1740

ATTGCCCCAA ACGCACCCCA ACCTGTCCGG ATCGACAACC CGGTTGGAGG ATTCAGCTTC    1800

GCGCTGCCTG CTGGCTGGGT GGAGTCTGAC GCCGCCCACT TCGACTACGG TTCAGCACTC    1860

CTCAGCAAAA CCACCGGGGA CCCGCCATTT CCCGGACAGC CGCCGCCGGT GGCCAATGAC    1920

ACCCGTATCG TGCTCGGCCG GCTAGACCAA AAGCTTTACG CCAGCGCCGA AGCCACCGAC    1980

TCCAAGGCCG CGGCCCGGTT GGGCTCGGAC ATGGGTGAGT TCTATATGCC CTACCCGGGC    2040

ACCCGGATCA ACCAGGAAAC CGTCTCGCTC GACGCCAACG GGGTGTCTGG AAGCGCGTCG    2100

TATTACGAAG TCAAGTTCAG CGATCCGAGT AAGCCGAACG GCCAGATCTG GACGGGCGTA    2160

ATCGGCTCGC CCGCGGCGAA CGCACCGGAC GCCGGGCCCC CTCAGCGCTG GTTTGTGGTA    2220

TGGCTCGGGA CCGCCAACAA CCCGGTGGAC AAGGGCGCGG CCAAGGCGCT GGCCGAATCG    2280

ATCCGGCCTT TGGTCGCCCC GCCGCCGGCG CCGGCACCGG CTCCTGCAGA GCCCGCTCCG    2340

GCGCCGGCGC CGGCCGGGGA AGTCGCTCCT ACCCCGACGA CACCGACACC GCAGCGGACC    2400

TTACCGGCCT GA                                                      2412
```

(2) INFORMATION FOR SEQ ID NO: 346:

(i) SEQUENCE CHARACTERISTICS:
        (A) LENGTH: 802 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 346:

```
Met Gly His His His His His Val Ile Asp Ile Ile Gly Thr Ser
 1               5                  10                  15

Pro Thr Ser Trp Glu Gln Ala Ala Glu Ala Val Gln Arg Ala Arg
                20                  25                  30

Asp Ser Val Asp Ile Arg Val Ala Arg Val Ile Glu Gln Asp Met
            35                  40                  45

Ala Val Asp Ser Ala Gly Lys Ile Thr Tyr Arg Ile Lys Leu Glu Val
        50                  55                  60

Ser Phe Lys Met Arg Pro Ala Gln Pro Arg Gly Ser Lys Pro Pro Ser
65                  70                  75                  80

Gly Ser Pro Glu Thr Gly Ala Gly Ala Gly Thr Val Ala Thr Pro
                85                  90                  95

Ala Ser Ser Pro Val Thr Leu Ala Glu Thr Gly Ser Thr Leu Leu Tyr
            100                 105                 110

Pro Leu Phe Asn Leu Trp Gly Pro Ala Phe His Glu Arg Tyr Pro Asn
        115                 120                 125
```

```
Val Thr Ile Thr Ala Gln Gly Thr Gly Ser Gly Ala Gly Ile Ala Gln
            130                 135                 140

Ala Ala Ala Gly Thr Val Asn Ile Gly Ala Ser Asp Ala Tyr Leu Ser
145                 150                 155                 160

Glu Gly Asp Met Ala Ala His Lys Gly Leu Met Asn Ile Ala Leu Ala
                165                 170                 175

Ile Ser Ala Gln Gln Val Asn Tyr Asn Leu Pro Gly Val Ser Glu His
            180                 185                 190

Leu Lys Leu Asn Gly Lys Val Leu Ala Met Tyr Gln Gly Thr Ile
            195                 200                 205

Lys Thr Trp Asp Asp Pro Gln Ile Ala Ala Leu Asn Pro Gly Val Asn
210                 215                 220

Leu Pro Gly Thr Ala Val Val Pro Leu His Arg Ser Asp Gly Ser Gly
225                 230                 235                 240

Asp Thr Phe Leu Phe Thr Gln Tyr Leu Ser Lys Gln Asp Pro Glu Gly
                245                 250                 255

Trp Gly Lys Ser Pro Gly Phe Gly Thr Thr Val Asp Phe Pro Ala Val
            260                 265                 270

Pro Gly Ala Leu Gly Glu Asn Gly Asn Gly Met Val Thr Gly Cys
            275                 280                 285

Ala Glu Thr Pro Gly Cys Val Ala Tyr Ile Gly Ile Ser Phe Leu Asp
            290                 295                 300

Gln Ala Ser Gln Arg Gly Leu Gly Glu Ala Gln Leu Gly Asn Ser Ser
305                 310                 315                 320

Gly Asn Phe Leu Leu Pro Asp Ala Gln Ser Ile Gln Ala Ala Ala
            325                 330                 335

Gly Phe Ala Ser Lys Thr Pro Ala Asn Gln Ala Ile Ser Met Ile Asp
            340                 345                 350

Gly Pro Ala Pro Asp Gly Tyr Pro Ile Ile Asn Tyr Glu Tyr Ala Ile
            355                 360                 365

Val Asn Asn Arg Gln Lys Asp Ala Ala Thr Ala Gln Thr Leu Gln Ala
370                 375                 380

Phe Leu His Trp Ala Ile Thr Asp Gly Asn Lys Ala Ser Phe Leu Asp
385                 390                 395                 400

Gln Val His Phe Gln Pro Leu Pro Pro Ala Val Val Lys Leu Ser Asp
                405                 410                 415

Ala Leu Ile Ala Thr Ile Ser Ser Ala Glu Met Lys Thr Asp Ala Ala
            420                 425                 430

Thr Leu Ala Gln Glu Ala Gly Asn Phe Glu Arg Ile Ser Gly Asp Leu
            435                 440                 445

Lys Thr Gln Ile Asp Gln Val Glu Ser Thr Ala Gly Ser Leu Gln Gly
            450                 455                 460

Gln Trp Arg Gly Ala Ala Gly Thr Ala Ala Gln Ala Ala Val Val Arg
465                 470                 475                 480

Phe Gln Glu Ala Ala Asn Lys Gln Lys Gln Glu Leu Asp Glu Ile Ser
                485                 490                 495

Thr Asn Ile Arg Gln Ala Gly Val Gln Tyr Ser Arg Ala Asp Glu Glu
            500                 505                 510

Gln Gln Gln Ala Leu Ser Ser Gln Met Gly Phe Val Pro Thr Thr Ala
            515                 520                 525

Ala Ser Pro Pro Ser Thr Ala Ala Ala Pro Pro Ala Pro Ala Thr Pro
530                 535                 540
```

```
Val Ala Pro Pro Pro Ala Ala Asn Thr Pro Asn Ala Gln Pro
545                 550             555             560

Gly Asp Pro Asn Ala Ala Pro Pro Ala Asp Pro Asn Ala Pro Pro
            565             570             575

Pro Pro Val Ile Ala Pro Asn Ala Pro Gln Pro Val Arg Ile Asp Asn
        580             585             590

Pro Val Gly Gly Phe Ser Phe Ala Leu Pro Ala Gly Trp Val Glu Ser
        595             600             605

Asp Ala Ala His Phe Asp Tyr Gly Ser Ala Leu Leu Ser Lys Thr Thr
        610             615             620

Gly Asp Pro Pro Phe Pro Gly Gln Pro Pro Val Ala Asn Asp Thr
625             630             635             640

Arg Ile Val Leu Gly Arg Leu Asp Gln Lys Leu Tyr Ala Ser Ala Glu
                645             650             655

Ala Thr Asp Ser Lys Ala Ala Arg Leu Gly Ser Asp Met Gly Glu
                660             665             670

Phe Tyr Met Pro Tyr Pro Gly Thr Arg Ile Asn Gln Glu Thr Val Ser
            675             680             685

Leu Asp Ala Asn Gly Val Ser Gly Ser Ala Ser Tyr Tyr Glu Val Lys
            690             695             700

Phe Ser Asp Pro Ser Lys Pro Asn Gly Gln Ile Trp Thr Gly Val Ile
705             710             715             720

Gly Ser Pro Ala Ala Asn Ala Pro Asp Ala Gly Pro Pro Gln Arg Trp
            725             730             735

Phe Val Val Trp Leu Gly Thr Ala Asn Asn Pro Val Asp Lys Gly Ala
            740             745             750

Ala Lys Ala Leu Ala Glu Ser Ile Arg Pro Leu Val Ala Pro Pro Pro
        755             760             765

Ala Pro Ala Pro Ala Pro Ala Glu Pro Ala Pro Ala Pro Ala
770             775             780

Gly Glu Val Ala Pro Thr Pro Thr Thr Pro Thr Pro Gln Arg Thr Leu
785             790             795             800

Pro Ala (2) INFORMATION FOR SEQ ID NO: 347:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 347:

GGATCCAAAC CACCGAGCGG TTCGCCTGAA ACGG                            34

(2) INFORMATION FOR SEQ ID NO: 348:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 348:

CGCTGCGAAT TCACCTCCGG AGGAAATCGT CGCGATC                         37
```

(2) INFORMATION FOR SEQ ID NO: 349:

(i) SEQUENCE CHARACTERISTICS:
        (A) LENGTH: 1962 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 349:

```
CATATGGGCC ATCATCATCA TCATCACGGA TCCAAACCAC CGAGCGGTTC GCCTGAAACG      60
GGCGCCGGCG CCGGTACTGT CGCGACTACC CCCGCGTCGT CGCCGGTGAC GTTGGCGGAG     120
ACCGGTAGCA CGCTGCTCTA CCCGCTGTTC AACCTGTGGG GTCCGGCCTT TCACGAGAGG     180
TATCCGAACG TCACGATCAC CGCTCAGGGC ACCGGTTCTG GTGCCGGGAT CGCGCAGGCC     240
GCCGCCGGGA CGGTCAACAT TGGGGCCTCC GACGCCTATC TGTCGGAAGG TGATATGGCC     300
GCGCACAAGG GGCTGATGAA CATCGCGCTA GCCATCTCCG CTCAGCAGGT CAACTACAAC     360
CTGCCCGGAG TGAGCGAGCA CCTCAAGCTG AACGGAAAAG TCCTGGCGGC CATGTACCAG     420
GGCACCATCA AAACCTGGGA CGACCCGCAG ATCGCTGCGC TCAACCCCGG CGTGAACCTG     480
CCCGGCACCG CGGTAGTTCC GCTGCACCGC TCCGACGGGT CCGGTGACAC CTTCTTGTTC     540
ACCCAGTACC TGTCCAAGCA AGATCCCGAG GGCTGGGCA AGTCGCCCGG CTTCGGCACC     600
ACCGTCGACT TCCCGGCGGT GCCGGGTGCG CTGGGTGAGA ACGGCAACGG CGGCATGGTG     660
ACCGGTTGCG CCGAGACACC GGGCTGCGTG GCCTATATCG GCATCAGCTT CCTCGACCAG     720
GCCAGTCAAC GGGGACTCGG CGAGGCCCAA CTAGGCAATA GCTCTGGCAA TTTCTTGTTG     780
CCCGACGCGC AAAGCATTCA GGCCGCGGCG GCTGGCTTCG CATCGAAAAC CCCGGCGAAC     840
CAGGCGATTT CGATGATCGA CGGGCCCGCC CCGGACGGCT ACCCGATCAT CAACTACGAG     900
TACGCCATCG TCAACAACCG GCAAAAGGAC GCCGCCACCG CGCAGACCTT GCAGGCATTT     960
CTGCACTGGG CGATCACCGA CGGCAACAAG GCCTCGTTCC TCGACCAGGT TCATTTCCAG    1020
CCGCTGCCGC CCGCGGTGGT GAAGTTGTCT GACGCGTTGA TCGCGACGAT TTCCTCCGGA    1080
GGTGGCAGTG GGGGAGGCTC AGGTGGAGGT TCTGGCGGGA GCGTGCCCAC AACGGCCGCC    1140
TCGCCGCCGT CGACCGCTGC AGCGCCACCC GCACCGGCGA CACCTGTTGC CCCCCCACCA    1200
CCGGCCGCCG CCAACACGCC GAATGCCCAG CCGGGCGATC CCAACGCAGC ACCTCCGCCG    1260
GCCGACCCGA ACGCACCGCC GCCACCTGTC ATTGCCCCAA ACGCACCCCA ACCTGTCCGG    1320
ATCGACAACC CGGTTGGAGG ATTCAGCTTC GCGCTGCCTG CTGGCTGGGT GGAGTCTGAC    1380
GCCGCCCACT TCGACTACGG TTCAGCACTC CTCAGCAAAA CCACCGGGGA CCCGCCATTT    1440
CCCGGACAGC CGCCGCCGGT GGCCAATGAC ACCCGTATCG TGCTCGGCCG GCTAGACCAA    1500
AAGCTTTACG CCAGCGCCGA AGCCACCGAC TCCAAGGCCG CGGCCCGGTT GGGCTCGGAC    1560
ATGGGTGAGT CTATATGCC CTACCCGGGC ACCCGGATCA ACCAGGAAAC CGTCTCGCTC    1620
GACGCCAACG GGGTGTCTGG AAGCGCGTCG TATTACGAAG TCAAGTTCAG CGATCCGAGT    1680
AAGCCGAACG CCAGATCTG GACGGGCGTA ATCGGCTCGC CCGCGGCGAA CGCACCGGAC    1740
GCCGGGCCCC CTCAGCGCTG GTTTGTGGTA TGGCTCGGGA CCGCCAACAA CCCGGTGGAC    1800
AAGGGCGCGG CCAAGGCGCT GGCCGAATCG ATCCGGCCTT TGGTCGCCCC GCCGCCGGCG    1860
CCGGCACCGG CTCCTGCAGA GCCCGCTCCG GCGCCGGCGC CGGCCGGGGA AGTCGCTCCT    1920
ACCCCGACGA CACCGACACC GCAGCGGACC TTACCGGCCT GA                      1962
```

(2) INFORMATION FOR SEQ ID NO: 350:

(i) SEQUENCE CHARACTERISTICS:
        (A) LENGTH: 652 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 350:

```
Met Gly His His His His His Gly Ser Lys Pro Pro Ser Gly Ser
 1               5                  10                  15

Pro Glu Thr Gly Ala Gly Ala Gly Thr Val Ala Thr Thr Pro Ala Ser
            20                  25                  30

Ser Pro Val Thr Leu Ala Glu Thr Gly Ser Thr Leu Leu Tyr Pro Leu
            35                  40                  45

Phe Asn Leu Trp Gly Pro Ala Phe His Glu Arg Tyr Pro Asn Val Thr
 50                  55                  60

Ile Thr Ala Gln Gly Thr Gly Ser Gly Ala Gly Ile Ala Gln Ala Ala
 65                  70                  75                  80

Ala Gly Thr Val Asn Ile Gly Ala Ser Asp Ala Tyr Leu Ser Glu Gly
                85                  90                  95

Asp Met Ala Ala His Lys Gly Leu Met Asn Ile Ala Leu Ala Ile Ser
            100                 105                 110

Ala Gln Gln Val Asn Tyr Asn Leu Pro Gly Val Ser Glu His Leu Lys
            115                 120                 125

Leu Asn Gly Lys Val Leu Ala Ala Met Tyr Gln Gly Thr Ile Lys Thr
130                 135                 140

Trp Asp Asp Pro Gln Ile Ala Ala Leu Asn Pro Gly Val Asn Leu Pro
145                 150                 155                 160

Gly Thr Ala Val Val Pro Leu His Arg Ser Asp Gly Ser Gly Asp Thr
                165                 170                 175

Phe Leu Phe Thr Gln Tyr Leu Ser Lys Gln Asp Pro Glu Gly Trp Gly
            180                 185                 190

Lys Ser Pro Gly Phe Gly Thr Thr Val Asp Phe Pro Ala Val Pro Gly
            195                 200                 205

Ala Leu Gly Glu Asn Gly Asn Gly Gly Met Val Thr Gly Cys Ala Glu
            210                 215                 220

Thr Pro Gly Cys Val Ala Tyr Ile Gly Ile Ser Phe Leu Asp Gln Ala
225                 230                 235                 240

Ser Gln Arg Gly Leu Gly Glu Ala Gln Leu Gly Asn Ser Ser Gly Asn
            245                 250                 255

Phe Leu Leu Pro Asp Ala Gln Ser Ile Gln Ala Ala Ala Gly Phe
            260                 265                 270

Ala Ser Lys Thr Pro Ala Asn Gln Ala Ile Ser Met Ile Asp Gly Pro
            275                 280                 285

Ala Pro Asp Gly Tyr Pro Ile Ile Asn Tyr Glu Tyr Ala Ile Val Asn
            290                 295                 300

Asn Arg Gln Lys Asp Ala Ala Thr Ala Gln Thr Leu Gln Ala Phe Leu
305                 310                 315                 320

His Trp Ala Ile Thr Asp Gly Asn Lys Ala Ser Phe Leu Asp Gln Val
                325                 330                 335

His Phe Gln Pro Leu Pro Pro Ala Val Val Lys Leu Ser Asp Ala Leu
            340                 345                 350
```

-continued

```
Ile Ala Thr Ile Ser Ser Gly Gly Gly Ser Gly Gly Gly Ser Gly Gly
        355                 360                 365

Gly Ser Gly Gly Ser Val Pro Thr Thr Ala Ala Ser Pro Pro Ser Thr
        370                 375                 380

Ala Ala Ala Pro Pro Ala Pro Ala Thr Pro Val Ala Pro Pro Pro Pro
385                 390                 395                 400

Ala Ala Ala Asn Thr Pro Asn Ala Gln Pro Gly Asp Pro Asn Ala Ala
                405                 410                 415

Pro Pro Pro Ala Asp Pro Asn Ala Pro Pro Pro Val Ile Ala Pro
                420                 425                 430

Asn Ala Pro Gln Pro Val Arg Ile Asp Asn Pro Val Gly Gly Phe Ser
        435                 440                 445

Phe Ala Leu Pro Ala Gly Trp Val Glu Ser Asp Ala Ala His Phe Asp
        450                 455                 460

Tyr Gly Ser Ala Leu Leu Ser Lys Thr Thr Gly Asp Pro Pro Phe Pro
465                 470                 475                 480

Gly Gln Pro Pro Val Ala Asn Asp Thr Arg Ile Val Leu Gly Arg
                485                 490                 495

Leu Asp Gln Lys Leu Tyr Ala Ser Ala Glu Ala Thr Asp Ser Lys Ala
                500                 505                 510

Ala Ala Arg Leu Gly Ser Asp Met Gly Glu Phe Tyr Met Pro Tyr Pro
        515                 520                 525

Gly Thr Arg Ile Asn Gln Glu Thr Val Ser Leu Asp Ala Asn Gly Val
        530                 535                 540

Ser Gly Ser Ala Ser Tyr Tyr Glu Val Lys Phe Ser Asp Pro Ser Lys
545                 550                 555                 560

Pro Asn Gly Gln Ile Trp Thr Gly Val Ile Gly Ser Pro Ala Ala Asn
                565                 570                 575

Ala Pro Asp Ala Gly Pro Pro Gln Arg Trp Phe Val Val Trp Leu Gly
                580                 585                 590

Thr Ala Asn Asn Pro Val Asp Lys Gly Ala Ala Lys Ala Leu Ala Glu
        595                 600                 605

Ser Ile Arg Pro Leu Val Ala Pro Pro Pro Ala Pro Ala Pro Ala Pro
        610                 615                 620

Ala Glu Pro Ala Pro Ala Pro Ala Pro Ala Gly Glu Val Ala Pro Thr
625                 630                 635                 640

Pro Thr Thr Pro Thr Pro Gln Arg Thr Leu Pro Ala
                645                 650
```